US011970494B2

(12) United States Patent
Masse et al.

(10) Patent No.: US 11,970,494 B2
(45) Date of Patent: Apr. 30, 2024

(54) 6-HETEROARYLOXY BENZIMIDAZOLES AND AZABENZIMIDAZOLES AS JAK2 INHIBITORS

(71) Applicant: Ajax Therapeutics, Inc., New York, NY (US)

(72) Inventors: Craig E. Masse, Cambridge, MA (US); Jeremy R. Greenwood, Brooklyn, NY (US); Jiayi Xu, Marlboro, NJ (US); Sayan Mondal, New York, NY (US); Phani Ghanakota, Edison, NJ (US)

(73) Assignee: Ajax Therapeutics, Inc., New York, NY (US)

( * ) Notice: Subject to any disclaimer, the term of this patent is extended or adjusted under 35 U.S.C. 154(b) by 0 days.

(21) Appl. No.: 17/982,663

(22) Filed: Nov. 8, 2022

(65) Prior Publication Data

US 2023/0167110 A1   Jun. 1, 2023

Related U.S. Application Data

(60) Provisional application No. 63/354,403, filed on Jun. 22, 2022, provisional application No. 63/277,343, filed on Nov. 9, 2021.

(51) Int. Cl.
 *C07D 471/04* (2006.01)
 *C07D 519/00* (2006.01)

(52) U.S. Cl.
 CPC ......... *C07D 471/04* (2013.01); *C07D 519/00* (2013.01)

(58) Field of Classification Search
 None
 See application file for complete search history.

(56) References Cited

U.S. PATENT DOCUMENTS

| | | |
|---|---|---|
| 5,270,148 A | 12/1993 | Morigaki et al. |
| 5,512,590 A | 4/1996 | George et al. |
| 5,616,537 A | 4/1997 | Yokota et al. |
| 5,702,877 A | 12/1997 | Odenwalder et al. |
| 5,814,633 A | 9/1998 | Muller et al. |
| 5,852,046 A | 12/1998 | Lang et al. |
| 5,994,629 A | 11/1999 | Bojsen et al. |
| 6,329,383 B1 | 12/2001 | Hedgecock et al. |
| 6,346,531 B1 | 2/2002 | Luengo et al. |
| 6,444,816 B1 | 9/2002 | Das et al. |
| 6,552,192 B1 | 4/2003 | Hanus et al. |
| 6,566,372 B1 | 5/2003 | Zhi et al. |
| 6,630,470 B1 | 10/2003 | Luengo et al. |
| 6,743,800 B1 | 6/2004 | Peyman et al. |
| 6,747,016 B1 | 6/2004 | Peyman et al. |
| 7,256,196 B1 | 8/2007 | Sabat et al. |
| 7,531,553 B2 | 5/2009 | Di Pietro et al. |
| 8,114,874 B2 | 2/2012 | Zou et al. |
| 8,293,923 B2 | 10/2012 | Guckian et al. |
| 8,614,330 B2 | 12/2013 | Amiri et al. |
| 8,846,697 B2 | 9/2014 | Carson et al. |
| 9,145,438 B2 | 9/2015 | Chesworth et al. |
| 9,200,020 B2 | 12/2015 | De Jersey et al. |
| 9,284,299 B2 | 3/2016 | Ji et al. |
| 10,766,888 B1 | 9/2020 | Biddle et al. |
| 11,691,963 B2 | 7/2023 | Masse et al. |
| 2001/0056090 A1 | 12/2001 | Aquila et al. |
| 2002/0010159 A1 | 1/2002 | Weigele et al. |
| 2002/0052368 A1 | 5/2002 | Marlowe et al. |
| 2002/0058677 A1 | 5/2002 | Marlowe et al. |
| 2002/0068721 A1 | 6/2002 | Weigele et al. |
| 2002/0094994 A1 | 7/2002 | Bourzat et al. |
| 2002/0120144 A1 | 8/2002 | Akama et al. |
| 2002/0165261 A1 | 11/2002 | Borisy et al. |
| 2002/0173506 A1 | 11/2002 | Clark et al. |
| 2003/0109714 A1 | 6/2003 | Wishart et al. |
| 2003/0187261 A1 | 10/2003 | Havlicek et al. |
| 2003/0199564 A1 | 10/2003 | Fenton et al. |
| 2004/0006117 A1 | 1/2004 | Blume et al. |
| 2004/0034224 A1 | 2/2004 | Hammarstrom et al. |
| 2004/0077633 A1 | 4/2004 | Watson et al. |
| 2004/0082583 A1 | 4/2004 | Cheung et al. |
| 2004/0087626 A1* | 5/2004 | Renhowe ............ C07D 413/14 548/161 |
| 2004/0122237 A1 | 6/2004 | Amiri et al. |
| 2004/0171630 A1 | 9/2004 | Kim et al. |
| 2004/0198725 A1 | 10/2004 | Sun et al. |
| 2005/0049263 A1 | 3/2005 | Kasibhatla et al. |
| 2005/0101647 A1 | 5/2005 | Oda et al. |
| 2005/0137234 A1 | 6/2005 | Bressi et al. |
| 2005/0192287 A1 | 9/2005 | Costales et al. |
| 2005/0209176 A1 | 9/2005 | Meutermans et al. |
| 2005/0239821 A1 | 10/2005 | Neyts et al. |
| 2005/0272765 A1 | 12/2005 | Feng et al. |
| 2005/0282802 A1 | 12/2005 | Kostik et al. |
| 2006/0042026 A1 | 3/2006 | Glenn et al. |
| 2006/0052331 A1 | 3/2006 | Koch et al. |
| 2006/0111362 A1 | 5/2006 | Kira et al. |
| 2006/0116383 A1 | 6/2006 | Bloxham et al. |
| 2006/0148830 A1 | 7/2006 | Terakado et al. |
| 2006/0154977 A1 | 7/2006 | Morand et al. |
| 2006/0160872 A1 | 7/2006 | Norman et al. |
| 2007/0032493 A1 | 2/2007 | Foley et al. |
| 2007/0043043 A1 | 2/2007 | Chen et al. |
| 2007/0049622 A1 | 3/2007 | Dimitroff et al. |
| 2007/0093544 A1 | 4/2007 | Parmee et al. |
| 2007/0105930 A1 | 5/2007 | Parmee et al. |
| 2007/0112048 A1 | 5/2007 | Bavari et al. |

(Continued)

FOREIGN PATENT DOCUMENTS

| | | |
|---|---|---|
| CN | 1148043 A | 4/1997 |
| CN | 101239980 A | 8/2008 |

(Continued)

OTHER PUBLICATIONS

International Search Report for PCT/US2022/049220, 4 pages (dated Feb. 6, 2023).

(Continued)

*Primary Examiner* — Noble E Jarrell
(74) *Attorney, Agent, or Firm* — Choate, Hall & Stewart LLP; Michael A. Shinall; Lauren E. Bertino

(57) ABSTRACT

The present disclosure provides 6-heteroaryloxy benzimidazole and azabenzimidazole compounds and compositions thereof useful for inhibiting JAK2.

30 Claims, No Drawings

(56) References Cited

U.S. PATENT DOCUMENTS

| | | |
|---|---|---|
| 2007/0173527 A1 | 7/2007 | Bressi et al. |
| 2007/0197450 A1 | 8/2007 | Fushimi et al. |
| 2007/0219235 A1 | 9/2007 | Mjalli et al. |
| 2007/0249637 A1 | 10/2007 | Collins et al. |
| 2007/0275984 A1 | 11/2007 | Imogai et al. |
| 2008/0008682 A1 | 1/2008 | Chong et al. |
| 2008/0009488 A1 | 1/2008 | Anand et al. |
| 2008/0032936 A1 | 2/2008 | Gai et al. |
| 2008/0058297 A1 | 3/2008 | Ono et al. |
| 2008/0096903 A1 | 4/2008 | Chen et al. |
| 2008/0132501 A1 | 6/2008 | Sun et al. |
| 2008/0161254 A1 | 7/2008 | Green et al. |
| 2008/0194803 A1 | 8/2008 | Sinclair et al. |
| 2008/0221148 A1 | 9/2008 | Ibrahim et al. |
| 2008/0284322 A1 | 11/2008 | Hosokawa et al. |
| 2009/0047249 A1 | 2/2009 | Graupe et al. |
| 2009/0118200 A1 | 5/2009 | Bergman et al. |
| 2009/0140637 A1 | 6/2009 | Hosokawa et al. |
| 2009/0176778 A1 | 7/2009 | Schmitz et al. |
| 2009/0232844 A1 | 9/2009 | Sutton et al. |
| 2009/0233946 A1 | 9/2009 | Krasinski et al. |
| 2009/0278115 A1 | 11/2009 | Hosokawa et al. |
| 2010/0010217 A1 | 1/2010 | Valiante et al. |
| 2010/0029709 A1 | 2/2010 | Menet et al. |
| 2010/0093747 A1 | 4/2010 | Goodhew |
| 2010/0197688 A1 | 8/2010 | Nantermet et al. |
| 2010/0204265 A1 | 8/2010 | Baskaran et al. |
| 2010/0210598 A1 | 8/2010 | Carson et al. |
| 2010/0216810 A1 | 8/2010 | Okaniwa et al. |
| 2010/0249119 A1 | 9/2010 | Hirose et al. |
| 2010/0256188 A1 | 10/2010 | Pfau et al. |
| 2010/0261679 A1 | 10/2010 | Sutton et al. |
| 2010/0267714 A1 | 10/2010 | Jorgensen et al. |
| 2011/0021518 A1 | 1/2011 | Magnuson et al. |
| 2011/0039895 A1 | 2/2011 | Chai et al. |
| 2011/0059962 A1 | 3/2011 | Alekshun et al. |
| 2011/0105498 A1 | 5/2011 | Pettus et al. |
| 2011/0117073 A1 | 5/2011 | Singh et al. |
| 2011/0172186 A1 | 7/2011 | Behnke et al. |
| 2011/0201605 A1 | 8/2011 | Baumann et al. |
| 2011/0237620 A1 | 9/2011 | Okaniwa |
| 2011/0263598 A1 | 10/2011 | Sampson et al. |
| 2011/0281865 A1 | 11/2011 | Muthuppalaniappan et al. |
| 2011/0312935 A1 | 12/2011 | Pfau et al. |
| 2012/0028969 A1 | 2/2012 | Barnes et al. |
| 2012/0115902 A1 | 5/2012 | Pfau et al. |
| 2012/0122930 A1 | 5/2012 | Pfau et al. |
| 2012/0172351 A1 | 7/2012 | Negoro et al. |
| 2012/0202287 A1 | 8/2012 | Adams et al. |
| 2012/0208839 A1 | 8/2012 | Priepke et al. |
| 2012/0214786 A1 | 8/2012 | Priepke et al. |
| 2012/0258967 A1 | 10/2012 | Qiao et al. |
| 2013/0059851 A1 | 3/2013 | Garraway et al. |
| 2013/0079342 A1 | 3/2013 | Dransfield et al. |
| 2013/0084346 A1 | 4/2013 | Wolkenberg et al. |
| 2013/0090327 A1 | 4/2013 | Hata et al. |
| 2013/0096136 A1 | 4/2013 | Hata et al. |
| 2013/0136782 A1 | 5/2013 | Blackwell et al. |
| 2013/0149717 A1 | 6/2013 | Krause et al. |
| 2013/0165446 A1 | 6/2013 | Fujita et al. |
| 2013/0184240 A1 | 7/2013 | Tonogaki et al. |
| 2013/0184248 A1 | 7/2013 | Grauert et al. |
| 2013/0190320 A1 | 7/2013 | Xu et al. |
| 2013/0224195 A1 | 8/2013 | Costales et al. |
| 2013/0225596 A1 | 8/2013 | Kai et al. |
| 2013/0261125 A1 | 10/2013 | Shipps, Jr. et al. |
| 2013/0310333 A1 | 11/2013 | Chesworth et al. |
| 2013/0345261 A1 | 12/2013 | Waters et al. |
| 2014/0011763 A1 | 1/2014 | Lakshman |
| 2014/0031339 A1 | 1/2014 | Abeywardane et al. |
| 2014/0155379 A1 | 6/2014 | Ho et al. |
| 2014/0194420 A1 | 7/2014 | Kojima et al. |
| 2014/0303102 A1 | 10/2014 | Choe et al. |
| 2014/0303360 A1 | 10/2014 | Schroeder et al. |
| 2014/0364386 A1 | 12/2014 | Choe et al. |
| 2015/0018291 A1 | 1/2015 | Choe et al. |
| 2015/0057309 A1 | 2/2015 | Vakkalanka et al. |
| 2015/0126436 A1 | 5/2015 | Phillips et al. |
| 2015/0133500 A1 | 5/2015 | Tafesse et al. |
| 2015/0152065 A1 | 6/2015 | Brookings et al. |
| 2015/0197497 A1 | 7/2015 | Abeywickrama et al. |
| 2015/0216168 A1 | 8/2015 | Frackenpohl et al. |
| 2015/0243903 A1 | 8/2015 | Zeng et al. |
| 2015/0249221 A1 | 9/2015 | Zeng et al. |
| 2016/0024072 A1 | 1/2016 | Kai et al. |
| 2016/0052922 A1 | 2/2016 | Chesworth et al. |
| 2016/0096804 A1 | 4/2016 | Shuttleworth et al. |
| 2016/0168165 A1 | 6/2016 | Koehler et al. |
| 2016/0176825 A1 | 6/2016 | Gray et al. |
| 2016/0229837 A1 | 8/2016 | Xi et al. |
| 2016/0257641 A1 | 9/2016 | Kobayashi et al. |
| 2016/0297795 A1 | 10/2016 | Heer et al. |
| 2016/0304511 A1 | 10/2016 | Jackson et al. |
| 2016/0304513 A1 | 10/2016 | Deligny et al. |
| 2017/0114078 A1 | 4/2017 | McGowan et al. |
| 2017/0121349 A1 | 5/2017 | Kim et al. |
| 2017/0129883 A1 | 5/2017 | Jackson et al. |
| 2017/0158688 A1 | 6/2017 | Jackson et al. |
| 2017/0222157 A1 | 8/2017 | Jatsch et al. |
| 2017/0333398 A1 | 11/2017 | Kojima et al. |
| 2018/0030453 A1 | 2/2018 | Zakharenko et al. |
| 2018/0072688 A1 | 3/2018 | Qian et al. |
| 2018/0079727 A1 | 3/2018 | Ohyabu et al. |
| 2018/0086725 A1 | 3/2018 | Kumar et al. |
| 2018/0153877 A1 | 6/2018 | Azam |
| 2018/0273511 A1 | 9/2018 | Long |
| 2019/0002442 A1 | 1/2019 | Zhao et al. |
| 2019/0022074 A1 | 1/2019 | Hadari et al. |
| 2019/0038603 A1 | 2/2019 | Jakobsson |
| 2019/0119217 A1 | 4/2019 | Long et al. |
| 2019/0134042 A1 | 5/2019 | Miao et al. |
| 2019/0135834 A1 | 5/2019 | Tamura et al. |
| 2019/0183866 A1 | 6/2019 | Tamura et al. |
| 2019/0382377 A1 | 12/2019 | Li et al. |
| 2019/0388426 A1 | 12/2019 | Nguyen et al. |
| 2020/0039933 A1 | 2/2020 | Gaisina et al. |
| 2020/0039961 A1 | 2/2020 | Campbell et al. |
| 2020/0039998 A1 | 2/2020 | Campbell et al. |
| 2020/0054635 A1 | 2/2020 | Campbell et al. |
| 2020/0062758 A1 | 2/2020 | Liu et al. |
| 2020/0101091 A1 | 4/2020 | Peyrottes et al. |
| 2020/0113901 A1 | 4/2020 | Campbell et al. |
| 2020/0113907 A1 | 4/2020 | Hagiwara et al. |
| 2020/0237717 A1 | 7/2020 | Jensen et al. |
| 2020/0268753 A1 | 8/2020 | Nguyen et al. |
| 2020/0274072 A1 | 8/2020 | Kugler |
| 2020/0317642 A1 | 10/2020 | Campbell et al. |
| 2021/0008046 A1 | 1/2021 | Bravo et al. |
| 2022/0127260 A1 | 4/2022 | Gray et al. |
| 2022/0127284 A1 | 4/2022 | Gray et al. |
| 2022/0411403 A1 | 12/2022 | Masse et al. |
| 2023/0099203 A1 | 3/2023 | Masse et al. |
| 2023/0146125 A1 | 5/2023 | Masse et al. |
| 2023/0265075 A1 | 8/2023 | Masse et al. |

FOREIGN PATENT DOCUMENTS

| | | |
|---|---|---|
| CN | 107383014 A | 11/2017 |
| CN | 108689942 A | 10/2018 |
| CN | 110092798 A | 8/2019 |
| EP | 639573 A1 | 2/1995 |
| EP | 3059225 A1 | 8/2016 |
| EP | 3279187 A1 | 2/2018 |
| EP | 3450435 A1 | 3/2019 |
| JP | H11-283746 A | 10/1999 |
| JP | 2000299186 A | 10/2000 |
| JP | 2004067629 A | 3/2004 |
| JP | 2005289921 A | 10/2005 |
| JP | 2009149589 A | 7/2009 |
| JP | 2016132649 A | 7/2016 |
| KR | 10-2019-0064508 A | 6/2019 |
| WO | WO-93/05163 A1 | 3/1993 |
| WO | WO-97/11065 A1 | 3/1997 |

(56) References Cited

FOREIGN PATENT DOCUMENTS

| | | |
|---|---|---|
| WO | WO-99/26932 A1 | 6/1999 |
| WO | WO-2001/044259 A1 | 6/2001 |
| WO | WO-2002/076960 A1 | 10/2002 |
| WO | WO-2003/082272 A1 | 10/2003 |
| WO | WO-2004/006849 A2 | 1/2004 |
| WO | WO-2004/085425 A1 | 10/2004 |
| WO | WO-2004/087153 A2 | 10/2004 |
| WO | WO-2005/032548 A1 | 4/2005 |
| WO | WO-2005/035526 A1 | 4/2005 |
| WO | WO-2005/037273 A1 | 4/2005 |
| WO | WO-2006/027365 A1 | 3/2006 |
| WO | WO-2006/128129 A2 | 11/2006 |
| WO | WO-2006/130469 A1 | 12/2006 |
| WO | WO-2007/091950 A1 | 8/2007 |
| WO | WO-2007/121484 A2 | 10/2007 |
| WO | WO-2008/016666 A2 | 2/2008 |
| WO | WO-2008/124145 A1 | 10/2008 |
| WO | WO-2008/144062 A1 | 11/2008 |
| WO | WO-2008/150015 A1 | 12/2008 |
| WO | WO-2009/011775 A1 | 1/2009 |
| WO | WO-2009/017954 A1 | 2/2009 |
| WO | WO-2009/034386 A1 | 3/2009 |
| WO | WO-2009/050228 A2 | 4/2009 |
| WO | WO-2009/155565 A1 | 12/2009 |
| WO | WO-2010/002492 A1 | 1/2010 |
| WO | WO-2010/141796 A2 | 12/2010 |
| WO | WO-2010/144909 A1 | 12/2010 |
| WO | WO-2011/063908 A1 | 6/2011 |
| WO | WO-2011/127833 A1 | 10/2011 |
| WO | WO-2012/016133 A2 | 2/2012 |
| WO | WO-2013/024078 A1 | 2/2013 |
| WO | WO-2014/069426 A1 | 5/2014 |
| WO | WO-2014/072435 A1 | 5/2014 |
| WO | WO-2014/175330 A1 | 10/2014 |
| WO | WO-2015/008861 A1 | 1/2015 |
| WO | WO-2016/014576 A1 | 1/2016 |
| WO | WO-2016/119700 A1 | 8/2016 |
| WO | WO-2017/143014 A1 | 8/2017 |
| WO | WO-2017/175068 A1 | 10/2017 |
| WO | WO-2018/039557 A1 | 3/2018 |
| WO | WO-2018/064498 A1 | 4/2018 |
| WO | WO-2018/066545 A1 | 4/2018 |
| WO | WO-2018/191146 A1 | 10/2018 |
| WO | WO-2018/200786 A1 | 11/2018 |
| WO | WO-2018/203099 A1 | 11/2018 |
| WO | WO-2018/204765 A1 | 11/2018 |
| WO | WO-2019/000683 A1 | 1/2019 |
| WO | WO-2019/018119 A1 | 1/2019 |
| WO | WO-2019/038683 A1 | 2/2019 |
| WO | WO-2019/079596 A1 | 4/2019 |
| WO | WO-2019/079607 A1 | 4/2019 |
| WO | WO-2019/088159 A1 | 5/2019 |
| WO | WO-2019/217838 A1 | 11/2019 |
| WO | WO-2020/014599 A1 | 1/2020 |
| WO | WO-2020/081450 A1 | 4/2020 |
| WO | WO-2020/089455 A1 | 5/2020 |
| WO | WO-2020/093905 A1 | 5/2020 |
| WO | WO-2020/097396 A1 | 5/2020 |
| WO | WO-2020/097398 A1 | 5/2020 |
| WO | WO-2020/097400 A1 | 5/2020 |
| WO | WO-2020/118045 A1 | 6/2020 |
| WO | WO-2020/165907 A1 | 8/2020 |
| WO | WO-2020/176597 A1 | 9/2020 |
| WO | WO-2020/180768 A1 | 9/2020 |
| WO | WO-2020/181050 A1 | 9/2020 |
| WO | WO-2020/210481 A1 | 10/2020 |
| WO | WO-2020/243457 A1 | 12/2020 |
| WO | WO-2021/067682 A1 | 4/2021 |
| WO | WO-2021/091575 A1 | 5/2021 |
| WO | WO-2021/113557 A1 | 6/2021 |
| WO | WO-2021/226261 A1 | 11/2021 |
| WO | WO-2022/140527 A1 | 6/2022 |
| WO | WO-2023/086319 A1 | 5/2023 |

OTHER PUBLICATIONS

Rai, S. et al., The Second Generation Type II JAK2 inhibitor, AJ1-10502, Demonstrates Enhanced Selectivity Improved Therapeutic Efficacy and Reduced Mutant Cell Fraction Compared to Type I JAK2 inhibitors in Models of Myeloproliferative Neoplasms (MPNs), 64th American Society of Hematology Annual Meeting, 1-4 (2022).

Rai, S. et al., The Second Generation Type II JAK2 inhibitor, AJ1-10502, Demonstrates Enhanced Selectivity Improved Therapeutic Efficacy and Reduced Mutant Cell Fraction Compared to Type I JAK2 inhibitors in Models of Myeloproliferative Neoplasms (MPNs), Poster (1 page), Presented at the 64th American Society of Hematology Annual Meeting from Dec. 10-13, 2022.

Steelman, L. S. et al., JAK/STAT, Raf/MEK/ERK, PI3K/Akt and BCR-ABL in cell cycle progression and leukemogenesis, Leukemia, 18:189-218 (2004).

U.S. Appl. No. 17/559,051, Ajax Therapeutics, Inc.

U.S. Appl. No. 17/982,664, Masse et al.

Aaronson, D. S. and Horvath, C. M., A Road Map for Those Who Don't Know JAK-STAT, Science, 296(5573):1653-1655 (2002).

Akhtar, W. et al., Therapeutic evolution of benzimidazole derivatives in the last quinquennial period, European Journal of Medicinal Chemistry, 126:705-753 (2017).

Andraos, R. et al., Modulation of activation-loop phosphorylation by JAK inhibitors is binding mode dependent, Cancer Discovery, 2(6):512-523 (2012).

Bundgard, Design of Prodrugs, Amsterdam, New York, Oxford, Elsevier, pp. 7-9, 21-24 (1985).

Choi, H.G. et al., Development of 'DFG-out' inhibitors of gatekeeper mutant kinases, Bioorganic & Medicinal Chemistry Letters, 22:5297-5302 (2012).

Clark, J. et al., Discovery and Development of Janus Kinase (JAK) Inhibitors for Inflammatory Diseases, Journal of Medicinal Chemistry, J. Med. Chem., 57:5023-5038 (2014).

Dymock et al., Inhibitors of JAK2 and JAK3: an update on the patent literature 2010-2012, Expert Opin Ther Pat., 23(4):449-501 (2013).

Elf, S. et al., Mutant calreticulin requires both its mutant C-terminus and the thrombopoietin receptor for oncogenic transformation, Science Discovery, 6(4):368-381 (2016).

Extended European Search Report for Application No. EP19882411.2, dated Jun. 21, 2022.

Extended European Search Report for EP 19882880.8 dated Jul. 11, 2022 (D0504.70172EP00).

Extended European Search Report for EP19881035.0 dated Jun. 29, 2022.

Harrison, C. et al., JAK Inhibition with Ruxolitinib versus Best Available Therapy for Myelofibrosis, The New England Journal of Medicine, 366(9):787-798 (2012).

International Search Report for PCT/US2019/060358, dated Mar. 3, 2020.

International Search Report for PCT/US2019/060360, dated Mar. 3, 2020.

International Search Report for PCT/US2019/060363, dated Mar. 9, 2020.

International Search Report for PCT/US2020/053922, dated Mar. 8, 2021.

International Search Report for PCT/US2021/030926, 7 pages (dated Sep. 8, 2021).

International Search Report for PCT/US2021/064830, 4 pages (dated Mar. 25, 2022).

Jaffer, T. and Ma, D., The emerging role of chemokine receptor CXCR2 in cancer progression, Transl. Cancer Res., 5(Suppl 4):S616-S628 (2016).

Jutzi, J. et al., LSD1 Inhibition Prolongs Survival in Mouse Models of MPN by Selectivity Targeting the Disease Clone, HemaSphere, 2:3, 13 pages (2018).

Koppikar, P. et al., Heterodimeric JAK-STAT Activation as a Mechanism of Persistence to JAK2 Inhibitor Therapy, Nature, 489(7414):155-159 (2012).

(56) References Cited

OTHER PUBLICATIONS

Leroy, E. et al., Rethinking JAK2 inhibition: towards novel strategies of more specific and versatile janus kinase inhibition, Leukemia, 31(5):1023-1038 (2017).
Levine, R. L., JAK-mutant Myeloproliferative Neoplasms, Current Topics in Microbiology and Immunology, 355:119-133 (2011).
Li, et al., AutoT&T v.2: An Efficient and Versatile Tool for Lead Structure Generation and Optimization, J. Chem. Inf. Model, 56(2):435-453 (2016).
Meyer, S. and Levine, R., Molecular Pathways: Molecular Basis for Sensitivity and Resistance to JAK Kinase Inhibitors, Clin. Cancer Res., 20(8):2051-2059 (2014).
O'Hare, T. et al., AP24534, a Pan-BCR-ABL Inhibitor for Chronic Myeloid Leukemia, Potently Inhibits the T3151 Mutant and Overcomes Mutation-Based Resistance, Cancer Cell, 16(5):401-412 (2009).
Okaniwa, et al., Design and synthesis of novel DFG-out RAF/ vascular endothelial growth factor receptor 2 (VEGF2) inhibitors. 1. Exploration of [5,6]-fused bicyclic scaffolds, J Med Chem., 55(7):3452-78 (2012).
O'Shea, J. et al., Janus kinase Inhibitors in autoimmune diseases, Ann Rheum. Dis., 72, 11 pages (2013).
Pandey, A. et al., Cloning of a receptor subunit required for signaling by thymic stromal lymphopoietin, Nature Immunology, 1(1):59-64 (2000).
Ramurthy, S. et al., Design and Synthesis of Orally Bioavailable Benzimidazoles as Raf Kinase Inhibitors, J. Med. Chem., 51:7049-7052 (2008).
Ramurthy, S. et al., Supporting Information Design and Synthesis of Benzimidazoles Amides as Raf Kinase Inibitors, Novartis Institutes of Biomedical Research, 38 pages (2018).
Roberts, K. G. et al., Targetable Kinase-Activating Lesions in Ph-like Acute Lymphoblastic Leukemia, New England Journal of Medicine, 371(11):1005-1015 (2014).
Rodrigues, M. and Torres, T., JAK/STAT inhibitors for the treatment of atopic dermatitis, Journal of Dermatological Treatment, 31(1):33-40 (2020).
Rui, L. et al., Cooperative Epigenetic Modulation by Cancer Amplicon Genes, Cancer Cell., 18(6):590-605 (2010).
Rzymski, T. et al., SEL120-34A is a novel CDK8 inhibitor active in AML cells with high levels of serine phosphorylation of STAT1 and STAT5 transactivation domains, Oncotarget, 8(20):33779-33795 (2017).
Shiels, M. S. et al., Cancer Burden in the HIV-Infected Population in the United States, J Natl Cancer Inst., 103(9):753-762 (2011).
Smith, A. et al., Imidazo[1,2-a]pyridin-6-yl-benzamide analogs as potent RAF inhibitors, Bioorg Med Chem Lett., 27(23):5221-5224 (2017).
Subramanian, S. et al., Design and Synthesis of Orally Bioavailable Benzimidazole Reverse Amides as Pan RAF Kinase Inhibitors, ACS Med. Chem. Lett., 5:989-992 (2014).
Vainchenker, W. et al., JAK inhibitors for the treatment of myeloproliferative neoplasms and other disorders, F1000 Research, 7(F1000 Faculty Rev), 19 pages (last updated Jan. 17, 2018).
Verstovsek, S. et al., A Double-Blind Placebo-Controlled Trial of Ruxolitinib for Myelofibrosis, N Engl J Med., 366(9):799-807 (2012).
Williams et al., Discovery of RAF265: A Potent mut-B-RAF Inhibitor for the Treatment of Metastatic Melanoma, ACS Med. Chem Lett., 6(9):961-965 (2015).
Wu, S. et al., Activity of the Type II JAK2 Inhibitor CHZ868 in B Cell Acute Lymphoblastic Leukemia, Cancer Cell, 28:29-41 (2015).
Yuanyuan, W. et al., Design, synthesis, biological evaluation and molecular modeling of novel 1H-pyrazolo [3,4-d] pyrimidine derivatives as BRAFV600Eand VEGFR-2 dual inhibitors, European Journal of Medicinal Chemistry, 155:210-228 (2018).
Yumeen, S. et al., JAK inhibition synergistically potentiates BCL2, BET, HDAC, and proteasome inhibition in advanced CTCL, Blood Advances, 4(10):2213-2226 (2020).
Zhao, et al., Exploration of type II binding mode: A privileged approach for kinase inhibitor focused drug discovery?, ACS Chem Biol., 9(6):1230-41 (2014).
Bain, J. et al., The selectivity of protein kinase inhibitors: a further update, Biochem. J., 408:297-315 (2007).
Fabian, M. A. et al., A small molecule-kinase interaction map for clinical kinase inhibitors, Nat. Biotech., 23(3):329-336 (2005).
International Preliminary Report on Patentability for PCT/US2022/049220, 6 pages (mailed Jan. 3, 2024).

\* cited by examiner

6-HETEROARYLOXY BENZIMIDAZOLES AND AZABENZIMIDAZOLES AS JAK2 INHIBITORS

RELATED APPLICATIONS

This application claims priority to and benefit of U.S. application Ser. No. 63/277,343, filed Nov. 9, 2021, and U.S. Application No. 63/354,403, filed Jun. 22, 2022, the entire contents of each of which are hereby incorporated by reference.

BACKGROUND

Janus kinase 2 (JAK2) is a non-receptor tyrosine kinase involved in the JAK-STAT signaling pathway, which plays a role in cell processes such as immunity, cell division, and cell death. Dysfunction of the JAK-STAT pathway is implicated in various diseases, including cancer and other proliferative diseases, as well as diseases of the immune system. For example, essentially all BCR-ABL1-negative myeloproliferative neoplasms are associated with mutations that activate JAK2. In particular, JAK2V617F is the most prevalent mutation in myeloproliferative neoplasms, occurring in approx. 70% of all patients, and in up to 95% of patients with polycythemia vera. (Vainchenker, W., Kralovics, R. Blood 2017, 129(6):667-79). Even less common mutations, such as in MPL and CALR, have been shown to effect activation of JAK2, thereby initiating and/or driving disease progression. (Vainchenker, W. et al., F1000Research 2018, 7(F1000 Faculty Rev):82). Furthermore, polymorphisms in JAK2 have been linked to various autoimmune diseases and inflammatory conditions, such as psoriasis and inflammatory bowel disease. (O'Shea, J. J. et al., Ann. Rheum. Dis. 2013 April, 72:ii111-ii115). Increased signaling through JAK2, as well as other members of the JAK family, is also associated with atopic dermatitis. (Rodrigues, M. A. and Torres, T. J. Derm. Treat. 2019, 31(1):33-40).

Inhibitors of JAKs (e.g., JAK2) are classified based on their binding mode. All currently approved JAK inhibitors are Type I inhibitors, which are those that bind the ATP-binding site in the active conformation of the kinase domain, thereby blocking catalysis (Vainchenker, W. et al.). However, increased phosphorylation of the JAK2 activation loop is observed with Type I inhibitors and may lead to acquired resistance in certain patients (Meyer S. C., Levine, R. L. Clin. Cancer Res. 2014, 20(8):2051-9). Type II inhibitors, on the other hand, bind the ATP-binding site of the kinase domain in the inactive conformation and, therefore, may avoid hyperphosphorylation observed with Type I inhibitors (Wu, S. C. et al. Cancer Cell 2015 Jul. 13, 28(1):29-41).

SUMMARY

The present disclosure provides compounds useful for inhibiting JAK2. In some embodiments, provided compounds are useful for, among other things, treating and/or preventing diseases, disorders, or conditions associated with JAK2.

In some embodiments, the present disclosure provides a compound of Formula I

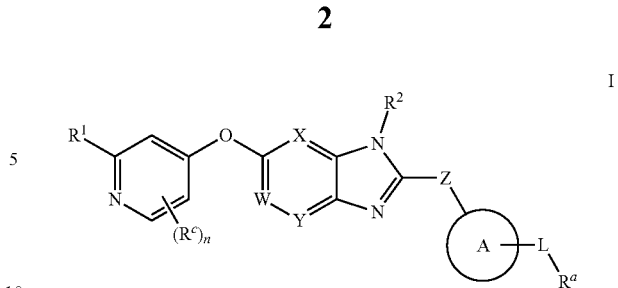

or a pharmaceutically acceptable salt thereof, wherein Ring A, n, L, W, X, Y, Z, $R^1$, $R^2$, $R^a$, and $R^c$ are as defined herein.

In some embodiments, the present disclosure provides a compound of Formula II

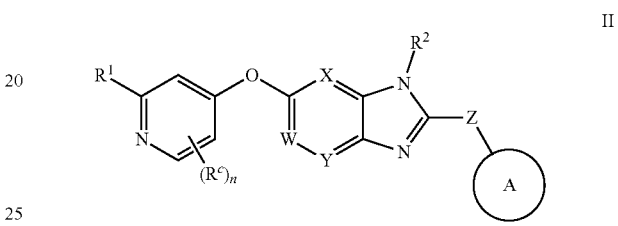

or a pharmaceutically acceptable salt thereof, wherein Ring A, n, W, X, Y, Z, $R^1$, $R^2$, and $R^c$ are as defined herein.

In some embodiments, the present disclosure provides a compound of Formula III

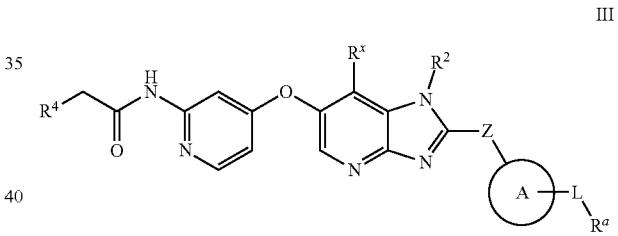

or a pharmaceutically acceptable salt thereof, wherein Ring A, L, Z, $R^2$, $R^4$, $R^a$, and $R^x$ are as defined herein.

In some embodiments, the present disclosure provides a compound of Formula IV

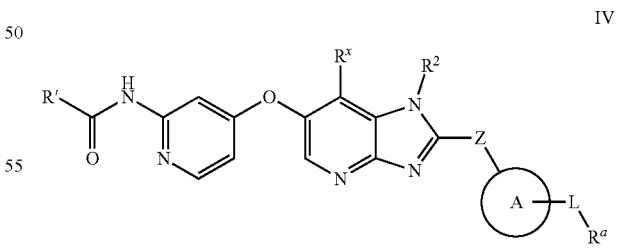

or a pharmaceutically acceptable salt thereof, wherein Ring A, L, Z, R', $R^2$, $R^a$, and $R^x$ are as defined herein.

DETAILED DESCRIPTION

Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Unless otherwise stated, structures depicted herein are meant to include all stereoisomeric (e.g., enantiomeric or diastereomeric) forms of the structure, as well as all geometric or conformational isomeric forms of the structure. For example, the R and S configurations of each stereocenter are contemplated as part of the disclosure. Therefore, single stereochemical isomers, as well as enantiomeric, diastereomic, and geometric (or conformational) mixtures of provided compounds are within the scope of the disclosure. For example, in some case, Table 1 shows one or more stereoisomers of a compound, and unless otherwise indicated, represents each stereoisomer alone and/or as a mixture. Unless otherwise stated, all tautomeric forms of provided compounds are within the scope of the disclosure.

Unless otherwise indicated, structures depicted herein are meant to include compounds that differ only in the presence of one or more isotopically enriched atoms. For example, compounds having the present structures including replacement of hydrogen by deuterium or tritium, or replacement of a carbon by $^{13}$C- or $^{14}$C-enriched carbon are within the scope of this disclosure.

Aliphatic: The term "aliphatic" refers to a straight-chain (i.e., unbranched) or branched, optionally substituted hydrocarbon chain that is completely saturated or that contains one or more units of unsaturation, or a monocyclic or bicyclic hydrocarbon that is completely saturated or that contains one or more units of unsaturation but which is not aromatic (also referred to herein as "carbocyclic" or "cycloaliphatic"), that has a single point of attachment to the rest of the molecule. Unless otherwise specified, aliphatic groups contain 1-12 aliphatic carbon atoms. In some embodiments, aliphatic groups contain 1-6 aliphatic carbon atoms (e.g., $C_{1-6}$). In some embodiments, aliphatic groups contain 1-5 aliphatic carbon atoms (e.g., $C_{1-5}$). In other embodiments, aliphatic groups contain 1-4 aliphatic carbon atoms (e.g., $C_{1-4}$). In still other embodiments, aliphatic groups contain 1-3 aliphatic carbon atoms (e.g., $C_{1-3}$), and in yet other embodiments, aliphatic groups contain 1-2 aliphatic carbon atoms (e.g., $C_{1-2}$). Suitable aliphatic groups include, but are not limited to, linear or branched, substituted or unsubstituted alkyl, alkenyl, alkynyl groups and hybrids thereof. In some embodiments, "aliphatic" refers to a straight-chain (i.e., unbranched) or branched, optionally substituted hydrocarbon chain that is completely saturated or that contains one or more units of unsaturation that has a single point of attachment to the rest of the molecule.

Alkyl: The term "alkyl", used alone or as part of a larger moiety, refers to a saturated, optionally substituted straight or branched hydrocarbon group having (unless otherwise specified) 1-12, 1-10, 1-8, 1-6, 1-4, 1-3, or 1-2 carbon atoms (e.g., $C_{1-12}$, $C_{1-10}$, $C_{1-8}$, $C_{1-6}$, $C_{1-4}$, $C_{1-3}$, or $C_{1-2}$). Exemplary alkyl groups include methyl, ethyl, propyl, butyl, pentyl, hexyl, and heptyl.

Carbocyclyl: The terms "carbocyclyl," "carbocycle," and "carbocyclic ring" as used herein, refer to saturated or partially unsaturated cyclic aliphatic monocyclic, bicyclic, or polycyclic ring systems, as described herein, having from 3 to 14 members, wherein the aliphatic ring system is optionally substituted as described herein. Carbocyclic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, "carbocyclyl" (or "cycloaliphatic") refers to an optionally substituted monocyclic $C_3$-$C_8$ hydrocarbon, or an optionally substituted $C_7$-$C_{10}$ bicyclic hydrocarbon that is completely saturated or that contains one or more units of unsaturation, but which is not aromatic, that has a single point of attachment to the rest of the molecule. The term "cycloalkyl" refers to an optionally substituted saturated ring system of about 3 to about 10 ring carbon atoms. In some embodiments, cycloalkyl groups have 3-6 carbons. Exemplary monocyclic cycloalkyl rings include cyclopropyl, cyclobutyl, cyclopentyl, cyclohexyl, and cycloheptyl. The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl, and cycloheptenyl.

Alkenyl: The term "alkenyl", used alone or as part of a larger moiety, refers to an optionally substituted straight or branched hydrocarbon chain having at least one double bond and having (unless otherwise specified) 2-12, 2-10, 2-8, 2-6, 2-4, or 2-3 carbon atoms (e.g., $C_{2-12}$, $C_{2-10}$, $C_{2-8}$, $C_{2-6}$, $C_{2-4}$, or $C_{2-3}$). Exemplary alkenyl groups include ethenyl, propenyl, butenyl, pentenyl, hexenyl, and heptenyl.

Alkynyl: The term "alkynyl", used alone or as part of a larger moiety, refers to an optionally substituted straight or branched chain hydrocarbon group having at least one triple bond and having (unless otherwise specified) 2-12, 2-10, 2-8, 2-6, 2-4, or 2-3 carbon atoms (e.g., $C_{2-12}$, $C_{2-10}$, $C_{2-8}$, $C_{2-6}$, $C_{2-4}$, or $C_{2-3}$). Exemplary alkynyl groups include ethynyl, propynyl, butynyl, pentynyl, hexynyl, and heptynyl.

Aryl: The term "aryl" refers to monocyclic and bicyclic ring systems having a total of six to fourteen ring members (e.g., $C_{6-14}$), wherein at least one ring in the system is aromatic and wherein each ring in the system contains three to seven ring members. The term "aryl" may be used interchangeably with the term "aryl ring". In some embodiments, "aryl" refers to an aromatic ring system which includes, but not limited to, phenyl, naphthyl, anthracyl and the like, which may bear one or more substituents. Unless otherwise specified, "aryl" groups are hydrocarbons.

Heteroaryl: The terms "heteroaryl" and "heteroar-", used alone or as part of a larger moiety, e.g., "heteroaralkyl", or "heteroaralkoxy", refer to monocyclic or bicyclic ring groups having 5 to 10 ring atoms (e.g., 5- to 6-membered monocyclic heteroaryl or 9- to 10-membered bicyclic heteroaryl); having 6, 10, or 14 π electrons shared in a cyclic array; and having, in addition to carbon atoms, from one to five heteroatoms. Exemplary heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridonyl, pyridazinyl, pyrimidinyl, pyrazinyl, indolizinyl, purinyl, naphthyridinyl, pteridinyl, imidazo[1,2-a]pyrimidinyl, imidazo[1,2-a]pyridinyl, thienopyrimidinyl, triazolopyridinyl, and benzoisoxazolyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring (i.e., a bicyclic heteroaryl ring having 1 to 3 heteroatoms). Nonlimiting examples include indolyl, isoindolyl, benzothienyl, benzofuranyl, dibenzofuranyl, indazolyl, benzimidazolyl, benzothiazolyl, benzothiadiazolyl, benzoxazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, and benzoisoxazolyl. The term "heteroaryl" may be used interchangeably with the terms "heteroaryl ring", "heteroaryl group", or "heteroaromatic", any of which terms include rings that are optionally substituted.

Heteroatom: The term "heteroatom" as used herein refers to nitrogen, oxygen, or sulfur, and includes any oxidized form of nitrogen or sulfur, and any quaternized form of a basic nitrogen.

Heterocycle: As used herein, the terms "heterocycle", "heterocyclyl", and "heterocyclic ring" are used interchangeably and refer to a stable 3- to 8-membered monocyclic or 7- to 10-membered bicyclic heterocyclic moiety that is either saturated or partially unsaturated, and having, in addition to carbon atoms, one or more, such as one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. A bicyclic heterocyclic ring also includes groups in which the heterocyclic ring is fused to one or more aryl, heteroaryl, or cycloaliphatic rings. Exemplary bicyclic heterocyclic groups include indolinyl, isoindolinyl, benzodioxolyl, 1,3-dihydroisobenzofuranyl, 2,3-dihydrobenzofuranyl, and tetrahydroquinolinyl. A bicyclic heterocyclic ring can also be a spirocyclic ring system (e.g., 7- to 11-membered spirocyclic fused heterocyclic ring having, in addition to carbon atoms, one or more heteroatoms as defined above (e.g., one, two, three or four heteroatoms)).

Partially Unsaturated: As used herein, the term "partially unsaturated", when referring to a ring moiety, means a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

Patient or subject: As used herein, the term "patient" or "subject" refers to any organism to which a provided composition is or may be administered, e.g., for experimental, diagnostic, prophylactic, cosmetic, and/or therapeutic purposes. Typical patients or subjects include animals (e.g., mammals such as mice, rats, rabbits, non-human primates, and/or humans). In some embodiments, a patient is a human. In some embodiments, a patient or a subject is suffering from or susceptible to one or more disorders or conditions.

In some embodiments, a patient or subject displays one or more symptoms of a disorder or condition. In some embodiments, a patient or subject has been diagnosed with one or more disorders or conditions. In some embodiments, a patient or a subject is receiving or has received certain therapy to diagnose and/or to treat a disease, disorder, or condition.

Substituted or optionally substituted: As described herein, compounds of this disclosure may contain "optionally substituted" moieties. In general, the term "substituted," whether preceded by the term "optionally" or not, means that one or more hydrogens of the designated moiety are replaced with a suitable substituent (i.e., as described below for optionally substituted groups). "Substituted" applies to one or more hydrogens that are either explicit or implicit from the structure

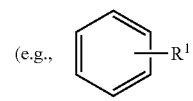

refers to at least

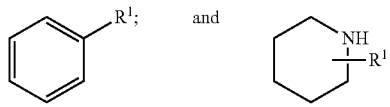

refers to at least

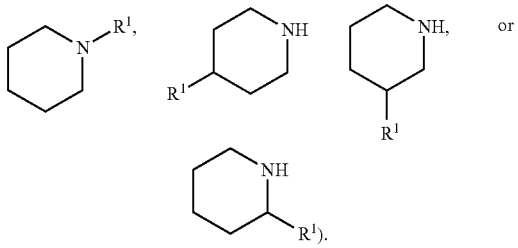

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes provided herein. Groups described as being "substituted" preferably have between 1 and 4 substituents, more preferably 1 or 2 substituents. Groups described as being "optionally substituted" may be unsubstituted or be "substituted" as described above.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH (OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —(CH$_2$)$_{0-4}$SC(O)R°; —(CH$_2$)$_{0-4}$C(O)NR°$_2$; —C(S)NR°$_2$; —C(S)SR°; —SC(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$—(5- to 6-membered heteroaryl ring), or a 3- to 6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3- to 12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R●, -(haloR●), —(CH$_2$)$_{0-2}$OH, —(CH$_2$)$_{0-2}$OR●, —(CH$_2$)$_{0-2}$CH(OR●)$_2$, —O(haloR●), —CN, —N$_3$, —(CH$_2$)$_{0-2}$C(O)R●, —(CH$_2$)$_{0-2}$C(O)OH, —(CH$_2$)$_{0-2}$C(O)OR●, —(CH$_2$)$_{0-2}$SR●, —(CH$_2$)$_{0-2}$SH, —(CH$_2$)$_{0-2}$NH$_2$, —(CH$_2$)$_{0-2}$NHR●, —(CH$_2$)$_{0-2}$NR●$_2$, —NO$_2$, —SiR●$_3$, —OSiR●$_3$, —C(O)SR●, —(C$_{1-4}$ straight or branched alkylene)C(O)OR●, or —SSR● wherein each R● is unsubstituted or where preceded by "halo" is substituted only with one or more halogens, and is independently selected from C$_{1-4}$ aliphatic, —CH$_2$Ph, —O(CH$_2$)$_{0-1}$Ph, or a 3- to 6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O ("oxo"), =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 3- to 6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 3- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, or an unsubstituted 3- to 6-membered saturated, partially unsaturated, or aryl ring having 0-4 heteroatoms independently selected from nitrogen, oxygen, or sulfur, or, notwithstanding the definition above, two independent occurrences of Rt, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur.

Suitable substituents on the aliphatic group of Rt are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 3- to 6-membered saturated, partially unsaturated, or aryl ring having 0-4 heteroatoms independently selected from nitrogen, oxygen, or sulfur.

Treat: As used herein, the term "treat" (also "treatment" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition.

Provided Compounds

In some embodiments, the present disclosure provides a compound of Formula I:

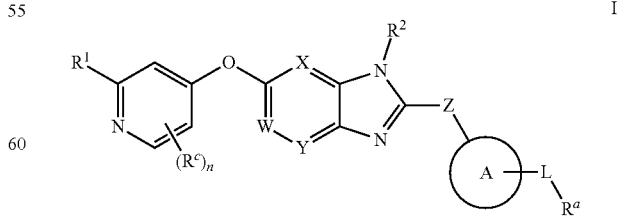

or a pharmaceutically acceptable salt thereof, wherein:
W is CR$^w$ or N;
X is CR$^x$ or N;
Y is CR$^y$ or N;

Z is —O— or —NR$^z$—;

R$^w$, R$^x$, and R$^y$ are each independently hydrogen, halogen, —OR$^3$, —N(R$^3$)$_2$, —SR$^3$, optionally substituted C$_{1-6}$ aliphatic, or —CN;

R$^z$ is hydrogen or optionally substituted C$_{1-6}$ aliphatic;

R$^1$ is —N(R)$_2$, —N(R)C(O)R', —C(O)N(R)$_2$, —N(R)C(O)N(R)$_2$, or —N(R)C(O)OR;

each R$^c$ is independently selected from halogen, —CN, —CO$_2$R, —C(O)N(R)$_2$, —NO$_2$, —N(R)$_2$, —OR, —SR, or optionally substituted C$_{1-6}$ aliphatic;

n is 0, 1, 2, or 3, provided that when R$^1$ is —N(R)$_2$, —N(R)C(O)R' or —C(O)N(R)$_2$, then n is 1, 2, or 3;

R$^2$ is optionally substituted C$_{1-6}$ aliphatic;

R$^3$ is hydrogen or optionally substituted C$_{1-6}$ aliphatic;

Ring A is optionally substituted phenyl, optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;

L is a covalent bond or a bivalent C$_{1-3}$ straight or branched hydrocarbon chain;

R$^a$ is hydrogen, halogen, optionally substituted C$_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;

each R is independently hydrogen, optionally substituted C$_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur; and each R' is independently optionally substituted C$_{1-6}$ aliphatic or optionally substituted 3- to 7-membered saturated or partially unsaturated carbocyclyl.

In some embodiments, the present disclosure provides a compound of Formula I-A:

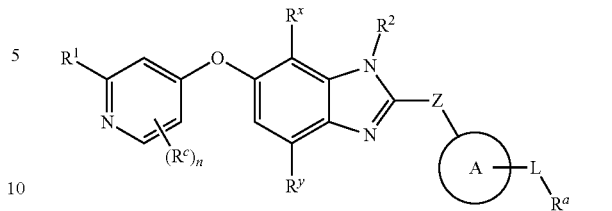

I-A or a pharmaceutically acceptable salt thereof, wherein Ring A, n, L, Z, R$^1$, R$^2$, R$^a$, R$^c$, R$^x$, and R$^y$ are as defined above for Formula I and described in classes and subclasses herein, both singly and in combination.

In some embodiments, the present disclosure provides a compound of Formula I-B:

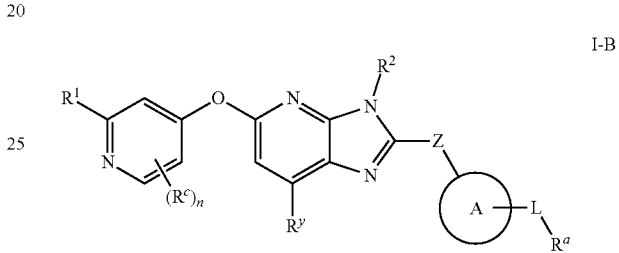

I-B or a pharmaceutically acceptable salt thereof, wherein Ring A, n, L, Z, R$^1$, R$^2$, R$^a$, R$^c$, and R$^y$ are as defined above for Formula I and described in classes and subclasses herein, both singly and in combination.

In some embodiments, the present disclosure provides a compound of Formula I-C:

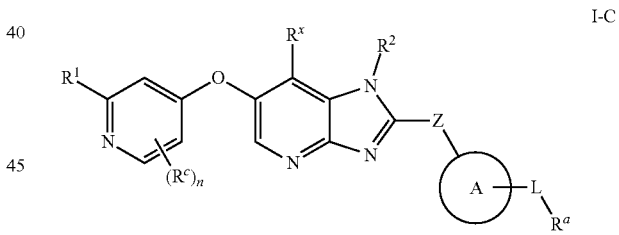

I-C or a pharmaceutically acceptable salt thereof, wherein Ring A, n, L, Z, R$^1$, R$^2$, R$^a$, R$^c$, and R$^x$ are as defined above for Formula I and described in classes and subclasses herein, both singly and in combination.

In some embodiments, the present disclosure provides a compound of Formula I-D:

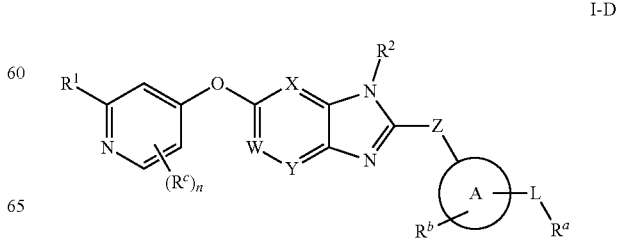

I-D or a pharmaceutically acceptable salt thereof, wherein Ring A, n, L, W, X, Y, Z, $R^1$, $R^2$, $R^a$, and $R^c$ are as defined above for Formula I and described in classes and subclasses herein, both singly and in combination; and $R^b$ is hydrogen, halogen, —CN, —OR, —O(CH$_2$)$_m$R, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted C$_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, or optionally substituted 5- to 6-membered monocyclic heteroaryl having 1-4 heteroatoms independently selected from nitrogen, oxygen, and sulfur; and m is 1, 2, or 3.

In some embodiments, the present disclosure provides a compound of Formula I-E:

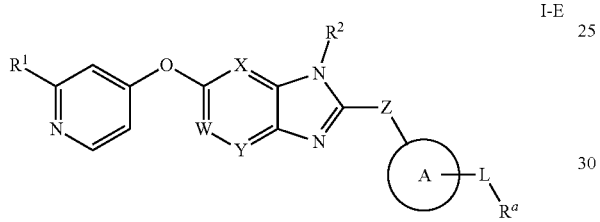

I-E or a pharmaceutically acceptable salt thereof, wherein Ring A, L, W, X, Y, Z, $R^1$, $R^2$, and $R^a$ are as defined above for Formula I and described in classes and subclasses herein, both singly and in combination.

In some embodiments, the present disclosure provides a compound of Formula II:

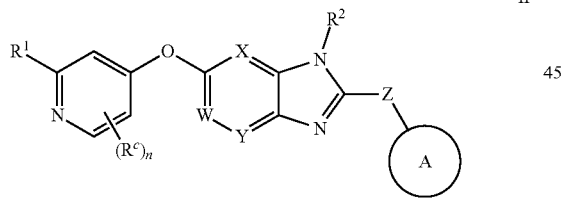

II or a pharmaceutically acceptable salt thereof, wherein:
W is CR$^w$ or N;
X is CR$^x$ or N;
Y is CR$^y$ or N;
Z is —O— or —NR$^z$—;
R$^w$, R$^x$, and R$^y$ are each independently hydrogen, halogen, —OR$^3$, —N(R$^3$)$_2$, —SR$^3$, optionally substituted C$_{1-6}$ aliphatic, or —CN;
R$^z$ is hydrogen or optionally substituted C$_{1-6}$ aliphatic;
$R^1$ is —N(R)$_2$, —N(R)C(O)R', —C(O)N(R)$_2$, —N(R)C(O)N(R)$_2$, or —N(R)C(O)OR;
each R$^c$ is independently selected from halogen, —CN, —CO$_2$R, —C(O)N(R)$_2$, —NO$_2$, —N(R)$_2$, —OR, —SR, or optionally substituted C$_{1-6}$ aliphatic;
n is 0, 1, 2, or 3;
$R^2$ is optionally substituted C$_{1-6}$ aliphatic;
$R^3$ is hydrogen or optionally substituted C$_{1-6}$ aliphatic;

Ring A is optionally substituted 9- to 16-membered bicyclic or tricyclic aryl, optionally substituted 8- to 10-membered bicyclic heteroaryl having 1-4 heteroatoms independently selected from nitrogen, oxygen, and sulfur, optionally substituted 10- to 16-membered polycyclic heteroaryl having 1-5 heteroatoms independently selected from nitrogen, oxygen, and sulfur, optionally substituted 7- to 10-membered bicyclic heterocyclyl having 1-4 heteroatoms independently selected from nitrogen, oxygen, and sulfur, or optionally substituted 10- to 16-membered polycyclic heterocyclyl having 1-5 heteroatoms independently selected from nitrogen, oxygen, and sulfur;

each R is independently hydrogen, optionally substituted C$_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur; and each R' is independently optionally substituted C$_{1-6}$ aliphatic or optionally substituted 3- to 7-membered saturated or partially unsaturated carbocyclyl.

In some embodiments, the present disclosure provides a compound of Formula II-A:

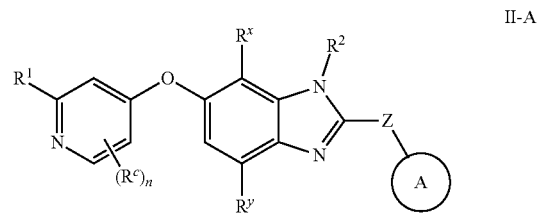

II-A or a pharmaceutically acceptable salt thereof, wherein Ring A, n, Z, $R^1$, $R^2$, $R^c$, $R^x$, and $R^y$ are as defined above for Formula II and described in classes and subclasses herein, both singly and in combination.

In some embodiments, the present disclosure provides a compound of Formula II-B:

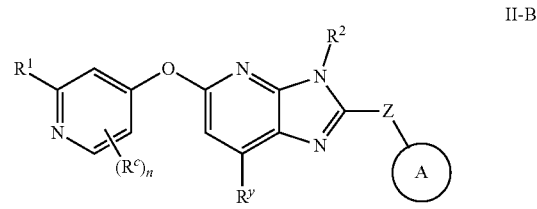

II-B or a pharmaceutically acceptable salt thereof, wherein Ring A, n, Z, $R^1$, $R^2$, $R^c$, and $R^y$ are as defined above for Formula II and described in classes and subclasses herein, both singly and in combination.

In some embodiments, the present disclosure provides a compound of Formula II-C:

13

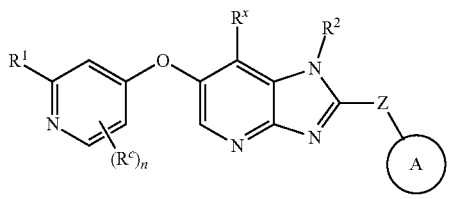

II-C or a pharmaceutically acceptable salt thereof, wherein Ring A, n, Z, $R^1$, $R^2$, $R^c$, and $R^x$ are as defined above for Formula II and described in classes and subclasses herein, both singly and in combination.

In some embodiments, the present disclosure provides a compound of Formula II-D:

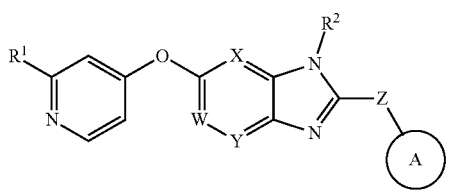

II-D or a pharmaceutically acceptable salt thereof, wherein Ring A, W, X, Y, Z, $R^1$, and $R^2$ are as defined above for Formula II and described in classes and subclasses herein, both singly and in combination.

In some embodiments, the present disclosure provides a compound of Formula II-E:

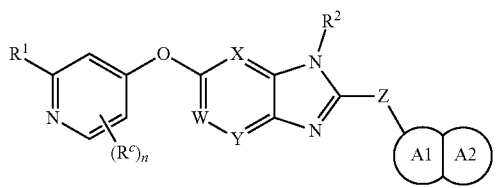

II-E or a pharmaceutically acceptable salt thereof, wherein n, W, X, Y, Z, $R^1$, $R^2$, and $R^c$ are as defined above for Formula II and described in classes and subclasses herein, both singly and in combination; and Ring A1 is an optionally substituted ring selected from phenyl, 5- to 6-membered monocyclic heteroaryl having 1-3 heteroatoms independently selected from nitrogen, oxygen, and sulfur, 5- to 7-membered saturated or partially unsaturated monocyclic carbocyclyl, and 5- to 7-membered saturated or partially unsaturated monocyclic heterocyclyl having 1-3 heteroatoms independently selected from nitrogen, oxygen, and sulfur; wherein Ring A1 is fused to Ring A2;

Ring A2 is an optionally substituted ring selected from phenyl, 5- to 6-membered monocyclic heteroaryl having 1-3 heteroatoms independently selected from nitrogen, oxygen, and sulfur, 5- to 7-membered saturated or partially unsaturated monocyclic carbocyclyl, and 5- to 7-membered saturated or partially unsaturated monocyclic heterocyclyl having 1-3 heteroatoms independently selected from nitrogen, oxygen, and sulfur;

14 wherein Ring A2 is optionally (i) further fused to Ring A3, or (ii) Ring A2 and Ring A3 combine to form a spirocycle; and Ring A3, when present, is an optionally substituted ring selected from phenyl, 5- to 6-membered monocyclic heteroaryl having 1-3 heteroatoms independently selected from nitrogen, oxygen, and sulfur, 3- to 7-membered saturated or partially unsaturated monocyclic carbocyclyl, and 3- to 7-membered saturated or partially unsaturated monocyclic heterocyclyl having 1-3 heteroatoms independently selected from nitrogen, oxygen, and sulfur.

In some embodiments, the present disclosure provides a compound of Formula II-F:

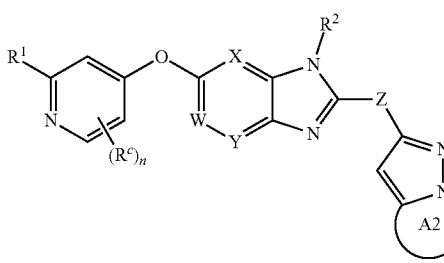

II-F or a pharmaceutically acceptable salt thereof, wherein Ring A2, n, W, X, Y, Z, $R^1$, $R^2$, and $R^c$ are as defined above for Formula II and described in classes and subclasses herein, both singly and in combination.

In some embodiments, the present disclosure provides a compound of Formula III:

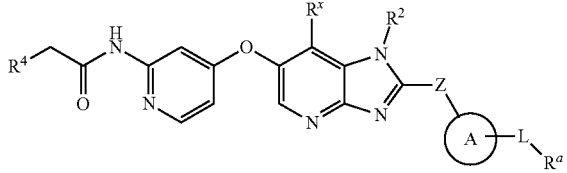

III or a pharmaceutically acceptable salt thereof, wherein:

Z is —O— or —N$R^z$—;

$R^x$ is hydrogen, halogen, —O$R^3$, —N$(R^3)_2$, —S$R^3$, optionally substituted $C_{1-6}$ aliphatic, or —CN;

$R^z$ is hydrogen or optionally substituted $C_{1-6}$ aliphatic;

$R^2$ is optionally substituted $C_{1-6}$ aliphatic;

$R^3$ is hydrogen or optionally substituted $C_{1-6}$ aliphatic;

$R^4$ is halogen, —OR, —N(R)$_2$, or optionally substituted 3- to 7-membered saturated or partially unsaturated monocyclic heterocyclyl having 1-3 heteroatoms independently selected from nitrogen, oxygen, and sulfur;

Ring A is optionally substituted phenyl, optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;

L is a covalent bond or a bivalent $C_{1-3}$ straight or branched hydrocarbon chain;

$R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur; and each R is independently hydrogen, optionally substituted $C_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur.

In some embodiments, the present disclosure provides a compound of Formula IV:

IV

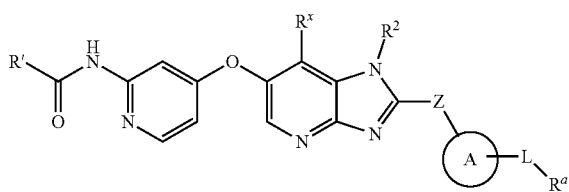

or a pharmaceutically acceptable salt thereof, wherein:
Z is —O— or —NR$^z$—;
$R^x$ is hydrogen, halogen, —OR$^3$, or —CN;
$R^z$ is hydrogen or optionally substituted $C_{1-6}$ aliphatic;
$R^2$ is optionally substituted $C_{1-6}$ aliphatic;
$R^3$ is hydrogen or optionally substituted $C_{1-6}$ aliphatic;

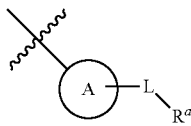

is selected from (i) or (ii):

(i)

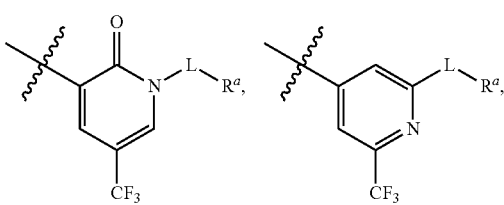

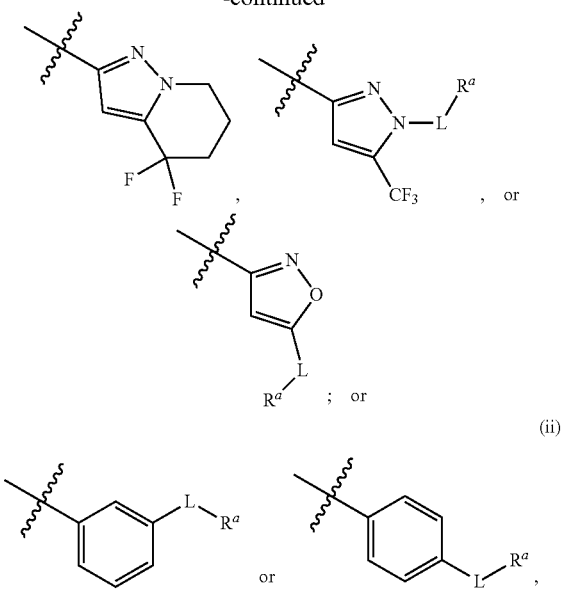

wherein Ring A is further substituted at least once, and at least one substituent on Ring A is $C_{1-6}$ haloalkyl;

L is a covalent bond or a bivalent $C_{1-3}$ straight or branched hydrocarbon chain;

$R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur; and R' is $C_{1-6}$ aliphatic or 3- to 7-membered saturated or partially unsaturated carbocyclyl.

In some embodiments of any of Formulae I, I-D, I-E, II, II-D, II-E, and II-F, W is CR$^w$. In some embodiments, W is N.

In some embodiments of any of Formulae I, I-D, I-E, II, II-D, II-E, and II-F, X is CR$^x$. In some embodiments, X is N.

In some embodiments of any of Formulae I, I-D, I-E, II, II-D, II-E, and II-F, Y is CR$^y$. In some embodiments, Y is N.

In some embodiments of any of Formulae I, I-D, I-E, II, II-D, II-E, and II-F, W is CR$^w$ or N, X is CR$^x$ or N, and Y is CR$^y$ or N, and no more than one of W, X, and Y is N. In some embodiments of any of Formulae I, I-D, I-E, II, II-D, II-E, and II-F, W is CR$^w$ or N, X is CR$^x$ or N, and Y is CR$^y$ or N, and no more than two of W, X, and Y is N.

In some embodiments of any of Formulae I, I-A, I-B, I-C, I-D, I-E, II, II-A, II-B, II-C, II-D, II-E, II-F, III, and IV, Z is —O—. In some embodiments, Z is —NR$^z$—. In some embodiments, Z is —NH—.

In some embodiments of any of Formulae I, I-D, I-E, II, II-D, II-E, and II-F, R$^w$ is hydrogen, halogen, or optionally substituted $C_{1-6}$ aliphatic. In some embodiments, R$^w$ is hydrogen. In some embodiments, R$^w$ is halogen. In some embodiments, R$^w$ is fluoro. In some embodiments, R$^w$ is chloro. In some embodiments, R$^w$ is —OR$^2$. In some embodiments, $R^w$ is —$OR^2$, wherein $R^2$ is optionally substituted $C_{1-6}$ aliphatic. In some embodiments, Y is N, W is $CR^w$, and $R^w$ is —$OR^2$ wherein $R^2$ is optionally substituted $C_{1-6}$ aliphatic. In some embodiments, $R^w$ is —$N(R^2)_2$. In some embodiments, $R^w$ is —$SR^2$. In some embodiments, $R^w$ is —$SR^2$, wherein $R^2$ is optionally substituted $C_{1-6}$ aliphatic. In some embodiments, Y is N, W is $CR^w$, and $R^w$ is —$SR^2$ wherein $R^2$ is optionally substituted $C_{1-6}$ aliphatic. In some embodiments, $R^w$ is optionally substituted $C_{1-6}$ aliphatic. In some embodiments, $R^w$ is optionally substituted straight-chain or branched $C_{1-6}$ aliphatic (i.e., optionally substituted acyclic $C_{1-6}$ aliphatic). In some embodiments, $R^w$ is optionally substituted $C_{1-6}$ alkyl. In some embodiments, $R^w$ is optionally substituted $C_{1-4}$ alkyl. In some embodiments, $R^w$ is optionally substituted $C_{1-2}$ alkyl. In some embodiments, $R^w$ is optionally substituted methyl (e.g., methyl optionally substituted with one or more fluoro). In some embodiments, $R^w$ is —CN.

In some embodiments of any of Formulae I, I-A, I-C, I-D, I-E, II, II-A, II-C, II-D, II-E, II-F, III, and IV, $R^x$ is hydrogen, halogen, —CN, —$OR^2$, or optionally substituted $C_{1-6}$ aliphatic. In some embodiments, $R^x$ is hydrogen, halogen, —CN, —O($C_{1-4}$ alkyl), or $C_{1-4}$ alkyl optionally substituted with one or more halogen. In some embodiments, $R^x$ is hydrogen, halogen, —$OR^2$, or optionally substituted $C_{1-6}$ aliphatic. In some embodiments, $R^x$ is hydrogen, halogen, —O($C_{1-4}$ alkyl), or $C_{1-4}$ alkyl optionally substituted with one or more halogen. In some embodiments, $R^x$ is hydrogen, halogen, or optionally substituted $C_{1-6}$ aliphatic. In some embodiments, $R^x$ is hydrogen, halogen, —CN, or $OR^2$. In some embodiments, $R^x$ is hydrogen, halogen, —CN, or O($C_{1-4}$ alkyl). In some embodiments, $R^x$ is halogen or —CN. In some embodiments, $R^x$ is hydrogen. In some embodiments, $R^x$ is halogen. In some embodiments, $R^x$ is fluoro. In some embodiments, $R^x$ is chloro. In some embodiments, $R^x$ is —$OR^2$. In some embodiments, $R^x$ is —$OR^2$, wherein $R^2$ is optionally substituted $C_{1-6}$ aliphatic (e.g., optionally substituted $C_{1-6}$ alkyl). In some embodiments, $R^x$ is —O($C_{1-4}$ alkyl). In some embodiments, $R^x$ is —$OCH_3$. In some embodiments, $R^x$ is —$N(R^2)_2$. In some embodiments, $R^x$ is —$SR^2$. In some embodiments, $R^x$ is —$SR^2$, wherein $R^2$ is optionally substituted $C_{1-6}$ aliphatic. In some embodiments, $R^x$ is optionally substituted $C_{1-6}$ aliphatic. In some embodiments, $R^x$ is optionally substituted straight-chain or branched $C_{1-6}$ aliphatic (i.e., optionally substituted acyclic $C_{1-6}$ aliphatic). In some embodiments, $R^x$ is optionally substituted $C_{1-6}$ alkyl (e.g., $C_{1-6}$ alkyl optionally substituted with one or more fluoro). In some embodiments, W is optionally substituted $C_{1-4}$ alkyl (e.g., $C_{1-4}$ alkyl optionally substituted with one or more fluoro). In some embodiments, $R^x$ is optionally substituted $C_{1-2}$ alkyl (e.g., $C_{1-2}$ alkyl optionally substituted with one or more fluoro). In some embodiments, $R^x$ is optionally substituted methyl (e.g., methyl optionally substituted with one or more fluoro, e.g., —$CHF_2$). In some embodiments, $R^x$ is —CN.

In some embodiments of any of Formulae I, I-A, I-B, I-D, I-E, II, II-A, II-B, II-D, II-E, II-F, $R^y$ is hydrogen, halogen, or optionally substituted $C_{1-6}$ aliphatic. In some embodiments, $R^y$ is hydrogen. In some embodiments, $R^y$ is halogen. In some embodiments, $R^y$ is fluoro. In some embodiments, $R^y$ is chloro. In some embodiments, $R^y$ is —$OR^2$. In some embodiments, $R^y$ is —$OR^2$, wherein $R^2$ is optionally substituted $C_{1-6}$ aliphatic. In some embodiments, W is N, Y is $CR^y$, and $R^y$ is —$OR^2$ wherein $R^2$ is optionally substituted $C_{1-6}$ aliphatic. In some embodiments, $R^y$ is —$N(R^2)_2$. In some embodiments, $R^y$ is —$SR^2$. In some embodiments, $R^y$ is —$SR^2$, wherein $R^2$ is optionally substituted $C_{1-6}$ aliphatic.

In some embodiments, W is N, Y is $CR^y$, and $R^y$ is —$SR^2$ wherein $R^2$ is optionally substituted $C_{1-6}$ aliphatic. In some embodiments, $R^y$ is optionally substituted $C_{1-6}$ aliphatic. In some embodiments, $R^y$ is optionally substituted straight-chain or branched $C_{1-6}$ aliphatic (i.e., optionally substituted acyclic $C_{1-6}$ aliphatic). In some embodiments, $R^y$ is optionally substituted $C_{1-6}$ alkyl. In some embodiments, $R^y$ is optionally substituted $C_{1-4}$ alkyl. In some embodiments, $R^y$ is optionally substituted $C_{1-2}$ alkyl. In some embodiments, $R^y$ is optionally substituted methyl (e.g., methyl optionally substituted with one or more fluoro). In some embodiments, $R^y$ is —CN.

In some embodiments of any of Formulae I, I-A, I-B, I-C, I-D, I-E, II, II-A, II-B, II-C, II-D, II-E, II-F, III, and IV, $R^z$ is hydrogen. In some embodiments, $R^z$ is optionally substituted $C_{1-6}$ aliphatic. In some embodiments, $R^z$ is optionally substituted straight-chain or branched $C_{1-6}$ aliphatic (i.e., optionally substituted acyclic $C_{1-6}$ aliphatic). In some embodiments, $R^z$ is optionally substituted $C_{1-6}$ alkyl. In some embodiments, $R^z$ is optionally substituted $C_{1-4}$ alkyl. In some embodiments, $R^z$ is unsubstituted $C_{1-4}$ alkyl. In some embodiments, $R^z$ is optionally substituted $C_{1-2}$ alkyl. In some embodiments, $R^z$ is unsubstituted $C_{1-2}$ alkyl.

In some embodiments of any of Formulae I, I-A, I-B, I-C, I-D, I-E, II, II-A, II-B, II-C, II-D, II-E, and II-F, $R^1$ is —N(R)C(O)N(R)$_2$ or —N(R)C(O)OR. In some embodiments, $R^1$ is —N(R)$_2$, —N(R)C(O)R', or —C(O)N(R)$_2$. In some embodiments, $R^1$ is —N(R)C(O)R' or —C(O)N(R)$_2$. In some embodiments, $R^1$ is —N(R)C(O)R', —C(O)N(R)$_2$, —N(R)C(O)N(R)$_2$, or —N(R)C(O)OR.

In some embodiments, when $R^1$ is —N(R)$_2$, —N(R)C(O)R', or —C(O)N(R)$_2$, then n is 1, 2, or 3. In some embodiments, when n is 0, then $R^1$ is —N(R)C(O)N(R)$_2$ or —N(R)C(O)OR.

In some embodiments, $R^1$ is —N(R)$_2$. In some embodiments, $R^1$ is —N(H)(R). In some embodiments, $R^1$ is —$NH_2$. In some embodiments, when $R^1$ is —N(R)$_2$, then n is 1, 2, or 3.

In some embodiments, $R^1$ is —N(R)C(O)R'. In some embodiments, $R^1$ is —N(H)C(O)R'. In some embodiments, $R^1$ is —N(R)C(O)(optionally substituted $C_{1-6}$ aliphatic). In some embodiments, $R^1$ is —N(H)C(O)(optionally substituted $C_{1-6}$ aliphatic). In some embodiments, $R^1$ is —N(R)C(O)($C_{1-6}$ aliphatic). In some embodiments, $R^1$ is —N(H)C(O)($C_{1-6}$ aliphatic). In some embodiments, $R^1$ is —N(R)C(O)(straight-chain or branched $C_{1-6}$ aliphatic). In some embodiments, $R^1$ is —N(H)C(O)(straight-chain or branched $C_{1-6}$ aliphatic). In some embodiments, $R^1$ is —N(R)C(O)(optionally substituted $C_{1-6}$ alkyl). In some embodiments, $R^1$ is —N(H)C(O)(optionally substituted $C_{1-6}$ alkyl). In some embodiments, $R^1$ is —N(R)C(O)R', wherein R' of $R^1$ is $C_{1-6}$ alkyl optionally substituted with halogen, —OH, —O($C_{1-6}$ alkyl), —NH(CH$_2$)$_2$O($C_{1-6}$ alkyl), —NH($C_{1-4}$ haloalkyl), or an optionally substituted 3- to 7-membered saturated monocyclic heterocyclyl having 1-2 heteroatoms independently selected from nitrogen, oxygen, and sulfur. In some embodiments, $R^1$ is —N(H)C(O)R', wherein R' of $R^1$ is $C_{1-6}$ alkyl optionally substituted with halogen, —OH, —O($C_{1-6}$ alkyl), —NH(CH$_2$)$_2$O($C_{1-6}$ alkyl), —NH($C_{1-4}$ haloalkyl), or an optionally substituted 3- to 7-membered saturated monocyclic heterocyclyl having 1-2 heteroatoms independently selected from nitrogen, oxygen, and sulfur. In some embodiments, $R^1$ is —N(R)C(O)($C_{1-6}$ alkyl). In some embodiments, $R^1$ is —N(H)C(O)($C_{1-6}$ alkyl). In some embodiments, $R^1$ is —N(R)C(O)(optionally substituted $C_{1-4}$ alkyl). In some embodiments, $R^1$ is —N(H)C(O)(optionally substituted $C_{1-4}$ alkyl). In some embodiments, $R^1$ is —N(R)C(O)R', wherein R' of $R^1$ is $C_{1-4}$ alkyl optionally substituted with halogen, —OH, —O($C_{1-6}$ alkyl), —NH(CH$_2$)$_2$O($C_{1-6}$ alkyl), —NH ($C_{1-4}$ haloalkyl), or an optionally substituted 3- to 7-membered saturated monocyclic heterocyclyl having 1-2 heteroatoms independently selected from nitrogen, oxygen, and sulfur. In some embodiments, $R^1$ is —N(H)C(O)R', wherein R' of $R^1$ is $C_{1-4}$ alkyl optionally substituted with halogen, —OH, —O($C_{1-6}$ alkyl), —NH(CH$_2$)$_2$O($C_{1-6}$ alkyl), —NH($C_{1-4}$ haloalkyl), or an optionally substituted 3- to 7-membered saturated monocyclic heterocyclyl having 1-2 heteroatoms independently selected from nitrogen, oxygen, and sulfur. In some embodiments, $R^1$ is —N(R)C(O)($C_{1-4}$ alkyl). In some embodiments, $R^1$ is —N(H)C(O)($C_{1-4}$ alkyl). In some embodiments, $R^1$ is —N(R)C(O)($C_{1-2}$ alkyl). In some embodiments, $R^1$ is —N(H)C(O)($C_{1-2}$ alkyl). In some embodiments, $R^1$ is —N(R)C(O)CH$_3$. In some embodiments, $R^1$ is —N(H)C(O)CH$_3$. In some embodiments, $R^1$ is —N(R)C(O)(optionally substituted $C_{3-7}$ cycloalkyl). In some embodiments, $R^1$ is —N(H)C(O)(optionally substituted $C_{3-7}$ cycloalkyl). In some embodiments, $R^1$ is —N(R)C(O)(optionally substituted cyclopropyl). In some embodiments, $R^1$ is —N(H)C(O)(optionally substituted cyclopropyl). In some embodiments, when $R^1$ is —N(R)C(O)R', then n is 1, 2, or 3.

In some embodiments, $R^1$ is —C(O)N(R)$_2$. In some embodiments, $R^1$ is —C(O)N(R)($C_{1-6}$ aliphatic). In some embodiments, $R^1$ is —C(O)N(H)($C_{1-6}$ aliphatic). In some embodiments, $R^1$ is —C(O)N(R)(straight-chain or branched $C_{1-6}$ aliphatic). In some embodiments, $R^1$ is —C(O)N(H)(straight-chain or branched $C_{1-6}$ aliphatic). In some embodiments, $R^1$ is —C(O)N(R)($C_{1-6}$ alkyl). In some embodiments, $R^1$ is —C(O)N(H)($C_{1-6}$ alkyl). In some embodiments, $R^1$ is —C(O)N(R)($C_{1-4}$ alkyl). In some embodiments, $R^1$ is —C(O)N(H)($C_{1-4}$ alkyl). In some embodiments, $R^1$ is —C(O)N(R)($C_{1-2}$ alkyl). In some embodiments, $R^1$ is —C(O)N(H)($C_{1-2}$ alkyl). In some embodiments, $R^1$ is —C(O)N(R)CH$_3$. In some embodiments, $R^1$ is —C(O)N(H)(R). In some embodiments, when $R^1$ is —C(O)N(R)$_2$, then n is 1, 2, or 3.

In some embodiments, $R^1$ is —N(R)C(O)N(R)$_2$. In some embodiments, $R^1$ is —N(H)C(O)N(R)$_2$. In some embodiments, $R^1$ is —N(H)C(O)N(optionally substituted $C_{1-6}$ aliphatic)$_2$. In some embodiments, $R^1$ is —N(H)C(O)N(optionally substituted $C_{1-6}$ alkyl)$_2$. In some embodiments, $R^1$ is —N(H)C(O)N(optionally substituted $C_{1-4}$ alkyl)$_2$. In some embodiments, $R^1$ is —N(H)C(O)N(optionally substituted $C_{1-2}$ alkyl)$_2$. In some embodiments, $R^1$ is —N(R)C(O)NH(R). In some embodiments, $R^1$ is —N(H)C(O)NH(R). In some embodiments, $R^1$ is —N(H)C(O)NH(optionally substituted $C_{1-6}$ aliphatic). In some embodiments, $R^1$ is —N(H)C(O)NH(optionally substituted $C_{1-6}$ alkyl). In some embodiments, $R^1$ is —N(H)C(O)NH(optionally substituted $C_{1-4}$ alkyl). In some embodiments, $R^1$ is —N(H)C(O)NH(optionally substituted $C_{1-2}$ alkyl). In some embodiments, $R^1$ is —N(H)C(O)NH(optionally substituted $C_{3-7}$ cycloaliphatic). In some embodiments, $R^1$ is —N(H)C(O)NH(optionally substituted $C_{3-7}$ cycloalkyl). In some embodiments, $R^1$ is —N(H)C(O)NH(optionally substituted cyclopropyl). In some embodiments, $R^1$ is —N(H)C(O)NH(optionally substituted 3- to 7-membered saturated or partially unsaturated monocyclic heterocyclyl having 1-3 heteroatoms independently selected from nitrogen, oxygen, and sulfur). In some embodiments, $R^1$ is —N(H)C(O)NH(optionally substituted 4- to 6-membered saturated monocyclic heterocyclyl having 1-2 heteroatoms independently selected from nitrogen, oxygen, and sulfur). In some embodiments, $R^1$ is —N(H)C(O)NH(optionally substituted oxetanyl). In some embodiments, $R^1$ is —N(R)C(O)N(R)$_2$, wherein the two R groups attached to the same nitrogen are taken together to form an optionally substituted 3- to 7-membered saturated or partially unsaturated monocyclic heterocyclyl having 0-2 additional heteroatoms independently selected from nitrogen, oxygen, and sulfur. In some embodiments, $R^1$ is —N(H)C(O)N(R)$_2$, wherein the two R groups attached to the same nitrogen are taken together to form an optionally substituted 3- to 7-membered saturated or partially unsaturated monocyclic heterocyclyl having 0-2 additional heteroatoms independently selected from nitrogen, oxygen, and sulfur. In some embodiments, $R^1$ is —N(H)C(O)N(R)$_2$, wherein the two R groups attached to the same nitrogen are taken together to form a 3- to 7-membered saturated or partially unsaturated monocyclic heterocyclyl having 0-2 additional heteroatoms independently selected from nitrogen, oxygen, and sulfur optionally substituted with one or more halogen, $C_{1-6}$ alkyl, —OH, and —O($C_{1-6}$ alkyl). In some embodiments, $R^1$ is —N(H)C(O)N(R)$_2$, wherein the two R groups attached to the same nitrogen are taken together to form an optionally substituted 4- to 6-membered saturated monocyclic heterocyclyl having 0-1 additional heteroatoms independently selected from nitrogen, oxygen, and sulfur. In some embodiments, $R^1$ is —N(H)C(O)N(R)$_2$, wherein the two R groups attached to the same nitrogen are taken together to form a 4- to 6-membered saturated monocyclic heterocyclyl having 0-1 additional heteroatoms independently selected from nitrogen, oxygen, and sulfur optionally substituted with one or more halogen, $C_{1-6}$ alkyl, —OH, and —O($C_{1-6}$ alkyl). In some embodiments, $R^1$ is selected from:

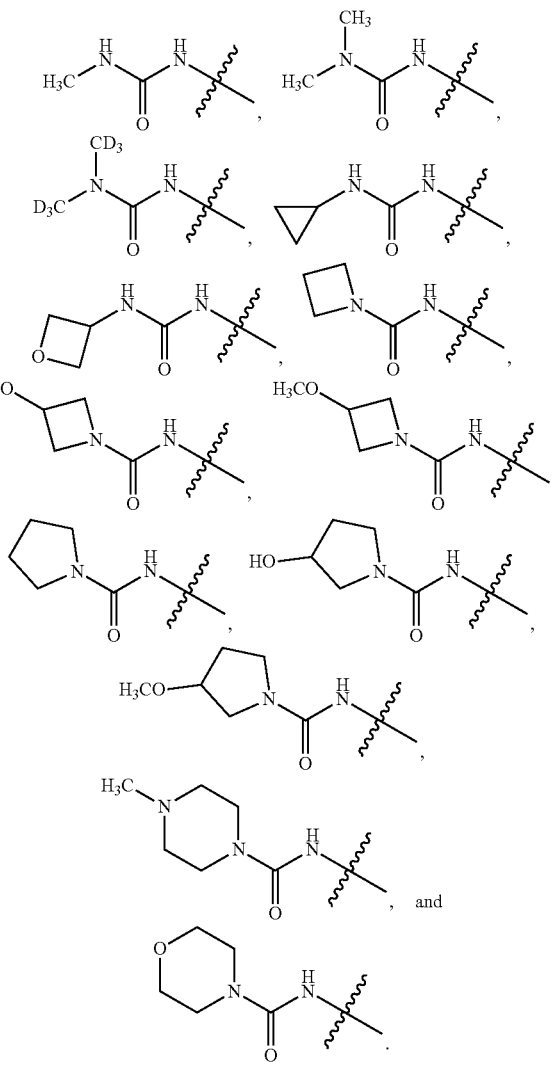

In some embodiments, $R^1$ is not

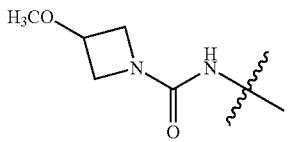

In some embodiments, when X is CH, then $R^1$ is not

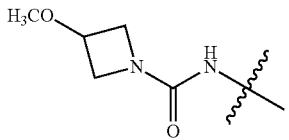

In some embodiments, $R^1$ is —N(R)C(O)OR. In some embodiments, $R^1$ is —N(H)C(O)OR. In some embodiments, $R^1$ is —N(H)C(O)OR, wherein R of $R^1$ is optionally substituted $C_{1-6}$ aliphatic or optionally substituted 3- to 7-membered saturated or partially unsaturated monocyclic heterocyclyl having 1-2 heteroatoms independently selected from nitrogen, oxygen, and sulfur. In some embodiments, $R^1$ is —N(H)C(O)OR, wherein R of $R^1$ is optionally substituted $C_{1-6}$ alkyl or optionally substituted 4- to 6-membered saturated monocyclic heterocyclyl having 1-2 heteroatoms independently selected from nitrogen, oxygen, and sulfur. In some embodiments, $R^1$ is —N(H)C(O)OR, wherein R of $R^1$ is $C_{1-6}$ alkyl optionally substituted with one or more —OH, —O($C_{1-6}$ alkyl), —N($C_{1-6}$ alkyl)$_2$, or 4- to 6-membered saturated monocyclic heterocyclyl having 1-2 heteroatoms independently selected from nitrogen, oxygen, and sulfur. In some embodiments, $R^1$ is —N(H)C(O)OR, wherein R of $R^1$ is 4- to 6-membered saturated monocyclic heterocyclyl having 1-2 heteroatoms independently selected from nitrogen, oxygen, and sulfur optionally substituted with one or more $C_{1-6}$ alkyl. In some embodiments, $R^1$ is selected from:

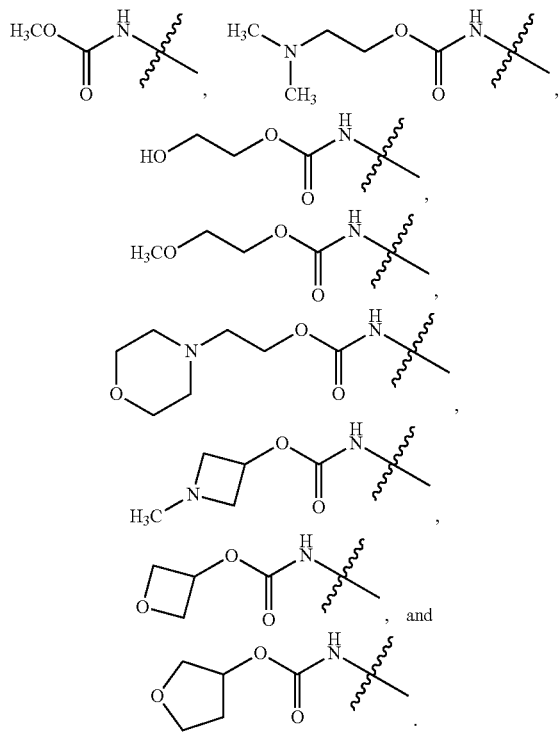

In some embodiments of any of Formulae I, I-A, I-B, I-C, I-D, I-E, II, II-A, II-B, II-C, II-D, II-E, II-F, III, and IV, $R^2$ is optionally substituted straight-chain or branched $C_{1-6}$ aliphatic (i.e., optionally substituted acyclic $C_{1-6}$ aliphatic). In some embodiments, $R^2$ is optionally substituted $C_{1-6}$ alkyl. In some embodiments, $R^2$ is optionally substituted $C_{1-4}$ alkyl. In some embodiments, $R^2$ is unsubstituted $C_{1-4}$ alkyl. In some embodiments, $R^2$ is optionally substituted $C_{1-2}$ alkyl. In some embodiments, $R^2$ is unsubstituted $C_{1-2}$ alkyl. In some embodiments, $R^2$ is methyl.

In some embodiments of any of Formulae I, I-A, I-B, I-C, I-D, I-E, II, II-A, II-B, II-C, II-D, II-E, II-F, III, and IV, each $R^3$ is independently hydrogen or optionally substituted $C_{1-4}$ aliphatic. In some embodiments, each $R^3$ is independently hydrogen or optionally substituted $C_{1-2}$ aliphatic. In some embodiments, each $R^3$ is hydrogen. In some embodiments, each $R^3$ is independently optionally substituted $C_{1-6}$ aliphatic. In some embodiments, each $R^3$ is independently optionally substituted straight-chain or branched $C_{1-6}$ aliphatic (i.e., optionally substituted acyclic $C_{1-6}$ aliphatic). In some embodiments, each $R^3$ is independently optionally substituted $C_{1-4}$ aliphatic. In some embodiments, each $R^3$ is independently optionally substituted straight-chain or branched $C_{1-4}$ aliphatic (i.e., optionally substituted acyclic $C_{1-4}$ aliphatic). In some embodiments, each $R^3$ is independently optionally substituted $C_{1-2}$ aliphatic. In some embodiments, each $R^3$ is independently hydrogen or $C_{1-6}$ alkyl. In some embodiments, each $R^3$ is independently hydrogen or $C_{1-4}$ alkyl. In some embodiments, each $R^3$ is independently hydrogen or $C_{1-2}$ alkyl.

In some embodiments of Formula III, $R^4$ is halogen. In some embodiments, $R^4$ is fluoro. In some embodiments, $R^4$ is chloro. In some embodiments, $R^4$ is —OR. In some embodiments, $R^4$ is —OH or —O(optionally substituted $C_{1-6}$ alkyl). In some embodiments, $R^4$ is —OH or —O($C_{1-6}$ alkyl). In some embodiments, $R^4$ is —OH or —OCH$_3$. In some embodiments, $R^4$ is —N(R)$_2$. In some embodiments, $R^4$ is —NH(R). In some embodiments, $R^4$ is —NH(optionally substituted $C_{1-6}$ alkyl). In some embodiments, $R^4$ is —NH(R wherein R of $R^4$ is $C_{1-6}$ alkyl optionally substituted with one or more halogen or —O($C_{1-6}$ alkyl). In some embodiments, $R^4$ is —NH(CH$_2$)$_2$F or —NH(CH$_2$)$_2$OCH$_3$. In some embodiments, $R^4$ is optionally substituted 3- to 7-membered saturated or partially unsaturated monocyclic heterocyclyl having 1-3 heteroatoms independently selected from nitrogen, oxygen, and sulfur. In some embodiments, $R^4$ is optionally substituted 4- to 6-membered saturated monocyclic heterocyclyl having 1-3 heteroatoms independently selected from nitrogen, oxygen, and sulfur. In some embodiments, $R^4$ is 4- to 6-membered saturated monocyclic heterocyclyl having 1-3 heteroatoms independently selected from nitrogen, oxygen, and sulfur optionally substituted with one or more $C_{1-6}$ alkyl. In some embodiments, $R^4$ is tetrahydropyranyl or morpholinyl optionally substituted with one or more $C_{1-6}$ alkyl.

In some embodiments of any of Formulae I, I-A, I-B, I-C, I-D, II, II-A, II-B, II-C, II-E, and II-F, each $R^c$ is independently selected from halogen, —CN, —CO$_2$R, —C(O)N(R)$_2$, —NO$_2$, —N(R)$_2$, —OR, —SR, or optionally substituted $C_{1-6}$ alkyl, wherein each R of $R^c$ is independently hydrogen or $C_{1-6}$ alkyl. In some embodiments, $R^c$ is halogen (e.g., fluoro). In some embodiments, $R^c$ is —CN, —CO$_2$R, —C(O)N(R)$_2$, or —NO$_2$. In some embodiments, $R^c$ is —N(R)$_2$, —OR, or —SR. In some embodiments, $R^c$ is optionally substituted $C_{1-6}$ aliphatic (e.g., $C_{1-6}$ alkyl).

In some embodiments of any of Formulae I, I-A, I-B, I-C, I-D, II, II-A, II-B, II-C, II-E, and II-F, n is 0 or 1. In some embodiments, n is 0. In some embodiments, n is 1. In some embodiments, n is 2. In some embodiments, n is 3.

In some embodiments of any of Formulae I, I-A, I-B, I-C, I-D, I-E, and III, Ring A is optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur. In some embodiments, Ring A is optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur. In some embodiments, Ring A is optionally substituted 5- to 6-membered monocyclic heteroaryl having 1-4 heteroatoms independently selected from nitrogen, oxygen, and sulfur or optionally substituted 8- to 10-membered bicyclic heteroaryl having 1-4 heteroatoms independently selected from nitrogen, oxygen, and sulfur.

In some embodiments, Ring A is optionally substituted phenyl. In some embodiments, Ring A is not optionally substituted phenyl.

In some embodiments, Ring A is optionally substituted 5- to 6-membered monocyclic heteroaryl having 1-4 heteroatoms independently selected from nitrogen, oxygen, and sulfur. In some embodiments, Ring A is optionally substituted 5- to 6-membered monocyclic heteroaryl having 1-2 heteroatoms independently selected from nitrogen, oxygen, and sulfur. In some embodiments, Ring A is optionally substituted 5-membered monocyclic heteroaryl having 1-4 heteroatoms independently selected from nitrogen, oxygen, and sulfur. In some embodiments, Ring A is optionally substituted pyrazolyl. In some embodiments, Ring A is optionally substituted 6-membered monocyclic heteroaryl having 1-4 heteroatoms independently selected from nitrogen, oxygen, and sulfur. In some embodiments, Ring A is optionally substituted pyridonyl.

In some embodiments, Ring A is optionally substituted 8- to 10-membered bicyclic heteroaryl having 1-4 heteroatoms independently selected from nitrogen, oxygen, and sulfur. In some embodiments, Ring A is optionally substituted 8-membered bicyclic heteroaryl having 1-4 heteroatoms independently selected from nitrogen, oxygen, and sulfur. In some embodiments, Ring A is optionally substituted 9-membered bicyclic heteroaryl having 1-4 heteroatoms independently selected from nitrogen, oxygen, and sulfur. In some embodiments, Ring A is optionally substituted tetrahydropyrazolo[1,5-a]pyridyl or dihydro-4H-pyrazolo[5,1-c][1,4]oxazinyl. In some embodiments, Ring A is optionally substituted 10-membered bicyclic heteroaryl having 1-4 heteroatoms independently selected from nitrogen, oxygen, and sulfur.

In some embodiments, Ring A is optionally substituted 3- to 7-membered saturated or partially unsaturated monocyclic carbocyclyl. In some embodiments, Ring A is optionally substituted 3-membered saturated or partially unsaturated monocyclic carbocyclyl. In some embodiments, Ring A is optionally substituted 4-membered saturated or partially unsaturated monocyclic carbocyclyl. In some embodiments, Ring A is optionally substituted 5-membered saturated or partially unsaturated monocyclic carbocyclyl. In some embodiments, Ring A is optionally substituted 6-membered saturated or partially unsaturated monocyclic carbocyclyl. In some embodiments, Ring A is not optionally substituted 6-membered saturated or partially unsaturated monocyclic carbocyclyl. In some embodiments, Ring A is optionally substituted 7-membered saturated or partially unsaturated monocyclic carbocyclyl.

In some embodiments, Ring A is optionally substituted 3- to 7-membered saturated or partially unsaturated monocyclic heterocyclyl having 1-3 heteroatoms independently selected from nitrogen, oxygen, and sulfur. In some embodiments, Ring A is optionally substituted 3-membered saturated or partially unsaturated monocyclic heterocyclyl having 1-2 heteroatoms independently selected from nitrogen, oxygen, and sulfur. In some embodiments, Ring A is optionally substituted 4-membered saturated or partially unsaturated monocyclic heterocyclyl having 1-3 heteroatoms independently selected from nitrogen, oxygen, and sulfur. In some embodiments, Ring A is optionally substituted 5-membered saturated or partially unsaturated monocyclic heterocyclyl having 1-3 heteroatoms independently selected from nitrogen, oxygen, and sulfur. In some embodiments, Ring A is optionally substituted 6-membered saturated or partially unsaturated monocyclic heterocyclyl having 1-3 heteroatoms independently selected from nitrogen, oxygen, and sulfur. In some embodiments, Ring A is optionally substituted 7-membered saturated or partially unsaturated monocyclic heterocyclyl having 1-3 heteroatoms independently selected from nitrogen, oxygen, and sulfur.

In some embodiments, Ring A is optionally substituted 7- to 10-membered saturated or partially unsaturated bicyclic heterocyclyl having 1-4 heteroatoms independently selected from nitrogen, oxygen, and sulfur. In some embodiments, Ring A is optionally substituted 7-membered saturated or partially unsaturated bicyclic heterocyclyl having 1-4 heteroatoms independently selected from nitrogen, oxygen, and sulfur. In some embodiments, Ring A is optionally substituted 8-membered saturated or partially unsaturated bicyclic heterocyclyl having 1-4 heteroatoms independently selected from nitrogen, oxygen, and sulfur. In some embodiments, Ring A is optionally substituted 9-membered saturated or partially unsaturated bicyclic heterocyclyl having 1-4 heteroatoms independently selected from nitrogen, oxygen, and sulfur. In some embodiments, Ring A is optionally substituted 10-membered saturated or partially unsaturated bicyclic heterocyclyl having 1-4 heteroatoms independently selected from nitrogen, oxygen, and sulfur.

In some embodiments, Ring A is

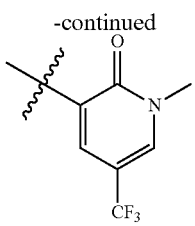

In some embodiments of any of Formulae II, II-A, II-B, II-C, II-D, II-E, and II-F, Ring A is optionally substituted 8- to 10-membered bicyclic heteroaryl having 1-4 heteroatoms independently selected from nitrogen, oxygen, and sulfur, optionally substituted 10- to 16-membered polycyclic heteroaryl having 1-5 heteroatoms independently selected from nitrogen, oxygen, and sulfur, optionally substituted 7- to 10-membered bicyclic heterocyclyl having 1-4 heteroatoms independently selected from nitrogen, oxygen, and sulfur, or optionally substituted 10- to 16-membered polycyclic heterocyclyl having 1-5 heteroatoms independently selected from nitrogen, oxygen, and sulfur. In some embodiments, Ring A is optionally substituted 8- to 10-membered bicyclic heteroaryl having 1-4 heteroatoms independently selected from nitrogen, oxygen, and sulfur or optionally substituted 10- to 16-membered polycyclic heteroaryl having 1-5 heteroatoms independently selected from nitrogen, oxygen, and sulfur. In some embodiments, Ring A is optionally substituted 7- to 10-membered bicyclic heterocyclyl having 1-4 heteroatoms independently selected from nitrogen, oxygen, and sulfur or optionally substituted 10- to 16-membered polycyclic heterocyclyl having 1-5 heteroatoms independently selected from nitrogen, oxygen, and sulfur.

In some embodiments, each ring in a bicyclic or polycyclic ring system of Ring A contains at least one heteroatom. In some embodiments, one and only one ring of a bicyclic or polycyclic ring system of Ring A contains no heteroatoms.

In some embodiments, each ring in a bicyclic or polycyclic ring system of Ring A is aromatic. In some embodiments, one and only one ring of a bicyclic or polycyclic ring system of Ring A is aromatic. In some embodiments, no ring in a bicyclic or polycyclic ring system of Ring A is aromatic.

In some embodiments, Ring A is optionally substituted 9- to 16-membered bicyclic or tricyclic aryl. In some embodiments, Ring A is optionally substituted 9- to 10-membered bicyclic aryl. In some embodiments, Ring A is optionally substituted 9-membered bicyclic aryl (e.g., a 5-membered carbocycle fused to a phenyl ring). In some embodiments, Ring A is not substituted indanyl (e.g., indanyl substituted with one or more halogens). In some embodiments, Ring A is optionally substituted 10-membered bicyclic aryl (e.g., naphthyl or a 6-membered carbocycle fused to a phenyl ring).

In some embodiments, Ring A is optionally substituted 8- to 10-membered bicyclic heteroaryl having 1-4 heteroatoms independently selected from nitrogen, oxygen, and sulfur. In some embodiments, Ring A is 8- to 10-membered bicyclic heteroaryl having 1-4 heteroatoms independently selected from nitrogen, oxygen, and sulfur optionally substituted with one or more oxo, halogen, or $C_{1-6}$ alkyl. In some embodiments, Ring A is optionally substituted 8-membered bicyclic heteroaryl having 1-4 heteroatoms independently selected from nitrogen, oxygen, and sulfur. In some embodiments, Ring A is optionally substituted dihydro-1H-imidazo[1,2-b]pyrazolyl, In some embodiments, Ring A is optionally substituted 9-membered bicyclic heteroaryl having 1-4 heteroatoms independently selected from nitrogen, oxygen, and sulfur. In some embodiments, Ring A is 9-membered bicyclic heteroaryl having 1-4 heteroatoms independently selected from nitrogen, oxygen, and sulfur optionally substituted with one or more oxo, halogen, or $C_{1-6}$ alkyl. In some embodiments, Ring A is optionally substituted tetrahydropyrazolo[1,5-a]pyridyl, dihydropyrazolo[1,5-a]pyrazin-4(5H)-onyl, tetrahydropyrazolo[1,5-a]pyrimidinyl, or dihydro-4H-pyrazolo[5,1-c][1,4]oxazinyl. In some embodiments, Ring A is optionally substituted 10-membered bicyclic heteroaryl having 1-4 heteroatoms independently selected from nitrogen, oxygen, and sulfur. In some embodiments, Ring A is 10-membered bicyclic heteroaryl having 1-4 heteroatoms independently selected from nitrogen, oxygen, and sulfur optionally substituted with one or more $C_{1-6}$ alkyl. In some embodiments, Ring A is optionally substituted tetrahydro-4H-pyrazolo[1,5-a][1,4]diazepinyl, tetrahydro-4H-pyrazolo[1,5-d][1,4]diazepinyl, tetrahydropyrazolo[1,5-d][1,4]oxazepinyl, or tetrahydro-4H-pyrazolo[1,5-a]azepinyl.

In some embodiments, Ring A is optionally substituted 10- to 16-membered polycyclic heteroaryl having 1-5 heteroatoms independently selected from nitrogen, oxygen, and sulfur. In some embodiments, Ring A is optionally substituted 11-membered polycyclic heteroaryl having 1-5 heteroatoms independently selected from nitrogen, oxygen, and sulfur. In some embodiments, Ring A is optionally substituted dihydrospiro[cyclobutane-1,4'-pyrrolo[1,2-b]pyrazolyl], dihydro-5'H-spiro[cyclopropane-1,4'-pyrazolo[1,5-a]pyridyl], dihydro-5'H-spiro[cyclopropane-1,4'-pyrazolo[1,5-a]pyrazine], or dihydro-4'H-spiro[cyclopropane-1,5'-pyrazolo[1,5-a]pyrimidinyl].

In some embodiments, Ring A is optionally substituted 7- to 10-membered bicyclic heterocyclyl having 1-4 heteroatoms independently selected from nitrogen, oxygen, and sulfur. In some embodiments, Ring A is optionally substituted 7- to 10-membered fused bicyclic heterocyclyl having 1-4 heteroatoms independently selected from nitrogen, oxygen, and sulfur. In some embodiments, Ring A is optionally substituted 7-membered bicyclic heterocyclyl having 1-3 heteroatoms independently selected from nitrogen, oxygen, and sulfur. In some embodiments, Ring A is optionally substituted 8-membered bicyclic heterocyclyl having 1-3 heteroatoms independently selected from nitrogen, oxygen, and sulfur. In some embodiments, Ring A is optionally substituted 9-membered bicyclic heterocyclyl having 1-3 heteroatoms independently selected from nitrogen, oxygen, and sulfur. In some embodiments, Ring A is optionally substituted 10-membered bicyclic heterocyclyl having 1-3 heteroatoms independently selected from nitrogen, oxygen, and sulfur.

In some embodiments, Ring A is optionally substituted 10- to 16-membered polycyclic heterocyclyl having 1-5 heteroatoms independently selected from nitrogen, oxygen, and sulfur.

In some embodiments, Ring A is selected from:

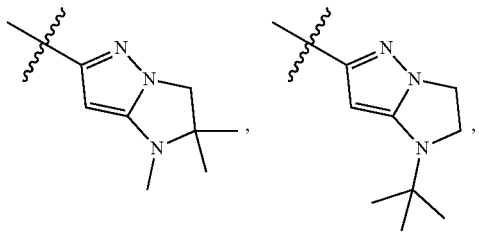

-continued

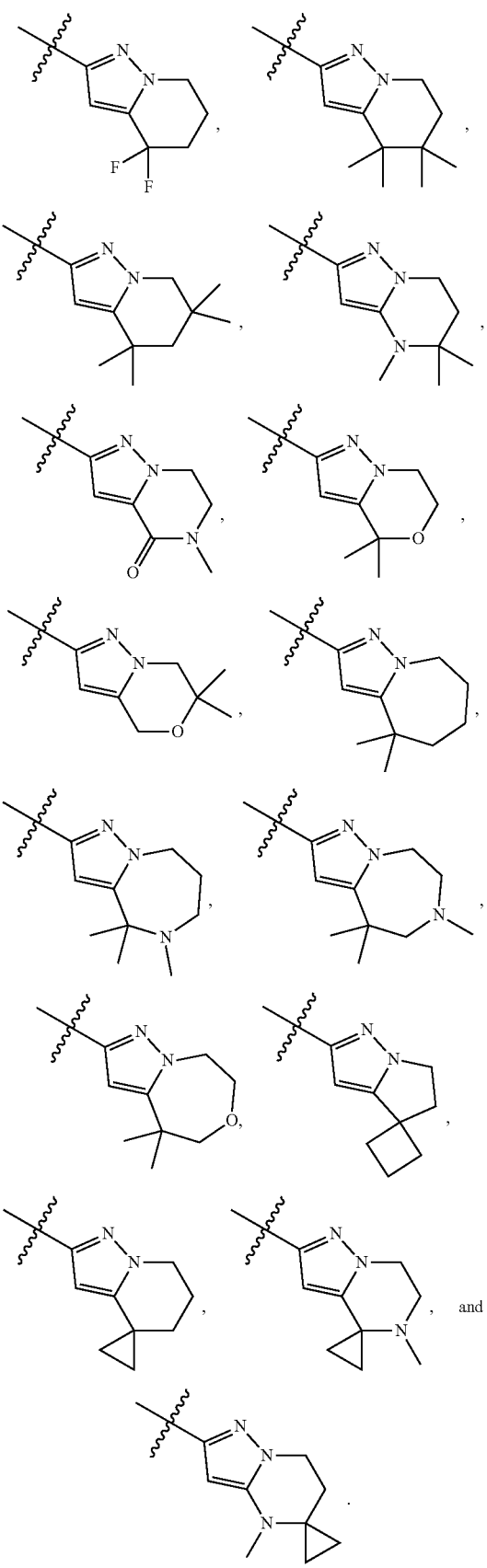

In some embodiments, Ring A is

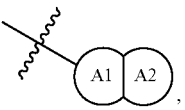

wherein Ring A1 and Ring A2 are defined as in Formula II-E and described in classes and subclasses herein, both singly and in combination; and Ring A1 is fused to Ring A2; and Ring A2 is optionally (i) further fused to Ring A3 or (ii) Ring A2 and Ring A3 combine to form a spirocycle.

In some embodiments, Ring A1 is an optionally substituted ring selected from 5- to 6-membered monocyclic heteroaryl having 1-3 heteroatoms independently selected from nitrogen, oxygen, and sulfur and 5- to 7-membered saturated or partially unsaturated monocyclic heterocyclyl having 1-3 heteroatoms independently selected from nitrogen, oxygen, and sulfur.

In some embodiments, Ring A1 is optionally substituted phenyl. In some embodiments, when Ring A1 is phenyl, Ring A2 contains at least one heteroatom.

In some embodiments, Ring A1 is optionally substituted 5- to 6-membered monocyclic heteroaryl having 1-3 heteroatoms independently selected from nitrogen, oxygen, and sulfur. In some embodiments, Ring A1 is unsubstituted 5- to 6-membered monocyclic heteroaryl having 1-3 heteroatoms independently selected from nitrogen, oxygen, and sulfur. In some embodiments, Ring A1 is optionally substituted 5-membered monocyclic heteroaryl having 1-3 heteroatoms independently selected from nitrogen, oxygen, and sulfur. In some embodiments, Ring A1 is optionally substituted pyrazole. In some embodiments, Ring A1 is optionally substituted 6-membered monocyclic heteroaryl having 1-3 heteroatoms independently selected from nitrogen, oxygen, and sulfur.

In some embodiments, Ring A1 is optionally substituted 5- to 7-membered saturated or partially unsaturated monocyclic carbocyclyl. In some embodiments, when Ring A1 is optionally substituted 5- to 7-membered saturated or partially unsaturated monocyclic carbocyclyl, Ring A2 contains at least one heteroatom. In some embodiments, when Ring A2 is not aromatic, Ring A1 is optionally substituted 5- to 7-membered saturated monocyclic carbocyclyl. In some embodiments, Ring A1 is optionally substituted 5- to 7-membered partially saturated monocyclic carbocyclyl.

In some embodiments, Ring A1 is optionally substituted 5- to 7-membered saturated or partially unsaturated monocyclic heterocyclyl having 1-3 heteroatoms independently selected from nitrogen, oxygen, and sulfur. In some embodiments, when Ring A2 is not aromatic, Ring A1 is optionally substituted 5- to 7-membered saturated monocyclic heterocyclyl having 1-3 heteroatoms independently selected from nitrogen, oxygen, and sulfur. In some embodiments, Ring A1 is optionally substituted 5- to 7-membered partially saturated monocyclic heterocyclyl having 1-3 heteroatoms independently selected from nitrogen, oxygen, and sulfur.

In some embodiments, optionally substituted Ring A1 fused to Ring A2 is

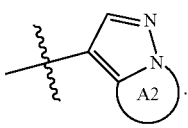

In some embodiments, Ring A2 is an optionally substituted ring selected from 5- to 6-membered monocyclic heteroaryl having 1-3 heteroatoms independently selected from nitrogen, oxygen, and sulfur and 5- to 7-membered saturated or partially unsaturated monocyclic heterocyclyl having 1-3 heteroatoms independently selected from nitrogen, oxygen, and sulfur.

In some embodiments, Ring A2 is optionally substituted phenyl. In some embodiments, when Ring A2 is phenyl, Ring A1 contains at least one heteroatom.

In some embodiments, Ring A2 is optionally substituted 5- to 6-membered monocyclic heteroaryl having 1-3 heteroatoms independently selected from nitrogen, oxygen, and sulfur. In some embodiments, Ring A2 is optionally substituted 5-membered monocyclic heteroaryl having 1-3 heteroatoms independently selected from nitrogen, oxygen, and sulfur. In some embodiments, Ring A2 is optionally substituted 6-membered monocyclic heteroaryl having 1-3 heteroatoms independently selected from nitrogen, oxygen, and sulfur.

In some embodiments, Ring A2 is optionally substituted 5- to 7-membered saturated or partially unsaturated monocyclic carbocyclyl. In some embodiments, when Ring A2 is optionally substituted 5- to 7-membered saturated or partially unsaturated monocyclic carbocyclyl, Ring A1 contains at least one heteroatom. In some embodiments, when Ring A1 is not aromatic, Ring A2 is optionally substituted 5- to 7-membered saturated monocyclic carbocyclyl. In some embodiments, Ring A2 is optionally substituted 5- to 7-membered partially saturated monocyclic carbocyclyl.

In some embodiments, Ring A2 is optionally substituted 5- to 7-membered saturated or partially unsaturated monocyclic heterocyclyl having 1-3 heteroatoms independently selected from nitrogen, oxygen, and sulfur. In some embodiments, when Ring A1 (and Ring A3, if present) is not aromatic, Ring A2 is optionally substituted 5- to 7-membered saturated monocyclic heterocyclyl having 1-3 heteroatoms independently selected from nitrogen, oxygen, and sulfur. In some embodiments, Ring A2 is optionally substituted 5- to 7-membered partially saturated monocyclic heterocyclyl having 1-3 heteroatoms independently selected from nitrogen, oxygen, and sulfur. In some embodiments, Ring A2 is optionally substituted 5-membered saturated or partially unsaturated monocyclic heterocyclyl having 1-2 heteroatoms independently selected from nitrogen, oxygen, and sulfur. In some embodiments, Ring A2 is 5-membered saturated or partially unsaturated monocyclic heterocyclyl having 1-2 heteroatoms independently selected from nitrogen, oxygen, and sulfur optionally substituted with one or more $C_{1-6}$ alkyl. In some embodiments, Ring A2 is optionally substituted pyrrolidine or imidazolidine. In some embodiments, Ring A2 is optionally substituted 6-membered saturated or partially unsaturated monocyclic heterocyclyl having 1-2 heteroatoms independently selected from nitrogen, oxygen, and sulfur. In some embodiments, Ring A2 is 6-membered saturated or partially unsaturated monocyclic heterocyclyl having 1-2 heteroatoms independently selected from nitrogen, oxygen, and sulfur optionally substituted with one or more oxo, halogen, and $C_{1-6}$ alkyl. In some embodiments, Ring A2 is optionally substituted piperidine, hexahydropyrimidine, morpholine, or piperazinone. In some embodiments, Ring A2 is optionally substituted 7-membered saturated or partially unsaturated monocyclic heterocyclyl having 1-3 heteroatoms independently selected from nitrogen, oxygen, and sulfur. In some embodiments, Ring A2 is 7-membered saturated or partially unsaturated monocyclic heterocyclyl having 1-3 heteroatoms independently selected from nitrogen, oxygen, and sulfur optionally substituted with one or more $C_{1-6}$ alkyl. In some embodiments, Ring A2 is azepane, diazepane, or oxazepane.

In some embodiments, optionally substituted Ring A2 fused to Ring A1 is selected from the group consisting of:

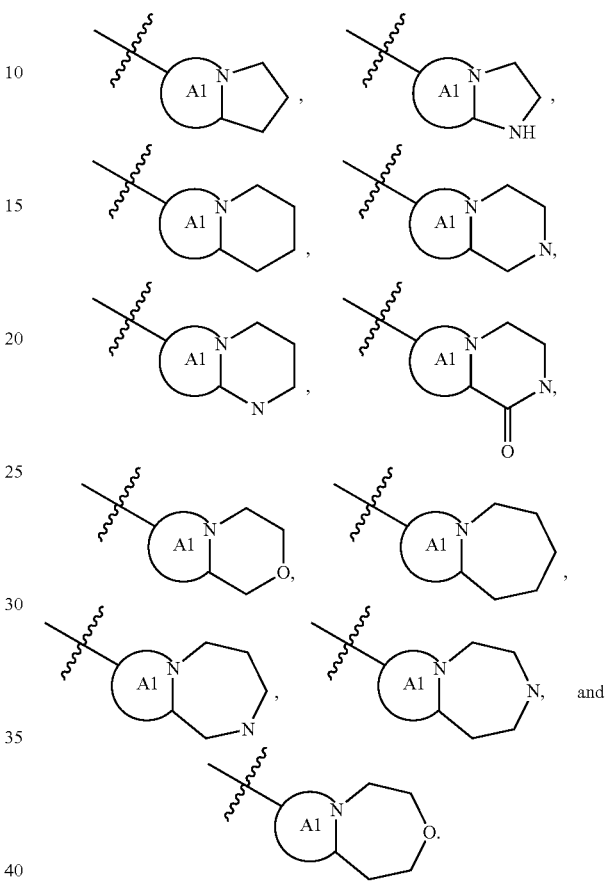

In some embodiments, Ring A1 is an optionally substituted 5- to 6-membered monocyclic heteroaryl having 1-3 heteroatoms independently selected from nitrogen, oxygen, and sulfur, and Ring A2 is an optionally substituted 5- to 7-membered saturated or partially unsaturated monocyclic heterocyclyl having 1-3 heteroatoms independently selected from nitrogen, oxygen, and sulfur. In some embodiments, Ring A1 is an optionally substituted 5-membered monocyclic heteroaryl having 1-3 heteroatoms independently selected from nitrogen, oxygen, and sulfur, and Ring A2 is an optionally substituted 5- to 7-membered saturated or partially unsaturated monocyclic heterocyclyl having 1-3 heteroatoms independently selected from nitrogen, oxygen, and sulfur. In some embodiments, Ring A1 is an optionally substituted 5-membered monocyclic heteroaryl having 1-2 heteroatoms independently selected from nitrogen, oxygen, and sulfur, and Ring A2 is an optionally substituted 5-membered saturated or partially unsaturated monocyclic heterocyclyl having 1-2 heteroatoms independently selected from nitrogen, oxygen, and sulfur. In some embodiments, Ring A1 is an optionally substituted 5-membered monocyclic heteroaryl having 1-2 heteroatoms independently selected from nitrogen, oxygen, and sulfur, and Ring A2 is an optionally substituted 6-membered saturated or partially unsaturated monocyclic heterocyclyl having 1-2 heteroatoms independently selected from nitrogen, oxygen, and sulfur. In some embodiments, Ring A1 is an optionally substituted 5-membered monocyclic heteroaryl having 1-2 heteroatoms independently selected from nitrogen, oxygen, and sulfur, and Ring A2 is an optionally substituted 7-membered saturated or partially unsaturated monocyclic heterocyclyl having 1-2 heteroatoms independently selected from nitrogen, oxygen, and sulfur.

In some embodiments, Ring A2 is further fused to Ring A3. In some embodiments, Ring A2 and Ring A3 combine to form a spirocycle. In some embodiments, when Ring A2 and Ring A3 combine to form a spirocycle, Ring A3 is optionally substituted 3- to 7-membered saturated or partially unsaturated monocyclic carbocyclyl or optionally substituted 3- to 7-membered saturated or partially unsaturated monocyclic heterocyclyl having 1-3 heteroatoms independently selected from nitrogen, oxygen, and sulfur.

In some embodiments, Ring A3, when present, is optionally substituted phenyl. In some embodiments, Ring A3, when present, is optionally substituted 5- to 6-membered monocyclic heteroaryl having 1-3 heteroatoms independently selected from nitrogen, oxygen, and sulfur. In some embodiments, Ring A3, when present, is optionally substituted 3- to 7-membered saturated or partially unsaturated monocyclic carbocyclyl. In some embodiments, Ring A3, when not fused to an aromatic Ring A2, is 3- to 7-membered saturated monocyclic carbocyclyl. In some embodiments, Ring A3 is 3- to 7-membered partially saturated monocyclic carbocyclyl. In some embodiments, Ring A3 is optionally substituted $C_3$-$C_7$ cycloalkyl (e.g., cyclopropyl or cyclobutyl). In some embodiments, Ring A3 is 3- to 7-membered saturated or partially unsaturated monocyclic heterocyclyl having 1-3 heteroatoms independently selected from nitrogen, oxygen, and sulfur. In some embodiments, Ring A3, when not fused to an aromatic Ring A2, is 3- to 7-membered saturated monocyclic heterocyclyl having 1-3 heteroatoms independently selected from nitrogen, oxygen, and sulfur. In some embodiments, Ring A3 is 3- to 7-membered partially saturated monocyclic heterocyclyl having 1-3 heteroatoms independently selected from nitrogen, oxygen, and sulfur.

In some embodiments, optionally substituted Ring A2 fused to Ring A1 and combined to form a spirocycle with Ring A3 is selected from:

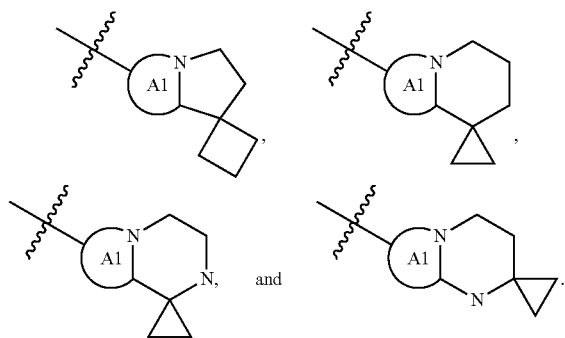

In some embodiments of any of Formulae I, I-A, I-B, I-C, I-D, I-E, II, II-A, II-B, II-C, II-D, II-E, II-F, III, and IV, Ring A is optionally substituted on a substitutable carbon atom with one or more groups independently selected from oxo, halogen, R°, —CN, —OR°, —O(CH$_2$)$_{1-4}$R°, —SR°, —N(R°)$_2$, —NO$_2$, —C(O)R°, —C(O)OR°, —C(O)NR°$_2$, —OC(O)R°, —OC(O)NR°$_2$, —OC(O)OR°, —OS(O)$_2$R°, —OS(O)$_2$NR°$_2$, —N(R°)C(O)R°, —N(R°)S(O)$_2$R°, —S(O)$_2$R°, —SO$_2$NR°$_2$, and —S(O)$_2$OR°, and (ii) optionally substituted on a substitutable nitrogen atom with one or more groups selected from —R†, —NR†$_2$, —C(O)R†, —C(O)OR†, —S(O)$_2$R†, and —S(O)$_2$NR†$_2$. In some embodiments, Ring A is (i) optionally substituted on a substitutable carbon atom with one or more groups independently selected from oxo, halogen, R°, —OR°, and —O(CH$_2$)$_{1-4}$R°, and (ii) optionally substituted on a substitutable nitrogen atom with one or more groups selected from —R†. In some embodiments, Ring A is (i) optionally substituted on a substitutable carbon atom with one or more groups independently selected from oxo, halogen, and R°, and (ii) optionally substituted on a substitutable nitrogen atom with one or more groups selected from —R†.

In some embodiments, Ring A is optionally substituted with one or more $R^b$ (e.g., in addition to being substituted with -L-$R^a$, when present), wherein $R^b$ is as defined in Formula I-D above and described in classes and subclasses herein. In some embodiments, Ring A is substituted with zero, one, two, three, four, or five $R^b$, as valency allows.

In some embodiments of any of Formulae I, I-A, I-B, I-C, I-D, I-E, III, and IV, L is a covalent bond. In some embodiments, L is a bivalent $C_{1-3}$ straight or branched hydrocarbon chain. In some embodiments, L is a bivalent $C_{1-2}$ straight or branched hydrocarbon chain. In some embodiments, L is methylene (i.e., —CH$_2$—). In some embodiments, L is —CH$_2$CH$_2$—. In some embodiments, L is —CH$_2$CH$_2$CH$_2$—. In some embodiments, L is —C(CH$_3$)$_2$—. In some embodiments, L is a covalent bond or —CH$_2$—.

In some embodiments of any of Formulae I, I-A, I-B, I-C, I-D, I-E, III, and IV, $R^a$ is halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur. In some embodiments, $R^a$ is optionally substituted $C_{1-6}$ aliphatic, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur. In some embodiments, $R^a$ is hydrogen, halogen, optionally substituted $C_{1-6}$ aliphatic, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

In some embodiments, $R^a$ is hydrogen. In some embodiments, $R^a$ is not hydrogen.

In some embodiments, $R^a$ is halogen. In some embodiments, $C_{1-6}$ is fluoro, chloro, bromo, or iodo. In some embodiments, $R^a$ is fluoro. In some embodiments, $R^a$ is chloro.

In some embodiments, $R^a$ is optionally substituted $C_{1-6}$ aliphatic. In some embodiments, $R^a$ is optionally substituted straight-chain or branched $C_{1-6}$ aliphatic (i.e., optionally substituted acyclic $C_{1-6}$ aliphatic). In some embodiments, $R^a$ is $C_{1-6}$ aliphatic optionally substituted with one or more halogen, —N($C_{1-6}$ alkyl)$_2$, —OH, or —O(optionally substituted 3- to 7-membered saturated or partially unsaturated monocyclic heterocyclyl). In some embodiments, $R^a$ is optionally substituted $C_{1-6}$ alkyl. In some embodiments, $R^a$ is $C_{1-6}$ alkyl optionally substituted with one or more halogen, —N($C_{1-6}$ alkyl)$_2$, —OH, or —O(optionally substituted 3- to 7-membered saturated or partially unsaturated monocyclic heterocyclyl). In some embodiments, $R^a$ is optionally substituted $C_{1-4}$ alkyl. In some embodiments, $R^a$ is $C_{1-4}$ alkyl optionally substituted with one or more halogen, —N($C_{1-6}$ alkyl)$_2$, —OH, or —O(optionally substituted 3- to 7-membered saturated or partially unsaturated monocyclic heterocyclyl). In some embodiments, $R^a$ is —CH$_3$, —CD$_3$, —CF$_3$, —CH$_2$N(CH$_3$)$_2$, —CH$_2$CH$_2$OH, or

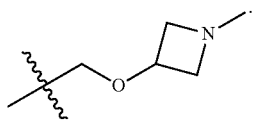 [SMILES: *COC1CN(C)C1]

In some embodiments, $R^a$ is optionally substituted phenyl.

In some embodiments, $R^a$ is optionally substituted 5- to 6-membered monocyclic heteroaryl having 1-4 heteroatoms independently selected from nitrogen, oxygen, and sulfur. In some embodiments, $R^a$ is optionally substituted 5- to 6-membered monocyclic heteroaryl having 1-2 heteroatoms independently selected from nitrogen, oxygen, and sulfur. In some embodiments, $R^a$ is optionally substituted 5-membered monocyclic heteroaryl having 1-4 heteroatoms independently selected from nitrogen, oxygen, and sulfur. In some embodiments, $R^a$ is optionally substituted 6-membered monocyclic heteroaryl having 1-4 heteroatoms independently selected from nitrogen, oxygen, and sulfur.

In some embodiments, $R^a$ is optionally substituted 3- to 7-membered saturated or partially unsaturated monocyclic carbocyclyl. In some embodiments, $R^a$ is optionally substituted 3- to 6-membered saturated monocyclic carbocyclyl. In some embodiments, $R^a$ is optionally substituted 3-membered saturated monocyclic carbocyclyl. In some embodiments, $R^a$ is optionally substituted 4-membered saturated monocyclic carbocyclyl. In some embodiments, $R^a$ is optionally substituted 5-membered saturated monocyclic carbocyclyl. In some embodiments, $R^a$ is optionally substituted 6-membered saturated monocyclic carbocyclyl. In some embodiments, $R^a$ is optionally substituted 7-membered saturated monocyclic carbocyclyl.

In some embodiments, $R^a$ is optionally substituted 3- to 7-membered saturated or partially unsaturated monocyclic heterocyclyl having 1-3 heteroatoms independently selected from nitrogen, oxygen, and sulfur. In some embodiments, $R^a$ is optionally substituted 4- to 7-membered saturated monocyclic heterocyclyl having 1-2 heteroatoms independently selected from nitrogen, oxygen, and sulfur. In some embodiments, $R^a$ is optionally substituted 3-membered saturated monocyclic heterocyclyl having 1 heteroatom independently selected from nitrogen, oxygen, and sulfur. In some embodiments, $R^a$ is optionally substituted 4-membered saturated monocyclic heterocyclyl having 1-2 heteroatoms independently selected from nitrogen, oxygen, and sulfur. In some embodiments, $R^a$ is optionally substituted 5-membered saturated monocyclic heterocyclyl having 1-3 heteroatoms independently selected from nitrogen, oxygen, and sulfur. In some embodiments, $R^a$ is optionally substituted pyrrolidinyl or tetrahydrofuranyl. In some embodiments, $R^a$ is optionally substituted 6-membered saturated monocyclic heterocyclyl having 1-3 heteroatoms independently selected from nitrogen, oxygen, and sulfur. In some embodiments, $R^a$ is optionally substituted 7-membered saturated monocyclic heterocyclyl having 1-3 heteroatoms independently selected from nitrogen, oxygen, and sulfur.

In some embodiments, $R^a$ is optionally substituted 7- to 10-membered saturated or partially unsaturated bicyclic heterocyclyl having 1-4 heteroatoms independently selected from nitrogen, oxygen, and sulfur. In some embodiments, $R^a$ is optionally substituted 7- to 10-membered saturated, spirocyclic, bicyclic heterocyclyl having 1-4 heteroatoms independently selected from nitrogen, oxygen, and sulfur. In some embodiments, $R^a$ is optionally substituted 7- to 9-membered saturated, spirocyclic, bicyclic heterocyclyl having 1-2 heteroatoms independently selected from nitrogen, oxygen, and sulfur. In some embodiments, $R^a$ is optionally substituted 7-membered saturated, spirocyclic, bicyclic heterocyclyl having 1-4 heteroatoms independently selected from nitrogen, oxygen, and sulfur. In some embodiments, $R^a$ is optionally substituted 2-oxaspiro[3.3]heptanyl. In some embodiments, $R^a$ is optionally substituted 8-membered saturated, spirocyclic, bicyclic heterocyclyl having 1-4 heteroatoms independently selected from nitrogen, oxygen, and sulfur. In some embodiments, $R^a$ is optionally substituted 9-membered saturated, spirocyclic, bicyclic heterocyclyl having 1-4 heteroatoms independently selected from nitrogen, oxygen, and sulfur. In some embodiments, $R^a$ is optionally substituted 7-oxaspiro[3.5]nonanyl. In some embodiments, $R^a$ is optionally substituted 10-membered saturated, spirocyclic, bicyclic heterocyclyl having 1-4 heteroatoms independently selected from nitrogen, oxygen, and sulfur.

In some embodiments of any of Formulae I, I-A, I-B, I-C, I-D, I-E, III, and IV,

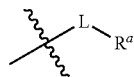

is —$R^a$ (i.e., L is a covalent bond). In some embodiments,

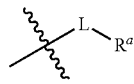

is —($C_{1-3}$ alkylene)-$R^a$ (i.e., L is a $C_{1-3}$ straight or branched hydrocarbon chain). In some embodiments,

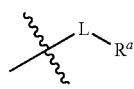

is —($C_{1-2}$ alkylene)-$R^a$ (i.e., L is a $C_{1-2}$ straight or branched hydrocarbon chain). In some embodiments,

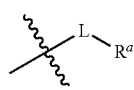

is —CH$_2$—$R^a$ (i.e., L is a $C_1$ hydrocarbon chain). In some embodiments,

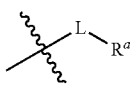

is —CH$_2$CH$_2$—R$^a$ (i.e., L is a C$_2$ straight hydrocarbon chain). In some embodiments,

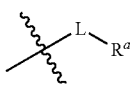

is —CH$_2$CH$_2$CH$_2$—R$^a$ (i.e., L is a C$_3$ straight hydrocarbon chain). In some embodiments, is —

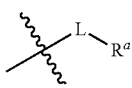

is —C(CH$_3$)$_2$—R$^a$ (i.e., L is a C$_3$ branched hydrocarbon chain).

In some embodiments of any of Formulae I, I-A, I-B, I-C, I-D, I-E, II, II-A, II-B, II-C, II-D, II-E, II-F, III, and IV, up to five occurrences of R$^b$ may be present, as allowed by valency rules, and is each independently halogen, —CN, —OR, —O(CH$_2$)$_m$R, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted C$_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, optionally substituted 5- to 6-membered monocyclic heteroaryl having 1-4 heteroatoms independently selected from nitrogen, oxygen, and sulfur. In some embodiments, each occurrence of R$^b$ is independently halogen, optionally substituted C$_{1-6}$ aliphatic, —OR, or —O(CH$_2$)$_m$R. In some embodiments, each occurrence of R$^b$ is independently halogen, optionally substituted C$_{1-6}$ alkyl, —OR, or —OCH$_2$R, wherein R of R$^b$ is optionally substituted 3- to 6-membered saturated or partially unsaturated monocyclic heterocyclyl having 1-3 heteroatoms independently selected from nitrogen, oxygen, and sulfur. In some embodiments, each occurrence of R$^b$ is halogen or C$_{1-6}$ alkyl optionally substituted with one or more halogen.

In some embodiments, one occurrence of R$^b$ is present. In some embodiments, two occurrences of R$^b$ are present. In some embodiments, three occurrences of R$^b$ are present. In some embodiments, four occurrences of R$^b$ are present. In some embodiments, five occurrences of R$^b$ are present. In some embodiments, R$^b$ is not present. In some embodiments, 1-4 occurrences of R$^b$ are present. In some embodiments, one or two occurrences of R$^b$ are present.

In some embodiments, R$^b$ is hydrogen.

In some embodiments, R$^b$ is halogen. In some embodiments, R$^b$ is fluoro, chloro, bromo, or iodo. In some embodiments, R$^b$ is fluoro. In some embodiments, R$^b$ is chloro.

In some embodiments, R$^b$ is —CN, —OR, —O(CH$_2$)$_m$R, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R, —SO$_2$N(R)$_2$, or —SO$_3$R'. In some embodiments, R$^b$ is —CN. In some embodiments, R$^b$ is —N(R)$_2$. In some embodiments, R$^b$ is —C(O)N(R)$_2$.

In some embodiments, R$^b$ is —OR. In some embodiments, R$^b$ is —OR, wherein R is optionally substituted 3- to 7-membered saturated or partially unsaturated monocyclic heterocyclyl having 1-3 heteroatoms independently selected from nitrogen, oxygen, and sulfur. In some embodiments, R$^b$ is —OR, wherein R is optionally substituted 4- to 6-membered saturated monocyclic heterocyclyl having 1-2 heteroatoms independently selected from nitrogen, oxygen, and sulfur. In some embodiments, R$^b$ is —OR, wherein R is 4- to 6-membered saturated monocyclic heterocyclyl having 1-2 heteroatoms independently selected from nitrogen, oxygen, and sulfur and optionally substituted with one or more C$_{1-6}$ alkyl (e.g., methyl). In some embodiments, R$^b$ is —OR, wherein R is optionally substituted azetidinyl or pyrrolidinyl. In some embodiments, R$^b$ is —OR, wherein R is azetidinyl or pyrrolidinyl optionally substituted with one or more C$_{1-6}$ alkyl (e.g., methyl). In some embodiments, R$^b$ is

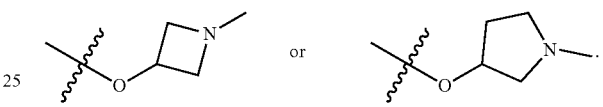

In some embodiments, R$^b$ is —O(CH$_2$)$_m$R. In some embodiments, R$^b$ is —OCH$_2$R. In some embodiments, R$^b$ is —O(CH$_2$)$_m$R, wherein R is optionally substituted 3- to 7-membered saturated or partially unsaturated monocyclic heterocyclyl having 1-3 heteroatoms independently selected from nitrogen, oxygen, and sulfur. In some embodiments, R$^b$ is —O(CH$_2$)$_m$R, wherein R is optionally substituted 4- to 6-membered saturated monocyclic heterocyclyl having 1-2 heteroatoms independently selected from nitrogen, oxygen, and sulfur. In some embodiments, R$^b$ is —O(CH$_2$)$_m$R, wherein R is 4- to 6-membered saturated monocyclic heterocyclyl having 1-2 heteroatoms independently selected from nitrogen, oxygen, and sulfur and optionally substituted with one or more C$_{1-6}$ alkyl (e.g., methyl). In some embodiments, R$^b$ is —O(CH$_2$)$_m$R, wherein R is optionally substituted pyrrolidinyl. In some embodiments, R$^b$ is —O(CH$_2$)$_m$R, wherein R is pyrrolidinyl optionally substituted with one or more C$_{1-6}$ alkyl (e.g., methyl). In some embodiments, R$^b$ is

In some embodiments, R$^b$ is optionally substituted C$_{1-6}$ aliphatic. In some embodiments, R$^b$ is optionally substituted straight-chain or branched C$_{1-6}$ aliphatic (i.e., optionally substituted acyclic C$_{1-6}$ aliphatic). In some embodiments, R$^b$ is optionally substituted C$_{1-6}$ alkyl. In some embodiments, R$^b$ is optionally substituted C$_{1-4}$ alkyl. In some embodiments, R$^b$ is C$_{1-4}$ alkyl optionally substituted with one or more of halogen. In some embodiments, R$^b$ is —CH$_3$, —CF$_3$, or —C(CH$_3$)$_3$.

In some embodiments, R$^b$ is optionally substituted 3- to 6-membered saturated or partially unsaturated monocyclic carbocyclyl. In some embodiments, R$^b$ is optionally substituted C$_3$-C$_6$ cycloalkyl.

In some embodiments, $R^b$ is optionally substituted 3- to 6-membered saturated or partially unsaturated monocyclic heterocyclyl having 1-3 heteroatoms independently selected from nitrogen, oxygen, and sulfur. In some embodiments, $R^b$ is optionally substituted 3- to 6-membered saturated monocyclic heterocyclyl having 1-2 heteroatoms independently selected from nitrogen, oxygen, and sulfur.

In some embodiments, $R^b$ is optionally substituted 5- to 6-membered monocyclic heteroaryl having 1-4 heteroatoms independently selected from nitrogen, oxygen, and sulfur.

In some embodiments of any of Formulae I, I-A, I-B, I-C, I-D, I-E, II, II-A, II-B, II-C, II-D, II-E, II-F, III, and IV, m is 1 or 2. In some embodiments, m is 1. In some embodiments, m is 2. In some embodiments, m is 3.

In some embodiments of any of Formulae I, I-A, I-B, I-C, I-D, I-E, and III, optionally substituted

In some embodiments, optionally substituted

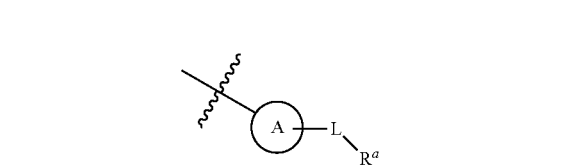

is optionally substituted

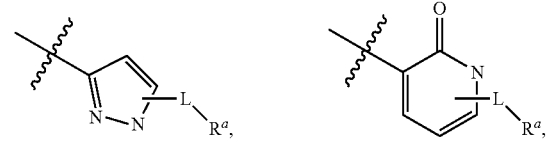

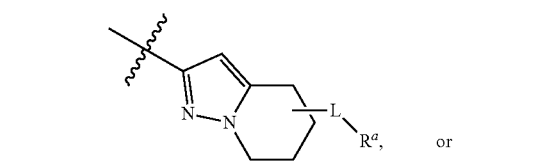

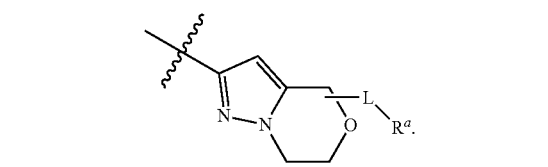

In some embodiments,

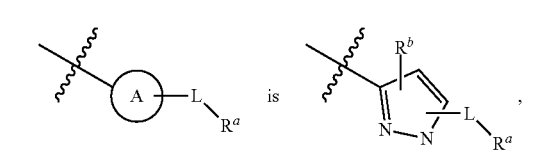

In some embodiments,

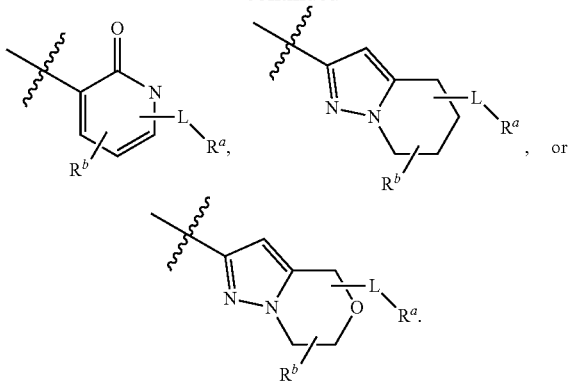

In some embodiments,

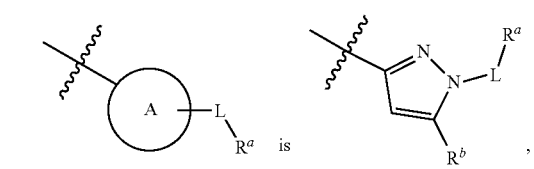

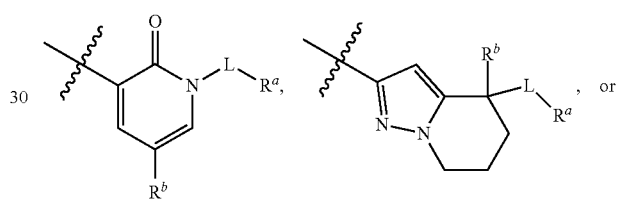

In some embodiments,

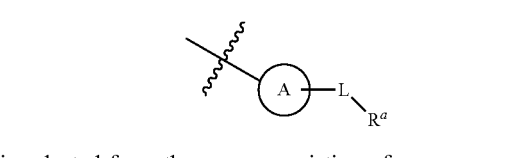

is selected from the group consisting of:

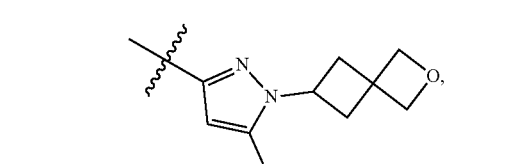

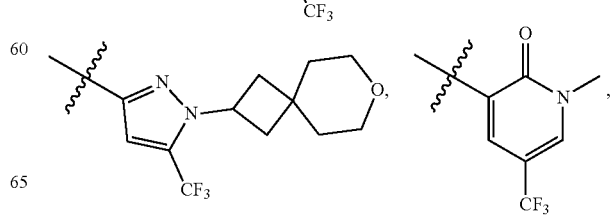

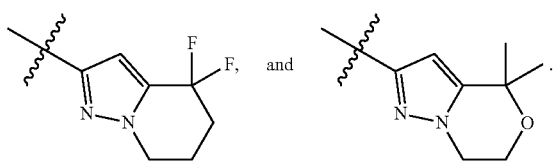

In some embodiments of Formula IV,

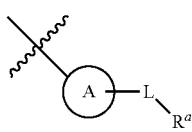

is selected from the group consisting of:

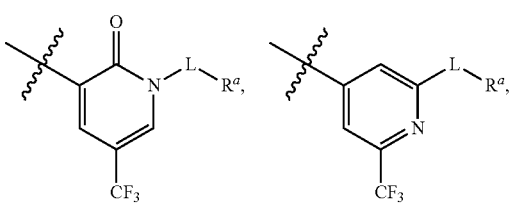

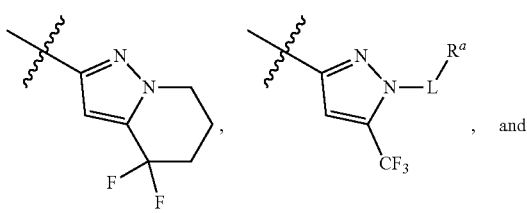

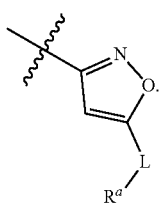

In some embodiments,

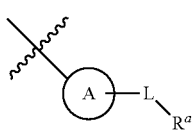

is selected from the group consisting of:

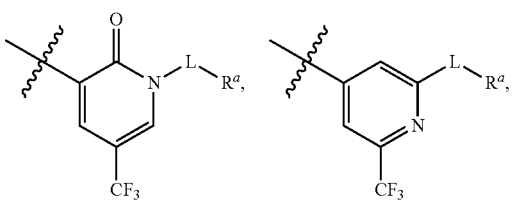

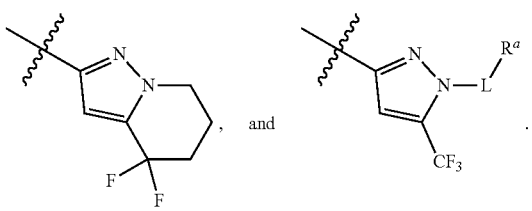

In some embodiments, when

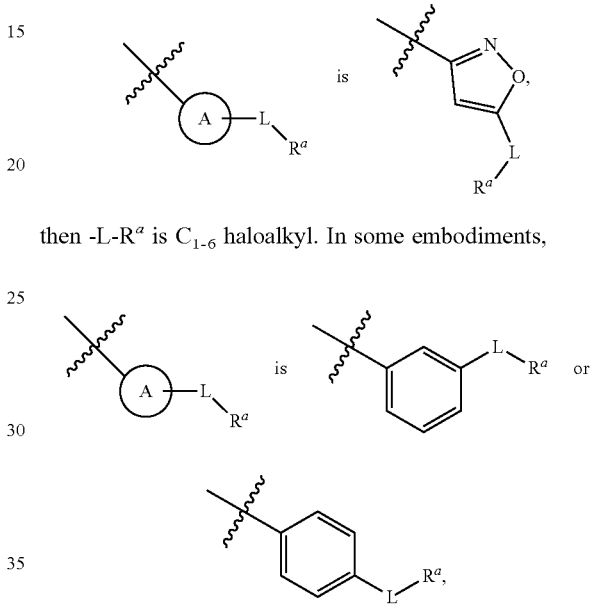

then -L-$R^a$ is $C_{1-6}$ haloalkyl. In some embodiments,

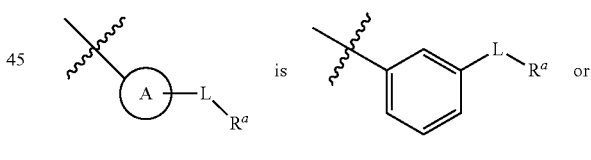

wherein Ring A is further substituted at least once, and at least one substituent on Ring A is $C_{1-6}$ haloalkyl (e.g., —$CF_3$). In some embodiments, when

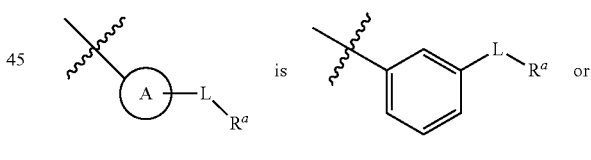

then Ring A is further substituted with $R^b$ as defined and described in classes and subclasses herein, and at least one substituent on Ring A (i.e., either $R^b$ or -L-$R^a$) is $C_{1-6}$ haloalkyl (e.g., —$CF_3$). In some embodiments,

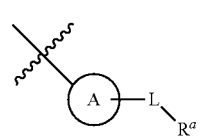

is selected from the group consisting of:
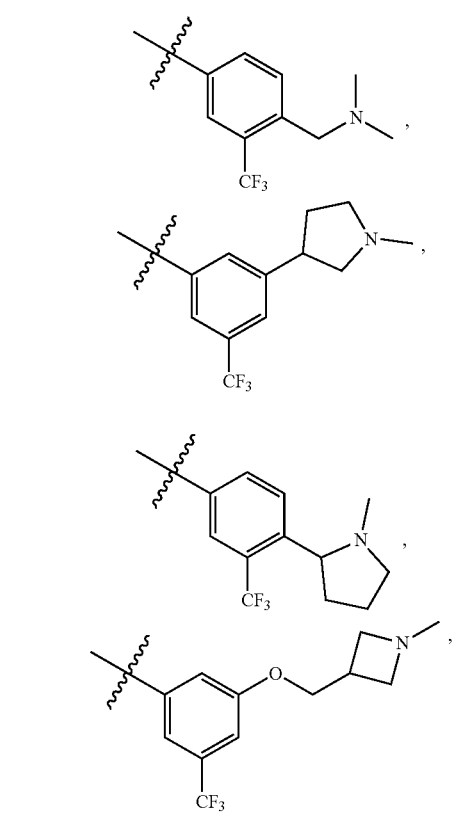
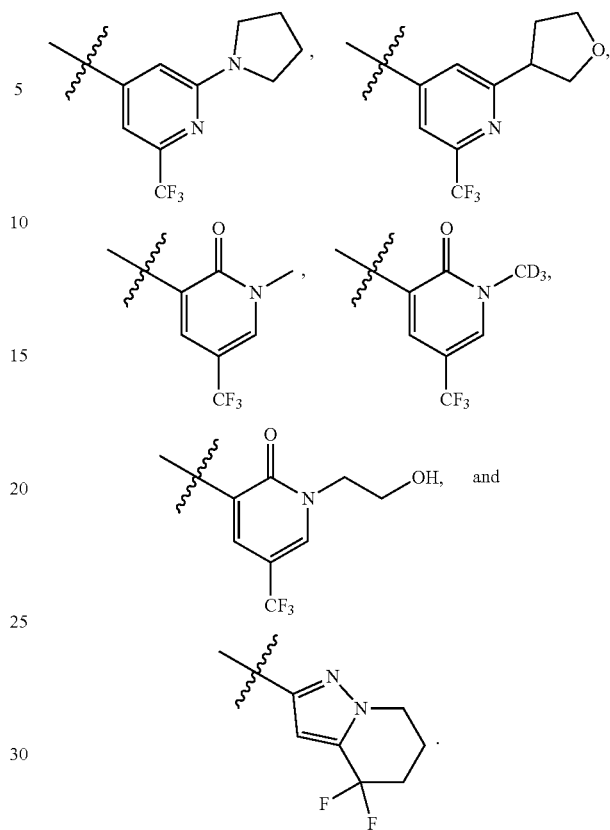
In some embodiments of any of Formulae II, II-A, II-B, II-C, II-D, II-E, and II-F, optionally substituted
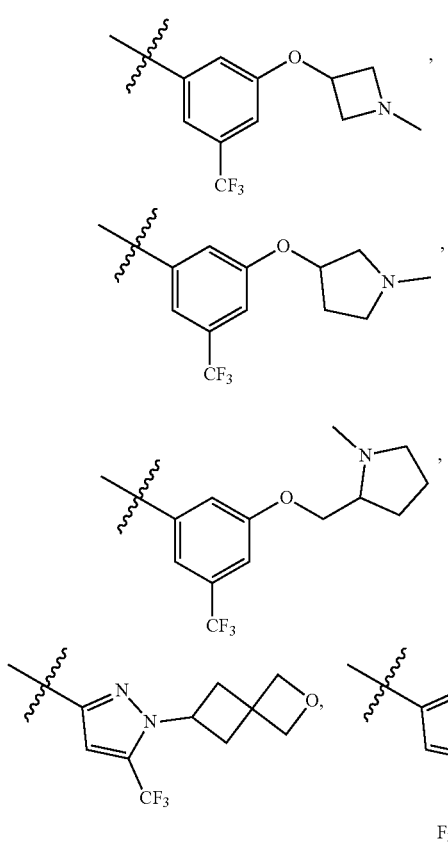
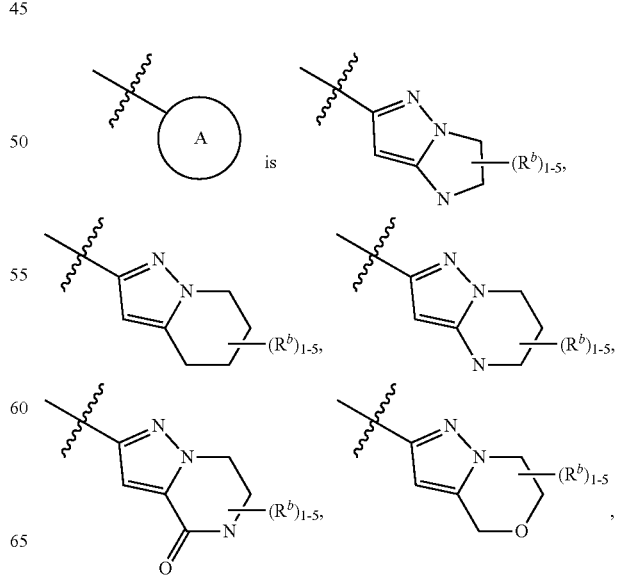
In some embodiments, optionally substituted

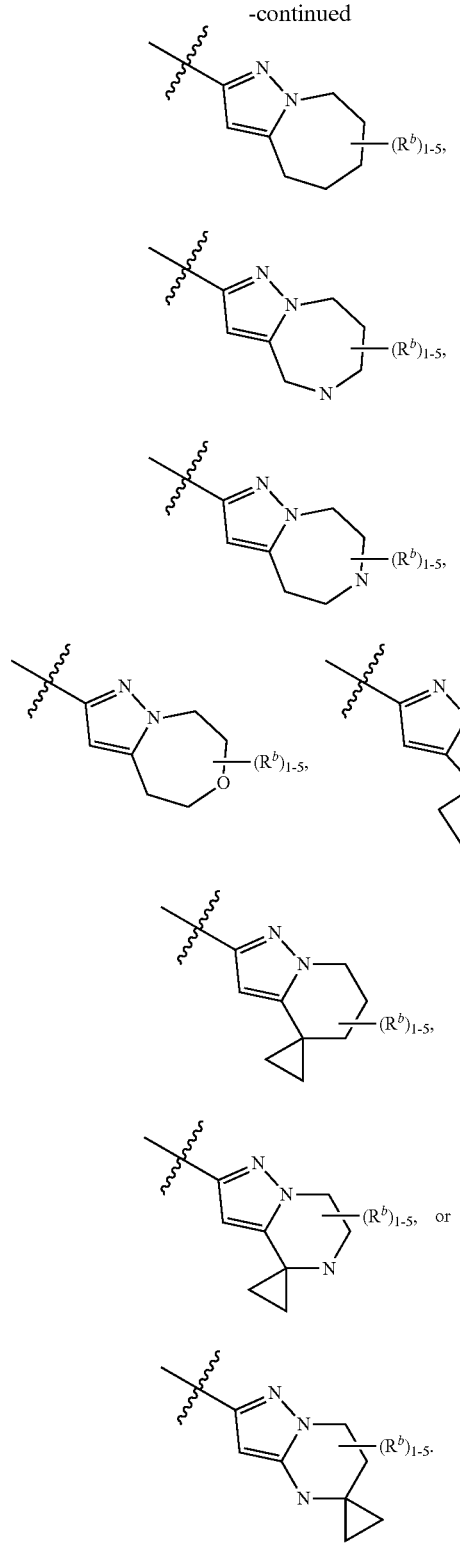
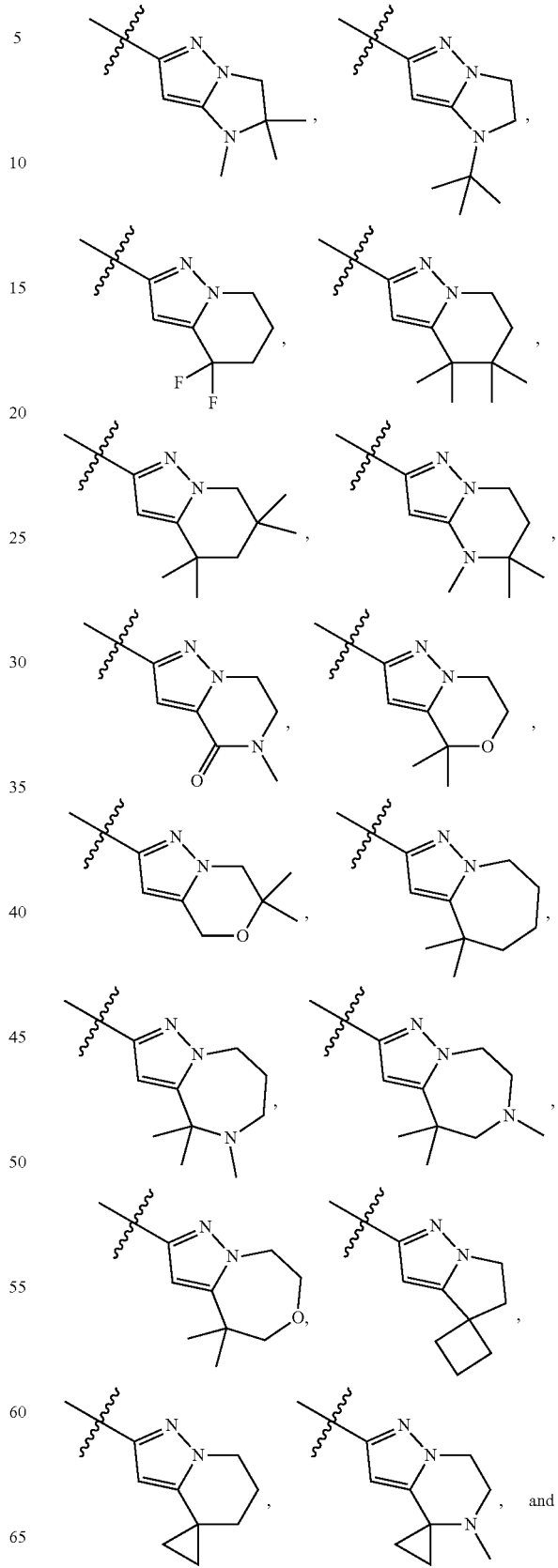
In some embodiments, optionally substituted
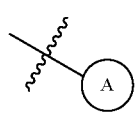
is selected from the group consisting of:

[Structure at top: pyrazolo-pyrimidine fused ring with cyclopropyl substituent]

In some embodiments of any of Formulae I, I-A, I-B, I-C, I-D, I-E, II, II-A, II-B, II-C, II-D, II-E, II-F, III, and IV, each R is independently hydrogen, optionally substituted $C_{1-6}$ aliphatic, or optionally substituted 3- to 7-membered saturated or partially unsaturated monocyclic heterocyclyl having 1-2 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur. In some embodiments, each R is independently hydrogen or optionally substituted $C_{1-6}$ aliphatic. In some embodiments, each R is independently hydrogen, optionally substituted $C_{1-6}$ aliphatic, or optionally substituted 3- to 7-membered saturated or partially unsaturated monocyclic heterocyclyl having 1-2 heteroatoms independently selected from nitrogen, oxygen, and sulfur. In some embodiments, each R is independently optionally substituted $C_{1-6}$ aliphatic or optionally substituted 3- to 7-membered saturated or partially unsaturated monocyclic heterocyclyl having 1-2 heteroatoms independently selected from nitrogen, oxygen, and sulfur. In some embodiments, each R is independently is hydrogen, optionally substituted $C_{1-6}$ alkyl or optionally substituted 4- to 6-membered saturated monocyclic heterocyclyl having 1-2 heteroatoms independently selected from nitrogen, oxygen, and sulfur.

In some embodiments, R is hydrogen.

In some embodiments, R is optionally substituted $C_{1-6}$ aliphatic. In some embodiments, R is optionally substituted straight-chain or branched $C_{1-6}$ aliphatic (i.e., optionally substituted acyclic $C_{1-6}$ aliphatic). In some embodiments, R is optionally substituted $C_{1-6}$ alkyl. In some embodiments, R is $C_{1-6}$ alkyl optionally substituted with one or more —OH, —O($C_{1-6}$ alkyl), —N($C_{1-6}$ alkyl)$_2$, or 4- to 6-membered saturated monocyclic heterocyclyl having 1-2 heteroatoms independently selected from nitrogen, oxygen, and sulfur. In some embodiments, R is optionally substituted $C_{1-4}$ alkyl. In some embodiments, R is optionally substituted $C_{1-2}$ alkyl.

In some embodiments, R is optionally substituted 3- to 7-membered saturated or partially unsaturated carbocyclyl. In some embodiments, R is optionally substituted $C_{3-7}$ cycloalkyl.

In some embodiments, R is optionally substituted 3- to 7-membered saturated or partially unsaturated monocyclic heterocyclyl having 1-3 heteroatoms independently selected from nitrogen, oxygen, and sulfur. In some embodiments, R is optionally substituted 4- to 6-membered saturated monocyclic heterocyclyl having 1-2 heteroatoms independently selected from nitrogen, oxygen, and sulfur. In some embodiments, R is 4- to 6-membered saturated monocyclic heterocyclyl having 1-2 heteroatoms independently selected from nitrogen, oxygen, and sulfur optionally substituted with one or more $C_{1-6}$ alkyl. In some embodiments, R is optionally substituted oxetanyl.

In some embodiments, two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur. In some embodiments, two R groups attached to the same nitrogen are taken together to form a 3- to 7-membered saturated or partially unsaturated monocyclic heterocyclyl having 0-2 additional heteroatoms independently selected from nitrogen, oxygen, and sulfur and optionally substituted with one or more halogen, $C_{1-6}$ alkyl, —OH, or —O($C_{1-6}$ alkyl). In some embodiments, two R groups attached to the same nitrogen are taken together to form an optionally substituted 4- to 6-membered saturated monocyclic heterocyclyl having 0-1 additional heteroatoms independently selected from nitrogen, oxygen, and sulfur. In some embodiments, two R groups attached to the same nitrogen are taken together to form a 4- to 6-membered saturated monocyclic heterocyclyl having 0-1 additional heteroatoms independently selected from nitrogen, oxygen, and sulfur optionally substituted with one or more halogen, $C_{1-6}$ alkyl, —OH, and —O($C_{1-6}$ alkyl).

In some embodiments of any of Formulae I, I-A, I-B, I-C, I-D, I-E, II, II-A, II-B, II-C, II-D, II-E, II-F, III, and IV, each R' is independently optionally substituted $C_{1-6}$ alkyl or optionally substituted $C_{3-7}$ cycloalkyl. In some embodiments, R' is optionally substituted $C_{1-6}$ aliphatic. In some embodiments, R' is optionally substituted straight-chain or branched $C_{1-6}$ aliphatic (i.e., optionally substituted acyclic $C_{1-6}$ aliphatic). In some embodiments, R' is optionally substituted $C_{1-6}$ alkyl. In some embodiments, R' is $C_{1-6}$ alkyl optionally substituted with halogen, —OH, —O($C_{1-6}$ alkyl), —NH(CH$_2$)$_2$O($C_{1-6}$ alkyl), —NH($C_{1-4}$ haloalkyl), or an optionally substituted 3- to 7-membered saturated monocyclic heterocyclyl having 1-2 heteroatoms independently selected from nitrogen, oxygen, and sulfur. In some embodiments, R' is optionally substituted $C_{1-4}$ alkyl. In some embodiments, R' is optionally substituted $C_{1-2}$ alkyl. In some embodiments, R' is methyl. In some embodiments, R' is optionally substituted 3- to 7-membered saturated or partially unsaturated carbocyclyl. In some embodiments, R' is optionally substituted $C_{3-7}$ cycloalkyl. In some embodiments, R' is optionally substituted cyclopropyl. In some embodiments, R' is cyclopropyl.

In some embodiments of any of Formulae described herein, the compound is not:

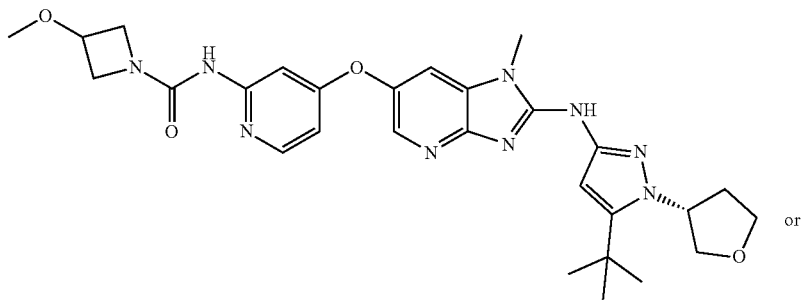

or

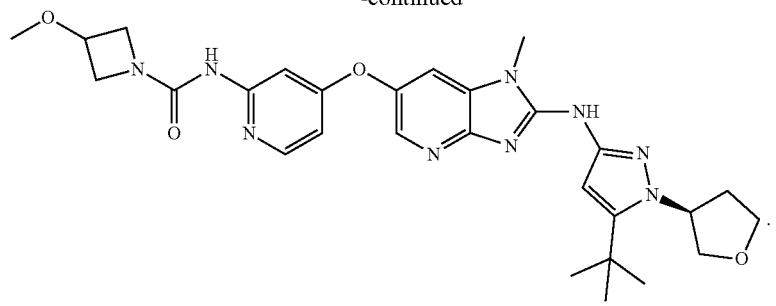
In some embodiments, the compound is not:
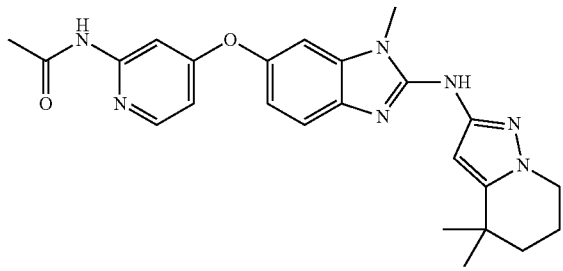
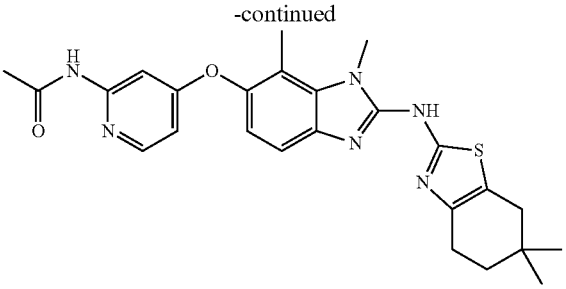
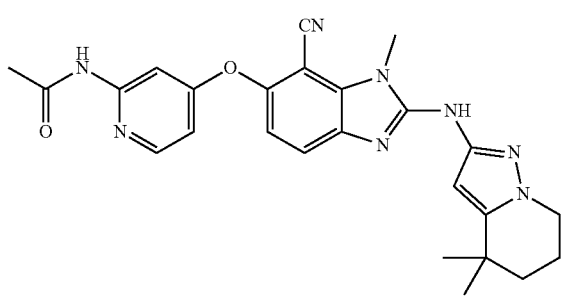
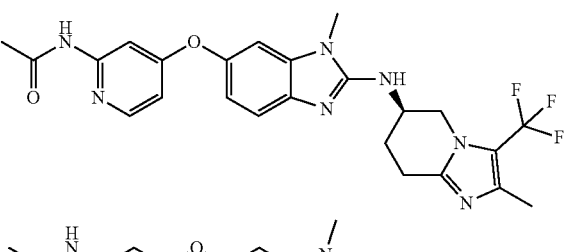
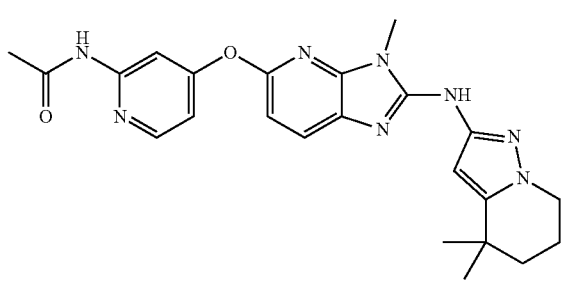
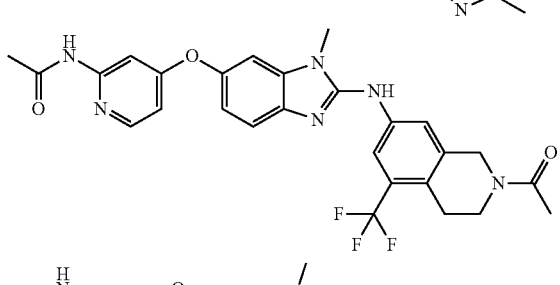
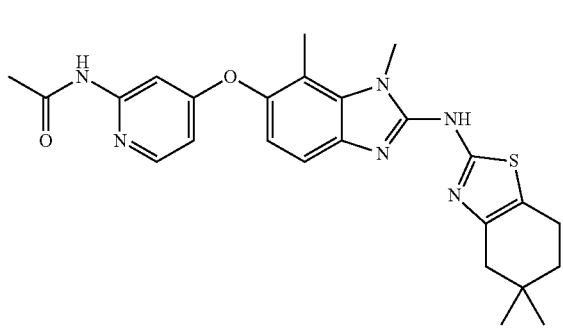
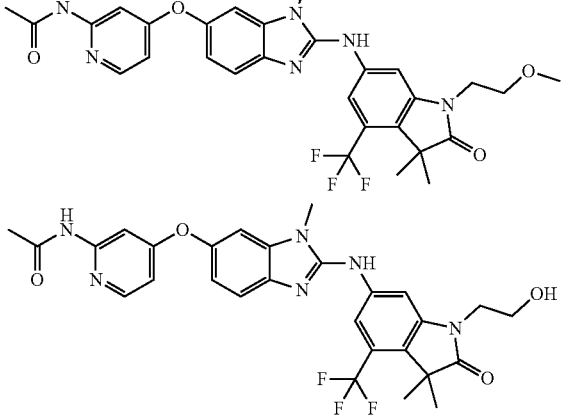

-continued
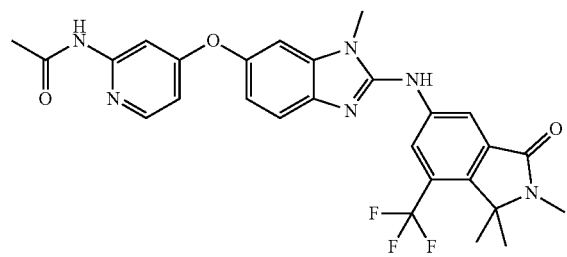
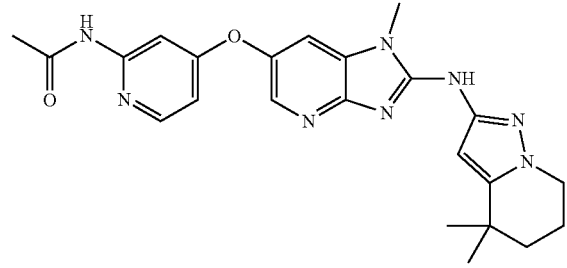
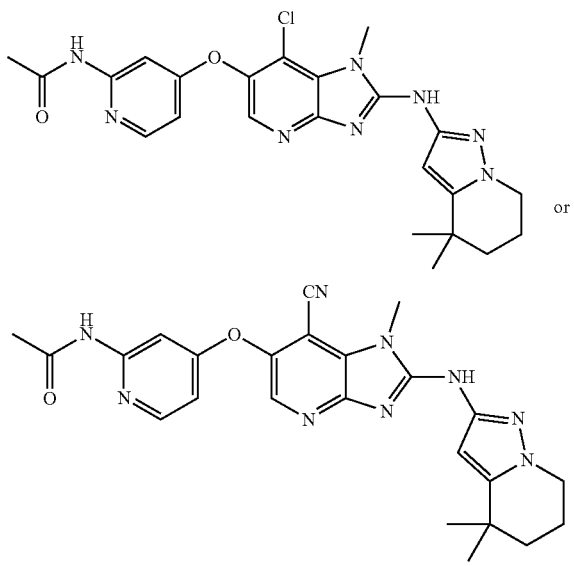
In some embodiments, the compound is not:
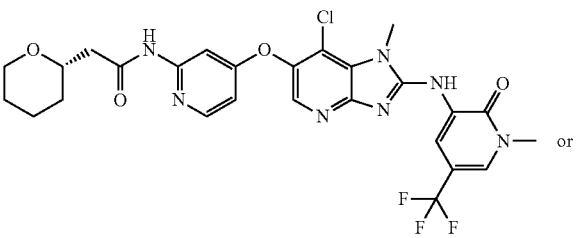
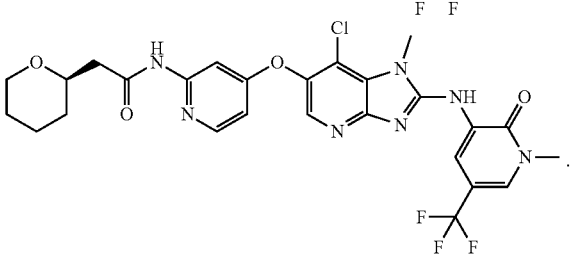
In some embodiments, the compound is not:
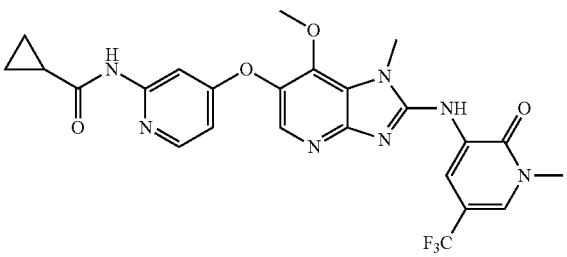
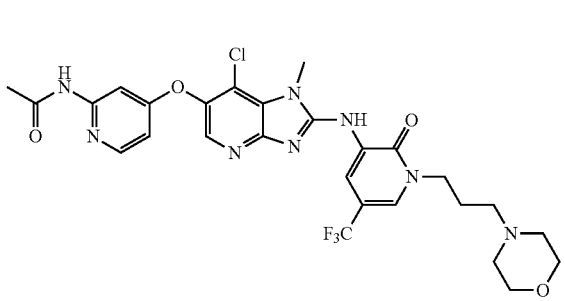
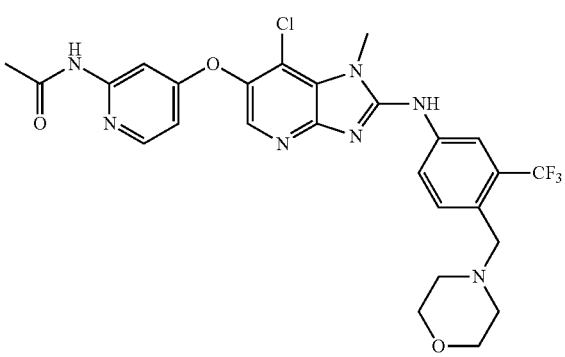
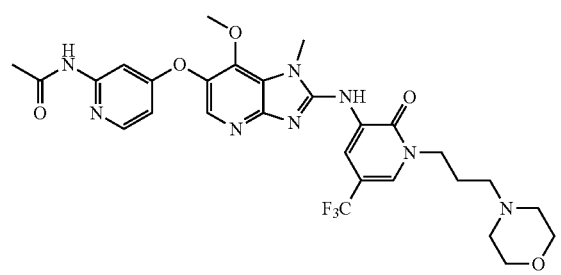
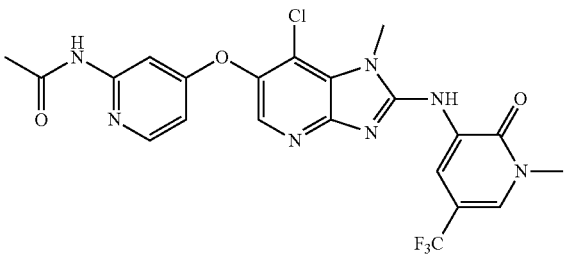

In some embodiments of any of Formulae I, I-A, I-B, I-C, I-D, and I-E, when $R^1$ is and Y is N, then $R^x$ is not hydrogen. In some embodiments, when $R^1$ is then Ring A is not pyrazolyl. In some embodiments, when Ring A is pyrazolyl, then $R^1$ is not —N(R)C(O)N(R)$_2$. In some embodiments, when Ring A is pyrazolyl and Y is N, then $R^x$ is not hydrogen.

In some embodiments of any of Formulae II, II-A, II-B, II-C, II-D, II-E, and II-F, Ring A is not In some embodiments, when Ring A is then $R^1$ is not —N(H)C(O)CH$_3$. In some embodiments, when Ring A is then X is not N and $R^x$ is not —CN.

In some embodiments of Formula III, $R^4$ is not tetrahydropyranyl. In some embodiments, when $R^4$ is tetrahydropyranyl and Y is N, then $R^x$ is not chloro.

In some embodiments of Formula IV, when Y is N and $R^x$ is not hydrogen, then -L-R$^a$ is not —CH$_3$ or In some embodiments, the present disclosure provides compounds selected from Table 1:

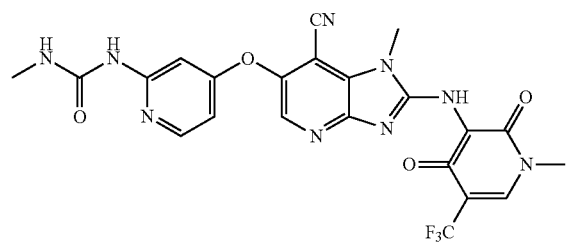
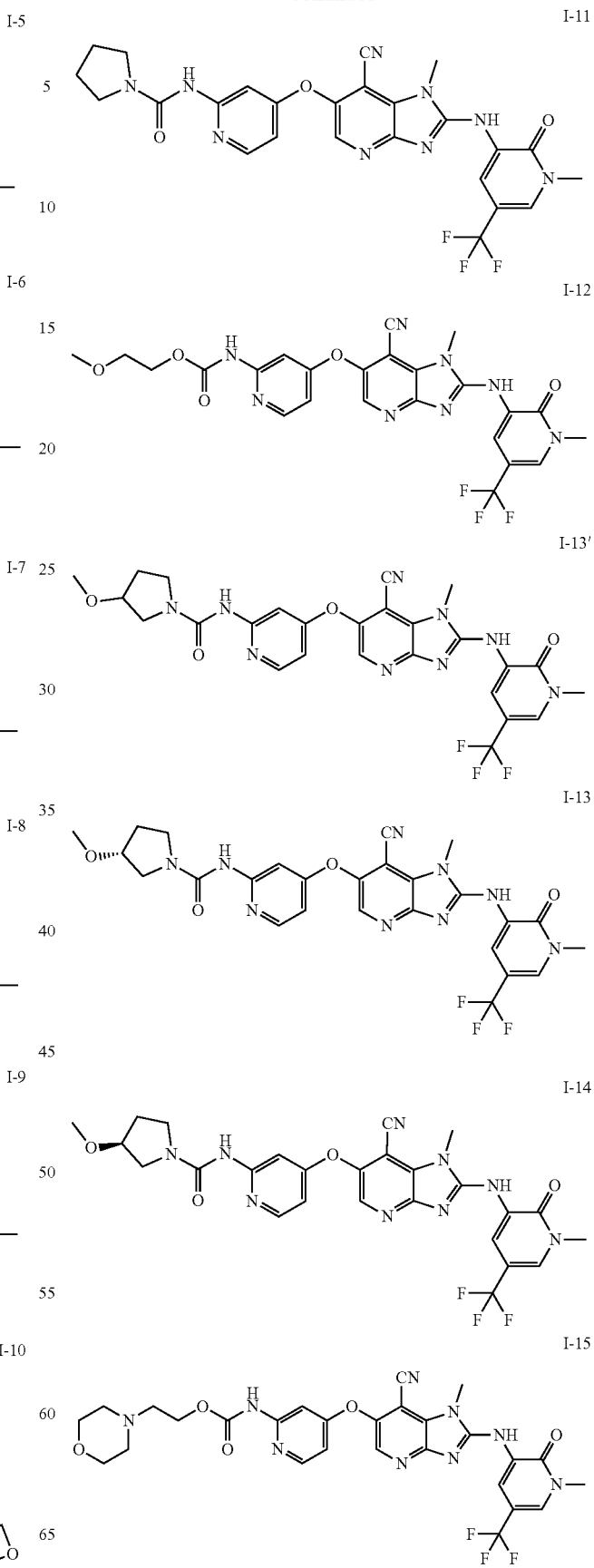

I-16
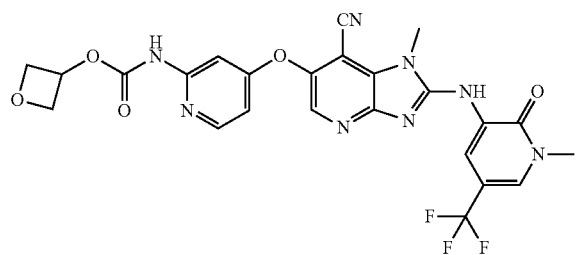
I-17'
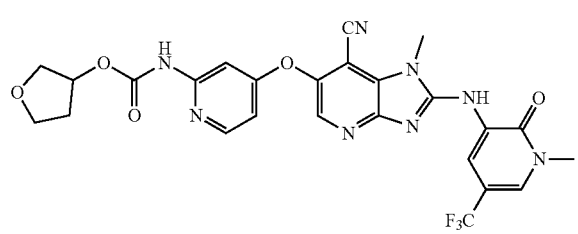
I-17
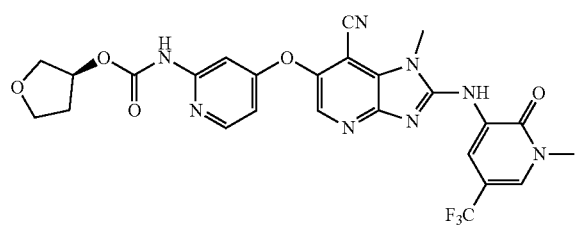
I-18
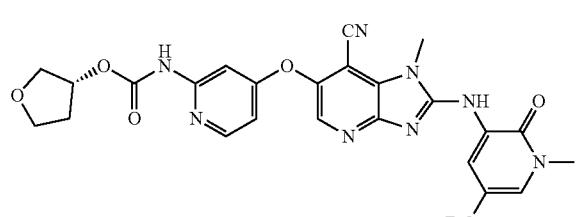
I-19
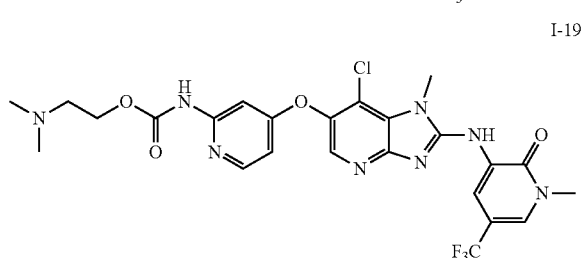
I-20
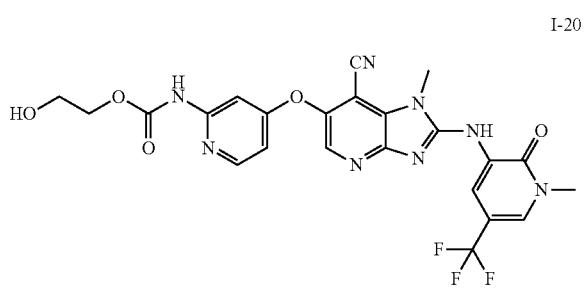
I-21
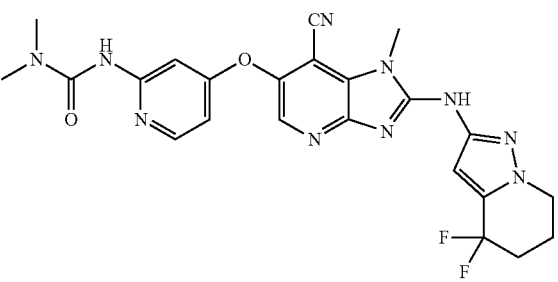
I-22
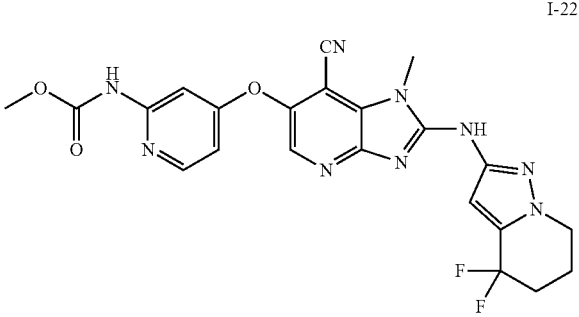
I-23
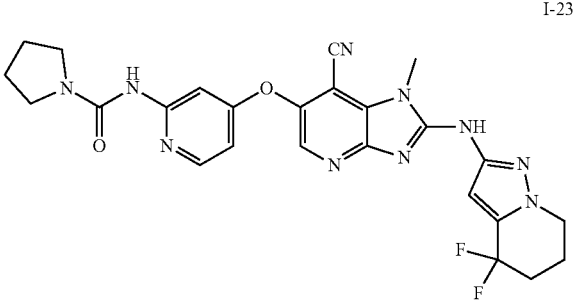
I-24
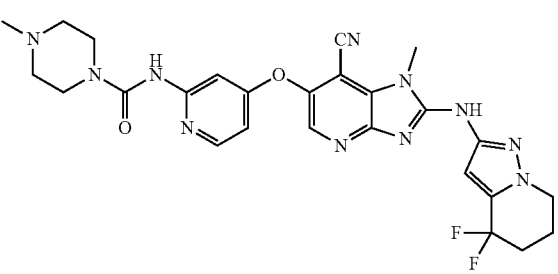
I-25
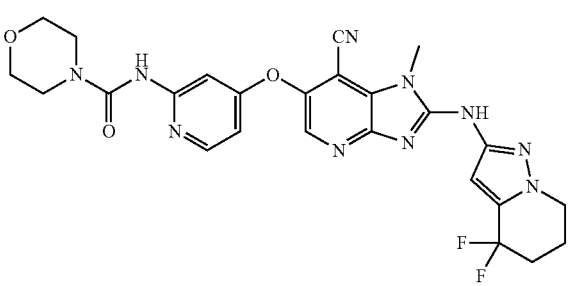

I-26
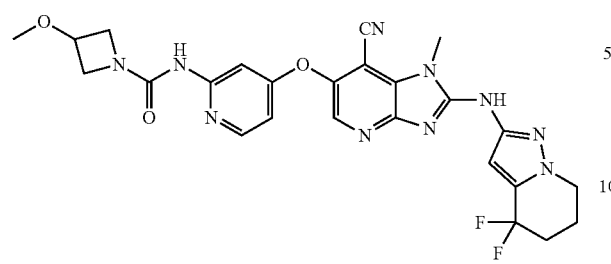
I-30
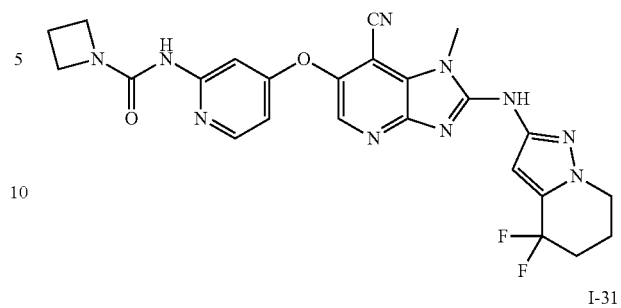
I-27
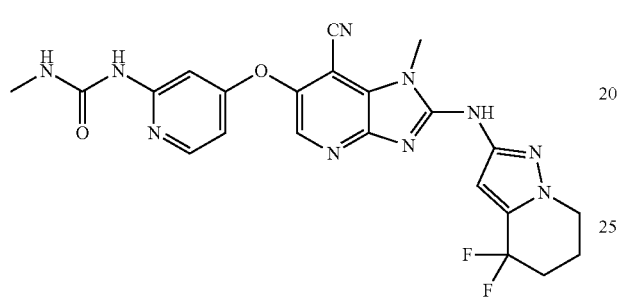
I-31
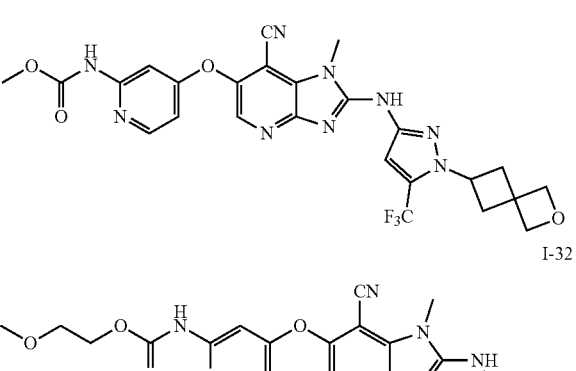
I-28'
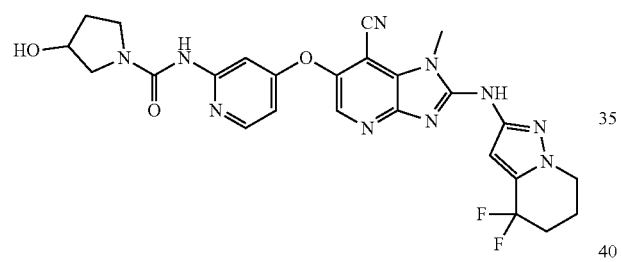
I-32
I-33'
I-28
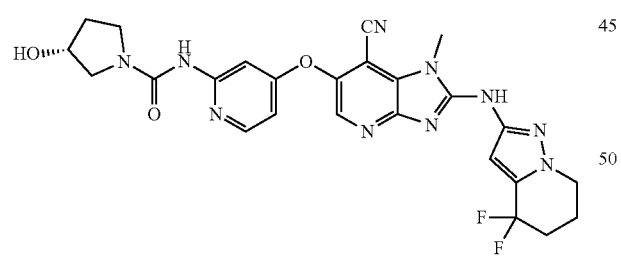
I-33
I-29
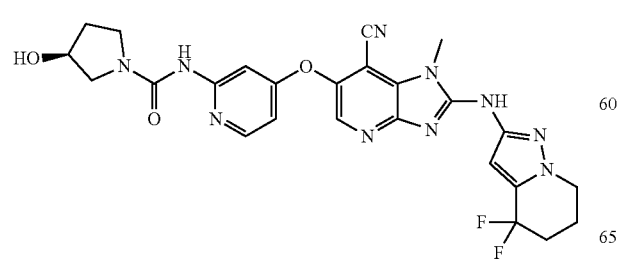
I-34

-continued
I-35
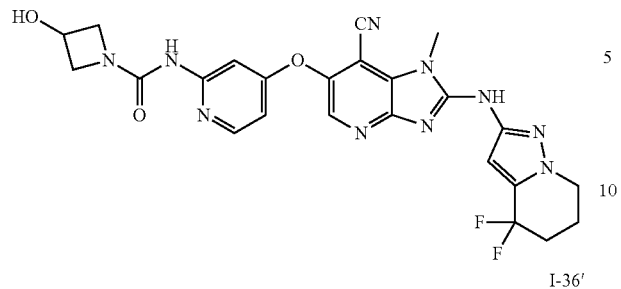
I-36'
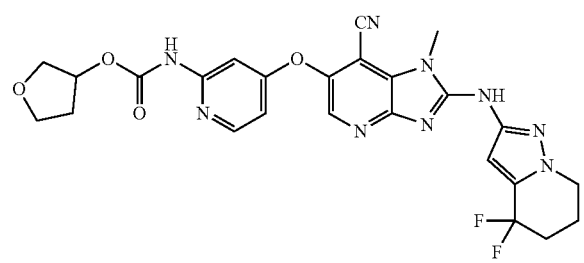
I-36
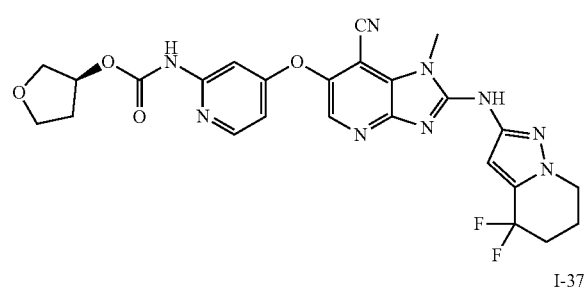
I-37
I-38
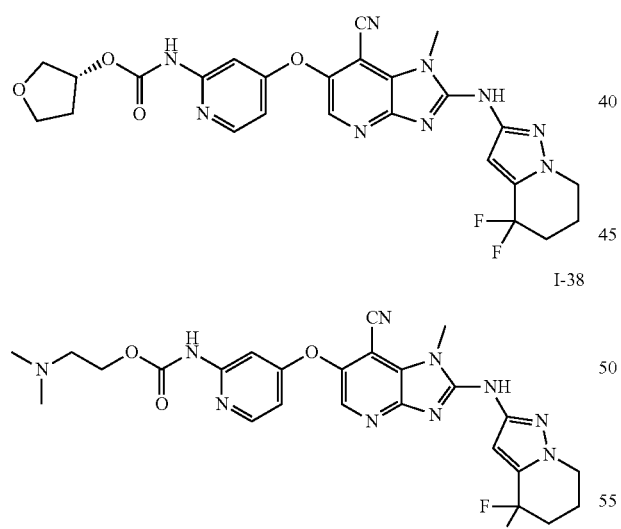
I-39
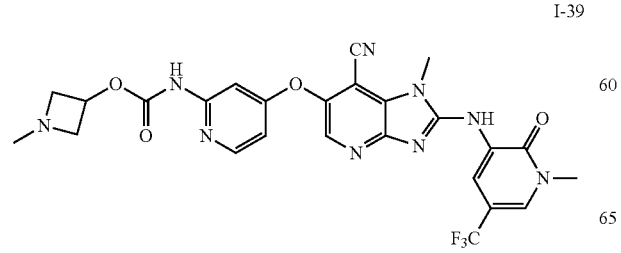
-continued
I-40
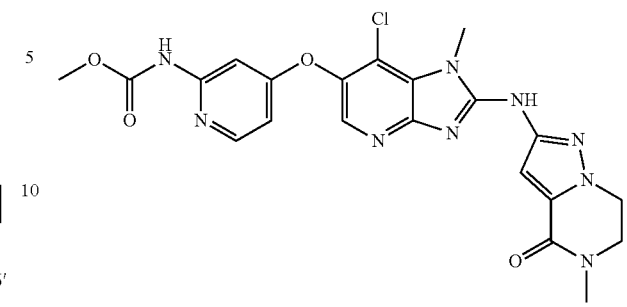
I-41
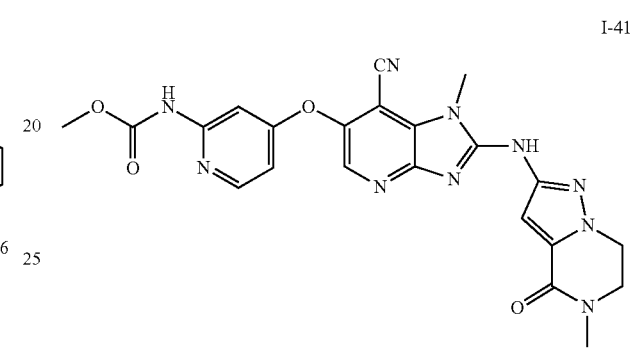
I-42
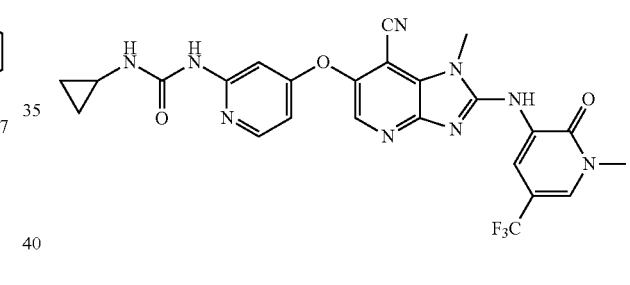
I-43
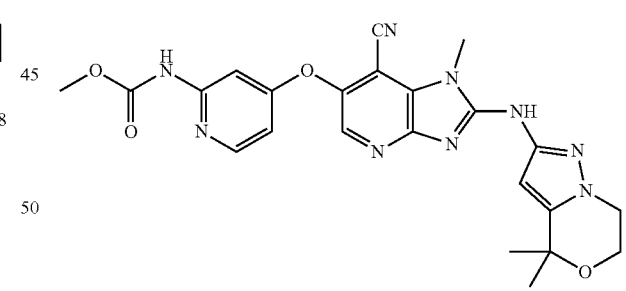
I-44
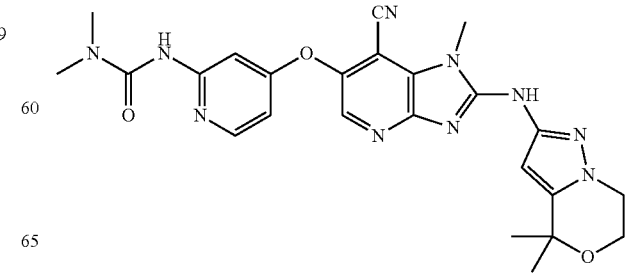

I-45
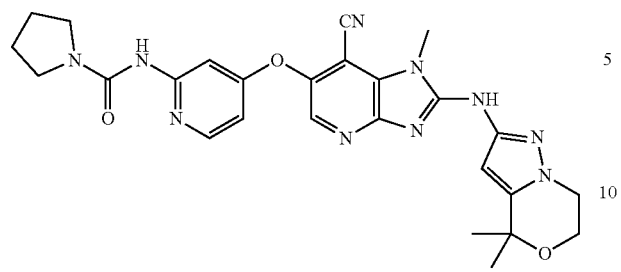
I-49
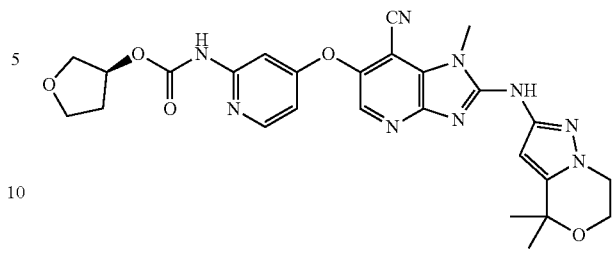
I-46
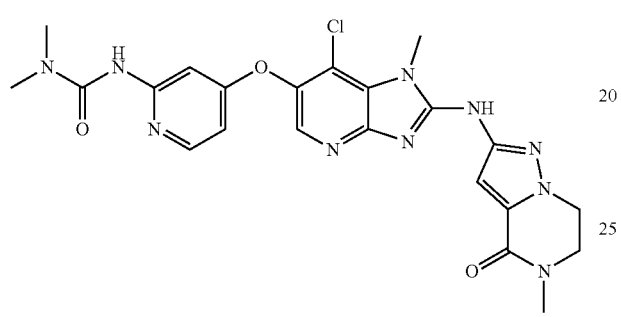
I-52
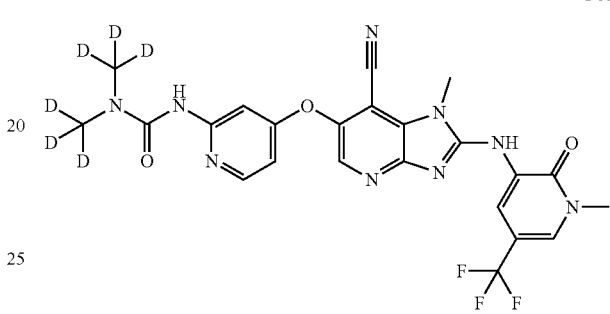
I-47
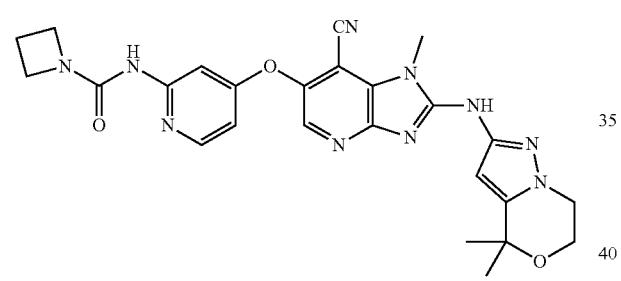
I-53'
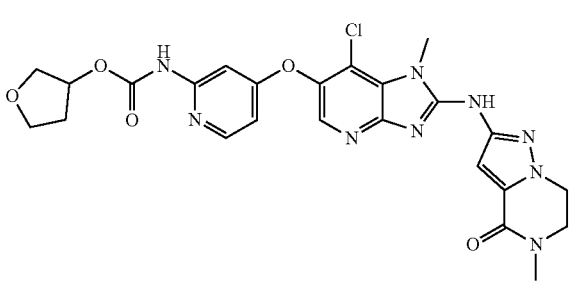
I-48'
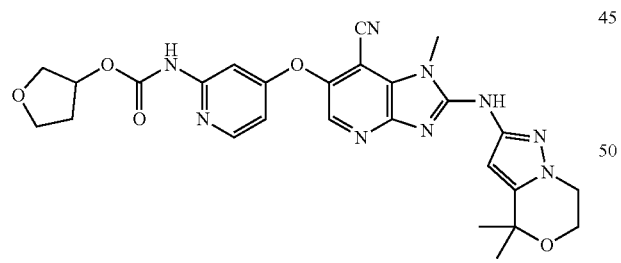
I-53
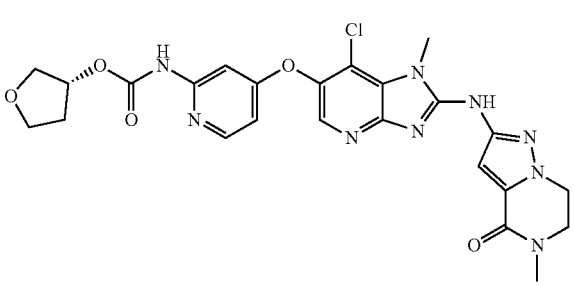
I-48
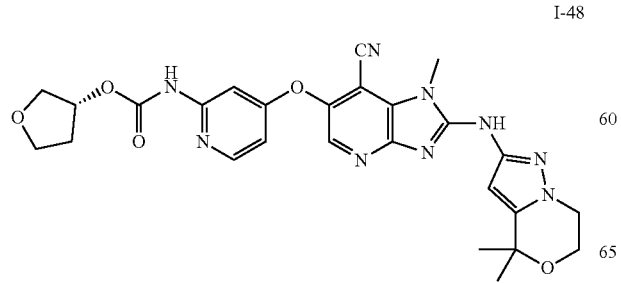
I-54
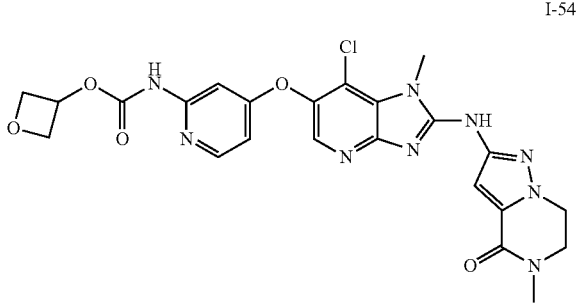

I-55
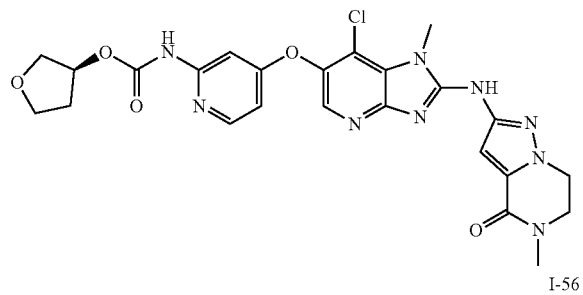
I-56
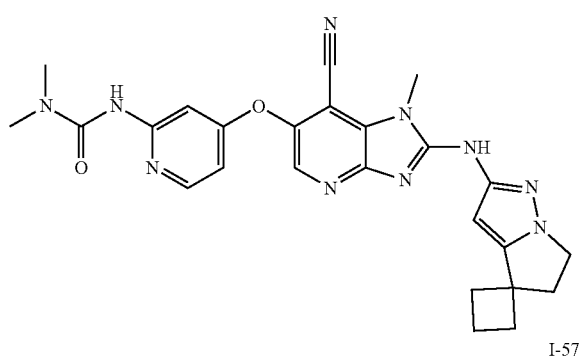
I-57
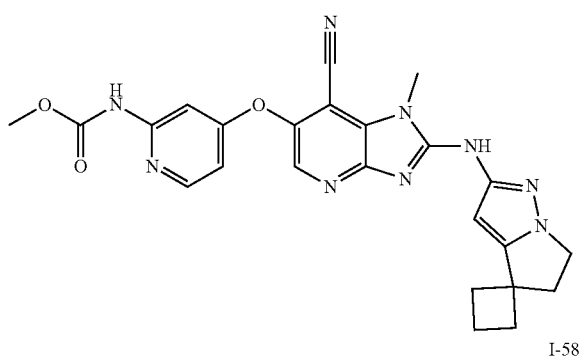
I-58
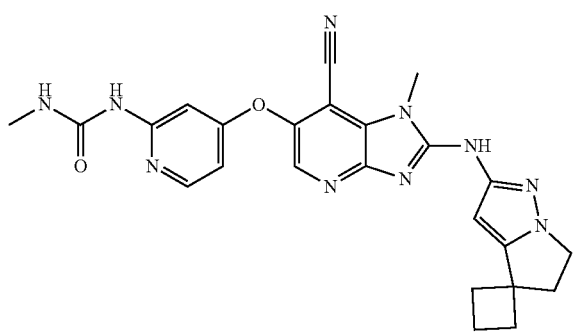
I-59'
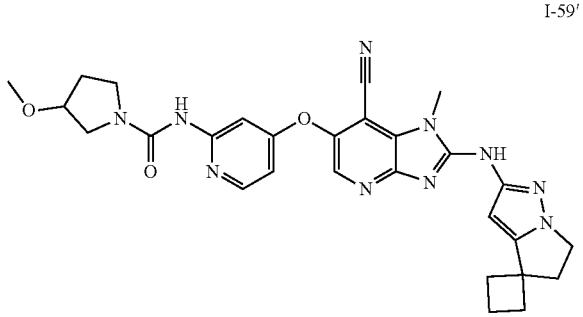
I-59
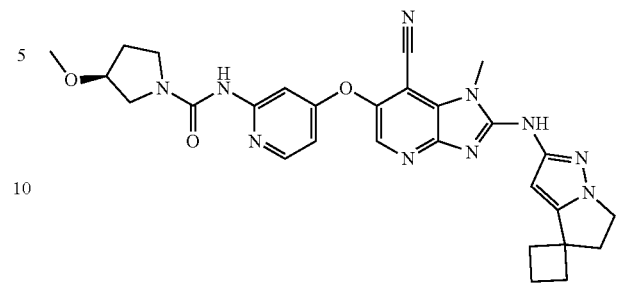
I-60
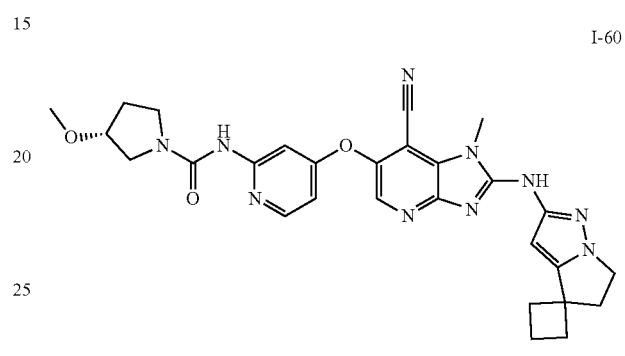
I-61
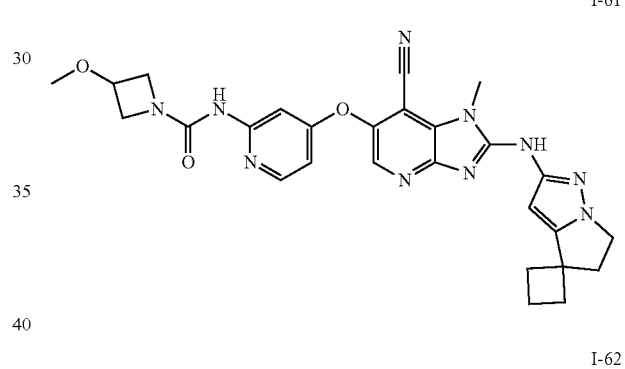
I-62
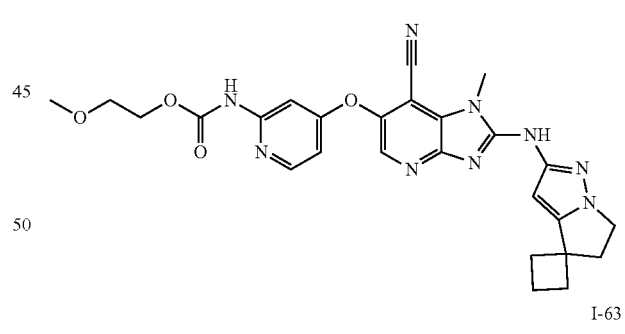
I-63
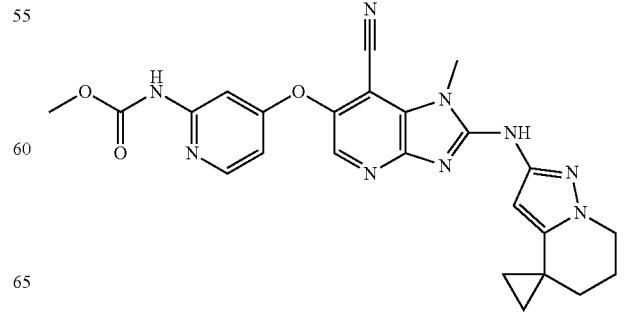

I-64
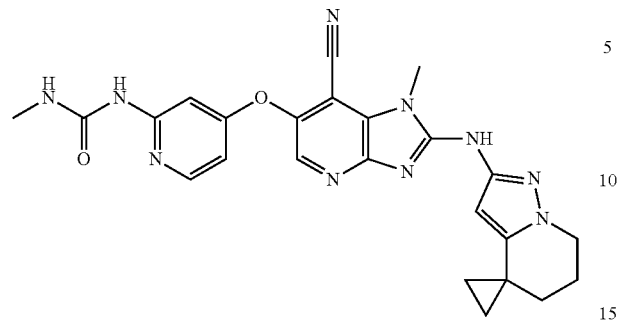
I-65
I-66
I-67
I-68
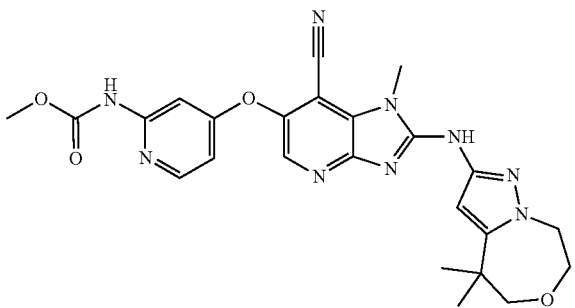
I-69
I-70
I-71

I-72
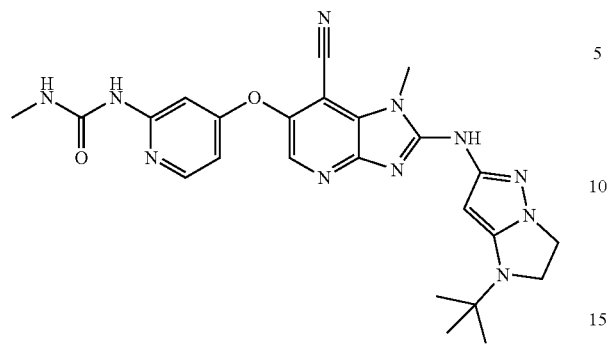
I-75
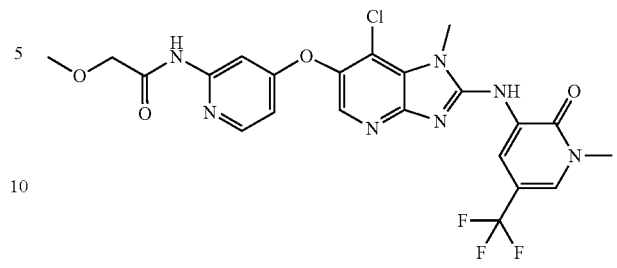
I-73
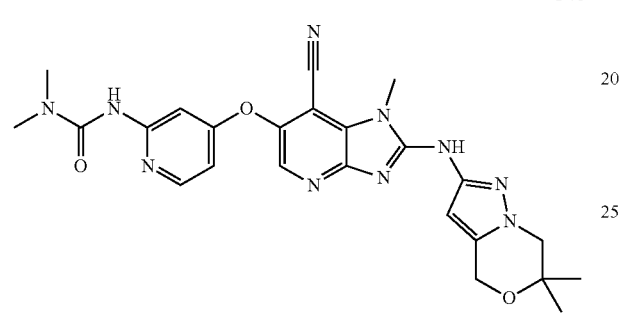
I-76
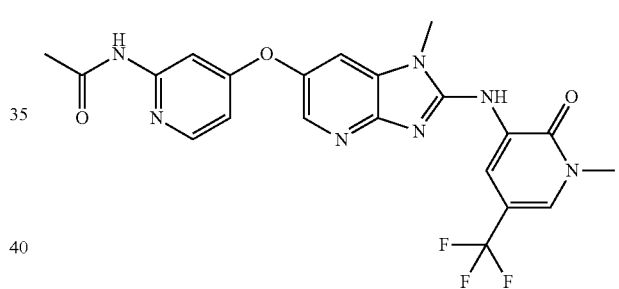
I-74
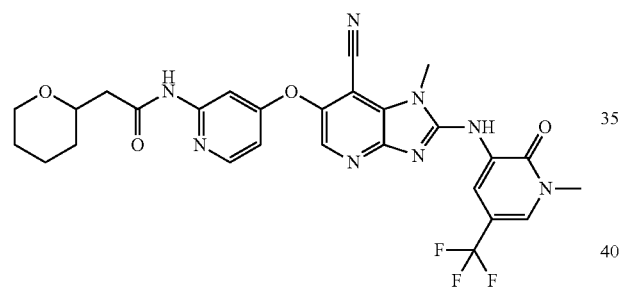
I-77
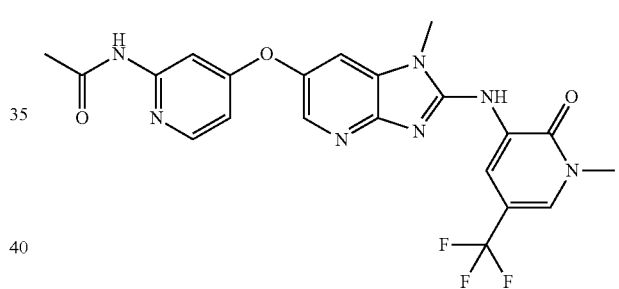
I-74-i
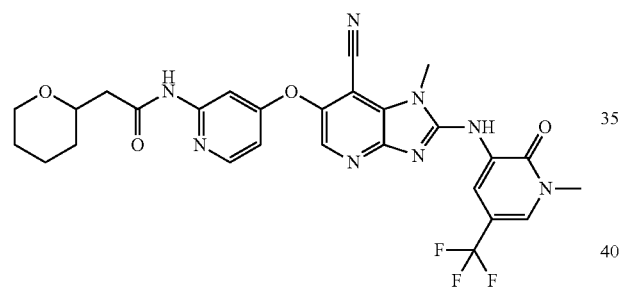
I-78
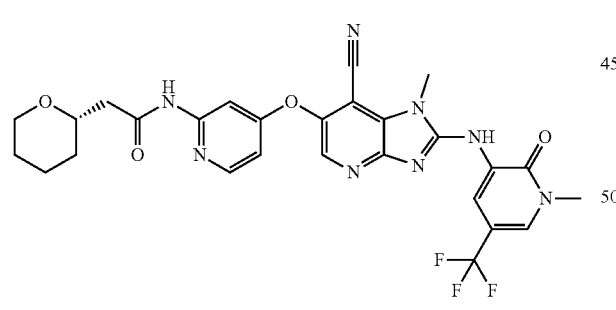
I-74-ii
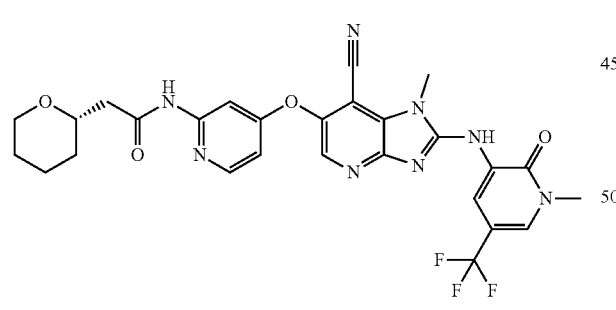
I-78-i
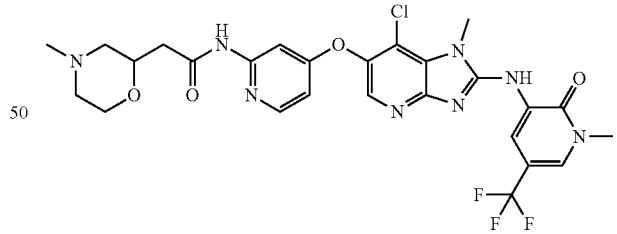

i-78-ii
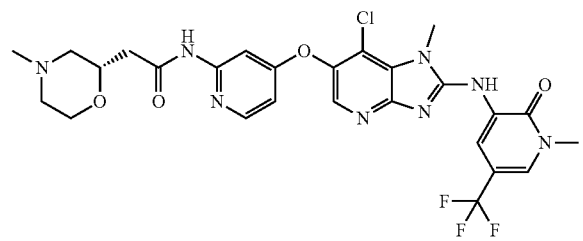
I-79
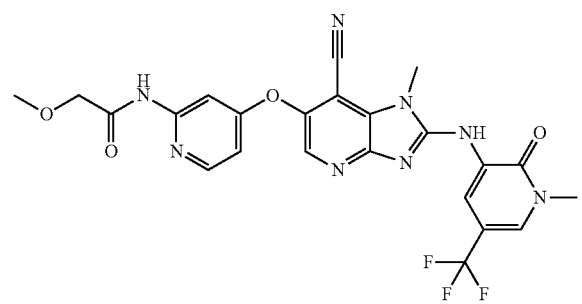
I-80
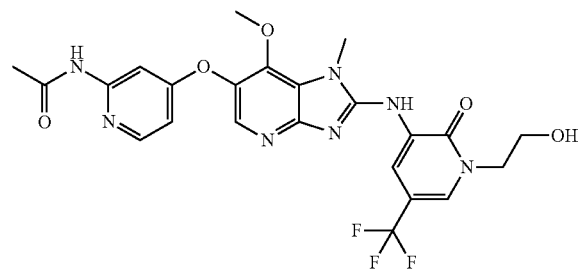
I-81
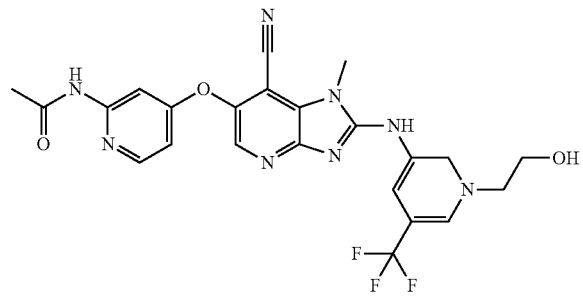
I-82
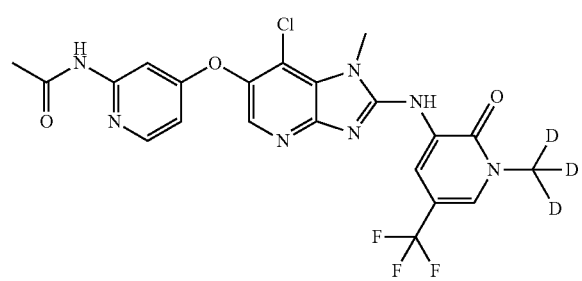
I-83
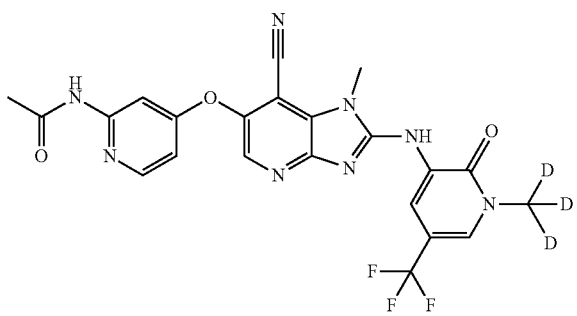
I-84
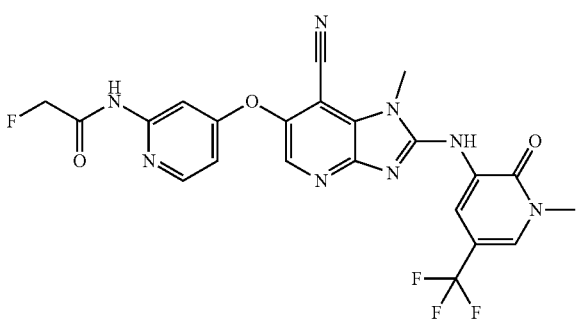
I-85
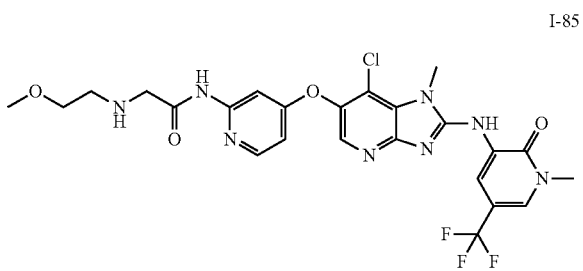
I-86
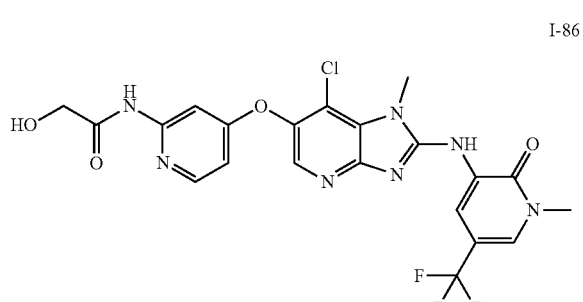
I-87
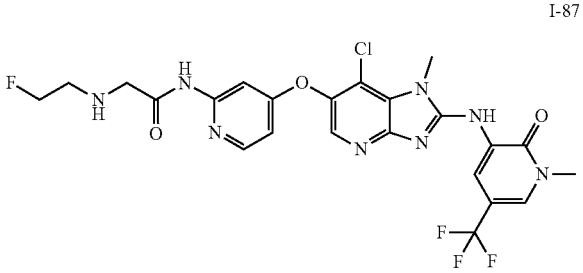

I-88
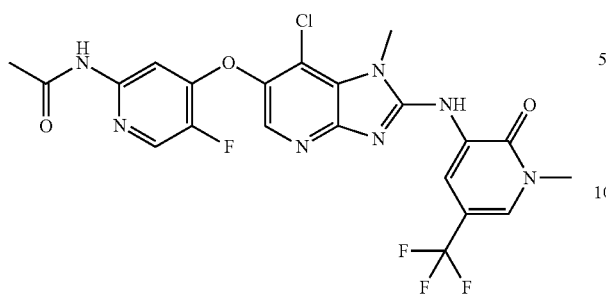
I-89
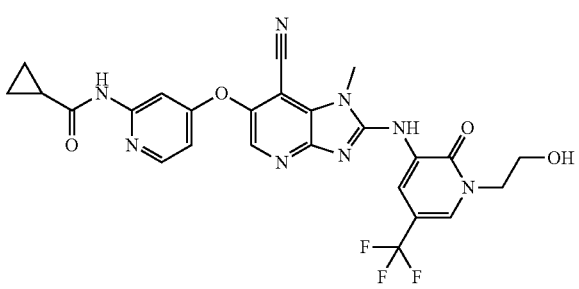
I-90'
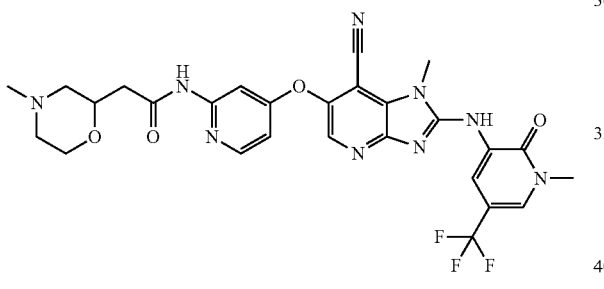
I-90-i
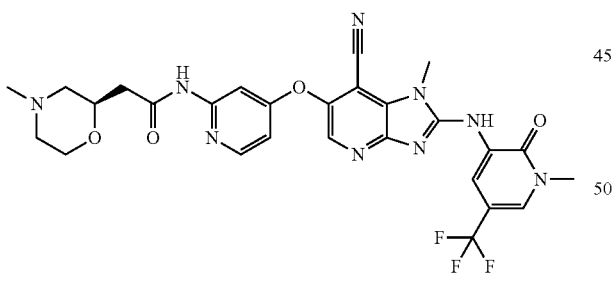
I-90-ii
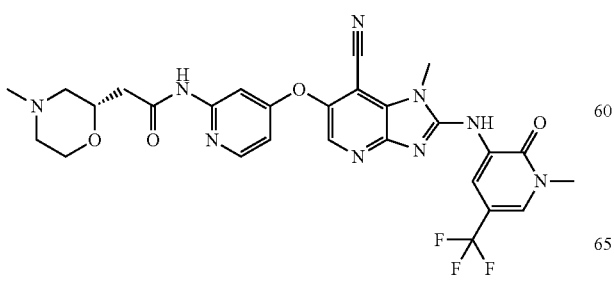
I-91'
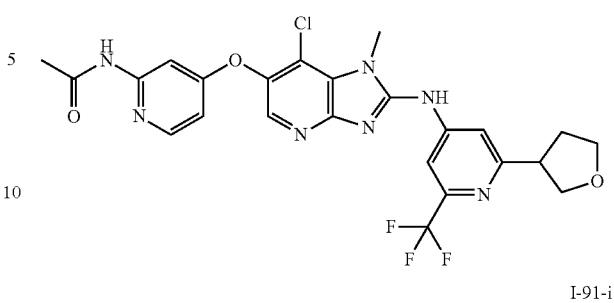
I-91-i
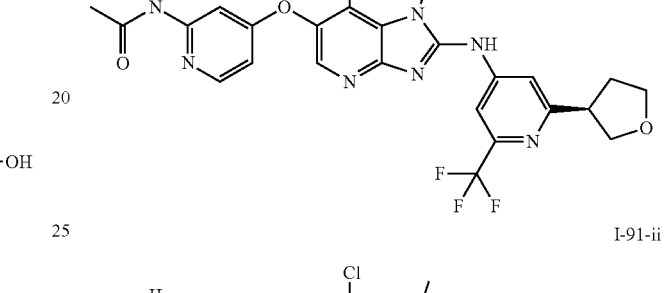
I-91-ii
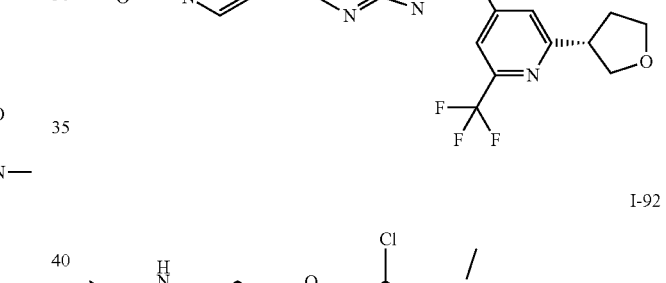
I-92
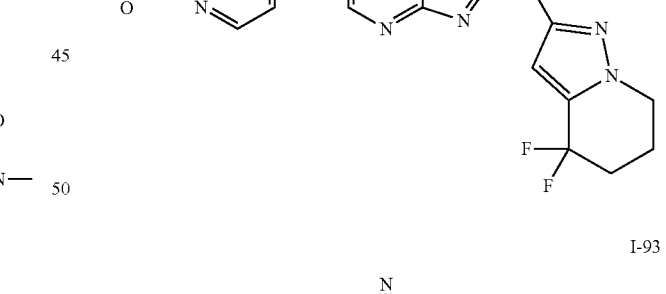
I-93
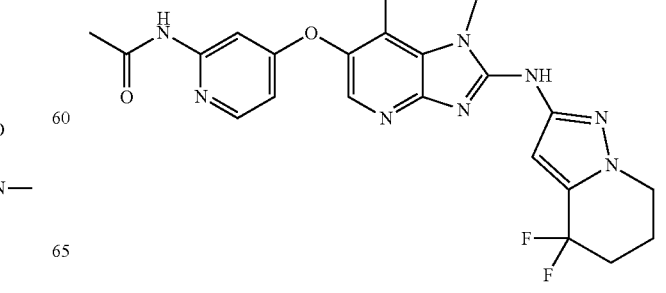

I-94
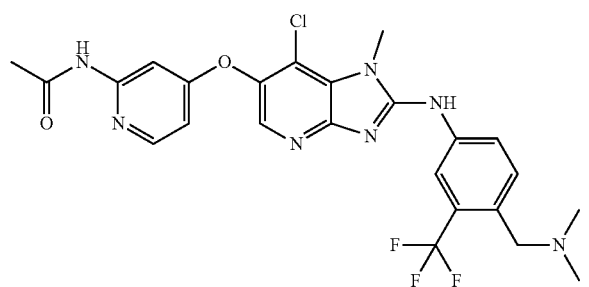
I-95'
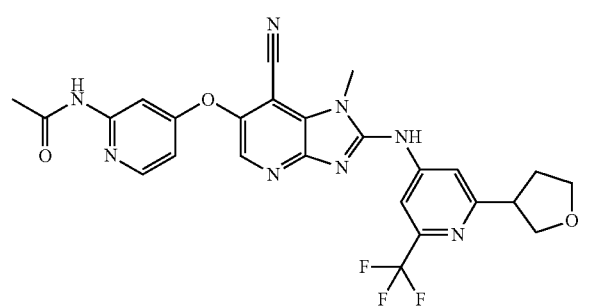
I-95-i
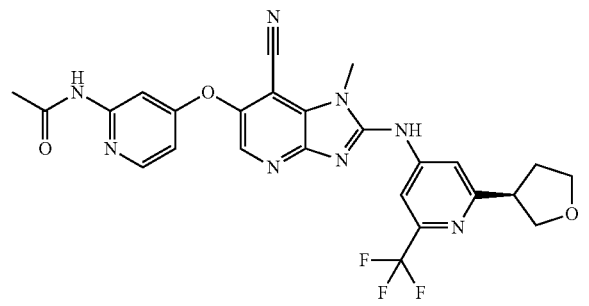
I-95-ii
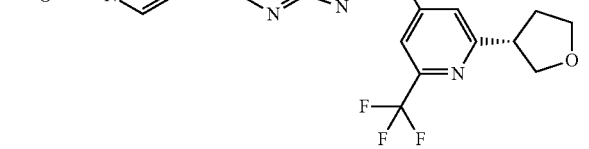
I-96'
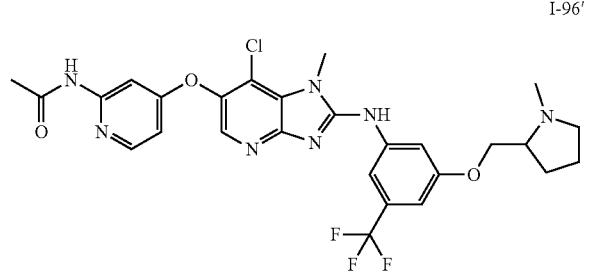
I-96
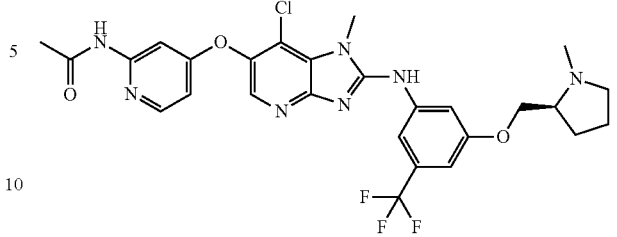
I-97
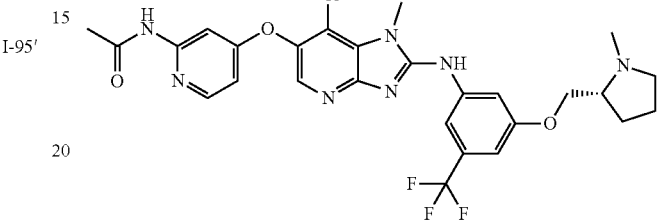
I-98
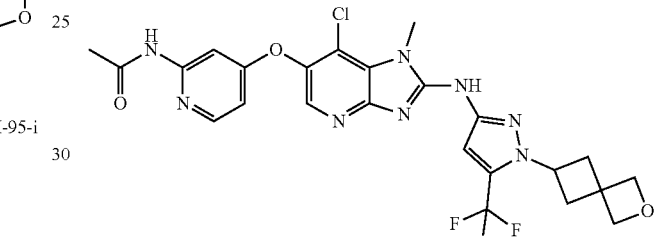
I-99'
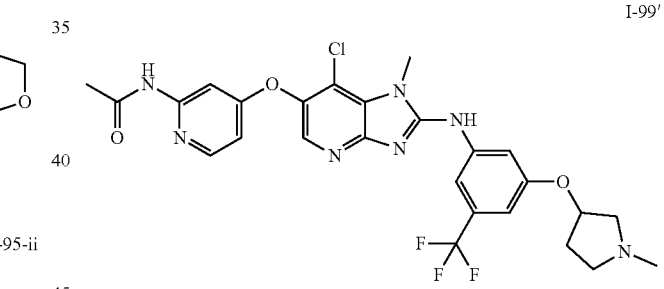
I-99
I-100
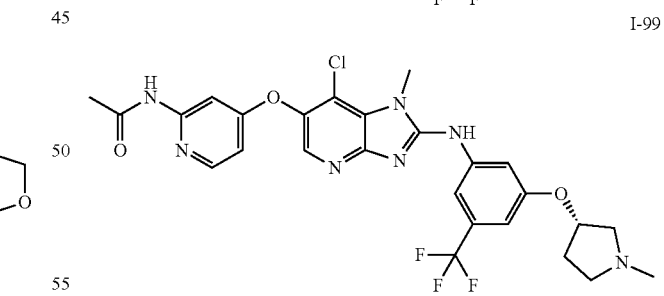

I-101
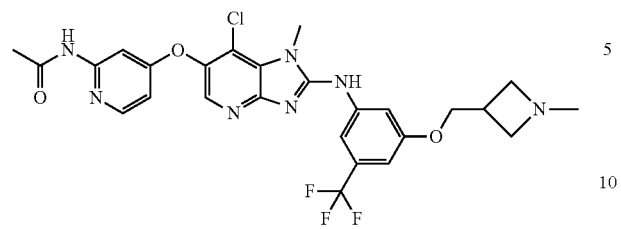
I-102
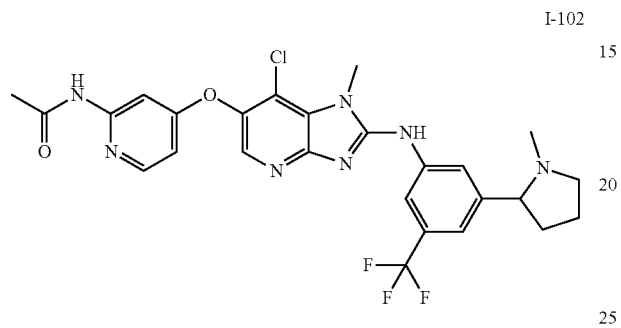
I-102-i
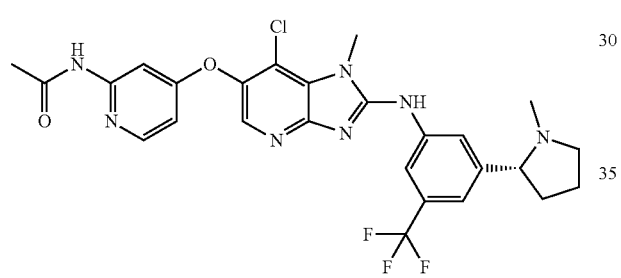
I-102-ii
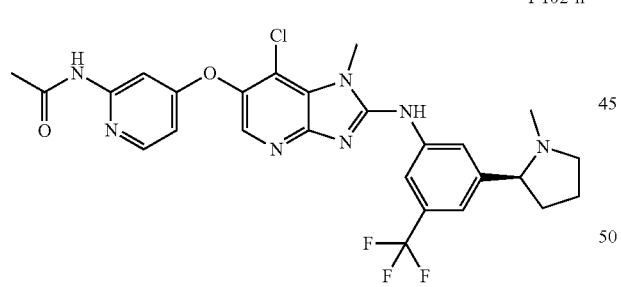
I-103
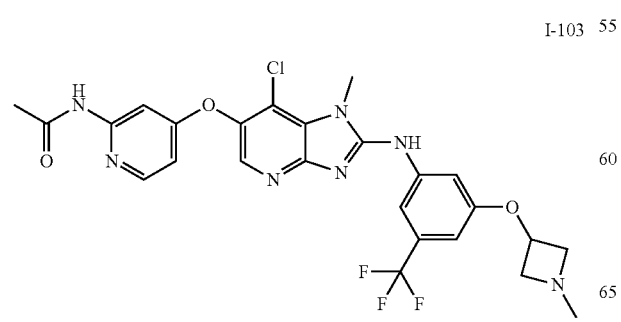
I-104
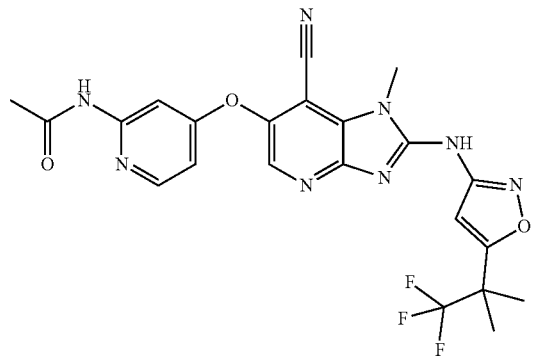
I-105
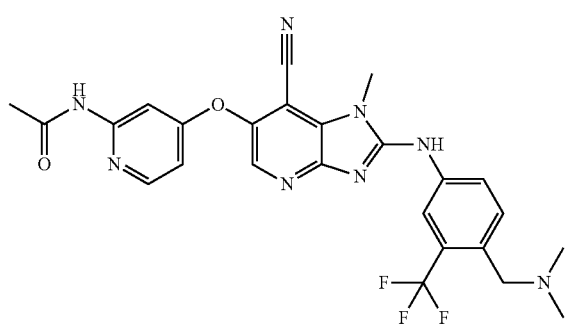
I-106
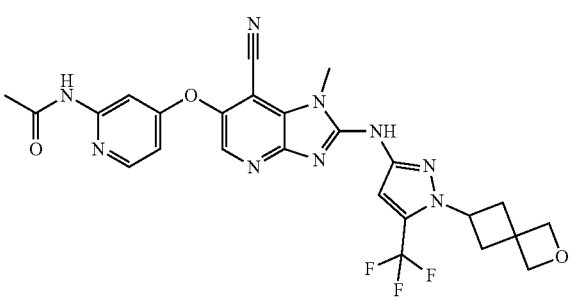
I-107
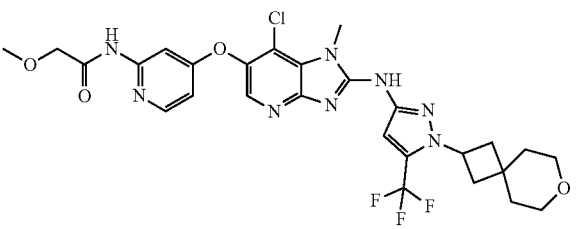
I-108
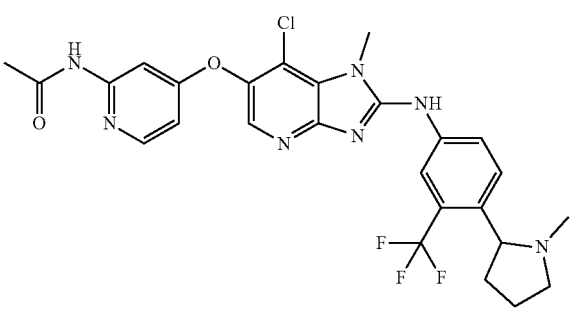

I-108-i
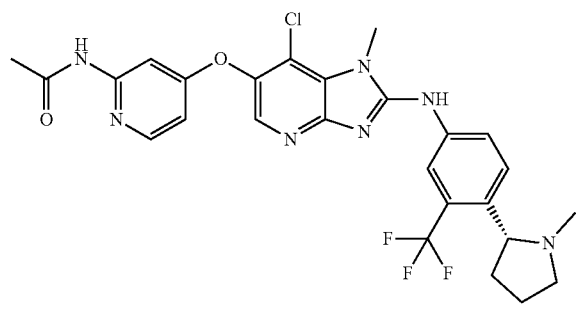
I-108-ii
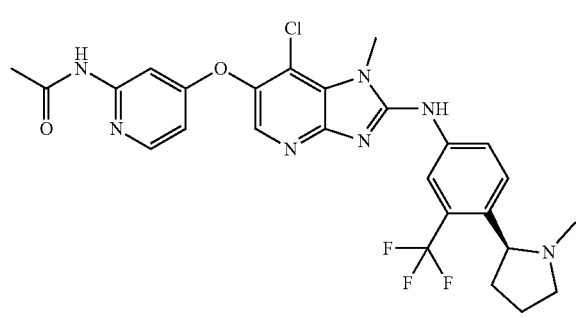
I-109
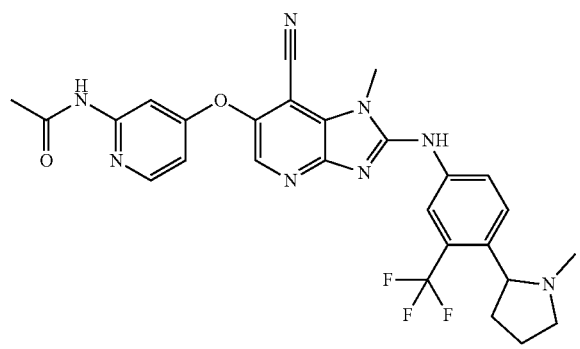
I-109-i
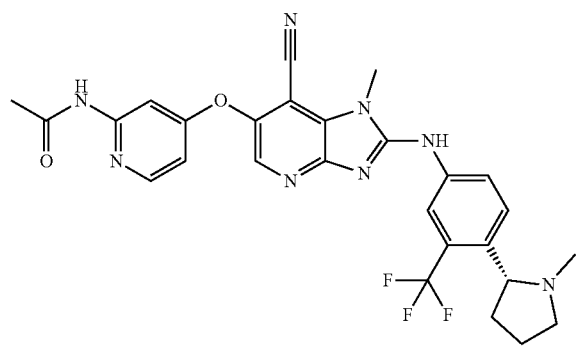
I-109-ii
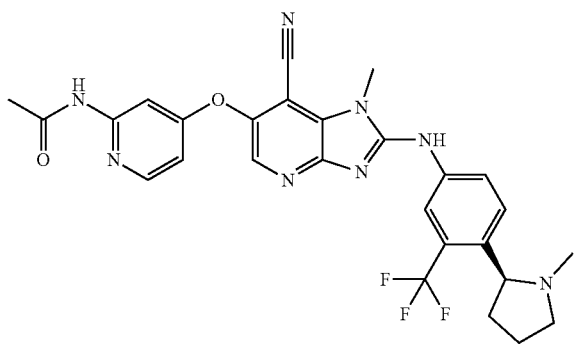
I-110
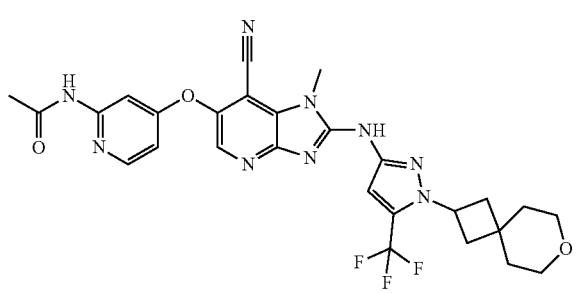
I-111
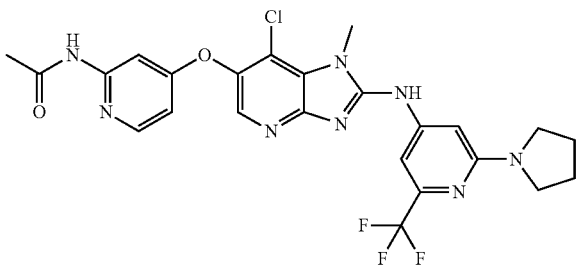
I-112
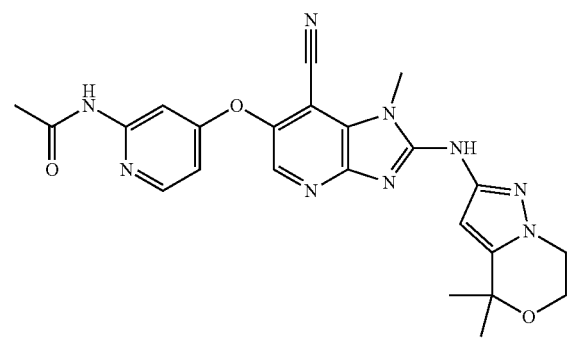

I-113
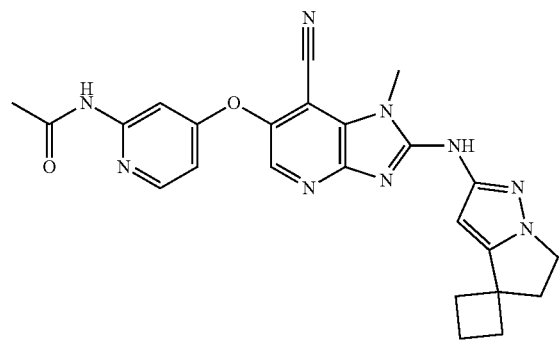
I-114
I-115
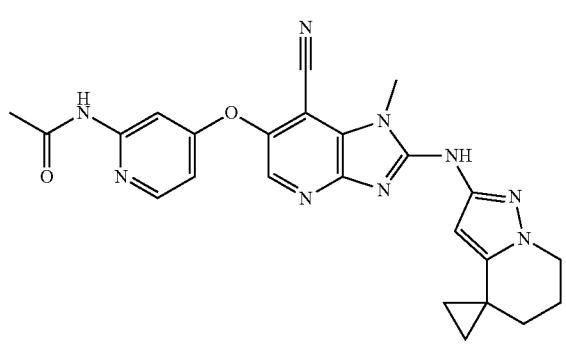
I-116
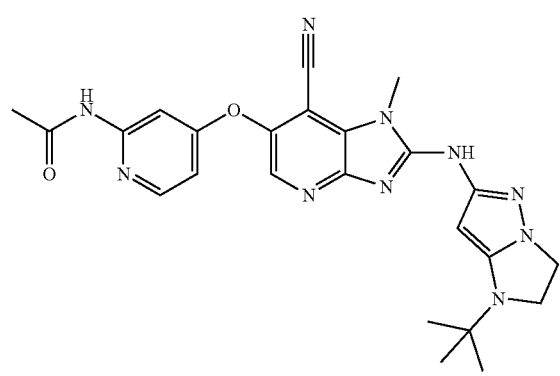
I-118
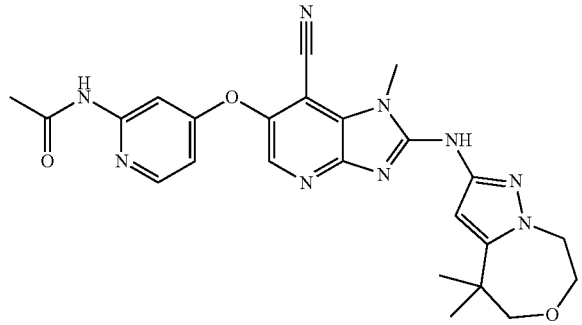
I-119
I-120'
I-120
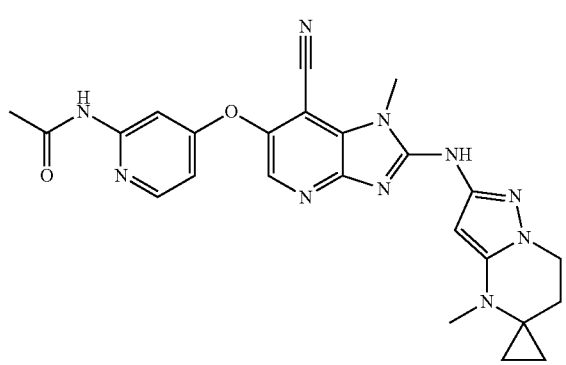
I-121

I-122

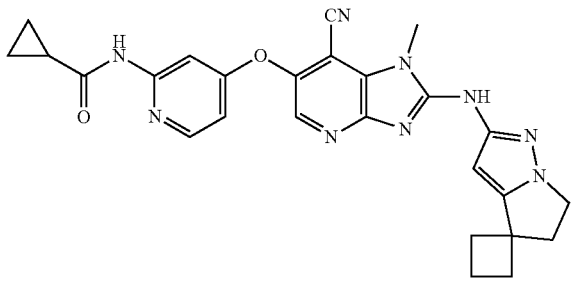

I-123

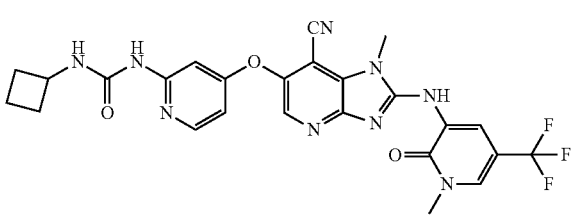

or a pharmaceutically acceptable salt thereof.

In some embodiments, the present disclosure encompasses the recognition that provided compounds display certain desirable characteristics, e.g., as compared to other known compounds. For example, in some embodiments, provided compounds are more potent in one or more biochemical or cellular assays (e.g., the JAK2 Binding Assay, SET2-pSTAT5 Cellular Assay, hPBMC-GMCSF-STAT5 Assay, hPBMC-IL12-STAT4 Assay, or hPBMC-IL2-STAT5 Assay described herein) and/or have one or more other characteristics that make them more suitable for drug development, such as better selectivity over other kinases and/or better ADME (absorption, distribution, metabolism, and excretion) properties including but not limited to better permeability, cytotoxicity, hepatocyte stability, solubility, and/or plasma protein binding profiles (e.g., based on assays described in the ensuing examples), than other known compounds. In some embodiments, provided compounds display certain desirable characteristics in one or more assays described herein, e.g., compared to other known compounds. Without wishing to be bound by any particular theory, the present disclosure encompasses the recognition that 6-heteroaryloxy benzimidazoles and azabenzimidazoles (e.g., compounds described herein) display certain more desirable characteristics (such as better properties in one or more assays described herein) than corresponding 5-heteroaryloxy benzimidazoles and azabenzimidazoles.

In some embodiments, provided compounds are provided and/or utilized in a salt form (e.g., a pharmaceutically acceptable salt form). Reference to a compound provided herein is understood to include reference to salts thereof, unless otherwise indicated. Pharmaceutically acceptable salt forms are known in the art. For example, S. M. Berge, et al. describes pharmaceutically acceptable salts in detail in J. Pharmaceutical Sciences, 66:1-19(1977).

It will be appreciated that throughout the present disclosure, unless otherwise indicated, reference to a compound of Formula I is intended to also include Formulae I, I-A, I-B, I-C, I-D, and I-E and compound species of such formulas disclosed herein; reference to a compound of Formula II is intended to also include Formulae II, II-A, II-B, II-C, II-D, II-E, and II-F and compound species of such formulas disclosed herein; reference to a compound of Formula III is intended to also include compound species of such formulas disclosed herein; and reference to a compound of Formula IV is intended to also include compound species of such formulas disclosed herein.

Preparing Provided Compounds

Provided compounds may generally be made by the processes described in the ensuing schemes and examples. In some embodiments, provided compounds are prepared according to the following Scheme:

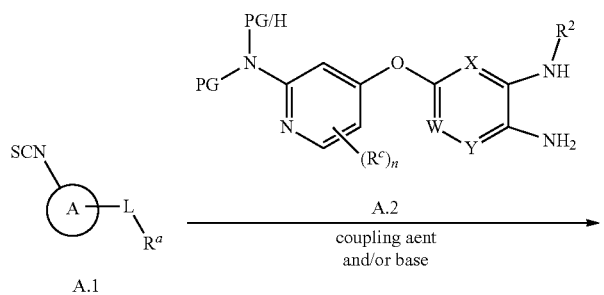

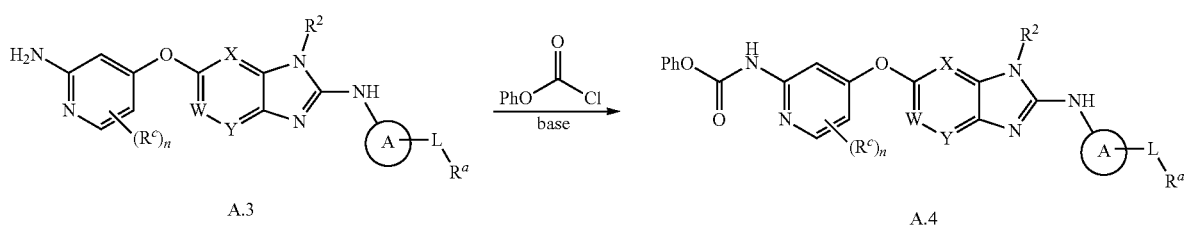

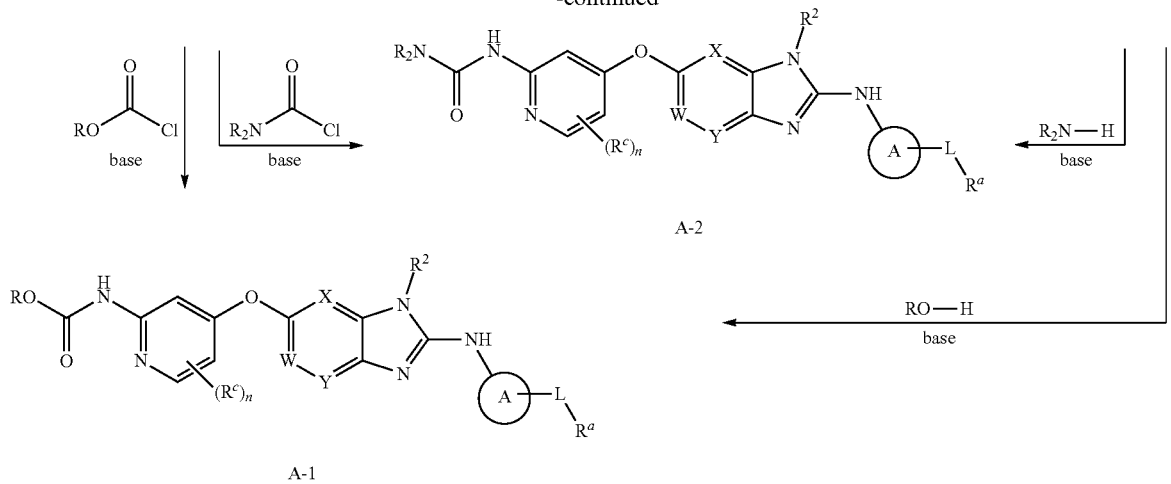

A-2

A-1 wherein PG is a suitable protecting group (e.g., p-methoxybenzyl, acetyl, methyl carbamate, etc.), and Ring A, n, L, W, X, Y, R, $R^2$, $R^a$, and $R^c$ are as defined above for Formula I and described in classes and subclasses herein, both singly and in combination. Accordingly, in some embodiments, intermediate A.3 is prepared by a process comprising contacting intermediate A.1 with intermediate A.2 in the presence of a suitable coupling agent and/or a suitable base (e.g., potassium tert-butoxide). In some embodiments, a process for preparing intermediate A.3 further comprises a deprotection step and/or a functionalization step (e.g., cyanation) under suitable conditions. In some embodiments, intermediate A.4 is prepared by a process comprising contacting intermediate A.3 with phenyl chloroformate in the presence of a suitable base (e.g., triethylamine). In some embodiments, compound A-1 is prepared by a process comprising contacting intermediate A.4 with RO—H, optionally in the presence of a suitable base (e.g., triethylamine). In some embodiments, compound A-1 is prepared by a process comprising contacting intermediate A.3 with RO—C(O)—Cl in the presence of a suitable base (e.g., triethylamine). In some embodiments, compound A-2 is prepared by a process comprising contacting intermediate A.4 with $R_2N$—H, optionally in the presence of a suitable base (e.g., triethylamine). In some embodiments, compound A-2 is prepared by a process comprising contacting intermediate A.3 with $R_2N$—C(O)—Cl in the presence of a suitable base (e.g., triethylamine).

In some embodiments, provided compounds are prepared according to the following Scheme:

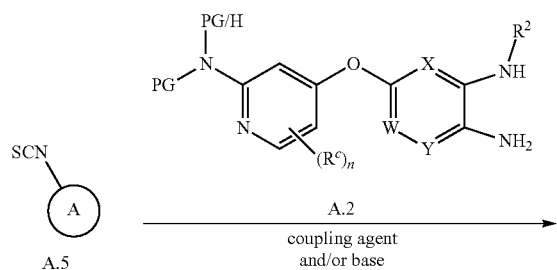

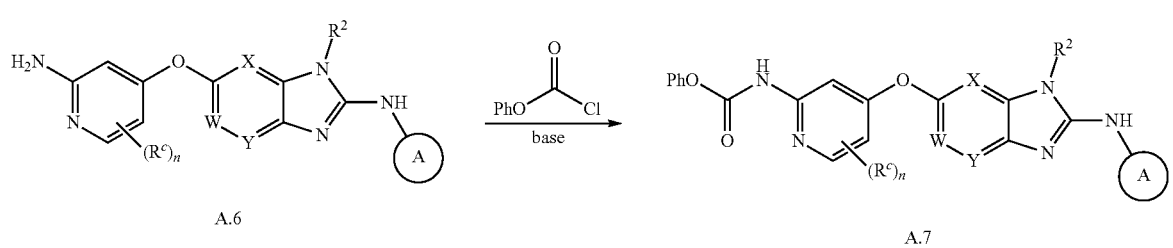

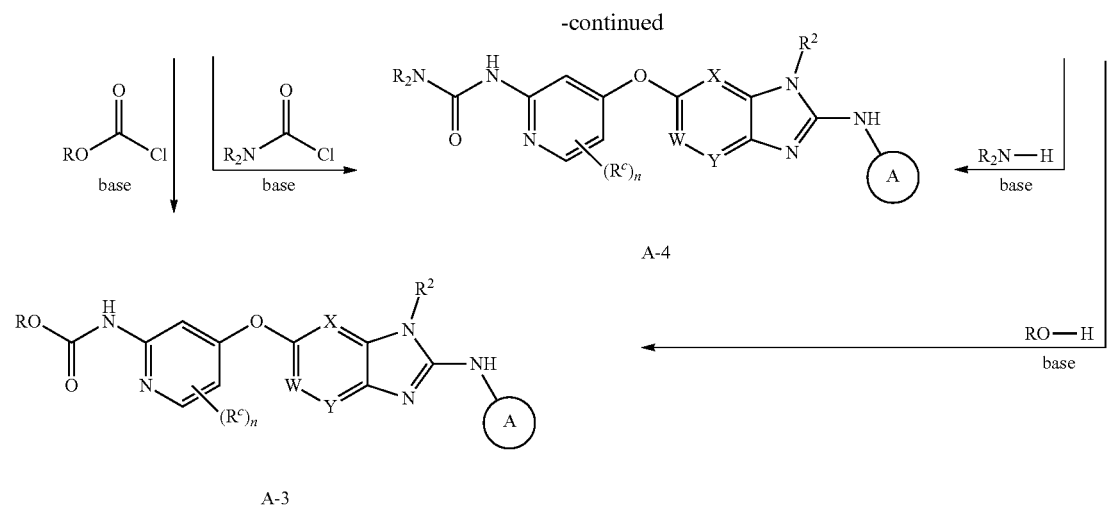

A-3 wherein PG is a suitable protecting group (e.g., p-methoxybenzyl, acetyl, methyl carbamate, etc.), and Ring A, n, W, X, Y, R, $R^2$, and $R^c$ are as defined above for Formula II and described in classes and subclasses herein, both singly and in combination. Accordingly, in some embodiments, intermediate A.6 is prepared by a process comprising contacting intermediate A.5 with intermediate A.2 in the presence of a suitable coupling agent and/or a suitable base (e.g., potassium tert-butoxide). In some embodiments, a process for preparing intermediate A.6 further comprises a deprotection step and/or a functionalization step (e.g., cyanation) under suitable conditions. In some embodiments, intermediate A.7 is prepared by a process comprising contacting intermediate A.6 with phenyl chloroformate in the presence of a suitable base (e.g., triethylamine). In some embodiments, compound A-3 is prepared by a process comprising contacting intermediate A.7 with RO—H, optionally in the presence of a suitable base (e.g., triethylamine). In some embodiments, compound A-3 is prepared by a process comprising contacting intermediate A.6 with RO—C(O)—Cl in the presence of a suitable base (e.g., triethylamine). In some embodiments, compound A-4 is prepared by a process comprising contacting intermediate A.7 with $R_2N$—H, optionally in the presence of a suitable base (e.g., triethylamine). In some embodiments, compound A-4 is prepared by a process comprising contacting intermediate A.6 with $R_2N$—C(O)—Cl in the presence of a suitable base (e.g., triethylamine).

In some embodiments, provided compounds are prepared according to the following Scheme:

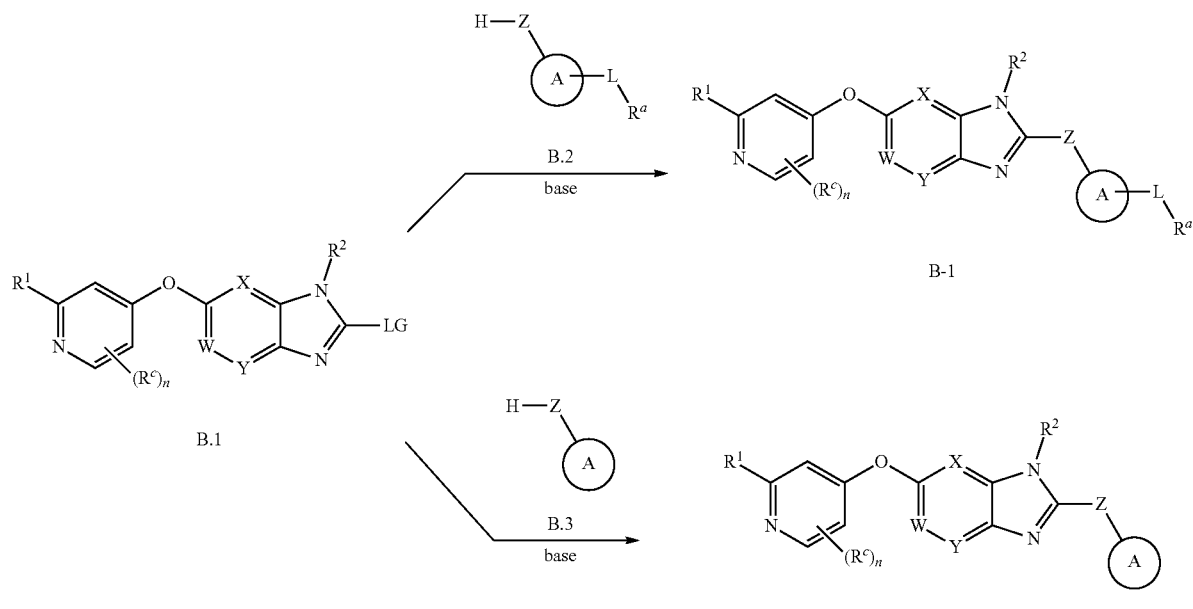

wherein LG is a suitable leaving group (e.g., halogen, e.g., chloro or bromo), and Ring A, n, L, W, X, Y, Z, $R^1$, $R^2$, $R^a$, and $R^c$ are as defined above for Formulae I and/or II and described in classes and subclasses herein, both singly and in combination. Accordingly, in some embodiments, compound B-1 is prepared by a process comprising contacting intermediate B.1 with intermediate B.2 in the presence of a suitable base (e.g., $K_3PO_4$, $K_2CO_3$, or $Cs_2CO_3$), and optionally in the presence of a suitable metal complex (e.g., a palladium complex such as tris(dibenzylideneacetone)dipalladium(0)) and/or a suitable ligand (e.g., 4,5-bis(diphenylphosphino)-9,9-dimethylxanthene). In some embodiments, compound B-2 is prepared by a process comprising contacting intermediate B.1 with intermediate B.3 in the presence of a suitable base (e.g., $K_3PO_4$, $K_2CO_3$, or $Cs_2CO_3$), and optionally in the presence of a suitable metal complex (e.g., a palladium complex such as tris(dibenzylideneacetone)dipalladium(0)) and/or a suitable ligand (e.g., 4,5-bis(diphenylphosphino)-9,9-dimethylxanthene). In some embodiments, a process for preparing compound B-1 or B-2 further comprises a deprotection step under suitable conditions. In some embodiments, a process for preparing compound B-1 or B-2 further comprises a funtionalization step (e.g., cyanation) under suitable conditions.

In some embodiments, provided compounds are prepared according to the following Scheme:

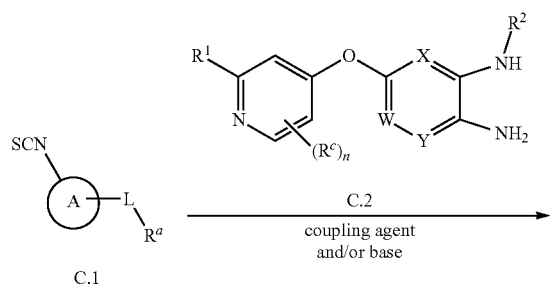

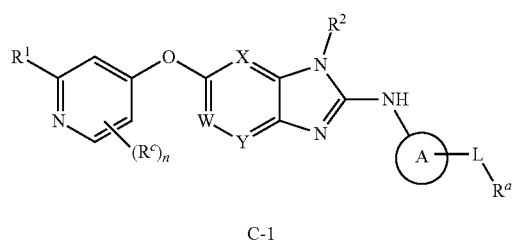

C-1 wherein Ring A, n, L, W, X, Y, $R^1$, $R^2$, $R^a$, and $R^c$ are as defined above for Formula I and described in classes and subclasses herein, both singly and in combination. Accordingly, in some embodiments, compound C-1 is prepared by a process comprising contacting intermediate C.1 with intermediate C.2 in the presence of a suitable coupling agent and/or a suitable base (e.g., potassium tert-butoxide). In some embodiments, a process for preparing compound C-1 further comprises a deprotection and/or functionalization (e.g., cyanation) step under suitable conditions.

In some embodiments, provided compounds are prepared according to the following Scheme:

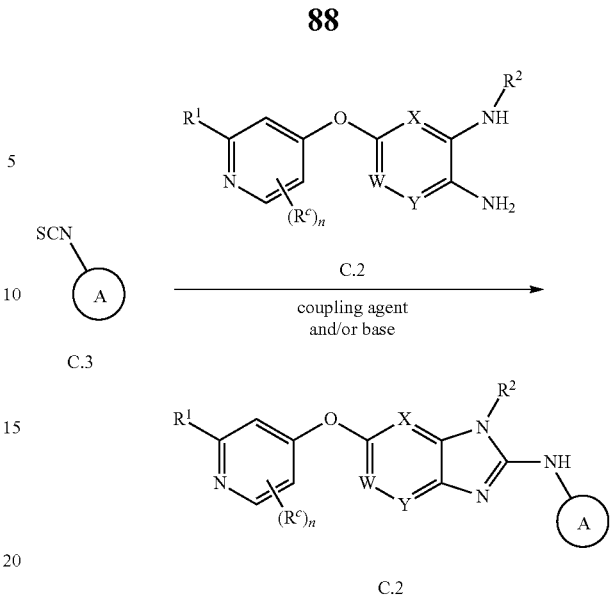

wherein Ring A, n, W, X, Y, $R^1$, $R^2$, and $R^c$ are as defined above for Formula II and described in classes and subclasses herein, both singly and in combination. Accordingly, in some embodiments, compound C-2 is prepared by a process comprising contacting intermediate C.3 with intermediate C.2 in the presence of a suitable coupling agent and/or a suitable base (e.g., potassium tert-butoxide). In some embodiments, a process for preparing compound C-2 further comprises a deprotection and/or functionalization (e.g., cyanation) step under suitable conditions.

Compositions

The present disclosure also provides compositions comprising a compound provided herein with one or more other components. In some embodiments, provided compositions comprise and/or deliver a compound described herein (e.g., compounds of Formulae I, I-A, I-B, I-C, I-D, I-E, II, II-A, II-B, II-C, II-D, II-E, II-F, III, and IV).

In some embodiments, a provided composition is a pharmaceutical composition that comprises and/or delivers a compound provided herein (e.g., compounds of Formulae I, I-A, I-B, I-C, I-D, I-E, II, II-A, II-B, II-C, II-D, II-E, II-F, III, and IV) and further comprises a pharmaceutically acceptable carrier. Pharmaceutical compositions typically contain an active agent (e.g., a compound described herein) in an amount effective to achieve a desired therapeutic effect while avoiding or minimizing adverse side effects. In some embodiments, provided pharmaceutical compositions comprise a compound described herein and one or more fillers, disintegrants, lubricants, glidants, anti-adherents, and/or anti-statics, etc. Provided pharmaceutical compositions can be in a variety of forms including oral dosage forms, topical creams, topical patches, iontophoresis forms, suppository, nasal spray and/or inhaler, eye drops, intraocular injection forms, depot forms, as well as injectable and infusible solutions. Methods of preparing pharmaceutical compositions are well known in the art.

In some embodiments, provided compounds are formulated in a unit dosage form for ease of administration and uniformity of dosage. The expression "unit dosage form" as used herein refers to a physically discrete unit of an active agent (e.g., a compound described herein) for administration to a subject. Typically, each such unit contains a predetermined quantity of active agent. In some embodiments, a unit dosage form contains an entire single dose of the agent. In some embodiments, more than one unit dosage form is administered to achieve a total single dose. In some embodiments, administration of multiple unit dosage forms is required, or expected to be required, in order to achieve an intended effect. A unit dosage form may be, for example, a liquid pharmaceutical composition containing a predetermined quantity of one or more active agents, a solid pharmaceutical composition (e.g., a tablet, a capsule, or the like) containing a predetermined amount of one or more active agents, a sustained release formulation containing a predetermined quantity of one or more active agents, or a drug delivery device containing a predetermined amount of one or more active agents, etc.

Provided compositions may be administered using any amount and any route of administration effective for treating or lessening the severity of any disease or disorder described herein.

Uses

The present disclosure provides uses for compounds and compositions described herein. In some embodiments, provided compounds and compositions are useful in medicine (e.g., as therapy). In some embodiments, provided compounds and compositions are useful in research as, for example, analytical tools and/or control compounds in biological assays.

In some embodiments, the present disclosure provides methods of administering provided compounds or compositions to a subject in need thereof. In some embodiments, the present disclosure provides methods of administering provided compounds or compositions to a subject suffering from or susceptible to a disease, disorder, or condition associated with JAK2.

In some embodiments, provided compounds are useful as JAK2 inhibitors. In some embodiments, provided compounds are useful as Type II JAK2 inhibitors. In some embodiments, the present disclosure provides methods of inhibiting JAK2 in a subject comprising administering a provided compound or composition. In some embodiments, the present disclosure provides methods of inhibiting JAK2 in a biological sample comprising contacting the sample with a provided compound or composition.

JAK (e.g., JAK2) has been implicated in various diseases, disorders, and conditions, such as myeloproliferative neoplasms (Vainchenker, W. et al., F1000Research 2018, 7(F1000 Faculty Rev):82), atopic dermatitis (Rodrigues, M. A. and Torres, T. J. Derm. Treat. 2019, 31(1), 33-40) and acute respiratory syndrome, hyperinflammation, and/or cytokine storm syndrome (*The Lancet*. doi:10.1016/S0140-6736(20)30628-0). Accordingly, in some embodiments, the present disclosure provides methods of treating a disease, disorder or condition associated with JAK2 in a subject in need thereof comprising administering to the subject a provided compound or composition. In some embodiments, a disease, disorder or condition is associated with overexpression of JAK2.

In some embodiments, the present disclosure provides methods of treating cancer, comprising administering a provided compound or composition to a subject in need thereof. In some embodiments, the present disclosure provides methods of treating proliferative diseases, comprising administering a provided compound or composition to a subject in need thereof.

In some embodiments, the present disclosure provides methods of treating a hematological malignancy, comprising administering a provided compound or composition to a subject in need thereof. In some embodiments, a hematological malignancy is leukemia (e.g., chronic lymphocytic leukemia, acute lymphoblastic leukemia, T-cell acute lymphoblastic leukemia, chronic myelogenous leukemia, acute myelogenous leukemia, or acute monocytic leukemia). In some embodiments, a hematological malignancy is lymphoma (e.g., Burkitt's lymphoma, Hodgkin's lymphoma, or non-Hodgkin's lymphoma). In some embodiments, a non-Hodgkin's lymphoma is a B-cell lymphoma. In some embodiments, a non-Hodgkin's lymphoma is a NK/T-cell lymphoma (e.g., cutaneous T-cell lymphoma). In some embodiments, a hematological malignancy is myeloma (e.g., multiple myeloma). In some embodiments, a hematological malignancy is myeloproliferative neoplasm (e.g., polycythemia vera, essential thrombocytopenia, or myelofibrosis). In some embodiments, a hematological malignancy is myelodysplastic syndrome.

In some embodiments, the present disclosure provides methods of treating an inflammatory disease, disorder, or condition (e.g., acute respiratory syndrome, hyperinflammation, and/or cytokine storm syndrome (including those associated with COVID-19) or atopic dermatitis), comprising administering a provided compound or composition to a subject in need thereof.

In some embodiments, a provided compound or composition is administered as part of a combination therapy. As used herein, the term "combination therapy" refers to those situations in which a subject is simultaneously exposed to two or more therapeutic or prophylactic regimens (e.g., two or more therapeutic or prophylactic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition.

For example, in some embodiments, a provided compound or composition is administered to a subject who is receiving or has received one or more additional therapies (e.g., an anti-cancer therapy and/or therapy to address one or more side effects of such anti-cancer therapy, or otherwise to provide palliative care). Exemplary additional therapies include BCL2 inhibitors (e.g., venetoclax), HDAC inhibitors (e.g., vorinostat), BET inhibitors (e.g., mivebresib), proteasome inhibitors (e.g., bortezomib), LSD1 inhibitors (e.g., IMG-7289), and CXCR2 inhibitors. Useful combinations of a JAK2 inhibitor with BCL2, HDAC, BET, and proteasome inhibitors have been demonstrated in cells derived from cutaneous T-cell lymphoma patients (Yumeen, S., et al., Blood Adv. 2020, 4(10), 2213-2226). A combination of a JAK2 inhibitor with a LSD1 inhibitor demonstrated good efficacy in a mouse model of myeloproliferative neoplasms (Jutzi, J. S., et al., HemaSphere 2018, 2(3), http://dx.doi.org/10.1097/HS9.0000000000000054). CXCR2 activity has been shown to modulate signaling pathways involved in tumor growth, angiogenesis, and/or metastasis, including the JAK-STAT3 pathway (Jaffer, T., Ma, D. Transl. Cancer Res. 2016, 5(Suppl. 4), S616-S628).

Exemplary Embodiments

The following numbered embodiments, while non-limiting, are exemplary of certain aspects of the present disclosure:

1. A compound of Formula I:

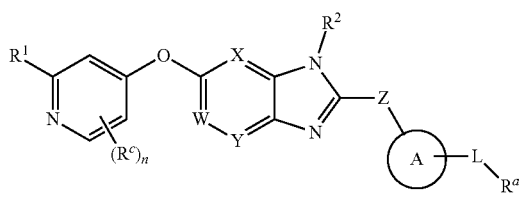

or a pharmaceutically acceptable salt thereof, wherein:
W is CR$^w$ or N;
X is CR$^x$ or N;
Y is CR$^y$ or N;
Z is —O— or —NR$^z$—;
R$^w$, R$^x$, and R$^y$ are each independently hydrogen, halogen, —OR$^3$, —N(R$^3$)$_2$, —SR$^3$, optionally substituted C$_{1-6}$ aliphatic, or —CN;
R$^z$ is hydrogen or optionally substituted C$_{1-6}$ aliphatic;
R$^1$ is —N(R)$_2$, —N(R)C(O)R', —C(O)N(R)$_2$, —N(R)C(O)N(R)$_2$, or —N(R)C(O)OR;
each R$^c$ is independently selected from halogen, —CN, —CO$_2$R, —C(O)N(R)$_2$, —NO$_2$, —N(R)$_2$, —OR, —SR, or optionally substituted C$_{1-6}$ aliphatic;
n is 0, 1, 2, or 3, provided that when R$^1$ is —N(R)$_2$, —N(R)C(O)R' or —C(O)N(R)$_2$, then n is 1, 2, or 3;
R$^2$ is optionally substituted C$_{1-6}$ aliphatic;
R$^3$ is hydrogen or optionally substituted C$_{1-6}$ aliphatic;
Ring A is optionally substituted phenyl, optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
L is a covalent bond or a bivalent C$_{1-3}$ straight or branched hydrocarbon chain;
R$^a$ is hydrogen, halogen, optionally substituted C$_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
each R is independently hydrogen, optionally substituted C$_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur; and
each R' is independently optionally substituted C$_{1-6}$ aliphatic or optionally substituted 3- to 7-membered saturated or partially unsaturated carbocyclyl.

2. The compound of embodiment 1, wherein the compound is not:

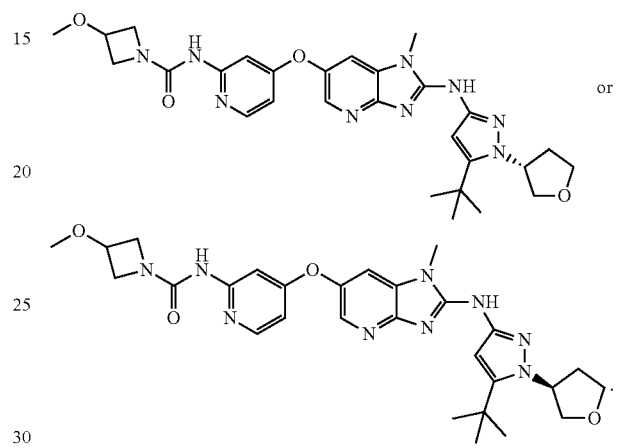

3. The compound of embodiment 1 or embodiment 2, wherein Ring A is optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

4. The compound of any one of the preceding embodiments, wherein Ring A is optionally substituted 5- to 6-membered monocyclic heteroaryl having 1-4 heteroatoms independently selected from nitrogen, oxygen, and sulfur or optionally substituted 8- to 10-membered bicyclic heteroaryl having 1-4 heteroatoms independently selected from nitrogen, oxygen, and sulfur.

5. The compound of any one of the preceding embodiments, wherein Ring A is optionally substituted 5- to 6-membered monocyclic heteroaryl having 1-4 heteroatoms independently selected from nitrogen, oxygen, and sulfur.

6. The compound of any one of the preceding embodiments, wherein R$^a$ is halogen, optionally substituted C$_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

7. The compound of any one of the preceding embodiments, wherein $R^a$ is optionally substituted $C_{1-6}$ aliphatic, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

8. The compound of any one of the preceding embodiments, wherein $R^a$ is optionally substituted $C_{1-6}$ aliphatic or optionally substituted 7- to 10-membered saturated or partially unsaturated bicyclic heterocyclyl having 1-4 heteroatoms independently selected from nitrogen, oxygen, and sulfur.

9. The compound of any one of the preceding embodiments, wherein:

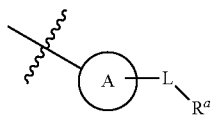

is substituted with 1-5 $R^b$, as valency allows; and
  each $R^b$ is independently hydrogen, halogen, —CN, —OR, —O(CH$_2$)$_m$R, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted $C_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, optionally substituted 5- to 6-membered monocyclic heteroaryl having 1-4 heteroatoms independently selected from nitrogen, oxygen, and sulfur; and
  m is 1, 2, or 3.

10. The compound of embodiment 9, wherein each $R^b$ is independently halogen, —CN, —OR, —O(CH$_2$)$_m$R, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted $C_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, optionally substituted 5- to 6-membered monocyclic heteroaryl having 1-4 heteroatoms independently selected from nitrogen, oxygen, and sulfur.

11. The compound of embodiment 9 or 10, wherein each $R^b$ is independently halogen or optionally substituted $C_{1-6}$ aliphatic.

12. The compound of any one of embodiments 9-11, wherein

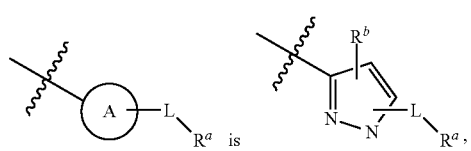

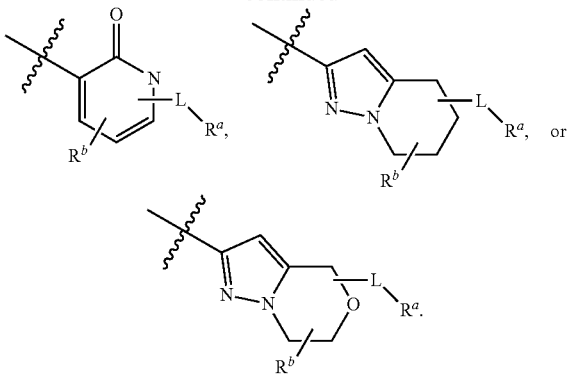

13. The compound of any one of the preceding embodiments, wherein L is a covalent bond.

14. The compound of any one of embodiments 1-12, wherein L is —CH$_2$—.

15. The compound of any one of the preceding embodiments, wherein the compound is of Formula I-C:

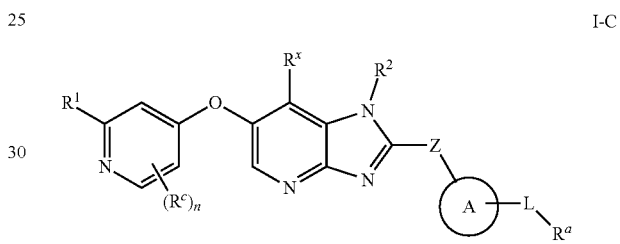

I-C or a pharmaceutically acceptable salt thereof.

16. The compound of any one of the preceding embodiments, wherein the compound is of Formula I-D:

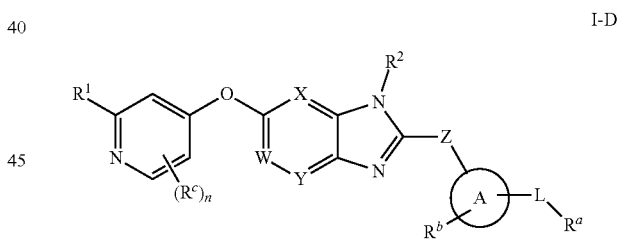

I-D or a pharmaceutically acceptable salt thereof, wherein:
  $R^b$ is hydrogen, halogen, —CN, —OR, —O(CH$_2$)$_m$R, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted $C_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, optionally substituted 5- to 6-membered monocyclic heteroaryl having 1-4 heteroatoms independently selected from nitrogen, oxygen, and sulfur; and
  m is 1, 2, or 3.

17. The compound of any one of the preceding embodiments, wherein the compound is of Formula I-E:

I-E

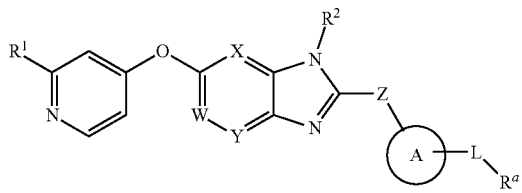

or a pharmaceutically acceptable salt thereof.

18. A compound of Formula II:

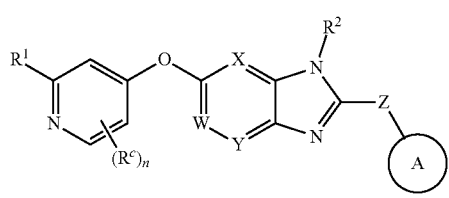

or a pharmaceutically acceptable salt thereof, wherein:
W is $CR^w$ or N;
X is $CR^x$ or N;
Y is $CR^y$ or N;
Z is —O— or —$NR^z$—;
$R^w$, $R^x$, and $R^y$ are each independently hydrogen, halogen, —$OR^3$, —$N(R^3)_2$, —$SR^3$, optionally substituted $C_{1-6}$ aliphatic, or —CN;
$R^z$ is hydrogen or optionally substituted $C_{1-6}$ aliphatic;
$R^1$ is —$N(R)_2$, —N(R)C(O)R', —C(O)N(R)$_2$, —N(R)C(O)N(R)$_2$, or —N(R)C(O)OR;
each $R^c$ is independently selected from halogen, —CN, —$CO_2R$, —C(O)N(R)$_2$, —$NO_2$, —N(R)$_2$, —OR, —SR, or optionally substituted $C_{1-6}$ aliphatic;
n is 0, 1, 2, or 3;
$R^2$ is optionally substituted $C_{1-6}$ aliphatic;
$R^3$ is hydrogen or optionally substituted $C_{1-6}$ aliphatic;
Ring A is optionally substituted 9- to 16-membered bicyclic or tricyclic aryl, optionally substituted 8- to 10-membered bicyclic heteroaryl having 1-4 heteroatoms independently selected from nitrogen, oxygen, and sulfur, optionally substituted 10- to 16-membered polycyclic heteroaryl having 1-5 heteroatoms independently selected from nitrogen, oxygen, and sulfur, optionally substituted 7- to 10-membered bicyclic heterocyclyl having 1-4 heteroatoms independently selected from nitrogen, oxygen, and sulfur, or optionally substituted 10- to 16-membered polycyclic heterocyclyl having 1-5 heteroatoms independently selected from nitrogen, oxygen, and sulfur;
each R is independently hydrogen, optionally substituted $C_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur; and
each R' is independently optionally substituted $C_{1-6}$ aliphatic or optionally substituted 3- to 7-membered saturated or partially unsaturated carbocyclyl.

19. The compound of embodiment 18, wherein the compound is not:

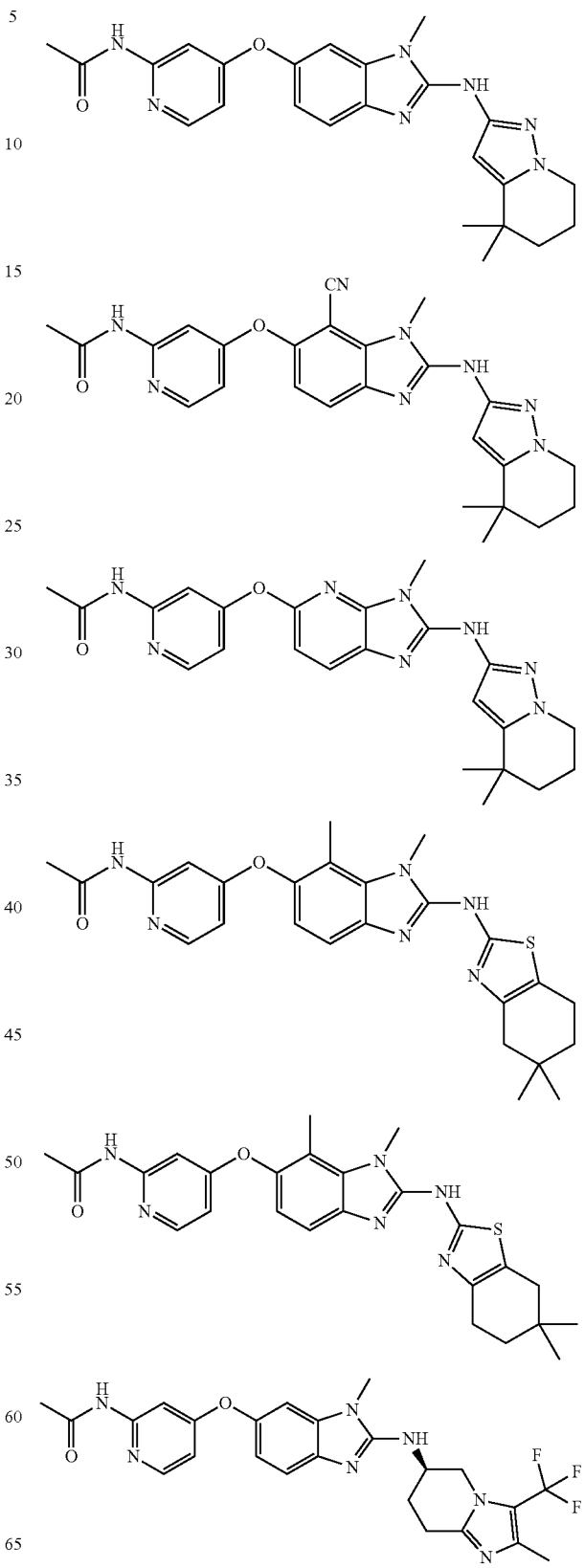

-continued

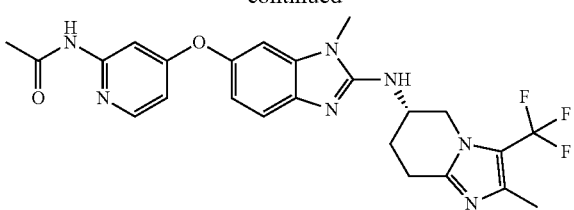
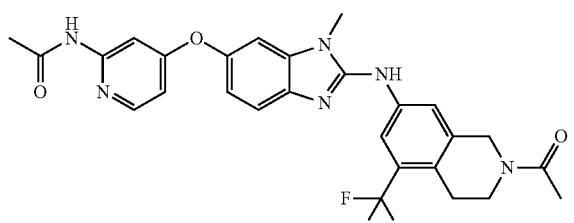
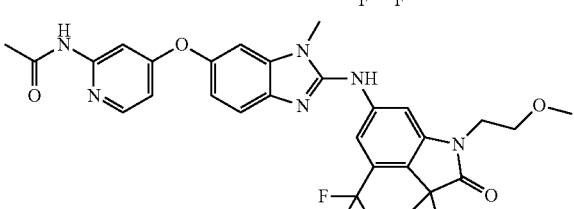
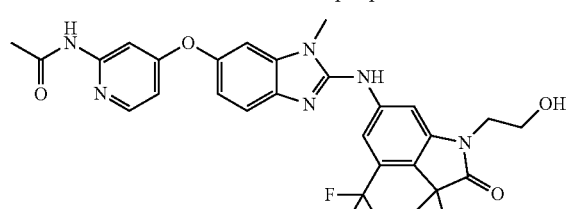
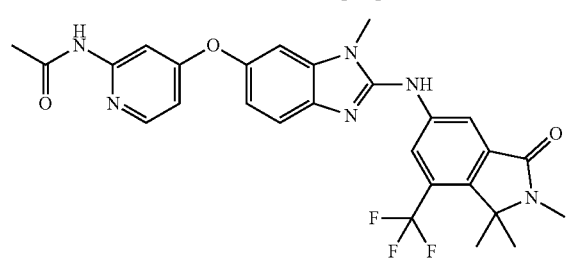
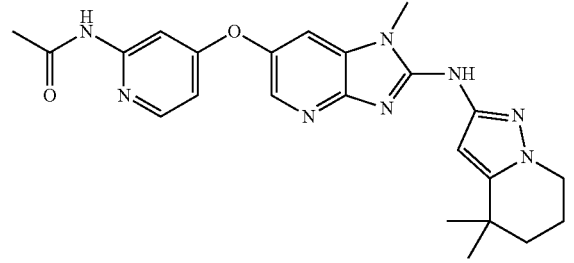
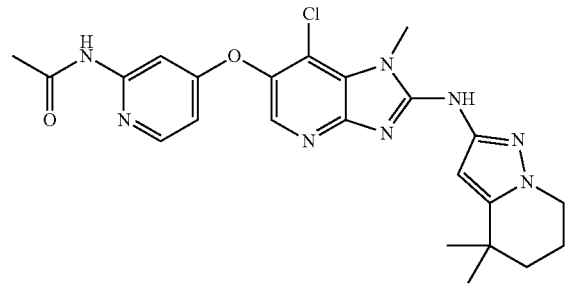

-continued

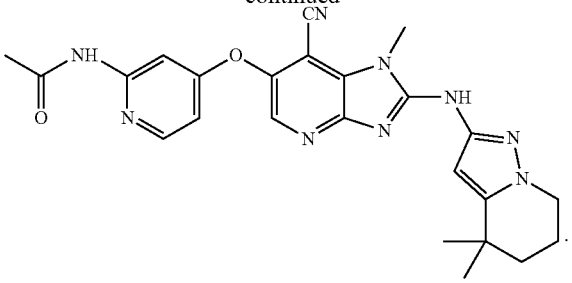

20. The compound of embodiment 18 or 19, wherein Ring A is optionally substituted 8- to 10-membered bicyclic heteroaryl having 1-4 heteroatoms independently selected from nitrogen, oxygen, and sulfur, optionally substituted 10- to 16-membered polycyclic heteroaryl having 1-5 heteroatoms independently selected from nitrogen, oxygen, and sulfur, optionally substituted 7- to 10-membered bicyclic heterocyclyl having 1-4 heteroatoms independently selected from nitrogen, oxygen, and sulfur, or optionally substituted 10- to 16-membered polycyclic heterocyclyl having 1-5 heteroatoms independently selected from nitrogen, oxygen, and sulfur.

21. The compound of any one of embodiments 18-20, wherein Ring A is optionally substituted 8- to 10-membered bicyclic heteroaryl having 1-4 heteroatoms independently selected from nitrogen, oxygen, and sulfur or optionally substituted 10- to 16-membered polycyclic heteroaryl having 1-5 heteroatoms independently selected from nitrogen, oxygen, and sulfur.

22. The compound of any one of embodiments 18-21, wherein Ring A is 8- to 10-membered bicyclic heteroaryl having 1-4 heteroatoms independently selected from nitrogen, oxygen, and sulfur optionally substituted with one or more oxo, halogen, or $C_{1-6}$ alkyl.

23. The compound of any one of embodiments 18-22, wherein Ring A is optionally substituted 10- to 16-membered polycyclic heteroaryl having 1-5 heteroatoms independently selected from nitrogen, oxygen, and sulfur.

24. The compound of any one of embodiments 18-23, wherein:
Ring A is

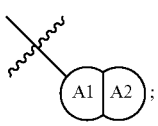

Ring A1 is an optionally substituted ring selected from phenyl, 5- to 6-membered monocyclic heteroaryl having 1-3 heteroatoms independently selected from nitrogen, oxygen, and sulfur, 5- to 7-membered saturated or partially unsaturated monocyclic carbocyclyl, and 5- to 7-membered saturated or partially unsaturated monocyclic heterocyclyl having 1-3 heteroatoms independently selected from nitrogen, oxygen, and sulfur;
wherein Ring A1 is fused to Ring A2;
Ring A2 is an optionally substituted ring selected from phenyl, 5- to 6-membered monocyclic heteroaryl having 1-3 heteroatoms independently selected from nitrogen, oxygen, and sulfur, 5- to 7-membered saturated or partially unsaturated monocyclic carbocyclyl, and 5- to 7-membered saturated or partially unsaturated monocyclic heterocyclyl having 1-3 heteroatoms independently selected from nitrogen, oxygen, and sulfur;
wherein Ring A2 is optionally (i) further fused to Ring A3,
or (ii) Ring A2 and Ring A3 combine to form a spirocycle; and
Ring A3, when present, is an optionally substituted ring selected from phenyl, 5- to 6-membered monocyclic heteroaryl having 1-3 heteroatoms independently selected from nitrogen, oxygen, and sulfur, 3- to 7-membered saturated or partially unsaturated monocyclic carbocyclyl, and 3- to 7-membered saturated or partially unsaturated monocyclic heterocyclyl having 1-3 heteroatoms independently selected from nitrogen, oxygen, and sulfur.

25. The compound of embodiment 24, wherein Ring A1 is optionally substituted 5- to 6-membered monocyclic heteroaryl having 1-3 heteroatoms independently selected from nitrogen, oxygen, and sulfur.

26. The compound of embodiment 24 or 25, wherein optionally substituted Ring A is

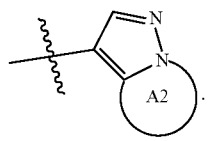

27. The compound of any one of embodiments 24-26, wherein Ring A2 is optionally substituted 5- to 7-membered partially saturated monocyclic heterocyclyl having 1-3 heteroatoms independently selected from nitrogen, oxygen, and sulfur.

28. The compound of any one of embodiments 24-27, wherein optionally substituted Ring A is selected from the group consisting of:

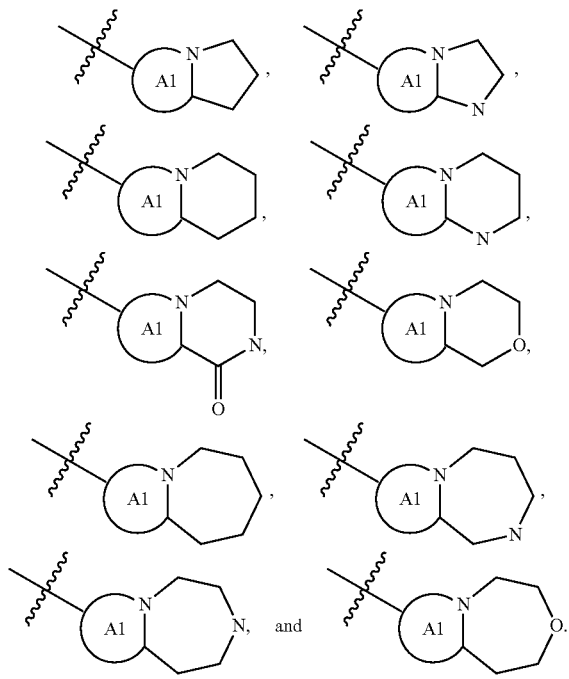

29. The compound of any one of embodiments 24-27, wherein optionally substituted Ring A is selected from the group consisting of:

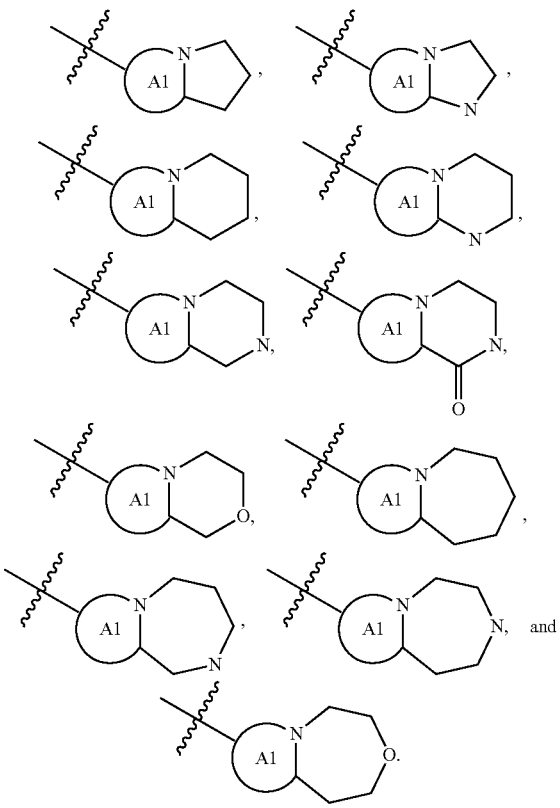

30. The compound of any one of embodiments 18-29, wherein:

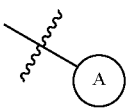

is substituted with 1-5 $R^b$, as valency allows; and
each $R^b$ is independently hydrogen, halogen, —CN, —OR, —O(CH$_2$)$_m$R, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted C$_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, optionally substituted 5- to 6-membered monocyclic heteroaryl having 1-4 heteroatoms independently selected from nitrogen, oxygen, and sulfur; and
m is 1, 2, or 3.

31. The compound of embodiment 30, wherein each $R^b$ is independently halogen, —CN, —OR, —O(CH$_2$)$_m$R, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted C$_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, optionally substituted 5- to 6-membered monocyclic heteroaryl having 1-4 heteroatoms independently selected from nitrogen, oxygen, and sulfur.

32. The compound of embodiment 30 or embodiment 31, wherein each $R^b$ is independently halogen, optionally substituted $C_{1-6}$ aliphatic, —OR, or —O(CH$_2$)$_m$R.

33. The compound of any one of embodiments 30-32, wherein

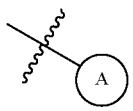

is selected from the group consisting of:

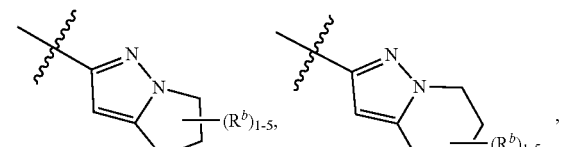

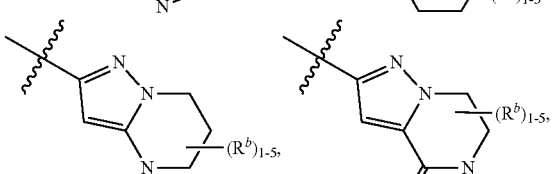

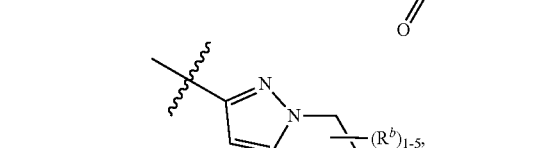

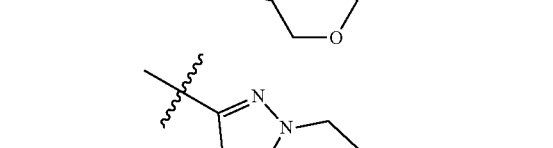

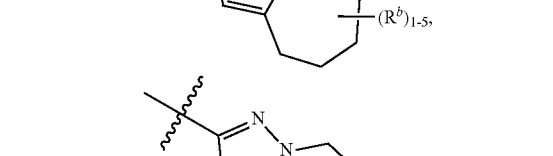

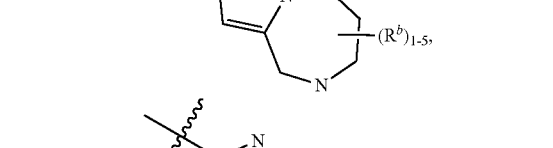

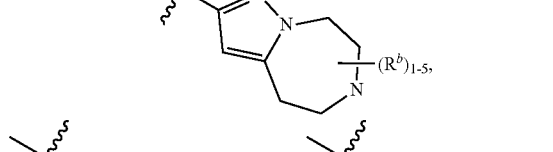

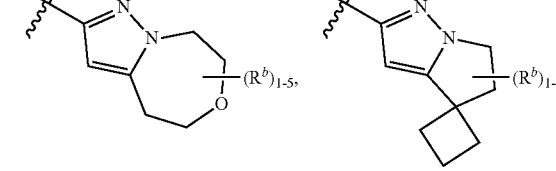

-continued

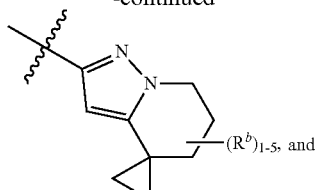

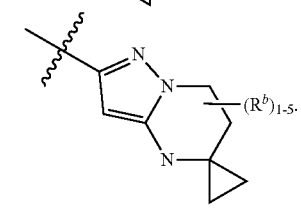

34. The compound of any one of embodiments 30-32, wherein

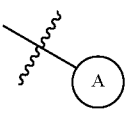

is selected from the group consisting of:

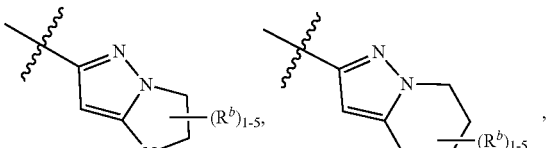

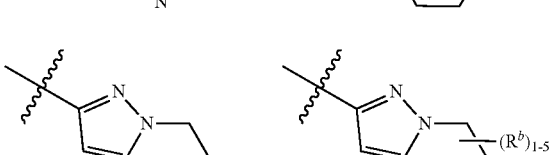

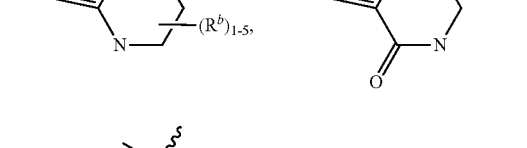

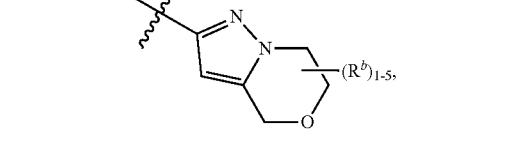

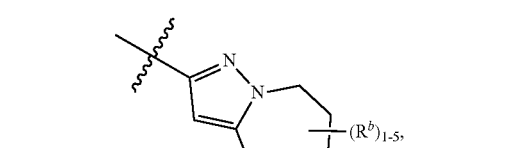

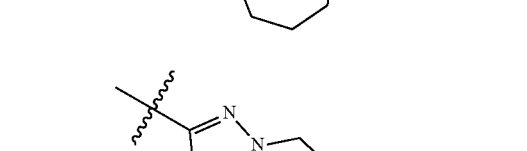

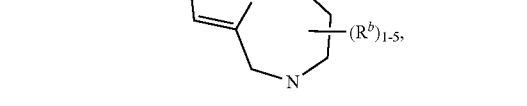

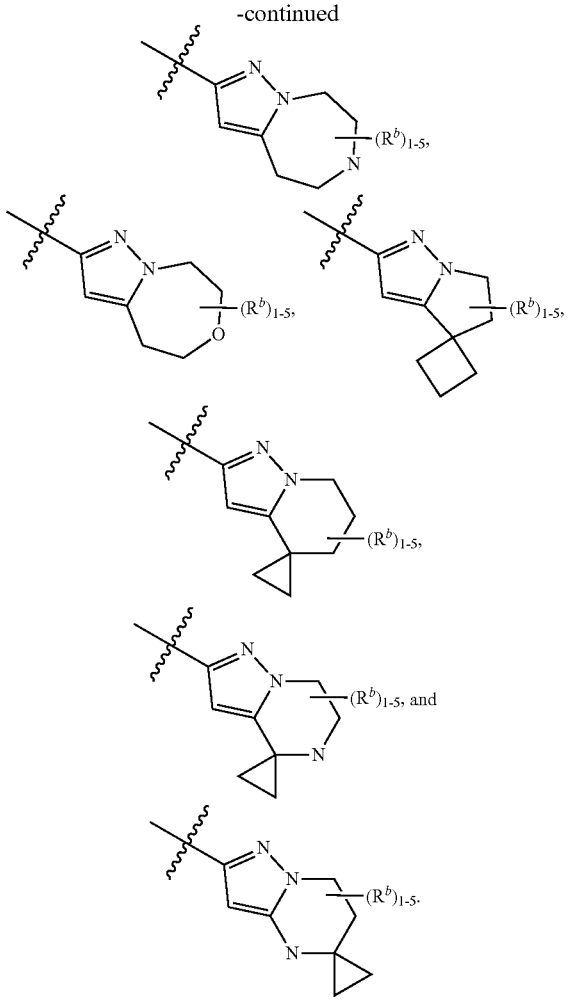

35. The compound of any one of embodiments 18-34, wherein the compound is of Formula II-C:

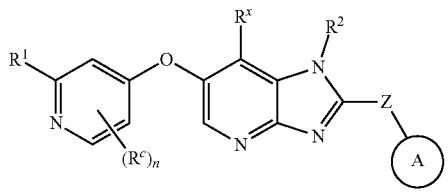

or a pharmaceutically acceptable salt thereof.

36. The compound of any one of embodiments 18-35, wherein the compound is of Formula II-D:

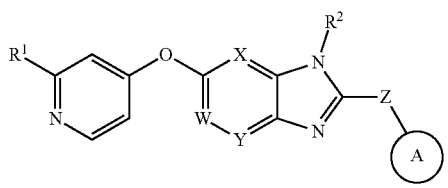

or a pharmaceutically acceptable salt thereof.

37. The compound of any one of embodiments 18-36, wherein the compound is of Formula II-E:

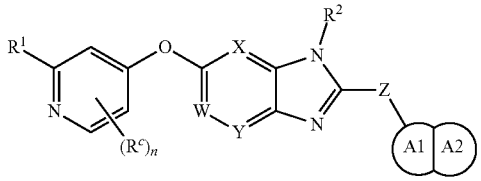

or a pharmaceutically acceptable salt thereof, wherein:

Ring A1 is an optionally substituted ring selected from phenyl, 5- to 6-membered monocyclic heteroaryl having 1-3 heteroatoms independently selected from nitrogen, oxygen, and sulfur, 5- to 7-membered saturated or partially unsaturated monocyclic carbocyclyl, and 5- to 7-membered saturated or partially unsaturated monocyclic heterocyclyl having 1-3 heteroatoms independently selected from nitrogen, oxygen, and sulfur; wherein Ring A1 is fused to Ring A2;

Ring A2 is an optionally substituted ring selected from phenyl, 5- to 6-membered monocyclic heteroaryl having 1-3 heteroatoms independently selected from nitrogen, oxygen, and sulfur, 5- to 7-membered saturated or partially unsaturated monocyclic carbocyclyl, and 5- to 7-membered saturated or partially unsaturated monocyclic heterocyclyl having 1-3 heteroatoms independently selected from nitrogen, oxygen, and sulfur; wherein Ring A2 is optionally (i) further fused to Ring A3, or (ii) Ring A2 and Ring A3 combine to form a spirocycle; and Ring A3, when present, is an optionally substituted ring selected from phenyl, 5- to 6-membered monocyclic heteroaryl having 1-3 heteroatoms independently selected from nitrogen, oxygen, and sulfur, 3- to 7-membered saturated or partially unsaturated monocyclic carbocyclyl, and 3- to 7-membered saturated or partially unsaturated monocyclic heterocyclyl having 1-3 heteroatoms independently selected from nitrogen, oxygen, and sulfur.

38. The compound of any one of the preceding embodiments, wherein W is $CR^w$.

39. The compound of embodiment 38, wherein $R^w$ is hydrogen.

40. The compound of any one of embodiments 1-37, wherein W is N.

41. The compound of any one of the preceding embodiments, wherein X is $CR^x$.

42. The compound of any one of the preceding embodiments, wherein $R^x$ is hydrogen, halogen, —CN, —$OR^3$, or optionally substituted $C_{1-6}$ aliphatic.

43. The compound of any one of embodiments 1-40, wherein X is N.

44. The compound of any one of the preceding embodiments, wherein Y is $CR^y$.

45. The compound of embodiment 44, wherein $R^y$ is hydrogen.

46. The compound of any one of embodiments 1-43, wherein Y is N.

47. The compound of any one of the preceding embodiments, wherein $R^1$ is —N(R)C(O)N(R)$_2$, or —N(R)C(O)OR.

48. The compound of any one of the preceding embodiments, wherein $R^1$ is —N(R)C(O)N(R)$_2$.

49. The compound of any one of the preceding embodiments, wherein $R^1$ is —N(H)C(O)N(R)$_2$, and each R of $R^1$ is independently hydrogen, optionally substituted $C_{1-6}$ aliphatic, or optionally substituted 3- to 7-membered saturated or partially unsaturated carbocyclyl, or the two R groups attached to the same nitrogen are taken together to form an optionally substituted 3- to 7-membered saturated or partially unsaturated monocyclic heterocyclyl having 0-2 additional heteroatoms independently selected from nitrogen, oxygen, and sulfur.

50. The compound of any one of embodiments 1-47, wherein $R^1$ is —N(R)C(O)OR.
51. The compound of any one of embodiments 1-47, wherein $R^1$ is —N(H)C(O)OR, and R of $R^1$ is optionally substituted $C_{1-6}$ aliphatic or optionally substituted 3- to 7-membered saturated or partially unsaturated monocyclic heterocyclyl having 1-2 heteroatoms independently selected from nitrogen, oxygen, and sulfur.
52. The compound of any one of embodiments 1-46, wherein $R^1$ is —N(R)C(O)R'.
53. The compound of any one of embodiments 1-46, wherein $R^1$ is —N(H)C(O)(optionally substituted $C_{1-6}$ aliphatic).
54. The compound of any one of the preceding embodiments, wherein each $R^c$ is independently halogen.
55. The compound of any one of the preceding embodiments, wherein n is 0.
56. A compound of Formula III:

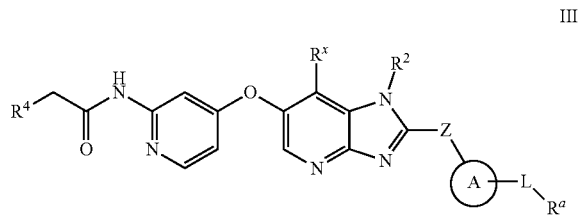

III or a pharmaceutically acceptable salt thereof, wherein:
Z is —O— or —$NR^z$—;
$R^x$ is hydrogen, halogen, —$OR^3$, —$N(R^3)_2$, —$SR^3$, optionally substituted $C_{1-6}$ aliphatic, or —CN;
$R^z$ is hydrogen or optionally substituted $C_{1-6}$ aliphatic;
$R^2$ is optionally substituted $C_{1-6}$ aliphatic;
$R^3$ is hydrogen or optionally substituted $C_{1-6}$ aliphatic;
$R^4$ is halogen, —OR, —$N(R)_2$, or optionally substituted 3- to 7-membered saturated or partially unsaturated monocyclic heterocyclyl having 1-3 heteroatoms independently selected from nitrogen, oxygen, and sulfur;
Ring A is optionally substituted phenyl, optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
L is a covalent bond or a bivalent $C_{1-3}$ straight or branched hydrocarbon chain;
$R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur; and each R is independently hydrogen, optionally substituted $C_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur.

57. The compound of embodiment 56, wherein the compound is not:

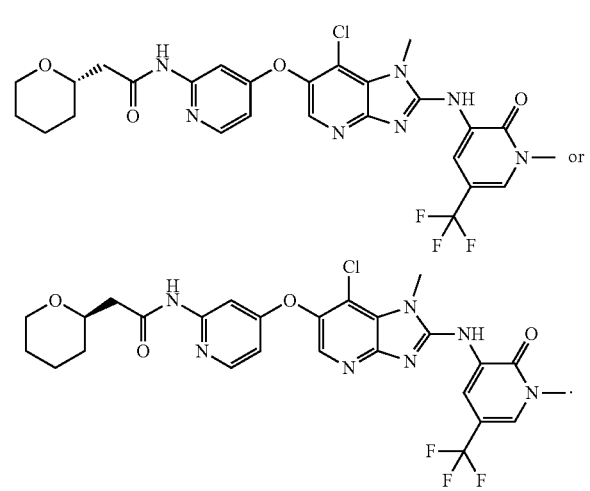

58. The compound of embodiment 56 or embodiment 57, wherein $R^4$ is halogen, —OR, —$N(R)_2$, or optionally substituted 3- to 7-membered saturated or partially unsaturated monocyclic heterocyclyl having 1-3 heteroatoms independently selected from nitrogen, oxygen, and sulfur, and each R of $R^4$ is independently hydrogen or optionally substituted $C_{1-6}$ aliphatic.
59. The compound of any one of embodiments 56-58, wherein Ring A is optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

60. The compound of any one of embodiments 56-59, wherein Ring A is optionally substituted 5- to 6-membered monocyclic heteroaryl having 1-4 heteroatoms independently selected from nitrogen, oxygen, and sulfur or optionally substituted 8- to 10-membered bicyclic heteroaryl having 1-4 heteroatoms independently selected from nitrogen, oxygen, and sulfur.

61. The compound of any one of embodiments 56-60, wherein Ring A is optionally substituted 5- to 6-membered monocyclic heteroaryl having 1-4 heteroatoms independently selected from nitrogen, oxygen, and sulfur.

62. The compound of any one of embodiments 56-61, wherein $R^a$ is halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

63. The compound of any one of embodiments 56-62, wherein $R^a$ is optionally substituted $C_{1-6}$ aliphatic.

64. The compound of any one of embodiments 56-63, wherein:

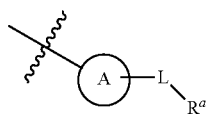

is substituted with 1-5 $R^b$, as valency allows; and
each $R^b$ is independently hydrogen, halogen, —CN, —OR, —O(CH$_2$)$_m$R, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted $C_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, optionally substituted 5- to 6-membered monocyclic heteroaryl having 1-4 heteroatoms independently selected from nitrogen, oxygen, and sulfur; and
m is 1, 2, or 3.

65. The compound of embodiment 64, wherein each $R^b$ is independently halogen, —CN, —OR, —O(CH$_2$)$_m$R, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted $C_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, optionally substituted 5- to 6-membered monocyclic heteroaryl having 1-4 heteroatoms independently selected from nitrogen, oxygen, and sulfur.

66. The compound of embodiment 64 or 65, wherein each $R^b$ is independently optionally substituted $C_{1-6}$ aliphatic.

67. The compound of any one of embodiments 64-66, wherein

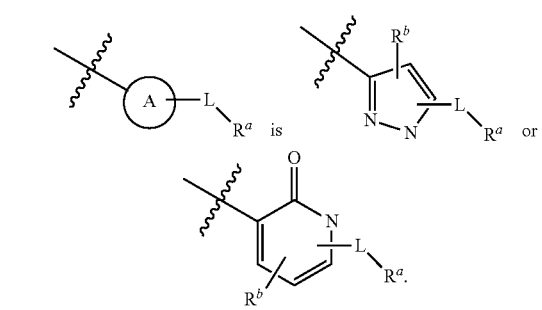

68. The compound of any one of embodiments 56-67, wherein L is a covalent bond.

69. The compound of any one of embodiments 56-67, wherein L is —CH$_2$—.

70. The compound of any one of the preceding embodiments, wherein each R is independently hydrogen, optionally substituted $C_{1-6}$ aliphatic, or optionally substituted 3- to 7-membered saturated or partially unsaturated monocyclic heterocyclyl having 1-2 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur.

71. The compound of any one of the preceding embodiments, wherein each R is independently hydrogen or optionally substituted $C_{1-6}$ aliphatic.

72. The compound of any one of the preceding embodiments, wherein each R' is independently optionally substituted $C_{1-6}$ alkyl or optionally substituted $C_{3-7}$ cycloalkyl.

73. The compound of any one of the preceding embodiments, wherein each R' is independently optionally substituted $C_{1-6}$ aliphatic.

74. A compound of Formula IV:

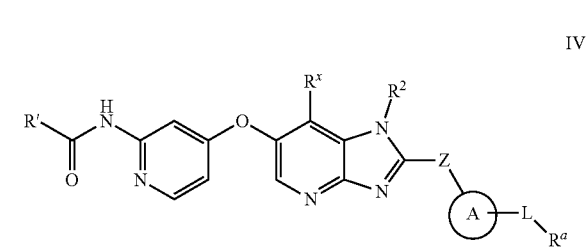

or a pharmaceutically acceptable salt thereof, wherein:
Z is —O— or —NR$^z$—;
R$^x$ is hydrogen, halogen, —OR$^3$, or —CN;
R$^z$ is hydrogen or optionally substituted $C_{1-6}$ aliphatic;
R$^2$ is optionally substituted $C_{1-6}$ aliphatic;
R$^3$ is hydrogen or optionally substituted $C_{1-6}$ aliphatic;

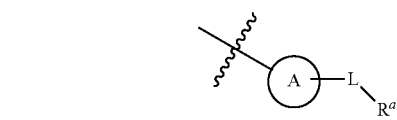

is selected from (i) or (ii):

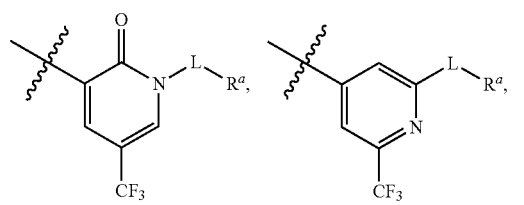

(i)

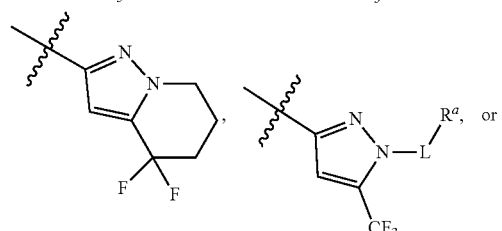

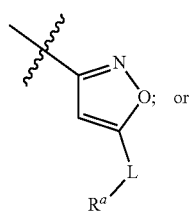

; or

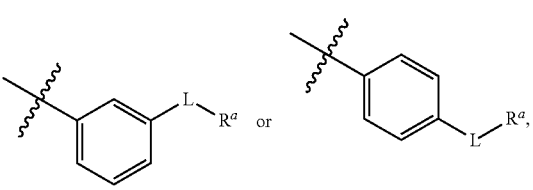

(ii)

wherein Ring A is further substituted at least once, and at least one substituent on Ring A is $C_{1-6}$ haloalkyl;

L is a covalent bond or a bivalent $C_{1-3}$ straight or branched hydrocarbon chain;

$R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur; and R' is $C_{1-6}$ aliphatic or 3- to 7-membered saturated or partially unsaturated carbocyclyl.

75. The compound of embodiment 74, wherein the compound is not:

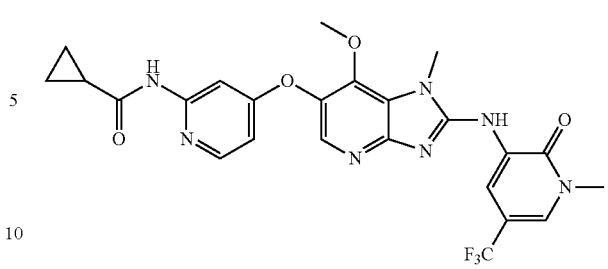

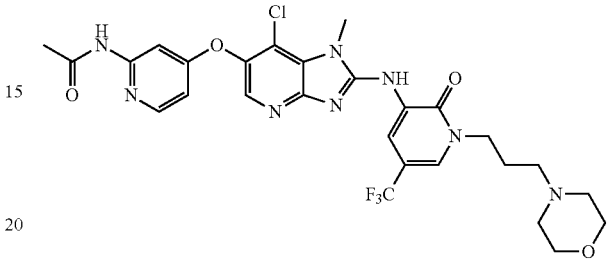

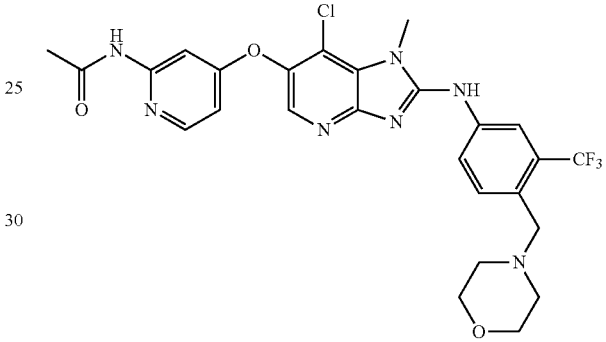

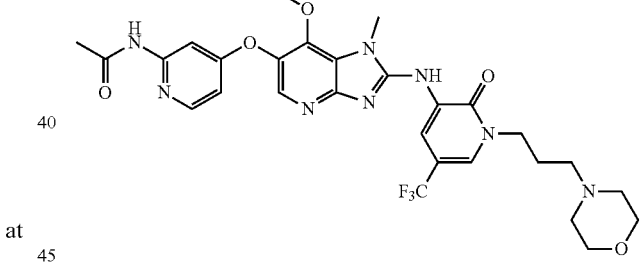

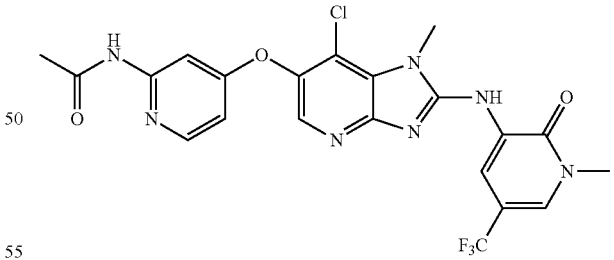

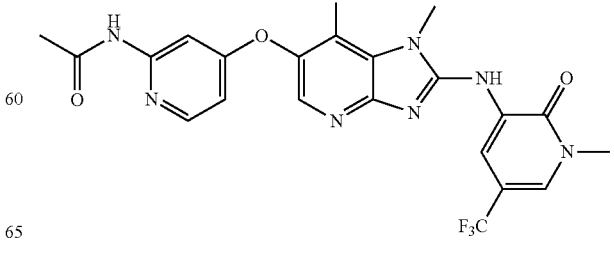

76. The compound of embodiment 74 or 75, wherein $R^a$ is halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

77. The compound of any one of embodiments 74-76, wherein $R^a$ is optionally substituted $C_{1-6}$ aliphatic, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

78. The compound of any one of embodiments 74-77, wherein L is a covalent bond.

79. The compound of any one of embodiments 74-77, wherein L is —CH$_2$—.

80. The compound of any one of embodiments 74-79, wherein R' is methyl or cyclopropyl.

81. The compound of any one of embodiments 56-80, wherein $R^x$ is hydrogen, halogen, —CN, —OR$^3$, or optionally substituted $C_{1-6}$ aliphatic.

82. The compound of any one of embodiments 56-81, wherein $R^x$ is hydrogen, halogen, —OR$^3$, or —CN.

83. The compound of any one of embodiments 56-82, wherein $R^x$ is halogen or —CN.

84. The compound of any one of the preceding embodiments, wherein $R^2$ is $C_{1-4}$ alkyl.

85. The compound of any one of the preceding embodiments, wherein Z is —O—.

86. The compound of any one of embodiments 1-84, wherein Z is —NR$^z$—.

87. The compound of embodiment 86, wherein $R^z$ is hydrogen.

88. A compound selected from Table 1, or a pharmaceutically acceptable salt thereof.

89. A pharmaceutical composition comprising a compound of any one of the preceding embodiments, or a pharmaceutically acceptable salt thereof, and a pharmaceutically acceptable carrier.

90. A method of inhibiting JAK2 in a subject comprising administering the compound of any one of embodiments 1-88 or the composition of embodiment 89.

91. A method of treating a disease, disorder, or condition associated with JAK2, comprising administering to a subject in need thereof the compound of any one of embodiments 1-88 or the composition of embodiment 89.

92. A method of treating cancer, comprising administering to a subject in need thereof the compound of any one of embodiments 1-88 or the composition of embodiment 89.

93. A method of treating a hematological malignancy, comprising administering to a subject in need thereof the compound of any one of embodiments 1-88 or the composition of embodiment 89.

94. The method of embodiment 93, wherein the hematological malignancy is leukemia or lymphoma.

95. A method of treating a myeloproliferative neoplasm, comprising administering to a subject in need thereof the compound of any one of embodiments 1-88 or the composition of embodiment 89.

96. The method of embodiment 95, wherein the myeloproliferative neoplasm is polycythemia vera, essential thrombocytopenia or myelofibrosis.

EXAMPLES

As described in the Examples below, in certain exemplary embodiments, compounds are prepared according to the following general procedures. It will be appreciated that, although the general methods depict the synthesis of certain compounds of the present disclosure, the following general methods and other methods known to one of ordinary skill in the art can be applied to all compounds and subclasses and species of each of these compounds, as described herein.

Preparation of Intermediates

Preparation of Intermediate Int-1:
5-fluoro-N-methyl-2-nitropyridin-3-amine

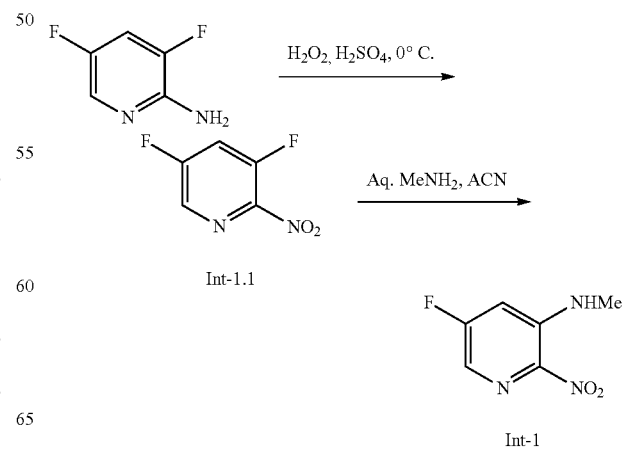

Synthesis of compound Int-1.1 Hydrogen peroxide (30 wt %, 31 mL) was added dropwise to concentrated sulfuric acid (60 mL) at 0° C. To the solution was added a solution of 3,5-difluoropyridin-2-amine (5.0 g, 38.43 mmol, 1.0 equiv) in concentrated sulfuric acid (60 mL) dropwise at 0° C. The reaction mixture was stirred at room temperature for 48 h. It was carefully poured over crushed ice and stirred. The aqueous mixture was basified with saturated aqueous sodium bicarbonate. Precipitates were removed by filtration and the filtrate was extracted with ethyl acetate. The combined organic layers were washed with brine, dried over anhydrous sodium sulfate, filtered and concentrated under reduced pressure to afford Int-1.1. $^1$H NMR (CDCl$_3$, 400 MHz): δ 8.35 (bs, 1H), 7.62-7.58 (m, 1H).

Synthesis of compound Int-1. To a solution of Int-1.1 (2.3 g, 14.37 mmol, 1.0 equiv) in acetonitrile (20 mL) was added aqueous methylamine solution (40%, 1.1 mL, 14.37 mmol, 1.0 equiv) dropwise at 0° C. The reaction mixture was stirred at room temperature for 1 h. It was poured over ice-water and extracted with ethyl acetate. The combined organic layers were washed with brine, dried over anhydrous sodium sulfate, filtered and concentrated under reduced pressure to afford Int-1. $^1$H NMR (CDCl$_3$, 400 MHz): δ 7.93 (bs, 1H), 7.78-7.75 (d, 1H), 7.02-6.99 (m, 1H), 3.06 (s, 3H).

Preparation of Intermediate Int-2:
4-chloro-5-fluoro-N-methyl-2-nitropyridin-3-amine

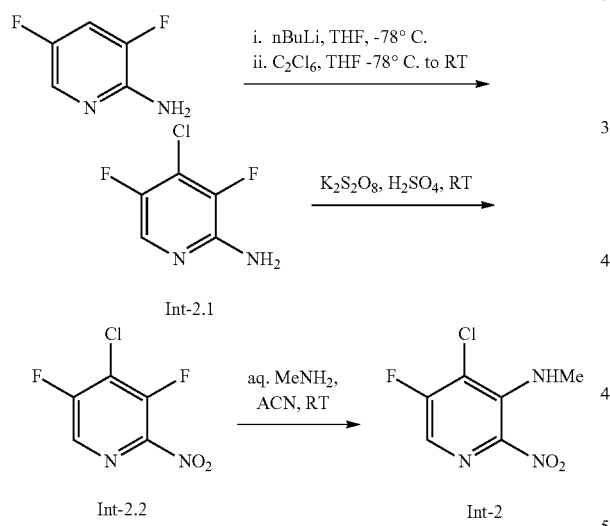

Synthesis of compound Int-2.1. To a solution of 3,5-difluoropyridin-2-amine (10 g, 76.87 mmol, 1.0 equiv) in THF (200 mL), was added n-butyllithium (2.5 M in hexane, 61.4 mL, 153.7 mmol, 2.0 equiv). The reaction mixture was stirred at −78° C. for 40 min. Hexachloroethane (36.3 g, 153.7 mmol, 2.0 equiv) was added and the reaction mixture was stirred at −78° C. for 30-40 min. A saturated ammonium chloride solution was added carefully to quenched the reaction. The mixture was warmed to room temperature and extracted with ethyl acetate. The combined organic layers were washed with brine, dried over anhydrous sodium sulfate, filtered and concentrated under reduced pressure. The residue was purified by flash column chromatography on silica gel (CombiFlash®, 12% ethyl acetate in hexane) to afford Int-2.1. $^1$H NMR (DMSO-d$_6$, 400 MHz): δ 7.98-7.94 (m, 1H), 6.48 (bs, 2H).

Synthesis of compound Int-2.2. Concentrated sulfuric acid (3 mL, 6 vol) was added dropwise to potassium persulfate (2.05 g, 7.6 mmol, 2.5 equiv) at room temperature and stirred for 15 min. To the mixture was added Int-2.1 (0.5 g, 3.04 mmol, 1.0 equiv) in small portions maintaining temperature at 30-40° C. The reaction mixture was stirred at room temperature for 3-4 h. It was poured over crushed ice, stirred, basified with saturated sodium bicarbonate and extracted with ethyl acetate. The combined organic layers were washed with brine, dried over anhydrous sodium sulfate, filtered and concentrated under reduced pressure. The residue was purified by flash column chromatography on silica gel (CombiFlash®, 2-3% ethyl acetate in hexane) to afford Int-2.2. $^1$H NMR (DMSO-d$_6$, 400 MHz): δ 8.78 (s, 1H).

Synthesis of compound Int-2. To a solution of Int-2.2 (0.970 g, 4.99 mmol, 1.0 equiv) in acetonitrile (10 mL) was added aqueous methylamine solution (40%, 0.8 mL, 9.98 mmol, 2.0 equiv) dropwise at 0° C. The reaction mixture was stirred at room temperature for 10-20 min. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane) to afford Int-2. $^1$H NMR (DMSO-d$_6$, 400 MHz): δ 7.98 (s, 1H), 7.05 (bs, 1H), 2.79 (d, 3H).

Preparation of Intermediate Int-3: (S)-5-(tert-butyl)-3-isothiocyanato-1-(tetrahydrofuran-3-yl)-1H-pyrazole

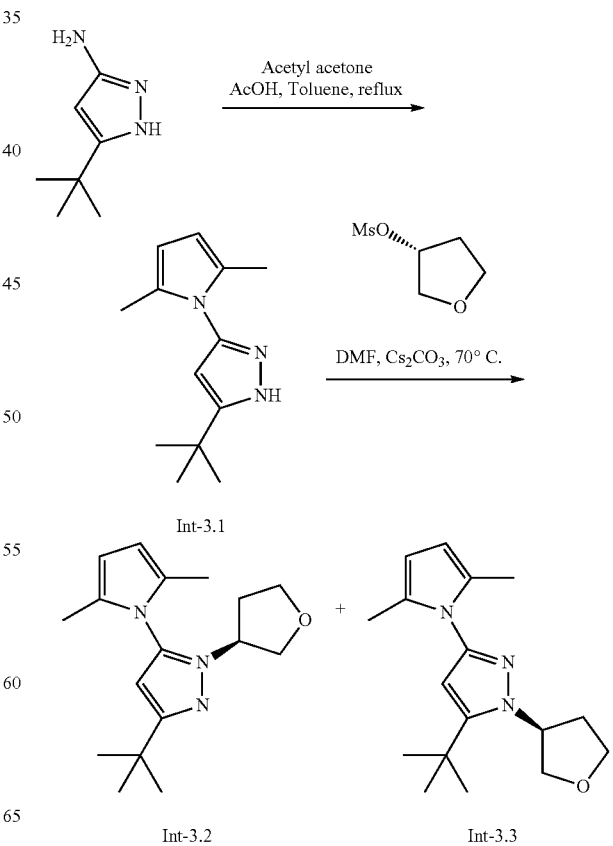

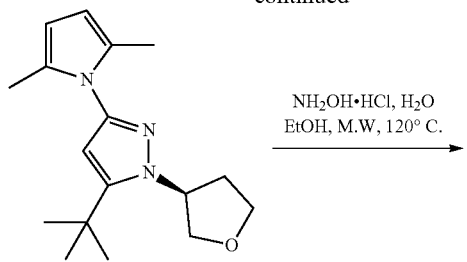

Int-3.3

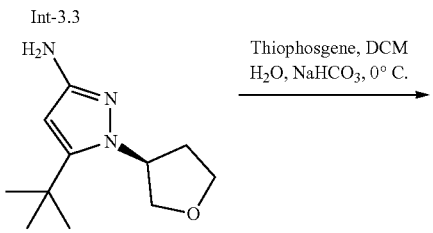

Int-3.4

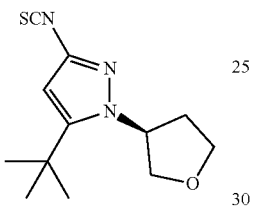

Int-3

Synthesis of compound Int-3.1. A round-bottom flask equipped with a Dean-Stark apparatus and a condenser was charged with 5-(tert-butyl)-1H-pyrazol-3-amine (5.0 g, 35.92 mmol, 1.0 equiv), 2,5-hexanedione (4.09 g, 35.92 mmol, 1.0 equiv), toluene (100 mL) and a few drops of acetic acid. The reaction mixture was heated to reflux for 3 hours. It was cooled rt and concentrated under reduced pressure. The residue was purified by flash column chromatography on silica gel (CombiFlash®, 12% ethyl acetate in hexane as eluant) to afford Int-3.1. MS (ES): m/z 218.3 [M+H]$^+$.

Synthesis of compound Int-3.2 and Int-3.3. A mixture of Int-3.1 (2.5 g, 11.50 mmol, 1.0 equiv), (R)-tetrahydrofuran-3-yl methanesulfonate (1.91 g, 11.50 mmol, 1.0 equiv) and cesium carbonate (7.49 g, 23 mmol, 2.0 equiv) in DMF (15 mL) was stirred at 70° C. for 12 h under nitrogen. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2% ethyl acetate in hexane as eluant) to afford Int-3.2. MS (ES): m/z 287.4 [M+H]$^+$ and Int-3.3. MS (ES): m/z 248.3 [M+H]$^+$.

Synthesis of compound Int-3.4. To a solution of Int-3.3 (0.120 g, 0.417 mmol, 1.0 equiv) in ethanol-water (2:1, 2 mL) was added hydroxylamine hydrochloride (0.287 g, 4.17 mmol, 10 equiv). The reaction mixture was stirred at 120° C. in a microwave reactor for 1 h. It was poured over ice-water, basified by 2 N sodium hydroxide and extracted with dichloromethane. The combined organic layers were washed with brine, dried over anhydrous sodium sulfate, filtered and concentrated under reduced pressure to afford Int-3.4. MS (ES): m/z 210.3 [M+H]$^+$.

Synthesis of compound Int-3. To a solution of Int-3.4 (0.070 g, 0.334 mmol, 1.0 equiv) in dichloromethane (2 mL) was added a solution of sodium bicarbonate (0.140 g, 1.67 mmol, 5.0 equiv) in water (1 mL) followed by thiophosgene (0.096 g, 0.835 mmol, 2.5 equiv) at 0° C. The reaction mixture was stirred at room temperature for 2 h. It was poured over ice-water and extracted with dichloromethane. The combined organic layers were washed with brine, dried over anhydrous sodium sulfate, filtered and concentrated under reduced pressure to afford Int-3. MS (ES): m/z 252.3 [M+H]$^+$.

Preparation of Intermediate Int-4: (R)-5-(tert-butyl)-3-isothiocyanato-1-(tetrahydrofuran-3-yl)-1H-pyrazole

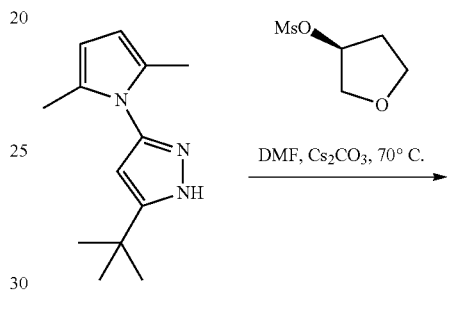

Int-4.3

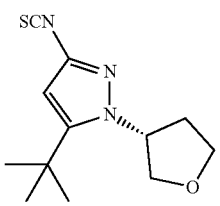

Int-4

Synthesis of compound Int-4. Compound Int-4 was prepared from Int-3.2, following the procedures described in the synthesis of Int-3. MS (ES): m/z 252.3 [M+H]⁺.

Preparation of Intermediate Int-5: 3-isothiocyanato-1-methyl-5-(trifluoromethyl)pyridin-2(1H)-one

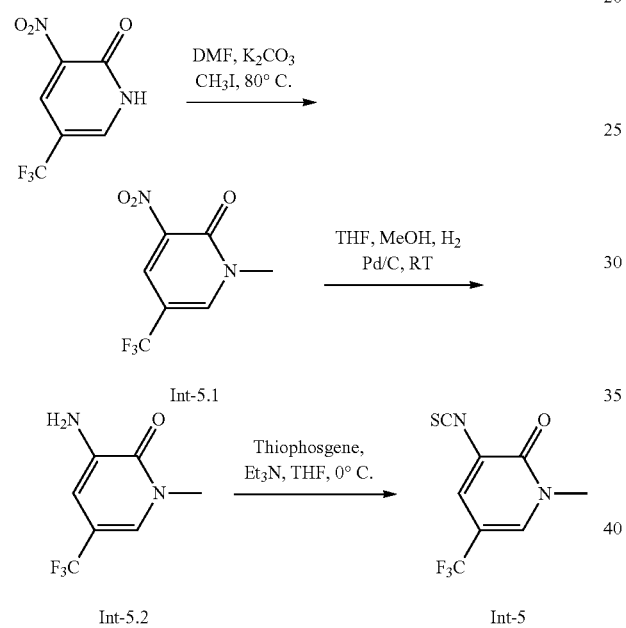

Synthesis of compound Int-5.1. A mixture of 3-nitro-5-(trifluoromethyl)pyridin-2(1H)-one (1.0 g, 4.81 mmol, 1.0 equiv) and potassium carbonate (1.3 g, 9.62 mmol, 2.0 equiv) in DMF (15 mL) was stirred for 15 min before the addition of methyl iodide (1.0 g, 7.21 mmol, 1.5 equiv). The reaction mixture was stirred at 70° C. for 2 h. It was transferred into ice-water and product was extracted with ethyl acetate. The combined organic layers were washed with brine, dried over anhydrous sodium sulfate, filtered, and concentrated under reduced pressure. The residue was purified by flash column chromatography on silica gel (CombiFlash®, 40% ethyl acetate in hexane) to afford Int-5.1. MS(ES): m/z 223.12 [M+H]⁺.

Synthesis of compound Int-5.2. A mixture of compound Int-5.1 (0.57 g, 2.57 mmol, 1.0 equiv) and 10% palladium on carbon (0.3 g) in methanol (18 mL) was stirred under hydrogen (1 atm) for 1 h. It was filtered through a pad of Celite® and rinsed with methanol. The filtrate was concentrated under reduced pressure to obtain Int-5.2. MS(ES): m/z 193.14 [M+H]⁺.

Synthesis of compound Int-5. To a solution of Int-5.2 (0.200 g, 1.04 mmol, 1.0 equiv) and triethylamine (0.4 mL, 2.49 mmol, 2.4 equiv) in THF (6 mL) was added thiophosgene (0.143 g, 1.25 mmol, 1.2 eq) at 0° C. The reaction mixture was stirred at room temperature for 30 min. It was transferred into ice-water and extracted with ethyl acetate. The combined organic layers were washed with brine, dried over anhydrous sodium sulfate, filtered, and concentrated under reduced pressure to afford Int-5. MS(ES): m/z 192.15 [M+H]⁺.

Preparation of Intermediate Int-6: 1-(2-oxaspiro[3.3]heptan-6-yl)-5-(trifluoromethyl)-1H-pyrazol-3-amine

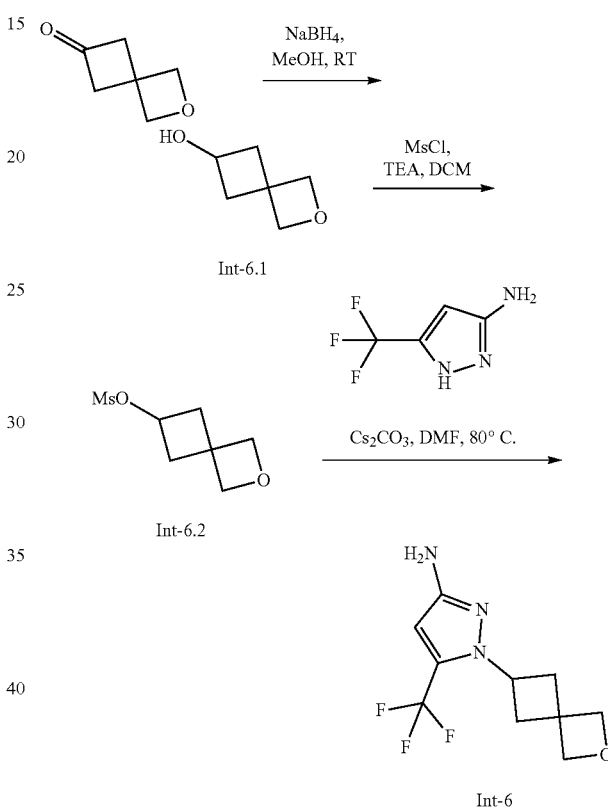

Synthesis of compound Int-6.1. To a solution of 2-oxaspiro[3.3]heptan-6-one (0.600 g, 5.35 mmol, 1.0 equiv) in methanol (10 mL), was added sodium borohydride (0.203 g, 5.35 mmol, 1.0 equiv) in portions at 0° C. The reaction mixture was stirred for 2 h. It was transferred into ice-water, stirred, and extracted with ethyl acetate. The combined organic layers were washed with brine, dried over anhydrous sodium sulfate, filtered, and concentrated under reduced pressure to obtain Int-6.1. MS (ES): m/z 115.2 [M+H]⁺.

Synthesis of compound. Int-6.2. To a solution of Int-6.1 (0.540 g, 4.73 mmol, 1.0 equiv) in dichloromethane (10 mL) was added triethylamine (1.64 mL, 11.82 mmol, 2.5 equiv) at 0° C. followed by addition of methanesulfonyl chloride (0.71 mL, 9.46 mmol, 2.0 equiv). The reaction mixture was stirred at room temperature for 12 h. It was transferred into ice-water, stirred, and extracted with dichloromethane. The combined organic layers were washed with brine, dried over anhydrous sodium sulfate, filtered, and concentrated under reduced pressure. The residue was purified by flash column chromatography on silica gel (CombiFlash®, 40% ethyl acetate in hexane) to afford Int-6.2. MS (ES): m/z 193.2 [M+H]⁺.

Synthesis of compound Int-6. To a solution of Int-6.2 (0.4 g, 2.08 mmol, 1.0 equiv) and 5-(trifluoromethyl)-1H-pyrazol-3-amine (0.314 g, 2.08 mmol, 1.0 equiv) in DMF (7 mL) was added cesium carbonate (1.352 g, 4.16 mmol, 2.0 equiv). The reaction mixture was heated at 80° C. for 5 h. It was transferred into ice-water, stirred, and extracted with ethyl acetate. The combined organic layers were washed with brine, dried over anhydrous sodium sulfate, filtered, and concentrated under reduced pressure. The residue was purified by preparative HPLC to obtain Int-6. MS (ES): m/z 248.2 [M+H]$^+$.

Preparation of Intermediate Int-7: 4,4-difluoro-2-isothiocyanato-4,5,6,7-tetrahydropyrazolo[1,5-a]pyridine

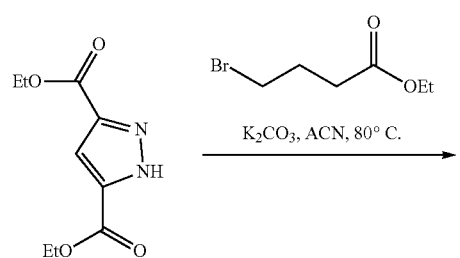
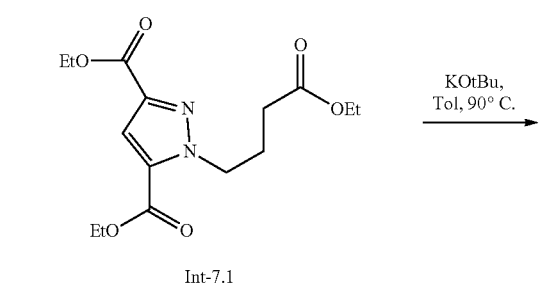
Int-7.1
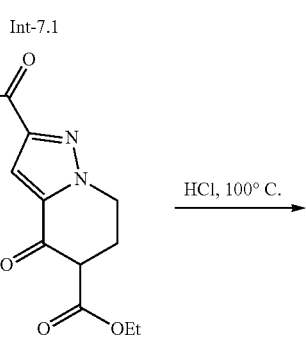
Int-7.2
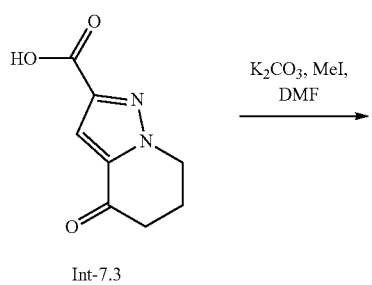
Int-7.3

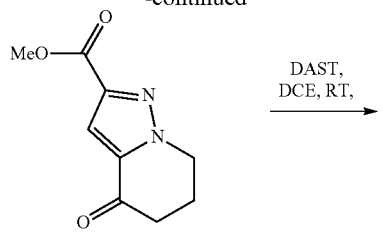
Int-7.4
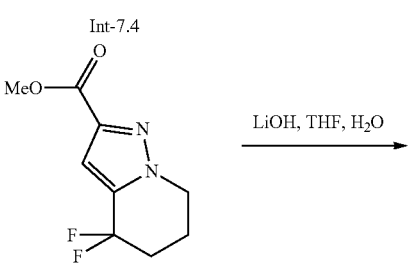
Int-7.5
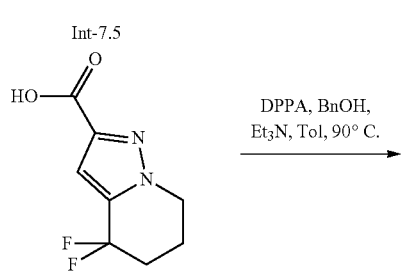
Int-7.6
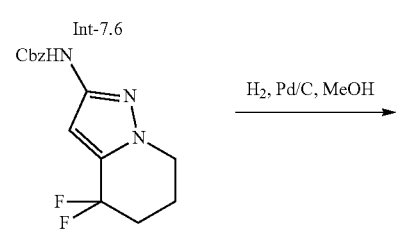
Int-7.7
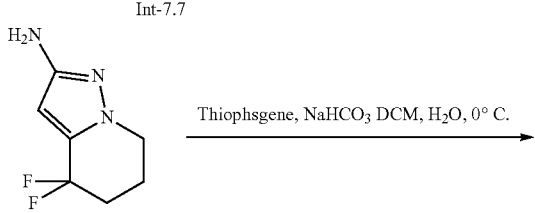
Int-7.8
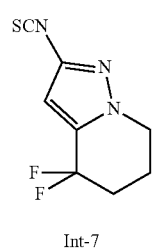
Int-7

Synthesis of compound Int-7.1. To a solution of diethyl 1H-pyrazole-3,5-dicarboxylate (100 g, 471 mmol, 1.0 equiv) and ethyl 4-bromobutanoate (91.92 g, 471 mmol, 1.0 equiv) in acetonitrile (1000 mL) was added potassium carbonate (64.99 g, 471 mmol, 1.0 equiv) and the reaction mixture was stirred at 80° C. for 4 h. It was poured into ice-water and extracted with ethyl acetate. The combined organic layers were washed with brine, dried over anhydrous sodium sulfate, filtered, and concentrated under reduced pressure. The residue was purified by trituration with diethyl ether to afford Int-7.1. MS(ES): m/z 327.2 [M+H]⁺.

Synthesis of compound Int-7.2. To a solution of Int-7.1 (120 g, 367 mmol, 1.0 equiv) in toluene (1000 mL) was added potassium tert-butoxide (1M in THF) (403 mL, 403.7 mmol, 1.1 equiv) at room temperature. The reaction mixture was stirred at 90° C. for 3 h. The reaction mixture was poured into ice-water, and product extracted with ethyl acetate. The combined organic layers were washed with brine, dried over anhydrous sodium sulfate, filtered, and concentrated under reduced pressure. The residue was purified by trituration with diethyl ether to afford Int-7.2. m/z: 281.2 [M+H]⁺.

Synthesis of compound Int-7.3. To Int-7.2 (65 g, 231 mmol 1.0 equiv) was added hydrochloric acid:water (2:1, 600 mL) and the reaction mixture heated 100° C. for 6 h. It was concentrated under reduced pressure. The residue was dissolved in acetonitrile-THF (1:4, 250 mL) and the solution was concentrated under reduced pressure to afford Int-7.3. MS(ES): m/z 181.1 [M+H]⁺.

Synthesis of compound Int-7.4. To a solution of Int-7.3 (38 g, 210 mmol, 1.0 equiv) in DMF (4000 mL) was added potassium carbonate (57.96 g, 420 mmol, 2.0 equiv) followed by methyl iodide (15.7 mL, 252 mmol, 1.2 equiv) and reaction mixture was stirred at room temperature for 4 h. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 25% ethyl acetate in hexane) to afford Int-7.4. MS(ES): m/z 195.0 [M+H]⁺.

Synthesis of compound Int-7.5. To a solution of Int-7.4 (22 g, 113.29 mmol, 1.0 equiv) in 1,2-dichloroethane (130 mL) was added diethylaminosulfur trifluoride (150 mL, 1132.9 mmol, 10.0 equiv) and the reaction mixture was stirred at room temperature for 5 days. It was transferred into ice-cold saturated sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 20% ethyl acetate in hexane) to afford Int-7.5. MS(ES): m/z 217.1 [M+H]+.

Synthesis of compound Int-7.6. To a solution of Int-7.5 (11.2 g, 51.81 mmol, 1.0 equiv) in THF (110 mL) was added lithium hydroxide (4.35 g, 103.62 mmol, 2.0 equiv) and water (11 mL). The reaction mixture was stirred at room temperature for 16 h. It was poured into ice-water, and adjusted pH to 5 by adding 2 M hydrochloric acid. Product was extracted with ethyl acetate. The combined organic layers were washed with brine, dried over anhydrous sodium sulfate, filtered, and concentrated under reduced pressure to afford Int-7.6. MS(ES): m/z 203.0 [M+H]⁺.

Synthesis of compound Int-7.7. To a suspension of Int-7.6 (8.0 g, 39.57 mmol, 1.0 equiv) in toluene (100 mL) was added triethylamine (11 mL, 79.14 mmol, 2.0 equiv), followed by benzyl alcohol (21.4 g, 197.85 mmol, 5.0 equiv) and diphenylphosphoryl azide (21.77 g, 79.14 mmol, 2.0 equiv). The reaction mixture was stirred at 90° C. for 16 h. It was poured into ice-water and extracted with ethyl acetate. The combined organic layers were washed with brine, dried over anhydrous sodium sulfate, filtered, and concentrated under reduced pressure to afford to afford crude material. This was further purified by flash column chromatography on silica gel (CombiFlash®, 15% ethyl acetate in hexane) to afford Int-7.7. MS(ES): m/z 308.2 [M+H]⁺.

Synthesis of compound Int-7.8. A mixture of Int-7.7 (5.4 g, 17.57 mmol, 1.0 equiv) and 10% palladium on charcoal (2.0 g) in methanol (100 mL) was stirred under hydrogen (1 atm) for 2 h. It was filtered through a pad of Celite® and rinsed with methanol. The filtrate was concentrated under reduced pressure to afford Int-7.8. MS(ES): m/z 174.1 [M+H]⁺.

Synthesis of compound Int-7. Compound Int-7 was prepared from Int-7.8 following the procedure described in the synthesis of Int-3. It was used without purification. MS(ES): m/z 216.2 [M+H]⁺.

Preparation of Intermediate Int-8: 2-isothiocyanato-5-methyl-6,7-dihydropyrazolo[1,5-a]pyrazin-4(5H)-one

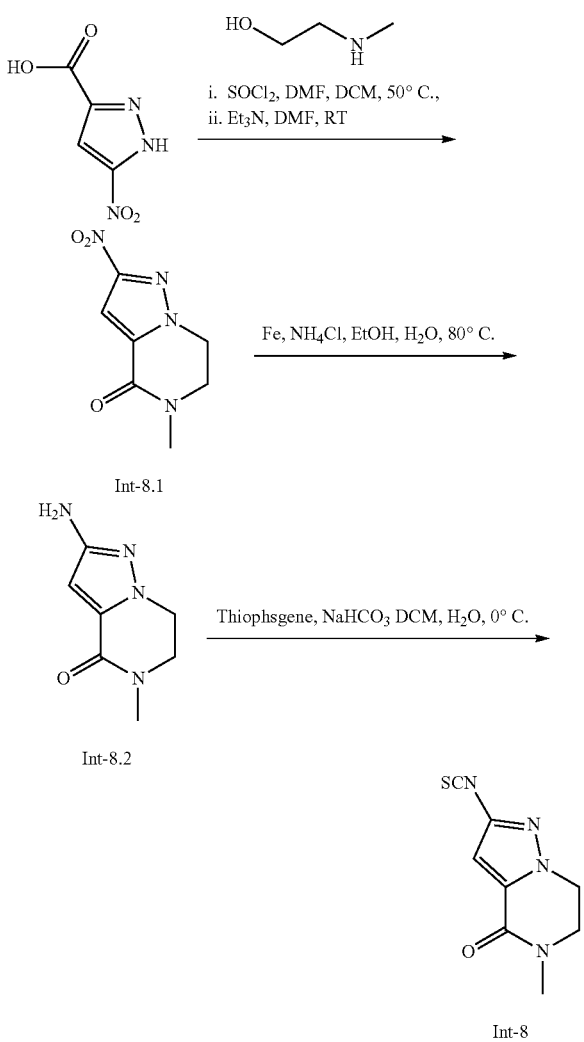

Synthesis of compound Int-8.1. To a solution of 5-nitro-1H-pyrazole-3-carboxylic acid (2.0 g, 12.73 mmol, 1.0 equiv) and 2-(methylamino)ethan-1-ol (1.43 g, 19.10 mmol, 1.5 equiv) in DCM (20 mL) were added dropwise thionyl chloride (4.6 mL, 63.65 mmol, 5.0 equiv) and a drop of DMF at −5° C. The reaction mixture was stirred for 10 and it was heated at 50° C. for 16 h. It was cooled to room temperature and concentrated under reduced pressure. The residue was dissolved in DMF (20 mL) and was added triethylamine (5.3 mL, 38.19 mmol, 3.0 equiv) stirred for 16 h. It was poured into ice-water and extracted with DCM. The combined organic layers were washed with brine, dried over anhydrous sodium sulfate, filtered, and concentrated under reduced pressure. The residue was purified by flash column chromatography on silica gel (CombiFlash®, 1.0% methanol in DCM) to afford Int-8.1. MS (ES): m/z 197.1 [M+H]⁺.

Synthesis of compound Int-8.2. A mixture of Int-8.1 (1.3 g, 6.63 mmol, 1.0 equiv), ammonium chloride (1.79 g, 33.15 mmol, 5.0 equiv) and iron powder (1.85 g, 33.15 mmol 5.0 equiv) in ethanol (20 mL) and water (7 mL) was stirred at 80° C. for 4 h. It was cooled to room temperature and filtered through a pad of Celite®. The filtrate was poured into ice-water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 1.5% methanol in DCM) to afford Int-8.2. MS(ES): m/z 167.0 [M+H]⁺.

Synthesis of compound Int-8. Compound Int-8 was prepared from Int-8.2 following the procedure described in the synthesis of Int-3. The product was purified by flash column chromatography on silica gel (CombiFlash®, 0.5% methanol in DCM). MS(ES): m/z 209.1 [M+H]⁺.

Preparation of Intermediate Int-9: 2-isothiocyanato-4,4-dimethyl-6,7-dihydro-4H-pyrazolo[5,1-c][1,4]oxazine

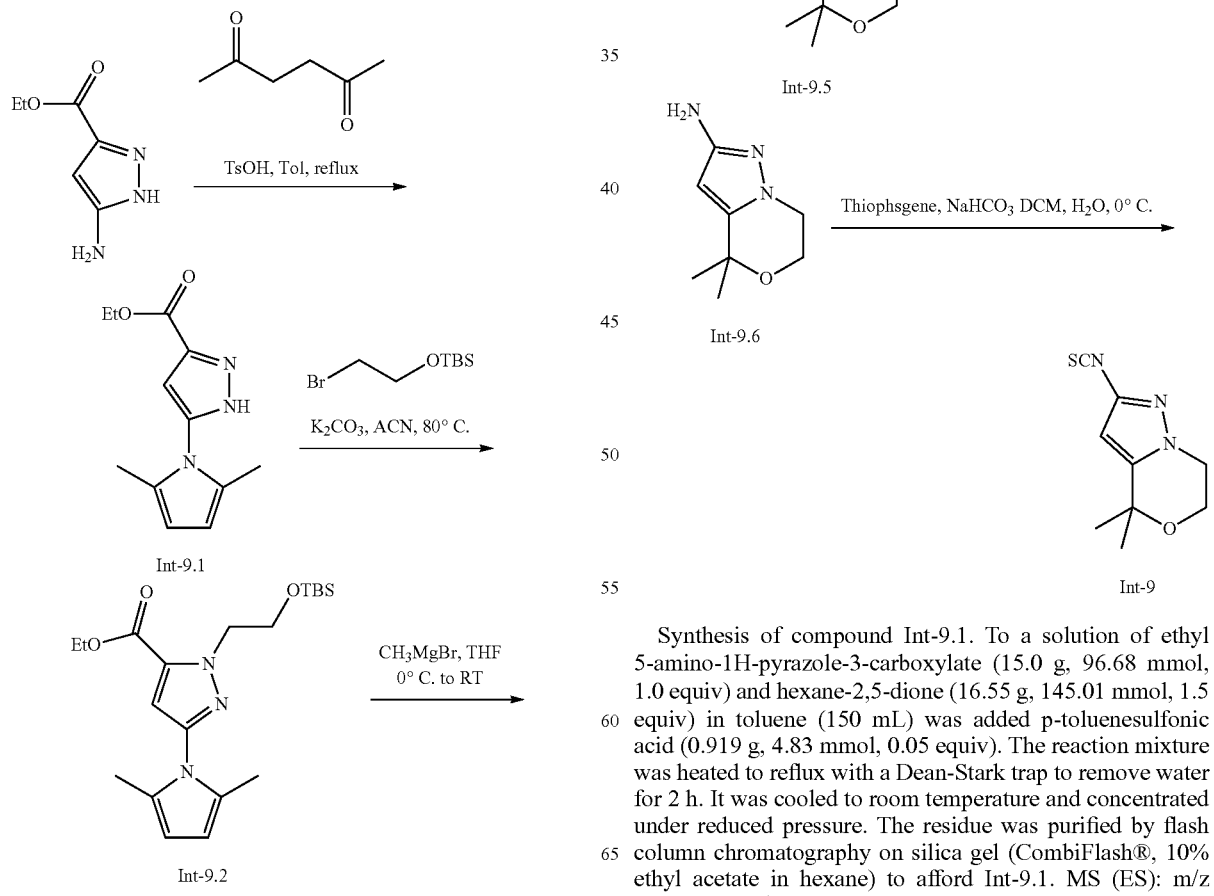

Synthesis of compound Int-9.1. To a solution of ethyl 5-amino-1H-pyrazole-3-carboxylate (15.0 g, 96.68 mmol, 1.0 equiv) and hexane-2,5-dione (16.55 g, 145.01 mmol, 1.5 equiv) in toluene (150 mL) was added p-toluenesulfonic acid (0.919 g, 4.83 mmol, 0.05 equiv). The reaction mixture was heated to reflux with a Dean-Stark trap to remove water for 2 h. It was cooled to room temperature and concentrated under reduced pressure. The residue was purified by flash column chromatography on silica gel (CombiFlash®, 10% ethyl acetate in hexane) to afford Int-9.1. MS (ES): m/z 234.2 [M+H]⁺.

Synthesis of compound Int-9.2. To a mixture of Int-9.1 (10 g, 42.87 mmol, 1.0 equiv), (2-bromoethoxy)(tert-butyl)dimethylsilane (15.38 g, 64.30 mmol, 1.0 equiv) and potassium carbonate (17.74 g, 128.61 mmol, 3.0 equiv) in acetonitrile (100 mL) was stirred at 80° C. for 1 h. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 15% ethyl acetate in hexane) to afford Int-9.2. MS(ES): m/z 392.2 [M+H]+.

Synthesis of compound Int-9.3. To a solution of Int-9.2 (7.2 g, 18.39 mmol, 1.0 equiv) in THF (70 mL) was added methyl magnesium bromide (3 M in diethyl ether, 18.4 mL, 55.17 mmol, 3.0 equiv) at 0° C. The reaction mixture was stirred at room temperature for 1 h. The reaction mixture was poured into ice-water, and product extracted with ethyl acetate. The combined organic layers were washed with brine, dried over anhydrous sodium sulfate, filtered, and concentrated under reduced pressure. The residue was purified by flash column chromatography on silica gel (CombiFlash®, 18% ethyl acetate in hexane) to afford Int-9.3. m/z: 378.5 [M+H]+.

Synthesis of compound Int-9.4. To a solution of Int-9.3 (5.3 g, 14.04 mmol, 1.0 equiv) in THF (50 mL) was added tetrabutylammonium fluoride solution (1 M in THF, 35 mL, 35.1 mmol, 2.5 equiv) at 0° C. The reaction mixture was stirred at room temperature for 1 h. It was poured into ice-water, and product extracted with ethyl acetate. The combined organic layers were washed with brine, dried over anhydrous sodium sulfate, filtered, and concentrated under reduced pressure. The residue was purified by flash column chromatography on silica gel (CombiFlash®, 25% ethyl acetate in hexane) to afford Int-9.4. m/z: 264.2 [M+H]+.

Synthesis of compound Int-9.5. To a solution of Int-9.4 (2.3 g, 8.73 mmol, 1.0 equiv) and 4-dimethylaminopyridine (0.010 g, 0.087 mmol, 0.01 equiv) in DCM (25 mL) was added a solution of 4-toluenesulfonyl chloride (2.16 g, 11.34 mmol, 1.3 equiv) in DCM (5 mL) and triethylamine (3.7 mL, 26.19 mmol, 3.0 equiv) at 0° C. The reaction mixture was stirred at room temperature for 1 h. It was poured into ice-water, and product extracted with DCM. The combined organic layers were washed with brine, dried over anhydrous sodium sulfate, filtered, and concentrated under reduced pressure to afford material. To the solution of this crude material in THF (50 mL) was added sodium hydride (1.05 g, 26.19 mmol, 3.0 equiv) at 0° C. The reaction mixture was stirred at room temperature for 30 min. It was poured into ice-water, and product extracted with ethyl acetate. The combined organic layers were washed with brine, dried over anhydrous sodium sulfate, filtered, and concentrated under reduced pressure. The residue was purified by flash column chromatography on silica gel (CombiFlash®, 30% ethyl acetate in hexane) to afford Int-9.5. m/z: 246.2 [M+H]+.

Synthesis of compound Int-9.6. To a solution of Int-9.5 (0.900 g, 3.67 mmol, 1.0 equiv) in ethanol-water (2:1, 20 mL) was added hydroxylamine hydrochloride (12.75 g, 183.5 mmol, 50 equiv). The reaction mixture was stirred at 120° C. for 1 h. It was poured into ice-water and neutralized by 2 N sodium hydroxide. The mixture was extracted with DCM. The combined organic layers were washed with brine, dried over anhydrous sodium sulfate, filtered, and concentrated under reduced pressure. The residue was purified by flash column chromatography on silica gel (CombiFlash®, 2% methanol in DCM) to afford Int-9.6. MS(ES): m/z 168.1 [M+H]+.

Synthesis of compound Int-9. Compound Int-9 was prepared from Int-9.6 following the procedure described in the synthesis of Int-3. The product was purified by flash column chromatography on silica gel (CombiFlash®, DCM). MS(ES): m/z 210.1 [M+H]+.

Preparation of Intermediate Int-10: 2'-isothiocyanato-5',6'-dihydrospiro[cyclobutane-1,4'-pyrrolo[1,2-b]pyrazole]

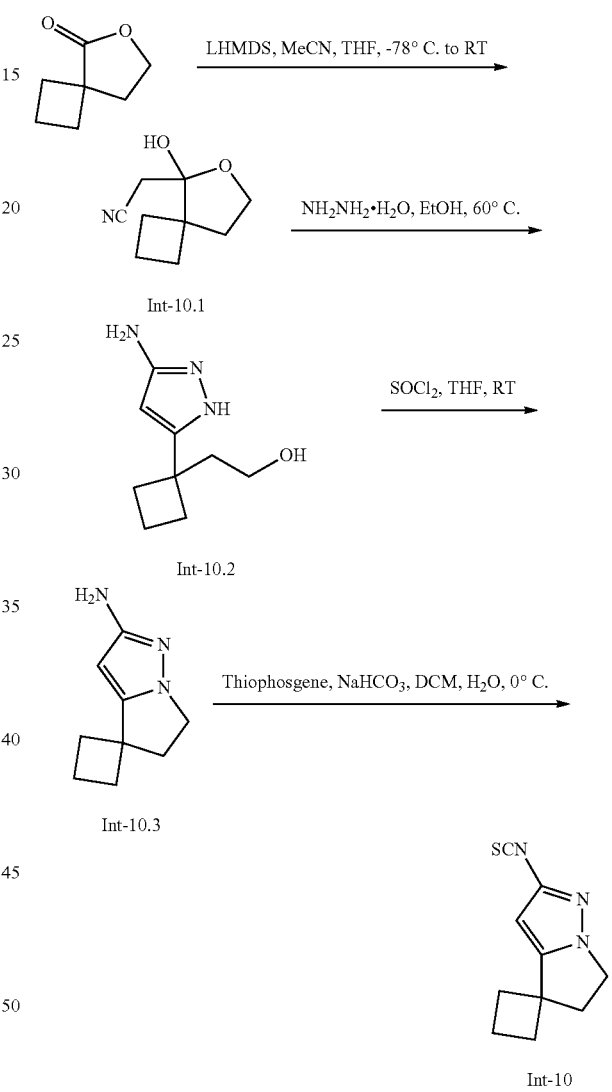

Synthesis of compound Int-10.1. To a solution of lithium bis(trimethylsilyl)amide (1 M in THF, 17.4 mL, 17.44 mmol, 2.2 equiv) in anhydrous tetrahydrofuran (25 mL) at −78° C. was added a solution of 6-oxaspiro[3.4]octan-5-one (1.0 g, 7.93 mmol, 1.0 equiv) and acetonitrile (0.83 mL, 15.86 mmol, 2.0 equiv) in tetrahydrofuran (8 mL). The reaction mixture was stirred at −78° C. for 30 min and it was allowed to warm to room temperature stirring for 2 h. It was transferred into saturated aqueous ammonium chloride solution and extracted with dichloromethane. The combined organic layers were washed with brine, dried over anhydrous sodium sulfate, filtered, and concentrated under reduced pressure to obtain residue which was purified by flash column chromatography on silica gel (CombiFlash®, 20% ethyl acetate in hexane) to afford Int-10.1. NMR (DMSO-$d_6$, 400 MHz): δ 4.01 (s, 1H), 3.76 (m, 1H), 3.66-3.62 (m, 1H), 2.84 (bs, 2H), 2.10 (bs, 2H), 1.99 (bs, 2H), 1.87-1.82 (m, 2H), 1.67 (bs, 2H).

Synthesis of compound Int-10.2. To a solution of Int-10.1 (0.800 g, 4.78 mmol, 1.0 equiv) in ethanol (10 mL) was added hydrazine monohydrate (0.358 g, 7.17 mmol, 1.5 equiv). The reaction mixture was heated at 60° C. for 72 h. The reaction mixture was cooled to room temperature and carbon dioxide was bubbled through it for 1 h. It was concentrated under reduced pressure. To the residue was added methanol (15 mL) and stirred for a while. The precipitated solids were removed by filtration. The filtration was concentrated under reduced pressure to obtain Int-10.2. MS(ES): m/z 182.1 [M+H]$^+$.

Synthesis of compound Int-10.3. To a solution of Int-10.2 (0.610 g, 3.37 mmol, 1.0 equiv) in THF (10 mL) was added thionyl chloride (1.22 mL, 16.85 mmol, 5.0 equiv). The reaction mixture was stirred at room temperature for 3 h. It was slowly transferred into (1:1) mixture of aqueous ammonium hydroxide and ice, stirred and extracted with dichloromethane. The combined organic layers were washed with brine, dried over anhydrous sodium sulfate, filtered, and concentrated under reduced pressure to obtain residue which was purified by flash column chromatography on silica gel (CombiFlash®, 2% methanol in dichloromethane) to afford Int-10.3. MS(ES): m/z 164.1 [M+H]$^+$.

Synthesis of compound Int-10. Compound Int-10 was prepared from Int-10.3 following the procedure described in the synthesis of Int-3. The product was purified by flash column chromatography on silica gel (CombiFlash®, dichloromethane). MS(ES): m/z 205.9 [M+H]$^+$.

Preparation of Intermediate Int-11: 2'-isothiocyanato-6',7'-dihydro-5'H-spiro[cyclopropane-1,4'-pyrazolo[1,5-a]pyridine]

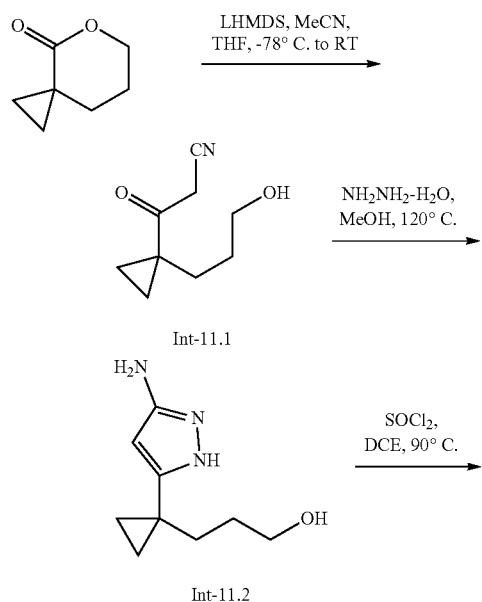

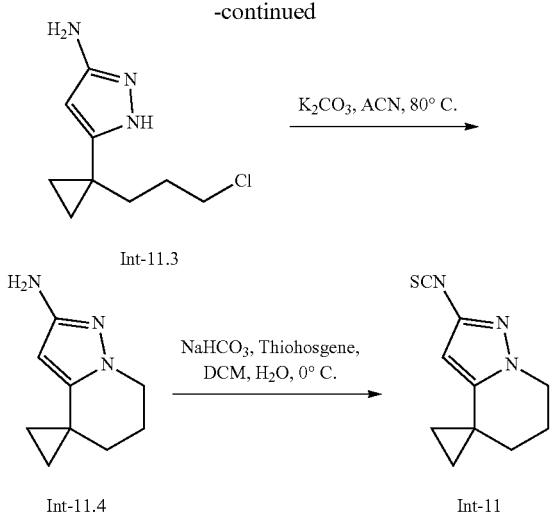

Synthesis of compound Int-11.1. To a solution of LiHMDS (35 mL, 35 mmol, 2.2 equiv) in THF (40 mL) at –78° C. was added acetonitrile (1.3 g, 32 mmol, 2 equiv) dropwise. The resulting solution was stirred for 1 h, and a solution of 5-oxaspiro[2.5]octan-4-one (2 g, 15.85 mmol, 1 equiv) in THF (10 mL) was added dropwise. The reaction mixture was stirred at –78° C. for another 2 h. It was allowed to warm to room temperature and quenched by a saturated ammonium chloride solution and extracted by DCM. The combined organic layers were washed with brine, dried over anhydrous sodium sulfate, filtered, and concentrated under reduced pressure to afford Int-11.1. MS(ES): m/z: 167.21 [M+H]$^+$.

Synthesis of compound Int-11.2. To a solution of Int-11.1 (1.7 g, 10.17 mmol, 1 equiv) in methanol (50 mL) was added hydrazine hydrate (1.52 g, 30.51 mmol, 3 equiv). The reaction mixture was stirred at in an autoclave at 120° C. for 16 h. The reaction mixture was cooled to room temperature and dry ice was added slowly over a period of 15 min. The solution was decanted, and solvent removed under reduced pressure. The residue was purified by flash column chromatography on silica gel (CombiFlash®, 6.0% methanol in DCM) to afford Int-11.2. MS(ES): m/z 181.24 [M+H]$^+$.

Synthesis of compound Int-11.3. To a stirred solution of Int-11.2 (1.2 g, 6.62 mmol, 1 equiv) in dichloroethane (24 mL) was added thionyl chloride (0.937 g, 7.94 mmol, 1.2 equiv) at room temperature. The reaction mixture was stirred at 90° C. for 1 h. The reaction mixture was cooled to room temperature, quenched by a saturated aqueous potassium carbonate solution and extracted by DCM. The combined organic layers were washed with brine, dried over anhydrous sodium sulfate, filtered, and concentrated under reduced pressure to afford Int-11.3. MS(ES): m/z: 199.68 [M+H]$^+$.

Synthesis of compound Int-11.4. A mixture of Int-11.3 (1 g, 5.01 mmol, 1 equiv) and $K_2CO_3$ (1.38 g, 10.02 mmol, 2 equiv) in acetonitrile (20 mL) was stirred at 80° C. for 16 h. It was cooled to room temperature, poured into water and extracted by DCM. The combined organic layers were washed with brine, dried over anhydrous sodium sulfate, filtered, and concentrated under reduced pressure. The residue was purified by flash column chromatography on silica gel (CombiFlash®, 5.0% methanol in DCM) to afford Int-11.4. MS(ES): m/z: 163.22 [M+H]$^+$.

Synthesis of compound Int-11. Compound Int-11 was prepared from Int-11.4, following the procedures described in the synthesis of Int-3. The product was purified by flash column chromatography on silica gel (CombiFlash®, 40% ethyl acetate in hexane). MS(ES): m/z 205.28 [M+H]+.
Preparation of Intermediate Int-12: 2-isothiocyanato-4,4-dimethyl-4,5,7,8-tetrahydropyrazolo[1,5-d][1,4]oxazepane
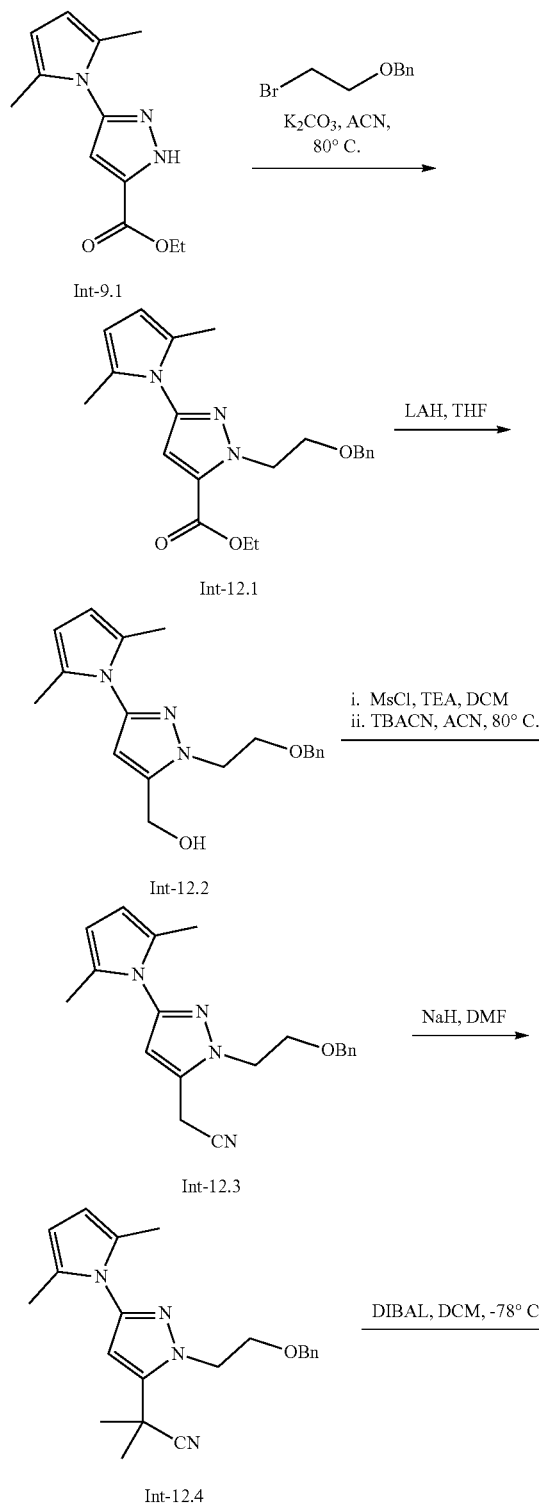
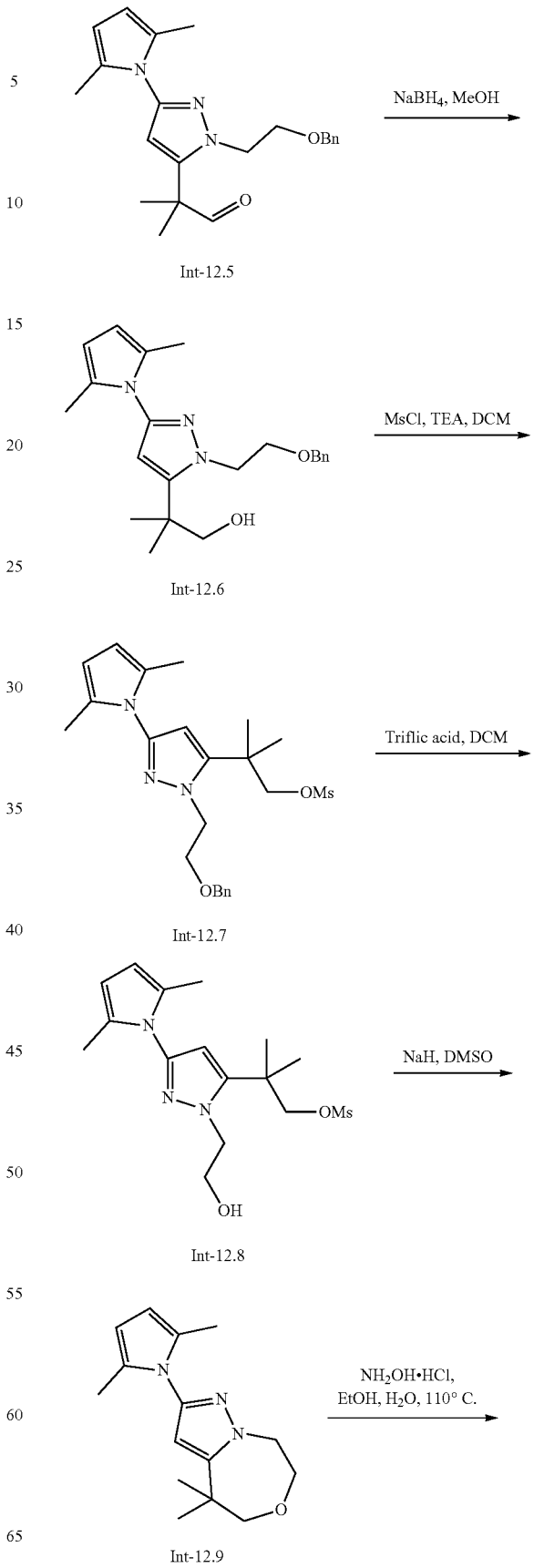

-continued

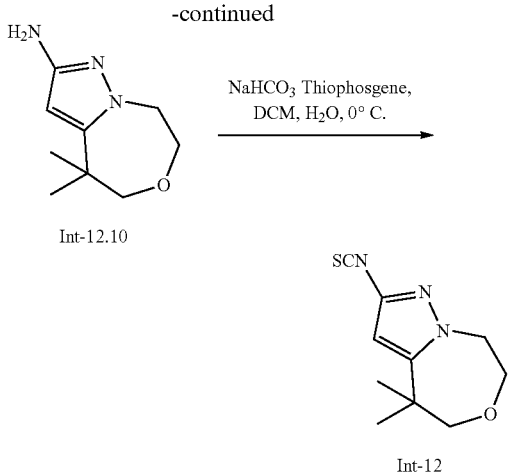

Synthesis of compound Int-12.1. A mixture of Int-9.1 (40 g, 171.67 mmol, 1.0 equiv), ((2-bromoethoxy)methyl)benzene (46.13 g, 214.59 mmol, 1.25 equiv) and potassium carbonate (71.07 g, 515.02 mmol, 3.0 equiv) in acetonitrile (100 mL) was stirred at 80° C. for 1 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 15% ethyl acetate in hexane) to afford Int-12.1. MS(ES): m/z 369.2 $[M+H]^+$.

Synthesis of compound Int-12.2. To a solution of Int-12.1 (34.8 g, 94.56 mmol, 1.0 equiv) in THF (350 mL) was added lithium aluminum hydride (1 M in THF, 60.0 mL, 94.56 mmol, 1.0 equiv) at 0° C. and was stirred for 30 min. It was poured into ethyl acetate and the precipitates were removed by filtering through a pad of Celite®. The filtrate was concentrated under reduced pressure to afford Int-12.2. MS(ES): m/z 326.1 $[M+H]^+$.

Synthesis of compound Int-12.3. To a solution of Int-12.2 (30.6 g, 94.15 mmol, 1.0 equiv) and triethylamine (23.77 g, 235.38 mmol, 2.5 equiv) in DCM (300 mL) was added methanesulfonyl chloride (16.1 g, 141.23 mmol, 1.5 equiv) at 0° C. and was stirred for 20 min. It was transferred into ice-water and extracted with DCM. The combined organic layers were dried over anhydrous sodium sulfate, filtered, and concentrated under reduced pressure. To the residue was added acetonitrile, followed by tetrabutylammoniumcyanide (55.59 g, 207.38 mmol, 2.0 equiv). The mixture was stirred at 80° C. for 1 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 28% ethyl acetate in hexane) to afford Int-12.3. MS(ES): m/z: 335.3 $[M+H]^+$.

Synthesis of compound Int-12.4. To a solution of Int-12.3 (20.8 g, 62.27 mmol, 1.0 equiv) in DMF (220 mL) was added sodium hydride (60%, 7.47 g, 186.82 mmol, 3.0 equiv) followed by methyl iodide (44.21 g, 311.37 mmol, 5.0 equiv) at 0° C. The reaction mixture was stirred at room temperature for 1 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 17% ethyl acetate in hexane) to afford Int-12.4. MS(ES): m/z: 363.61 $[M+H]^+$.

Synthesis of compound Int-12.5. To a solution of Int-12.4 (2.0 g, 5.52 mmol, 1.0 equiv) in DCM (25 mL) was added diisobutylaluminum hydride (1.0 M in hexane, 10.0 mL) at −78° C. and was stirred for 30 min. The reaction mixture was poured into a saturated aqueous solution of sodium potassium tartrate and was stirred for 1 h. It was filtered through a pad of Celite® and the filtrate was extracted with ethyl acetate. The combined organic layers were washed with brine, dried over anhydrous sodium sulfate, filtered, and concentrated under reduced pressure. The residue was purified by flash column chromatography on silica gel (CombiFlash®, 20% ethyl acetate in hexane) to afford Int-12.5. MS(ES): m/z: 366.61 $[M+H]^+$.

Synthesis of compound Int-12.6. To a solution of Int-12.5 (11.4 g, 31.23 mmol, 1.0 equiv) in methanol (125 mL) was added sodium borohydride (11.4 g, 62.46 mmol, 2.0 equiv) at 0° C. and was stirred for 1 h. It was poured into dilute hydrochloric acid (30 mL) and extracted with ethyl acetate. The combined organic layers were washed with brine, dried over anhydrous sodium sulfate, filtered, and concentrated under reduced pressure. The residue was purified by flash column chromatography on silica gel (CombiFlash®, 40% ethyl acetate in hexane) to afford Int-12.6. MS(ES): m/z: 368.41 $[M+H]^+$.

Synthesis of compound Int-12.7. To a solution of Int-12.6 (9.75 g, 26.56 mmol, 1.0 equiv) and triethylamine (10.7 g, 106.26 mmol, 4.0 equiv) in DCM (130 mL) was added methanesulfonyl chloride (6.05 g, 53.13 mmol, 2.0 equiv) at 0° C. The reaction mixture was stirred at room temperature for 30 min, transferred into water and extracted with DCM. The combined organic layers were washed with brine, dried over anhydrous sodium sulfate, filtered, and concentrated under reduced pressure. The residue was purified by flash column chromatography on silica gel (CombiFlash®, 28% ethyl acetate in hexane) to afford Int-12.7. MS(ES): m/z: 446.81 $[M+H]^+$.

Synthesis of compound Int-12.8. To a solution of Int-12.7 (7.8 g, 17.52 mmol, 1.0 equiv) in DCM (150 mL) was added trifluoromethanesulfonic acid (20.0 mL) at 0° C. and was stirred for 15 min. It was poured into a saturated aqueous solution of sodium bicarbonate and extracted with DCM. The combined organic layers were washed with brine, dried over anhydrous sodium sulfate, filtered, and concentrated under reduced pressure. The residue was purified by flash column chromatography on silica gel (CombiFlash®, 2% methanol in DCM) to afford Int-12.8. MS(ES): m/z: 356.36 $[M+H]^+$.

Synthesis of compound Int-12.9. To a solution of Int-12.8 (4.1 g, 11.54 mmol, 1.0 equiv) in dimethyl sulfoxide (60 mL) was added sodium hydride (60%, 2.30 g, 57.74 mmol, 5.0 equiv) at room temperature and was stirred for 2 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 25% ethyl acetate in hexane) to afford Int-12.9. MS(ES): m/z: 260.26 $[M+H]^+$.

Synthesis of compound. Int-12.10. To a solution of Int-12.9 (1.9 g, 7.33 mmol, 1.0 equiv) in ethanol and water (1:1, 25 mL) was added hydroxylamine hydrochloride (20.24 g, 293.43 mmol, 40.0 equiv) at room temperature. The reaction mixture was stirred at 120° C. for 4 h. It was poured into a saturated aqueous solution of sodium bicarbonate and extracted with DCM. The combined organic layers were washed with brine, dried over anhydrous sodium sulfate, filtered, and concentrated under reduced pressure. The residue was purified by flash column chromatography on silica gel (CombiFlash®, 4.2% methanol in DCM) to afford Int-12.10. MS(ES): m/z: 182.27 [M+H]$^+$.

Synthesis of compound Int-12. Compound Int-12 was prepared from Int-12.10, following the procedures described in the synthesis of Int-3. The product was purified by flash column chromatography on silica gel (CombiFlash®, DCM). MS(ES): m/z 224.1 [M+H]$^+$.

Preparation of Intermediate Int-13: 1-(tert-butyl)-6-isothiocyanato-2,3-dihydro-1H-imidazo[1,2-b]pyrazole

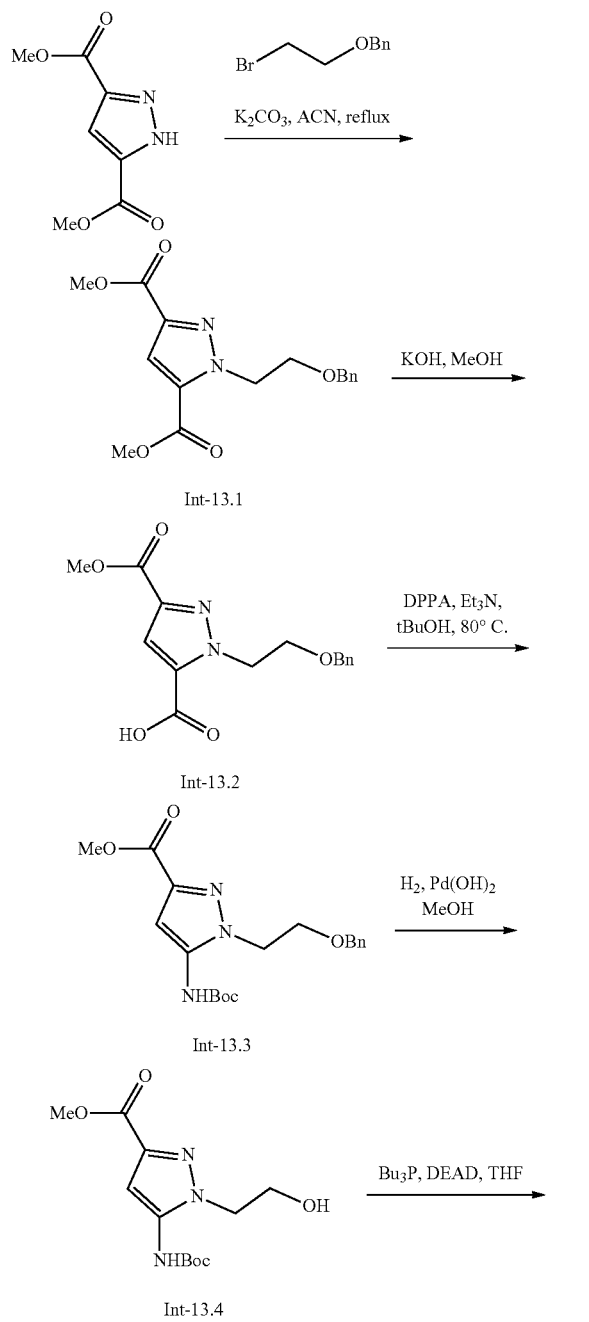
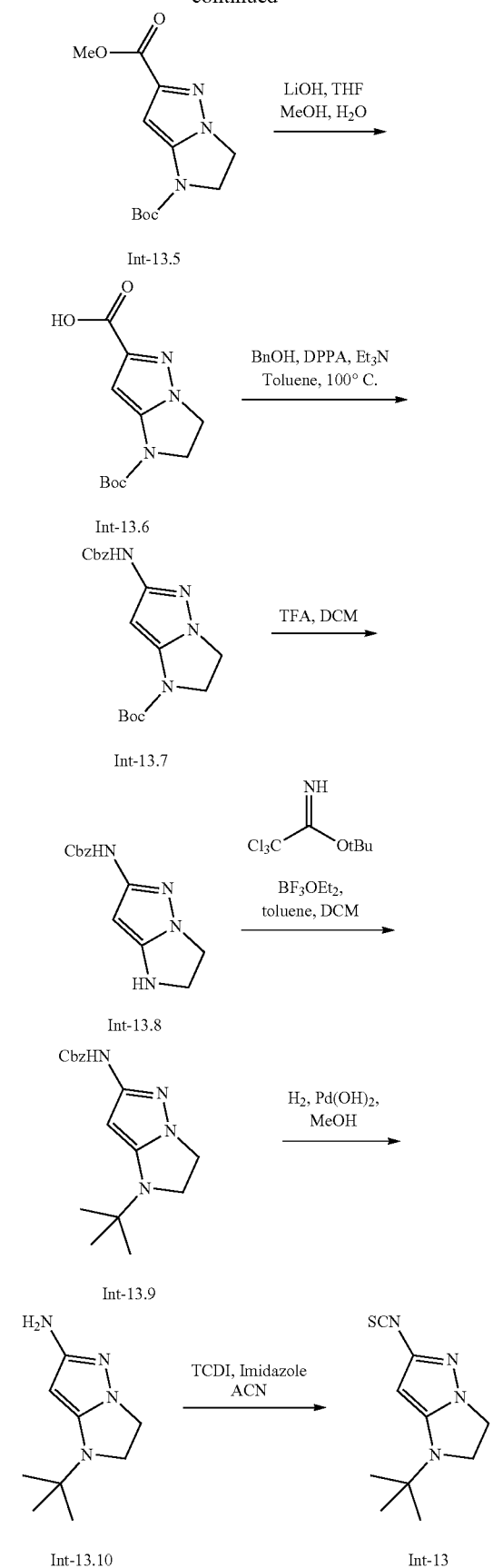

Synthesis of compound Int-13.1. A mixture of dimethyl 1H-pyrazole-3,5-dicarboxylate (25 g, 135.76 mmol, 1.0 equiv), potassium carbonate (28.10 g, 203.64 mmol, 1.5 equiv) and ((2-bromoethoxy)methyl)benzene (37.96 g, 176.49 mmol, 1.3 equiv) in acetonitrile (250 mL) was stirred at 80° C. for 4 h. It was cooled to room temperature, transferred into ice-water, and extracted with ethyl acetate. The combined organic layers were washed with brine, dried over anhydrous sodium sulfate, filtered, and concentrated under reduced pressure to afford Int-13.1. MS(ES): m/z 319.1 [M+H]$^+$.

Synthesis of compound Int-13.2. To a solution of Int-13.1 (32.5 g, 102.10 mmol, 1.0 equiv) and potassium hydroxide (5.61 g, 102.10 mmol, 1.0 equiv) in methanol (200 mL) was stirred at room temperature under nitrogen atmosphere for 16 h. It was concentrated under reduced pressure. The residue was added to water, acidified with dilute hydrochloric acid and extracted with ethyl acetate. The combined organic layers were washed with brine, dried over anhydrous sodium sulfate, filtered, and concentrated under reduced pressure to afford Int-13.2 MS(ES): m/z 305.2 [M+H]$^+$.

Synthesis of compound Int-13.3. To a solution of compound Int-13.2 (28.50 g, 93.66 mmol, 1.0 equiv) and triethylamine (16.2 mL, 112.39 mmol, 1.2 equiv) in tert-butanol (40 mL) was added diphenyl phosphoryl azide (30.9 g, 112.39 mmol, 1.2 equiv) under nitrogen at room temperature. The reaction mixture was stirred at 80° C. for 3 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 25-30% ethyl acetate in hexane) to afford Int-13.3. MS(ES): m/z: 376.7 [M+H]$^+$.

Synthesis of compound Int-13.4. A mixture of compound Int-133 (21.0 g, 55.94 mmol, 1.0 equiv) and 20% palladium on hydroxide (5.25 g) in methanol (210 mL) was stirred under hydrogen for 8 h. It was filtered through a pad of Celite® and rinsed with methanol. The filtrate was concentrated under reduced pressure to afford Int-13.4. MS(ES): m/z: 286 [M+H]$^+$.

Synthesis of compound Int-13.5. To a solution of compound Int-13.4 (15 g, 52.58 mmol, 1.0 equiv) in THF (300 mL) was added tri-cert-butyl phosphine (15.93, 78.87 mmol, 1.5 equiv) followed by diethyl azodicarboxylate (19.87 g, 78.87 mmol, 1.5 equiv) at 0° C. The reaction mixture was stirred at room temperature for 2 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 50-55% ethyl acetate in hexane) to afford Int-13.5. MS(ES): m/z: 268.7 [M+H]$^+$.

Synthesis of compound Int-13.6. To a solution of Int-13.5 (13.0 g, 48.64 mmol, 1.0 equiv) in a mixture of THF and methanol (100 mL, 5:1) was added lithium hydroxide (6.1 g, 145.92 mmol, 3.0 equiv) solution in water, and stirred at room temperature for 2 h. The reaction mixture was concentrated under reduced pressure. To the residue was added water and pH adjusted to 3-4 with 1N hydrochloric acid. The mixture was extracted with ethyl acetate. The combined organic layers were washed with brine, dried over anhydrous sodium sulfate, filtered, and concentrated under reduced pressure to afford Int-13.6. MS(ES): m/z 254.5 [M+H]$^+$.

Synthesis of compound Int-13.7. To a suspension of compound Int-13.6 (9.5 g, 37.51 mmol, 1.0 equiv) in toluene (20 mL) was added benzyl alcohol (4.8 g, 45.01 mmol, 1.2 equiv), diphenyl phosphoryl azide (12.33 g, 45.01 mmol, 1.2 equiv) and triethylamine (6.8 mL, 48.76 mmol, 1.3 equiv) at room temperature. The reaction mixture was stirred at 100° C. for 6 h. It was transferred into ice-water and extracted with ethyl acetate. The combined organic layers were washed with brine, dried over anhydrous sodium sulfate, filtered, and concentrated under reduced pressure. The residue was purified by trituration in a mixture of ethyl acetate: methanol (1:1) to afford Int-13.7. MS(ES): m/z: 359.7 [M+H]$^+$.

Synthesis of compound Int-13.8. To a solution of Int-13.7 (8.2 g, 22.88 mmol, 1.0 equiv) in DCM (5 mL) was added trifluoroacetic acid (82 mL) at room temperature. The reaction mixture was stirred for 3 h. It was transferred into a mixture of ice and saturated aqueous solution of sodium bicarbonate and extracted with 10% methanol in DCM. The combined organic layers were washed with brine, dried over anhydrous sodium sulfate, filtered, and concentrated under reduced pressure to afford Int-13.8. MS(ES): m/z 259 [M+H]$^+$.

Synthesis of compound. Int-13.9. To a solution of Int-13.8 (7.0 g, 27.10 mmol, 1.0 equiv) in a mixture of DCM:toluene (1:1, 350 mL) was added boron trifluoride etherate (7 mL) followed by tert-butyl 2,2,2-trichloroacetimidate (11.84 g, 54.20 mmol, 2.0 equiv) at room temperature. The reaction mixture was stirred for 16 h. It was transferred into an aqueous solution of sodium bicarbonate and extracted with DCM. The combined organic layers were washed with brine, dried over anhydrous sodium sulfate, filtered, and concentrated under reduced pressure. The residue was purified by flash column chromatography on silica gel (CombiFlash®, 2.3-2.5% methanol in DCM) to afford Int-13.9. MS(ES): m/z 315.2 [M+H]$^+$.

Synthesis of compound Int-13.10. A mixture of compound Int-13.9 (2.8 g, 8.91 mmol, 1.0 equiv) and 20% palladium on hydroxide (0.700 g) in methanol (42 mL) was stirred under hydrogen (1 atm) for 3 h. The reaction mixture was filtered through a pad of Celite® and rinsed with methanol. The filtrate was concentrated under reduced pressure. The residue was purified by flash column chromatography on silica gel (CombiFlash®, 3-3.5% methanol in DCM) to afford Int-13.10. MS(ES): m/z: 181.6 [M+H]$^+$.

Synthesis of compound Int-13. To a solution of Int-13.10 (1.0 g, 5.55 mmol, 1.0 equiv) in acetonitrile (15 mL) was added imidazole (0.096 g, 1.66 mmol, 0.3 equiv) followed by thiocarbonyldiimidazole (1.9 g, 11.1 mmol, 2.0 equiv) and was stirred at room temperature for 1 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 100% DCM) to afford Int-13. MS(ES): m/z: 223 [M+H]$^+$.

Preparation of Intermediate Int-14: 2-isothiocyanato-6,6-dimethyl-6,7-dihydro-4H-pyrazolo[5,1-c][1,4]oxazine

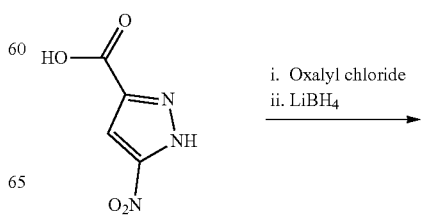

i. Oxalyl chloride
ii. LiBH$_4$

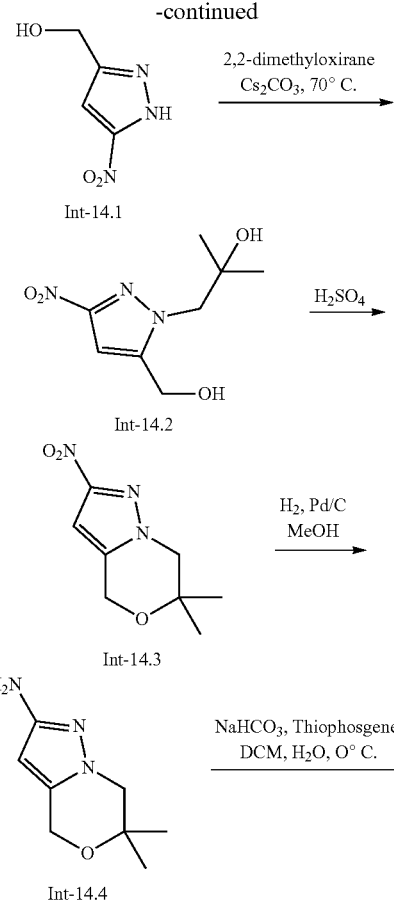

tography on silica gel (CombiFlash®, 1.2% methanol in DCM) to afford Int-14.2. MS (ES): m/z 216.81 [M+H]$^+$.

Synthesis of compound Int-14.3. A solution of Int-14.2 (0.5 g, 2.32 mmol, 1.0 equiv) in sulfuric acid (10 mL) was stirred at 45° C. for 16 h. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 0.5% methanol in DCM) to afford Int-14.3. MS (ES): m/z 198.19 [M+H]$^+$.

Synthesis of compound Int-14.4. A mixture of palladium on carbon (10%; 0.200 g) and compound Int-14.3 (350 g, 5.72 mmol, 1.0 equiv) in methanol (5 mL) was stirred under hydrogen for 2 h. The reaction mixture was filtered through a pad of Celite® and rinsed with methanol. The filtrate was concentrated under reduced pressure to afford Int-14.4. MS(ES): m/z 168.21 [M+H]$^+$.

Synthesis of compound Int-14. Compound Int-14 was prepared from Int-14.4, following the procedures described in the synthesis of Int-3. The product was purified by flash column chromatography on silica gel (CombiFlash®, 1.5% methanol in DCM). MS (ES): m/z 210.27 [M+H]$^+$.

Preparation of Intermediate Int-15: 1-(2-(benzyloxy)ethyl)-3-isothiocyanato-5-(trifluoromethyl)pyridin-2(1H)-one

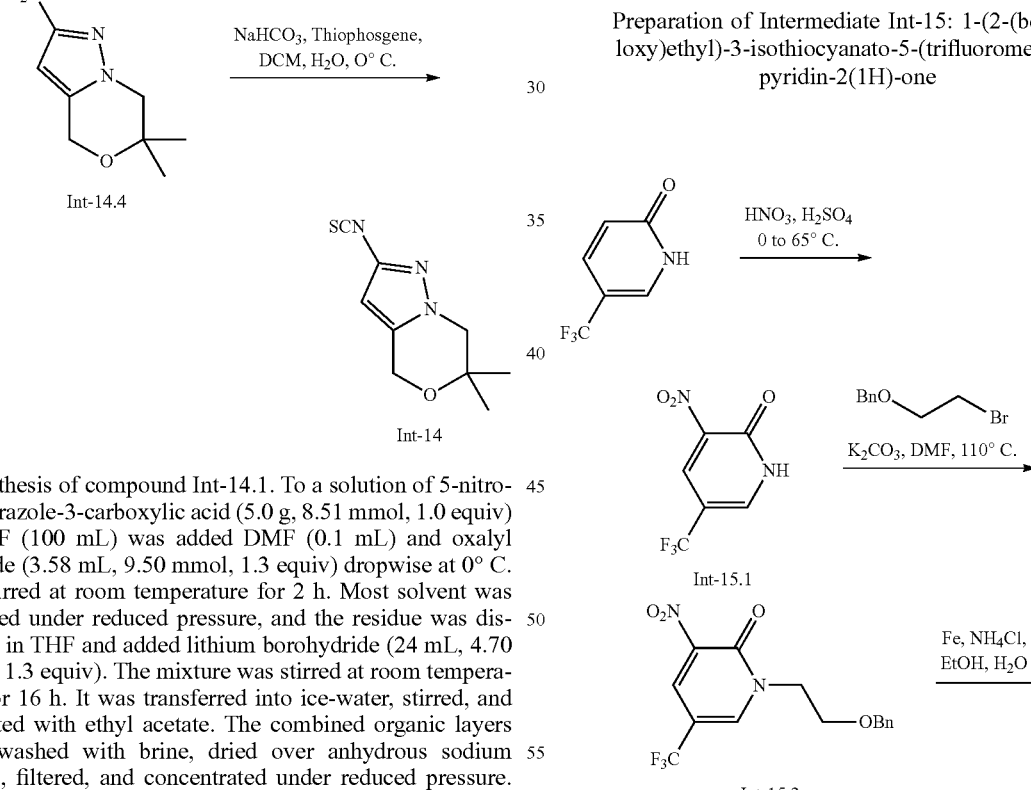

Synthesis of compound Int-14.1. To a solution of 5-nitro-1H-pyrazole-3-carboxylic acid (5.0 g, 8.51 mmol, 1.0 equiv) in THF (100 mL) was added DMF (0.1 mL) and oxalyl chloride (3.58 mL, 9.50 mmol, 1.3 equiv) dropwise at 0° C. and stirred at room temperature for 2 h. Most solvent was removed under reduced pressure, and the residue was dissolved in THF and added lithium borohydride (24 mL, 4.70 mmol, 1.3 equiv). The mixture was stirred at room temperature for 16 h. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford Int-14.1. MS (ES): m/z 143.10 [M+H]$^+$.

Synthesis of compound Int-14.2. A mixture of Int-14.1 (1.7 g, 11.77 mmol, 1.0 equiv) and cesium carbonate (0.772 g, 2.377 mmol, 0.2 equiv) in 2,2-dimethyloxirane (30 mL) was stir at 70° C. for 3 h. It was transferred into ice-water, stirred, and extracted with ethyl acetate. The combined organic layers were washed with brine, dried over anhydrous sodium sulfate, filtered, and concentrated under reduced pressure. The residue was purified by flash column chroma- -continued

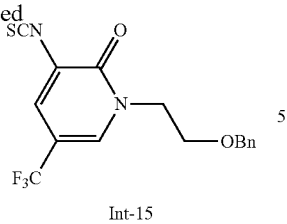

Int-15

Synthesis of compound Int-15.1. To a solution of 5-(trifluoromethyl)pyridin-2(1H)-one (5.0 g, 30.66 mmol, 1.0 equiv) in concentrated sulfuric acid (25 mL) was added fuming nitric acid (8 mL) at 0° C. The reaction mixture was stirred at 65° C. for 6 h. It was transferred into crushed ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford Int-15.1. MS(ES): m/z 209.10 [M+H]⁺.

Synthesis of compound Int-15.2. A mixture of Int-15.1 (0.5 g, 2.4 mmol, 1.0 equiv) and potassium carbonate (0.662 g, 4.8 mmol, 2.0 equiv) in DMF (7 mL) was stirred for 15 min. To the mixture was added ((2-bromoethoxy)methyl) benzene (0.775 g, 3.6 mmol, 1.5 equiv) and stirred at 110° C. for 2 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 30% ethyl acetate in hexane) to afford Int-15.2. MS(ES): m/z 343.2 [M+H]⁺.

Synthesis of compound Int-15.3. A mixture of Int-15.2 (0.322 g, 0.940 mmol, 1.0 equiv), iron powder (0.263 g, 4.7 mmol, 5.0 equiv) and ammonium chloride (0.253 g, 4.7 mmol, 5.0 equiv) in ethanol:water (2:1, 10 mL) was stirred at 80° C. for 2 h. It was transferred into ice-water, filtered, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford Int-15.3. MS(ES): m/z 313.3 [M+H]⁺.

Synthesis of compound Int-15. Compound Int-15 was prepared from Int-15.3, following the procedures described in the synthesis of Int-3. The product was purified by flash column chromatography on silica gel (CombiFlash®, 1.5% methanol in DCM). MS(ES): m/z 355.3 [M+H]⁺.

Preparation of Intermediate Int-16: 3-isothiocyanato-1-(methyl-d₃)-5-(trifluoromethyl)pyridin-2(1H)-one

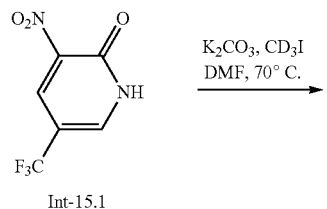

Int-15.1

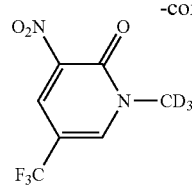

Int-16.1

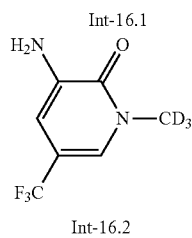

Int-16.2

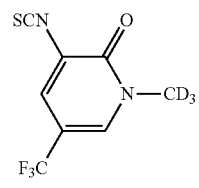

Int-16

Synthesis of compound Int-16.1. A mixture of Int-15.1 (12 g, 57.67 mmol, 1.0 equiv) and potassium carbonate (23.87 g, 173.01 mmol, 3.0 equiv) in DMF (140 mL) was stirred for 15 min before the addition of iodomethane-d₃ (10.03 g, 69.20 mmol, 1.2 equiv). The reaction mixture was stirred at 70° C. for 1 h. It was transferred into water, stirred, and extracted with ethyl acetate. The combined organic layers were washed with brine, dried over anhydrous sodium sulfate, filtered, and concentrated under reduced pressure to afford Int-16.1. MS(ES): m/z 226.1 [M+H]⁺.

Synthesis of compound Int-16.2. A mixture of Int-16.1 (10 g, 44.42 mmol, 1.0 equiv), iron powder (12.43 g, 222.1 mmol, 5.0 equiv), acetic acid (17.76 g, 222.1 mmol, 5.0 equiv) in ethanol (100 mL) and water (20 mL) was stirred at 80° C. for 3 h. The reaction mixture was concentrated under reduced pressure. The residue was transferred into saturated sodium bicarbonate and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford Int-16.2. MS(ES): m/z 196.2 [M+H]⁺.

Synthesis of compound Int-16. Compound Int-16 was prepared from Int-16.2, following the procedures described in the synthesis of Int-3. The product was purified by flash column chromatography on silica gel (CombiFlash®, 30% ethyl acetate in hexane). MS(ES): m/z 238.1 [M+H]⁺.

Preparation of Intermediate (±)-Int-17: 2-(tetrahydrofuran-3-yl)-6-(trifluoromethyl)pyridin-4-amine

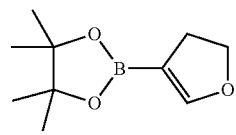

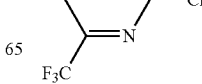

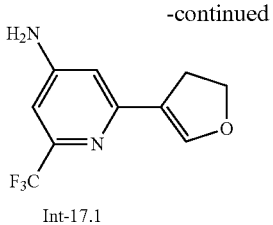

Int-17.1

H₂, Pd(OH)₂
MeOH
→

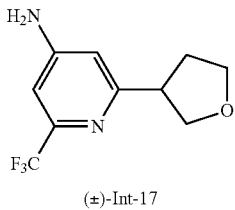

(±)-Int-17

Synthesis of compound Int-17.1. A mixture of 2-chloro-6-(trifluoromethyl)pyridin-4-amine (0.600 g, 3.05 mmol, 1.0 equiv), 2-(4,5-dihydrofuran-3-yl)-4,4,5,5-tetramethyl-1,3,2-dioxaborolane (0.898 g, 4.58 mmol, 1.5 equiv) and potassium carbonate (1.26 g, 9.15 mmol, 3.0 equiv) in 1,4-dioxane (10 mL) and water (1 mL) was degassed by bubbling through a stream of argon for 10 min. [1,1-Bis(diphenylphosphino)ferrocene]dichloropalladium(II)-DCM complex (0.125 g, 0.152 mmol, 0.05 equiv) was added and degassed for 5 min. The reaction mixture was stirred at 120° C. for 3 h. It was cooled to room temperature, filtered through a pad of Celite®. The filtrate was transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 1% methanol in DCM) to afford Int-17.1. MS(ES): m/z 231.19 [M+H]⁺.

Synthesis of compound (±)-Int-17. A mixture of palladium on carbon (10%, 0.2 g) and compound Int-17.1 (0.308 g, 1.34 mmol, 1.0 equiv) in methanol (5 mL) was stirred under hydrogen (1 atm) for 12 h. The reaction mixture was filtered through a pad of Celite® and rinsed with methanol. The filtrate was concentrated under reduced pressure to afford (±)-Int-17. MS(ES): m/z 233.21 [M+H]⁺.

Preparation of Intermediate Int-18: 1-(4-isothiocyanato-2-(trifluoromethyl)phenyl)-N,N-dimethylmethanamine

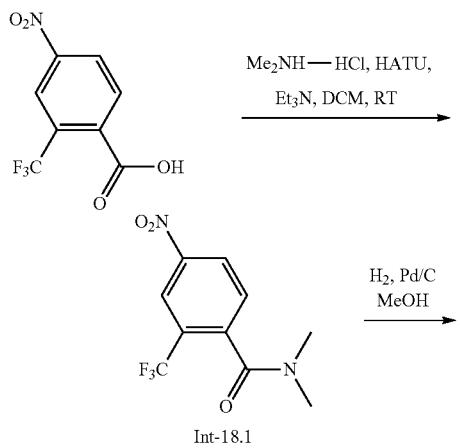

Int-18.1

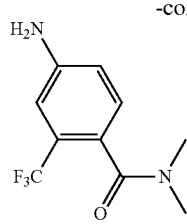

Int-18.2

LAH, THF, 70° C.
→

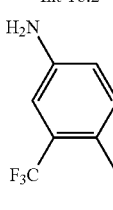

Int-18.3

TCDI, ACN
→

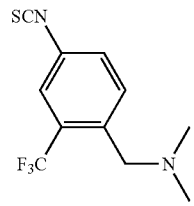

Int-18

Synthesis of compound Int-18.1. A solution of 4-nitro-2-(trifluoromethyl)benzoic acid (2.0 g, 8.51 mmol, 1.0 equiv), HATU (1.2 g, 2.92 mmol, 1.1 equiv) and triethylamine (3.5 g, 2.92 mmol, 3.0 equiv) in DCM (30 mL) was stirred at room temperature for 30 min. Dimethyl amine (4.1 mL, 2.9 mmol, 2.5 equiv) and was added and stirred for 16 h. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.4 methanol in DCM to afford Int-18.1. MS (ES): m/z 262.19 [M+H]⁺.

Synthesis of compound Int-18.2. A mixture of palladium on carbon (10%, 0.800 g) and compound Int-18.1 (1.5 g, 5.72 mmol, 1.0 equiv) in methanol (5 mL) was stirred under hydrogen (1 atm) for 2 h. The reaction mixture was filtered through a pad of Celite® and rinsed with methanol. The filtrate was concentrated under reduced pressure to afford Int-18.2. MS(ES): m/z 233.21 [M+H]⁺.

Synthesis of compound Int-18.3. To a solution of Int-18.2 (0.900 g, 4.58 mmol, 1.0 equiv) in THF (15 mL) was added lithium aluminum hydride (1.088 g, 13.76 mmol, 5.0 equiv). The mixture was heated to reflux for 1 h. It was cooled to rt and quenched by stirring with sodium sulfate hydrate powder. It was filtered and washed with ethyl acetate. The organic layer was concentrated under reduced pressure. The residue was purified by flash column chromatography on silica gel (CombiFlash®, 2.8% methanol in DCM) to afford Int-18.3. MS(ES): m/z 219.22 [M+H]⁺.

Synthesis of compound Int-18. Compound Int-18 was prepared from Int-18.3, following the procedure described in the synthesis of Int-13. The product was purified by flash column chromatography on silica gel (CombiFlash®, 2.4% methanol in DCM). MS(ES): m/z 261.28 [M+H]⁺.

Preparation of Intermediate Int-19: (S)-2-((3-isothiocyanato-5-(trifluoromethyl)phenoxy)methyl)-1-methylpyrrolidine

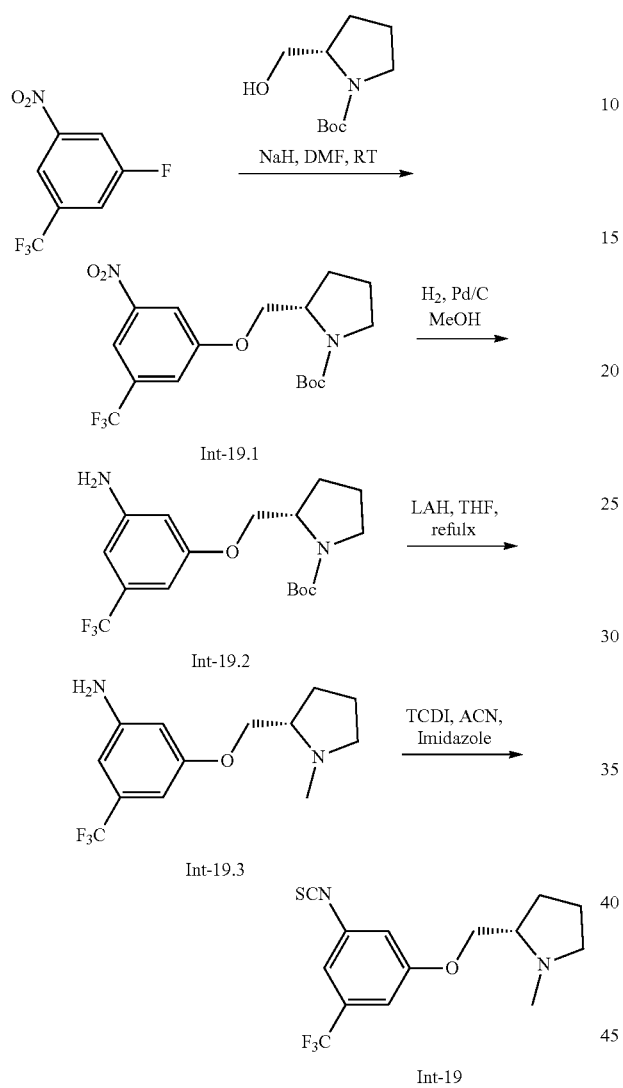

Int-19.1

Int-19.2

Int-19.3

Int-19

Synthesis of compound Int-19.1. To solution of 1-fluoro-3-nitro-5-(trifluoromethyl)benzene (0.7 g, 3.35 mmol, 1.0 equiv) and tert-butyl (S)-2-(hydroxymethyl)pyrrolidine-1-carboxylate (0.808 g, 4.02 mmol, 1.2 equiv) in DMF (12 mL) was added sodium hydride (0.201 g, 5.025 mmol, 1.5 equiv) at 0° C. and reaction mixture was stirred at room temperature for 30 min. It was transferred into ice-water and extracted with ethyl acetate. The combined organic layers were washed with brine, dried over anhydrous sodium sulfate The residue was purified by flash column chromatography on silica gel (CombiFlash®, 15-17% ethyl acetate in hexane) to afford Int-19.1 MS(ES): m/z 391.0 [M+H]+.

Synthesis of compound Int-19.2. A mixture of compound Int-19.1 (0.420 g, 1.08 mmol, 1.0 equiv) and 10% palladium on carbon (0.200 g) in methanol (10 mL) was stirred under hydrogen (1 atm) for 2 h. The reaction mixture was filtered through a pad of Celite® and rinsed with methanol. The filtrate was concentrated under reduced pressure. The residue was purified by flash column chromatography on silica gel (CombiFlash®, 20-23% ethyl acetate in hexane) to afford Int-19.2. MS(ES): m/z 361.2 [M+H]+.

Synthesis of compound Int-19.3. To a solution of Int-19.2 (0.270 g, 0.749 mmol, 1.0 equiv) in THF (5 mL) was added lithium aluminum hydride (1 M in THF, 5.2 mL, 5.243 mmol, 7.0 equiv) at 0° C. The reaction mixture was heated to reflux for 30 min. It was cooled to room temperature, transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 60-65% ethyl acetate in hexane) to afford Int-19.3. MS(ES): m/z 275.1 [M+H]+.

Synthesis of compound Int-19. Compound Int-19 was prepared from Int-19.3, following the procedure described in the synthesis of Int-13. The product was purified by flash column chromatography on silica gel (CombiFlash®, 1.5% methanol in DCM). MS(ES): m/z 317.2 [M+H]+.

Preparation of Intermediate Int-20: (R)-2-((3-isothiocyanato-5-(trifluoromethyl)phenoxy)methyl)-1-methylpyrrolidine

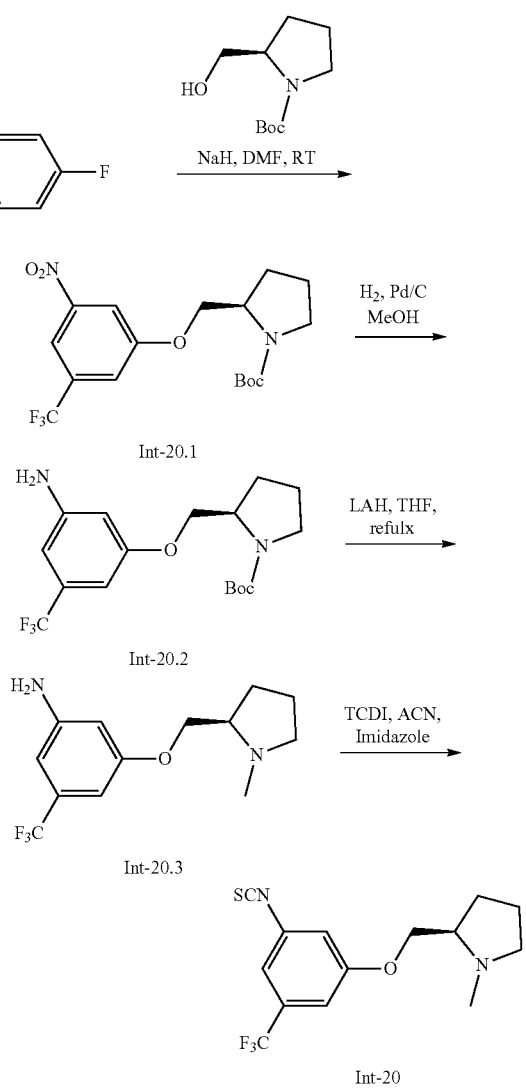

Int-20.1

Int-20.2

Int-20.3

Int-20

Synthesis of compound Int-20. Compound Int-20 was prepared by following the procedures described in the synthesis of Int-19. The product was purified by flash column chromatography on silica gel (CombiFlash®, 1.5% methanol in DCM). MS(ES): m/z 317.3 [M+H]⁺.

Preparation of Intermediate Int-21: (S)-3-(3-isothiocyanato-5-(trifluoromethyl)phenoxy)-1-methylpyrrolidine

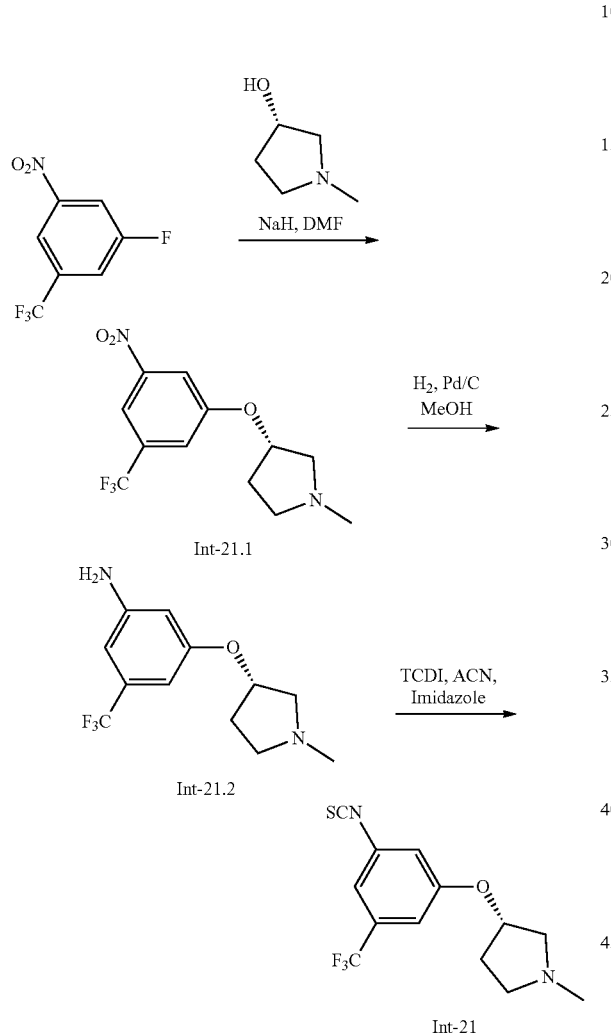

Synthesis of compound Int-21.1. To solution of 1-fluoro-3-nitro-5-(trifluoromethyl)benzene (1.0 g, 4.78 mmol, 1.0 equiv) and (S)-1-methylpyrrolidin-3-ol (0.580 g, 5.74 mmol, 1.2 equiv) in DMF (10 mL) was added sodium hydride (0.382 g, 9.56 mmol, 2.0 equiv) at 0° C. and stirred at room temperature for 30 min. It was transferred into ice-water and extracted with ethyl acetate. The combined organic layers were washed with brine, dried over anhydrous sodium sulfate The residue was purified by flash column chromatography on silica gel (CombiFlash®, 3.0% methanol in DCM) to afford Int-21.1. MS(ES): m/z 291.2 [M+H]⁺.

Synthesis of compound Int-21.2. A mixture of compound Int-21.1 (0.670 g, 2.31 mmol, 1.0 equiv) and 10% palladium on carbon (0.350 g) in methanol (5 mL) was stirred under hydrogen (1 atm) for 1 h. The reaction mixture was filtered through a pad of Celite® and rinsed with methanol. The filtrate was concentrated under reduced pressure to afford Int-21.1. MS(ES): m/z 261.1 [M+H]⁺.

Synthesis of compound Int-21. Compound Int-21 was prepared from Int-21.2, following the procedure described in the synthesis of Int-13. The product was purified by flash column chromatography on silica gel (CombiFlash®, 2.0% methanol in DCM). MS(ES): m/z 303.2 [M+H]⁺.

Preparation of compound Int-22: (S)-3-(3-isothiocyanato-5-(trifluoromethyl)phenoxy)-1-methylpyrrolidine

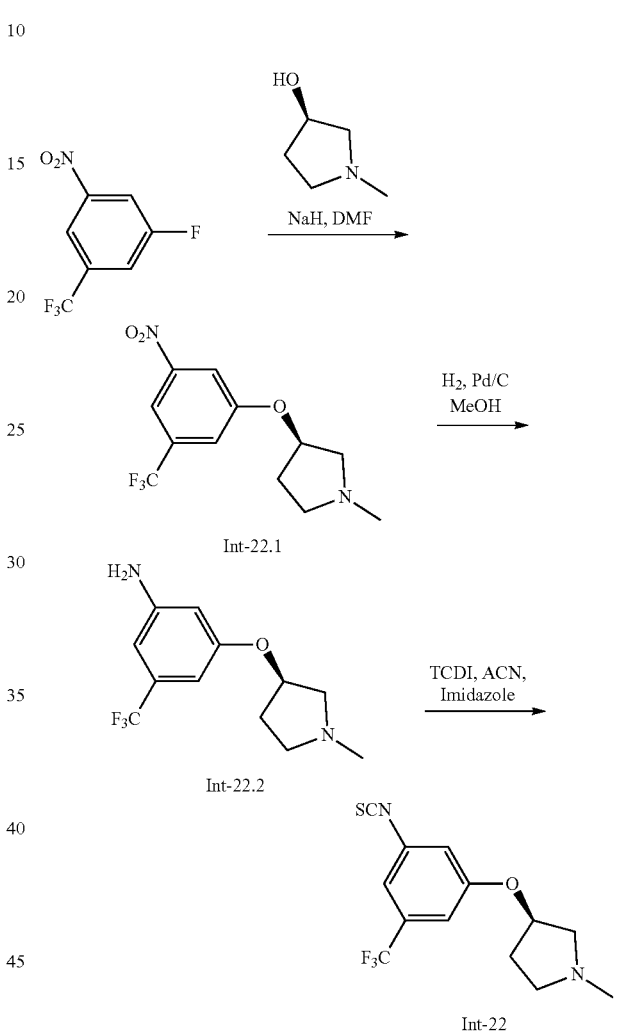

Synthesis of compound Int-22. Compound Int-22 was prepared by following the procedures described in the synthesis of Int-21. The product was purified by flash column chromatography on silica gel (CombiFlash®, 2.0% methanol in DCM). MS(ES): m/z 303.2 [M+H]⁺.

Preparation of Intermediate Int-23: tert-butyl 3-((3-amino-5-(trifluoromethyl)benzyl)oxy)azetidine-1-carboxylate

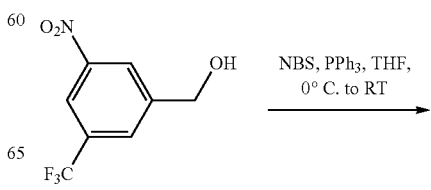

-continued

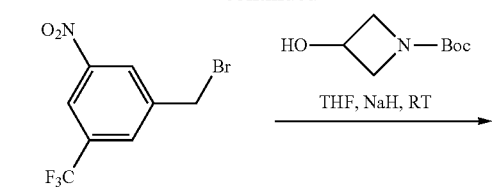

Int-23.1

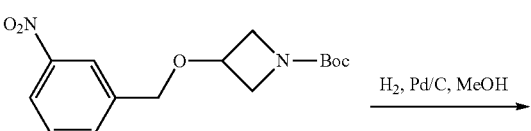

Int-23.2

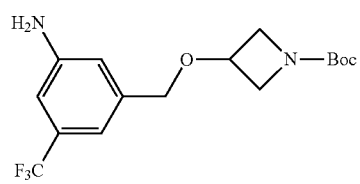

Int-23

Synthesis of compound Int-23.1. To a solution of (3-nitro-5-(trifluoromethyl)phenyl)methanol (2.0 g, 9.04 mmol, 1.0 equiv) in THF (30 mL) was added triphenylphosphine (4.74 g, 18.09 mmol, 2.0 equiv) followed by N-bromosuccinimide (3.22 g, 18.09 mmol, 2.0 equiv) at 0° C. The reaction mixture was stirred at room temperature for 16 h. It was transferred into a saturated aqueous solution of sodium bicarbonate and extracted with ethyl acetate. The combined organic layers were washed with brine, dried over anhydrous sodium sulfate, filtered, and concentrated under reduced pressure. The residue was purified by flash column chromatography on silica gel (CombiFlash®, 15% ethyl acetate in hexane) to afford Int-23.1. MS(ES): m/z 285.32 [M+H]⁺.

Synthesis of compound Int-23.2. To a solution of Int-23.1 (0.800 g, 4.62 mmol, 1.0 equiv) in THF (10 mL) was added NaH (60%, 0.277 g, 6.93 mmol, 1.5 equiv) in portions at 0° C. stirred for 20 min. A solution of tert-butyl 3-hydroxyazetidine-1-carboxylate (1.6 g, 5.54 mmol, 1.2 equiv) in THF (5 mL) was added dropwise at 0° C. The reaction mixture was stirred at room temperature for 16 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 20% ethyl acetate in hexane) to afford Int-23.2. MS(ES): m/z 377.62 [M+H]⁺.

Synthesis of compound Int-23. A mixture of Int-23.2 (0.850 g, 2.26 mmol, 1.0 equiv) and 10% palladium on carbon (0.450 g) in methanol (15 mL) was stirred under hydrogen (1 atm) for 2 h. The reaction mixture was filtered through a pad of Celite® and rinsed with methanol. The filtrate was concentrated under reduced pressure to afford Int-23. MS(ES): m/z 347.51 [M+H]⁺.

Preparation of Intermediate Int-24-a and I-24-b: (R)-2-(3-isothiocyanato-5-(trifluoromethyl)phenyl)-1-methylpyrrolidine and (S)-2-(3-isothiocyanato-5-(trifluoromethyl)phenyl)-1-methylpyrrolidine

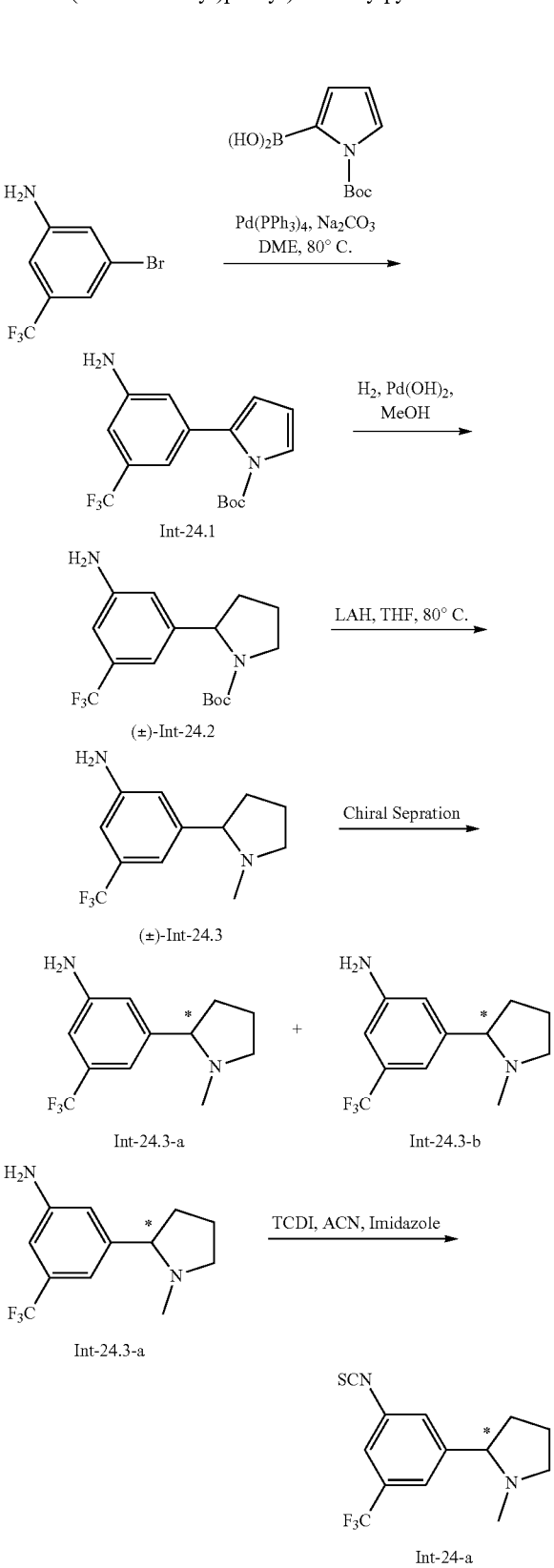

149

-continued

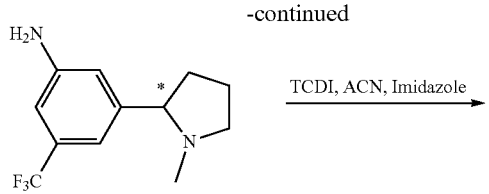

Int-24.3-b

TCDI, ACN, Imidazole →

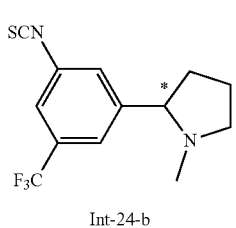

Int-24-b

Synthesis of compound Int-24.1. A mixture of 3-bromo-5-(trifluoromethyl)aniline (2.5 g, 10.42 mmol, 1.0 equiv), (1-(tert-butoxycarbonyl)-1H-pyrrol-2-yl)boronic acid (4.4 g, 20.83 mmol, 2.0 equiv) and sodium carbonate (3.31 g, 31.26 mmol, 3.0 equiv) in dimethoxyethane (25 mL) was degassed by bubbling through a stream of argon for 10 min. Tetrakis(triphenylphosphine)palladium(0) (1.2 g, 1.042 mmol, 0.1 equiv) was added and degassed for 5 min. The reaction mixture was stirred at 80° C. for 5 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford Int-24.1. MS(ES): m/z 327.2 [M+H]⁺.

Synthesis of compound (±)-Int-24.2. A mixture of compound Int-24.1 (2.1 g, 6.44 mmol, 1.0 equiv) and 20% palladium hydroxide (1.0 g) in methanol (20 mL) was stirred under hydrogen (1 atm) for 1 h. The reaction mixture was filtered through a pad of Celite® and rinsed with methanol. The filtrate was concentrated under reduced pressure to afford (±)-Int-24.2. MS(ES): m/z 331.1 [M+H]⁺.

Synthesis of compound (±)-Int-24.3. To a solution of (±)-Int-24.2 (1.37 g, 4.15 mmol, 1.0 equiv) in THF (10 mL) was added lithium aluminum hydride (1 M in THF, 29 mL, 29.05 mmol, 7.0 equiv) at 0° C. The reaction mixture was heated to reflux for 30 min. It was cooled to room temperature, transferred into ice, stirred, and extracted with ethyl acetate. The combined organic layers were washed with brine, dried over anhydrous sodium sulfate, filtered, and concentrated under reduced pressure to afford (±)-Int-24.3. MS(ES): m/z 245.1 [M+H]⁺. The racemate was subjected to chiral HPLC separation (column CHIRALPAK AD-H (250 mm*21 mm, 5 μm); mobile phases: (A) 0.1% DEA in n-hexane (B) 0.1% DEA in isopropanol; flow rate=30 mL/min) to afford first eluting fraction (Int-24.3-a) and second eluting fraction (Int-24.3-b). MS(ES): m/z: 245.1 [M+H]⁺.

Synthesis of compound Int-24-a and Int-24-b. Compound Int-24-a and Int-24-b were prepared from Int-24.3-a and Int-24.4-b respectively, following the procedure described in the synthesis of Int-13. The products were purified by flash column chromatography on silica gel (CombiFlash®, 12% ethyl acetate in hexane). MS(ES): m/z 287.2 [M+H]⁺.

150

Preparation of Intermediate Int-25: tert-butyl 3-(3-amino-5-(trifluoromethyl)phenoxy)azetidine-1-carboxylate

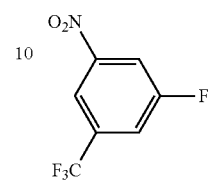 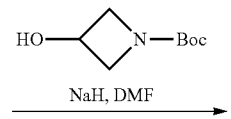

NaH, DMF →


Int-25.1

Fe, NH₄Cl, H₂O
EtOH, 80° C. →

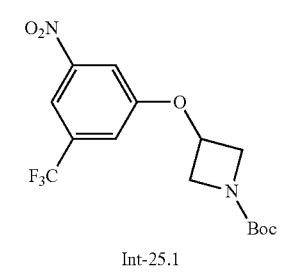

Int-25

Synthesis of compound Int-25.1. To a solution of 1-fluoro-3-nitro-5-(trifluoromethyl)benzene (1.0 g, 4.78 mmol, 1.0 equiv) in DMF (10 mL) was added sodium hydride (0.313 g, 7.17 mmol, 1.5 equiv) at 0° C. and stirred for 1 h. To the mixture was added tert-butyl 3-hydroxyazetidine-1-carboxylate (1.24 g, 7.17 mmol, 1.5 equiv). The reaction mixture was stirred at room temperature for 2 h. It was transferred into ice water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 38% ethyl acetate in hexane) to afford Int-25.1. MS(ES): m/z: 363.31 [M+H]⁺.

Synthesis of compound Int-25. A mixture of Int-25.1 (0.700 g, 1.93 mmol, 1.0 equiv), iron powder (0.541 g, 9.66 mmol, 5.0 equiv) and ammonium chloride (0.512 g, 9.66 mmol, 5.0 equiv) in ethanol:water (8:2, 6 mL) was stirred at 80° C. for 2 h. The reaction mixture was filtered through a pad of Celite® and rinsed with ethanol. The filtrate was concentrated under reduced pressure. The residue was purified by flash column chromatography on silica gel (CombiFlash®, 63% ethyl acetate in hexane) to afford Int-25. MS(ES): m/z 333.32 [M+H]⁺.

Preparation of Intermediate Int-26: 3-isothiocyanato-1-(7-oxaspiro[3.5]nonan-2-yl)-5-(trifluoromethyl)-1H-pyrazole

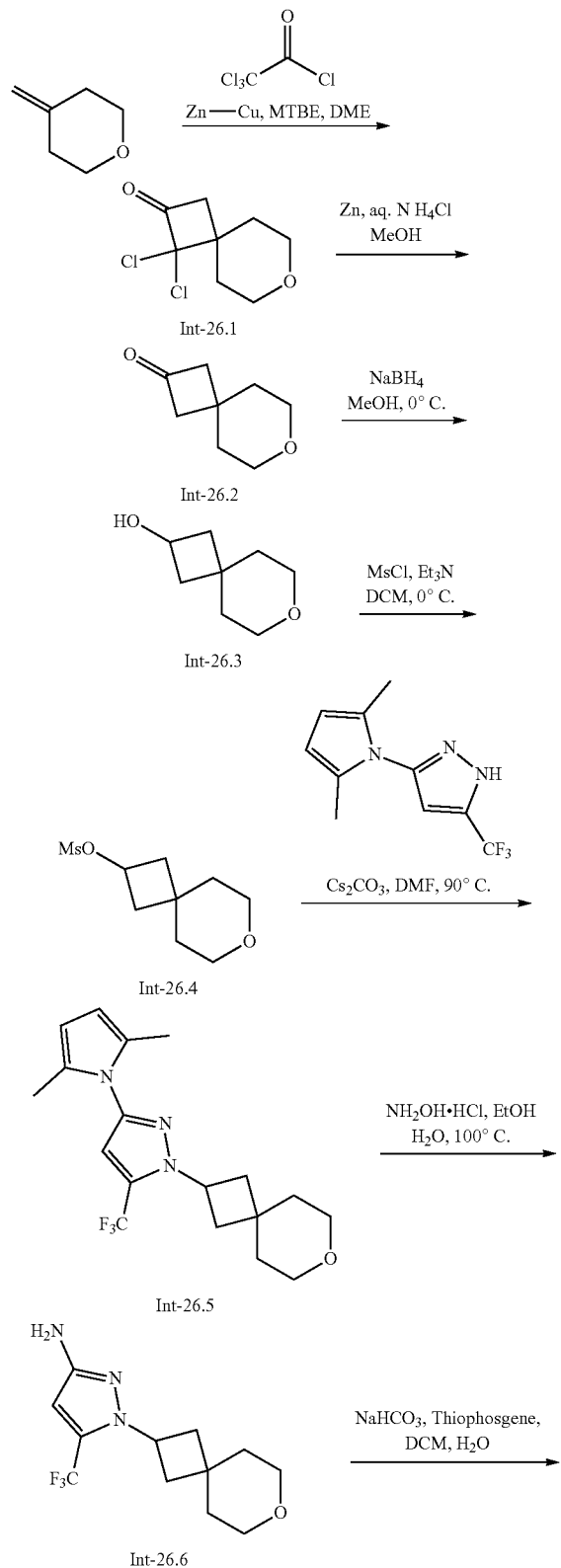

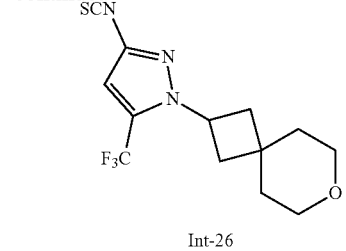

Synthesis of compound Int-26.1. To a solution of 4-methylenetetrahydro-2H-pyran (5.0 g, 50.95 mmol, 1.0 equiv) in tert-butyl methyl ether (100 mL) was added zinc-copper couple (71.73 g, 560.45 mmol, 11.0 equiv) followed by a solution of diphosgene (37.10 g, 204.08 mmol, 4.0 equiv) in dimethoxyethane (40 mL) at 0° C. The mixture was stirred at room temperature for 18 h. It was filtered through a pad of Celite®, and the filtrate was washed with solution of sodium bicarbonate and brine. The organic layer was separated, dried over anhydrous sodium sulfate, filtered, and concentrated under reduced pressure to afford Int-26.1. MS(ES): m/z: 210.0 [M+H]$^+$.

Synthesis of compound Int-26.2. A mixture of Int-26.1 (8.9 g, 42.58 mmol, 1.0 equiv), saturated aqueous ammonium chloride and zinc (27.67 g, 425.8 mmol, 10.0 equiv) in methanol (200 mL) was stirred at room temperature for 16 h. The reaction mixture was filtered through a pad of Celite®, rinsed with diethyl ether and concentrated under reduced pressure. The residue was purified by flash column chromatography on silica gel (CombiFlash®, 30% ethyl acetate in hexane) to afford Int-26.2. MS(ES): m/z: 141.1 [M+H]$^+$.

Synthesis of compound Int-26.3. To a solution of Int-26.2 (3.9 g, 27.82 mmol, 1.0 equiv) in methanol (40 mL) was added sodium borohydride (0.308 g, 8.34 mmol, 0.3 equiv) at 0° C. and stirred at room temperature for 16 h. It was transferred into ice-water and extracted with ethyl acetate. The combined organic layers were washed with brine, dried over anhydrous sodium sulfate, filtered, and concentrated under reduced pressure to afford Int-26.3. MS(ES): m/z: 143.1 [M+H]$^+$.

Synthesis of compound Int-26.4. To a solution of Int-26.3 (3.0 g, 21.1 mmol, 1.0 equiv) and triethylamine (8.8 mL, 63.3 mmol, 3.0 equiv) in DCM (30 mL) at 0° C. was added methanesulfonyl chloride (2.4 mL, 31.65 mmol, 1.5 equiv). The reaction mixture was stirred at room temperature for 30 min. It was transferred into ice-water, stirred, and extracted with DCM. The combined organic layers were washed with saturated sodium bicarbonate followed by brine, dried over anhydrous sodium sulfate, filtered, and concentrated under reduced pressure to afford Int-26.4. MS(ES): m/z: 221.0 [M+H]$^+$.

Synthesis of compound Int-26.5. A mixture of Int-26.4 (2.8 g, 12.22 mmol, 1.0 equiv), 3-(2,5-dimethyl-1H-pyrrol-1-yl)-5-(trifluoromethyl)-1H-pyrazole (4.04 g, 18.32 mmol, 1.3 equiv) and cesium carbonate (7.94 g, 24.44 mmol, 2.0 equiv) in DMF (15 mL) was stirred at 90° C. for 4 h. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.0% ethyl acetate in hexane) to afford Int-26.5. MS(ES): m/z 354.2 [M+H]$^+$.

Synthesis of compound Int-26.6. A solution of Int-26.5 (1.5 g, 4.24 mmol, 1.0 equiv) and hydroxylamine hydrochloride (11.4 g, 169.6 mmol, 40 equiv) in ethanol:water (2:1, 50 mL) was heated to reflux for 3 h. It was transferred into ice-water and 2 N sodium hydroxide was added to adjust pH to 10. The mixture was extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford Int-26.6. MS(ES): m/z 276.0 [M+H]+.

Synthesis of compound Int-26. Compound Int-26 was prepared from Int-26.6, following the procedures described in the synthesis of Int-3. The product was purified by flash column chromatography on silica gel (CombiFlash®, DCM). MS(ES): m/z 318.2 [M+H]+.

Preparation of Intermediate Int-27-a and Int-27-b: (R)-2-(4-isothiocyanato-2-(trifluoromethyl)phenyl)-1-methylpyrrolidine and (S)-2-(4-isothiocyanato-2-(trifluoromethyl)phenyl)-1-methylpyrrolidine

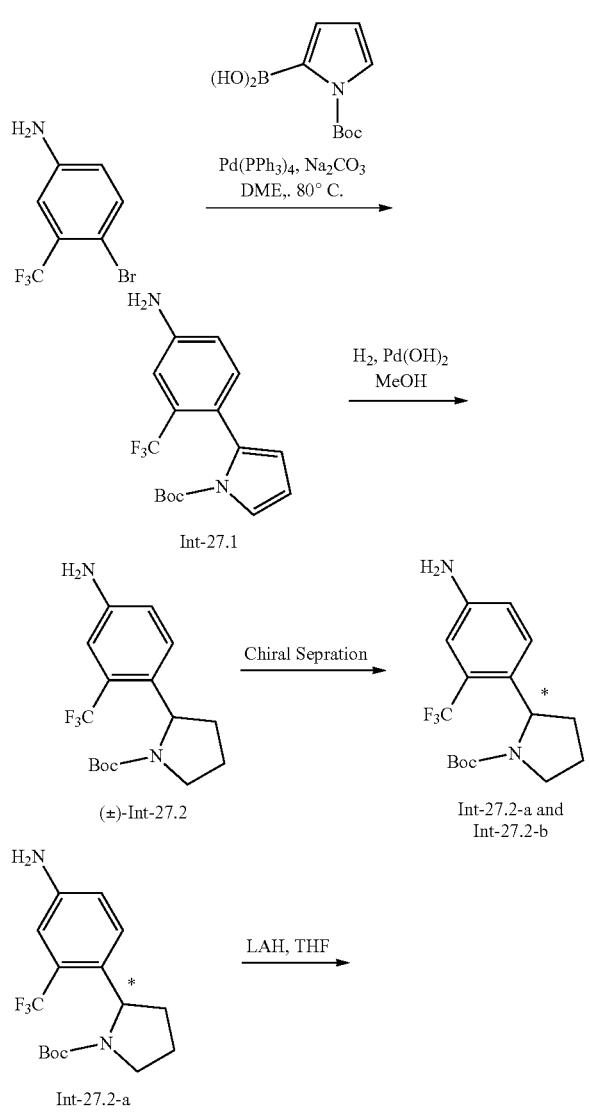

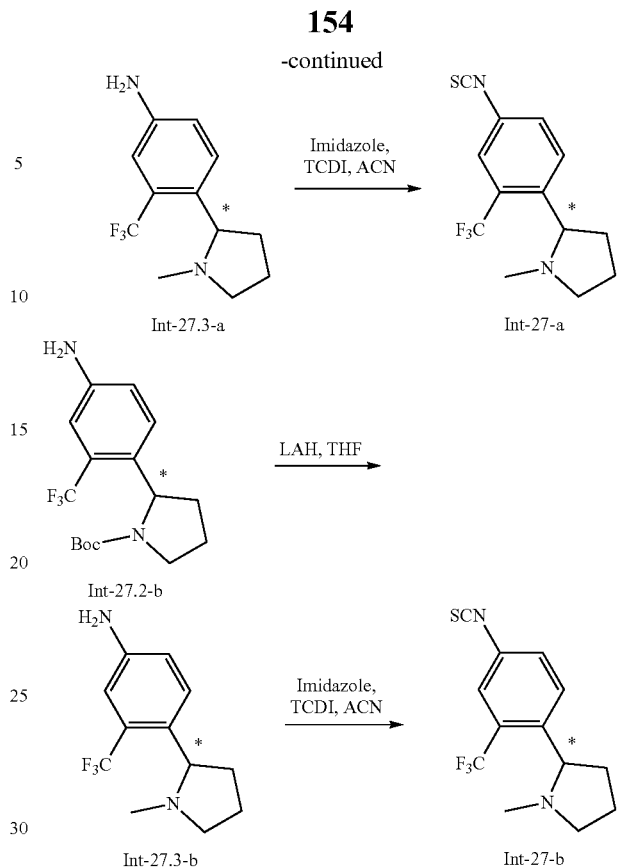

Synthesis of compound Int-27.1. To mixture of 4-bromo-3-(trifluoromethyl)aniline (3.0 g, 12.5 mmol, 1.0 equiv), (1-(tort-butoxycarbonyl)-1H-pyrrol-2-yl)boronic acid (3.9 g, 18.7 mmol, 1.5 equiv) and sodium carbonate (5.2 g, 50.02 mmol, 4.0 equiv) in dimethoxyethane (40 mL) was degassed by bubbling argon through for 10 min. Tetrakis(triphenylphosphine)palladium(0) (1.2 g, 1.3 mmol, 0.9 equiv) was added, and degassed for 5 min. The reaction mixture was stirred at 80° C. for 5 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 8.0% methanol in DCM) to afford Int-27.1. MS(ES): m/z 327.32 [M+H]+.

Synthesis of compound (±)-Int-27.2. A mixture of compound Int-27.1 (1.4 g, 4.29 mmol, 1.0 equiv) and 20% palladium hydroxide (1.0 g) in methanol (38 mL) was stirred under hydrogen (1 atm) for 7 h. The reaction mixture was filtered through a pad of Celite® and rinsed with methanol. The filtrate was concentrated under reduced pressure to afford (±)-Int-27.2. MS(ES): m/z 331.35 [M+H]+. The racemate was subjected to chiral SFC separation: (column CHIRALPAK AD-H (250 mm*4.6 mm, 5 µm); mobile phases: (A) CO2 (B) 0.1% diethylamine in isopropanol: acetonitrile (50:50); flow rate=75 mL/min) to afford first eluting faction (Int-27.2-a) and second eluting fraction (Int-27.2-b).

Synthesis of compound Int-27.3-a and Int-27.3-b. To a solution of Int-27.2-a (0.410 g, 1.24 mmol, 1.0 equiv) in THF (10 mL) was added lithium aluminum hydride (1 M in THF, 8.6 mL, 8.69 mmol, 7.0 equiv) at 0° C. The reaction mixture was heated to reflux for 30 min. It was cooled to room temperature and stirred with sodium sulfate decahydrate. The solids were removed by filtration and rinsed with ethyl acetate. The organic layer was separated and washed with brine, dried over anhydrous sodium sulfate, filtered, and concentrated under reduced pressure to afford Int-27.2-a. MS(ES): m/z 245.26 [M+H]+. Int-27.3-b was prepared from Int-27.2-b, following the same procedure.

Synthesis of compound Int-27-a and Int-27-b. Compound Int-27-a was prepared from Int-27.3-a, following the procedure described in the synthesis of Int-13. The product was purified by flash column chromatography on silica gel (CombiFlash®, 2.1% methanol in DCM). MS(ES): m/z 287.32 [M+H]+. Int-27-b was prepared from Int-27.3-b in the same manner.

Preparation of Intermediate Int-28: 4-isothiocyanato-2-(pyrrolidin-1-yl)-6-(trifluoromethyl)pyridine

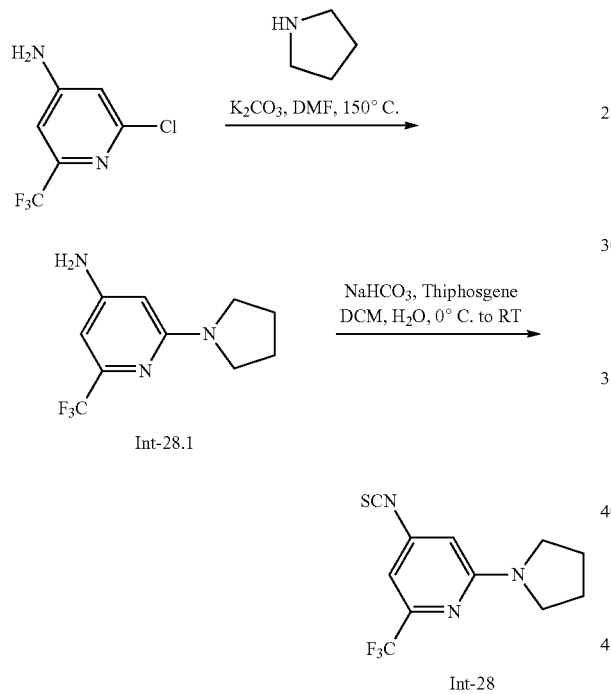

Preparation of Intermediate Int-29: 2'-isothiocyanato-5',6'-dihydrospiro[cyclobutane-1,4'-pyrrolo[1,2-b]pyrazole]

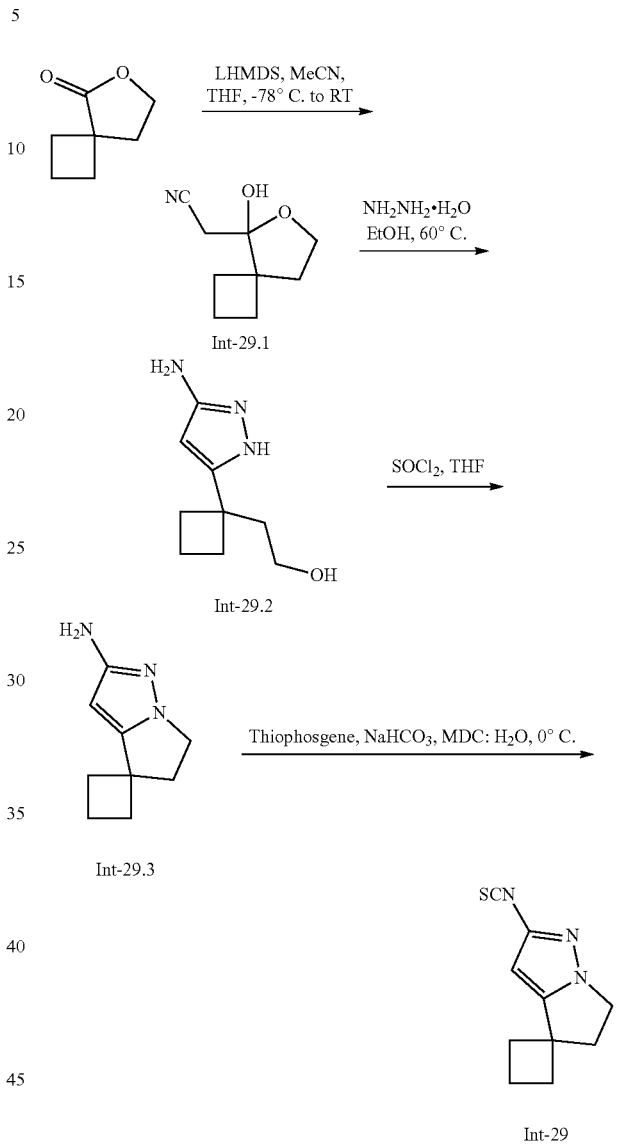

Synthesis of compound. Int-28.1. A mixture of 2-chloro-6-(trifluoromethyl)pyridin-4-amine (0.500 g, 2.54 mmol, 1.0 equiv), pyrrolidine (0.271 g, 3.82 mmol, 1.5 equiv) and potassium carbonate (1.05 g, 7.62 mmol, 3.0 equiv) in DMF (5 mL) was stirred at 150° C. for 18 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 20-30% ethyl acetate in hexane) to afford Int-28.1. MS(ES): m/z 232.5 [M+H]+.

Synthesis of compound Int-28. Compound Int-28 was prepared from Int-28.1, following the procedures described in the synthesis of Int-3. The product was purified by flash column chromatography on silica gel (CombiFlash®, 5-10% ethyl acetate in hexane). MS(ES): m/z 274.5 [M+H]+.

Synthesis of compound Int-29.1. To a solution of lithium bis(trimethylsilyl)amide (1 M in THF, 17.4 mL, 17.44 mmol, 2.2 equiv) in anhydrous THF (25 mL) at −78° C. was added solution of 6-oxaspiro[3.4]octan-5-one (1.0 g, 7.93 mmol, 1.0 equiv) and acetonitrile (0.83 mL, 15.86 mmol, 2.0 equiv) in THF (8 mL). The reaction mixture was stirred at −78° C. for 30 min and it was allowed to warm to room temperature, stirring for 2 h. It was transferred into saturated aqueous ammonium chloride solution and extracted with DCM. The combined organic layers were washed with brine, dried over anhydrous sodium sulfate, filtered, and concentrated under reduced pressure to afford residue which was purified by flash column chromatography on silica gel (CombiFlash®, 20% ethyl acetate in hexane) to afford Int-29.1.

Synthesis of compound Int-29.2. To a solution of Int-29.1 (0.800 g, 4.78 mmol, 1.0 equiv) in ethanol (10 mL) was added hydrazine monohydrate (0.358 g, 7.17 mmol, 1.5 equiv). The reaction mixture was stirred at 60° C. for 72 h.

The reaction mixture was cooled to room temperature and carbon dioxide was bubbled through it for 1 h. The reaction mixture was concentrated under reduced pressure. To the residue was added methanol (15 mL), stirred, and the precipitated solids were removed by filtration. The filtrate was concentrated under reduced pressure to afford Int-29.2. MS(ES): m/z 182.1 [M+H]$^+$.

Synthesis of compound Int-29.3. To a solution of Int-29.2 (0.610 g, 3.37 mmol, 1.0 equiv) in THF (10 mL) was added thionyl chloride (1.22 mL, 16.85 mmol, 5.0 equiv). The reaction mixture was stirred at room temperature for 3 h. It was slowly was transferred into a mixture of aqueous ammonium hydroxide and ice, stirred, and extracted DCM. The combined organic layers were washed with brine, dried over anhydrous sodium sulfate, filtered, and concentrated under reduced pressure to afford residue which was purified by flash column chromatography on silica gel (Combi-Flash®, 2% methanol in DCM) to afford Int-29.3. MS(ES): m/z 164.1 [M+H]$^+$.

Synthesis of compound Int-29. Compound Int-29 was prepared from Int-29.3, following the procedures described in the synthesis of Int-3. The product was purified by flash column chromatography on silica gel (CombiFlash®, DCM). MS(ES): m/z 205.9 [M+H]$^+$.

Preparation of Intermediate Int-30: 2'-isothiocyanato-5'-methyl-6',7'-dihydro-5'H-spiro[cyclopropane-1,4'-pyrazolo[1,5-c]pyrazine]

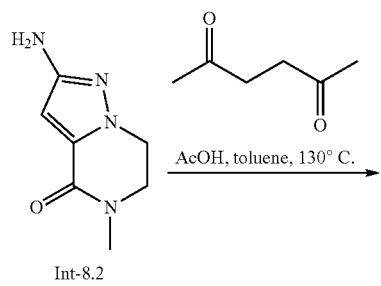

Int-8.2

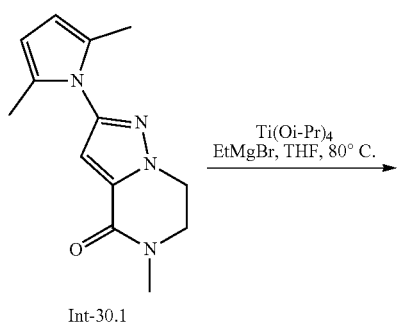

Int-30.1

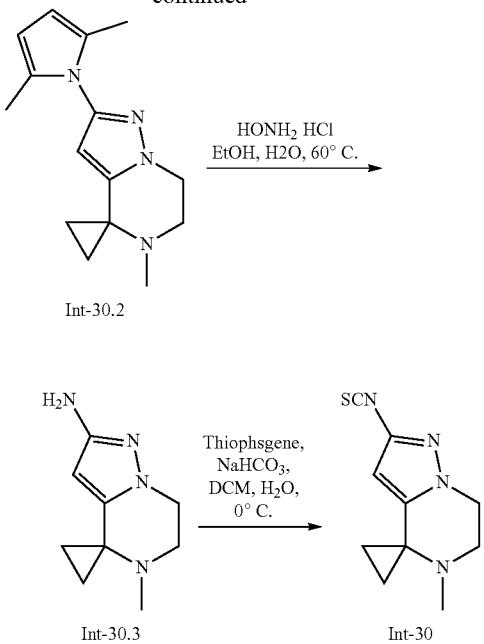

Synthesis of compound Int-30.1. To a solution of Int-8.2 (0.600 g, 4.81 mmol, 1.0 equiv) in toluene (6 mL) was added hexane-2,5-dione (0.618 g, 5.41 mmol, 1.5 equiv) followed by acetic acid (catalytic) at room temperature. The reaction mixture was stirred at 130° C. for 3 hr. It was cooled to rt and concentrated under reduced pressure. The residue was purified by flash column chromatography on silica gel (CombiFlash®, 0.5% methanol in DCM) to afford Int-30.1. MS(ES): m/z 245 [M+H]$^+$.

Synthesis of compound Int-30.2. To a solution of Int-30.2 (0.500 g, 2.55 mmol, 1.0 equiv) in THF (10 mL) was added titanium isopropoxide (1.45 g, 5.102 mmol, 2.0 equiv) followed by ethyl magnesium bromide (1 M in THF, 3.4 mL, 10.2 mmol, 4.0 equiv) at 80° C. The reaction mixture was stirred for 30 min. It was transferred into ice-water and extracted with ethyl acetate. The combined organic layers were washed with brine, dried over anhydrous sodium sulfate, filtered, and concentrated under reduced pressure to afford material. The residue was purified by flash column chromatography on silica gel (CombiFlash®, 15% ethyl acetate in hexane) to afford Int-30.2. MS(ES): m/z: 257 [M+H]$^+$.

Synthesis of compound Int-30.3. To solution of Int-30.3 (0.450 g, 1.75 mmol, 1.0 equiv) in ethanol (8 mL) and water (2 mL) was added hydroxylamine hydrochloride (3.65 g, 52.5 mmol, 30.0 equiv). The reaction mixture was stirred at 60° C. for 1 h. It was transferred into ice-cold saturated aqueous solution of sodium bicarbonate and extracted with DCM. The combined organic layers were washed with brine, dried over anhydrous sodium sulfate, filtered, and concentrated under reduced pressure. The residue was purified by trituration with diethyl ether to afford Int-30.3. MS(ES): m/z: 179 [M+H]$^+$.

Synthesis of compound Int-30. Compound Int-30 was prepared from Int-30.3, following the procedures described in the synthesis of Int-3. The product was purified by flash column chromatography on silica gel (CombiFlash®, 0.5% methanol in DCM). MS(ES): m/z 221 [M+H]⁺.

Preparation of Provided Compounds

Example 1: (R)-N-(4-((2-((5-(tert-butyl)-1-(tetrahydrofuran-3-yl)-1H-pyrazol-3-yl)amino)-1-methyl-1H-imidazo[4,5-b]pyridin-6-yl)oxy)pyridin-2-yl)-3-methoxyazetidine-1-carboxamide

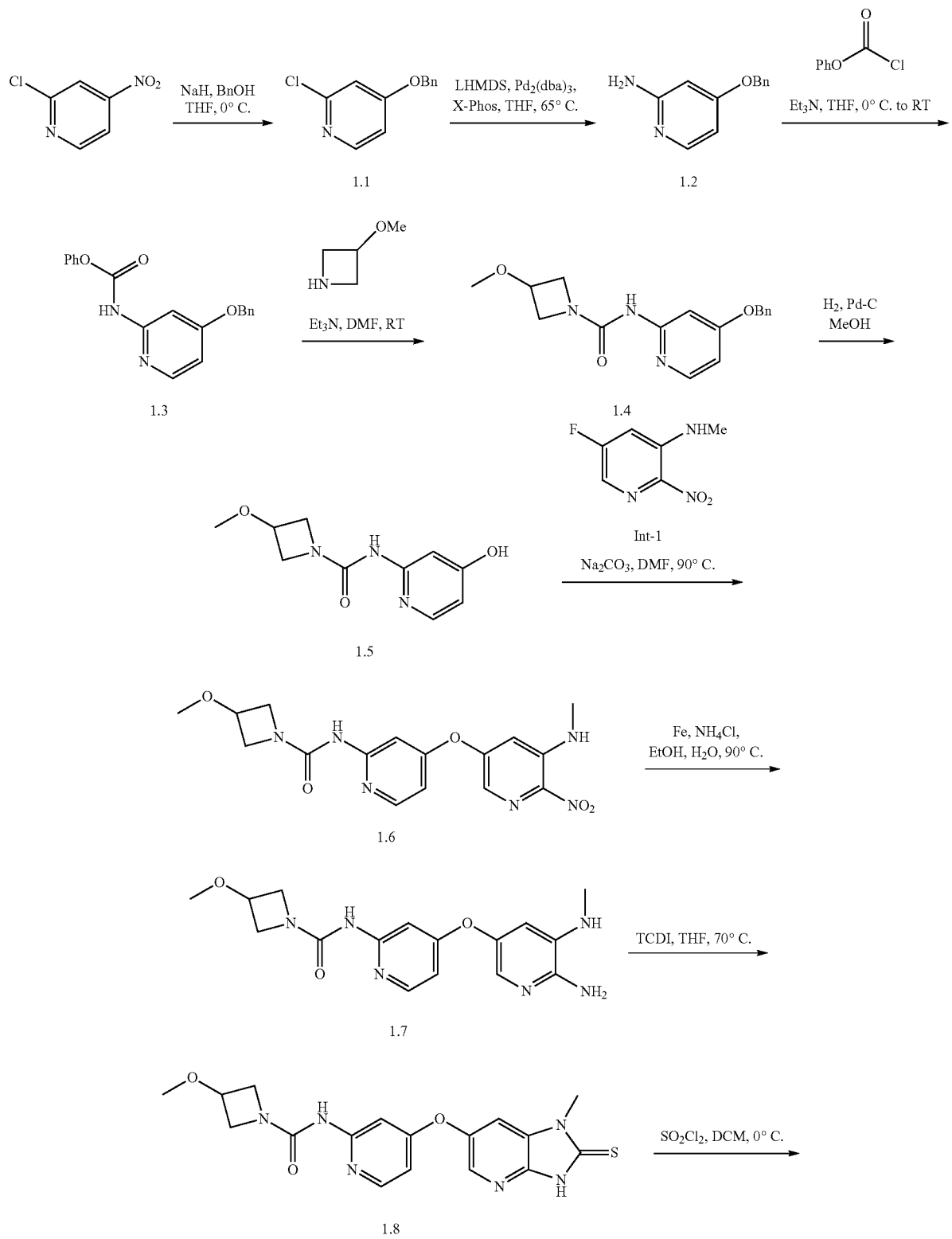

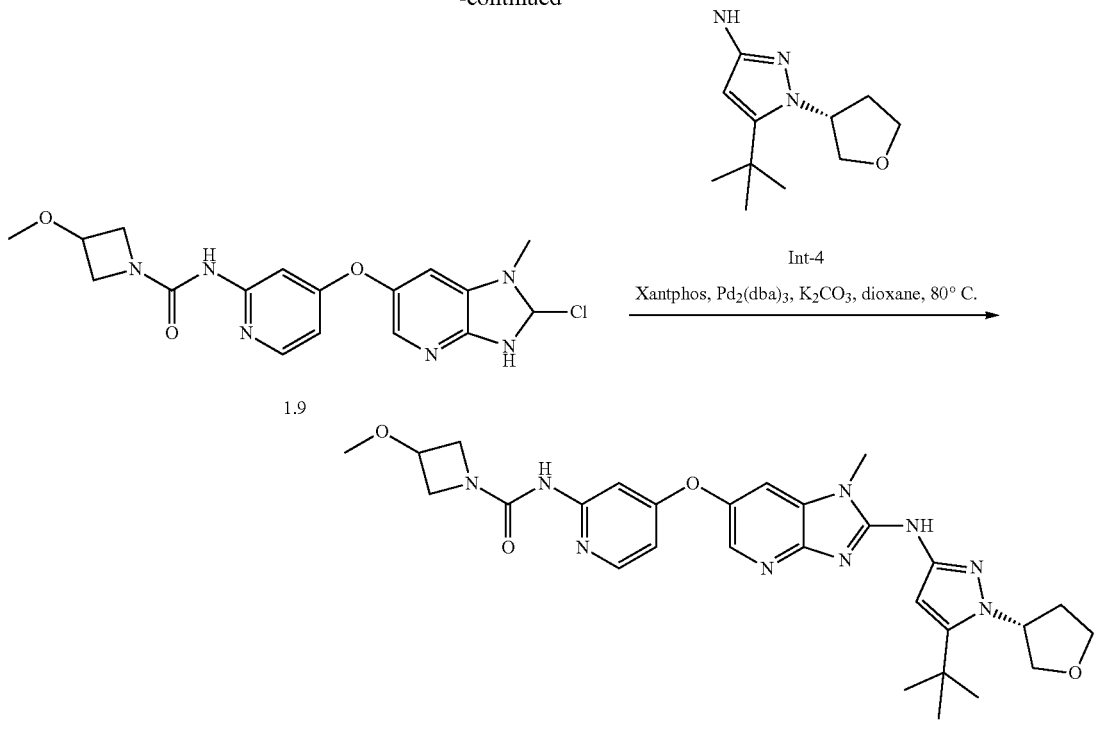

Synthesis of compound 1.1. To a solution of benzyl alcohol (17.05 g, 157.69 mmol, 1.0 equiv) in THF (250 mL) at 0° C. was added sodium hydride (12.61 g, 315.38 mmol, 2.0 equiv) in small portions. The mixture was stirred for 1 h and 2-chloro-4-nitropyridine (25 g, 157.69 mmol, 1.0 equiv) was added in portions. The reaction mixture was stirred at 0° C. for 2 h. It was poured over ice, stirred, and extracted with ethyl acetate three times. The combined organic layers were washed with brine, dried over anhydrous sodium sulfate, filtered, and concentrated under reduced pressure. The residue was purified by flash column chromatography on silica gel (CombiFlash®, 10% ethyl acetate in hexane as eluant) to afford 1.1. MS (ES): m/z 220.13 [M+H]$^+$.

Synthesis of compound 1.2. A solution of compound 1.1 (20 g, 91.05 mmol, 1.0 equiv) in THF (200 mL) was degassed by bubbling argon through for 10 min. 2-dicyclohexylphosphino-2',4',6'-triisopropylbiphenyl (4.34 g, 9.105 mmol, 0.1 equiv) and tris(dibenzylideneacetone)dipalladium (4.17 g, 4.55 mmol, 0.05 equiv) were added under argon atmosphere and degassed by bubbling through a stream of argon for 5 min. To the mixture was added a solution of lithium bis(trimethylsilyl)amide (1 M in THF, 182 mL, 182.1 mmol, 2.0 equiv) and it was stirred at 60° C. for 1 h. The reaction mixture was cooled to room temperature, poured over ice-water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3% methanol in DCM as eluant) to afford 1.2. MS (ES): m/z 201.2 [M+H]$^+$.

Synthesis of compound 1.3. To a solution of 1.2 (2.0 g, 9.99 mmol, 1.0 equiv) and triethylamine (4.2 mL, 29.97 mmol, 3.0 equiv) in THF (20 mL) was added phenyl chloroformate (4.67 g, 29.97 mmol, 3.0 equiv) dropwise at 0° C. The reaction mixture was stirred at room temperature for 3 h. It was transferred into water and extracted with ethyl acetate. The combined organic layers were washed with brine, dried over anhydrous sodium sulfate, filtered, and concentrated under reduced pressure to afford 1.1. MS (ES): m/z 321.3 [M+H]$^+$. It was used in the next step without further purification.

Synthesis of compound 1.4. To a solution of 1.3 (3.0 g, 9.36 mmol, 1.0 equiv) and triethylamine (12.5 mL, 84.24 mmol, 9.0 equiv) in DMF (20 mL) was added 3-methoxyazetidine (1.06 g, 12.17 mmol, 1.3 equiv) dropwise at 0° C. The reaction mixture was stirred at room temperature for 16 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford 1.4. MS (ES): m/z 314.3 [M+H]$^+$.

Synthesis of compound 1.5. A mixture of compound 1.4 (1.1 g, 3.51 mmol, 1.0 equiv) and 10% palladium on carbon (0.5 g) in methanol (10 mL) was stirred under hydrogen (1 atm) for 3 h. It was filtered through a pad of Celite® and rinsed with methanol. The filtrate was concentrated under reduced pressure to afford 1.5. MS(ES): m/z 224.2 [M+H]$^+$.

Synthesis of compound 1.6. A mixture of 1.5 (0.760 g, 3.4 mmol, 1.0 equiv) in DMF (10 mL), Int-1 (0.699 g, 4.09 mmol, 1.2 equiv) and sodium carbonate (0.720 g, 6.8 mmol, 2.0 equiv) was stirred at 90° C. for 12 h. It was cooled to room temperature, poured into ice-water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.8% methanol in DCM) to afford 1.6. MS(ES): m/z 375.3 [M+H]+.

Synthesis of compound 1.7. To a solution of 1.6 (0.700 g, 1.87 mmol, 1.0 equiv) in ethanol-water (2:1, 10 mL) was added iron powder (0.733 g, 13.09 mmol, 7.0 equiv) followed by ammonium chloride (0.706 g, 13.09 mmol, 7.0 equiv). The reaction mixture was stirred at 90° C. for 3 h. It was poured into ice-water, filtered, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.5% methanol in DCM) to afford 1.6. MS(ES): m/z 345.5 [M+H]+.

Synthesis of compound 1.8. To a solution of 1.7 (0.400 g, 1.16 mmol, 1.0 equiv) in THF (5 mL) was added 1,1'-thiocarbonyldiimidazole (1.03 g, 5.8 mmol, 5.0 equiv). The reaction mixture was stirred at 70° C. for 1 h. It was cooled to room temperature and poured into ice-water. The solids precipitated were collected by filtration and triturated with hexane to afford 1.8. MS(ES): m/z: 387.4 [M+H]+.

Synthesis of compound 1.9. To a solution of 1.8 (0.350 g, 0.905 mmol, 1.0 equiv) in DCM (5 mL) was added sulfuryl chloride (2.7 mL, 33.48 mmol, 37 equiv) at 0° C. and stirred for 10 min. It was transferred into a saturated sodium bicarbonate solution, stirred, and extracted with DCM. The combined organic layers were washed with brine, dried over anhydrous sodium sulfate, filtered, and concentrated under reduced pressure. The residue was purified by flash column chromatography on silica gel (CombiFlash®, 2.4% methanol in DCM) to afford 1.9. MS (ES): m/z 389.8 [M+H]+.

Synthesis of compound 1. A mixture of 1.9 (0.080 g, 0.205 mmol, 1.0 equiv), Int-3 (0.052 g, 0.246 mmol, 1.2 equiv) and potassium carbonate (0.070 g, 0.512 mmol, 2.5 equiv) in 1,4-dioxane (2 mL) was degassed by bubbling through a stream of argon for 10 min. 4,5-Bis(diphenylphosphino)-9,9-dimethylxanthene (0.023 g, 0.041 mmol, 0.2 equiv) and tris(dibenzylideneacetone)dipalladium(0) (0.01 g, 0.021 mmol, 0.1 equiv) were added, and degassed for another 5 min. The reaction mixture was stirred at 80° C. for 3 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.0% methanol in DCM) to afford compound 1. MS(ES): m/z: 562.6 [M+H]+, $^1$H NMR (DMSO-$d_6$, 400 MHz): δ 9.89 (s, 1H), 9.20 (s, 1H), 8.11-8.10 (d, J=5.6 Hz, 1H), 7.96-7.95 (d, J=2.4 Hz, 1H), 7.63-7.62 (d, J=2.4 Hz, 1H), 7.47 (bs, 1H), 6.60-6.58 (m, 2H), 5.77 (s, 1H), 5.26 (bs, 1H), 4.13-4.07 (m, 5H), 3.88-3.83 (m, 2H), 3.75-3.73 (m, 2H), 3.68 (s, 3H), 3.19 (s, 3H), 2.27-2.24 (m, 1H), 1.41 (s, 9H).

Example 3: Methyl (4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)carbamate

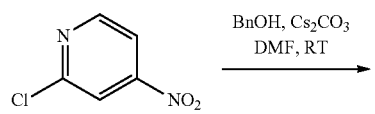

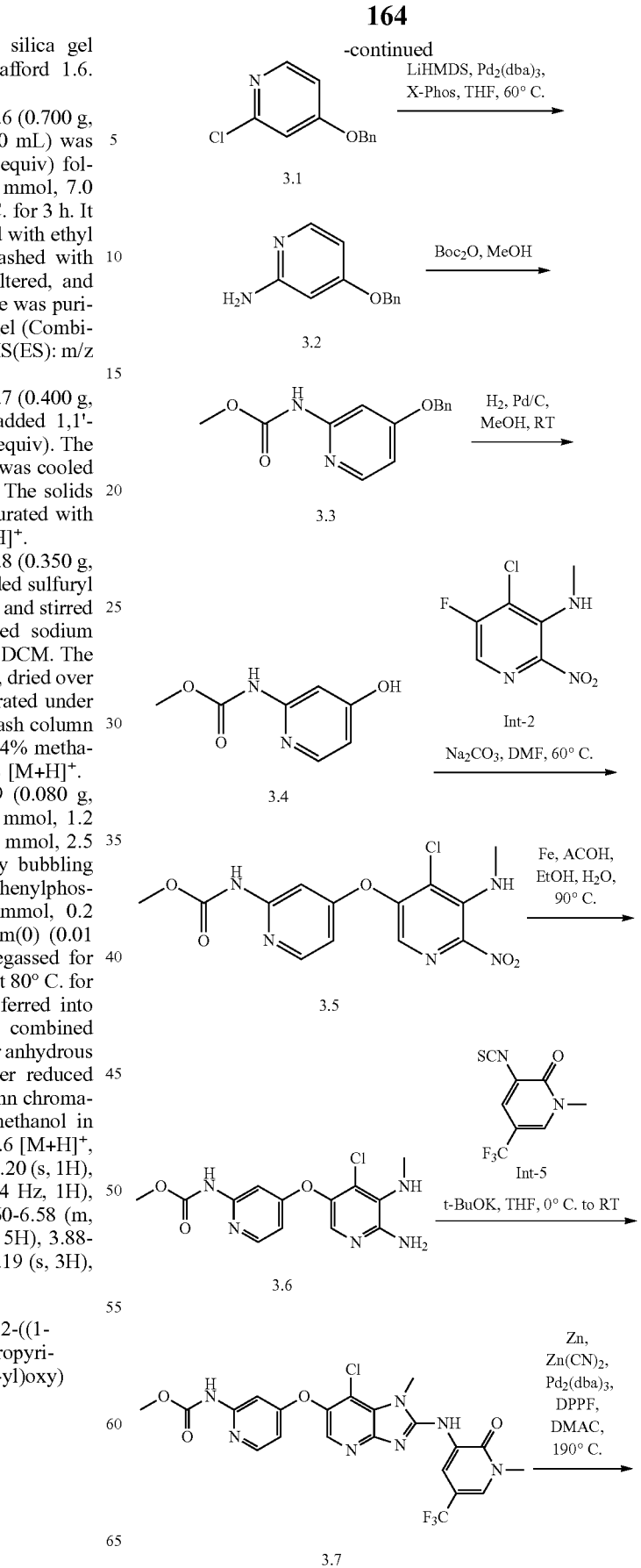

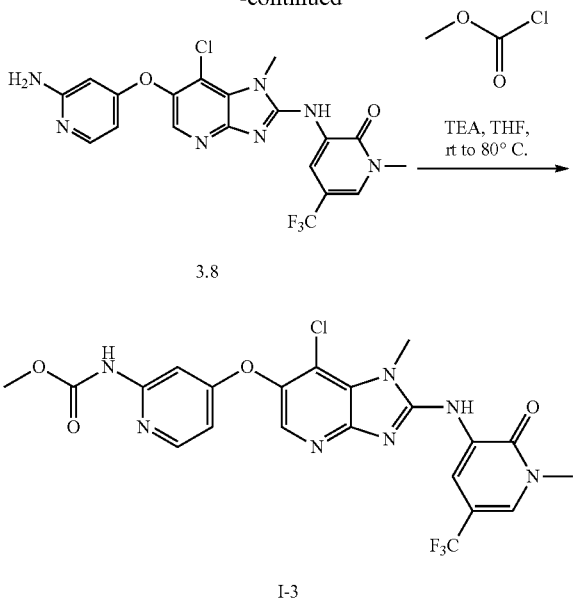

Synthesis of compound 3.1. A mixture of benzyl alcohol (102.3 g, 946.13 mmol, 1.0 equiv) and cesium carbonate (768.7 g, 2365.3 mmol, 2.5 equiv) in DMF (1000 mL) was stirred at room temperature for 2 h. A solution of 2-chloro-4-nitropyridine (150 g, 946.13 mmol, 1.0 equiv) in DMF (500 mL) was added and stirred for 16 h. It was poured into ice-water, stirred, and precipitated solids were collected by filtration and dried under vacuum to afford 3.1. MS (ES): m/z 220.5 [M+H]$^+$.

Synthesis of compound 3.2. A solution of 3.1 (150 g, 682.85 mmol, 1.0 equiv) in THF (1500 mL) was degassed by bubbling through a stream of argon for 10 min. To the solution was added 2-dicyclohexyl[2',4',6'-tris(propan-2-yl)[1,1'-biphenyl]-2-yl]phosphane (32.55 g, 68.28 mmol, 0.1 equiv) and tris(dibenzylideneacetone)dipalladium(0) (31.26 g, 34.14 mmol, 0.05 equiv) and degassed for another 10 min. Lithium bis(trimethylsilyl)amide solution (1 M in THF, 1365 mL, 1365.7 mmol, 2.0 equiv) was added and the reaction mixture was stirred at 60° C. for 1 h. It was concentrated under reduced pressure. The residue was added to ice and 6 N hydrochloric acid (1500 mL) slowly and extracted with ethyl acetate. The aqueous layer was separated and neutralized with solid sodium bicarbonate and extracted with DCM. The combined organic layers were washed with brine, dried over anhydrous sodium sulfate, filtered, and concentrated under reduced pressure to afford 3.2. MS(ES): m/z 201.2 [M+H]$^+$. It was used in the next step without purification.

Synthesis of compound 3.3. To a solution of 3.2 (100 g, 499 mmol, 1.0 equiv) in methanol (1000 mL) was added di-tert-butyl dicarbonate (130.5 g, 598.8 mmol, 1.2 equiv) at 0° C. The reaction mixture was stirred at room temperature for 3 h. After completion of reaction, precipitated solid was filtered out and rinsed with methanol, dried under vacuum to afford 3.3. MS(ES): m/z 259.2 [M+H]$^+$.

Synthesis of compound 3.4. A mixture of 3.3 (106 g, 410.4 mmol, 1.0 equiv) and 10% palladium on carbon (100 g) in methanol (1000 mL) was stirred under hydrogen (1 atm) for 1 h. It was filtered through a pad of Celite® and rinsed with methanol. The filtrate was concentrated under reduced pressure to afford 3.4. MS(ES): m/z 169.1 [M+H]$^+$.

Synthesis of compound 3.5. To a solution of 3.4 (66 g, 392.5 mmol, 1.0 equiv) in DMF (660 mL) was added Int-2 (64.55 g, 314 mmol, 0.8 equiv) followed by sodium carbonate (124.8 g, 1177.5 mmol, 3.0 equiv). The reaction mixture was stirred at 60° C. for 3 h. It was poured into ice-water, and precipitated solids were collected by filtration, dried under vacuum to afford 3.5. MS(ES): m/z 354.5 [M+H]$^+$.

Synthesis of compound 3.6. Compound 3.6 was prepared from compound 3.5 following the procedure described in the synthesis of compound 1.7. The product was purified by flash column chromatography on silica gel (CombiFlash®, 7.0% methanol in DCM) to afford 3.6. MS(ES): m/z 324.5 [M+H]$^+$.

Synthesis of compound 3.7. To a solution of 3.6 (38 g, 117.38 mmol, 1.0 equiv) and Int-5 (41.23 g, 176 mmol, 1.5 equiv) in THF (1300 mL) was added potassium tert-butoxide (1 M in THF, 704 mL, 704.28 mmol, 6.0 equiv) at 0° C. The reaction mixture was stirred at room temperature for 1 h. It was poured into ice-water, and product extracted with ethyl acetate. The combined organic layers were washed with brine, dried over anhydrous sodium sulfate, filtered, and concentrated under reduced pressure. The residue was purified by flash column chromatography on silica gel (CombiFlash®, 12% methanol in DCM) to afford 3.7. MS(ES): m/z: 524.2 [M+H]$^+$.

Synthesis of compound 3.8. To a solution of 3.7 (0.500 g, 0.954 mmol, 1.0 equiv) in DMA (11 mL) were added zinc (0.012 g, 0.190 mmol, 0.2 equiv) and zinc cyanide (0.056 g, 0.477 mmol, 0.5 equiv). The reaction mixture was degassed by bubbling through a stream of argon for 10 min. Tris(dibenzylideneacetone)dipalladium(0) (0.131 g, 0.143 mmol, 0.15 equiv) and 1,1'-bis(diphenylphosphino)ferrocene (0.158 g, 0.286 mmol, 0.3 equiv) were added, and degassed for 5 min. The reaction mixture was stirred at 190° C. in a microwave reactor for 2 h. It was cooled to room temperature, transferred into water, and extracted with ethyl acetate. The combined organic layers were washed with brine, dried over anhydrous sodium sulfate, filtered, and concentrated under reduced pressure to afford material.

Synthesis of I-3. To a solution of 3.8 (9.6 g, 21.03 mmol, 1.0 equiv) in THF (200 mL) was added triethylamine (5.9 mL, 42.06 mmol, 2.0 equiv) at 0° C. followed by methyl chloroformate (1.8 mL, 23.13 mmol, 1.1 equiv). The reaction mixture was stirred at room temperature for 4 h. It was poured into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.4% methanol in DCM) to afford I-3. MS(ES): m/z: 515.2 [M+H]$^+$. $^1$H NMR (DMSO-$d_6$, 400 MHz): δ 10.41 (s, 1H), 9.07 (s, 1H), 8.66 (s, 1H), 8.34 (s, 1H), 8.23-8.21 (d, J=6.8 Hz 2H), 7.49 (s, 1H), 6.76-6.75 (d, J=5.2 Hz 1H), 3.98 (s, 3H), 3.68 (s, 3H), 3.64 (s, 3H).

Example 4: 3-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-1,1-dimethylurea

Example 5: 1-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-3-methylurea

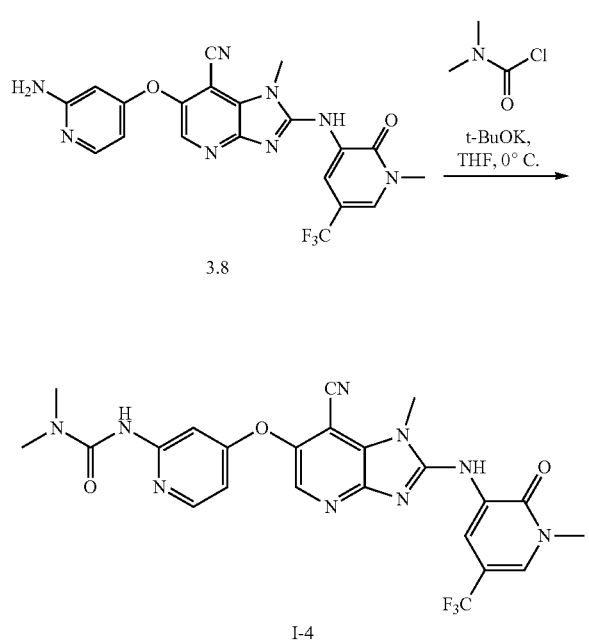

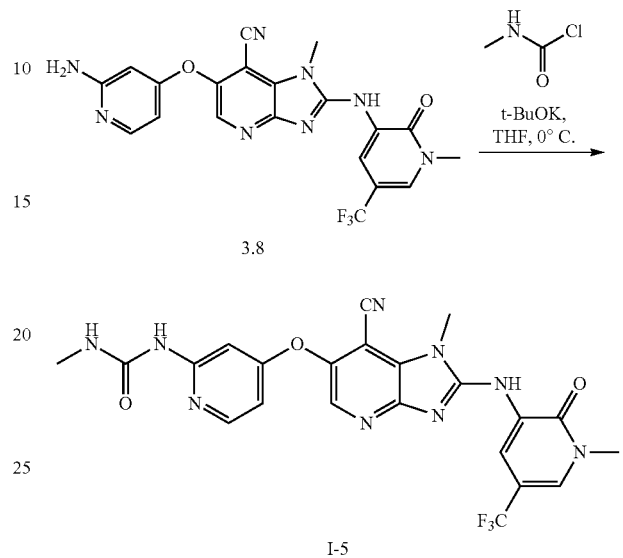

Synthesis of I-4. To a solution of 3.8 (0.040 g, 0.087 mmol, 1.0 equiv) and dimethylcarbamic chloride (0.010 g, 0.096 mmol, 1.1 equiv) in THF (2 mL) was added potassium tert-butoxide (1M in THF) (0.52 mL, 0.522 mmol, 6.0 equiv) at 0° C. and stirred at same temperature for 15 min. The reaction mixture was poured into ice-water, and product extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford I-4. MS(ES): m/z: 528.3 [M+H]$^+$, $^1$H NMR (DMSO-d$_6$, 400 MHz): δ 9.04-9.03 (d, J=6.8 Hz 2H), 8.66 (s, 1H), 8.31 (s, 1H), 8.19 (s, 1H), 8.17 (s, 1H), 7.48 (s, 1H), 6.69 (bs, 1H), 3.97 (s, 3H), 3.67 (s, 3H), 2.90 (s, 6H).

Synthesis of I-5. To a solution of 3.8 (0.040 g, 0.087 mmol, 1.0 equiv) and methylcarbamic chloride (0.009 g, 0.105 mmol, 1.2 equiv) in THF (2 mL) was added potassium tert-butoxide (1M in THF) (0.35 mL, 0.348 mmol, 4.0 equiv) at 0° C. and stirred at same temperature for 15 min. The reaction mixture was poured into ice-water, and product extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.5% methanol in DCM) to afford I-5. MS(ES): m/z: 514.2 [M+H]$^+$. NMR (DMSO-d$_6$, 400 MHz): δ 9.21 (s, 1H), 9.07 (s, 1H), 8.66-8.65 (d, J=1.6 Hz, 1H), 8.32 (s, 1H), 8.20 (s, 1H), 8.14-8.13 (d, J=6.0 Hz, 1H), 7.80 (bs, 1H), 7.09-7.07 (d, J=7.2 Hz, 1H), 7.04 (s, 1H), 3.98 (s, 3H), 3.67 (s, 3H), 2.70-2.69 (d, 3H).

Example 6: N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-4-methylpiperazine-1-carboxamide

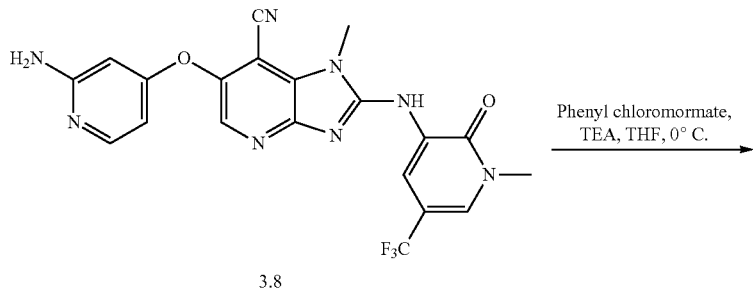

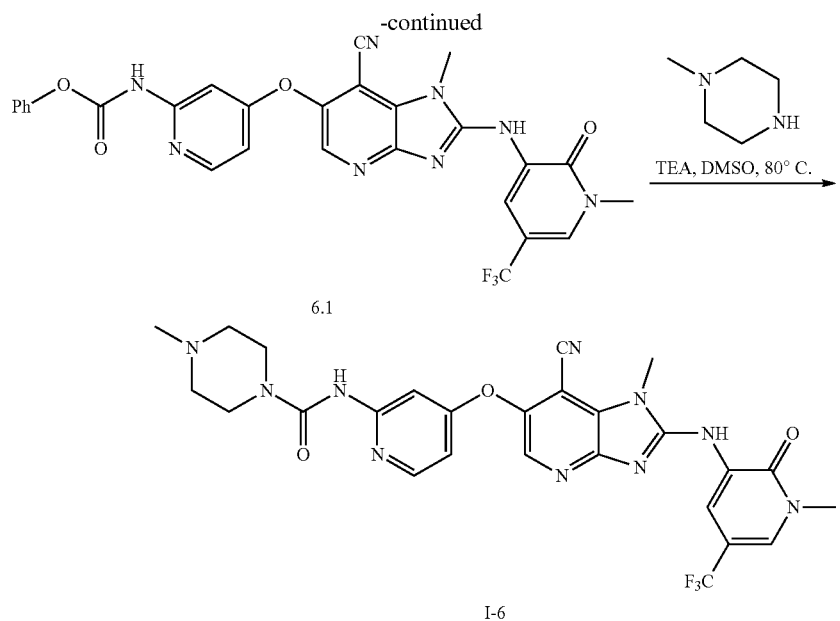

Synthesis of compound 6.1 To a solution of 3.8 (0.025 g, 0.054 mmol, 1.0 equiv) and triethylamine (0.016 g, 0.162 mmol, 3.0 equiv) in THF (3 mL) was added phenyl chloroformate (0.012 g, 0.081 mmol, 1.5 equiv) at 0° C. The reaction mixture was stirred at 0° C. for 15 min. It was poured into ice-water, stirred, and extracted with ethyl acetate. The combined organic layers were washed with brine, dried over anhydrous sodium sulfate, filtered, and concentrated under reduced pressure to afford 6.1. MS(ES): m/z: 577.4 [M+H]$^+$.

Synthesis of I-6. To a solution of 6.1 (0.030 g, 0.052 mmol, 1.0 equiv) and triethylamine (0.015 g, 0.156 mmol, 3.0 equiv) in dimethyl sulfoxide (3 mL) was added 1-methylpiperazine (0.008 g, 0.078 mmol, 1.5 equiv). The reaction mixture was stirred at 80° C. for 15 min. It was transferred into water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 7.0% methanol in DCM) to afford 1-6. MS(ES): m/z: 583.3 [M+H]$^+$, $^1$H NMR (DMSO-d$_6$, 400 MHz): δ 9.37 (s, 1H), 9.06 (s, 1H), 8.67 (s, 1H), 8.32 (s, 1H), 8.20 (bs, 2H), 7.47 (s, 1H), 6.70 (s, 1H), 3.98 (s, 3H), 3.68 (s, 3H), 3.43 (bs, 4H), 2.45 (bs, 4H), 2.29 (s, 3H).

Example 7: N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)azetidine-1-carboxamide

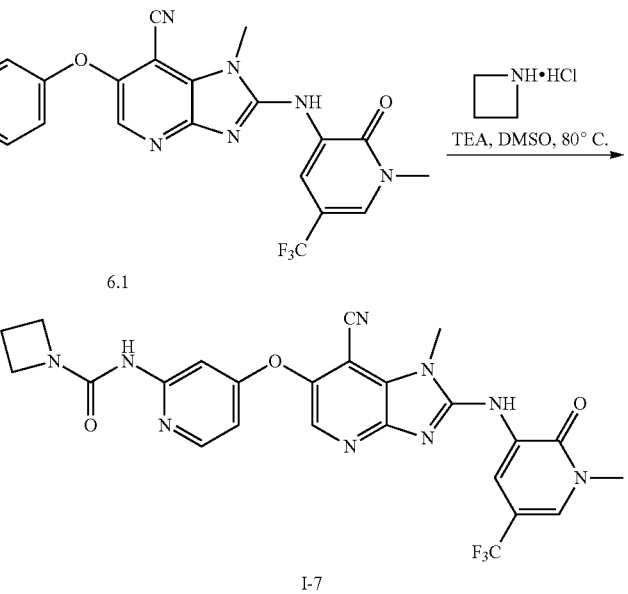

Synthesis of I-7. Compound I-7 was prepared from 6.1 and azetidine hydrochloride, following the procedure described in the synthesis of I-6. The product was purified by preparative HPLC. MS(ES): m/z: 540.4 [M+H]$^+$. $^1$H NMR (DMSO-d$_6$, 400 MHz): δ 9.23 (s, 1H), 9.06 (s, 1H), 8.66 (s, 1H), 8.31 (s, 1H), 8.20 (bs, 1H), 8.18-8.17 (d, J=6 Hz, 1H), 7.58 (s, 1H), 6.68 (s, 1H), 3.98 (s, 3H), 3.95 (bs, 4H), 3.67 (s, 3H), 2.16-2.12 (m, 2H).

Example 8: N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)hydroxyazetidine-1-carboxamide

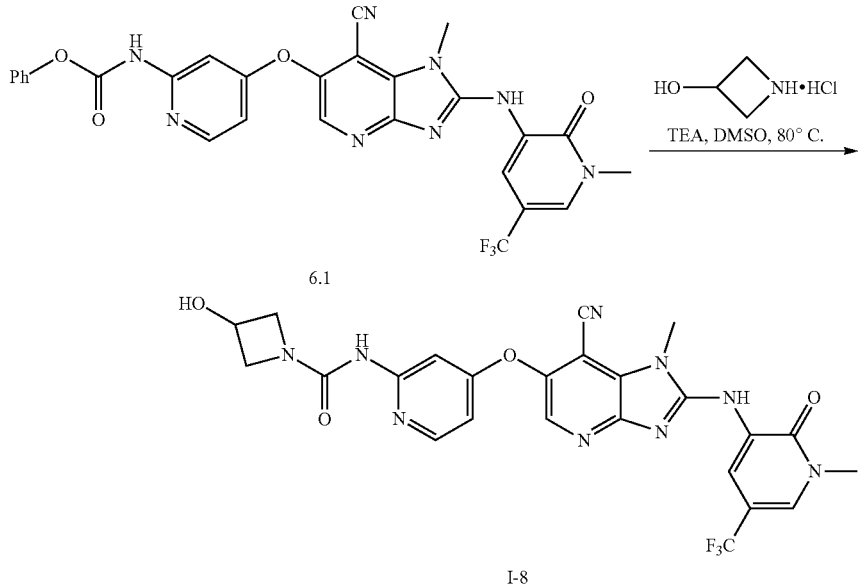

Synthesis of I-8. Compound I-8 was prepared from 6.1 and azetidin-3-ol hydrochloride, following the procedure described in the synthesis of I-6. The product was purified by flash column chromatography on silica gel (CombiFlash®, 3.0% methanol in DCM). MS(ES): m/z: 556.3 [M+H]$^+$, $^1$H NMR (DMSO-d$_6$, 400 MHz): δ 9.29 (s, 1H), 9.05 (s, 1H), 8.66 (s, 1H), 8.31 (s, 1H), 8.20 (bs, 1H), 8.18-8.17 (d, J=5.6 Hz, 1H), 7.58 (bs, 1H), 6.69-6.67 (m, 1H), 5.63-5.62 (d, J=6.4 Hz, 1H), 4.40-4.38 (m, 1H), 4.14-4.11 (m, 2H), 3.97 (s, 3H), 3.67 (s, 3H), 3.19-3.17 (m, 2H).

Example 9: N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-3-methoxyazetidine-1-carboxamide

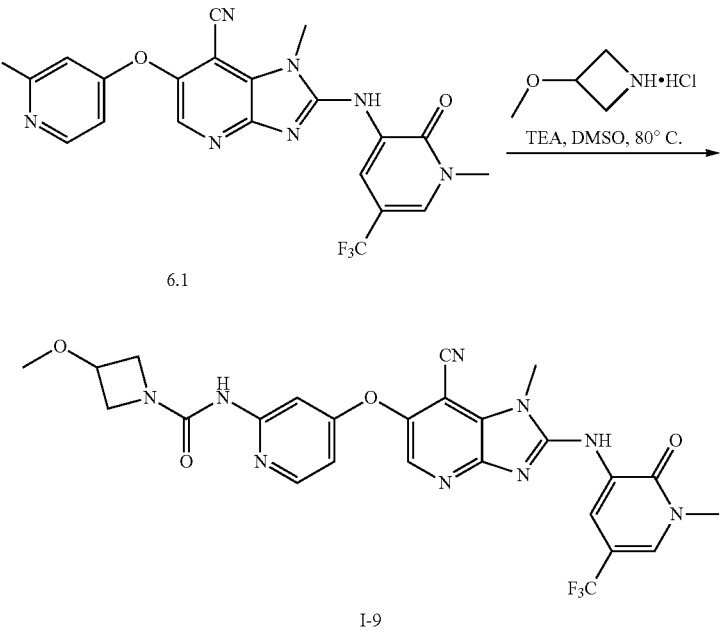

Synthesis of I-9. Compound I-9 was prepared from 6.1 and 3-methoxyazetidine hydrochloride, following the procedure described in the synthesis of I-6. The product was purified by flash column chromatography on silica gel (CombiFlash®, 3.0% methanol in DCM). MS(ES): m/z: 570.3 [M+H]$^+$, $^1$H NMR (DMSO-d$_6$, 400 MHz): δ 9.38 (s, 1H), 9.05 (s, 1H), 8.66 (s, 1H), 8.32 (s, 1H), 8.19-8.18 (m, 2H), 7.57 (bs, 1H), 6.69 (bs, 1H), 4.14 (bs, 4H), 3.98 (s, 3H), 3.76 (bs, 1H), 3.68 (s, 3H), 3.20 (s, 3H).

Example 10: Methyl(4-((2-((1-(2-oxaspiro[3.3]heptan-6-yl)-5-(trifluoromethyl)-1H-pyrazol-3-yl)amino)-7-chloro-1-methyl-1H-imidazo[4,5-b]pyridin-6-yl)oxy)pyridin-2-yl)carbamate

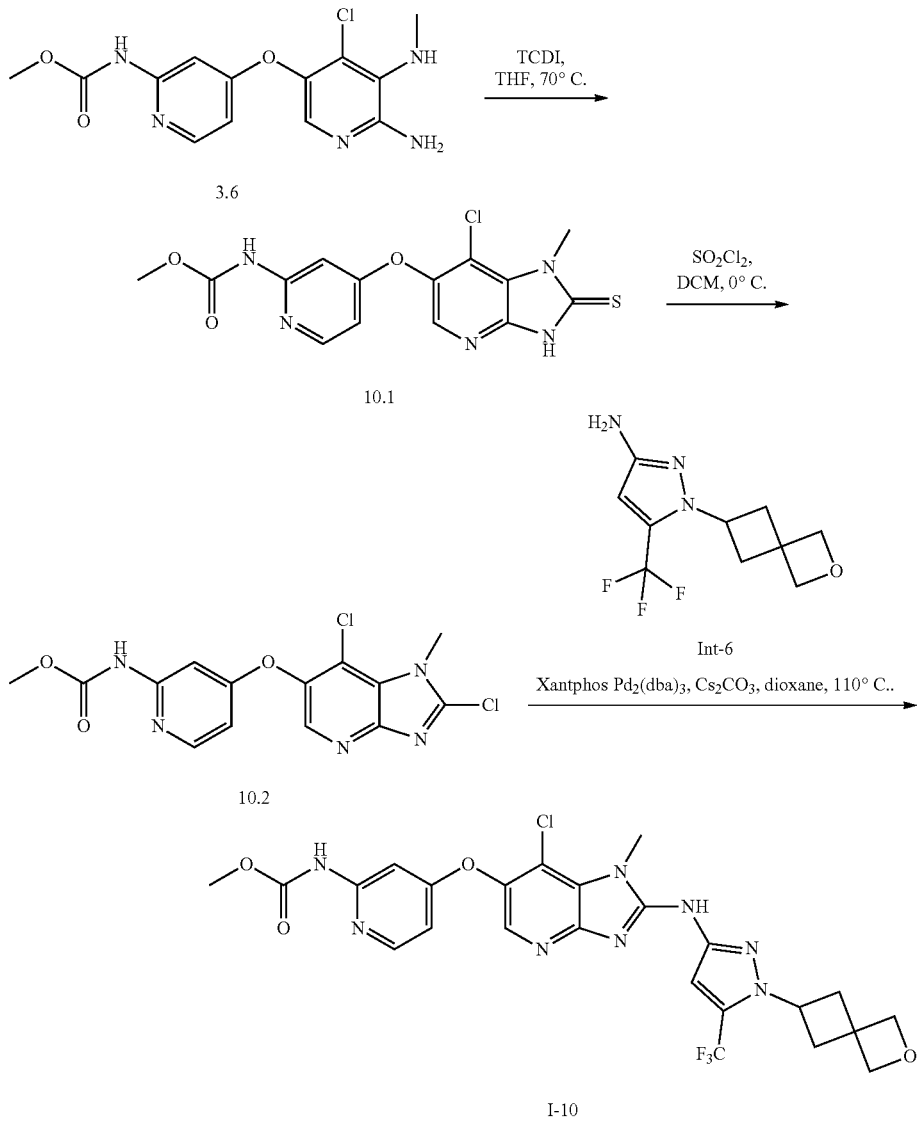

Synthesis of compound 10.1. To a solution of 3.6 (8.0 g, 24.71 mmol, 1.0 equiv) in THF (80 mL) was added 1,1'-thiocarbonyldiimidazole (21.99 g, 123.5 mmol, 5.0 equiv). The reaction mixture was stirred at 70° C. for 1 h. It was cooled to room temperature and poured into ice-water. The solids precipitated were collected by filtration and triturated with hexane to afford 10.1. MS(ES): m/z: 332.2 [M+H]$^+$.

Synthesis of compound 10.2. To a solution of 10.1 (2.0 g, 5.47 mmol, 1.0 equiv) in DCM (20 mL) was added sulfuryl chloride (16.4 mL, 202.39 mmol, 37 equiv) at 0° C. and the reaction mixture was stirred for 10 min. It was transferred into saturated sodium bicarbonate solution, stirred, and extracted with DCM. The combined organic layers were washed with brine, dried over anhydrous sodium sulfate, filtered, and concentrated under reduced pressure. The residue was purified by flash column chromatography on silica gel (CombiFlash®, 2.3% methanol in DCM) to afford 10.2. MS (ES): m/z 369.1 [M+H]⁺.

Synthesis of I-10. A mixture of 10.2 (0.050 g, 0.135 mmol, 1.0 equiv) and Int-6 (0.043 g, 0.176 mmol, 1.3 equiv) and cesium carbonate (0.131 g, 0.405 mmol, 3.0 equiv) in 1,4-dioxane (2 mL) was degassed by bubbling through a stream of argon for 10 min. 4,5-Bis(diphenylphosphino)-9,9-dimethylxanthene (0.015 g, 0.027 mmol, 0.2 equiv) and tris(dibenzylideneacetone)dipalladium(0) (0.012 g, 0.013 mmol, 0.1 equiv) were added, and degassed for 5 min. The reaction mixture was stirred at 110° C. for 2 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.0% methanol in DCM) to afford I-10. MS(ES): m/z: 579.4 [M+H]⁺, ¹H NMR (DMSO-d₆, 400 MHz): δ 10.58 (s, 1H), 10.32 (s, 1H), 8.15 (bs, 2H), 7.36 (s, 1H), 7.31 (s, 1H), 6.65-6.64 (d, J=3.6 Hz, 1H), 4.88-4.82 (m, 1H), 4.70 (bs, 2H), 4.58 (bs, 2H), 3.96 (s, 3H), 3.60 (s, 3H), 2.81 (bs, 4H).

Example 11: N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)pyrrolidine-1-carboxamide

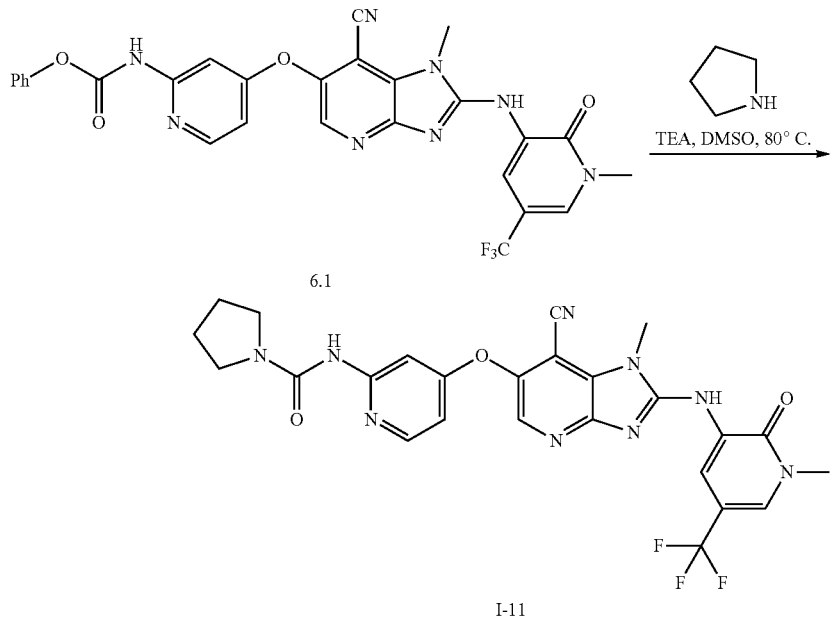

Synthesis of I-11. Compound I-11 was prepared from 6.1 and pyrrolidine, following the procedure described in the synthesis of I-6. The product was purified by flash column chromatography on silica gel (CombiFlash®, 3.2% methanol in DCM). MS(ES): m/z: 554.3 [M+H]⁺. ¹H NMR (DMSO-d₆, 400 MHz): δ 9.05 (s, 1H), 8.85 (s, 1H), 8.67-8.66 (d, J=2.0 Hz, 1H), 8.32 (s, 1H), 8.20-8.18 (m, 2H), 7.57 (bs, 1H), 6.70-6.69 (d, J=3.2 Hz, 1H), 3.98 (s, 3H), 3.68 (s, 3H), 2.47 (bs, 4H), 1.82 (bs, 4H).

Example 12: 2-methoxyethyl(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)carbamate

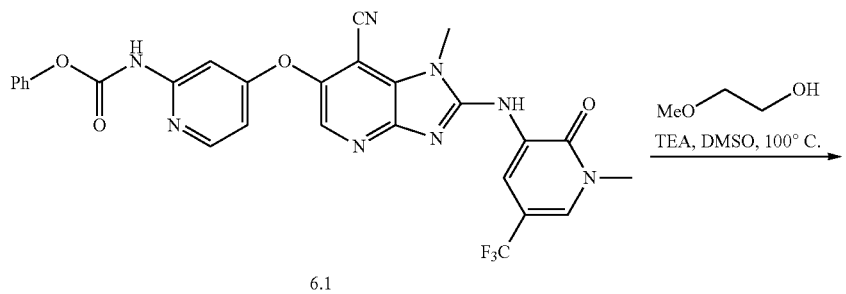

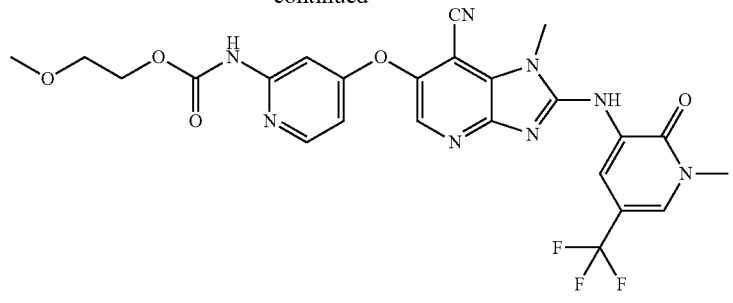

I-12

Synthesis of I-12. A solution of 6.1 (0.110 g, 0.190 mmol, 1.0 equiv), 2-methoxyethan-1-ol (0.022 g, 0.286 mmol, 1.5 equiv) and triethylamine (0.115 g, 1.14 mmol, 6.0 equiv) in dimethyl sulfoxide (5 mL) was stirred at 100° C. for 16 h. It was transferred into water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.5% methanol in DCM) to afford I-12. MS(ES): m/z: 559.2 [M+H]$^+$, $^1$H NMR (DMSO-$d_6$, 400 MHz): δ 10.41 (s, 1H), 9.06 (s, 1H), 8.66 (s, 1H), 8.34 (s, 1H), 8.22-8.21 (m, 2H), 7.47 (bs, 1H), 6.76-6.75 (d, J=2.8 Hz, 1H), 4.19 (bs, 2H), 3.98 (s, 3H), 3.68 (s, 3H), 3.53 (bs, 2H), 3.27 (s, 3H).

Example 13: (R)-N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)methoxypyrrolidine-1-carboxamide

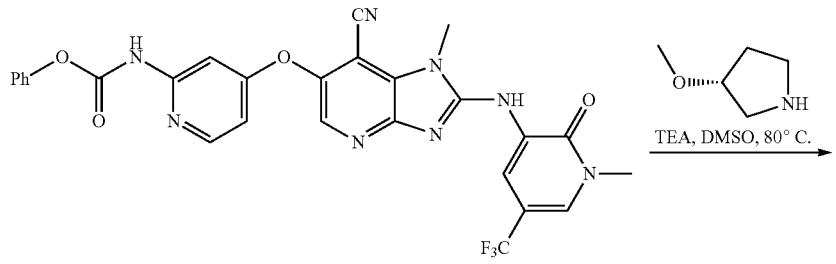

6.1

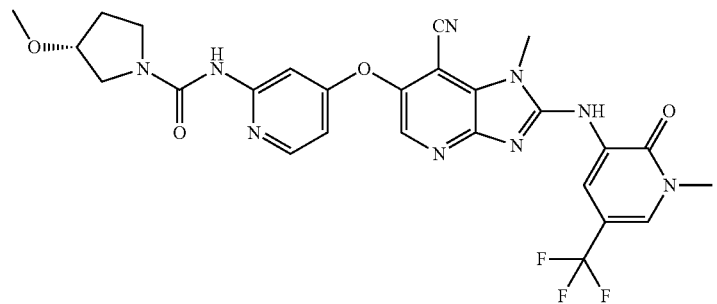

I-13

Synthesis of I-13. Compound I-13 was prepared from 6.1 and (R)-3-methoxypyrrolidine, following the procedure described in the synthesis of I-6. The product was purified by flash column chromatography on silica gel (CombiFlash®, 4.7% methanol in DCM). MS(ES): m/z: 584.3 [M+H]$^+$, $^1$H NMR (DMSO-$d_6$, 400 MHz): δ 9.04 (s, 1H), 8.94 (s, 1H), 8.65 (s, 1H), 8.31 (s, 1H), 8.19-8.17 (m, 2H), 7.55-7.54 (d, J=2.0 Hz, 1H), 6.70-6.68 (m, 1H), 3.96 (s, 3H), 3.66 (s, 3H), 3.46 (bs, 2H), 3.38 (bs, 1H), 3.21 (s, 3H), 2.54 (bs, 2H), 1.93 (bs, 2H).

Example 14: (S)-N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-3-methoxypyrrolidine-1-carboxamide

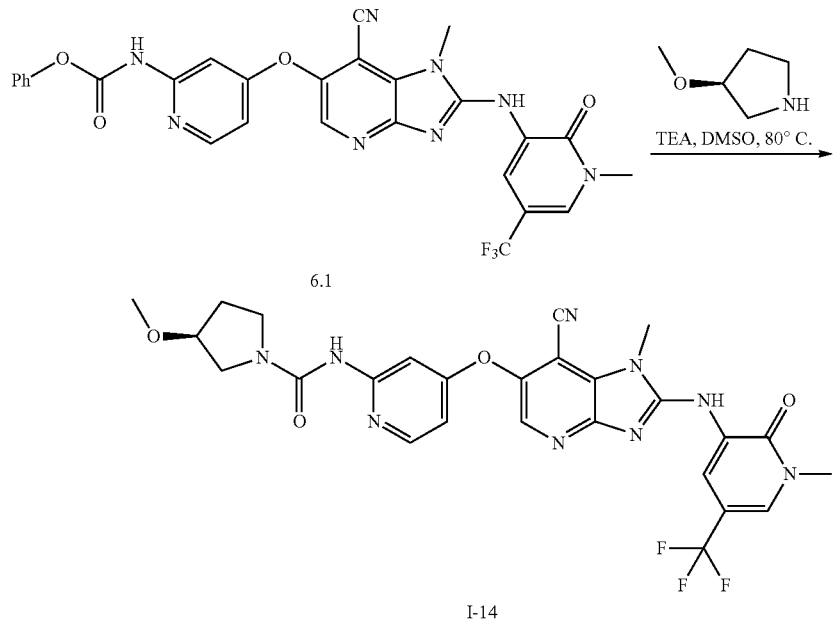

Synthesis of I-14. Compound I-14 was prepared from 6.1 and (S)-3-methoxypyrrolidine, following the procedure described in the synthesis of I-6. The product was purified by flash column chromatography on silica gel (CombiFlash®, 4.9% methanol in DCM). MS(ES): m/z: 584.3 [M+H]$^+$, $^1$H NMR (DMSO-d$_6$, 400 MHz): δ 9.04 (s, 1H), 8.94 (s, 1H), 8.65 (s, 1H), 8.31 (s, 1H), 8.18-8.17 (m, 2H), 7.54 (z, 1H), 6.69-6.68 (m, 1H), 3.96 (s, 3H), 3.66 (s, 3H), 3.46 (bs, 2H), 3.39 (bs, 1H), 3.21 (s, 3H), 2.54 (bs, 2H), 1.93 (bs, 2H).

Example 15: 2-Morpholinoethyl(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)carbamate

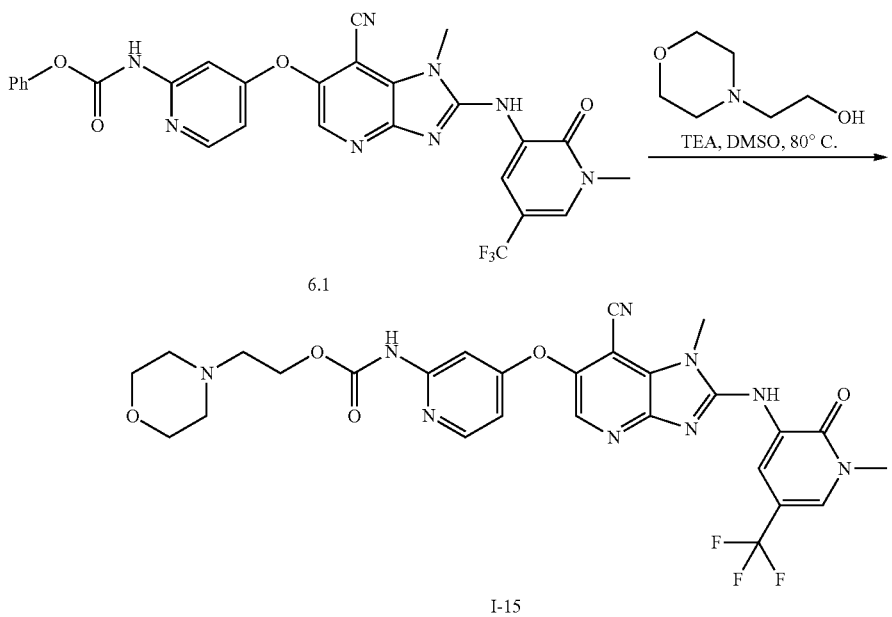

Synthesis of I-15. Compound I-15 was prepared from 6.1 and 2-morpholinoethan-1-ol, following the procedure described in the synthesis of I-6. The product was purified by flash column chromatography on silica gel (CombiFlash®, 2.5% methanol in DCM). MS(ES): m/z: 614.3 [M+H]$^+$, $^1$H NMR (DMSO-d$_6$, 400 MHz): δ 10.37 (s, 1H), 9.06 (s, 1H), 8.65 (s, 1H), 8.33 (s, 1H), 8.19 (bs, 2H), 7.45 (s, 1H), 6.74 (s, 1H), 4.16 (bs, 2H), 3.96 (s, 3H), 3.66 (s, 3H), 3.53 (bs, 4H), 2.40 (bs, 6H).

Example 16: Oxetan-3-yl(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)carbamate

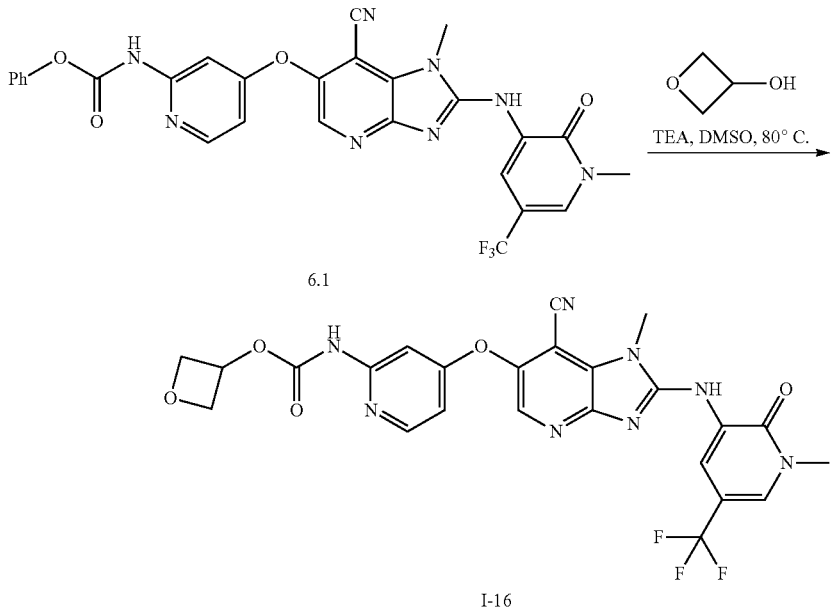

Synthesis of I-16. Compound I-16 was prepared from 6.1 and oxetan-3-ol, following the procedure described in the synthesis of I-6. The product was purified by flash column chromatography on silica gel (CombiFlash®, 2.7% methanol in DCM). MS(ES): m/z: 557.2 [M+H]$^+$, $^1$H NMR (DMSO-d$_6$, 400 MHz): δ 10.63 (s, 1H), 9.05 (s, 1H), 8.65 (s, 1H), 8.32 (s, 1H), 8.23-8.22 (d, J=5.6 Hz, 1H), 8.19 (s, 1H), 7.40 (s, 1H), 6.78 (bs, 1H), 5.36 (bs, 1H), 4.77-4.75 (m, 2H), 4.50 (bs, 2H), 3.96 (s, 3H), 3.66 (s, 3H).

Example 17: (S)-Tetrahydrofuran-3-yl(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)carbamate

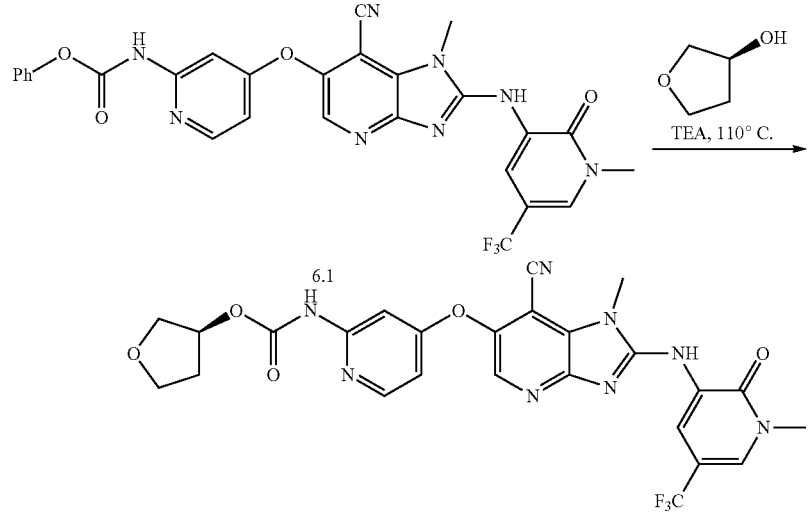

Synthesis of I-17. Compound 6.1 (0.110 g, 0.190 mmol, 1.0 equiv) and (S)-tetrahydrofuran-3-ol (0.084 g, 0.954 mmol, 5.0 equiv) in triethylamine (1.0 mL) was stirred at 110° C. for 6 h. It was transferred into water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.2% methanol in DCM) to afford I-17. MS(ES): m/z: 571.3 [M+H]$^+$. $^1$H NMR (DMSO-d$_6$, 400 MHz): δ 10.37 (s, 1H), 9.06 (s, 1H), 8.65 (s, 1H), 8.33 (s, 1H), 8.21-8.20 (m, 2H), 7.43 (s, 1H), 6.76-6.75 (d, J=4.0 Hz, 1H), 5.20 (bs, 1H), 3.96 (s, 3H), 3.78-3.72 (m, 4H), 3.66 (s, 3H), 2.16-2.10 (m, 1H), 1.92-1.89 (m, 1H).

Example 18: (R)-Tetrahydrofuran-3-yl(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)carbamate

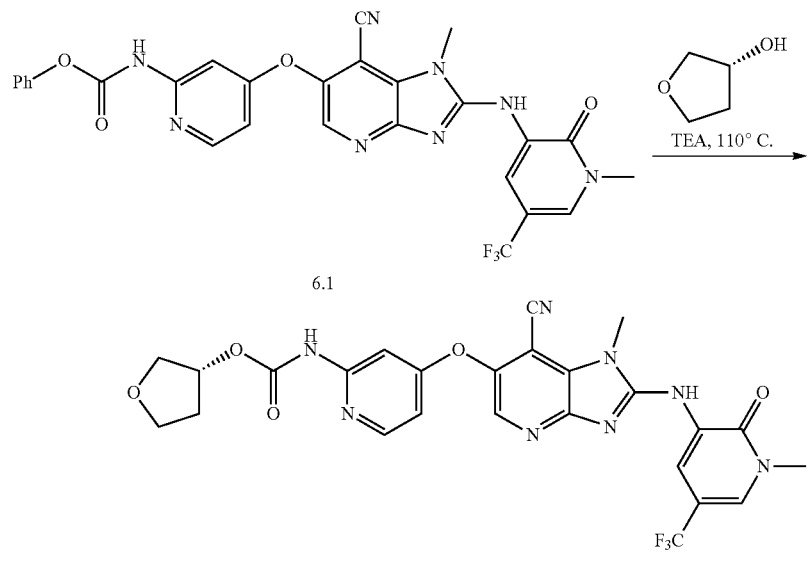

Synthesis of I-18. Compound I-18 was prepared from 6.1 and (R)-tetrahydrofuran-3-ol, following the procedure described in the synthesis of I-17. The product was purified by flash column chromatography on silica gel (CombiFlash®, 3.2% methanol in DCM). MS(ES): m/z: 571.3 [M+H]$^+$. $^1$H NMR (DMSO-d$_6$, 400 MHz): δ 10.38 (s, 1H), 9.07 (s, 1H), 8.67 (s, 1H), 8.34 (s, 1H), 8.22-8.21 (m, 2H), 7.45 (s, 1H), 6.77 (bs, 1H), 5.21 (bs, 1H), 3.98 (s, 3H), 3.79-3.70 (m, 4H), 3.68 (s, 3H), 2.15-2.11 (m, 1H), 1.92 (bs, 1H).

Example 19: 2-(Dimethylamino)ethyl(4-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)carbamate

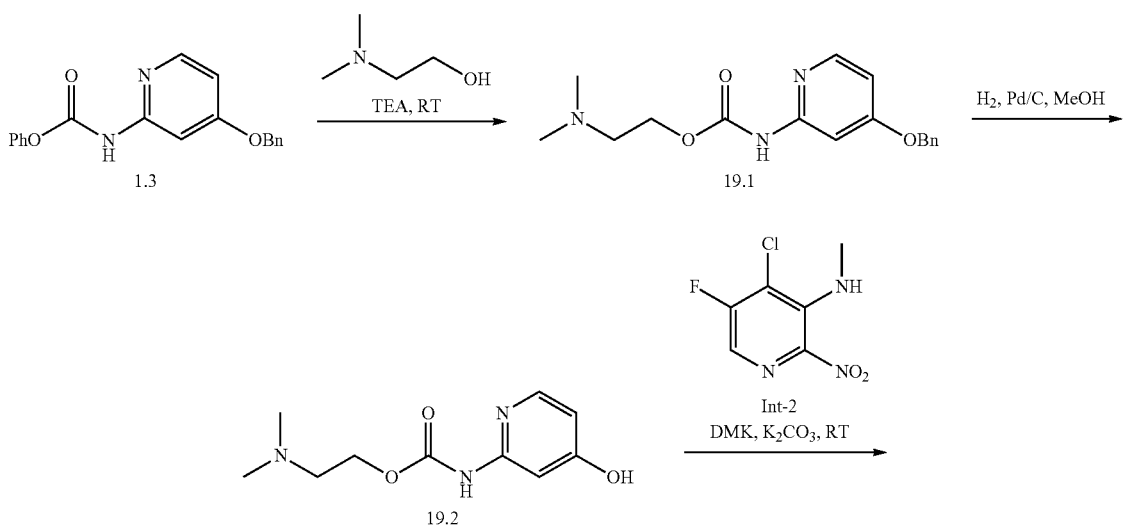

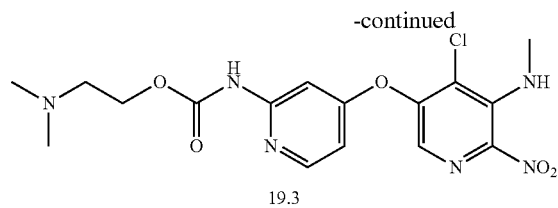

19.3

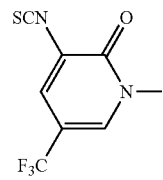

Int-5 i. t-BuOK, THF, 0° C.
ii. EDC—HCl, 70° C.

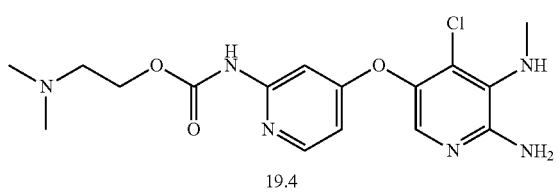

19.4

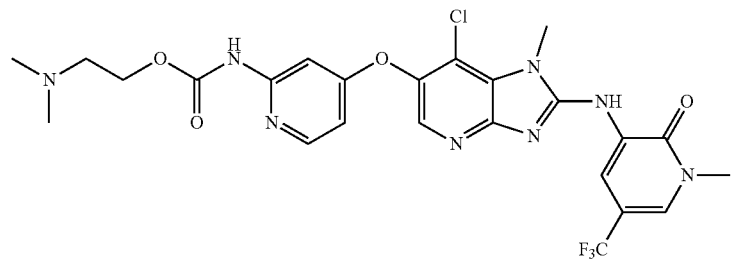

I-19

Synthesis of compound 19.1. A solution of 1.3 (0.400 g, 1.25 mmol, 1.0 equiv), triethylamine (0.87 mL, 6.25 mmol, 5.0 equiv) and 2-(dimethylamino)ethan-1-ol (0.166 g, 1.87 mmol, 1.5 equiv) was stirred at 70° C. for 30 min. It was transferred into water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.0% methanol in DCM) to afford 19.1. MS(ES): m/z: 316.3 [M+H]+.

Synthesis of compound 19.2. A mixture of compound 19.1 (0.230 g, 0.729 mmol, 1.0 equiv) and 10% palladium on carbon (0.200 g) in methanol (5 mL) was stirred under hydrogen (1 atm) for 30 min. It was filtered through a pad of Celite® and rinsed with methanol. The filtrate was concentrated under reduced pressure to afford 19.2. MS(ES): m/z 226.1 [M+H]+.

Synthesis of compound 19.3. A mixture of 19.2 (0.150 g, 0.665 mmol, 1.0 equiv), Int-2 (0.109 g, 0.532 mmol, 0.8 equiv) and potassium carbonate (0.275 g, 1.995 mmol, 3.0 equiv)) in DMF (5 mL) was stirred at room temperature for 1.5 h. It was poured into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 7.0% methanol in DCM) to afford 19.3. MS(ES): m/z 411.5 [M+H]+.

Synthesis of compound 19.4. Compound 19.4 was prepared from 19.3 following the procedure described in the synthesis of compound 3.6. The product was purified by flash column chromatography on silica gel (CombiFlash®, 9.0% methanol in DCM). MS(ES): m/z 381.5 [M+H]+.

Synthesis of I-19. To a solution of 19.4 (0.080 g, 0.210 mmol, 1.0 equiv) in THF (3.0 mL) was added Int-5 (0.098 g, 0.420 mmol, 2.0 equiv) followed by addition of potassium tert-butoxide (1 M in THF, 0.63 mL, 0.630 mmol, 3.0 equiv) at 0° C. The reaction mixture was stirred at 0° C. for 30 min. The reaction mixture was poured into ice-water, and product extracted with ethyl acetate. The combined organic layers were washed with brine, dried over anhydrous sodium sulfate, filtered, and concentrated under reduced pressure. The residue was dissolved in THF (3.0 mL) and N-(3-dimethylaminopropyl)-N'-ethylcarbodiimide hydrochloride (0.120 g, 0.630 mmol, 3.0 equiv) was added. The reaction mixture was stirred at 70° C. for 1.5 h. It was transferred into water and product extracted with ethyl acetate. This was further purified by flash column chromatography on silica gel (CombiFlash®, 10% methanol in DCM) to afford I-19. MS(ES): m/z: 581.2 [M+H]+. $^1$H NMR (DMSO-$d_6$, 400 MHz): δ 10.31 (s, 1H), 8.87 (s, 1H), 8.63 (s, 1H), 8.25 (s, 1H), 8.16 (bs, 2H), 7.36 (s, 1H), 6.67 (bs, 1H), 4.17 (bs, 2H), 3.99 (s, 3H), 3.66 (s, 3H), 3.52-3.45 (m, 2H), 2.30 (bs, 6H).

Example 20: 2-Hydroxyethyl(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)carbamate

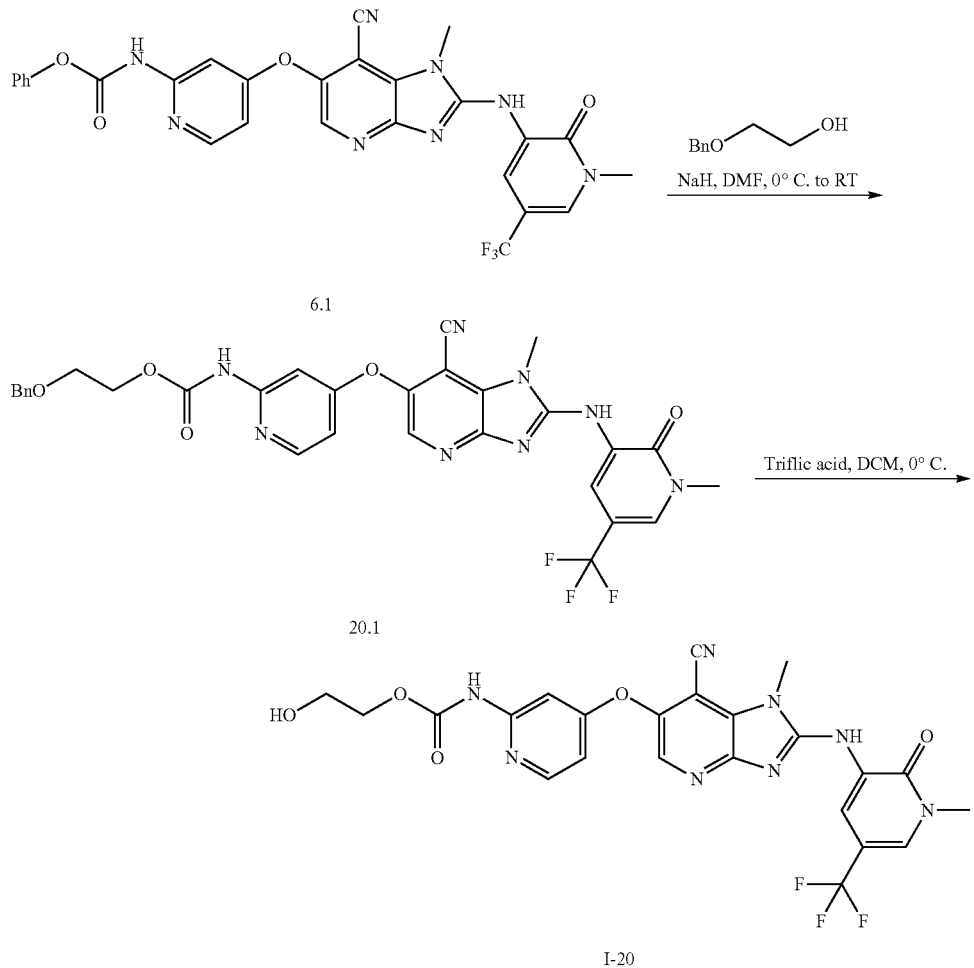

Synthesis of compound 20.1. To a solution of 2-(benzyloxy)ethan-1-ol (0.063 g, 0.416 mmol, 1.0 equiv) in DMF (5 mL) was sodium hydride (0.049 g, 1.248 mmol, 3.0 equiv) at 0° C. and stirred for 30 min. To the mixture was added 6.1 (0.200 g, 0.346 mmol, 1.0 equiv) and stirred at room temperature for 30 min. It was poured into ice-water and extracted with ethyl acetate. The combined organic layers were washed with brine, dried over anhydrous sodium sulfate, filtered, and concentrated under reduced pressure to afford material This was further purified by flash column chromatography on silica gel (CombiFlash®, 2.2% methanol in DCM) to afford 20.1. MS(ES): m/z: 635.4 [M+H]⁺.

Synthesis of I-20. To solution of 20.1 (0.040 g, 0.063 mmol, 1.0 equiv) in DCM (3 mL) was added triflic acid (1 mL) at 0° C. and stirred for 10 min. It was transferred into ice-cold saturated sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 3.0% methanol in DCM) to afford I-20. MS(ES): m/z: 545.2 [M+H]⁺. ¹H NMR (DMSO-$d_6$, 400 MHz): δ 10.63 (s, 1H), 8.99 (s, 1H), 8.60 (s, 1H), 8.27 (s, 1H), 8.14 (bs, 2H), 7.41 (s, 1H), 6.68 (bs, 1H), 4.74 (s, 1H), 4.02 (bs, 2H), 3.91 (s, 3H), 3.61 (s, 3H), 3.51 (bs, 2H).

Example 21: 3-(4-((7-cyano-2-((4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)-1,1-dimethylurea

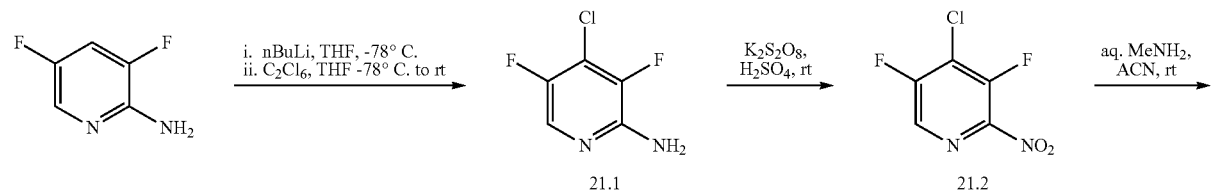

-continued
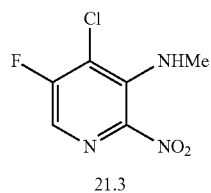 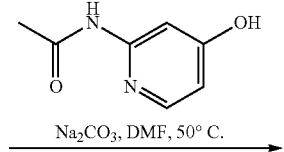 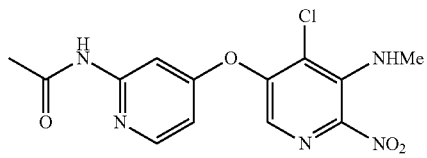
21.3
21.4
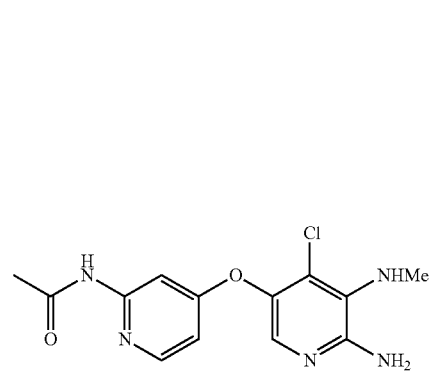
21.5
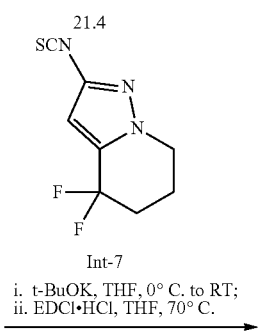
Int-7
i. t-BuOK, THF, 0° C. to RT;
ii. EDCl·HCl, THF, 70° C.
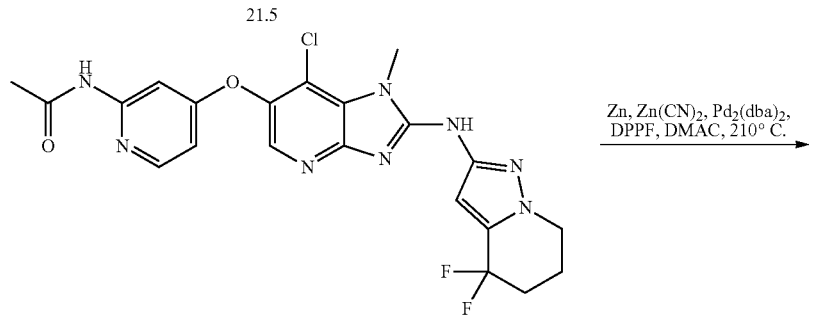
21.6
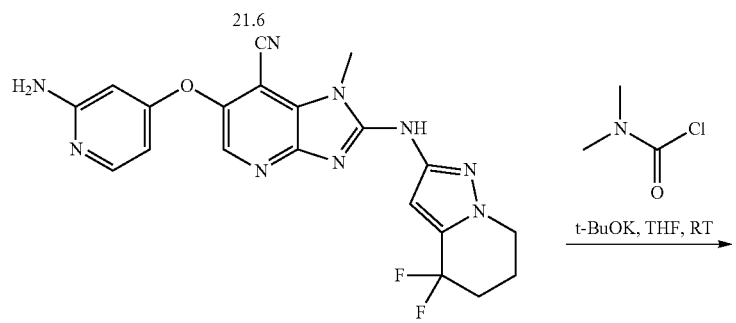
21.7
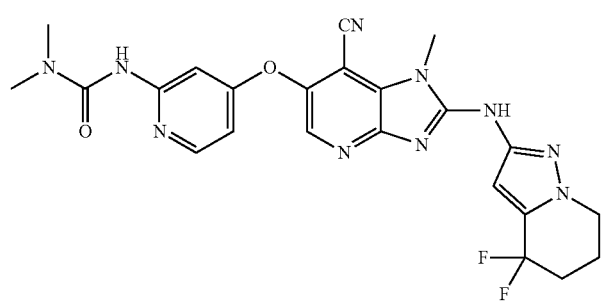
I-21
Synthesis of compound 21.1. To a solution of 3,5-difluoropyridin-2-amine (10 g, 76.87 mmol, 1.0 equiv) in THF (200 mL), was added n-butyl lithium (2.5M in hexane) (61.4 mL, 153.7 mmol, 2.0 equiv) at −78° C. and stirred for 40 min. Hexachloroethane (36.3 g, 153.7 mmol, 2.0 equiv) was added and the reaction mixture was stirred at −78° C. for 40 min. A saturated aqueous ammonium chloride solution was added carefully to quench the reaction. The mixture was extracted with ethyl acetate. The combined organic layers were washed with brine, dried over anhydrous sodium sulfate, filtered, and concentrated under reduced pressure. The residue by flash column chromatography on silica gel (CombiFlash®, 12% ethyl acetate in hexane) to afford 21.1. $^1$H NMR (DMSO-d$_6$, 400 MHz): δ 7.98-7.94 (m, 1H), 6.48 (bs, 2H).

Synthesis of compound 21.2. Concentrated sulfuric acid (3 mL) was added dropwise to potassium persulfate (2.05 g, 7.6 mmol, 2.5 equiv) at room temperature and stirred for 15 min. To the mixture was added 21.1 (0.5 g, 3.04 mmol, 1.0 equiv) in small portions while maintaining temperature in the range of 30-40° C. After the addition the reaction mixture was stirred at room temperature for 3-4 h. It was poured over crushed ice, stirred and basified with saturated sodium bicarbonate and extracted with ethyl acetate. The combined organic layers were washed with brine solution, dried over anhydrous sodium sulfate, filtered and concentrated under reduced pressure. The residue was purified by flash column chromatography on silica gel (CombiFlash®, 2-3% ethyl acetate in hexane) to afford 21.2. $^1$H NMR (DMSO-d$_6$, 400 MHz): δ 8.78 (s, 1H).

Synthesis of compound 21.3. To a solution of 21.2 (0.970 g, 4.99 mmol, 1.0 equiv) in acetonitrile (10 mL) was added aqueous methylamine solution (40%) (0.8 mL, 9.98 mmol, 2.0 equiv) dropwise at 0° C. The reaction mixture was allowed to warm to at room temperature and stirred for 20 min. It was poured over ice-water and extracted with ethyl acetate. The combined organic layers were washed with brine solution, dried over anhydrous sodium sulfate, filtered and concentrated under reduced pressure. The residue was purified by flash column chromatography on silica gel (CombiFlash®, 10% ethyl acetate in hexane) to afford 21.3. $^1$H NMR (DMSO-d$_6$, 400 MHz): δ 7.98 (s, 1H), 7.05 (bs, 1H), 2.79 (d, 3H).

Synthesis of compound 21.4. A mixture of 21.3 (0.930 g, 4.52 mmol, 1.0 equiv), N-(4-hydroxypyridin-2-yl)acetamide (0.895 g, 5.88 mmol, 1.3 equiv) and sodium carbonate (0.958 g, 9.04 mmol, 2.0 equiv) in DMF (10 mL) was stirred at 50° C. for 6 h. The reaction mixture was cooled to room temperature, poured over ice-water. The precipitated solids were collected by filtration, rinsed with water and dried under vacuum to afford 21.4. MS (ES): m/z 338.7 [M+H]$^+$.

Synthesis of compound 21.5. To a solution of compound 21.4 (0.850 g, 2.52 mmol, 1.0 equiv) in ethanol-water (8:2, 10 mL) was added iron powder (0.705 g, 12.6 mmol, 5.0 equiv) followed by ammonium chloride (0.673 g, 12.6 mmol, 5.0 equiv). The reaction mixture was stirred at 80° C. for 2 h. It was filtered through a pad of Celite® and rinsed with ethanol. The filtrate was concentrated under reduced pressure. The residue was purified by flash column chromatography on silica gel (CombiFlash®, 2.4% methanol in dichloromethane) to afford 21.5. MS (ES): m/z 308.5 [M+H]$^+$.

Synthesis of compound 21.6. Compound 21.6 was prepared from 21.5 and Int-7, following the procedure described in the synthesis of I-19. The product was purified by flash column chromatography on silica gel (CombiFlash®, 3.0% methanol in DCM). MS(ES): m/z: 489.6 [M+H]$^+$.

Synthesis of compound 21.7. To a solution of 21.6 (0.230 g, 0.470 mmol, 1.0 equiv) in DMA (5 mL) was added zinc (0.006 g, 0.094 mmol, 0.2 equiv) and zinc cyanide (0.275 g, 2.35 mmol, 5.0 equiv). The reaction mixture was degassed by bubbling through a stream of argon for 10 min. Tris (dibenzylideneacetone)dipalladium(0) (0.030 g, 0.032 mmol, 0.07 equiv) and 1,1'-bis(diphenylphosphino)ferrocene (0.039 g, 0.070 mmol, 0.15 equiv) were added, and degassed for 5 min. The reaction mixture was stirred at 210° C. in a microwave reactor for 1 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.5% methanol in DCM as eluent to afford to afford 21.7. MS (ES): m/z 438.2 [M+H]$^+$.

Synthesis of I-21. To a solution of 21.7 (0.050 g, 0.114 mmol, 1.0 equiv) in THF (2 mL) was added dimethylcarbamic chloride (0.013 g, 0.125 mmol, 1.1 equiv) followed by addition of potassium tert-butoxide (1M in THF) (0.57 mL, 0.57 mmol, 5.0 equiv) at 0° C. and stirred at same temperature for 15 min. The reaction mixture was poured into ice-water, and product extracted with ethyl acetate. The combined organic layers were washed with brine, dried over anhydrous sodium sulfate, filtered, and concentrated under reduced pressure. The residue was purified by preparative HPLC to afford I-21. MS(ES): m/z: 509.3 [M+H]$^+$. $^1$H NMR (DMSO-d$_6$, 400 MHz): δ 10.69 (s, 1H), 9.01 (s, 1H), 8.19 (s, 1H), 8.16-8.15 (d, J=6.0 Hz, 1H), 7.45 (s, 1H), 7.10 (s, 1H), 6.66-6.65 (d, J=3.6 Hz, 1H), 4.16 (bs, 2H), 3.92 (s, 3H), 2.89 (s, 6H), 2.69-2.67 (m, 2H), 2.19 (bs, 2H).

Example 22: Methyl(4-((7-cyano-2-((4,4-difluoro-4,5,6,7-tetrahydropyrazolo[1,5-a]dpyridin-2-yl)amino)-1-methyl-1H-imidazo[4,5-b]pyridin-6-yl)oxy)pyridin-2-yl)carbamate

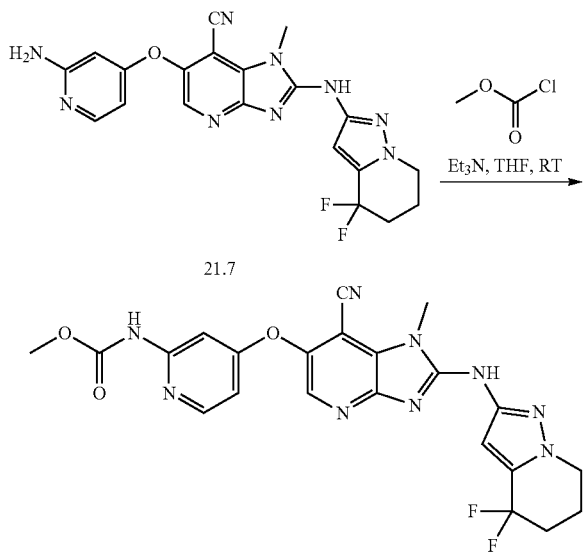

Synthesis of I-22. To a solution of 21.7 (0.050 g, 0.114 mmol, 1.0 equiv) and triethylamine (0.023 g, 0.228 mmol, 2.0 equiv) in THF (2 mL) was added methyl chloroformate (0.011 g, 0.125 mmol, 1.1 equiv) at 0° C. The reaction mixture was stirred at room temperature for 4 h. It was poured into ice-water, stirred, and extracted with ethyl acetate. The combined organic layers were washed with brine, dried over anhydrous sodium sulfate, filtered, and concentrated under reduced pressure. The residue was purified by preparative HPLC to afford I-22. MS(ES): m/z: 496.2 [M+H]$^+$. $^1$H NMR (DMSO-$d_6$, 400 MHz): δ 10.72 (s, 1H), 10.43 (s, 1H), 8.22-8.21 (d, J=2.4 Hz, 1H), 8.19 (s, 1H), 7.43 (s, 1H), 7.08 (s, 1H), 6.74-6.73 (m, 1H), 4.16 (bs, 2H), 3.92 (s, 3H), 3.63 (s, 3H), 2.45 (bs, 2H), 2.19 (bs, 2H).

Example 23: N-(4-((7-cyano-2-((4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)pyrrolidine-1-carboxamide

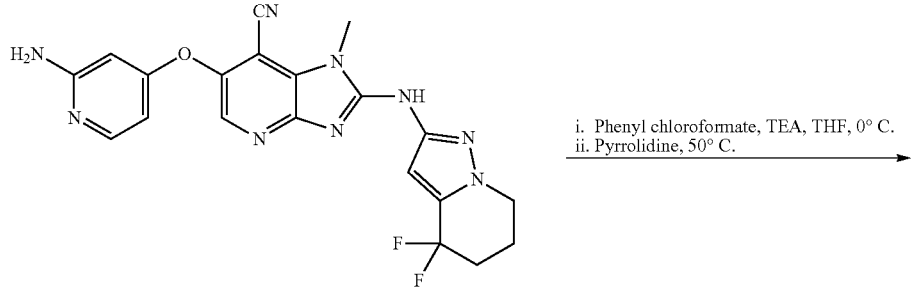

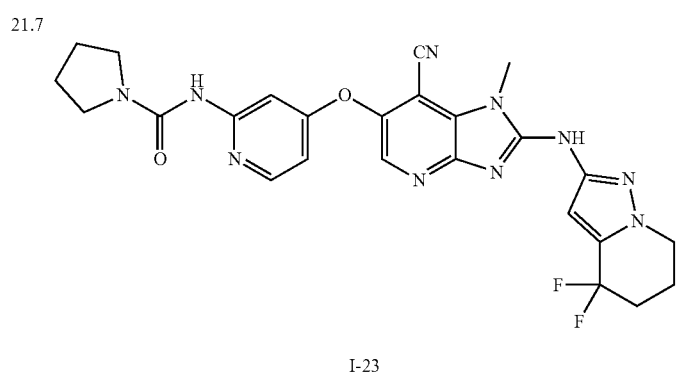

Synthesis of I-23. To a solution of 21.7 (0.050 g, 0.114 mmol, 1.0 equiv) and triethylamine (0.034 g, 0.342 mmol, 3.0 equiv) in THF (3 mL) was added phenyl chloroformate (0.027 g, 0.171 mmol, 1.5 equiv) at 0° C. The reaction mixture was stirred for 15 min before added pyrrolidine (0.040 g, 0.57 mmol, 5.0 equiv). The reaction mixture was stirred at 50° C. for 15 min. It was transferred into water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.5% methanol in DCM) to afford I-23. MS(ES): m/z: 535.4 [M+H]$^+$. $^1$H NMR (DMSO-$d_6$, 400 MHz): δ 10.67 (s, 1H), 8.80 (s, 1H), 8.19 (s, 1H), 8.16-8.15 (d, J=5.6 Hz, 1H), 7.54 (s, 1H), 7.09 (s, 1H), 6.83-6.81 (d, J=7.2 Hz, 1H), 4.16 (bs, 2H), 3.93 (s, 3H), 3.39-3.33 (m, 4H), 1.92-1.84 (m, 4H), 1.80-1.76 (m, 4H).

Example 24: N-(4-((7-cyano-2-((4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)-4-methylpiperazine-1-carboxamide

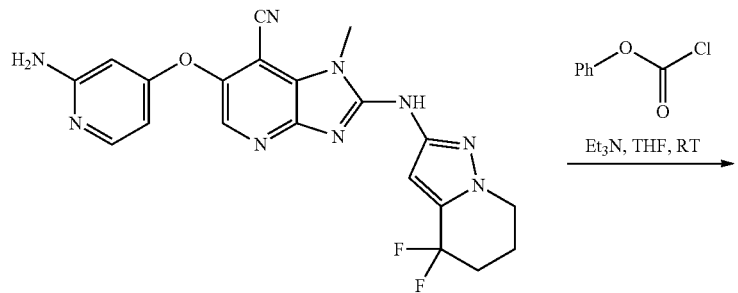

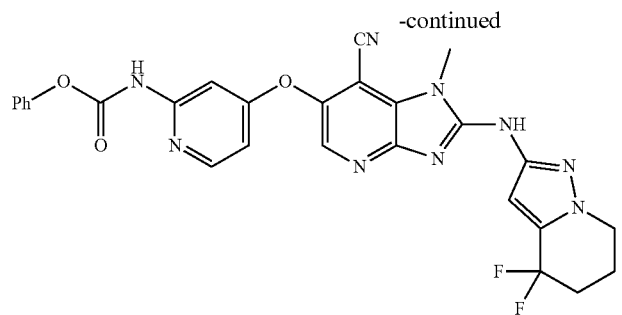 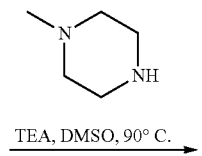

24.1

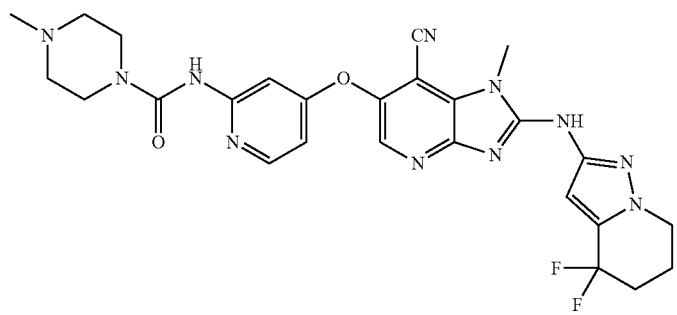

I-24

Synthesis of compound 24.1. To a solution of 21.7 (0.080 g, 0.182 mmol, 1.0 equiv) and triethylamine (0.055 g, 0.546 mmol, 3.0 equiv) in THF (3 mL) was added phenyl chloroformate (0.042 g, 0.274 mmol, 1.5 equiv) at 0° C. The reaction mixture was stirred for 15 min. It was poured into ice-water, stirred, and extracted with ethyl acetate. The combined organic layers were washed with brine, dried over anhydrous sodium sulfate, filtered, and concentrated under reduced pressure to afford 24.1. MS(ES): m/z: 558.4 [M+H]$^+$.

Synthesis of I-24. To a solution of 24.1 (0.090 g, 0.161 mmol, 1.0 equiv) and triethylamine (0.097 g, 0.966 mmol, 6.0 equiv) in dimethyl sulfoxide (3 mL) was added N-methylpiperazine (0.024 g, 0.242 mmol, 1.5 equiv). The reaction mixture was stirred at 90° C. for 15 min. It was transferred into water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 7.5% methanol in DCM) to afford I-24. MS(ES): m/z: 562.5 [M−H]$^+$. $^1$H NMR (DMSO-d$_6$, 400 MHz): δ 10.67 (s, 1H), 9.33 (s, 1H), 8.19-8.18 (d, J=4.0 Hz, 1H), 8.17 (s, 1H), 7.45 (s, 1H), 7.10 (s, 1H), 6.84 (bs, 1H), 4.17 (bs, 2H), 3.93 (s, 3H), 3.43 (bs, 4H), 2.31 (bs, 4H), 2.20 (s, 3H), 1.56 (bs, 2H), 1.25 (bs, 2H).

Example 25: N-(4-((7-cyano-2-((4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)morpholine-4-carboxamide

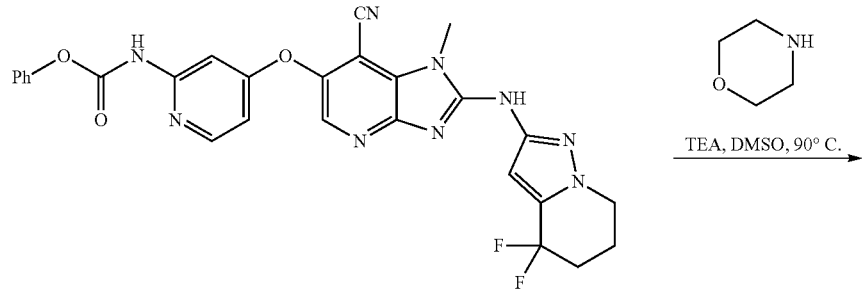

24.1

-continued

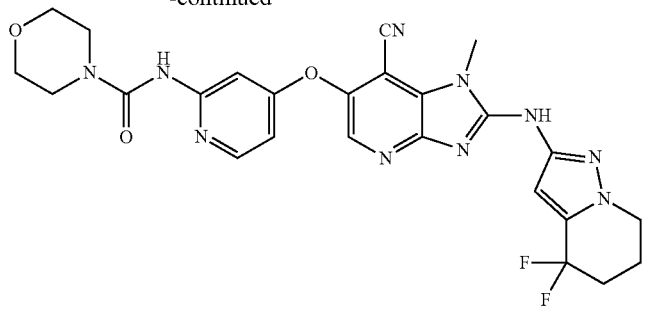

I-25

Synthesis of I-25. Compound I-25 was prepared from 24.1 and morpholine, following the procedure of the synthesis of I-24. The product was purified by flash column chromatography on silica gel (CombiFlash®, 3.0% methanol in DCM). MS(ES): m/z: 551.3 [M+H]⁺. ¹H NMR (DMSO-d₆, 400 MHz): δ 10.68 (s, 1H), 9.36 (s, 1H), 8.19-8.18 (d, J=4.0 Hz, 1H), 8.16 (s, 1H), 7.09 (s, 1H), 7.06 (s, 1H), 6.83 (bs, 1H), 4.16 (bs, 2H), 3.92 (s, 3H), 3.55 (bs, 4H), 3.40 (bs, 4H), 1.55 (bs, 2H), 1.23 (bs, 2H).

Example 26: N-(4-((7-cyano-2-((4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)-3-methoxyazetidine-1-carboxamide

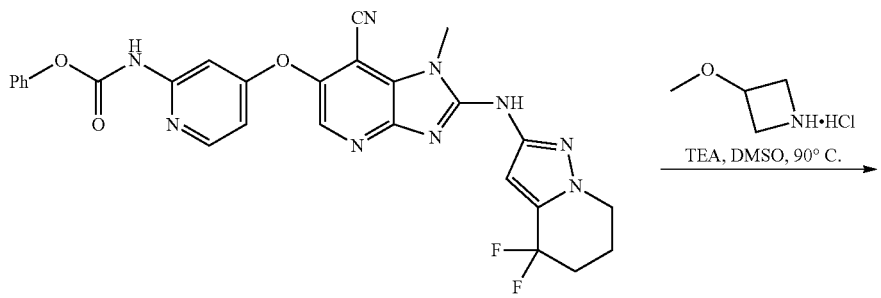

24.1

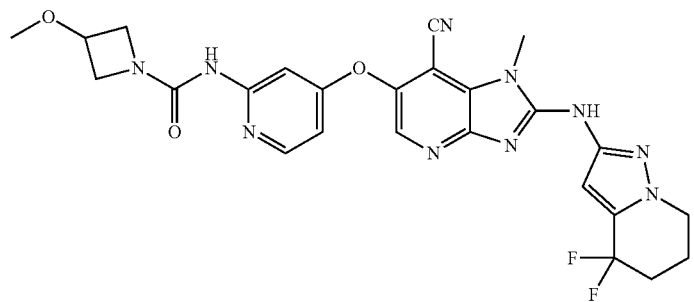

I-26

Synthesis of I-26. Compound I-26 was prepared from 24.1 and 3-methoxyazetidine hydrochloride, following the procedure of the synthesis of I-24. The product was purified by flash column chromatography on silica gel (CombiFlash®, 3.2% methanol in DCM). MS(ES): m/z: 551.4 [M+H]⁺, ¹H NMR (DMSO-d₆, 400 MHz): δ 10.73 (s, 1H), 10.05 (s, 1H), 8.26 (bs, 1H), 7.32 (s, 1H), 7.08 (s, 1H), 6.96 (s, 1H), 6.84 (s, 1H), 4.18 (bs, 4H), 3.96 (bs, 2H), 3.94 (s, 3H), 3.82 (s, 3H), 3.74 (bs, 1H), 2.21 (bs, 2H), 1.56 (bs, 2H).

Example 27: 1-(4-((7-cyano-2-((4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)-3-methylurea

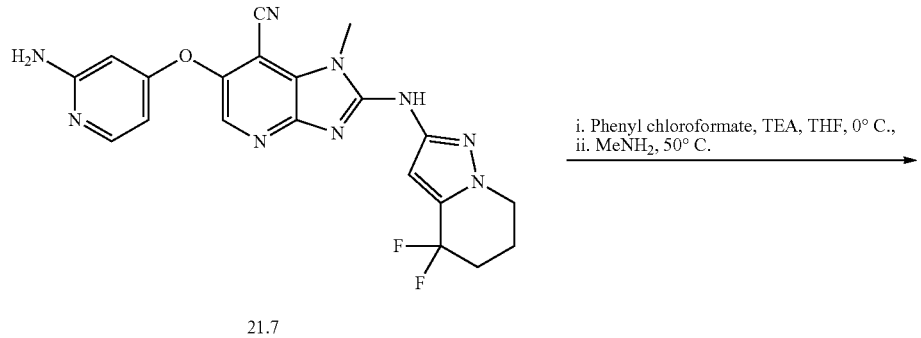

Synthesis of I-27. Compound I-27 was prepared from 21.7 and methylamine, following the procedure of the synthesis of I-23. The product was purified by flash column chromatography on silica gel (CombiFlash®, 4.0% methanol in DCM). MS(ES): m/z: 495.3 [M+H]$^+$, $^1$H NMR (DMSO-d$_6$, 400 MHz): δ 10.67 (s, 1H), 8.80 (s, 1H), 8.19 (s, 1H), 8.16-8.15 (d, J=5.6 Hz, 1H), 7.54 (s, 1H), 7.09 (s, 1H), 6.83 (bs, 1H), 6.66-6.65 (d, J=3.6 Hz, 1H), 4.16 (bs, 2H), 3.93 (s, 3H), 3.38 (s, 3H), 2.19 (bs, 2H), 1.89-1.87 (m, 2H).

Example 28: (R)-N-(4-((7-cyano-2-((4,4-difluoro-4,5,6,7-tetrahydropyrazolo[1,5-c]pyridin-2-yl)amino)-1-methyl-1H-imidazo[4,5-b]pyridin-6-yl)oxy)pyridin-2-yl)-3-hydroxypyrrolidine-1-carboxamide

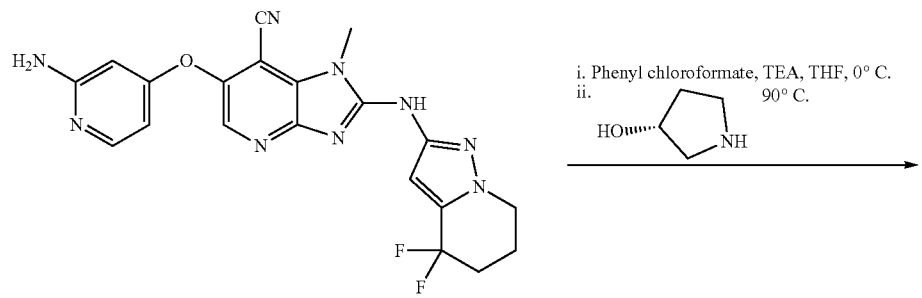

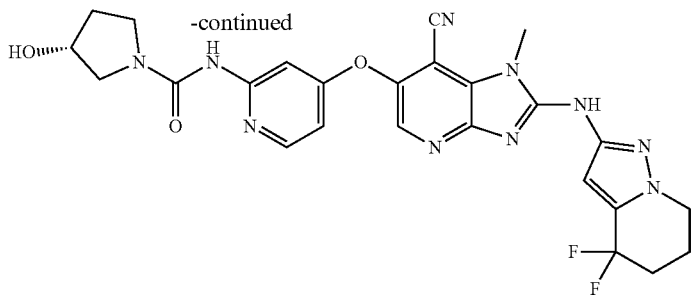

I-28

Synthesis of I-28. Compound I-28 was prepared from 21.7 and (R)-pyrrolidin-3-ol, following the procedure of the synthesis of I-23. The product was purified by flash column chromatography on silica gel (CombiFlash®, 3.4% methanol in DCM). MS(ES): m/z: 551.4 [M+H]+, $^1$H NMR (DMSO-$d_6$, 400 MHz): δ 10.68 (s, 1H), 8.86 (s, 1H), 8.20-8.16 (m, 2H), 7.54 (s, 1H), 7.10 (s, 1H), 6.84 (s, 1H), 5.36 (s, 1H), 4.95 (bs, 2H), 4.26 (bs, 1H), 4.11 (bs, 2H), 4.00 (bs, 2H), 3.94 (s, 3H), 2.20 (bs, 2H), 1.56 (bs, 4H).

Example 29: (S)-N-(4-((7-cyano-2-((4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)-3-hydroxypyrrolidine-1-carboxamide

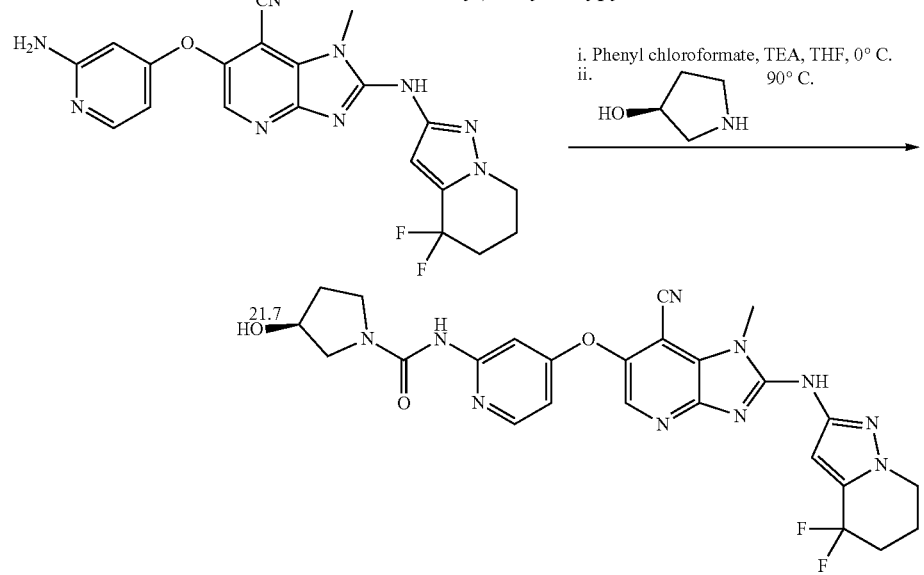

I-29

Synthesis of I-29. Compound I-29 was prepared from 21.7 and (S)-pyrrolidin-3-ol, following the procedure of the synthesis of I-23. The product was purified by flash column chromatography on silica gel (CombiFlash®, 3.5% methanol in DCM). MS(ES): m/z: 551.4 [M+H]+, $^1$H NMR (DMSO-$d_6$, 400 MHz): δ 10.69 (s, 1H), 8.86 (s, 1H), 8.20-8.16 (m, 2H), 7.54 (s, 1H), 7.11 (s, 1H), 6.84 (s, 1H), 5.36 (s, 1H), 4.95 (bs, 2H), 4.26 (s, 1H), 4.11 (bs, 2H), 4.00 (bs, 2H), 3.94 (s, 3H), 2.20 (bs, 2H), 1.56 (bs, 4H).

Example 30: 6-((2-Aminopyridin-4-yl)oxy)-2-((4,4-difluoro-4,5,6,7-tetrahydropyrazolo[1,5-a]pyridin-2-yl)amino)-1-methyl-1H-imidazo[4,5-b]pyridine-7-carbonitrile

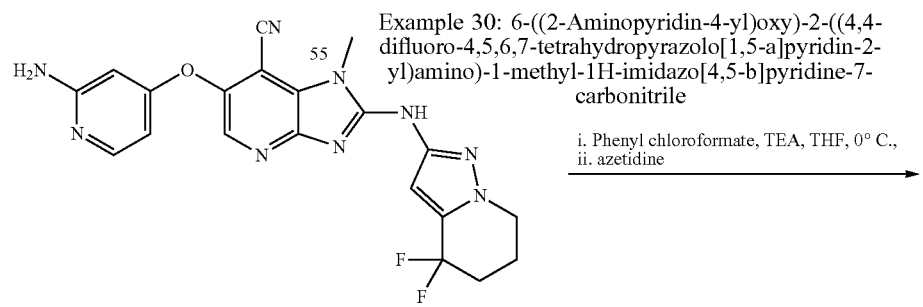

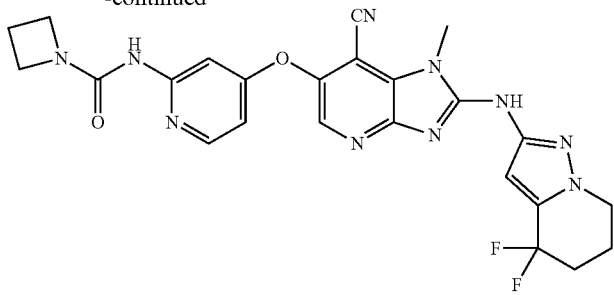

I-30

Synthesis of I-30. Compound I-30 was prepared from 21.7 and azetidine, following the procedure of the synthesis of I-23. The product was purified by flash column chromatography on silica gel (CombiFlash®, 4.0% methanol in DCM). MS(ES): m/z: 521.4 [M+H]⁺. LCMS purity: 98.49%, HPLC purity: 96.93%, ¹H NMR (DMSO-d$_6$, 400 MHz): δ 10.69 (s, 1H), 9.18 (s, 1H), 8.18 (s, 1H), 8.15 (bs, 1H), 7.55 (s, 1H), 7.09 (s, 1H), 6.23 (bs, 1H), 4.16 (bs, 2H), 3.95 (bs, 4H), 3.92 (s, 3H), 2.19-2.13 (m, 6H).

Example 31: Methyl(4-((2-((1-(2-oxaspiro[3.3]heptan-6-yl)-5-(trifluoromethyl)-1H-pyrazol-3-yl)amino)-7-cyano-1-methyl-1H-imidazo[4,5-b]pyridin-6-yl)oxy)pyridin-2-yl)carbamate

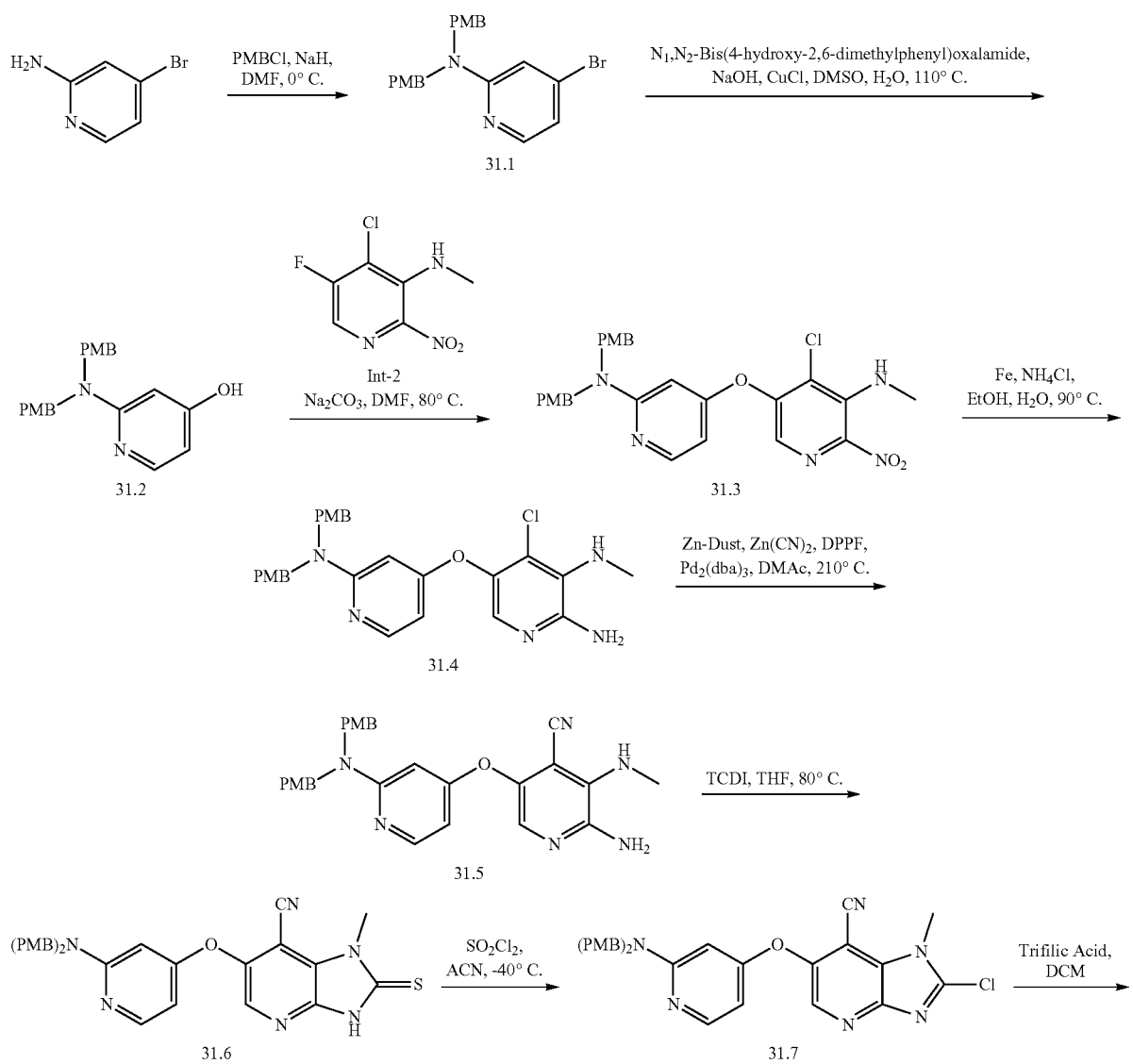

-continued

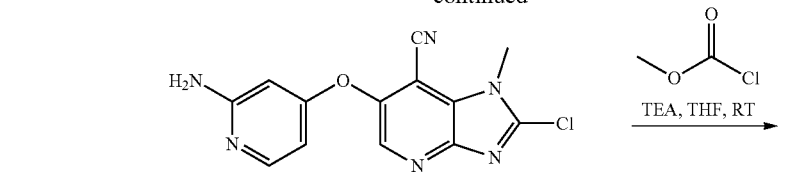

31.8

TEA, THF, RT →

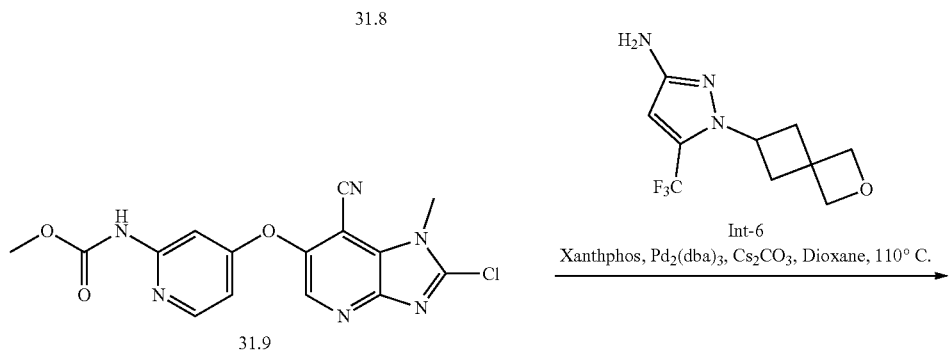

31.9

Int-6
Xanthphos, Pd$_2$(dba)$_3$, Cs$_2$CO$_3$, Dioxane, 110° C.
→

I-31

Synthesis of compound 31.1 To a solution of 4-bromopyridin-2-amine (100 g, 577.9 mmol, 1.0 equiv) in DMF (1300 mL) was added sodium hydride (111 g, 2773.9 mmol, 4.8 equiv) at 0° C. in portions and stirred for 2 h. To the mixture was added 4-methoxybenzyl chloride (434 g, 2773.9 mmol, 4.8 equiv) and stirred at 0° C. for 30 min. It was transferred into ice-water, precipitated solid was filtered, and dried under vacuum to afford 1.1 (150 g, yield: 62.79%) MS(ES): m/z 414.2 [M+H]$^+$.

Synthesis of compound 31.2. To a solution of 31.1 (60 g, 145 mmol, 1.0 equiv) in DMSO (1000 mL) was added copper(I) chloride (1.14 g, 11.6 mmol, 0.08 equiv) followed by addition of N1,N2-bis(4-hydroxy-2,6-dimethylphenyl) oxalamide (3.8 g, 11.6 mmol, 0.08 equiv). The reaction mixture was stirred at room temperature for 10 min and was added an aqueous solution of sodium hydroxide (11.6 g, 290 mmol, 2.0 equiv). The mixture was stirred at 110° C. for 48 h. It was cooled to room temperature, transferred into ice cold water, stirred, and extracted with ethyl acetate. The combined organic layers were washed with brine, dried over anhydrous sodium sulfate, filtered, and concentrated under reduced pressure. The residue was purified by trituration with diethyl ether to afford 31.2. MS(ES): m/z 351.2 [M+H]$^+$.

Synthesis of compound 31.3. A mixture of 31.2 (39 g, 111.3 mmol, 1.0 equiv), sodium carbonate (23.59 g, 222.6 mmol, 2.0 equiv) and Int-2 (18.3 g, 89.04 mmol, 0.8 eq) in DMF (390 mL) stirred at 80° C. for 1 h. It was filtered, and the filtrate was transferred into water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 28% ethyl acetate in hexane) to afford 31.3. MS(ES): m/z 536.6 [M+H]$^+$.

Synthesis of compound 31.4. Compound 31.4 was prepared from 31.3 following the procedure described in the synthesis of compound 3.6. The product was purified by flash column chromatography on silica gel (CombiFlash®, 70% ethyl acetate in hexane). MS(ES): m/z 506.9 [M+H]$^+$.

Synthesis of compound 31.5. Compound 31.5 was prepared from 31.4 following the procedure described in the synthesis of compound 21.7. The product further purified by flash column chromatography on silica gel (CombiFlash®, 1.8% methanol in DCM). MS (ES): m/z 497.5 [M+H]$^+$.

Synthesis of compound 31.6. To a solution of 31.5 (1.0 g, 2.01 mmol, 1.0 equiv) in THF (10 mL) was added 1,1'-thiocarbonyldiimidazole (1.788 g, 10.05 mmol, 5.0 equiv). The reaction mixture was stirred at 80° C. for 6 h. It was concentrated under reduced pressure. The residue was purified by flash column chromatography on silica gel (CombiFlash®, 30% ethyl acetate in hexane) to afford 31.6. MS(ES): m/z: 539.5 [M+H]$^+$.

Synthesis of compound 31.7. To a solution of 31.6 (0.510 g, 0.946 mmol, 1.0 equiv) in acetonitrile (7 mL) was added sulfuryl chloride (0.15 mL, 1.892 mmol, 2.0 equiv) at −40° C. and reaction mixture was stirred for 10 min. It was transferred into saturated sodium bicarbonate solution, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 40% ethyl acetate in hexane) to afford 31.7. MS (ES): m/z 541.9 [M+H]$^+$.

Synthesis of compound 31.8. To solution of 31.7 (0.230 g, 0.425 mmol, 1.0 equiv) in DCM (8 mL) was added trifluoromethanesulfonic acid (0.2 mL) at 0° C. and stirred for 5 min. It was transferred into ice-cold saturated sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 3.0% methanol in DCM) to afford 31.8. MS(ES): m/z: 301.5 [M+H]$^+$.

Synthesis of compound 31.9. To a solution of 31.8 (0.070 g, 0.232 mmol, 1.0 equiv) in THF (3 mL) was added triethylamine (0.070 g, 0.696 mmol, 3.0 equiv) at 0° C. followed by addition of methyl chloroformate (0.033 g, 0.349 mmol, 1.5 equiv). The reaction mixture was stirred at room temperature for 15 min. It was concentrated under reduced pressure. The residue was purified by flash column chromatography on silica gel (CombiFlash®, 2.8% methanol in DCM) to afford 31.9. MS(ES): m/z: 359.5 [M+H]$^+$.

Synthesis of I-31. Compound I-31 was prepared from 31.9 and Int-6, following the procedure of the synthesis of I-10. The product was purified by flash column chromatography on silica gel (CombiFlash®, 3.5% methanol in DCM). MS(ES): m/z: 570.3 [M+H]$^+$, $^1$H NMR (DMSO-d$_6$, 400 MHz): δ 10.59 (s, 1H), 10.32 (s, 1H), 8.17 (bs, 2H), 7.37 (s, 1H), 7.33 (s, 1H), 6.66-6.65 (d, J=3.2 Hz, 1H), 4.88-4.85 (m, 1H), 4.71 (bs, 2H), 4.61 (bs, 2H), 3.98 (s, 3H), 3.62 (s, 3H), 2.82 (bs, 4H).

Example 32: 2-Methoxyethyl(4-((7-cyano-2-((4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)carbamate

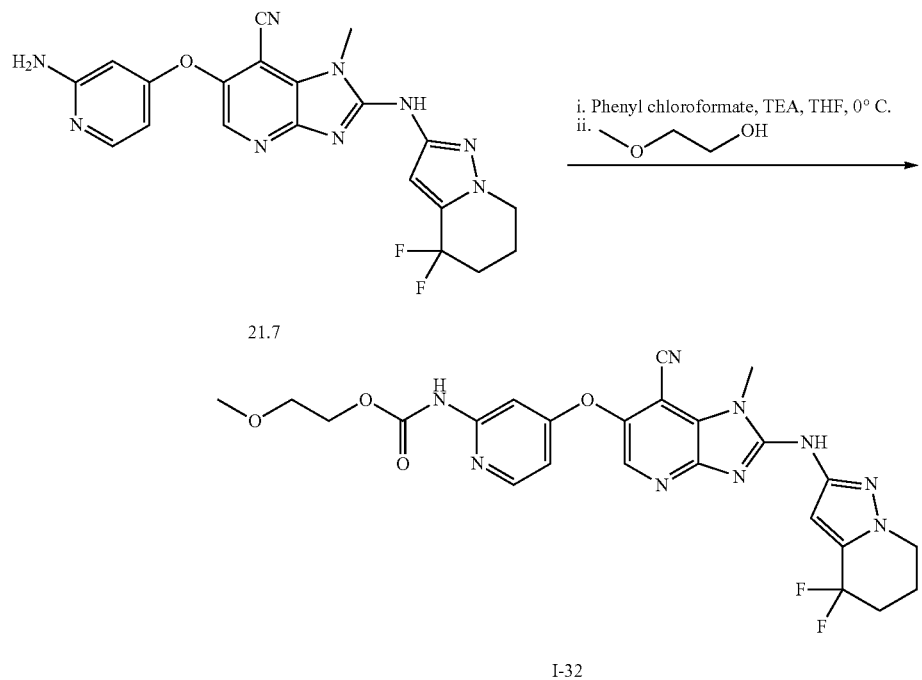

Synthesis of I-32. Compound I-32 was prepared from 21.7 and 2-methoxyethan-1-ol, following the procedure of the synthesis of I-23. The product was purified by flash column chromatography on silica gel (CombiFlash®, 3.5% methanol in DCM). MS(ES): m/z: 540.2 [M+H]$^+$, $^1$H NMR (DMSO-d$_6$, 400 MHz): δ 10.70 (s, 1H), 10.39 (s, 1H), 8.22-8.19 (m, 2H), 7.44 (s, 1H), 7.10 (s, 1H), 6.73-6.71 (m, 1H), 4.18 (bs, 3H), 3.93 (s, 3H), 3.53-3.51 (m, 2H), 3.26 (bs, 4H), 2.46 (bs, 2H), 2.20 (bs, 2H).

Example 33: (R)-N-(4-((7-cyano-2-(4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)-3-methoxypyrrolidine-1-carboxamide

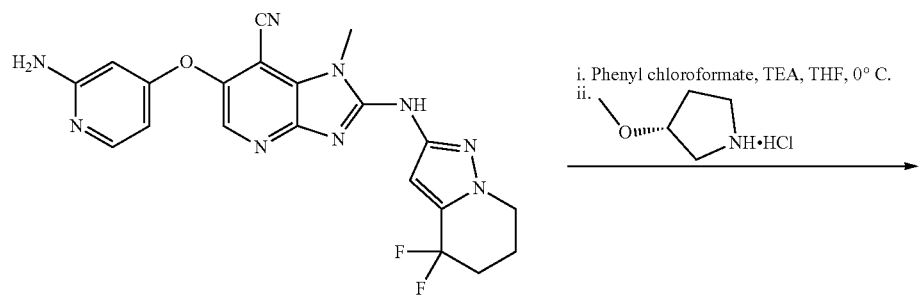

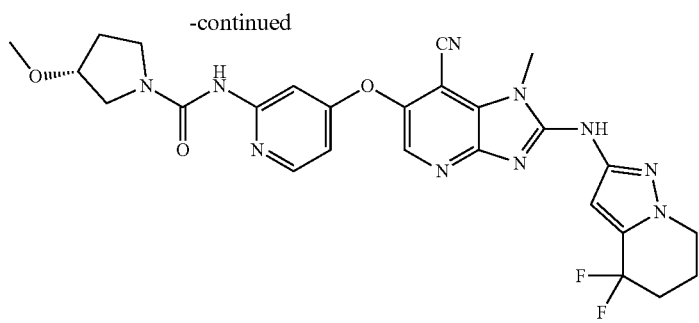

I-33

Synthesis of I-33. Compound I-33 was prepared from 21.7 and (R)-3-methoxypyrrolidine hydrochloride, following the procedure of the synthesis of I-23. The product was purified by flash column chromatography on silica gel (CombiFlash®, 3.3% methanol in DCM). MS(ES): m/z: 565.4 [M+H]$^+$, $^1$H NMR (DMSO-d$_6$, 400 MHz): δ 10.69 (s, 1H), 8.92 (s, 1H), 8.19-8.17 (d, J=7.2 Hz, 1H), 7.52 (s, 1H), 7.08-7.07 (d, J=7.6 Hz, 1H), 6.83-6.81 (d, J=7.2 Hz, 1H), 6.68-6.67 (d, J=3.6 Hz, 1H), 5.36-5.35 (m, 1H), 4.16 (bs, 2H), 3.99 (bs, 2H), 3.92 (s, 3H), 3.50 (bs, 2H), 3.17 (s, 3H), 2.19 (bs, 2H), 1.93 (bs, 2H), 1.55 (bs, 2H).

Example 34: (S)-N-(4-((7-cyano-2-((4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)-3-methoxypyrrolidine-1-carboxamide

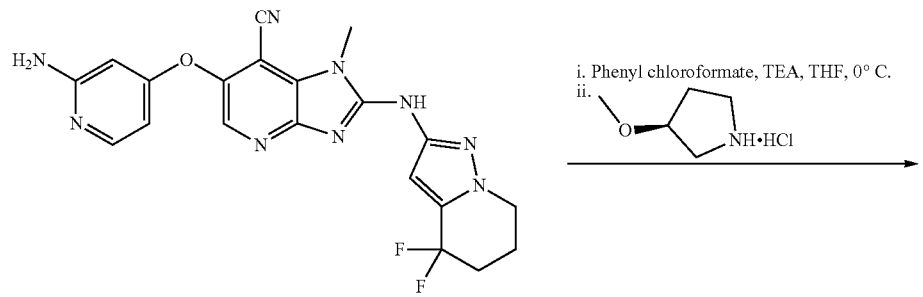

21.7

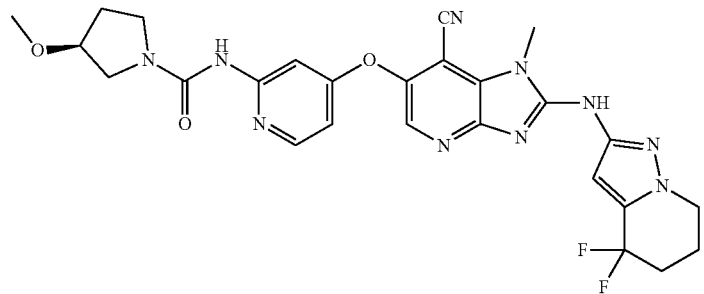

I-34

Synthesis of I-34. Compound I-34 was prepared from 21.7 and (S)-3-methoxypyrrolidine hydrochloride, following the procedure of the synthesis of I-23. The product was purified by flash column chromatography on silica gel (CombiFlash®, 3.3% methanol in DCM). MS(ES): m/z: 565.3 [M+H]$^+$, $^1$H NMR (DMSO-d$_6$, 400 MHz): δ 10.70 (s, 1H), 8.93 (s, 1H), 8.19-8.17 (d, J=7.2 Hz, 1H), 7.54 (s, 1H), 7.11 (bs, 1H), 6.85 (bs, 1H), 6.69 (bs, 1H), 5.37 (bs, 1H), 4.17 (bs, 2H), 4.01 (bs, 2H), 3.94 (s, 3H), 3.50 (bs, 2H), 3.23 (s, 3H), 2.21 (bs, 2H), 1.95 (bs, 2H), 1.57 (bs, 2H).

Example 35: N-(4-((7-cyano-2-((4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)-3-hydroxyazetidine-1-carboxamide

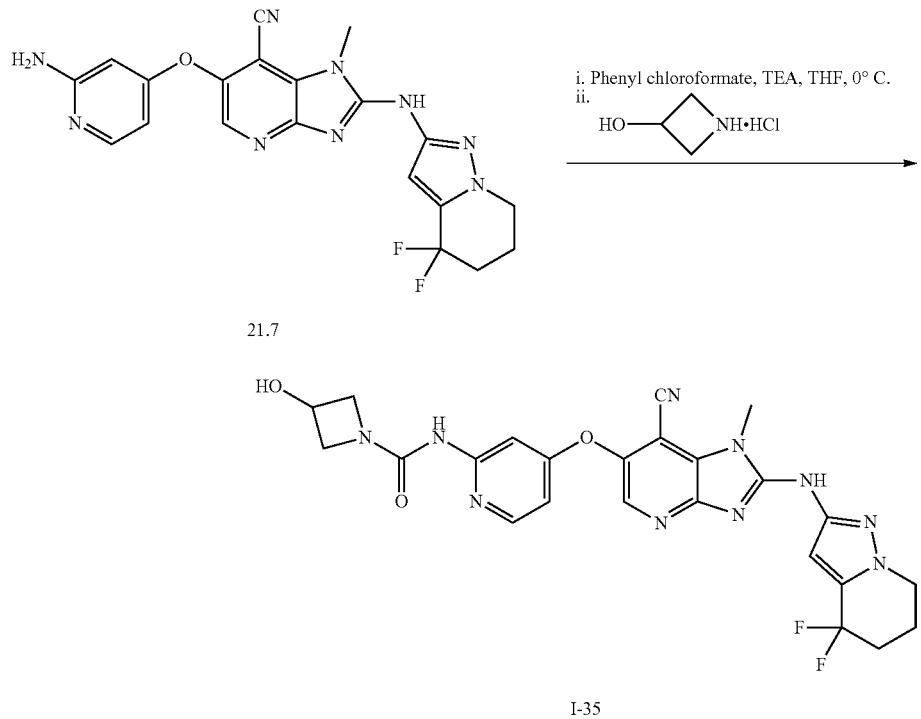

Synthesis of I-35. Compound I-35 was prepared from 21.7 and azetidin-3-ol hydrochloride, following the procedure of the synthesis of I-23. The product was purified by flash column chromatography on silica gel (CombiFlash®, 4.2% methanol in DCM). MS(ES): m/z: 537.3 [M+H]$^+$, $^1$H NMR (DMSO-d$_6$, 400 MHz): δ 10.70 (s, 1H), 9.27 (s, 1H), 8.20 (s, 1H), 8.17-8.16 (d, J=5.6 Hz, 1H), 7.56 (s, 1H), 7.11 (bs, 1H), 6.85 (bs, 1H), 5.64-5.62 (m, 1H), 4.38 (bs, 1H), 4.17-4.14 (m, 4H), 3.94 (s, 3H), 3.70 (bs, 2H), 2.21 (bs, 2H), 1.57 (bs, 2H).

Example 36: (S)-tetrahydrofuran-3-yl(4-((7-cyano-2-((4,4-difluoro-4,5,6,7-tetrahydropyrazolo[1,5-a]pyridin-2-yl)amino)-1-methyl-1H-imidazo[4,5-b]pyridin yl)oxy)pyridin-2-yl)carbamate

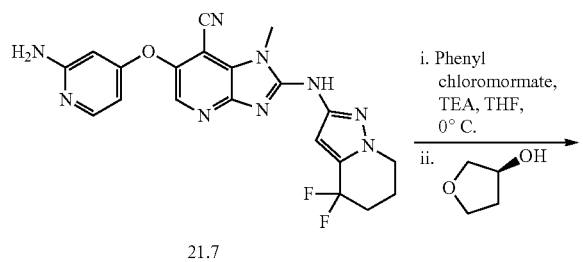

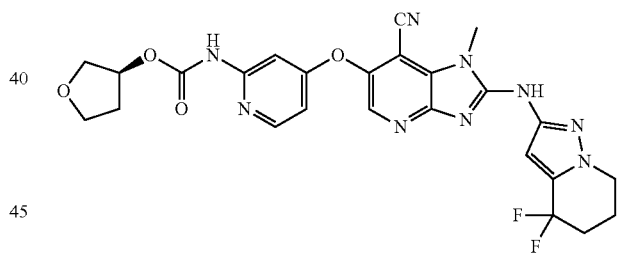

Synthesis of I-36. Compound I-36 was prepared from 21.7 and (S)-tetrahydrofuran-3-ol, following the procedure of the synthesis of I-23. The product was purified by flash column chromatography on silica gel (CombiFlash®, 4.2% methanol in DCM). MS(ES): m/z: 552.3 [M+H]$^+$, $^1$H NMR (DMSO-d$_6$, 400 MHz): δ 10.71 (s, 1H), 10.36 (s, 1H), 8.23 (bs, 2H), 7.42 (s, 1H), 7.11 (s, 1H), 6.75 (s, 1H), 5.21 (s, 1H), 4.17 (bs, 2H), 3.94 (s, 3H), 3.77-3.71 (m, 4H), 2.21 (bs, 4H), 1.94 (bs, 2H).

Example 37: (R)-tetrahydrofuran-3-yl(4-((7-cyano-2-((4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)carbamate

Example 38: 2-(Dimethylamino)ethyl(4-((7-cyano-2-((4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)carbamate

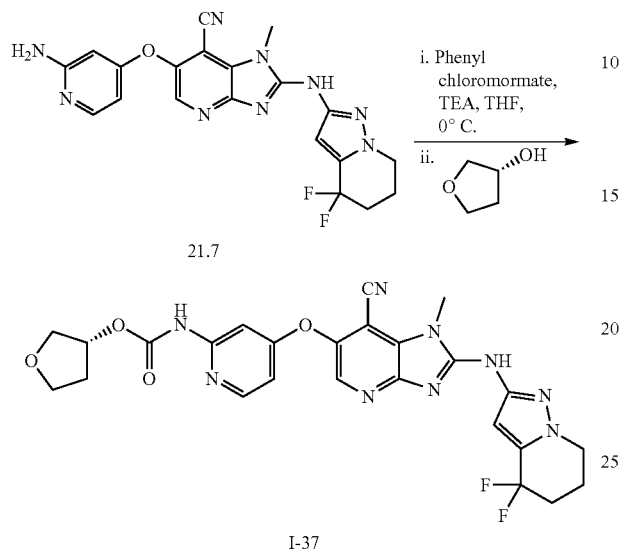

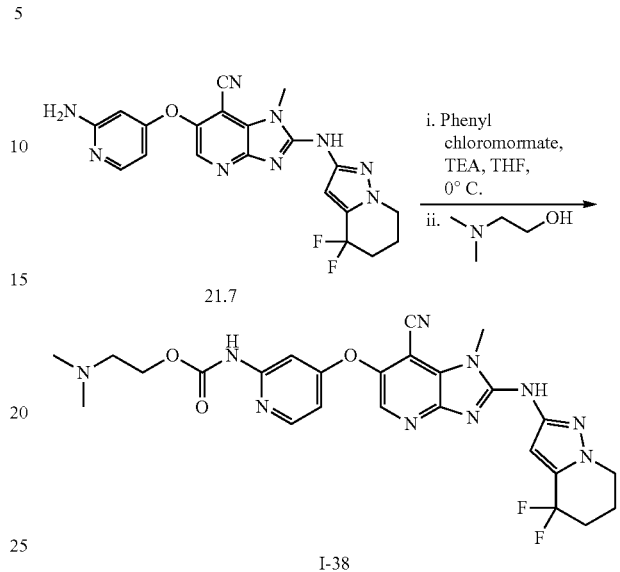

Synthesis of I-37. Compound I-37 was prepared from 21.7 and (R)-tetrahydrofuran-3-ol, following the procedure of the synthesis of I-23. The product was purified by flash column chromatography on silica gel (CombiFlash®, 4.2% methanol in DCM). MS(ES): m/z: 552.3 [M+H]$^+$, $^1$H NMR (DMSO-d$_6$, 400 MHz): δ 10.70 (s, 1H), 10.36 (s, 1H), 8.21-8.19 (m, 2H), 7.41 (s, 1H), 7.10 (s, 1H), 6.73 (s, 1H), 5.20 (s, 1H), 4.16 (bs, 2H), 3.93 (s, 3H), 3.75-3.70 (m, 4H), 2.20 (bs, 4H), 1.91 (bs, 2H).

Synthesis of I-38. Compound I-38 was prepared from 21.7 and 2-(dimethylamino)ethan-1-ol, following the procedure of the synthesis of I-23. The product was purified by flash column chromatography on silica gel (CombiFlash®, 4.5% methanol in DCM). MS(ES): m/z: 553.4 [M+H]$^+$, $^1$H NMR (DMSO-d$_6$, 400 MHz): δ 10.71 (s, 1H), 10.35 (s, 1H), 8.22-8.20 (m, 2H), 7.46 (s, 1H), 7.09 (s, 1H), 6.73 (s, 1H), 4.16 (bs, 4H), 3.93 (s, 3H), 2.49 (bs, 2H), 2.20 (bs, 10H).

Example 39: 1-Methylazetidin-3-yl(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)carbamate

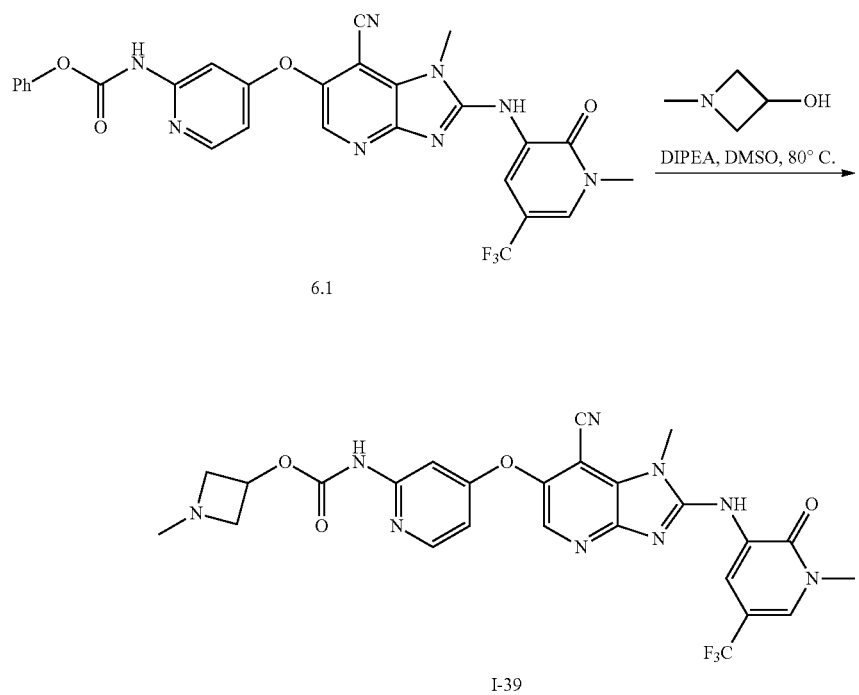

Synthesis of I-39. To a solution of 6.1 (0.150 g, 0.260 mmol, 1.0 equiv), N,N-diisopropylethylamine (0.100 g, 0.780 mmol, 3.0 equiv) and 1-methylazetidin-3-ol (0.034 g, 0.390 mmol, 1.5 equiv) in dimethyl sulfoxide (3 mL) was stirred at 80° C. for 16 h. It was transferred into water, stirred, and extracted with ethyl acetate. The combined organic layers were washed with brine, dried over anhydrous sodium sulfate, filtered, and concentrated under reduced pressure. The residue was purified by preparative HPLC to afford I-39. MS(ES): m/z: 570.4 [M+H]$^+$, $^1$H NMR (DMSO-d$_6$, 400 MHz): δ 9.04 (s, 1H), 8.66 (s, 1H), 8.28 (s, 1H), 8.26-8.25 (d, J=5.6 Hz, 1H), 8.19 (s, 1H), 7.53 (s, 1H), 6.77 (bs, 1H), 5.30 (bs, 1H), 4.10 (bs, 1H), 3.97 (s, 3H), 3.87-3.84 (m, 2H), 3.67 (s, 3H), 3.52-3.50 (m, 2H), 2.83 (s, 3H).

Example 40: Methyl(4-((7-chloro-1-methyl-2-((5-methyl-4-oxo-4,5,6,7-tetrahydropyrazolo[1,5-a]pyrazin-2-yl)amino)-1H-imidazo[4,5-b]pyridin-6-yl)oxy)pyridin-2-yl)carbamate

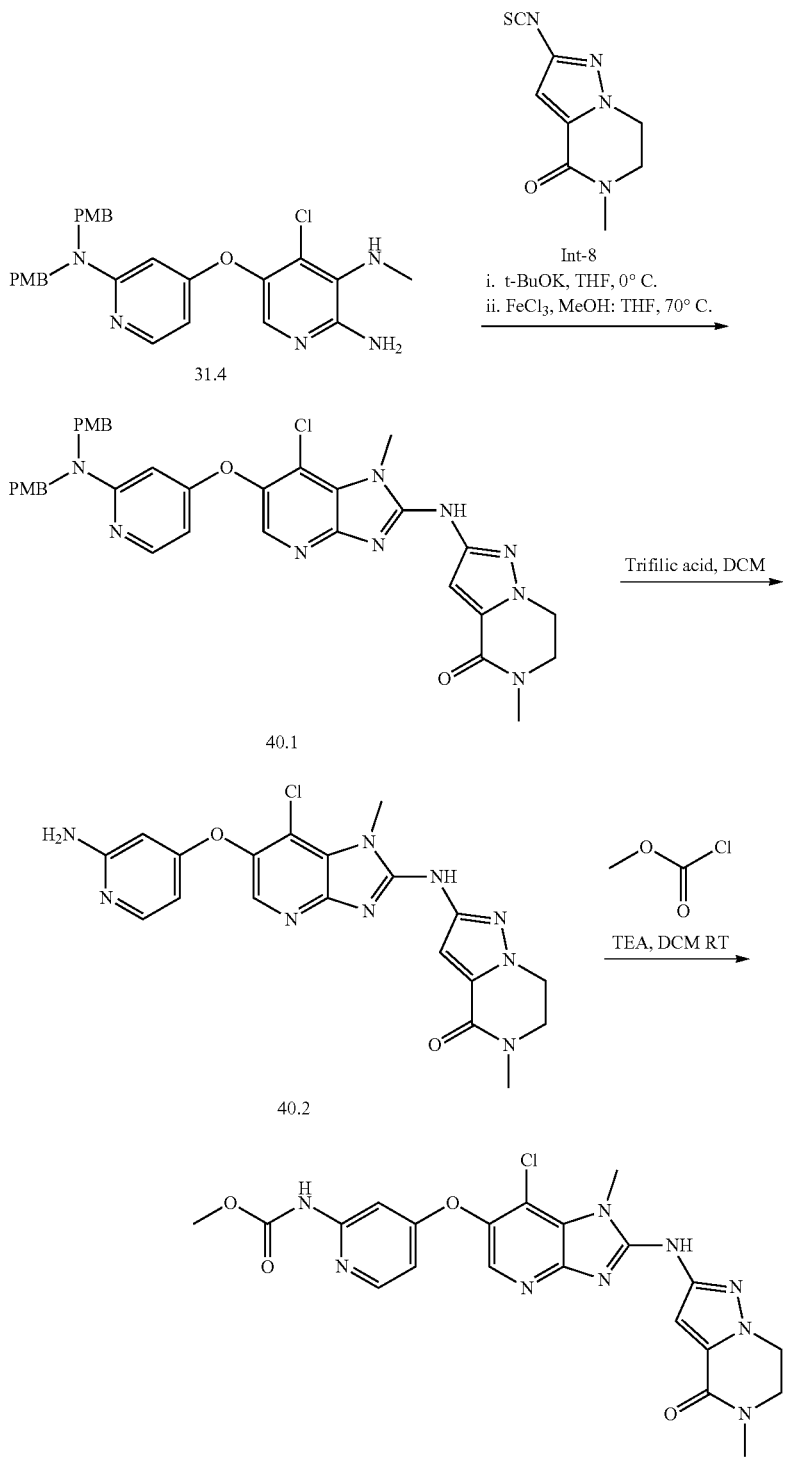

Synthesis of compound 40.1. To a solution of 31.4 (0.500 g, 0.988 mmol, 1.0 equiv) and Int-8 (0.308 g, 1.48 mmol, 1.5 equiv) in THF (5 mL) was added potassium tert-butoxide (1 M in THF, 2.96 mL, 2.964 mmol, 3.0 equiv) at 0° C. The reaction mixture was stirred at same temperature for 30 min. The reaction mixture was poured into ice-water, and product extracted with ethyl acetate. The combined organic layers were washed with brine, dried over anhydrous sodium sulfate, filtered, and concentrated under reduced pressure. The residue was dissolved in methanol-THF (1:1, 10 mL) and ferric chloride (0.272 g, 1.68 mmol, 1.5 equiv) was added. The reaction mixture was stirred at 70° C. for 1 h. The reaction mixture was transferred into water and product extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.0% methanol in DCM) to afford 40.1. MS(ES): m/z: 681.1 [M+H]$^+$.

Synthesis of compound 40.2. To solution of 40.1 (0.300 g, 0.441 mmol, 1.0 equiv) in DCM (5 mL) was added trifluoromethanesulfonic acid (0.3 mL) at 0° C. and stirred for 5 min. It was transferred into ice-cold saturated sodium bicarbonate solution and extracted with DCM. The combined organic layers were washed with brine, dried over anhydrous sodium sulfate, filtered, and concentrated under reduced pressure. The residue was purified by trituration with diethyl ether to afford 40.2. MS(ES): m/z: 440.5 [M+H]$^+$.

Synthesis of compound I-40. To a solution of 40.2 (0.060 g, 0.136 mmol, 1.0 equiv) and triethylamine (0.041 g, 0.408 mmol, 3.0 equiv) in THF (2 mL) was added methyl chloroformate (0.015 g, 0.163 mmol, 1.2 equiv) at 0° C. The reaction mixture was stirred at room temperature for 2 h. It was concentrated under reduced pressure. The residue was purified by flash column chromatography on silica gel (CombiFlash®, 5.0% methanol in DCM) to afford I-40. MS(ES): m/z: 498.3 [M+H]$^+$, $^1$H NMR (DMSO-d$_6$, 400 MHz): δ 10.28 (s, 1H), 8.12 (bs, 1H), 7.81 (s, 1H), 7.36 (s, 1H), 7.07 (bs, 1H), 6.83 (bs, 1H), 6.62 (bs, 1H), 3.87 (bs, 2H), 3.76 (s, 3H), 3.61-3.59 (m, 5H), 3.01 (s, 3H).

Example 41: Methyl(4-((7-cyano-1-methyl-2-((5-methyl-4-oxo-4,5,6,7-tetrahydropyrazolo[1,5-a]pyrazin-2-yl)amino)-1H-imidazo[4,5-b]pyridin-6-yl)oxy)pyridin-2-yl)carbamate

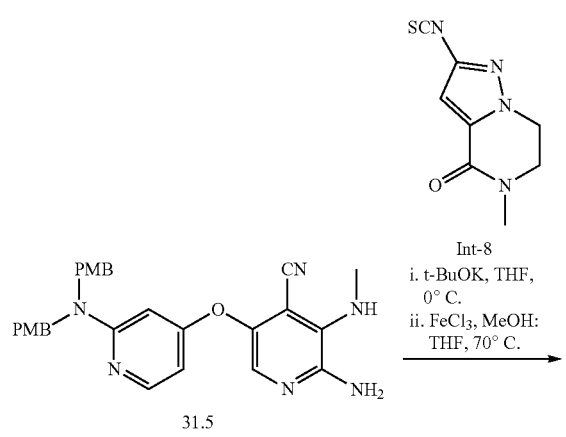

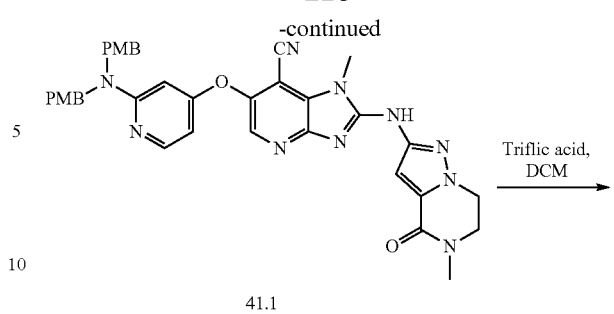

41.1

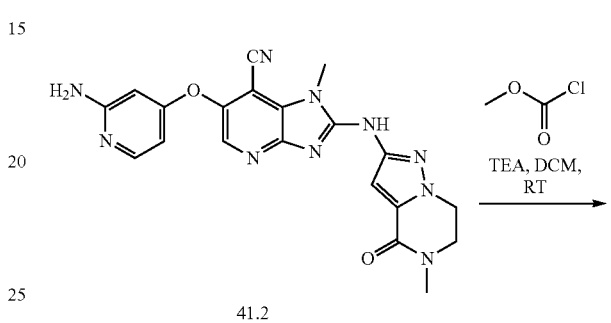

41.2

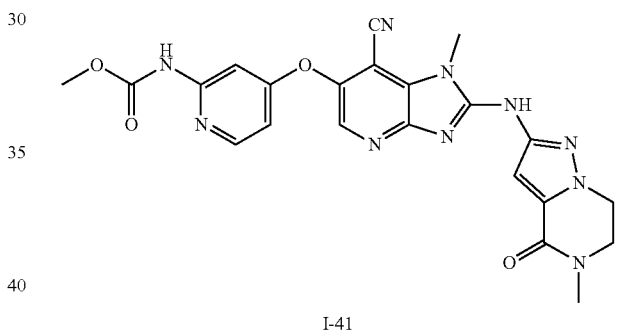

I-41

Synthesis of compound 41.1. Compound 41.1 was prepared from 31.5 and Int-8, following the procedure described in the synthesis of 40.1. The product was purified by flash column chromatography on silica gel (CombiFlash®, 4.5% methanol in DCM). MS(ES): m/z: 671.5 [M+H]$^+$.

Synthesis of compound 41.2. Compound 41.2 was prepared from 41.1, following the procedure described in the synthesis of 40.2. The product was purified by trituration with diethyl ether. MS(ES): m/z: 431.2 [M+H]$^+$.

Synthesis of compound I-41. Compound I-41 was prepared from 41.2, following the procedure described in the synthesis of I-40. The product was purified by flash column chromatography on silica gel (CombiFlash®, 4.0% methanol in DCM). MS(ES): m/z: 489.3 [M+H]$^+$, $^1$H NMR (DMSO-d$_6$, 400 MHz): δ 10.72 (s, 1H), 10.39 (s, 1H), 8.23 (bs, 2H), 7.47 (s, 1H), 7.26 (s, 1H), 6.74 (bs, 1H), 4.35 (bs, 2H), 3.94 (s, 3H), 3.84 (bs, 2H), 3.64 (s, 3H), 3.05 (s, 3H).

Example 42: 1-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-3-cyclopropylurea

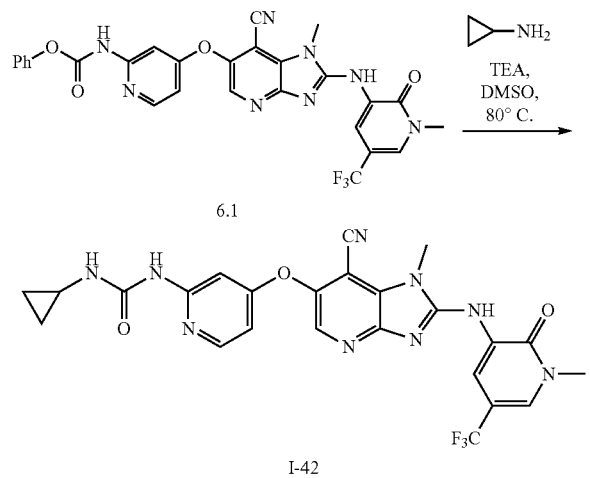

Synthesis of I-42. Compound I-42 was prepared from 6.1 and cyclopropanamine, following the procedure described in the synthesis of I-6. The product was purified by flash column chromatography on silica gel (CombiFlash®, 4.0% methanol in DCM). MS(ES): m/z: 540.3 [M+H]+, 1H NMR (DMSO-d6, 400 MHz): δ 9.06 (bs, 2H), 8.64 (s, 1H), 8.31 (s, 1H), 8.19 (s, 1H), 8.13-8.11 (d, J=6.0 Hz, 1H), 7.83 (s, 1H), 7.12 (s, 1H), 6.65-6.64 (d, J=3.6 Hz, 1H), 3.96 (s, 3H), 3.66 (s, 3H), 1.23 (bs, 1H), 0.63-0.62 (m, 2H), 0.40 (bs, 2H).

Example 43: Methyl(4-((7-cyano-2-((4,4-dimethyl-6,7-dihydro-4H-pyrazolo[5,1-c][1,4]oxazin-2-yl)amino)-1-methyl-1H-imidazo[4,5-b]pyridin-6-yl)oxy)pyridin-2-yl)carbamate

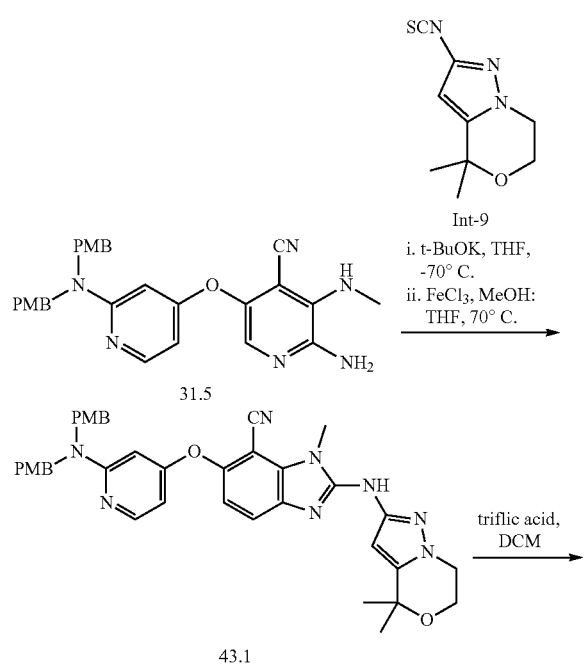

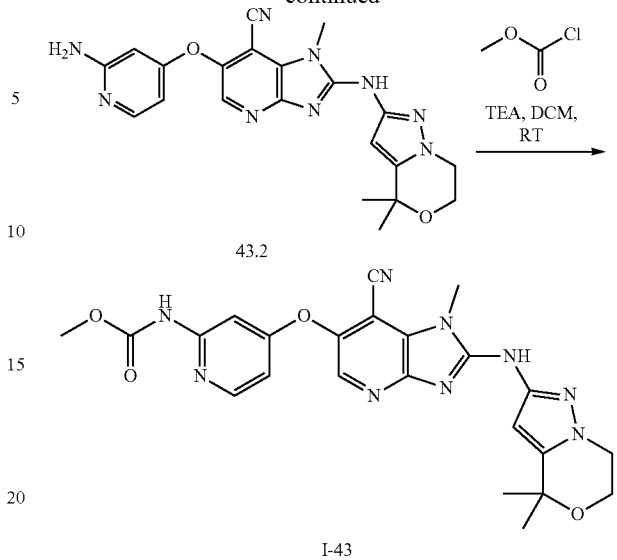

Synthesis of compound 43.1. Compound 43.1 was prepared from 31.5 and Int-9, following the procedure described in the synthesis of 40.1. The product was purified by flash column chromatography on silica gel (CombiFlash®, 2.0% methanol in DCM). MS(ES): m/z: 672.5 [M+H]+.

Synthesis of compound 43.2. Compound 43.2 was prepared from 43.1, following the procedure described in the synthesis of 40.2. The product was purified by trituration with diethyl ether. MS(ES): m/z: 432.3 [M+H]+.

Synthesis of compound I-43. Compound I-43 was prepared from 43.2, following the procedure described in the synthesis of I-40. The product was purified by flash column chromatography on silica gel (CombiFlash®, 3.5% methanol in DCM). MS(ES): m/z: 490.4 [M+H]+, 1H NMR (DMSO-d6, 400 MHz): δ 10.46 (s, 1H), 10.38 (s, 1H), 8.18 (bs, 2H), 7.44 (s, 1H), 6.72-6.71 (d, J=4.0 Hz, 1H), 6.64 (s, 1H), 4.09 (bs, 2H), 4.00 (bs, 2H), 3.91 (s, 3H), 3.62 (s, 3H), 1.53 (s, 6H).

Example 44: 3-(4-((7-cyano-2-((4,4-dimethyl-6,7-dihydro-4H-pyrazolo[5,1-c][1,4]oxazin-2-yl)amino)-1-methyl-1H-imidazo[4,5-b]pyridin-6-yl)oxy)pyridin-2-yl)-1,1-dimethylurea

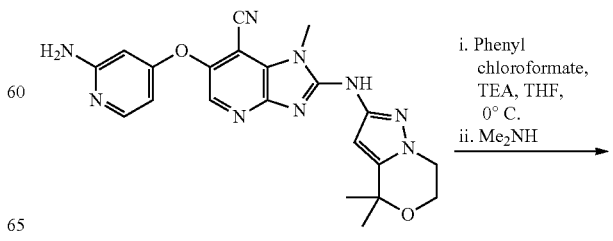

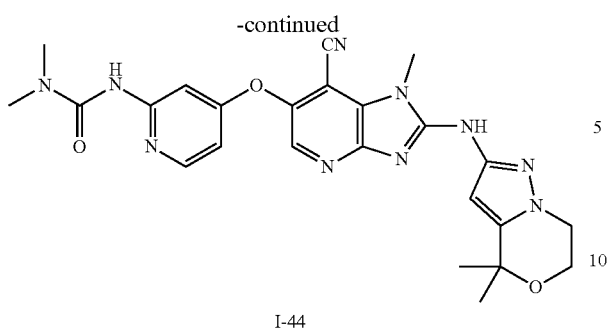

I-44

Synthesis of I-44. Compound I-44 was prepared from 43.2 and dimethylamine, following the procedure of the synthesis of I-23. The product was purified by flash column chromatography on silica gel (CombiFlash®, 3.0% methanol in DCM). MS(ES): m/z: 503.4 [M+H]$^+$, $^1$H NMR (DMSO-d$_6$, 400 MHz): δ 10.45 (s, 1H), 9.01 (s, 1H), 8.15 (bs, 2H), 7.44 (s, 1H), 6.66-6.64 (d, J=5.6 Hz, 2H), 4.09 (bs, 2H), 4.00 (bs, 2H), 3.90 (s, 3H), 2.89 (s, 6H), 1.53 (s, 6H).

Example 45: N-(4-((7-cyano-2-((4,4-dimethyl-6,7-dihydro-4H-pyrazolo[5,1-c][1,4]oxazin-2-yl)amino)-1-methyl-1H-imidazo[4,5-b]pyridin-6-yl)oxy)pyridin-2-yl)pyrrolidine-1-carboxamide

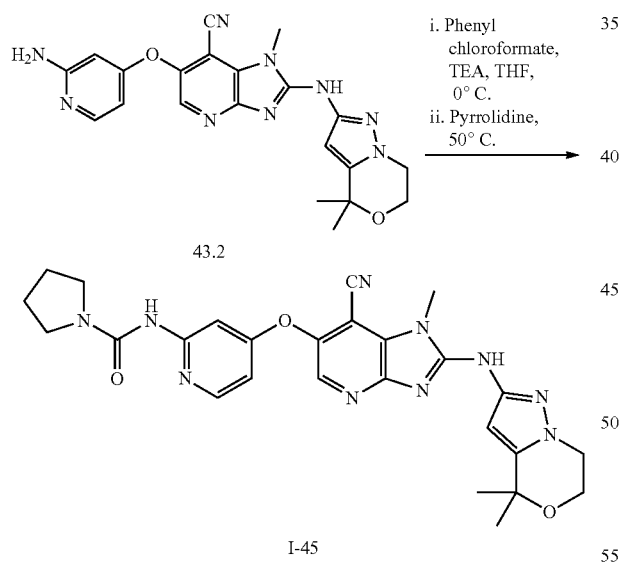

Synthesis of I-45. Compound I-45 was prepared from 43.2 and pyrrolidine, following the procedure of the synthesis of I-23. The product was purified by flash column chromatography on silica gel (CombiFlash®, 4.0% methanol in DCM). MS(ES): m/z: 529.4 [M+H]$^+$, $^1$H NMR (DMSO-d$_6$, 400 MHz): δ 10.45 (s, 1H), 8.82 (s, 1H), 8.16 (bs, 2H), 7.53-7.52 (d, J=1.6 Hz, 1H), 6.66-6.63 (m, 2H), 4.09 (bs, 2H), 4.00 (bs, 2H), 3.90 (s, 3H), 3.33 (bs, 4H), 1.80 (bs, 4H), 1.53 (bs, 6H).

Example 46: 3-(4-((7-chloro-1-methyl-2-((5-methyl-4-oxo-4,5,6,7-tetrahydropyrazolo[1,5-a]pyrazin-2-yl)amino)-1H-imidazo[4,5-b]pyridin-6-yl)oxy)pyridin-2-yl)-1,1-dimethylurea

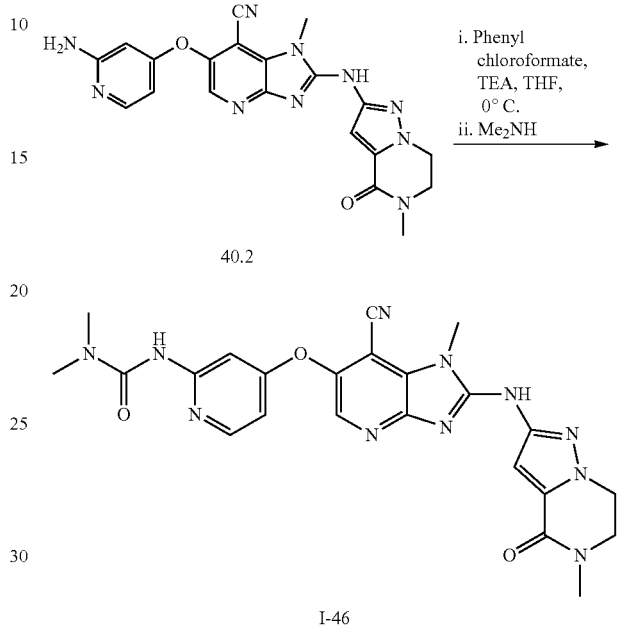

I-46

Synthesis of I-46. Compound I-46 was prepared from 40.2 and dimethylamine, following the procedure of the synthesis of I-23. The product further purified by flash column chromatography on silica gel (CombiFlash®, 3.5% methanol in DCM). MS(ES): m/z: 511.4 [M+H]$^+$, $^1$H NMR (DMSO-d$_6$, 400 MHz): δ 10.39 (s, 1H), 8.93 (s, 1H), 8.11 (s, 1H), 7.36 (s, 1H), 7.23 (s, 1H), 7.07 (bs, 1H), 6.83 (bs, 1H), 4.32 (bs, 2H), 3.95 (s, 3H), 3.81 (bs, 2H), 3.03 (s, 3H), 2.88 (s, 6H).

Example 47: N-(4-((7-cyano-2-((4,4-dimethyl-6,7-dihydro-4H-pyrazolo[5,1-c][1,4]oxazin-2-yl)amino)-1-methyl-1H-imidazo[4,5-b]pyridin-6-yl)oxy)pyridin-2-yl)azetidine-1-carboxamide

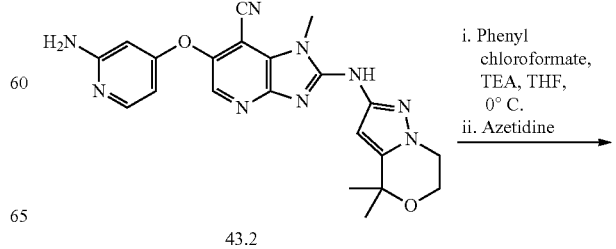

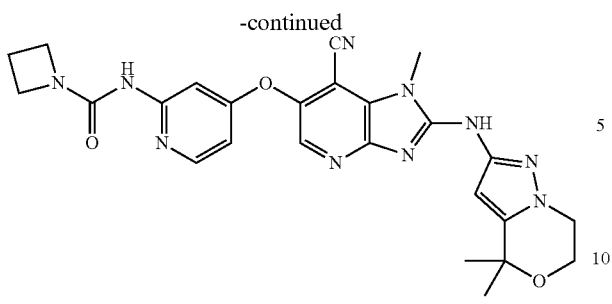

I-47

Synthesis of I-47. Compound I-47 was prepared from 43.2 and azetidine, following the procedure of the synthesis of I-23. The product was purified by flash column chromatography on silica gel (CombiFlash®, 4.0% methanol in DCM). MS(ES): m/z: 515.2 [M+H]+, 1H NMR (DMSO-d6, 400 MHz): δ 10.45 (s, 1H), 9.20 (s, 1H), 8.15 (bs, 2H), 7.54 (s, 1H), 7.07 (s, 1H), 6.83 (bs, 1H), 4.10 (bs, 2H), 4.00 (bs, 4H), 3.94 (bs, 2H), 3.91 (s, 3H), 2.14-2.11 (m, 2H), 1.53 (s, 6H).

Example 48: (R)-Tetrahydrofuran-3-yl(4-((7-cyano-2-((4,4-dimethyl-6,7-dihydro-4H-pyrazolo[5,1-c][1,4]oxazin-2-yl)amino)-1-methyl-1H-imidazo[4,5-b]pyridin-6-yl)oxy)pyridin-2-yl)carbamate

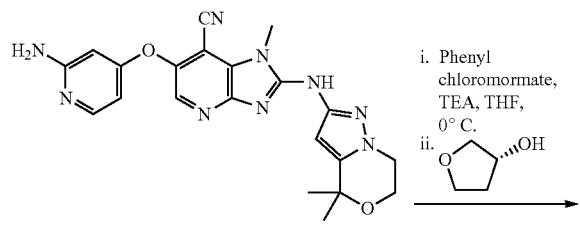

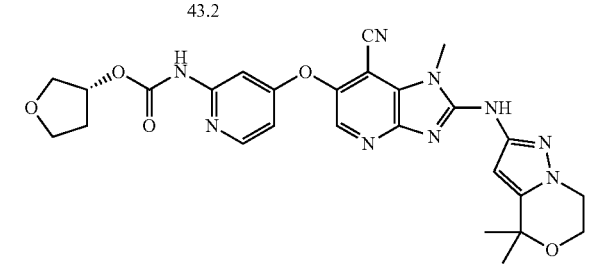

I-48

Synthesis of I-48. Compound I-48 was prepared from 43.2 and (R)-tetrahydrofuran-3-ol, following the procedure of the synthesis of I-23. The product was purified by flash column chromatography on silica gel (CombiFlash®, 3.8% methanol in DCM). MS(ES): m/z: 546.5 [M+H]+, 1H NMR (DMSO-d6, 400 MHz): δ 10.42 (s, 1H), 10.33 (s, 1H), 8.21-8.18 (m, 2H), 7.38 (s, 1H), 6.76-6.75 (d, J=3.6 Hz, 1H), 6.62 (s, 1H), 5.21 (s, 1H), 4.09 (bs, 2H), 4.00 (bs, 2H), 3.90 (s, 3H), 3.78-3.70 (m, 4H), 2.16-2.11 (m, 1H), 1.93-1.89 (m, 1H), 1.53 (s, 6H).

Example 49: (S)-Tetrahydrofuran-3-yl(4-((7-cyano-2-((4,4-dimethyl-6,7-dihydro-4H-pyrazolo[5,1-c][1,4]oxazin-2-yl)amino)-1-methyl-1H-imidazo[4,5-b]pyridin-6-yl)oxy)pyridin-2-yl)carbamate

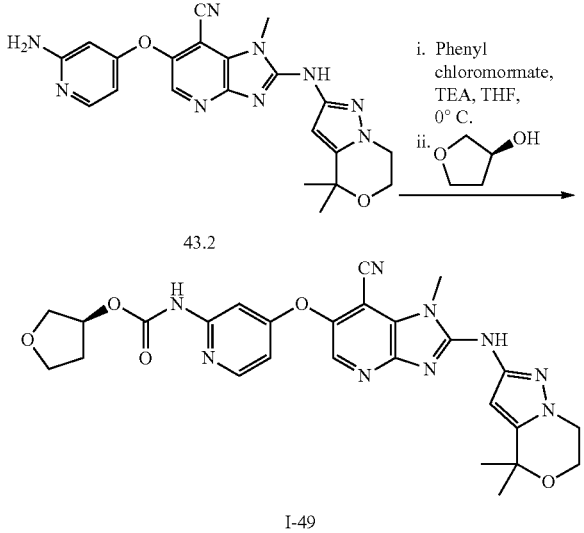

I-49

Synthesis of I-49. Compound I-49 was prepared from 43.2 and (S)-tetrahydrofuran-3-ol, following the procedure of the synthesis of I-23. The product was purified by flash column chromatography on silica gel (CombiFlash®, 4.0% methanol in DCM). MS(ES): m/z: 546.5 [M+H]+, 1H NMR (DMSO-d6, 400 MHz): δ 10.46 (s, 1H), 10.35 (s, 1H), 8.20-8.17 (m, 2H), 7.40 (s, 1H), 6.73-6.72 (d, J=3.2 Hz, 1H), 6.63 (s, 1H), 5.20 (bs, 1H), 4.09 (bs, 2H), 4.00 (bs, 2H), 3.90 (s, 3H), 3.77-3.69 (m, 4H), 2.15-2.10 (m, 1H), 1.92-1.88 (m, 1H), 1.53 (s, 6H).

Example 51: N-(4-((7-chloro-1-methyl-2-((1-(methyl-d3)-2-oxo-5-(trifluoromethyl)-1,2-dihydropyridin-3-yl)amino)-1H-imidazo[4,5-b]pyridin-6-yl)oxy)pyridin-2-yl)acetamide

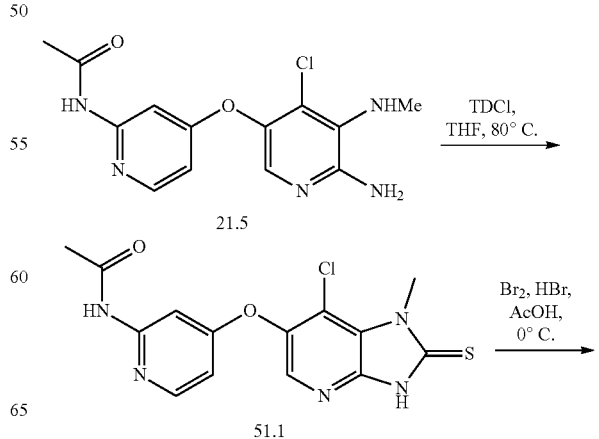

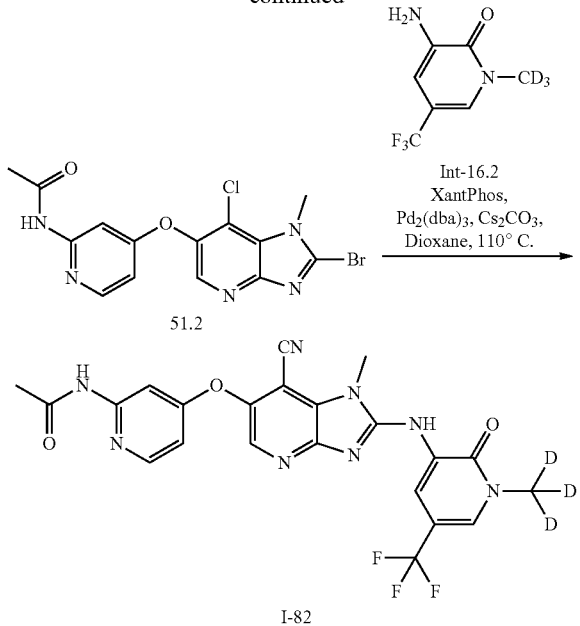

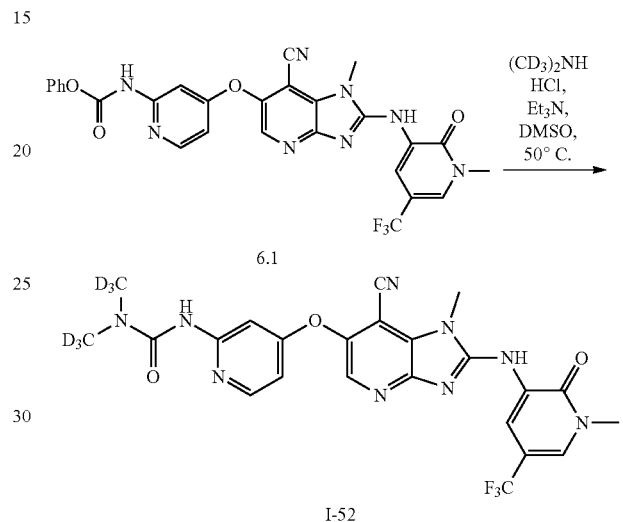

synthesis of I-10. The product was purified by flash column chromatography on silica gel (CombiFlash®, 2.3% methanol in DCM) to afford I-82. MS(ES): m/z: 511.2 [M]+, $^1$H NMR (DMSO-d$_6$, 400 MHz): δ 10.59 (s, 1H), 8.85 (s, 1H), 8.64 (d, J=2.4 Hz, 1H), 8.25 (s, 1H), 8.20 (d, J=6.0 Hz, 1H), 8.15 (s, 1H), 7.67 (s, 1H), 6.68-6.66 (m, 1H), 4.00 (s, 3H), 2.05 (s, 3H).

Example 52: 3-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-1,1-bis(methyl-d$_3$)urea Synthesis of compound 51.1. To a solution of 21.5 (0.150 g, 0.487 mmol, 1.0 equiv) in THF (2 mL) was added 1,1'-thiocarbonyldiimidazole (0.433 g, 2.43 mmol, 5.0 equiv). The reaction mixture was stirred at 80° C. for 1 h. It was cooled to room temperature and transferred into ice-water. The precipitated solids were collected by filtration and triturated with hexane to afford 51.1. MS(ES): m/z: 350.7 [M+H]+.

Synthesis of compound 51.2. To a solution of 51.1 (0.110 g, 0.314 mmol, 1.0 equiv) in acetic acid (5 mL) was added aqueous hydrobromic acid (0.037 g, 0.471 mmol, 1.5 equiv) at 0° C. followed by bromine (0.200 g, 1.25 mmol, 4.0 equiv). The reaction mixture was stirred for 10 min. It was transferred into saturated sodium bicarbonate solution, stirred, and extracted with ethyl acetate. The combined organic layers were washed with brine, dried over anhydrous sodium sulfate, and concentrated under reduced pressure. The residue was purified by flash column chromatography on silica gel (CombiFlash®, 2.5% methanol in DCM) to afford 51.2. MS (ES): m/z 397.6 [M+H]+.

Synthesis of I-82. Compound I-82 was prepared from 51.2 and Int-16.2, following the procedure described in the Synthesis of I-52. Compound I-52 was prepared from 6.1 and dimethylamine hydrochloride (d$_6$), following the procedure described in the synthesis of I-6. The product was purified by flash column chromatography on silica gel (CombiFlash®, 4.0% methanol in DCM). MS(ES): m/z: 540.3 [M+H]+; $^1$H NMR (DMSO-d$_6$, 400 MHz): δ 9.04 (d, J=10.8 Hz, 2H), 8.67 (s, 1H), 8.32 (s, 1H), 7.50 (s, 1H), 7.10-7.09 (bs, 1H), 6.86-6.83 (bs, 1H), 6.71-6.696 (bs, 1H), 4.00 (s, 3H), 3.69 (s, 3H).

Example 53: (R)-tetrahydrofuran-3-yl(4-((7-chloro-1-methyl-2-((5-methyl-4-oxo-4,5,6,7-tetrahydropyrazolo[1,5-a]pyrazin-2-yl)amino)-1H-imidazo[4,5-b]pyridin-6-yl)oxy)pyridin-2-yl)carbamate

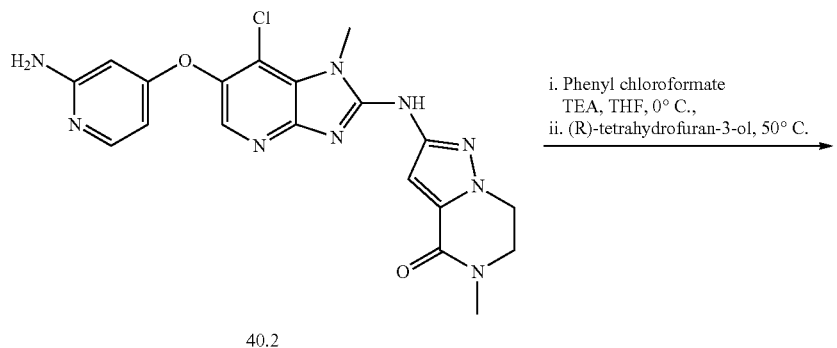

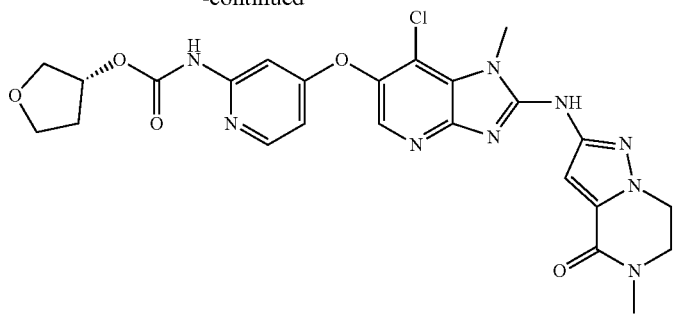

I-53

Synthesis of I-53. To a solution of 40.2 (0.080 g, 0.181 mmol, 1.0 equiv) in THF (3 mL) was added triethylamine (0.055 g, 0.545 mmol, 3.0 equiv) at 0° C. followed by phenyl chloroformate (0.042 g, 0.272 mmol, 1.5 equiv). The reaction mixture was stirred at 0° C. for 15 min. (R)-tetrahydrofuran-3-ol (0.080 g, 0.909 mmol, 5.0 equiv) was added and the mixture was stirred at 80° C. for 16 h. It was transferred into water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.5% methanol in DCM) to afford I-53. MS(ES): m/z: 554.4 [M+H]$^+$; $^1$H NMR (DMSO-d$_6$, 400 MHz): δ 10.41 (s, 1H), 10.28 (s, 1H), 8.15 (d, J=5 Hz, 2H), 7.32 (s, 1H), 7.23 (s, 1H), 6.66 (d, J=5 Hz, 1H), 5.19 (bs, 1H), 4.34 (t, J=7.5 Hz, 3H), 4.12-4.11 (m, 1H), 3.96 (s, 4H), 3.83-3.61 (m, 9H), 3.24 (m, 2H), 3.03 (s, 3H), 2.17-2.09 (m, 2H), 1.90-1.87 (m, 1H)

Example 54: oxetan-3-yl(4-((7-chloro-1-methyl-2-((5-methyl-4-oxo-4,5,6,7-tetrahydropyrazolo[1,5-a]pyrazin-2-yl)amino)-1H-imidazo[4,5-b]pyridin-6-yl)oxy)pyridin-2-yl)carbamate

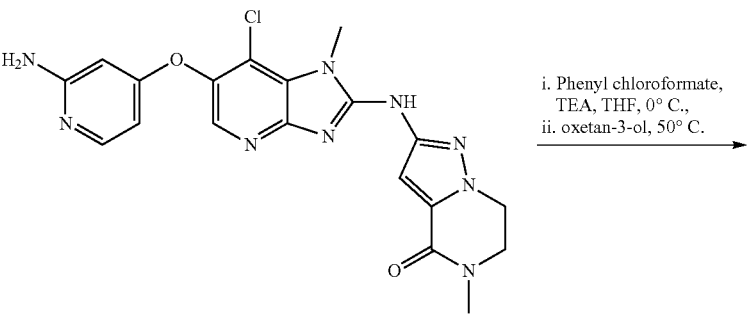

40.2

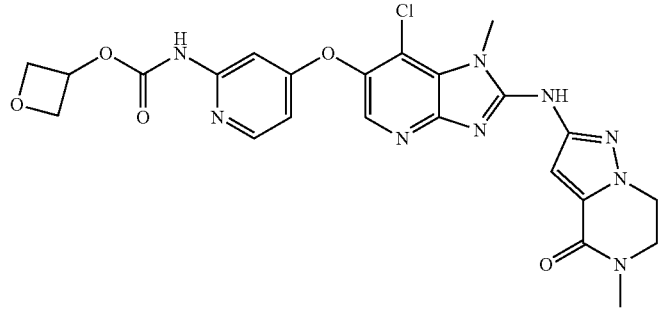

I-54

Synthesis of I-54. Compound I-54 was prepared from 40.2 and oxetan-3-ol, following the procedure described in the synthesis of I-53. The product was purified by flash column chromatography on silica gel (CombiFlash®, 3.5% methanol in DCM). MS(ES): m/z: 540.4 [M+H]$^+$; $^1$H NMR (DMSO-d$_6$, 400 MHz): δ 10.54 (s, 1H), 10.41 (s, 1H), 8.18-8.13 (m, 2H), 7.29-7.23 (m, 2H), 4.78-4.74 (m, 2H), 4.49 (bs, 2H), 4.33 (bs, 2H), 4.13-4.11 (bs, 2H), 3.952 (s, 4H), 3.821 (bs, 2H), 3.18-3.16 (m, 4H), 3.03 (s, 4H), 2.17-2.09 (m, 2H), 1.55 (s, 1H).

Example 55: (S)-tetrahydrofuran-3-yl(4-((7-chloro-1-methyl-2-((5-methyl-4-oxo-4,5,6,7-tetrahydropyrazolo[1,5-a]pyrazin-2-yl)amino)-1H-imidazo[4,5-b]pyridin-6-yl)oxy)pyridinyl)carbamate

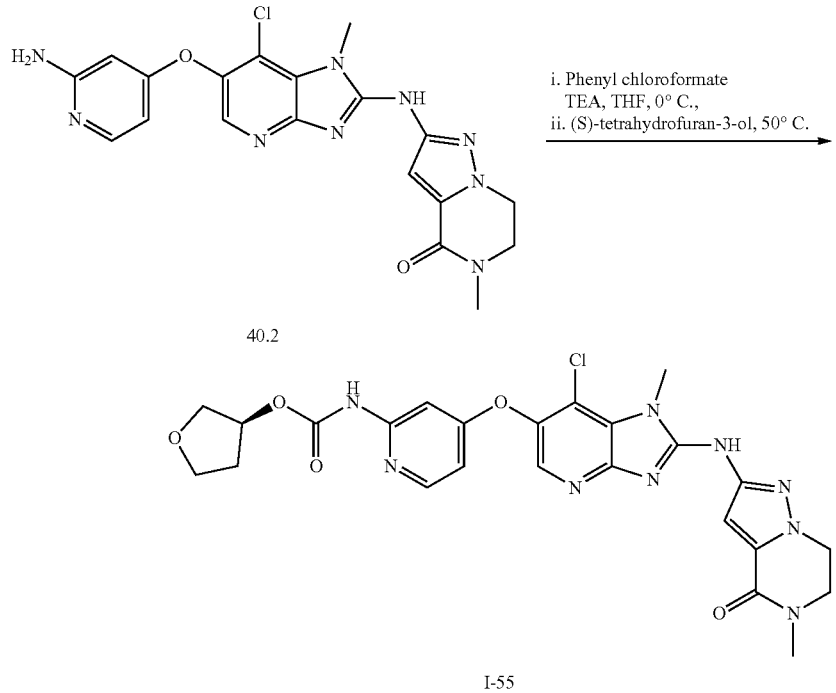

Synthesis of I-55. Compound I-55 was prepared from 40.2 and (S)-tetrahydrofuran-3-ol, following the procedure described in the synthesis of I-53. The product was purified by flash column chromatography on silica gel (Combi-Flash®, 3.5% methanol in DCM). MS(ES): m/z: 554.4 [M+H]+; 1H NMR (DMSO-$d_6$, 400 MHz): δ 10.41 (s, 1H), 10.28 (s, 1H), 8.15 (d, J=5 Hz, 2H), 7.32 (s, 1H), 7.23 (s, 1H), 6.66 (d, J=5 Hz, 1H), 5.19 (bs, 1H), 4.33 (t, J=7.5 Hz, 3H), 4.12-4.11 (m, 1H), 3.96 (s, 4H), 3.83-3.61 (m, 9H), 3.24 (m, 2H), 3.03 (s, 3H), 2.17-2.09 (m, 2H), 1.90-1.87 (m, 1H).

Example 56: 3-(4-((7-cyano-2-((5',6'-dihydrospiro[cyclobutane-1,4'-pyrrolo[1,2-b]pyrazol]-2'-yl)amino)-1-methyl-1H-imidazo[4,5-b]pyridin-6-yl)oxy)pyridin-2-yl)-1,1-dimethylurea

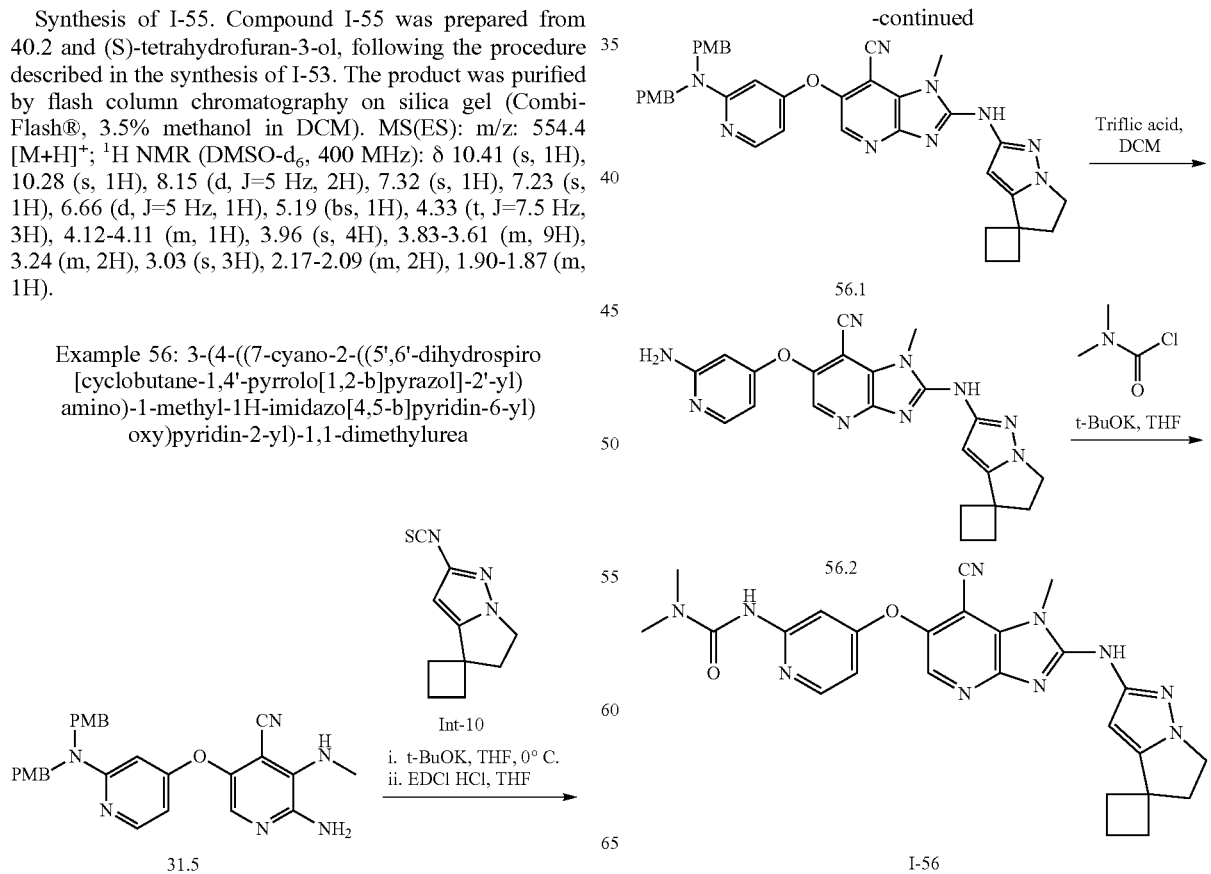

Synthesis of compound 56.1. Compound 56.1 was prepared from 31.5 and Int-10, following the procedure described in the synthesis of I-19. The product was purified by flash column chromatography on silica gel (CombiFlash®, DCM). MS(ES): m/z 668 [M+H]$^+$.

Synthesis of compound 56.2. Compound 56.2 was prepared from 56.1, following the procedure described in the synthesis of 40.2. The product was purified by trituration using diethyl ether and used in the next step without further purification. MS(ES): m/z 428 [M+H]$^+$.

Synthesis of I-56. Compound I-56 was prepared from 56.2 following the procedure described in the synthesis of I-21. The product was purified by flash column chromatography on silica gel (CombiFlash®, 3.2% DCM: methanol). MS(ES): m/z 499.35 [M+H]$^+$; $^1$H NMR (DMSO-d$_6$, 400 MHz): δ 10.38 (s, 1H), 9.011 (s, 1H), 8.17 (s, 2H), 7.44 (m, 2H), 6.72 (s, 3H), 4.07-4.04 (m, 2H), 3.92 (s, 3H), 2.91 (s, 3H), 2.79-2.656 (m, 2H), 2.37 (m, 2H), 2.01 (s, 2H), 1.25 (s, 2H).

Example 57: methyl(4-((7-cyano-2-((5',6'-dihydrospiro[cyclobutane-1,4'-pyrrolo[1,2-b]pyrazol]-2'-yl)amino)-1-methyl-1H-imidazo[4,5-b]pyridin-6-yl)oxy)pyridin-2-yl)carbamate

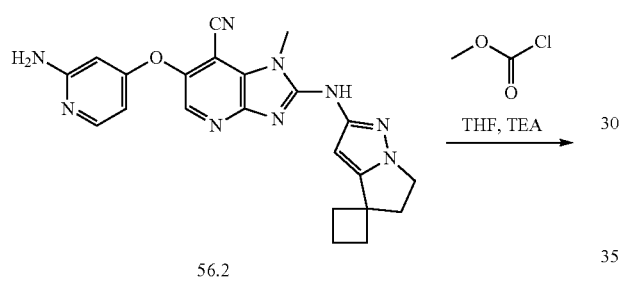

56.2

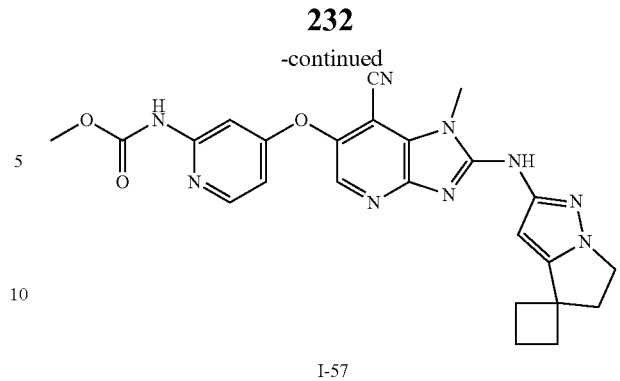

I-57

Synthesis of I-57. Compound I-57 was prepared from 56.2 following the procedure described in the synthesis of I-22. The product was purified by flash column chromatography on silica gel (CombiFlash®, 2% DCM: methanol). MS(ES): m/z 486.35 [M+H]$^+$. $^1$H NMR (DMSO-d$_6$, 400 MHz): δ 10.38 (s, 1H), 8.18 (s, 1H), 7.62 (s, 1H), 7.45 (m, 2H), 6.72 (s, 2H), 4.10-3.91 (m, 2H), 3.62 (s, 3H), 2.65 (s, 3H), 2.50-2.35 (m, 2H), 2.27 (s, 2H), 2.02 (s, 2H), 1.23 (s, 2H).

Example 58: 1-(4-((7-cyano-2-((5',6'-dihydrospiro[cyclobutane-1,4'-pyrrolo[1,2-b]pyrazol]-2'-yl)amino)-1-methyl-1H-imidazo[4,5-b]pyridin-6-yl)oxy)pyridin-2-yl)-3-methylurea

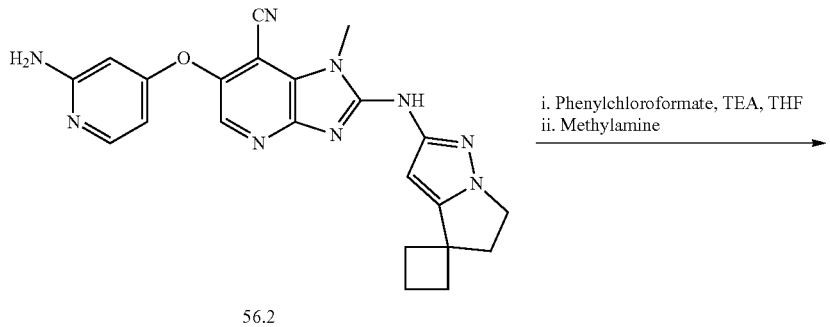

56.2 i. Phenylchloroformate, TEA, THF
ii. Methylamine

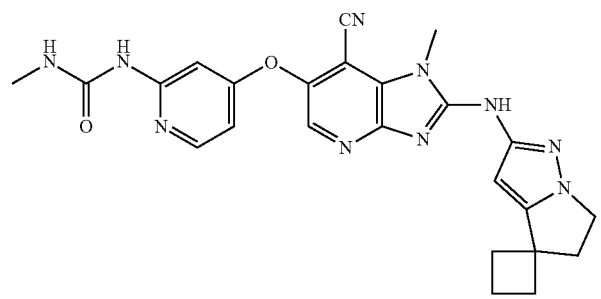

I-58

Synthesis of I-58. Compound I-58 was prepared from 56.2 and methylamine, following the procedure described in the synthesis of I-23. The product was purified by flash column chromatography on silica gel (CombiFlash®, 3.5% methanol in DCM). MS(ES): m/z: 485.39 [M+H]$^+$; $^1$H NMR (DMSO-d$_6$, 400 MHz): δ 10.39 (s, 1H), 9.19 (s, 1H), 8.17 (m, 2H), 7.84 (bs, 2H), 7.07-6.98 (m, 2H), 4.04 (bs, 2H), 3.91 (s, 3H), 2.68 (s, 3H), 2.10-2.00 (m, 4H), 1.72-1.56 (m, 2H), 1.24 (s, 2H).

Example 59: (S)-N-(4-((7-cyano-2-((5',6'-dihydrospiro[cyclobutane-1,4'-pyrrolo[1,2-b]pyrazol]-2'-yl)amino)-1-methyl-1H-imidazo[4,5-b]pyridin-6-yl)oxy)pyridin-2-yl)-3-methoxypyrrolidine-1-carboxamide

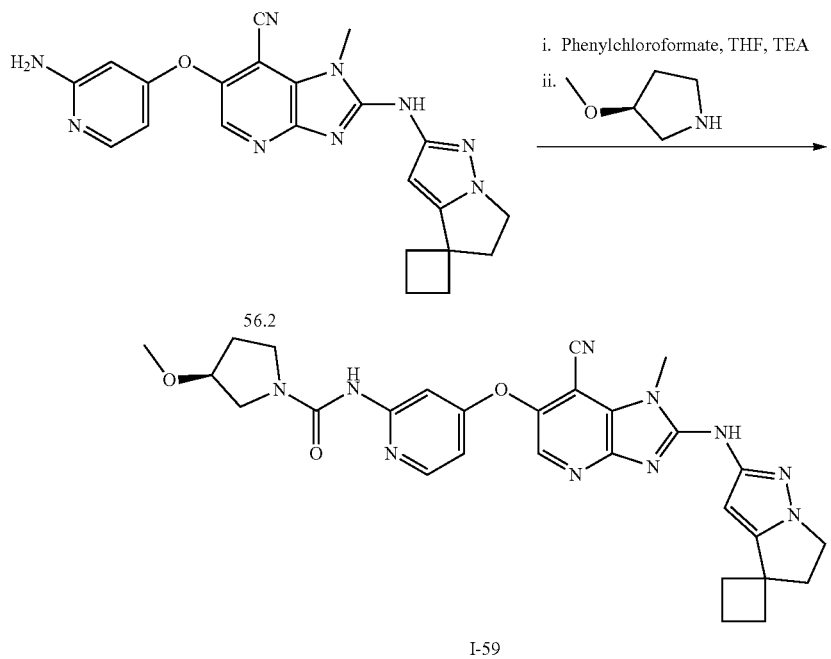

Synthesis of I-59. Compound I-59 was prepared from 56.2 and (S)-3-methoxypyrrolidine, following the procedure described in the synthesis of I-23. The product was purified by flash column chromatography on silica gel (CombiFlash®, 3.5% methanol in DCM). MS(ES): m/z: 555.40 [M+H]$^+$; $^1$H NMR (DMSO-d$_6$, 400 MHz): δ 10.37 (s, 1H), 8.90 (s, 1H), 8.16 (d, J=4.8 Hz, 2H), 7.52 (s, 1H) 6.71 (m, 2H), 4.05 (t, J=6.4 Hz, 3H), 3.90 (s, 3H), 3.36 (bs, 4H), 3.21 (s, 3H), 2.67 (bs, 2H), 2.37 (m, 2H), 2.27 (bs, 2H), 2.03 (m, 2H), 1.93 (m, 2H).

Example 60: (R)-N-(4-((7-cyano-2-((5',6'-dihydrospiro[cyclobutane-1,4'-pyrrolo[1,2-b]pyrazol]-2'-yl)amino)-1-methyl-1H-imidazo[4,5-b]pyridin-6-yl)oxy)pyridin-2-yl)-3-methoxypyrrolidine-1-carboxamide

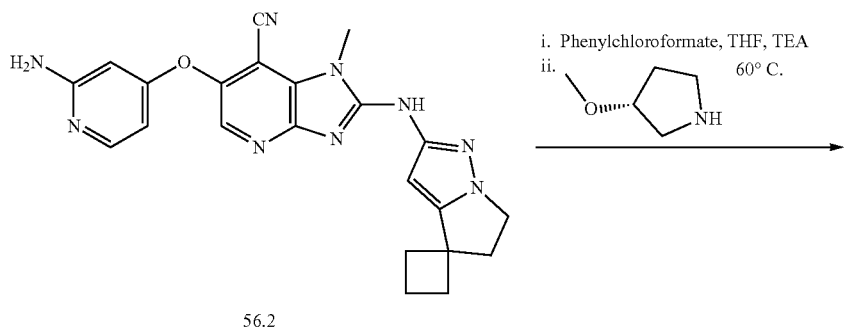

-continued

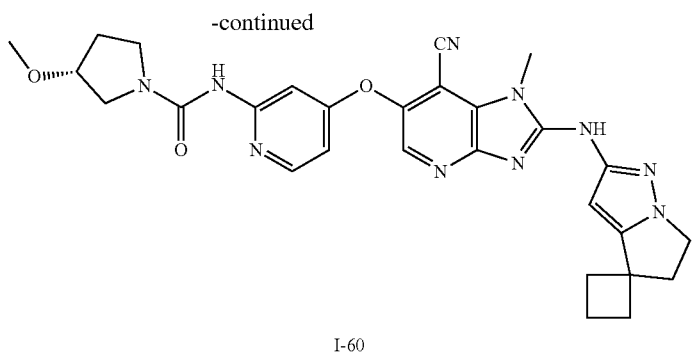

I-60

Synthesis of I-60. Compound I-60 was prepared from 56.2 and (R)-3-methoxypyrrolidine, following the procedure described in the synthesis of I-23. The product was purified by flash column chromatography on silica gel (Combi-Flash®, 3.5% methanol in DCM). MS(ES): m/z: 555.42 [M+H]$^+$; $^1$H NMR (DMSO-d$_6$, 400 MHz): δ 10.38 (s, 1H), 8.91 (s, 1H), 8.15 (d, J=4.8 Hz, 2H) 7.51 (s, 1H), 6.71 (m, 2H), 4.05 (m, 1H), 4.04 (m, 2H), 3.90 (s, 3H), 3.36 (bs, 4H), 3.21 (s, 3H), 2.67 (bs, 2H), 2.37 (m, 2H), 2.27 (bs, 2H) 2.03 (m, 2H), 1.93 (m, 2H).

Example 61: N-(4-((7-cyano-2-((5',6'-dihydrospiro[cyclobutane-1,4'-pyrrolo[1,2-b]pyrazol]-2'-yl)amino)-1-methyl-1H-imidazo[4,5-b]pyridin-6-yl)oxy)pyridin-2-yl)-3-methoxyazetidine carboxamide

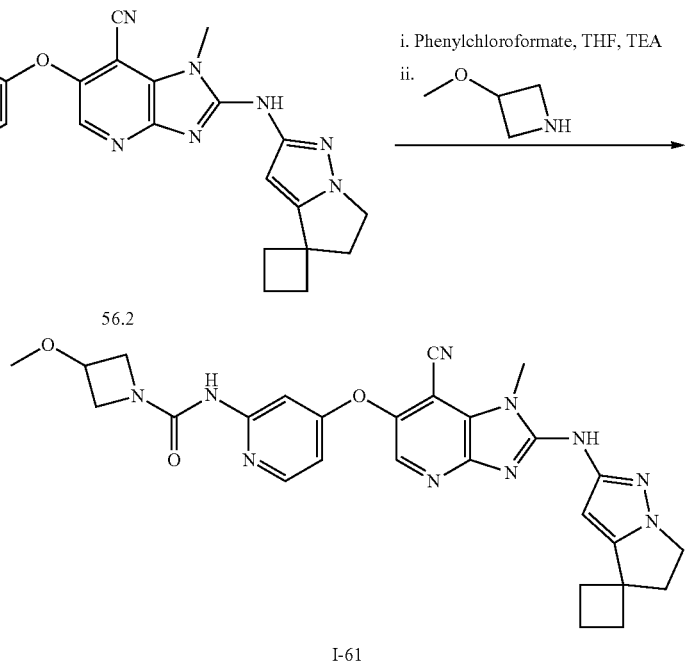

Synthesis of I-61. Compound I-61 was prepared from 56.2 and 3-methoxyazetidine, following the procedure described in the synthesis of I-23. The product was purified by flash column chromatography on silica gel (Combi-Flash®, 3.5% methanol in DCM). MS(ES): m/z: 541.43 [M+H]$^+$; $^1$H NMR (DMSO-d$_6$, 400 MHz): δ 10.42 (s, 1H), 9.39 (s, 1H), 8.19 (s, 2H) 7.55 (m, 1H), 6.72 (m, 3H), 4.16 (s, 2H), 4.07 (t, J=6.8 Hz, 2H), 3.93 (s, 3H), 3.79 (d, J=5.6 Hz, 2H), 3.21 (s, 3H), 2.701 (m, 2H), 2.31 (m, 2H), 2.06 (m, 2H), 1.26 (s, 2H).

Example 62: 2-methoxyethyl(4-((7-cyano-2-((5',6'-dihydrospiro[cyclobutane-1,4'-pyrrolo[1,2-b]pyrazol]-2'-yl)amino)-1-methyl-1H-imidazo[4,5-b]pyridin-6-yl)oxy)pyridin-2-yl)carbamate

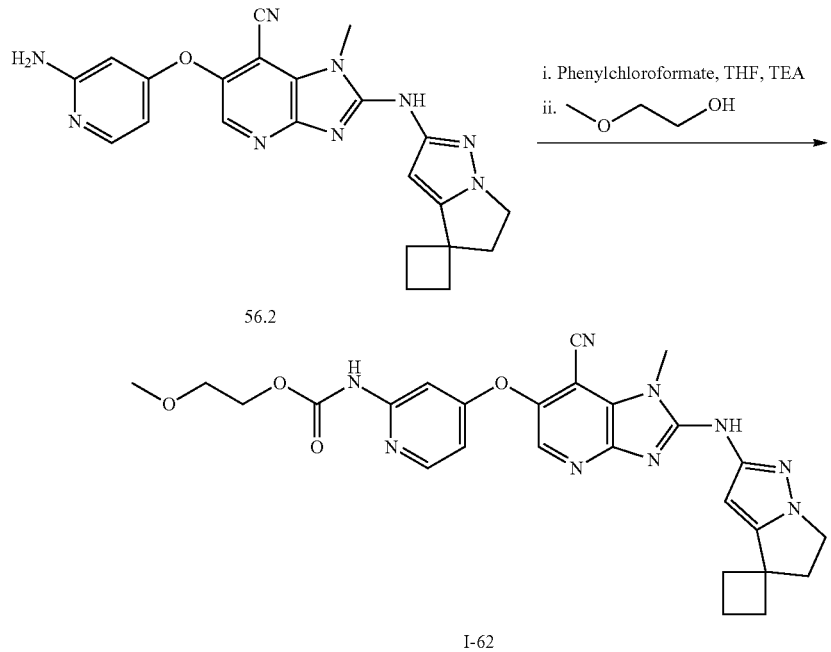

Synthesis of I-62. Compound I-62 was prepared from 56.2 and 2-methoxyethan-1-ol, following the procedure described in the synthesis of I-23. The product was purified by flash column chromatography on silica gel (Combi-Flash®, 3.5% methanol in DCM). MS(ES): m/z: 530.39 [M+H]$^+$; $^1$H NMR (DMSO-$d_6$, 400 MHz): δ 10.38 (s, 1H), 8.18 (s, 1H), 7.43 (s, 1H), 6.71 (m, 2H), 4.71 (m, 3H), 4.04 (m, 3H), 3.90 (s, 3H), 3.52 (m, 2H), 3.25 (s, 3H), 2.65 (bs, 2H), 2.50 (m, 2H), 2.35 (m, 2H), 2.27 (bs, 2H) 2.03 (m, 2H).

Example 63: methyl (4-((7-cyano-2-((6',7'-dihydro-5'H-spiro[cyclopropane-1,4'-pyrazolo[1,5-a]pyridin]-2'-yl)amino)-1-methyl-1H-imidazo[4,5-b]pyridin-6-yl)oxy)pyridin-2-yl)carbamate

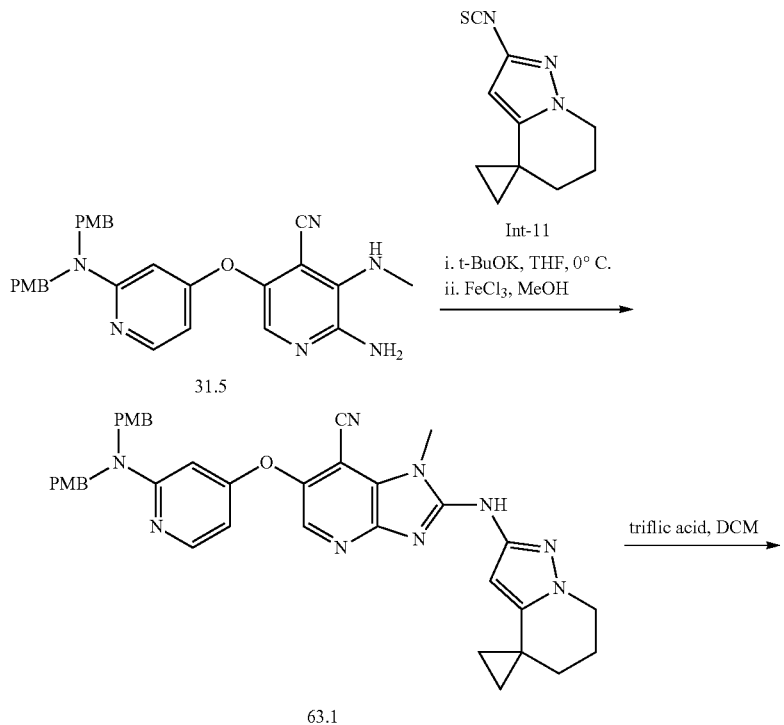

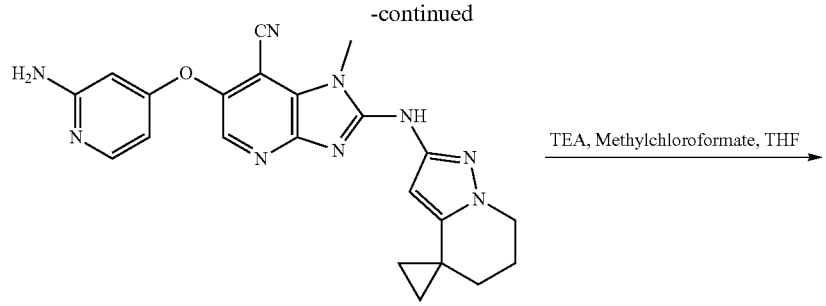

63.2

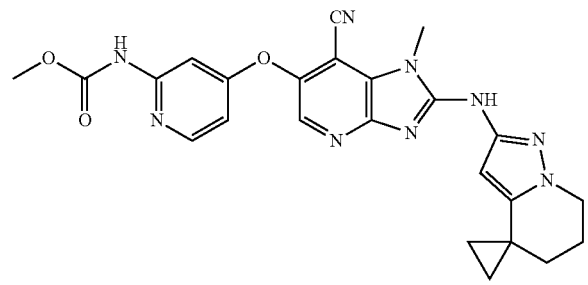

I-63

Synthesis of compound 63.1. Compound 63.1 was prepared from 31.5 and Int-11, following the procedure described in the synthesis of 40.1. The product was purified by flash column chromatography on silica gel (CombiFlash®, 2% methanol in DCM). MS(ES): m/z 667.77 [M+H]⁺.

Synthesis of compound 63.2. Compound 63.2 was prepared from 63.1, following the procedure described in the synthesis of 40.2. The product was triturated by diethyl ether and used in the next step without further purification. MS(ES): m/z 427.47 [M+H]⁺.

Synthesis of compound I-63. Compound I-63 was prepared from 63.1, following the procedure described in the synthesis of I-22. The product was purified by flash column chromatography on silica gel (CombiFlash®, 3% methanol in DCM). MS(ES): m/z 485.51 [M+H]⁺; ¹H NMR (DMSO-$d_6$, 400 MHz): δ 10.43 (s, 1H), 8.22-8.20 (bs, 1H), 7.45 (s, 1H), 7.26-7.00 (bs, 2H), 6.75 (s, 1H), 6.22 (s, 1H), 4.10 (bs, 2H), 3.91 (s, 3H), 3.65 (s, 3H), 2.11 (bs, 2H), 1.74 (bs, 2H), 1.26 (bs, 2H), 0.96-0.87 (bs, 2H).

Example 64: 1-(4-((7-cyano-2-((6',7'-dihydro-5'H-spiro[cyclopropane-1,4'-pyrazolo[1,5-a]pyridin]-2'-yl)amino)-1-methyl-1H-imidazo[4,5-b]pyridin-6-yl)oxy)pyridin-2-yl)-3-methylurea

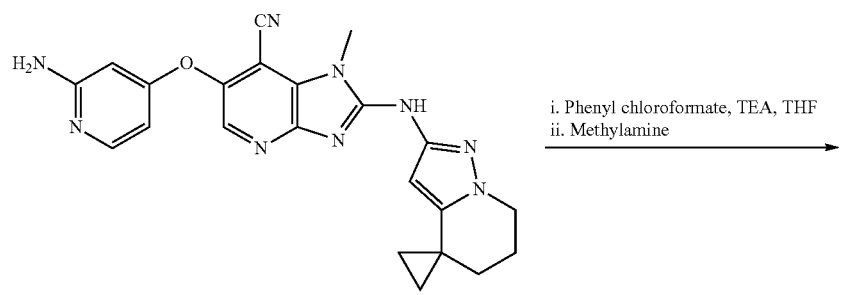

63.2

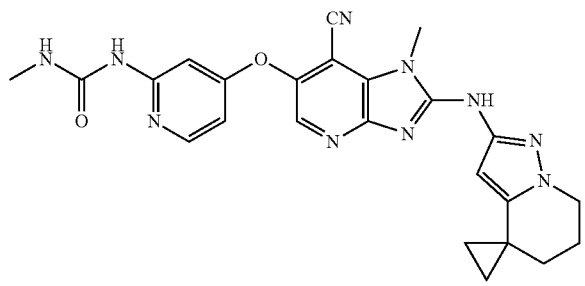

I-64

Synthesis of I-64. Compound I-64 was prepared from 63.2 and methylamine, following the procedure described in the synthesis of I-23. The product was purified by flash column chromatography on silica gel (CombiFlash®, 3.5% methanol in DCM). MS(ES): m/z: 484.52 [M+H]$^+$; $^1$H NMR (DMSO-d$_6$, 400 MHz): δ 9.17 (s, 1H), 8.10 (bs, 1H), 7.82 (bs, 1H), 7.07 (bs, 2H), 6.83 (bs, 2H), 6.20 (s, 1H), 5.34 (s, 1H), 4.09 (bs, 1H), 3.99 (s, 3H), 3.90 (s, 3H), 3.10 (bs, 2H), 1.55 (s, 2H), 1.18 (bs, 2H), 0.94 (bs, 2H).

Example 65: 3-(4-((7-cyano-2-((6',7'-dihydro-5'H-spiro[cyclopropane-1,4'-pyrazolo[1,5-a]pyridin]-2'-yl)amino)-1-methyl-1H-imidazo[4,5-b]pyridin-6-yl)oxy)pyridin-2-yl)-1,1-dimethylurea

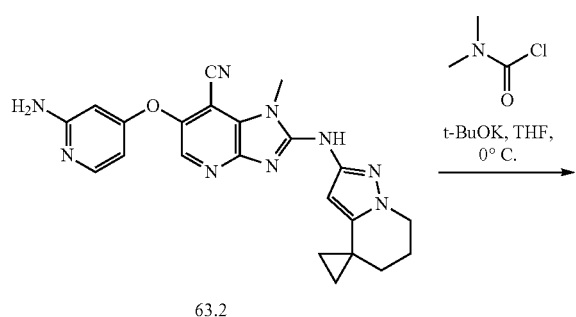

63.2

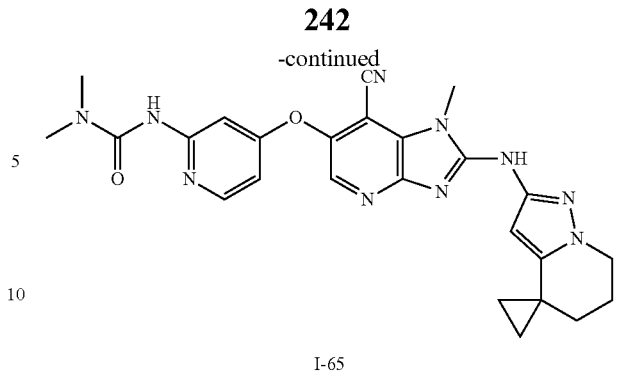

I-65

Synthesis of I-65. Compound I-65 was prepared from 63.2 and dimethyl carbonyl chloride, following the procedure described in the synthesis of I-21. The product was purified by flash column chromatography on silica gel (CombiFlash®, 3.5% methanol in DCM). MS(ES): m/z: 498.55 [M+H]$^+$; $^1$H NMR (DMSO-d$_6$, 400 MHz): δ 8.98 (s, 1H), 8.16-8.08 (bs, 1H), 7.74 (s, 1H), 7.44-7.42 (bs, 1H), 6.65-6.59 (bs, 1H), 6.22 (s, 1H), 5.67 (s, 1H), 3.75 (s, 3H), 3.58-3.51 (bs, 2H), 2.89-2.87 (bs, 6H), 2.16-2.09 (bs, 1H), 1.93 (bs, 1H), 1.72-1.66 (bs, 2H), 1.23-1.24 (bs, 2H), 1.02-0.91 (bs, 2H).

Example 66: oxetan-3-yl (4-((7-cyano-2-((5',6'-dihydrospiro[cyclobutane-1,4'-pyrrolo[1,2-b]pyrazol]-2'-yl)amino)-1-methyl-1H-imidazo[4,5-b]pyridin-6-yl)oxy)pyridin-2-yl)carbamate

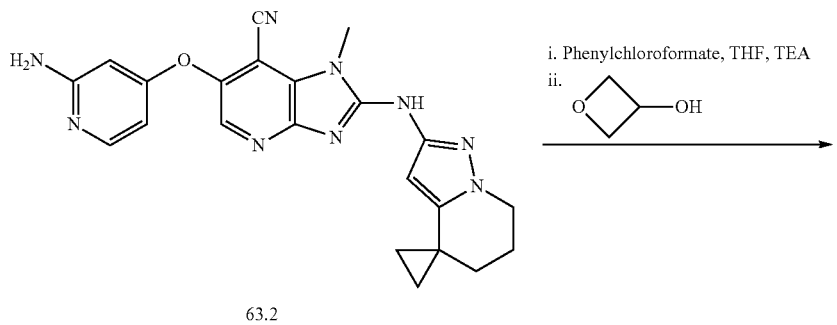

63.2

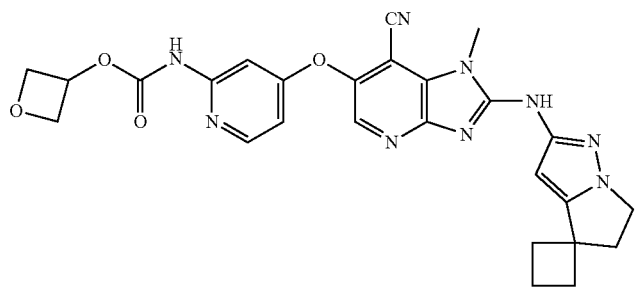

I-66

Synthesis of I-66. Compound I-66 was prepared from 63.2 and oxetan-3-ol, following the procedure described in the synthesis of I-23. The product was purified by flash column chromatography on silica gel (CombiFlash®, 3.5% methanol in DCM) followed by HPLC. MS(ES): m/z: 528.41 [M+H]$^+$; $^1$H NMR (DMSO-d$_6$, 400 MHz): δ 10.58 (s, 1H), 10.36 (s, 1H), 8.20 (m, 2H), 7.36 (s, 1H), 6.74 (m, 2H), 5.34 (t, J=5.6 Hz, 1H), 4.75 (t, J=6.8 Hz, 2H), 4.48 (t, J=5.6 Hz, 2H), 4.02 (t, J=6.4 Hz, 2H), 3.88 (s, 3H), 2.65 (m, 2H), 2.48 (m, 2H), 2.35 (m, 2H), 2.25 (bs, 2H), 2.02 (m, 2H).

Example 67: 3-(4-((7-cyano-2-((4,4-dimethyl-4,5,7,8-tetrahydropyrazolo[1,5-d][1,4]oxazepin yl)amino)-1-methyl-1H-imidazo[4,5-b]pyridin-6-yl)oxy)pyridin-2-yl)-1,1-dimethylurea

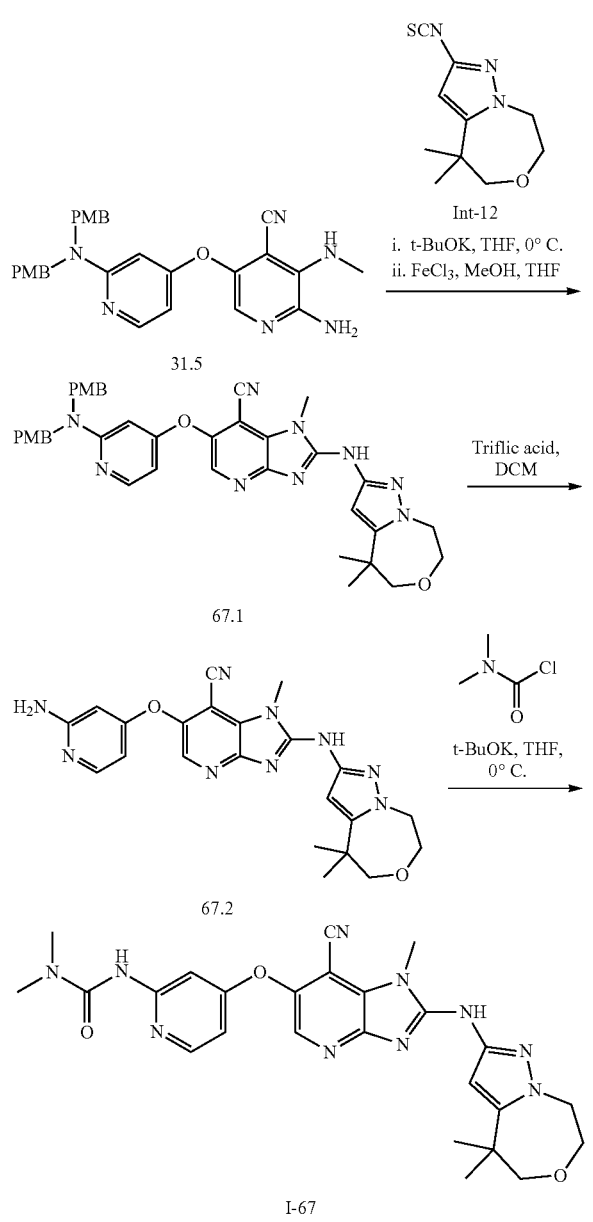

Synthesis of compound 67.1. Compound 67.1 was prepared from 31.5 and Int-12, following the procedure described in the synthesis of 40.1. The product was purified by flash column chromatography on silica gel (CombiFlash®, 4.1% methanol in DCM). MS(ES): m/z: 686.52 [M+H]$^+$.

Synthesis of compound 67.2. Compound 67.2 was prepared from 67.1, following the procedure described in the synthesis of 40.2. The product was purified by trituration with diethyl ether and used in the next step without further purification. MS(ES): m/z: 446.35 [M+H]$^+$.

Synthesis of I-67. Compound I-67 was prepared from 67.2, following the procedure described in the synthesis of I-21. The product was purified by flash column chromatography on silica gel (CombiFlash®, 4.1% methanol in DCM). MS(ES): m/z: 517.41 [M+H]$^+$; $^1$H NMR (DMSO-d$_6$, 400 MHz): δ 10.36 (s, 1H), 9.01 (s, 1H), 8.17 (d, J=6.8 Hz, 2H), 7.44 (s, 1H), 6.67 (s, 2H), 4.38 (s, 2H), 3.91-3.86 (m, 5H), 3.59 (s, 2H), 2.91 (s, 6H), 1.32 (s, 6H).

Example 68: methyl(4-((7-cyano-2-((4,4-dimethyl-4,5,7,8-tetrahydropyrazolo[1,5-d][1,4]oxazepin-2-yl)amino)-1-methyl-1H-imidazo[4,5-b]pyridin-6-yl)oxy)pyridin-2-yl)carbamate

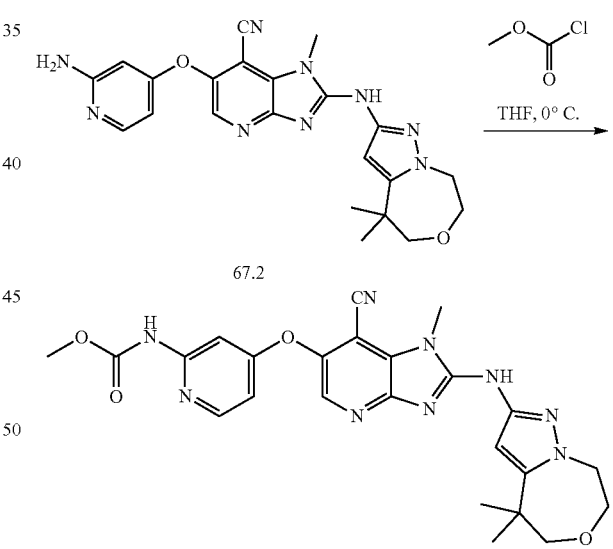

Synthesis of I-68. Compound I-68 was prepared from 67.2, following the procedure described in the synthesis of I-22. The product was purified by flash column chromatography on silica gel (CombiFlash®, 3.9% methanol in DCM). MS(ES): m/z: 504.36 [M+H]$^+$; $^1$H NMR (DMSO-d$_6$, 400 MHz): δ 10.66 (s, 1H), 10.38 (s, 1H), 8.24 (d, J=5.6 Hz, 1H), 8.17 (s, 1H), 7.73 (s, 1H), 6.74 (d, J=3.2 Hz, 1H), 6.67 (s, 1H), 4.38 (s, 2H), 3.90 (s, 3H), 3.86 (s, 2H), 3.58 (s, 2H), 2.06 (s, 3H), 1.31 (s, 6H).

245

Example 69: 1-(4-((7-cyano-2-((4,4-dimethyl-4,5,7,8-tetrahydropyrazolo[1,5-d][1,4]oxazepin-2-yl)amino)-1-methyl-1H-imidazo[4,5-b]pyridin-6-yl)oxy)pyridin-2-yl)-3-methylurea

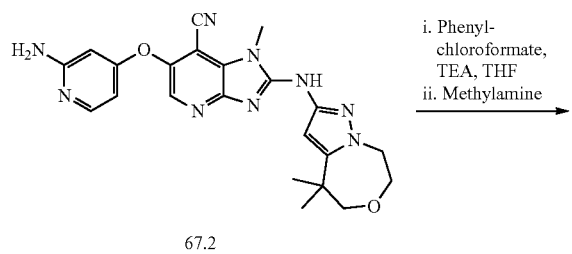

67.2 i. Phenylchloroformate, TEA, THF
ii. Methylamine

246

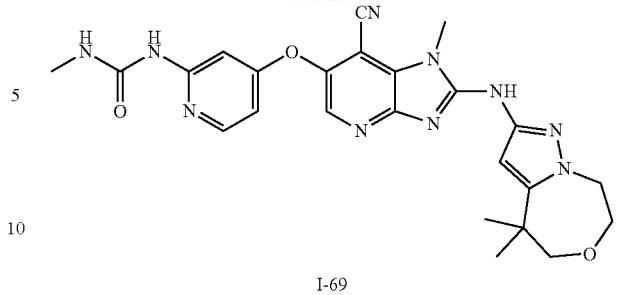

I-69

Synthesis of I-69. Compound I-69 was prepared from 67.2 and methylamine, following the procedure described in the synthesis of I-23. The product was purified by flash column chromatography on silica gel (CombiFlash®, 4.4% methanol in DCM). MS(ES): m/z: 503.38 [M+H]$^+$; $^1$H NMR (DMSO-$d_6$, 400 MHz): δ 10.38 (s, 1H), 9.20 (s, 1H), 8.17 (s, 1H), 8.2 (d, J=5.6 Hz, 1H), 7.84 (bs, 1H), 6.99 (s, 1H), 6.66 (s, 1H), 6.63 (d, J=5.2 Hz, 1H), 4.38 (s, 2H), 3.91 (s, 3H), 3.86 (s, 2H), 3.58 (s, 2H), 2.69 (s, 3H), 1.31 (s, 6H).

Example 70: 3-(4-((2-((1-(tert-butyl)-2,3-dihydro-1H-imidazo[1,2-b]pyrazol-6-yl)amino)-7-cyano-1-methyl-1H-imidazo[4,5-b]pyridin-6-yl)oxy)pyridin-2-yl)-1,1-dimethylurea

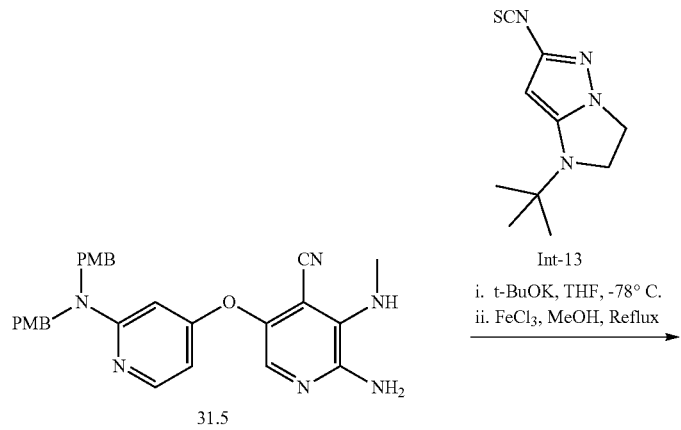

i. t-BuOK, THF, -78° C.
ii. FeCl$_3$, MeOH, Reflux

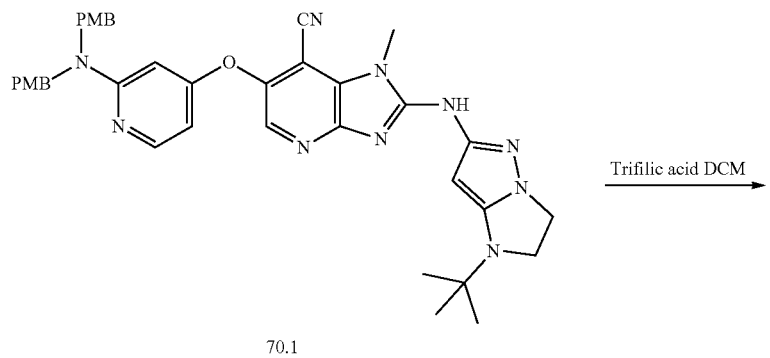

70.1

Triflic acid DCM

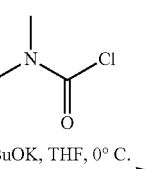
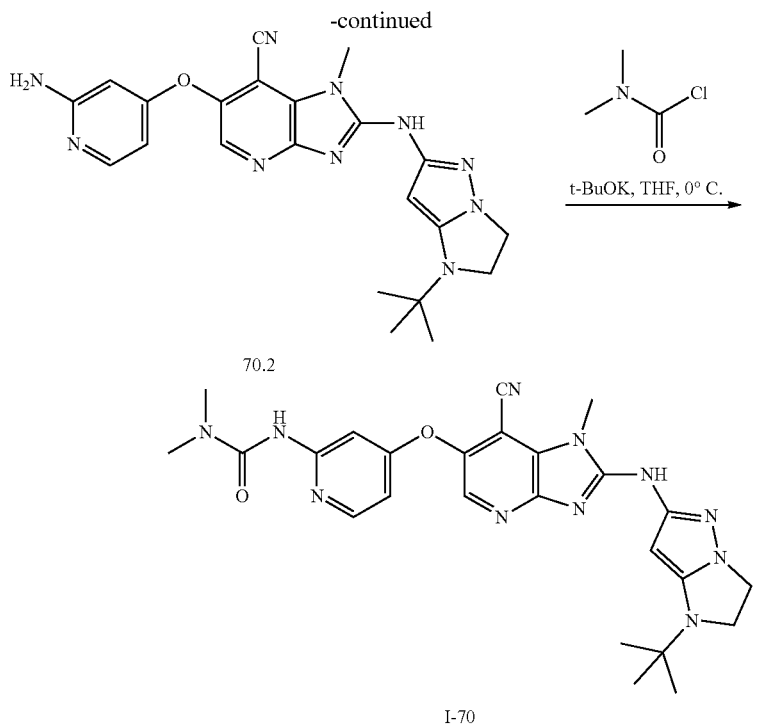

Synthesis of compound 70.1. Compound 70.1 was prepared from 31.5 and Int-13, following the procedure described in the synthesis of 40.1. The product was purified by flash column chromatography on silica gel (CombiFlash®, 2.0% methanol in DCM. MS(ES): m/z 685.83 [M+H]$^+$.

Synthesis of compound 70.2. Compound 70.2 was prepared from 70.1, following the procedure described in the synthesis of 40.2. The product was purified by trituration using diethyl ether and used in the next step without further purification. MS(ES): m/z: 445.2 [M+H]$^+$.

Synthesis of I-70. Compound I-70 was prepared from 70.2, following the procedure described in the synthesis of I-21. The product was purified by flash column chromatography on silica gel (CombiFlash®, 2.3-2.6% methanol in DCM). MS(ES): m/z: 516.32 [M+H]$^+$; $^1$H NMR (DMSO-d$_6$, 400 MHz): δ 8.95 (s, 1H), 8.14-8.07 (m, 1H), 7.76 (s, 1H), 7.41 (s, 1H), 6.61 (s, 1H), 6.05 (s, 1H), 4.06-3.87 (m, 2H), 3.74-3.65 (m, 3H), 3.56-3.49 (m, 2H), 2.88-2.86 (m, 6H), 1.27 (s, 9H).

Example 71: methyl(4-((2-((1-(tert-butyl)-2,3-dihydro-1H-imidazo[1,2-b]pyrazol-6-yl)amino)-7-cyano-1-methyl-1H-imidazo[4,5-b]pyridin-6-yl)oxy)pyridin-2-yl)carbamate

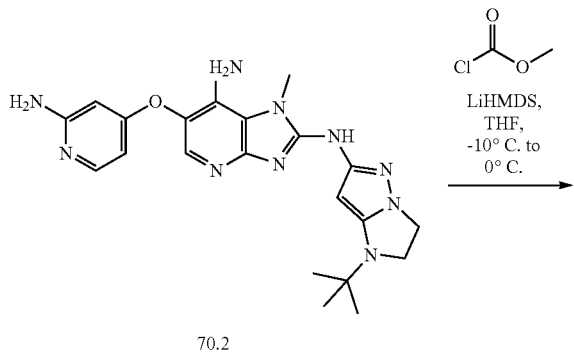
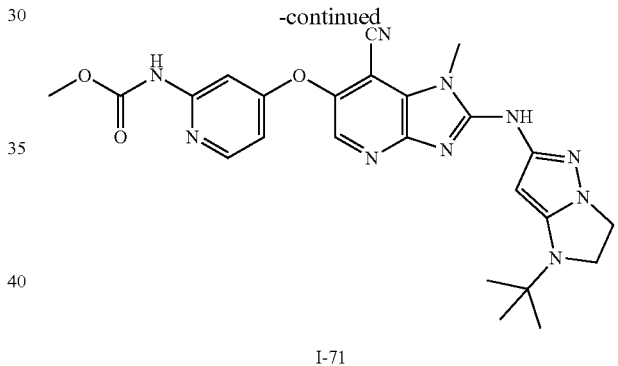

Synthesis of I-71. To a solution of 70.2 (0.050 g, 0.112 mmol, 1.0 equiv) in THF (5 mL) was added lithium bis(trimethylsilyl)amide (0.33 mL, 0.336 mmol, 3.0 equiv) at 0° C. and stirred for 10 min. It was cooled to 10° C. and methyl chloroformate (0.018 g, 0.168 mmol, 1.5 equiv) was added. The reaction mixture was stirred for 30 min. It was transferred into water and extracted with ethyl acetate. The combined organic layers were washed with brine, dried over anhydrous sodium sulfate, filtered, and concentrated under reduced pressure. To a solution of residue in methanol (5 mL) was added potassium carbonate (0.154 g, 1.112 mmol, 10 equiv), and stirred at room temperature for 1 h. The reaction mixture was filtered through a pad of Celite®. The filtrate was concentrated under reduced pressure. The residue was purified by flash column chromatography on silica gel (CombiFlash®, 3.5-4.1% methanol in DCM). MS(ES): m/z: 503.53 [M+H]$^+$; $^1$H NMR (DMSO-d$_6$, 400 MHz): δ 10.34 (s, 1H), 10.23 (s, 1H), 8.18-8.13 (m, 2H), 7.43 (s, 1H), 6.69-6.68 (d, J=3.2, 1H), 6.04 (s, 1H), 3.95-3.91 (m, 2H), 3.87 (s, 3H), 3.66-3.61 (m, 5H), 1.26 (s, 9H).

Example 72: 1-(4-((2-((1-(tert-butyl)-2,3-dihydro-1H-imidazo[1,2-b]pyrazol-6-yl)amino)-7-cyano-1-methyl-1H-imidazo[4,5-b]pyridin-6-yl)oxy)pyridin-2-yl)-3-methylurea

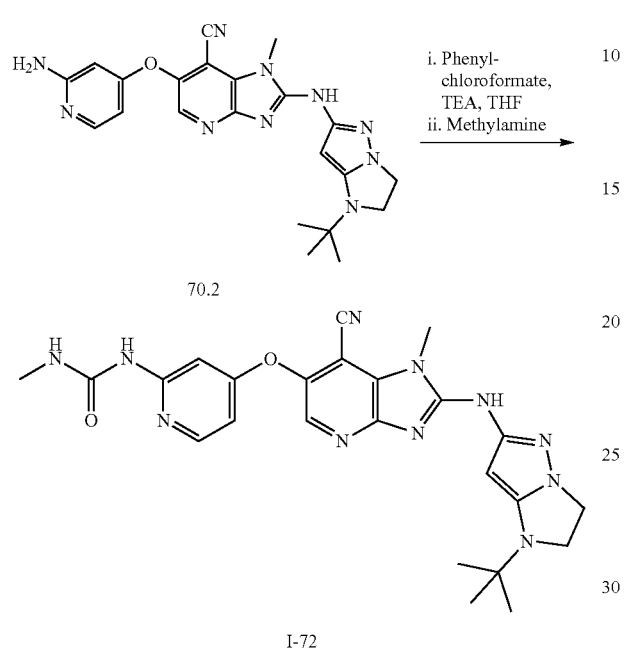

Synthesis of I-72. Compound I-72 was prepared from 70.2 and methylamine, following the procedure described in the synthesis of I-23. The product was purified by preparative HPLC. MS(ES): m/z: 502.4 [M+H]⁺, ¹H NMR (DMSO-$d_6$, 400 MHz): δ 9.16 (s, 1H), 8.18 (s, 1H), 8.11-8.08 (m, 2H), 7.80 (s, 1H), 6.97 (s, 1H), 6.60-6.58 (m, 1H), 6.01 (s, 1H), 3.95-3.91 (m, 2H), 3.66-3.63 (m, 2H), 3.15 (s, 3H), 2.67-2.65 (m, 3H), 1.26 (s, 9H).

Example 73: 3-(4-((7-cyano-2-((6,6-dimethyl-6,7-dihydro-4H-pyrazolo[5,1-c][1,4]oxazin-2-yl)amino)-1-methyl-1H-imidazo[4,5-b]pyridin-6-yl)oxy)pyridin-2-yl)-1,1-dimethylurea

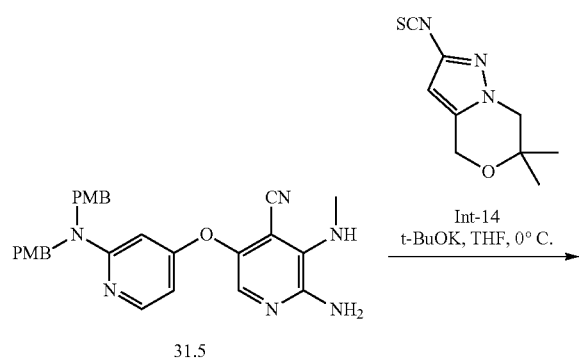

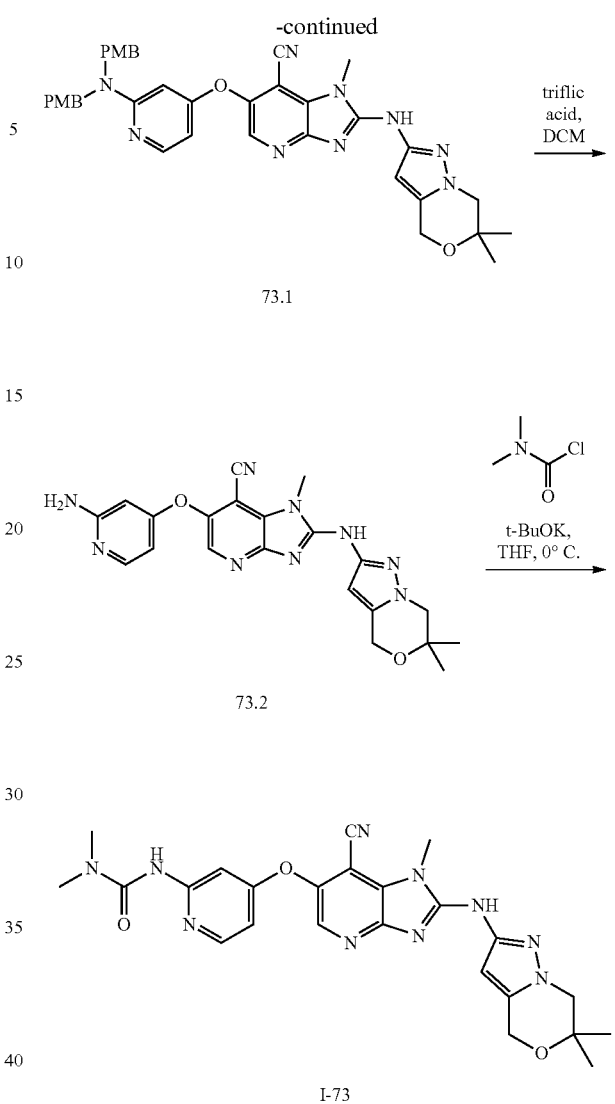

Synthesis of compound 73.1. Compound 73.1 was prepared from 31.5 and methylamine, following the procedure described in the synthesis of 3.7. The product was purified by flash column chromatography on silica gel (CombiFlash®, 5.2% methanol in DCM). MS(ES): m/z: 672.52 [M+H]⁺.

Synthesis of compound 73.2. Compound 73.2 was prepared from 73.1, following the procedure described in the synthesis of 40.2. The product was purified by flash column chromatography on silica gel (CombiFlash®, 5.8% methanol in DCM). MS(ES): m/z 432.46 [M+H]⁺.

Synthesis of I-73. Compound I-73 was prepared from 73.2, following the procedure described in the synthesis of I-21. The product was purified by flash column chromatography on silica gel (CombiFlash®, 2.4% methanol in DCM). MS(ES): m/z: 503.54 [M+H]⁺; ¹H NMR (DMSO-$d_6$, 400 MHz): δ 10.44 (s, 1H), 8.99 (s, 1H), 8.15 (s, 2H), 7.44 (s, 1H), 6.64 (s, 2H), 4.83 (s, 2H), 3.91-3.88 (m, 5H), 2.89 (s, 6H), 1.31 (s, 6H).

Example 74: (S)-N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-2-(tetrahydro-2H-pyran-2-yl)acetamide and (R)-N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-2-(tetrahydro-2H-yl)pyran-2-yl)acetamide

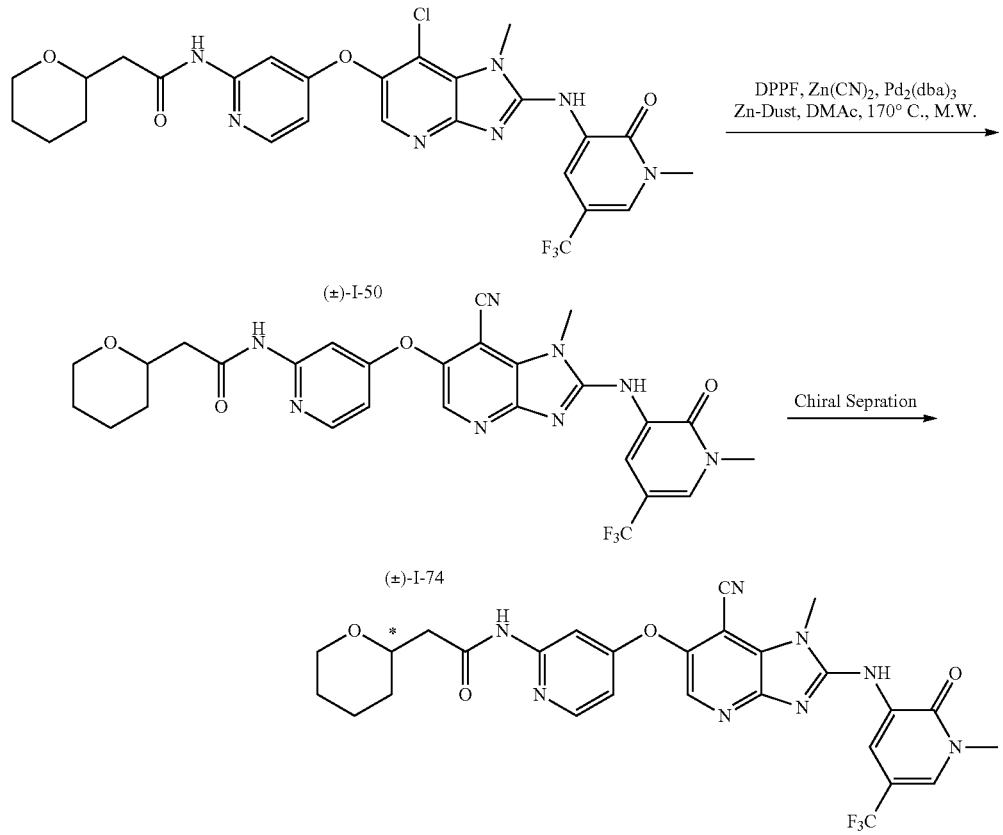

Synthesis of compound (±)-I-74. A mixture of (±)-I-50 (0.130 g, 0.219 mmol, 1.0 equiv), zinc powder (0.002 g, 0.043 mmol, 0.2 equiv), and zinc cyanide (0.128 g, 1.09 mmol, 5.0 equiv) in N,N-dimethylacetamide (10 mL) was degassed by bubbling through a stream of argon for 5 min. Tris(dibenzylideneacetone)dipalladium(0) (0.030 g, 0.032 mmol, 0.15 equiv) and 1,1'-bis(diphenylphosphino)ferrocene (0.035 g, 0.065 mmol, 0.3 equiv) were added and degassed for 5 min. The reaction mixture was stirred at 170° C. in a microwave reactor for 2 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.3% methanol in DCM) to afford (±)-I-74. MS(ES): m/z: 583.54 [M+H]⁺.

I-74-a and I-74-b. The racemate was subjected to chiral HPLC (CHIRALPAK OX-H (250 mm*21 mm, 5 μm; mobile phases: (A) 0.1% DEA in n-hexane (B) 0.1% DEA in propane-2-ol:acetonitrile (70:30); flow rate=20 mL/min) to afford first eluting fraction (I-74-a) and second eluting fraction (I-74-b).

I-74-a: MS(ES): m/z: 583.54 [M+H]⁺, ¹H NMR (DMSO-d₆, 400 MHz): δ 10.59 (s, 1H), 9.05 (s, 1H), 8.67 (s, 1H), 8.34 (s, 1H), 8.26 (d, J=8.0 Hz, 1H), 8.20 (s, 1H), 7.78 (s, 1H), 6.80 (s, 1H), 3.98 (s, 2H), 3.83-3.80 (m, 1H), 3.68 (s, 3H), 3.34 (s, 3H), 2.44-2.43 (bs, 2H), 1.74 (bs, 1H), 1.60-1.57 (m, 1H), 1.44 (s, 2H), 1.22-1.19 (m, 2H).

I-74-b: MS(ES): m/z: 583.54 [M+H]⁺, ¹H NMR (DMSO-d₆, 400 MHz): 10.59 (s, 1H), 9.05 (s, 1H), 8.67 (s, 1H), 8.34 (s, 1H), 8.26 (d, J=8.0 Hz, 1H), 8.20 (s, 1H), 7.78 (s, 1H), 6.80 (s, 1H), 3.98 (s, 2H), 3.83-3.80 (m, 1H), 3.68 (s, 3H), 3.39 (s, 3H), 2.44-2.40 (bs, 2H), 1.72 (bs, 1H), 1.60-1.57 (m, 1H), 1.44 (bs, 2H), 1.22-1.12 (m, 2H).

Example 75: N-(4-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-2-methoxyacetamide

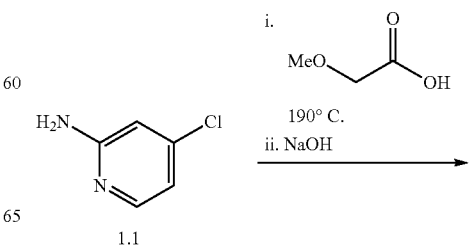

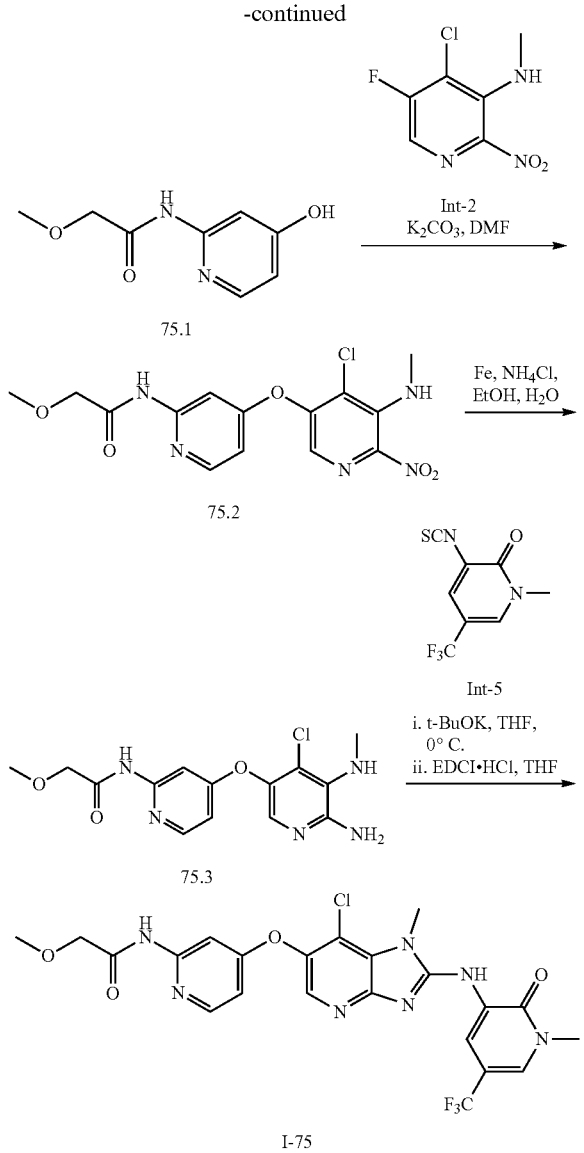

75.1

75.2

Int-5

75.3

I-75

Synthesis of compound 75.1. A mixture of 1.1 (1.0 g, 7.78 mmol, 1.0 equiv) and 2-methoxyacetic acid (3.5 g, 38.89 mmol, 5 equiv) was stirred at in a microwave reactor at 190° C. for 2 h. The reaction mixture was cooled to room temperature, transferred into methanol and concentrated under reduced pressure. To the residue was added 1N sodium hydroxide solution (5 mL) and stirred at for 1 h. It was neutralized using 1N hydrochloric acid. The precipitates were collected by filtration and dried under reduced pressure to afford 75.1. MS(ES): m/z 183.3 [M+H]$^+$.

Synthesis of compound 75.2. A mixture of 75.1 (0.500 g, 2.74 mmol, 1.0 equiv), Int-2 (0.617 g, 3.01 mmol, 1.1 equiv) and potassium carbonate (0.756 g, 5.48 mmol, 2.0 equiv) in DMF (10 mL) was stirred at room temperature for 1 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 30% ethyl acetate in hexane) to afford 75.2. MS(ES): m/z 368.5 [M+H]$^+$.

Synthesis of compound 75.3. A mixture of 75.2 (0.350 g, 0.951 mmol, 1.0 equiv), iron powder (0.266 g, 4.775 mmol, 5.0 equiv) and ammonium chloride (0.256 g, 4.775 mmol, 5.0 equiv) in ethanol:water (4:1, 7 mL) was stirred at 90° C. for 1 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 1.7% methanol in DCM) to afford 75.3. MS(ES): m/z 338.5 [M+H]$^+$.

Synthesis of compound I-75. Compound I-75 was prepared from 75.3 and Int-5, following the procedure described in the synthesis of I-19. The product was purified by flash column chromatography on silica gel (CombiFlash®, 3.1% methanol in DCM). MS(ES): m/z 538.11 [M+H]$^+$. NMR (DMSO-d$_6$, 400 MHz): δ 10.136 (s, 1H), 8.85 (s, 1H), 8.64 (s, 1H), 8.27 (s, 1H), 8.23 (d, J=5.6 Hz, 1H), 8.16 (s, 1H), 7.66 (s, 1H), 6.73 (d, J=3.2 Hz, 1H), 4.03 (s, 2H), 4.00 (s, 3H), 3.67 (s, 3H), 3.34 (d, J=2.4 Hz, 3H).

Example 76: N-(4-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-2-fluoroacetamide

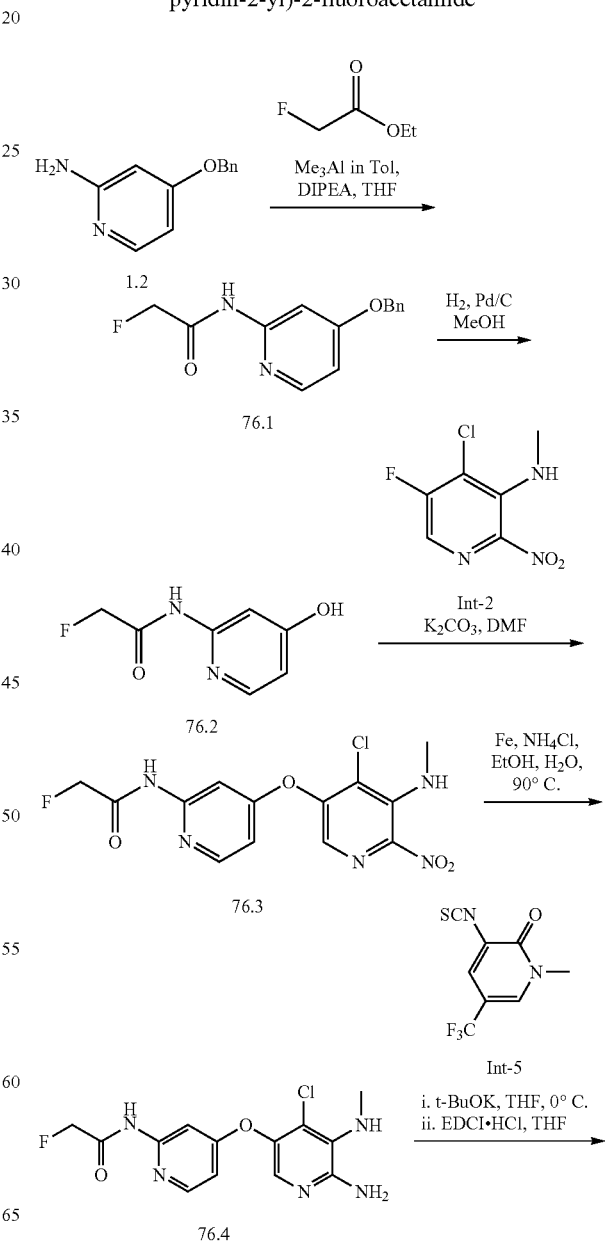

1.2

76.1

76.2

76.3

Int-5

76.4

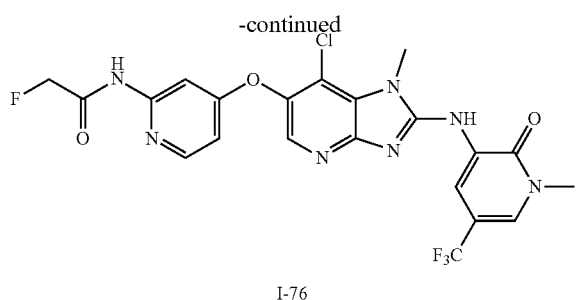

I-76

Synthesis of compound 76.1. To a solution of 1.2 (2.0 g, 9.99 mmol, 0.8 equiv), ethyl 2-fluoroacetate (1.32 g, 12.48 mmol, 1.0 equiv) and N,N-diisopropylethylamine (3.2 g, 24.96 mmol, 0.5 equiv) in THF (20 mL) was stirred at room temperature for 30 min. To the reaction was added trimethylaluminum (1 M solution in toluene, 50 mL, 50 mmol, 5.0 equiv) and stirred for 2 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 15-20% ethyl acetate in hexane) to afford 76.1. MS(ES): m/z 261.1 [M+H]$^+$.

Synthesis of compound 76.2. A mixture of compound 76.1 (0.400 g, 1.54 mmol, 1.0 equiv) and 10% palladium on charcoal (0.100 g) in methanol (10 mL) was stirred under hydrogen (1 atm) for 1 h. The reaction mixture was filtered through a pad of Celite® and rinsed with methanol. The filtrate concentrated under reduced pressure. The residue was purified by flash column chromatography on silica gel (CombiFlash®, 12% ethyl acetate in hexane) to afford 76.2. MS(ES): m/z 171.2 [M+H]$^+$.

Synthesis of compound 76.3. A mixture of 76.3 (0.260 g, 1.53 mmol, 1.0 equiv), Int-2 (0.345 g, 1.683 mmol, 1.1 equiv) and potassium carbonate (0.422 g, 3.06 mmol, 2.0 equiv) in DMF (10 mL) was stirred at room temperature for 1 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 38% ethyl acetate in hexane) to afford 76.3. MS(ES): m/z 356.5 [M+H]$^+$. 104331 Synthesis of compound 76.4. A mixture of 76.3 (0.350 g, 0.983 mmol, 1.0 equiv), iron powder (0.275 g, 4.915 mmol, 5.0 equiv) and ammonium chloride (0.265 g, 4.915 mmol, 5.0 equiv) in ethanol:water (2:1, 8 mL) was stirred at 90° C. for 1 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 1.7% methanol in DCM) to afford 76.4. MS(ES): m/z 326.5 [M+H]$^+$.

Synthesis of I-76. Compound I-76 was prepared from 76.4 and Int-5, following the procedure described in the synthesis of I-19. The product was purified by flash column chromatography on silica gel (CombiFlash®, 2.5% methanol in DCM). MS(ES): m/z: 526.13 [M+H]$^+$; NMR (DMSO-d$_6$, 400 MHz): δ 10.67 (s, 1H), 8.86 (s, 1H), 8.64 (d, J=2 Hz, 1H), 8.26-8.23 (m, 2H), 8.16 (s, 1H), 7.61 (s, 1H), 6.75-6.73 (m, 1H), 5.06 (s, 1H), 4.94 (s, 1H), 4.00 (s, 3H), 3.67 (s, 3H).

Example 77: N-(4-((1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide

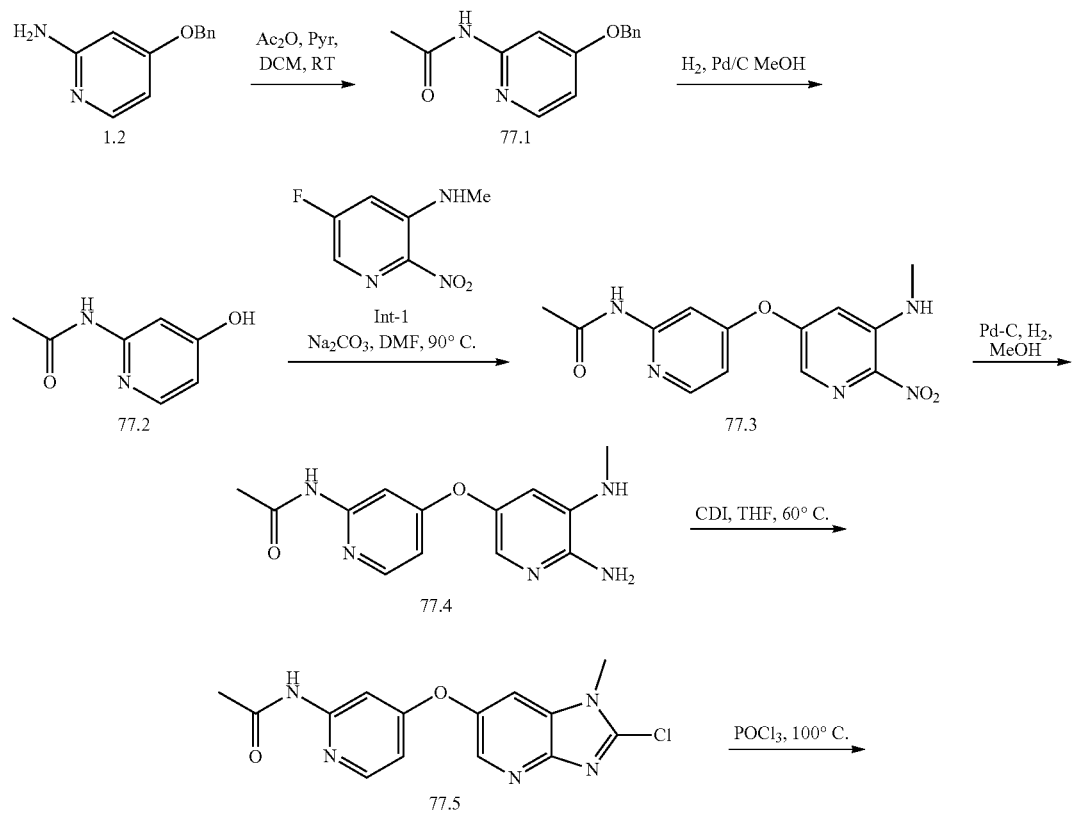

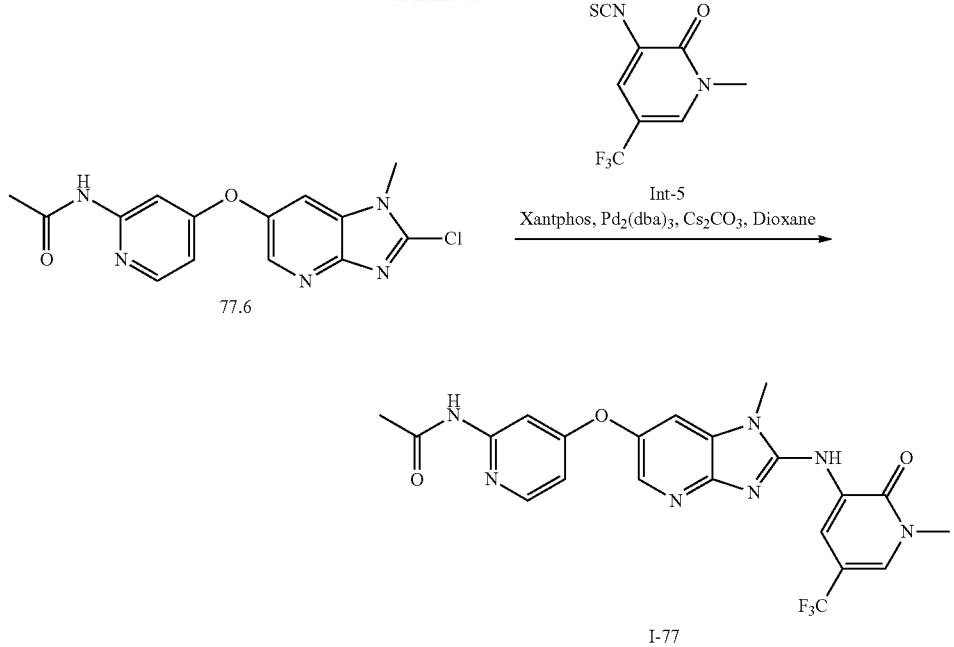

Synthesis of compound 77.1. To a solution of 1.2 (11.2 g, 55.93 mmol, 1.0 equiv) and pyridine (6.3 mL, 78.30 mmol, 1.4 equiv) in DCM (110 mL) was added acetic anhydride (6.34 mL, 67.11 mmol, 1.2 equiv) and was stirred for 1 h. It was transferred into ice, stirred, and extracted with DCM. The combined organic layers were washed with brine, dried over anhydrous sodium sulfate, filtered, and concentrated under reduced pressure. The residue was purified by flash column chromatography on silica gel (CombiFlash®, 1% methanol in DCM) to afford 77.1. MS (ES): m/z 243.21 $[M+H]^+$.

Synthesis of compound 77.2. A mixture of compound 77.1 (6.1 g, 25.18 mmol, 1.0 equiv) and 10% palladium on carbon (2 g) in methanol (60 mL) was stirred under hydrogen (1 atm) for 2 h. The reaction mixture was filtered through a pad of Celite® and rinsed with methanol. The filtrate was concentrated under reduced pressure. The residue was purified by flash column chromatography on silica gel (CombiFlash®, 5% methanol in DCM) to afford 77.2. MS(ES): m/z 153.2 $[M+H]^+$.

Synthesis of compound 77.3. Compound 77.3 was prepared from 77.2 and Int-1, following the procedure described in the synthesis of 1.6. The product was purified by flash column chromatography on silica gel (CombiFlash®, 2% methanol in DCM). MS(ES): m/z 304.3 $[M+H]^+$.

Synthesis of compound 77.4. A mixture of compound 77.3 (0.960 g, 3.17 mmol, 1.0 equiv) and 10% palladium on carbon (0.500 g) in methanol (5 mL) was stirred under hydrogen (1 atm) for 1 h. The reaction mixture was filtered through a pad of Celite® and rinsed with methanol. The filtrate was concentrated under reduced pressure to afford 77.4. MS(ES): m/z 274.3 $[M+H]^+$.

Synthesis of compound 77.5. To a solution of 77.4 (0.550 g, 2.01 mmol, 1.0 equiv) in THF (6 mL) was added 1,1'-carbonyldiimidazole (1.041 g, 6.43 mmol, 3.2 equiv). The reaction mixture was stirred at 70° C. for 3 h. It was cooled to room temperature and was transferred into ice-water. Precipitated solid was filtered out and triturated with hexane to afford 77.5. MS(ES): m/z: 300.3 $[M+H]^+$.

Synthesis of compound 77.6. A solution of 77.5 (0.370 g, 1.24 mmol, 1.0 equiv) in phosphoryl chloride (10 mL) was stirred at 100° C. for 8 h. It was cooled and was transferred into saturated solution of sodium bicarbonate, stirred, and extracted with DCM. The combined organic layers were washed with brine, dried over anhydrous sodium sulfate, filtered, and concentrated under reduced pressure. The residue was purified by flash column chromatography on silica gel (CombiFlash®, 3.2% methanol in DCM) to afford 77.6. MS (ES): m/z 318.7 $[M+H]^+$.

Synthesis of compound I-77. Compound I-77 was prepared from 77.6 and Int-5, following the procedure of the synthesis of I-10. The product was purified by flash column chromatography on silica gel (CombiFlash®, 3.8% methanol in DCM). MS(ES): m/z: 474.88 $[M+H]^+$; $^1H$ NMR (DMSO-$d_6$, 400 MHz): δ 10.55 (s, 1H), 8.69 (s, 2H), 8.19 (d, J=5.2 Hz, 1H), 8.11 (s, 2H), 7.87 (s, 1H), 7.67 (s, 1H), 6.68 (s, 1H), 3.77 (s, 3H), 3.66 (s, 3H), 2.03 (s, 3H).

Example 78: (R)-N-(4-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-2-(4-methylmorpholin-2-yl)acetamide and (S)-N-(4-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-2-(4-methylmorpholin-2-yl)acetamide
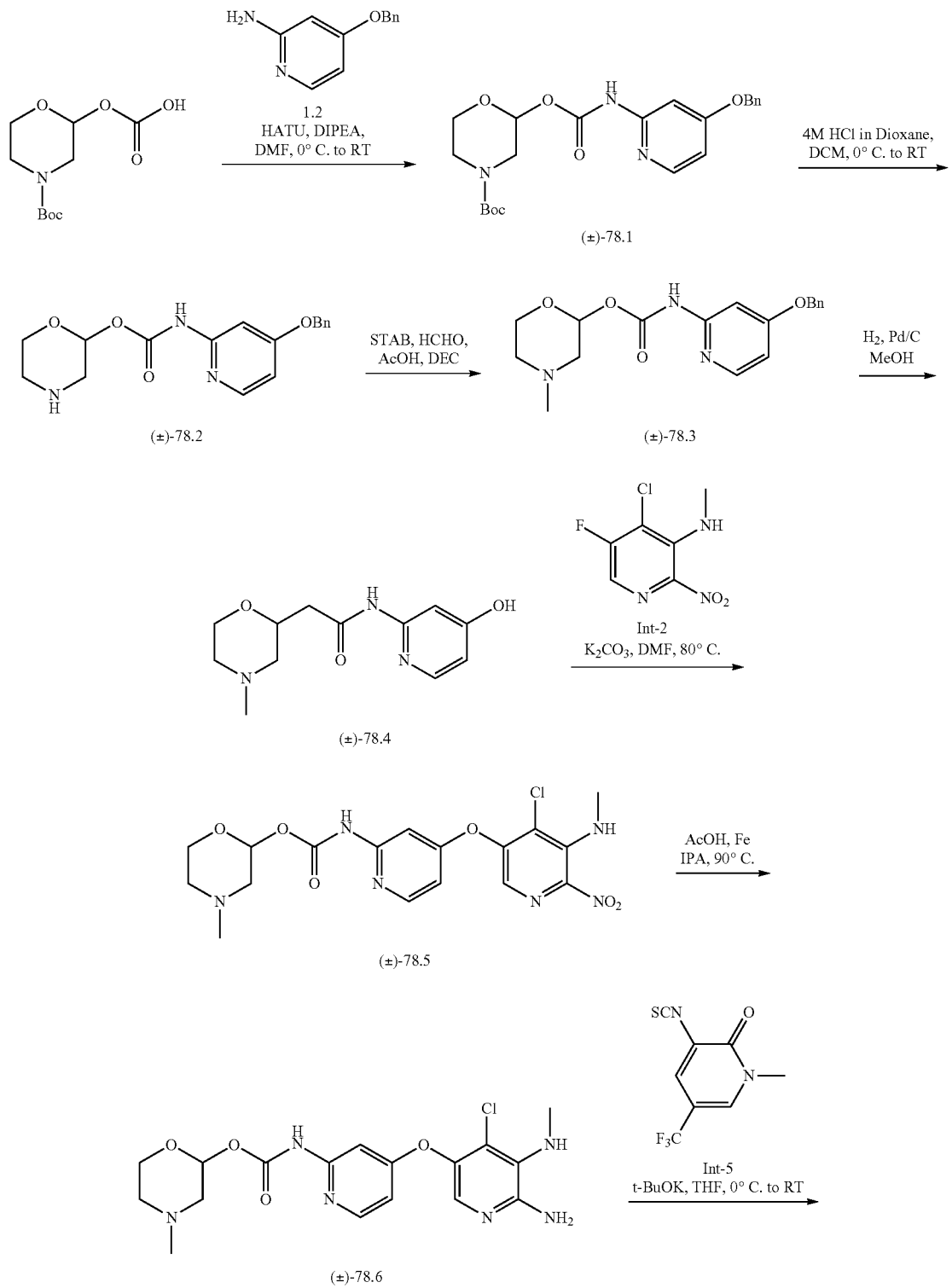

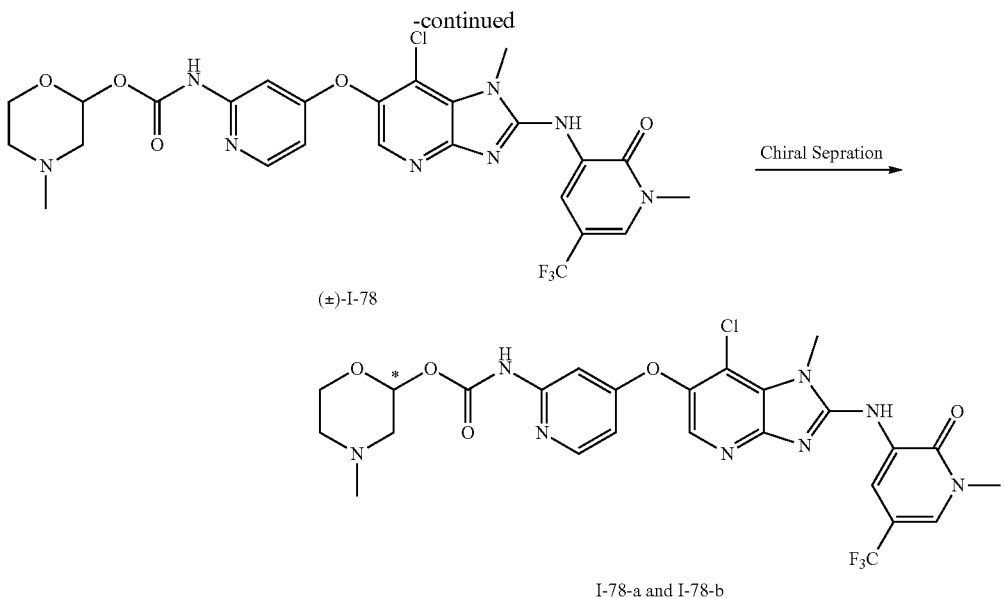

(±)-I-78

I-78-a and I-78-b

Synthesis of compound (±)-78.1. To a solution of 2-(4-(tert-butoxycarbonyl)morpholin-2-yl)acetic acid (3 g, 12.23, 1.0 equiv) in DMF (30 mL) at 0° C. and added HATU (7.0 g, 18.36 mmol, 1.5 equiv) and stirred for 15 min. To the mixture was added 1.2 (2.9 g, 14.68 mmol, 1.2 equiv), followed by N,N-diisopropylethylamine (4.7 g, 36.73 mmol, 3.0 equiv) and the reaction mixture was stirred at room temperature overnight. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford (±)-78.1. MS(ES): m/z: 428.5 [M+H].

Synthesis of compound (±)-78.2. To a solution of (±)-78.1 (1.42 g, 3.32 mmol, 1.0 equiv) in DCM (15 mL) at to 0° C. was added HCl in dioxane (4 M, 10 mL). The reaction mixture was stirred at room temperature for 1 h. It was transferred into ice-water and neutralized with sodium bicarbonate and was extracted with DCM. The combined organic layers were washed with brine, dried over anhydrous sodium sulfate, filtered, and concentrated under reduced pressure. The residue was used in the next step without purification. MS(ES): m/z: 328.7 [M+H].

Synthesis of compound (±)-78.3. A solution of (±)-78.2 (0.910 g, 2.78 mmol, 1.0 equiv), formaldehyde solution (37% in $H_2O$, 0.338 g, 4.1 mmol, 1.5 equiv) and acetic acid (0.525 g, 8.3 mmol, 3.0 equiv) in 1,2-dichloroethane (15 mL) was stirred at 0° C. for 15 min. To the mixture was added sodium triacetoxyborohydride (1.77 g, 8.3 mmol, 3.0 equiv) and stirred at rt for 16 h. It was transferred into water and extracted with DCM. The combined organic layers were washed with brine, dried over anhydrous sodium sulfate, filtered, and concentrated under reduced pressure. The residue was purified by flash column chromatography on silica gel (CombiFlash®, 3.2% methanol in DCM) to afford (±)-78.3. MS(ES): m/z: 342.4 [M+H].

Synthesis of compound (±)-78.4. A mixture of 10% palladium on carbon (0.3 g) and (±)-78.3 (0.75 g, 2.20 mmol, 1.0 equiv) was stirred under hydrogen (1 atm) for 2 h at room temperature. The reaction mixture was filtered through a pad of Celite®. The filtrate was concentrated under reduced pressure to afford (±)-78.4. MS(ES): m/z 252.6 [M+H]$^+$.

Synthesis of compound (±)-78.5. A mixture of (±)-78.4 (0.389 g, 1.55 mmol, 1.0 equiv), potassium carbonate (0.641 g, 4.64 mmol, 3.0 equiv) and Int-2 (0.318 g, 1.55 mmol, 1.0 equiv) in DMF (10 mL) were stirred at 80° C. for 2 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3% methanol in DCM) to afford (±)-78.5. MS(ES): m/z 437.9 [M+H]$^+$.

Synthesis of compound (±)-78.6. A mixture of (±)-78.5 (0.350 g, 0.801 mmol, 1.0 equiv), iron powder (0.224 g, 4.01 mmol, 5.0 equiv) and acetic acid (0.240 g, 4.01 mmol 5.0 equiv) in isopropanol (10 mL) and water (4 mL) was stirred at 90° C. for 2 h. The reaction mixture was filtered through a pad of Celite®. The filtrate was concentrated under reduced pressure. The residue was purified by flash column chromatography on silica gel (CombiFlash®, 3.2% methanol in DCM) to afford (±)-78.6. MS(ES): m/z 407.8 [M+H]$^+$.

Synthesis of compound (±)-I-78. Compound (±)-I-78 was prepared from compound (±)-78.6 following the procedure described in the synthesis of compound 3.7. The product was purified by flash column chromatography on silica gel (CombiFlash®, 3.2% methanol in DCM). MS(ES): m/z: 608.5 [M+H]$^+$.

I-78-a and I-78-b. The racemate was separated by chiral HPLC (CHIRALPAK IH (250 mm*21 mm, 5 μm; mobile phases: (A) 0.1% DEA in n-hexane (B) 0.1% DEA in propane-2-ol:acetonitrile (70:30); flow rate=20 mL/min) to afford first eluting fraction (I-78-a) and second eluting fraction (I-78-b).

I-78-a: MS(ES): m/z 607.4 [M+H]$^+$; $^1$H NMR (DMSO-$d_6$, 400 MHz): δ 10.58 (s, 1H), 8.82 (bs, 1H), 8.63 (s, 1H), 8.24 (s, 1H), 8.20 (d, J=4 Hz, 1H), 8.15 (s, 1H), 7.66 (s, 1H), 6.71-6.70 (m, 1H), 4.66-4.59 (m, 1H), 3.99 (s, 3H), 3.78 (bs, 1H), 3.71-3.66 (m, 4H), 3.45-3.40 (m, 1H), 2.67-2.64 (m, 1H), 2.50-2.40 (m, 2H), 2.13 (s, 3H), 1.94-1.88 (m, 1H), 1.71-1.66 (m, 1H).

I-78-b: MS(ES): m/z 607.4 [M+H]$^+$; $^1$H NMR (DMSO-$d_6$, 400 MHz): δ 10.59 (s, 1H), 8.86 (bs, 1H), 8.64 (s, 1H), 8.24 (s, 1H), 8.21 (d, J=4 Hz, 1H), 8.15 (s, 1H), 7.67 (s, 1H), 6.72-6.70 (m, 1H), 4.66-4.60 (m, 1H), 3.99 (s, 3H), 3.80 (bs,

1H), 3.72-3.67 (m, 4H), 3.43 (m, 1H), 2.66 (m, 1H), 2.51-2.40 (m, 2H), 2.14 (s, 3H), 1.92 (m, 1H), 1.73 (m, 1H).

Example 79: N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-2-methoxyacetamide

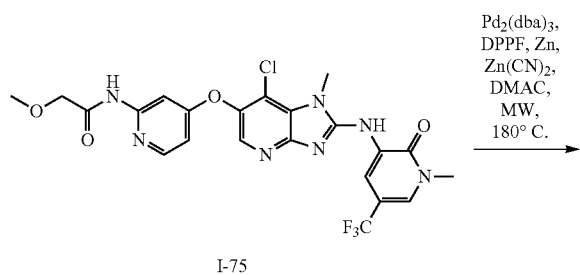

I-75

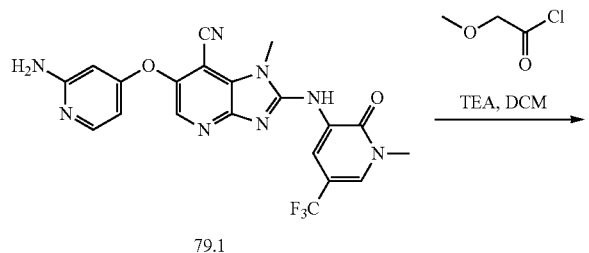

79.1

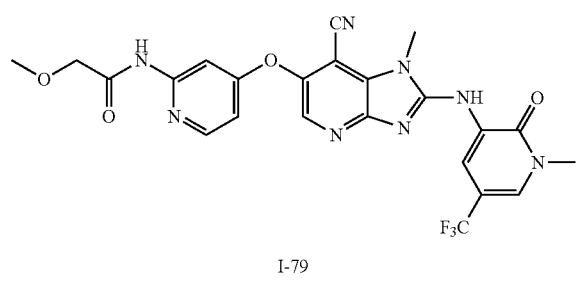

I-79

Synthesis of compound 79.1. A mixture of I-75 (0.125 g, 0.232 mmol, 1.0 equiv), zinc (0.003 g, 0.04 mmol, 0.2 equiv) and zinc cyanide (0.135 g, 1.16 mmol, 5 equiv) in N,N-dimethylacetamide (3 mL) was degassed by bubbling through a stream of argon for 10 min. Tris(dibenzylideneacetone)dipalladium(0) (0.031 g, 0.034 mmol, 0.15 equiv) and 1,1'-bis(diphenylphosphino)ferrocene (0.038 g, 0.069 mmol, 0.3 equiv) were added and degassed for 5 min. The reaction mixture was stirred at 180° C. for 1 h in a microwave reactor. The reaction mixture was cooled to room temperature, transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.6% methanol in DCM) to afford 79.1. MS(ES): m/z: 457.3 [M+H]$^+$.

Synthesis of I-79. To a solution of 79.1 (0.060 g, 0.131 mmol, 1.0 equiv) and triethylamine (0.05 mL, 0.393 mmol, 3 equiv) in DCM (6 mL) at 0° C. was added 2-methoxyacetyl chloride (0.060 g, 0.131 mmol, 1.0 equiv) dropwise. The reaction mixture was stirred for 2 h. It was transferred into ice-water, filtered, and extracted with DCM. The combined organic layers were washed with brine, dried over anhydrous sodium sulfate, filtered, and concentrated under reduced pressure. The residue was purified by flash column chromatography on silica gel (CombiFlash®, 2.4% methanol in DCM) to afford I-79. MS(ES): m/z 529.42 [M+H]$^+$; $^1$H NMR (DMSO-d$_6$, 400 MHz): δ 10.22 (s, 1H), 9.04 (s, 1H), 8.65 (s, 1H), 8.33 (s, 1H), 8.27 (d, J=4 Hz, 1H), 8.19 (s, 1H), 7.74 (s, 1H), 6.81 (d, J=2.8 Hz, 1H), 4.04 (s, 2H), 3.96 (s, 3H), 3.66 (s, 3H), 3.36 (s, 3H).

Example 80: N-(4-((2-((1-(2-hydroxyethyl)-2-oxo-5-(trifluoromethyl)-1,2-dihydropyridin-3-yl)amino)-7-methoxy-1-methyl-1H-imidazo[4,5-b]pyridin-6-yl)oxy)pyridin-2-yl)acetamide

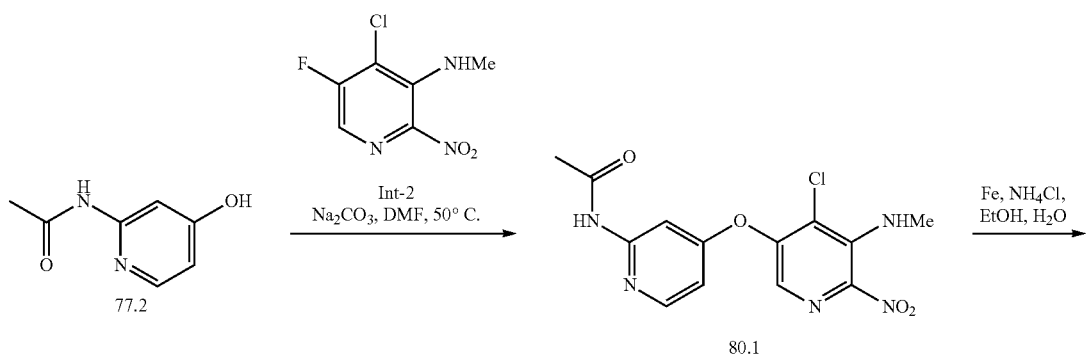

80.1

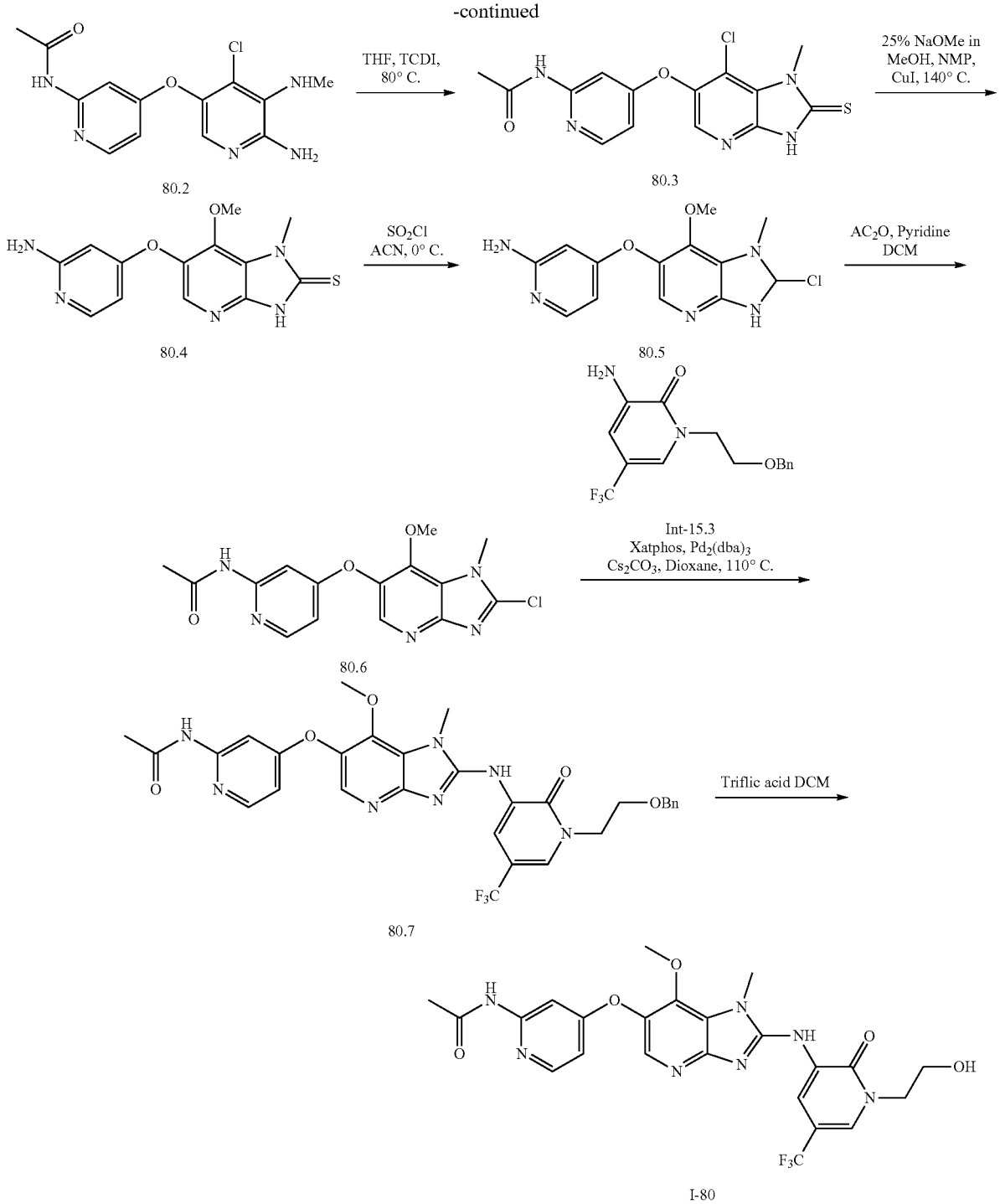

Synthesis of compound 80.1. A mixture of 77.2 (0.930 g, 4.52 mmol, 1.0 equiv), Int-2 (0.895 g, 5.88 mmol, 1.3 equiv) and sodium carbonate (0.958 g, 9.04 mmol, 2.0 equiv) in DMF (10 mL) was stirred at 50° C. for 6 h. It was cooled to room temperature, transferred into ice-water, and stirred. The precipitates were collected by filtration, rinsed with water, and dried to afford 80.1. MS(ES): m/z 338.7 [M+H]+.

Synthesis of compound 80.2. A mixture of compound 80.1 (0.850 g, 2.52 mmol, 1.0 equiv), iron powder (0.705 g, 12.6 mmol, 5.0 equiv) and ammonium chloride (0.673 g, 12.6 mmol, 5.0 equiv) in ethanol:water (8:2, 10 mL) was stirred at 80° C. for 2 h. The reaction mixture was filtered through a pad of Celite® and rinsed with ethanol. The filtrate was concentrated under reduced pressure. The residue was purified by flash column chromatography on silica gel (CombiFlash®, 2.4% methanol in DCM) to afford 80.2. MS(ES): m/z 308.5 [M+H]+.

Synthesis of compound 80.3. A solution of 80.2 (0.150 g, 0.487 mmol, 1.0 equiv) and 1,1'-thiocarbonyldiimidazole (0.433 g, 2.43 mmol, 5.0 equiv) in THF (2 mL) stirred at 80° C. for 1 h. It was cooled to room temperature and was transferred into ice-water. The precipitated solids were collected by filtration and triturated with hexane to afford 80.3. MS(ES): m/z: 350.7 [M+H]⁺.

Synthesis of compound 80.4. To a solution of 80.3 (1.0 g, 2.86 mmol, 1.0 equiv) in methanol (7 mL) and NMP (15 mL) was added sodium methoxide solution (25%, 8 mL, 37.18 mmol, 13 equiv) and copper iodide (0.119 g, 0.629 mmol, 0.22 equiv). The reaction mixture was stirred at 140° C. for 4 h. It was cooled to room temperature, transferred into ice-water, and extracted with DCM. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford 80.4. MS(ES): m/z: 304.3 [M+H]⁺.

Synthesis of compound 80.5. To a solution of 80.4 (0.050 g, 0.164 mmol, 1.0 equiv) in acetonitrile (5 mL) was added sulfuryl chloride (0.49 mL, 6.06 mmol, 37 equiv) at 0° C. and stirred for 15 min. It was transferred into a saturated solution of sodium bicarbonate, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.0% methanol in DCM) to afford 80.5. MS (ES): m/z 306.7 [M+H]⁺.

Synthesis of compound 80.6. To a solution of 80.5 (0.025 g, 0.081 mmol, 1.0 equiv) and pyridine (0.03 mL) in DCM (2 mL) at 0° C. was added acetic anhydride (0.019 mL, 0.202 mmol, 2.5 equiv) and the reaction mixture was stirred for 5 min. It was transferred into saturated solution of sodium bicarbonate, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.8% methanol in DCM) to afford 80.6. MS (ES): m/z 348.7 [M+H]⁺.

Synthesis of compound 80.7. Compound 80.7 was prepared from 80.6 and Int-15.3, following the procedure of the synthesis of I-10. The product was purified by flash column chromatography on silica gel (CombiFlash®, 2.0% methanol in DCM). MS(ES): m/z: 624.3 [M+H]⁺.

Synthesis of I-80. Compound I-80 was prepared from 80.7, following the procedure described in the synthesis of 40.2. The product was purified by flash column chromatography on silica gel (CombiFlash®, 2.8% methanol in DCM). MS(ES): m/z. 534.45 [M+H]⁺; ¹H NMR (DMSO-d₆, 400 MHz): δ 10.58 (s, 1H), 8.66 (s, 2H), 8.19 (d, J=4 Hz, 1H), 7.95 (s, 1H), 7.69 (s, 1H), 6.67 (d, J=4 Hz, 1H), 5.00 (d, J=8 Hz, 1H), 4.18 (s, 2H), 3.95-3.90 (m, 6H), 3.74-3.73 (bs, 2H), 2.56 (s, 3H).

Example 81: (N-(4-((7-cyano-2-((1-(2-hydroxyethyl)-2-oxo-5-(trifluoromethyl)-1,2-dihydropyridin-3-yl)amino)-1-methyl-1H-imidazo[4,5-b]pyridin-6-yl)oxy)pyridin-2-yl)acetamide

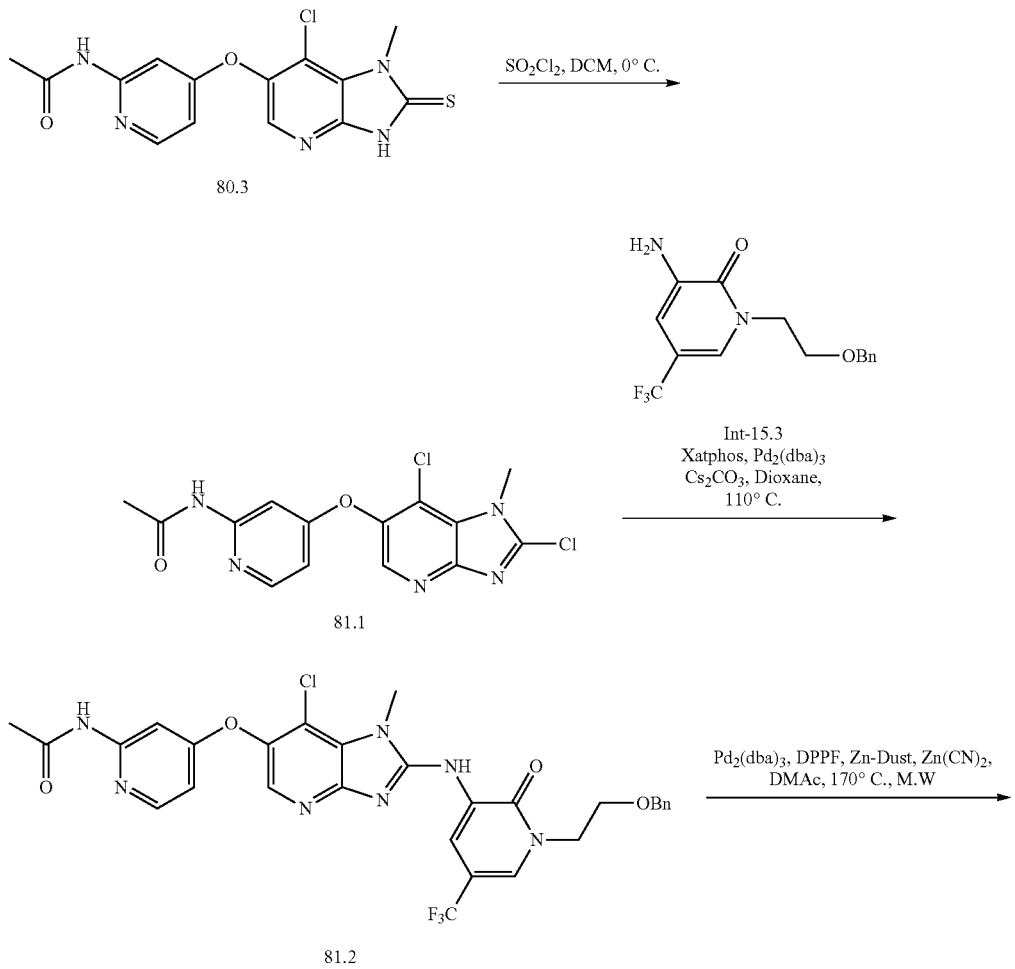

-continued

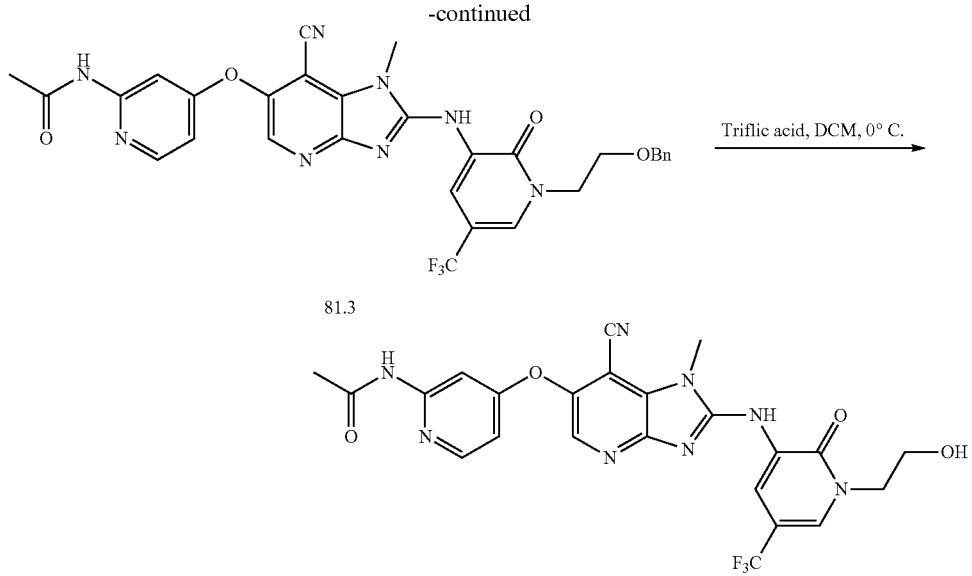

Synthesis of compound 81.1. To a solution of 80.3 (30.5 g, 87.19 mmol, 1.0 equiv) in DCM (600 mL) was added sulphuryl chloride (435.5 g, 3226 mmol, 37 equiv) at 0° C. and stirred for 15 min. It was transferred into a saturated solution of sodium bicarbonate, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford 81.1. MS (ES): m/z 353.6 [M+H]$^+$.

Synthesis of compound 81.2. Compound 81.2 was prepared from 81.1 and Int-15.3, following the procedure of the synthesis of I-10. The product was purified by flash column chromatography on silica gel (CombiFlash®, 2.1% methanol in DCM. MS(ES): m/z: 629.32 [M+H]$^+$.

Synthesis of compound 81.3. Compound 81.3 was prepared from 81.2, following the procedure of the synthesis of (±)-I-74. The product was purified by flash column chromatography on silica gel (CombiFlash®, 2.0% methanol in DCM). MS (ES): m/z 619.

Synthesis of I-81. Compound I-81 was prepared from 81.3, following the procedure described in the synthesis of 40.2. The product was purified by flash column chromatography on silica gel (CombiFlash®, 4.0% methanol in DCM). MS(ES): m/z: 529.41 [M+H]$^+$; $^1$H NMR (DMSO-d$_6$, 400 MHz): δ 10.71 (s, 1H), 8.66 (s, 1H), 8.32 (s, 1H), 8.25 (d, J=5.6 Hz, 1H), 8.02 (s, 1H), 7.71 (s, 1H), 6.79-6.78 (m, 1H), 4.19 (m, 2H), 3.96 (s, 3H), 3.17 (m, 2H), 2.06 (s, 3H).

Example 82: N-(4-((7-chloro-1-methyl-2-((1-(methyl-d$_3$)-2-oxo-5-(trifluoromethyl)-1,2-dihydropyridin-3-yl)amino)-1H-imidazo[4,5-b]pyridin-6-yl)oxy)pyridin-2-yl)acetamide

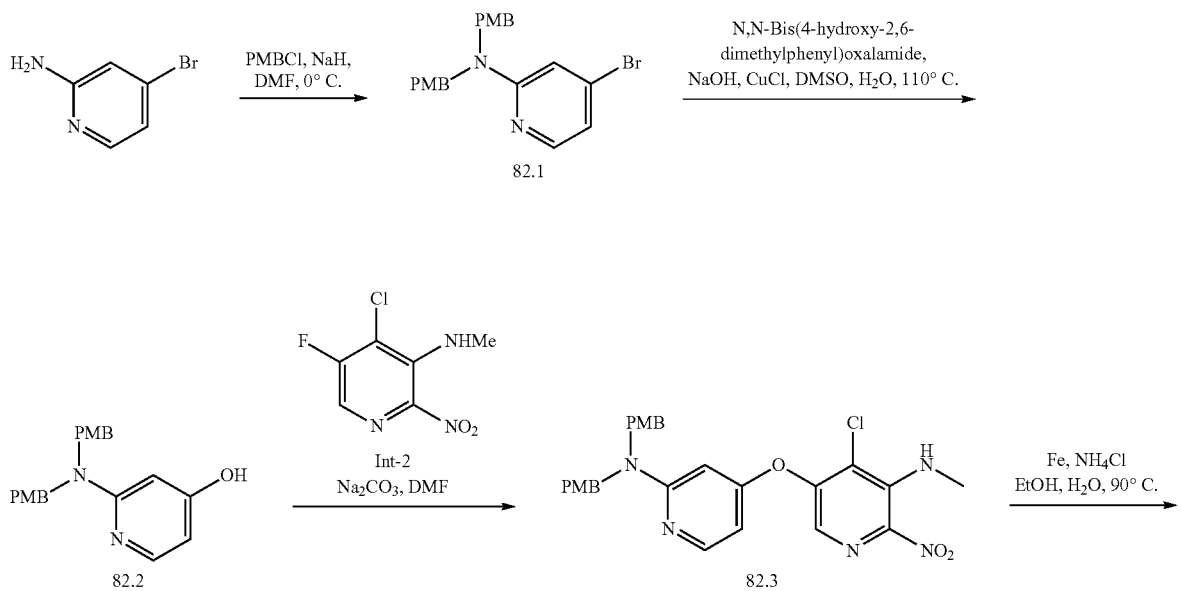

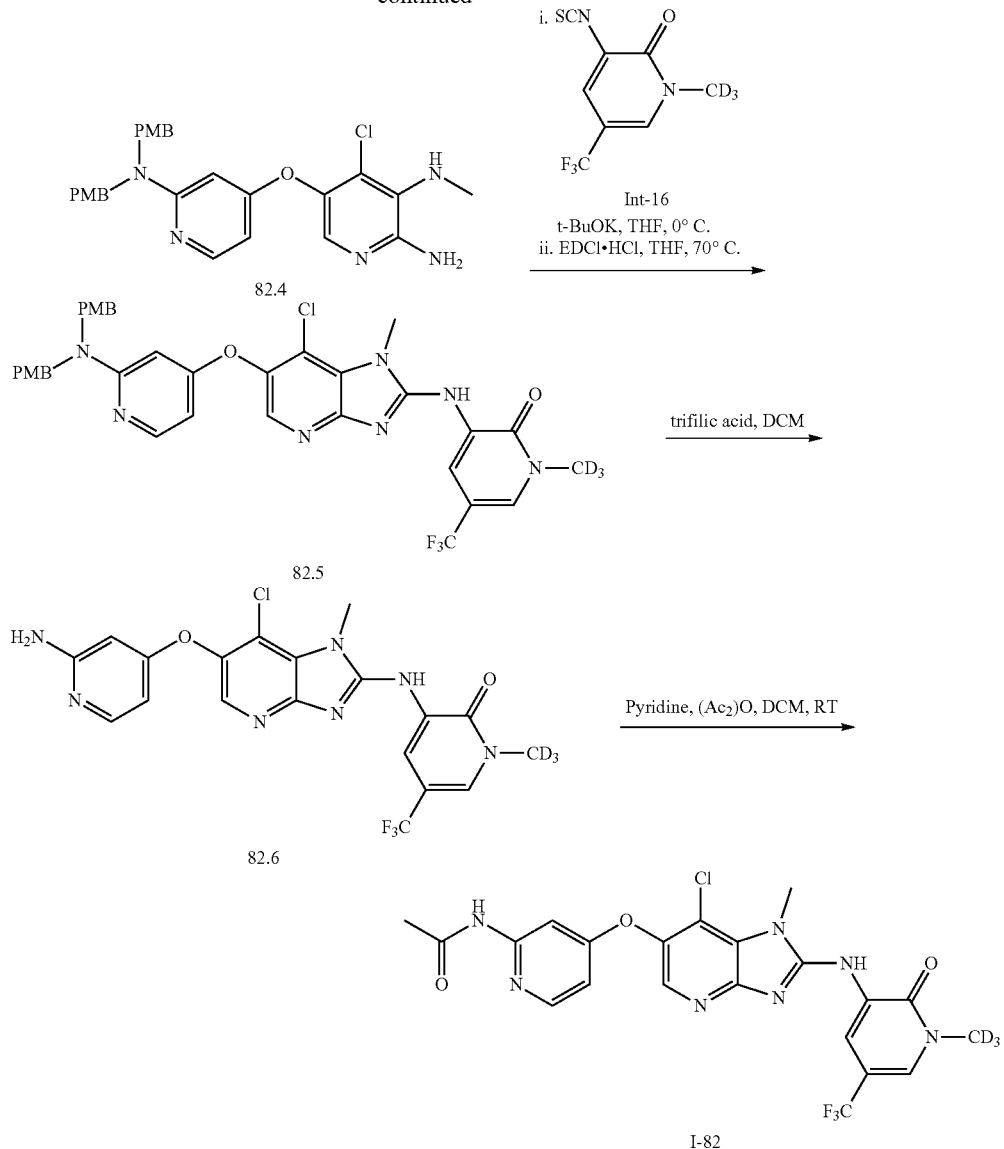

Synthesis of compound 82.1 To a solution of 4-bromopyridin-2-amine (100 g, 577.9 mmol, 1.0 equiv) in DMF (1300 mL) was added sodium hydride (111 g, 2773.9 mmol, 4.8 equiv) at 0° C. in portions. The reaction mixture was stirred for 2 h and 4-methoxybenzyl chloride (434 g, 2773.9 mmol, 4.8 equiv) was added slowly. After the addition, it was stirred at 0° C. for 30 min, transferred into ice-water, and stirred. The precipitated solids were collected by filtration and dried to afford 82.1. MS(ES): m/z 414.2 [M+H]⁺.

Synthesis of compound 82.2. To a solution of 82.1 (60 g, 145 mmol, 1.0 equiv), copper(I) chloride (1.14 g, 11.6 mmol, 0.08 equiv) and N,N-bis(4-hydroxy-2,6-dimethylphenyl)oxalamide (3.8 g, 11.6 mmol, 0.08 equiv) in DMSO (1000 mL) was added sodium hydroxide (11.6 g, 290 mmol, 2.0 equiv). The reaction mixture was stirred at 110° C. for 48 h. The reaction mixture cooled to room temperature, transferred into ice-water, stirred, and extracted with ethyl acetate. The combined organic layers were washed with brine, dried over anhydrous sodium sulfate, filtered, and concentrated under reduced pressure. The residue was purified by trituration with diethyl ether to afford 82.2. MS(ES): m/z 351.2 [M+H]⁺.

Synthesis of compound 82.3. A mixture of 82.2 (39 g, 111.3 mmol, 1.0 equiv), sodium carbonate (23.59 g, 222.6 mmol, 2.0 equiv) and Int-2 (18.3 g, 89.04 mmol, 0.8 equiv) in DMF (390 mL) was stirred at 80° C. for 1 h. The reaction mixture was filtered, and the filtrate was transferred into water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 28% ethyl acetate in hexane) to afford 82.3. MS(ES): m/z 536.6 [M+H]⁺.

Synthesis of compound 82.4. A mixture of 82.3 (46 g, 85.82 mmol, 1.0 equiv), ammonium chloride (23.17 g, 429.1 mmol, 5.0 equiv) and iron powder (24.03 g, 429.1 mmol 5.0 equiv) in ethanol (700 mL) and water (250 mL) was stirred at 90° C. for 4 h. The reaction mixture was filtered through a pad of Celite®. The filtrate was transferred into ice-water and extracted with ethyl acetate. The combined organic layers were washed with brine, dried over anhydrous sodium sulfate, filtered, and concentrated under reduced pressure.

The residue was purified by flash column chromatography on silica gel (CombiFlash®, 70% ethyl acetate in hexane) to afford 82.4. MS(ES): m/z 506.9 [MH-H]+.

Synthesis of compound 82.5. Compound 82.5 was prepared from 82.4 and Int-16, following the procedure described in the synthesis of I-19. The product was purified by flash column chromatography on silica gel (CombiFlash®, 2.8% methanol in DCM). MS(ES): m/z: 710.1 [M+H]+.

Synthesis of compound 82.6. Compound 82.6 was prepared from 82.5, following the procedure described in the synthesis of 40.2. The product was purified by trituration with diethyl ether. MS(ES): m/z: 469.5 [M+H]+.

Synthesis of I-82. To solution of 82.6 (7.0 g, 14.93 mmol, 1.0 equiv) and pyridine (24 mL, 298.6 mmol, 20 equiv) in DCM (70 mL) was acetic anhydride (56.6 mL, 599.2 mmol, 40 equiv) stirred at room temperature for 24 h. The reaction mixture was concentrated under reduced pressure. The residue was purified by flash column chromatography on silica gel (CombiFlash®, 5-6% methanol in DCM) to afford I-82. MS(ES): m/z: 511.3 [M+H]+; $^1$H NMR (DMSO-$d_6$, 400 MHz): δ 10.62 (bs, 1H), 8.86 (d, J=7.2 Hz, 1H), 8.65 (d, J=5.2 Hz, 1H), 8.26 (d, J=8.0 Hz, 1H), 8.22 (d, J=6.0 Hz, 1H), 8.17 (bs, 1H), 7.68 (bs, 1H), 6.70-6.68 (m, 1H), 4.02 (s, 3H), 2.07 (s, 3H).

Example 83: N-(4-((7-cyano-1-methyl-2-((1-(methyl-d₃)-2-oxo-5-(trifluoromethyl)-1,2-dihydropyridin-3-yl)amino)-1H-imidazo[4,5-b]pyridin-6-yl)oxy)pyridin-2-yl)acetamide

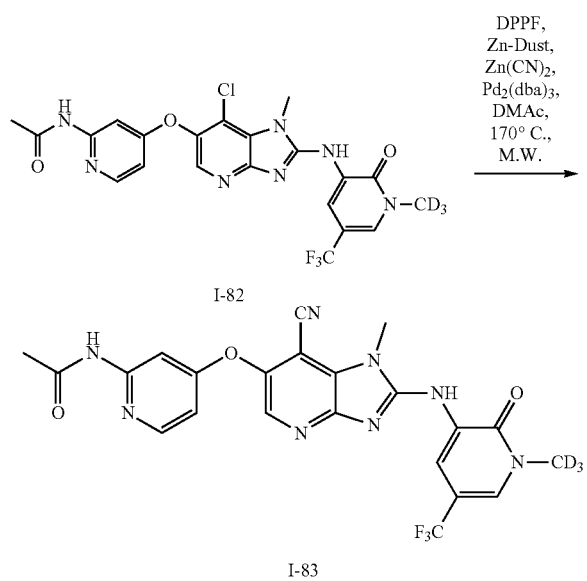

Synthesis of I-83. Compound I-83 was prepared from I-82, following the procedure described in the synthesis of (±)-I-74. The product was purified by flash column chromatography on silica gel (CombiFlash®, 2.5% methanol in DCM) t. MS(ES): m/z 501.44 [M+H]+; $^1$H NMR (DMSO-$d_6$, 400 MHz): δ 10.64 (s, 1H), 9.04 (bs, 1H), 8.65 (s, 1H), 8.30 (s, 1H), 8.24 (d, J=8 Hz, 1H), 8.17 (s, 1H), 7.75 (s, 1H), 6.76-6.55 (t, J=4 Hz, 1H), 3.96 (s, 3H), 2.06 (s, 3H).

Example 84: N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-2-fluoroacetamide

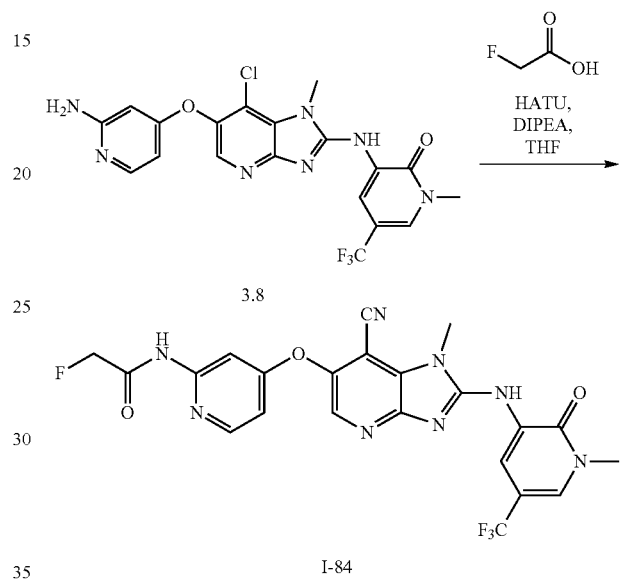

Synthesis of I-84. To a solution of 3.8 (0.070 g, 0.153 mmol, 1.0 equiv) in THF (5 mL) was added HATU (0.088 g, 0.229 mmol, 1.5 equiv) and stirred for 30 min. To the mixture was added N,N-diisopropylethylamine (0.049 g, 0.382 mmol, 2.5 equiv) and 2-fluoroacetic acid (0.023 g, 0.306 mmol, 1.5 equiv). The reaction mixture was stirred at room temperature for 2 h. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3% methanol in DCM) to afford I-84. MS(ES): m/z 517.88 [M+H]+; 99.31%, $^1$H NMR (DMSO-$d_6$, 400 MHz): δ 10.72 (s, 1H), 9.03 (s, 1H), 8.65 (s, 1H), 8.33 (s, 1H), 8.27 (d, J=1.6 Hz, 1H), 8.19 (s, 1H), 7.70 (s, 1H), 6.83 (d, J=5.6 Hz, 1H), 5.07 (s, 1H), 4.95 (s, 1H), 3.96 (s, 3H), 3.36 (s, 3H).

Example 85: N-(4-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-2-((2-methoxyethyl)amino)acetamide

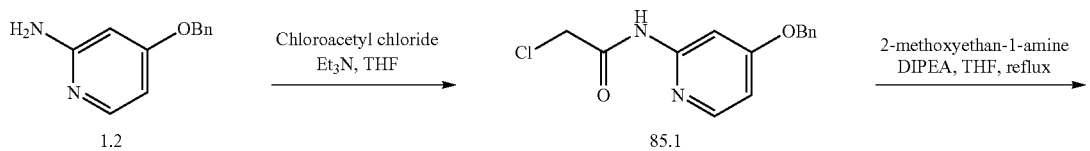

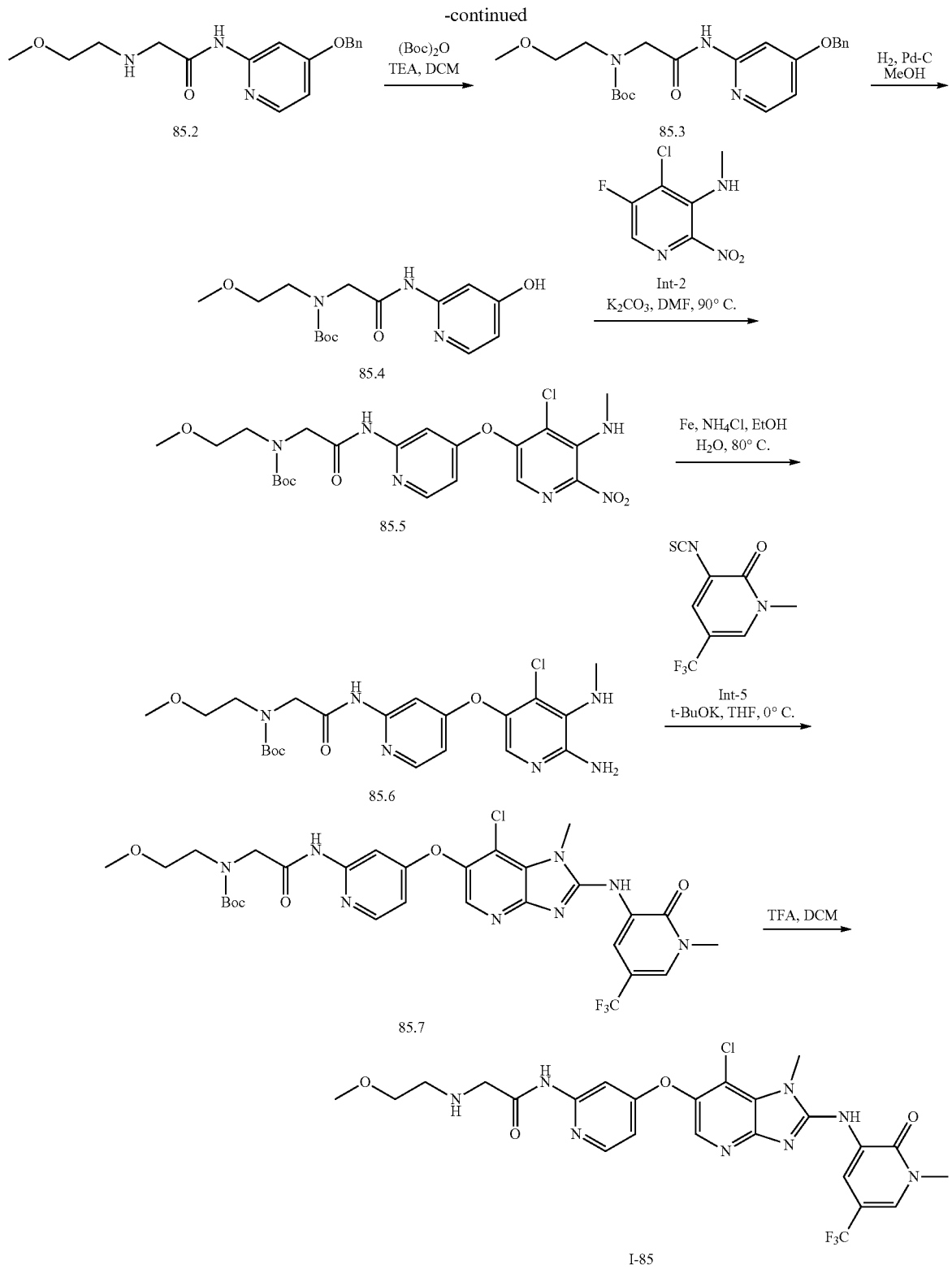

Synthesis of compound 85.1 To a solution of 1.2 (5.00 g, 25.0 mmol, 1.0 equiv) and trimethylamine (7.575 g, 75.0 mmol, 3.0 equiv) in THF (50 mL) at 0° C. was added chloroacetyl chloride (4.235 g, 37.5 mmol, 1.5 equiv). The reaction mixture was stirred at room temperature for 2 h. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.8% methanol in DCM) to afford 85.1. MS(ES): m/z: 277.62 [M+H]$^+$.

Synthesis of compound 85.2. To a solution of 85.1 (4.0 g, 14.45 mmol, 1.0 equiv) and N,N-diisopropylethylamine (5.60 g, 43.36 mmol, 3.0 equiv) in THF (40 mL) was added 2-methoxyethan-1-amine (1.63 g, 21.73 mmol, 1.5 equiv). The reaction mixture was stirred at 80° C. for 1 h. It was transferred into water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 1.8% methanol in DCM) to afford 85.2. MS(ES): m/z: 316.37 [M+H]$^+$.

Synthesis of compound 85.3. To a solution of 85.2 (2.60 g, 8.25 mmol, 1.0 equiv) and triethylamine (2.5 g, 24.76 mmol, 3.0 equiv) in DCM (26 mL) at 0° C. was added di-tert-butyl dicarbonate (2.70 g, 12.38 mmol, 1.5 equiv). The reaction mixture was stirred at room temperature for 2 h. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 1.2% methanol in DCM) to afford 85.3. MS(ES): m/z: 416.49 [M+H]$^+$.

Synthesis of compound 85.4. A mixture of compound 85.3 (1.6 g, 25.18 mmol, 1.0 equiv) and 10% palladium on carbon (0.800 g) in methanol (16 mL) was stirred under hydrogen (1 atm) for 2 h. The reaction mixture was filtered through a pad of Celite® and rinsed with methanol. The filtrate was concentrated under reduced pressure to afford 85.4. MS(ES): m/z 326.37 [M+H]$^+$.

Synthesis of compound 85.5. A mixture of 85.4 (1.06 g, 3.25 mmol, 1.0 equiv), Int-2 (0.802 g, 3.91 mmol, 1.2 equiv) and potassium carbonate (0.900 g, 6.52 mmol, 2.0 equiv) in DMF (10 mL) was stirred at 90° C. for 2 h. It was cooled to room temperature, transferred into ice-water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2% methanol in DCM to afford 85.5. MS(ES): m/z 511.93 [M+H]$^+$.

Synthesis of compound 85.6. A mixture of compound 85.5 (0.655 g, 1.28 mmol, 1.0 equiv), iron powder (0.358 g, 6.42 mmol, 5.0 equiv) and ammonium chloride (0.343 g, 6.42 mmol, 5.0 equiv) in ethanol:water (8:2, 6 mL) was stirred at 80° C. for 2 h. The reaction mixture was filtered through a pad of Celite® and rinsed with ethanol. The filtrate was concentrated under reduced pressure. The residue was purified by flash column chromatography on silica gel (CombiFlash®, 2.8% methanol in DCM) to afford 85.6. MS(ES): m/z 481.95 [M+H]$^+$.

Synthesis of compound 85.7. Compound 85.7 was prepared from compound 85.6 following the procedure described in the synthesis of compound 3.7. The product was purified by flash column chromatography on silica gel (CombiFlash®, 4.1% methanol in DCM). MS(ES): m/z 682.05 [M+H]$^+$.

Synthesis of I-85. To a solution of 85.7 (0.080 g, 0.117 mmol, 1.0 equiv) in DCM (4 mL) was added trifluoroacetic acid (0.267 g, 2.348 mmol, 20.0 equiv) at 0° C. The reaction mixture was stirred at room temperature for 1 h. It was transferred into ice-water and basified with a saturated aqueous solution of sodium bicarbonate and extracted with DCM. The combined organic layers were washed with brine, dried over anhydrous sodium sulfate, filtered, and concentrated under reduced pressure. The residue was purified by flash column chromatography on silica gel (CombiFlash®, 6.3% methanol in DCM) to afford I-85. MS(ES): m/z: 581.95 [M+H]$^+$; $^1$H NMR (DMSO-d$_6$, 400 MHz): δ 10.32 (s, 1H), 8.85 (s, 1H), 8.63 (s, 1H), 8.25 (s, 1H), 8.21 (d, J=3.7 Hz, 1H), 8.15 (s, 1H), 7.66 (s, 1H), 6.73 (d, J=3.6 Hz, 1H), 3.99 (s, 3H), 3.66 (s, 3H), 3.38-3.33 (m, 4H), 3.23 (s, 3H), 2.71-2.68 (d, J=4.8 Hz, 2H).

Example 86: N-(4-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)hydroxyacetamide

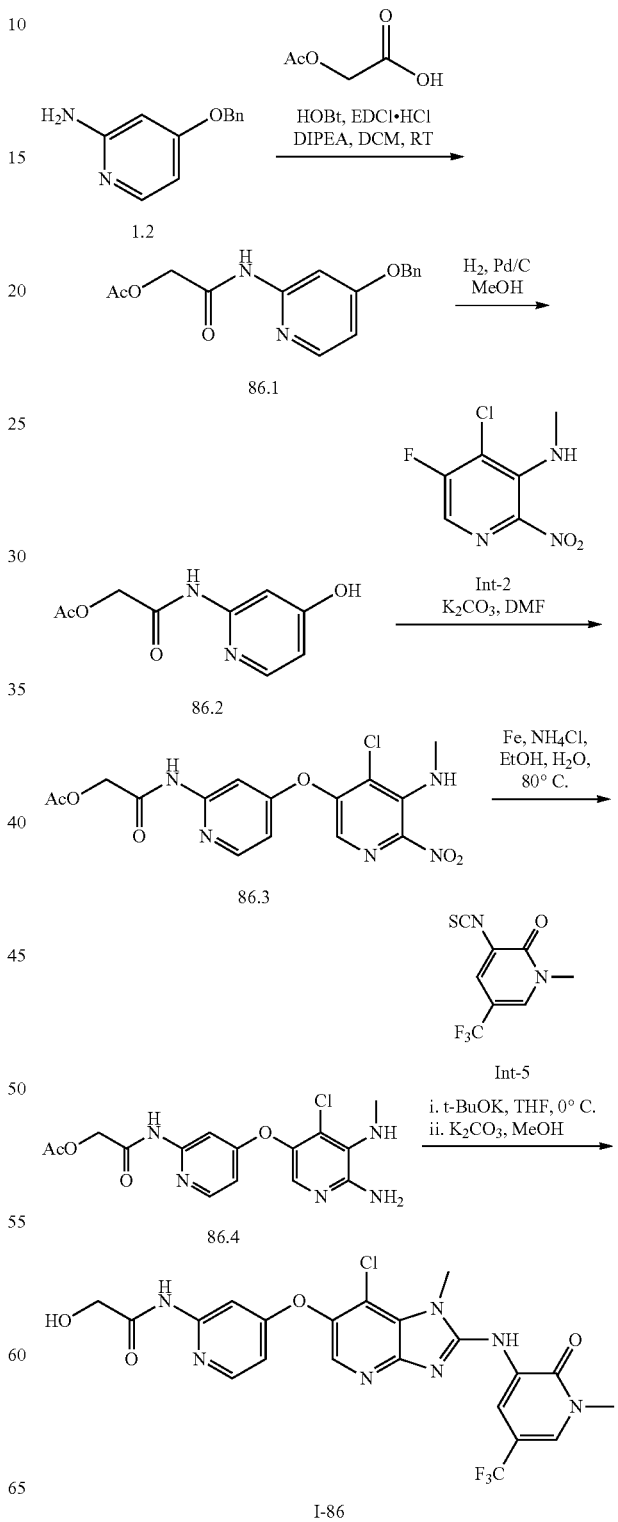

Synthesis of compound 86.1. To a solution of 1.2 (2.0 g, 16.94 mmol, 1.0 equiv), 1-hydroxybenzotriazole hydrate (2.51 g, 18.64 mmol, 1.1 equiv) and N-(3-dimethylaminopropyl)-N'-ethylcarbodiimide hydrochloride (4.88 g, 25.42 mmol, 1.5 equiv) in DCM (40 mL) was added N,N-diisopropylethylamine (5.13 g, 50.84 mmol, 3.0 equiv). The reaction mixture was stirred at 0° C. for 15 min and 2-acetoxyacetic acid (3.0 g, 18.63 mmol, 1.5 equiv) was added. The reaction mixture was stirred for 16 h. It was transferred into ice-water and extracted with ethyl acetate. The combined organic layers were washed with brine, dried over anhydrous sodium sulfate, filtered, and concentrated under reduced pressure to afford material. The residue was purified by flash column chromatography on silica gel (CombiFlash®, 5.0% methanol in DCM) to afford 86.1. MS(ES): m/z: 301.31 [M+H]$^+$.

Synthesis of compound 86.2. A mixture of Pd—C (10%; 0.7 g) and 86.1 (1.45 g, 4.83 mmol, 1.0 equiv) in methanol (40 mL) was stirred under hydrogen (1 atm) for 2 h. The reaction mixture was filtered through a pad of Celite® and rinsed with methanol. The filtrate was concentrated under reduced pressure to afford 86.2. MS(ES): m/z 211.13 [M+H]$^+$.

Synthesis of compound 86.3. A mixture of 86.2 (0.910 g, 4.33 mmol, 1.0 equiv), Int-2 (0.712 g, 3.46 mol, 0.8 equiv) and potassium carbonate (1.8 g, 12.99 mmol, 3.0 equiv) in DMF (20 mL) was stirred at rt for 6 h. It was cooled to room temperature, transferred into ice-water, and stirred. The precipitated solids were collected by filtration, rinsed with water, and dried to afford 86.3. MS(ES): m/z 396.76 [M+H]$^+$.

Synthesis of compound 86.4. A mixture of compound 86.3 (0.330 g, 0.833 mmol, 1.0 equiv), iron powder (0.705 g, 4.16 mmol, 5.0 equiv) and ammonium chloride (0.225 g, 4.16 mmol, 5.0 equiv) in ethanol:water (8:2, 10 mL) was stirred at 80° C. for 2 h. The reaction mixture was filtered through a pad of Celite® and rinsed with ethanol. The filtrate was concentrated under reduced pressure. The residue was purified by flash column chromatography on silica gel (CombiFlash®, 2.4% methanol in DCM) to afford 86.4. MS(ES): m/z 366.77 [M+H]$^+$.

Synthesis of I-86. A mixture of 86.4 (0.155 g, 0.423 mmol, 1.0 equiv), Int-5 (0.148 g, 0.635 mmol, 1.5 equiv) and potassium tert-butoxide (1 M in THF, 1.3 mL, 1.3 mmol, 3.0 equiv) in THF (5 mL) was stirred at room temperature for 1 h. It was transferred into ice-water and extracted with ethyl acetate. The combined organic layers were washed with brine, dried over anhydrous sodium sulfate, filtered, and concentrated under reduced pressure. The residue was dissolved in methanol (10 mL) and potassium carbonate (0.05 g) was added at rt. The reaction mixture was stirred at room temperature for 30 min. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.9% methanol in DCM) to afford I-86. MS(ES): m/z: 524.18 [M+H]$^+$; $^1$H NMR (DMSO-d$_6$, 400 MHz): δ 9.83 (s, 1H), 8.87 (s, 1H), 8.64 (s, 1H), 8.27 (s, 1H), 8.23 (d, J=6.8 Hz, 1H), 8.17 (s, 1H), 7.68 (s, 1H), 6.75 (d, J=4 Hz, 1H), 5.68 (t, J=4 Hz, 1H), 4.00 (s, 5H), 3.67 (s, 3H).

Example 87: N-(4-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-2-((2-fluoroethyl)amino)acetamide

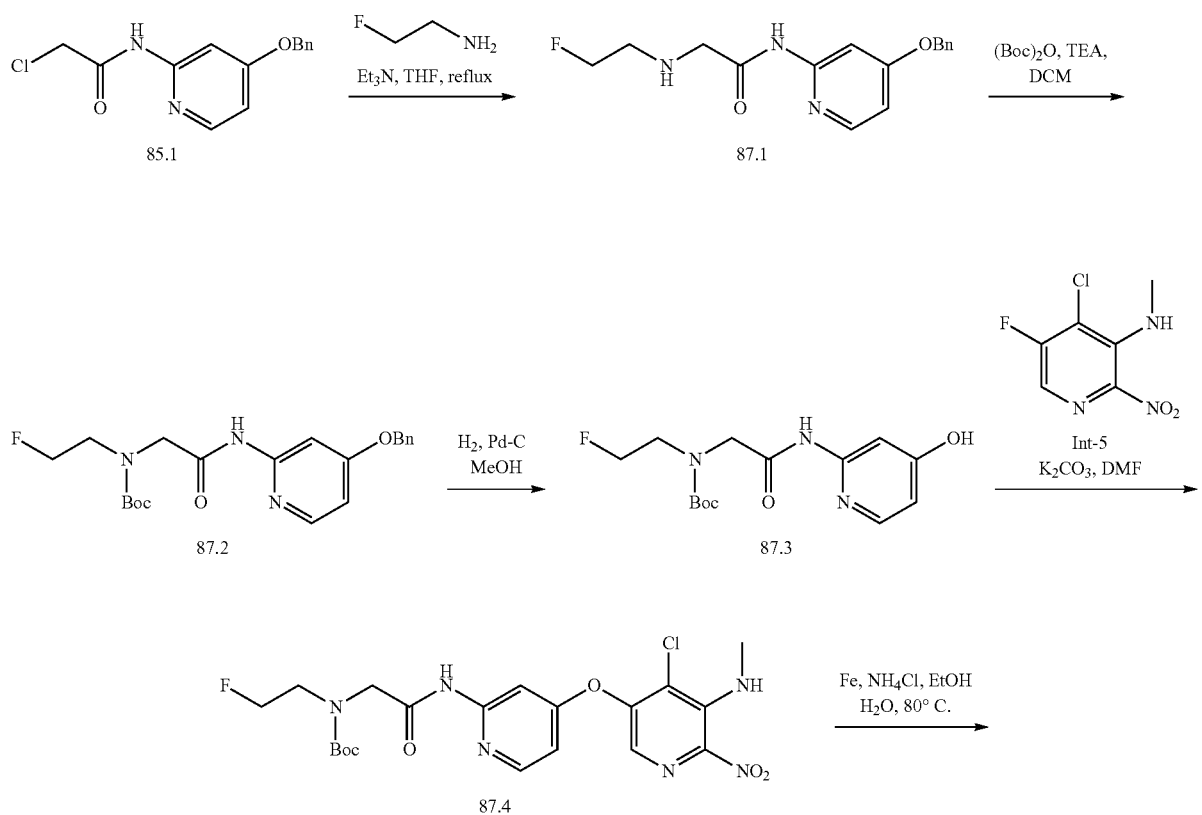

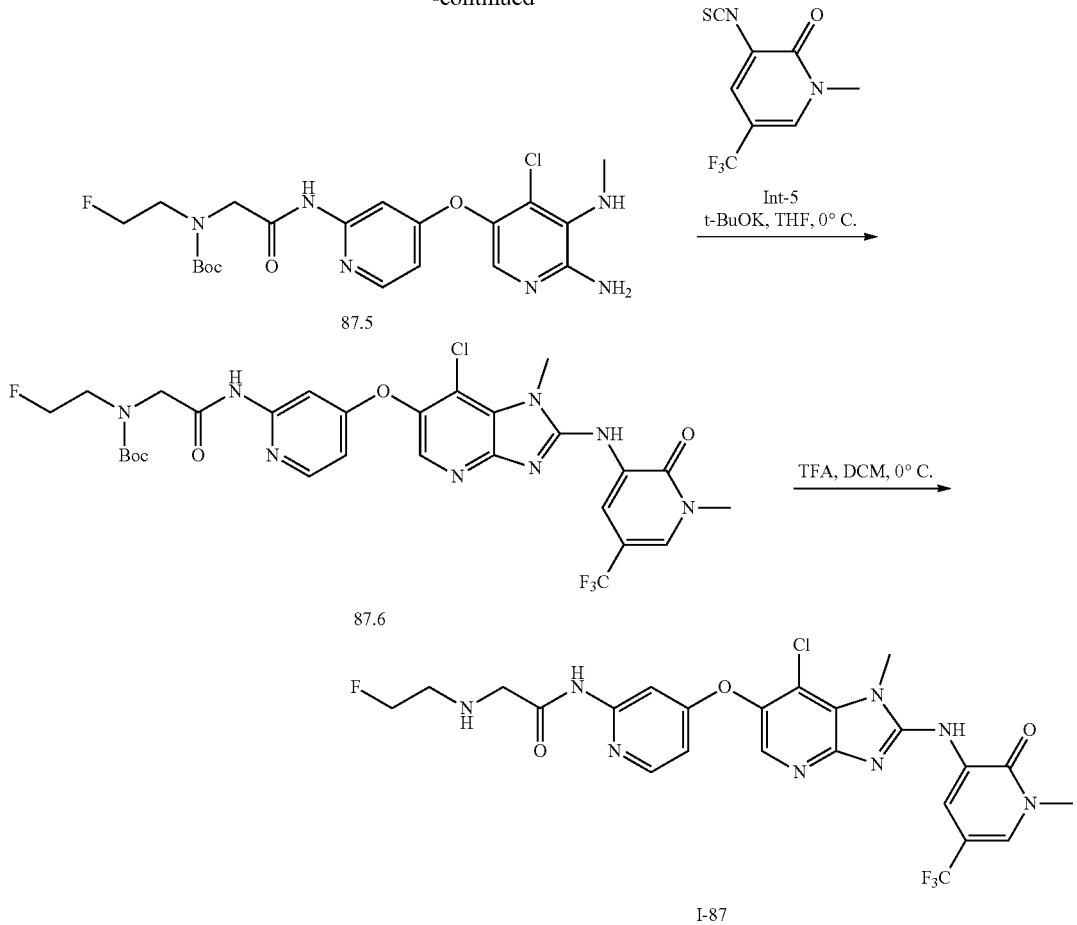

Synthesis of compound 87.1. To a solution of 85.1 (1.0 g, 3.62 mmol, 1.0 equiv), 2-fluoroethan-1-amine (1.07 g, 10.86 mmol, 3.0 equiv) and TEA (1.83 g, 18.15 mmol, 5.0 equiv) in THF (15 mL) was stirred at 80° C. for 20 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 48% ethyl acetate in hexane) to afford 87.1. MS(ES): m/z 304.2 [M+H]⁺.

Synthesis of compound 87.2. A solution of 87.1 (0.910 g, 3.00 mmol, 1.0 equiv), triethylamine (0.606 g, 6.00 mmol, 2.0 equiv) and Boc anhydride (0.784 g, 3.6 mmol, 1.2 equiv) in DCM (15 mL) was stirred at room temperature for 14 h. It was transferred into water and extracted with DCM. The combined organic layers were washed with brine, dried over anhydrous sodium sulfate, filtered, and concentrated under reduced pressure. The residue was purified by flash column chromatography on silica gel (CombiFlash®, 32% ethyl acetate in hexane) to afford 87.2. m/z: 404.58 [M+H]⁺.

Synthesis of compound 87.3. A mixture of 87.3 (1.05 g, 2.59 mmol, 1.0 equiv) and 10% palladium on carbon (0.800 g) in methanol (15 mL) was stirred under hydrogen (1 atm) for 1.5 h. The reaction mixture was filtered through a pad of Celite® and rinsed with methanol. The filtrate was concentrated under reduced pressure to afford 87.3. MS(ES): m/z 314.37 [M+H]⁺.

Synthesis of compound 87.4. A mixture of 87.3 (1.05 g, 3.35 mmol, 1.0 equiv), Int-5 (0.687 g, 3.35 mmol, 1.0 equiv) and potassium carbonate (0.924 g, 6.7 mmol, 2.0 equiv) in DMF (15 mL) was stirred at room temperature for 2 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 35% ethyl acetate in hexane) to afford 87.4. MS(ES): m/z 499.52 [M+H]⁺.

Synthesis of compound 87.5. A mixture of compound 87.4 (0.820 g, 1.64 mmol, 1.0 equiv), iron powder (0.461 g, 8.23 mmol, 5.0 equiv) and ammonium chloride (0.436 g, 8.23 mmol, 5.0 equiv) in ethanol:water (8:2, 12 mL) was stirred at 80° C. for 2 h. The reaction mixture was filtered through a pad of Celite® and rinsed with ethanol. The filtrate was concentrated under reduced pressure. The residue was purified by flash column chromatography on silica gel (CombiFlash®, 2.3% methanol in DCM) to afford 87.5. MS(ES): m/z 469.45 [M+H]⁺.

Synthesis of compound 87.6. Compound 87.6 was prepared from compound 87.5 following the procedure described in the synthesis of compound 3.7. The product was purified by flash column chromatography on silica gel (CombiFlash®, 2.8% methanol in DCM). MS(ES): m/z: 670.5 [M+H]⁺.

Synthesis of I-87. To solution of 87.6 (0.120 g, 0.178 mmol, 1.0 equiv) in DCM (6 mL) was added trifluoroacetic acid (1.0 mL) at 0° C. and stirred for 1.5 h. It was transferred into a mixture of ice and saturated aqueous solution of sodium bicarbonate, stirred, and extracted with DCM. The combined organic layers were washed with brine, dried over anhydrous sodium sulfate, filtered, and concentrated under reduced pressure. The residue was purified by trituration with diethyl ether to afford I-87. MS(ES): m/z: 569.82 [M+H]$^+$; $^1$H NMR (DMSO-d$_6$, 400 MHz): 10.39 (s, 1H), 8.86 (s, 1H), 8.63 (s, 1H), 8.26 (s, 1H), 8.22 (d, J=6.0 Hz, 2H), 8.15 (s, 1H), 7.65 (s, 1H), 6.75-6.73 (dd, J=2.0 Hz, 1H), 4.54 (t, J=4.4 Hz, 1H), 4.42 (t, J=4.8 Hz, 1H), 3.99 (s, 3H), 3.66 (s, 3H), 3.34 (s, 2H), 2.92 (t, J=4.8 Hz, 1H), 2.84 (t, J=4.4 Hz, 1H).

Example 88: N-(4-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)-5-fluoropyridin-2-yl)acetamide

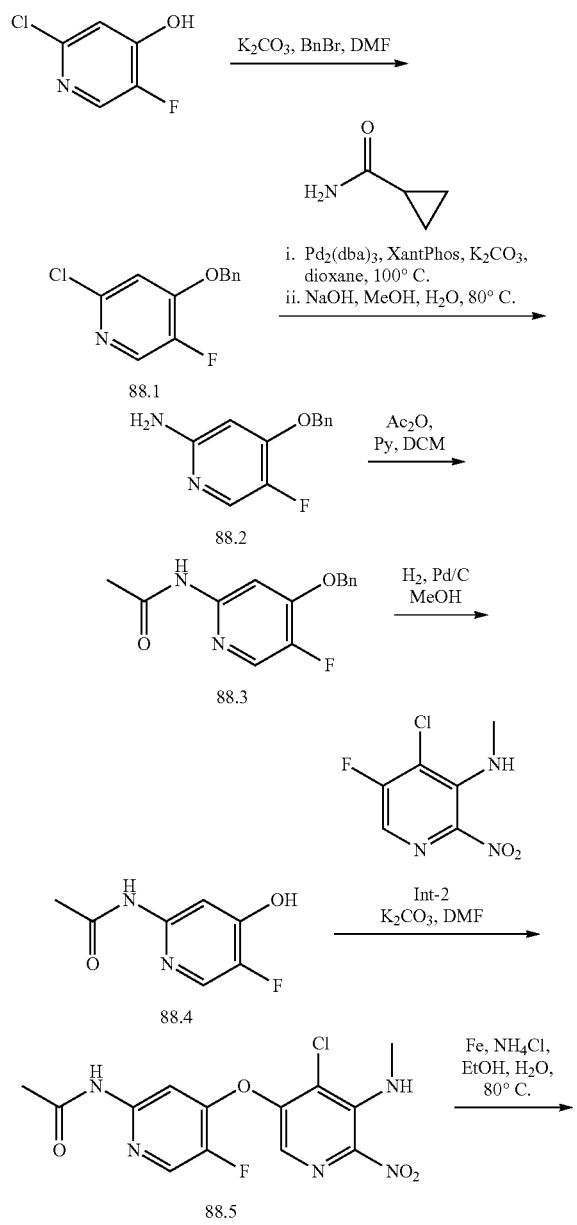

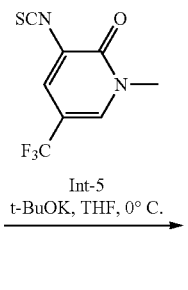

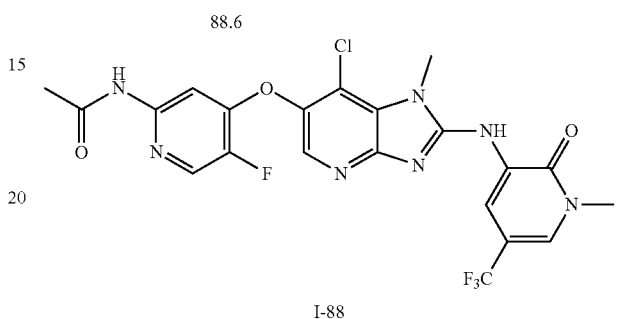

Synthesis of compound 88.1. A mixture of 2-chloro-5-fluoropyridin-4-ol, potassium carbonate (6.1 g, 44.730 mmol, 3.0 equiv) and benzyl bromide (5.1 g, 29.820 mmol, 2.0 equiv) in DMF (120 mL) was stirred at room temperature for 2 h. The reaction mixture was poured in water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 21% ethyl acetate in hexane) to afford 88.1. MS(ES): m/z 237.66 [M+H]$^+$.

Synthesis of compound 88.2 A mixture of 88.1 (1.7 g, 7.15 mmol, 1.0 equiv), cyclopropanecarboxamide (0.608 g, 7.15 mmol, 1.2 equiv) and potassium carbonate (1.97 g, 14.30 mmol, 2.0 equiv) in dioxane (15 mL) was purged with argon for 5 min before the addition of 4,5-bis(diphenylphosphino)-9,9-dimethylxanthene (0.413 g, 0.715 mmol, 0.1 equiv) and tris(dibenzylideneacetone)dipalladium(0) (0.327 g, 0.357 mmol, 0.05 equiv). The reaction mixture was purged with argon for another 5 min and stirred at 100° C. for 2 h. It was poured in water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.5% methanol in DCM). The product was dissolved in methanol and an aqueous solution of sodium hydroxide (2.0 g, 5.00 mmol, 10 equiv) was added. The reaction mixture was stirred at 80° C. for 4 h. It was poured in water and extracted with ethyl acetate. The combined organic layers were washed with brine, dried over anhydrous sodium sulfate, and concentrated under reduced pressure. The residue was purified by flash column chromatography on silica gel (CombiFlash®, 7.0% methanol in DCM) to to afford 88.2. MS(ES): m/z 218.23 [M+H]$^+$.

Synthesis of compound 88.3. To a solution of 88.2 (1.0 g, 4.58 mmol, 1.0 equiv) and pyridine (1.088 g, 13.76 mmol, 5.0 equiv) in DCM (15 mL) was added acetic anhydride (1.40 g, 13.76 mmol, 3.0 equiv). The reaction mixture was stirred at room temperature for 16 h. It was poured into water and extracted with DCM. The combined organic layers were washed with brine, dried over anhydrous sodium sulfate, filtered, and concentrated under reduced pressure. The residue was purified by flash column chromatography on silica gel (CombiFlash®, 26% ethyl acetate in hexane) to afford 88.3. MS(ES): m/z 260.27 [M+H]⁺.

Synthesis of compound 88.4. A mixture of palladium on carbon (10 wt %, 0.400 g) and compound 88.3 (0.700 g, 2.69 mmol, 1.0 equiv) in methanol (20 mL) was stirred under hydrogen (1 atm) for 2 h. The reaction mixture was filtered through a pad of Celite® and rinsed with methanol. The filtrate was concentrated under reduced pressure to afford 88.4. MS(ES): m/z 171.14 [M+H]⁺.

Synthesis of compound 88.5. A mixture of 88.4 (0.45 g, 2.65 mmol, 1.0 equiv), Int-2 (0.543 g, 2.65 mol, 1.0 equiv) and potassium carbonate (1.09 g, 7.94 mmol, 3.0 equiv) in DMF (20 mL) was stirred at rt for 6 h. It was transferred into ice-water and stirred. The precipitated solids were collected by filtration, rinsed with water and dried to 88.5. MS(ES): m/z 356.71 [M+H]⁺.

Synthesis of compound 88.6. A mixture of 88.5 (0.350 g, 0.983 mmol, 1.0 equiv), iron powder (0.256 g, 4.91 mmol, 5.0 equiv) and ammonium chloride (0.240 g, 4.91 mmol, 5.0 equiv) in ethanol:water (8:2, 10 mL) was stirred at 80° C. for 5 h. The reaction mixture was filtered through a pad of Celite® and rinsed with ethanol. The filtrate was concentrated under reduced pressure. The residue was purified by flash column chromatography on silica gel (CombiFlash®, 2.4% methanol in DCM) to afford 88.6. MS(ES): m/z 326.73 [M+H]⁺.

Synthesis of I-88. Compound I-88 was prepared from compound 88.6 following the procedure described in the synthesis of compound 3.7. The product was purified by flash column chromatography on silica gel (CombiFlash®, 3.9% methanol in DCM). MS(ES): m/z. 526.85 [M+H]⁺; ¹H NMR (DMSO-d₆, 400 MHz): δ 10.64 (s, 1H), 8.88 (s, 1H), 8.65 (s, 1H), 8.42-8.35 (bs, 2H), 8.17 (s, 1H), 7.54 (d, J=5.6 Hz, 1H), 4.01 (s, 3H), 3.68 (s, 3H), 1.97 (s, 3H).

Example 89: N-(4-((7-cyano-2-((1-(2-hydroxyethyl)-2-oxo-5-(trifluoromethyl)-1,2-dihydropyridin-3-yl)amino)-1-methyl-1H-imidazo[4,5-b]pyridin-6-yl)oxy)pyridin-2-yl)cyclopropanecarboxamide

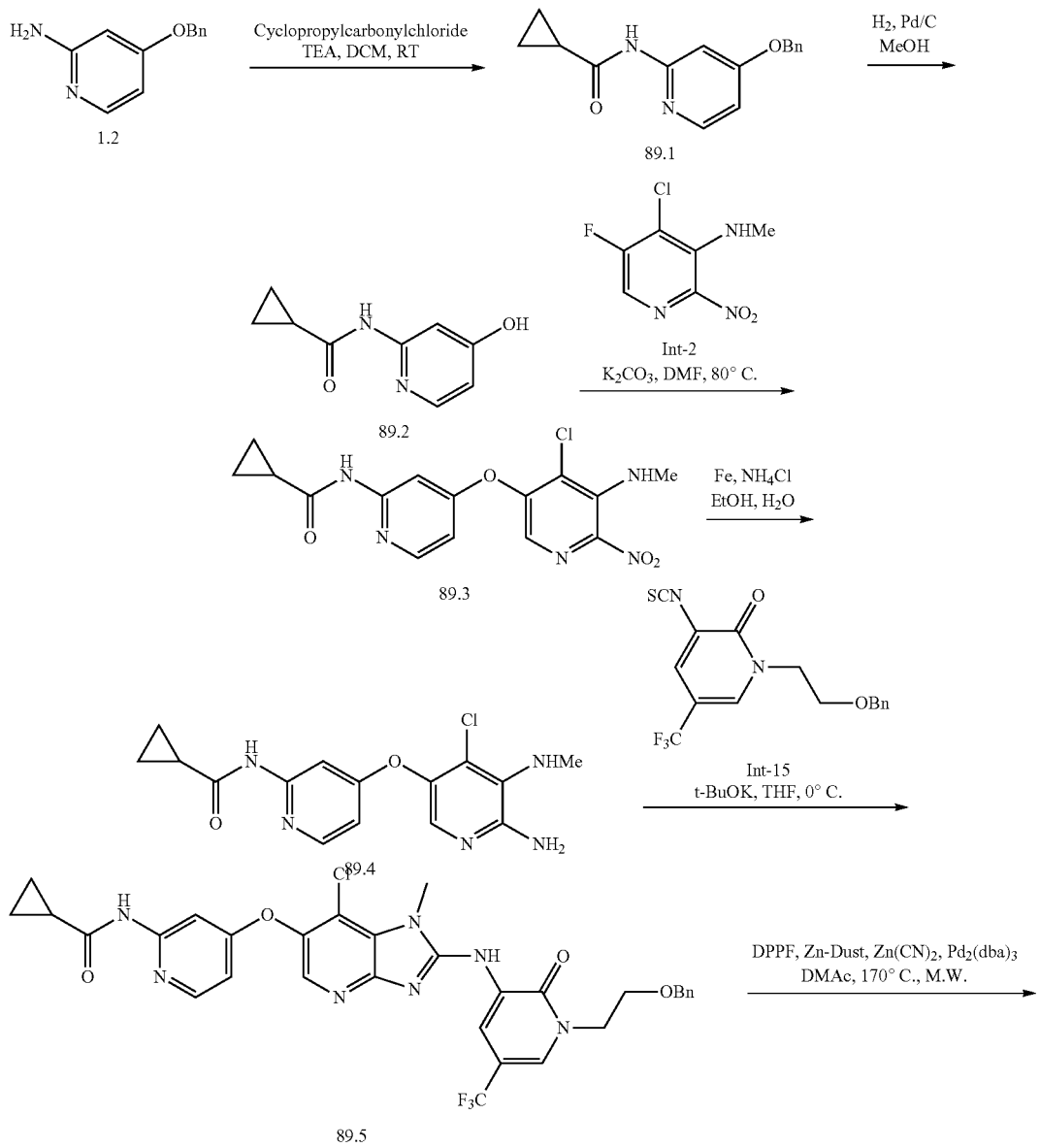

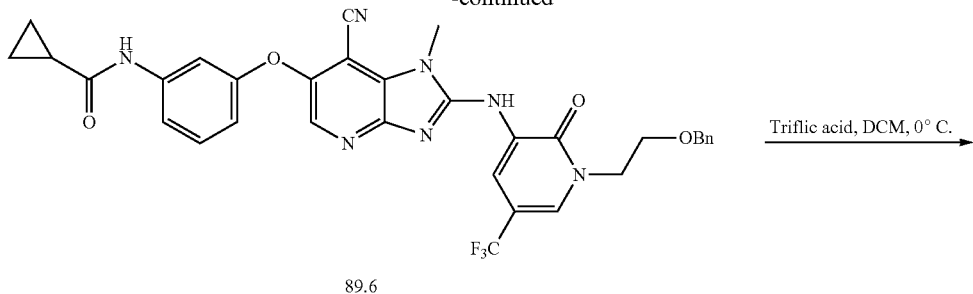

89.6

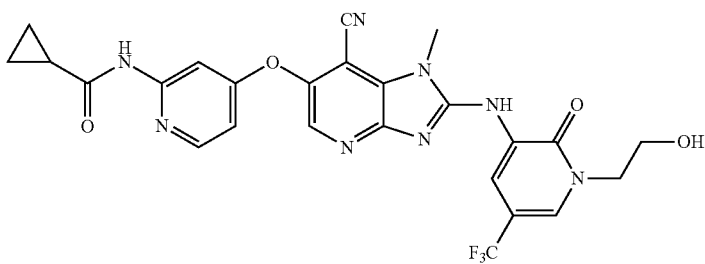

I-89

Synthesis of compound 89.1. To a solution of 1.2 (2.0 g, 9.99 mmol, 1.0 equiv) and triethylamine (4.17 mL, 29.97 mmol, 3.0 equiv) in DCM (20 mL) was added cyclopropylcarbonyl chloride (1.24 g, 11.98 mmol, 1.2 equiv) at room temperature and stirred for 1 h. It was transferred into ice, stirred, and extracted with DCM. The combined organic layers were washed with brine, dried over anhydrous sodium sulfate, filtered, and concentrated under reduced pressure. The residue was purified by flash column chromatography on silica gel (CombiFlash®, 1.2% methanol in DCM) to afford 89.1. MS (ES): m/z 269.3 [M+H]$^+$.

Synthesis of compound 89.2. A mixture of compound 89.1 (0.87 g, 3.24 mmol, 1.0 equiv) and 10% palladium on carbon (0.4 g) in methanol (5 mL) was stirred under hydrogen (1 atm) for 2 h. The reaction mixture was filtered through a pad of Celite® and rinsed with methanol. The filtrate was concentrated under reduced pressure. The residue was purified by flash column chromatography on silica gel (CombiFlash®, 4.5% methanol in DCM) to afford 89.2. MS(ES): m/z 179.2 [M+H]$^+$.

Synthesis of compound 89.3. A mixture of 89.2 (0.433 g, 2.43 mmol, 1.0 equiv), Int-2 (0.500 g, 2.43 mmol, 1.0 equiv) and potassium carbonate (0.838 g, 6.07 mmol, 2.5 equiv) in DMF (5 mL) was stirred at 80° C. for 2 h. It was cooled to room temperature, transferred into ice-water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.7% methanol in DCM) to afford 89.3. MS(ES): m/z 364.3 [M+H]$^+$.

Synthesis of compound 89.4. A mixture of 89.3 (0.590 g, 1.62 mmol, 1.0 equiv), iron powder (0.445 g, 8.1 mmol, 5 equiv) and ammonium chloride (0.445 g, 8.1 mmol, 5 equiv) in ethanol:water (2:1, 10 mL) was stirred at 80° C. for 1 h. It was transferred into ice-water, filtered, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.3% methanol in DCM) to afford 89.4. MS(ES): m/z 334.7 [M+H]$^+$.

Synthesis of compound 89.5. Compound 89.5 was prepared from compound 89.4 following the procedure described in the synthesis of compound 3.7. The product was purified by flash column chromatography on silica gel (CombiFlash®, 2.0% methanol in DCM). MS(ES): m/z: 655.5 [M+H]$^+$.

Synthesis of compound 89.6. Compound 89.6 was prepared from compound 89.5 following the procedure described in the synthesis of compound (±)-I-74. The product was purified by flash column chromatography on silica gel (CombiFlash®, 2.3% methanol in DCM. MS (ES): m/z 645.41 [M+H]$^+$.

Synthesis of I-89. Compound I-89 was prepared from 89.6, following the procedure described in the synthesis of 40.2. The product was purified by flash column chromatography on silica gel (CombiFlash®, 4.5% methanol in DCM). MS(ES): m/z: 555.26 [M+H]$^+$; $^1$H NMR (DMSO-d$_6$, 400 MHz): δ 10.97 (s, 1H), 9.06 (s, 1H), 8.67 (s, 1H), 8.31 (s, 1H), 8.25 (d, J=5.6 Hz, 1H), 8.02 (s, 1H), 7.72 (s, 1H), 6.79 (t, J=2.0 Hz, 1H), 5.00 (t, J=5.2 Hz, 1H), 4.18 (s, 2H), 3.96 (s, 3H), 3.74 (d, J=4.8 Hz, 2H), 1.97 (bs, 1H), 0.78-0.76 (m, 4H).

Example 90: (R)-N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-2-(4-methylmorpholin-2-yl)acetamide and (S)-N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-2-(4-methylmorpholin-2-yl)acetamide
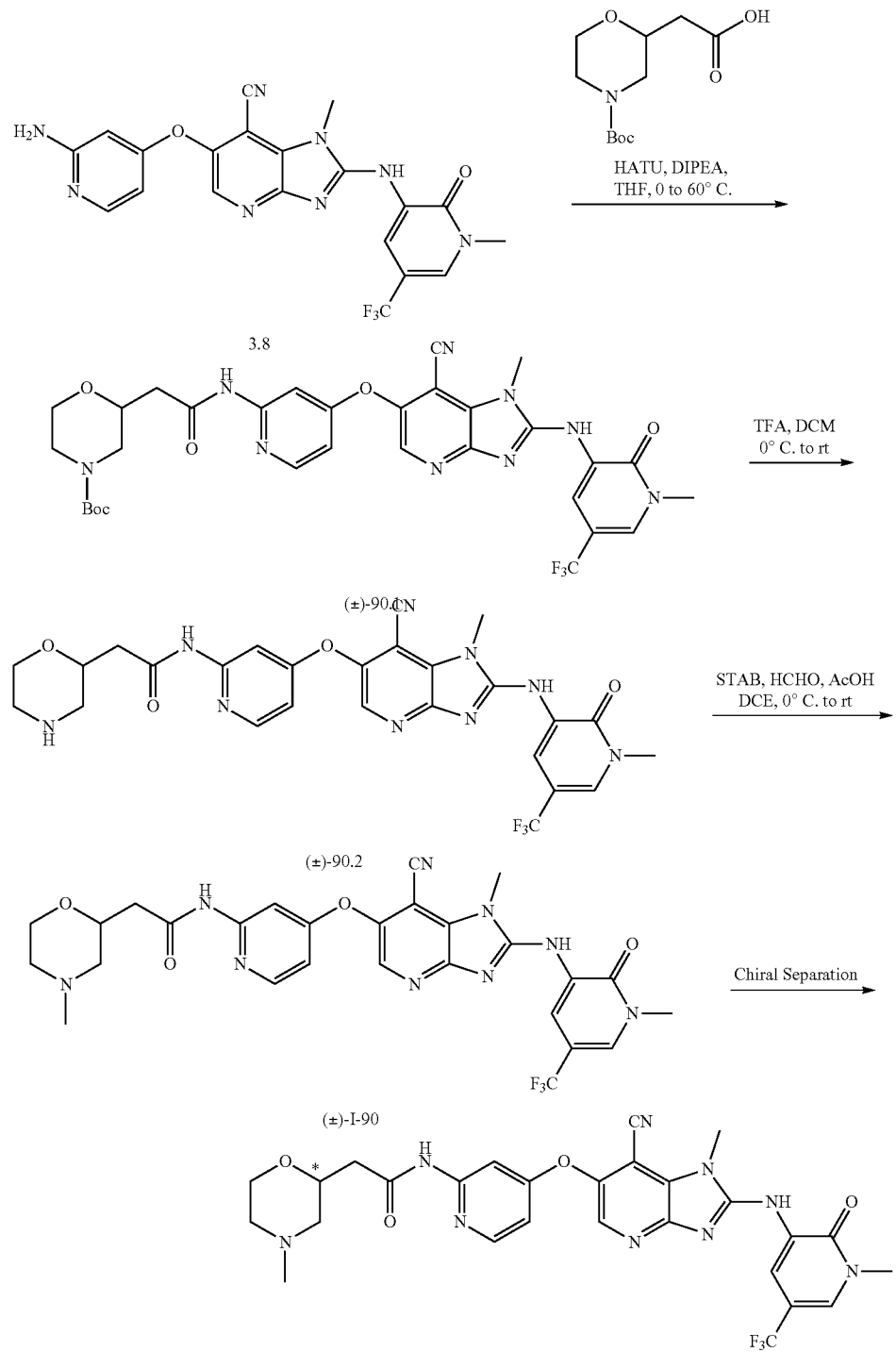

Synthesis of compound (±)-90.1. To a solution of 2-(4-(tert-butoxycarbonyl)morpholin-2-yl)acetic acid (0.2 g, 0.81 mmol, 1.0 equiv) in THF (8 mL) at 0° C. was added HATU (0.465 g, 1.22 mmol, 1.5 equiv) and stirred for 15 min. To the mixture was added compound 3.8 (0.446 g, 0.98 mmol, 1.2 equiv) and N,N-diisopropylethylamine (0.316 g, 2.44 mmol, 3.0 equiv). The reaction mixture was stirred at 60° C. overnight. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.8% methanol in DCM) to afford (±)-90.1. MS(ES): m/z: 684.2 [M+H]$^+$.

Synthesis of compound (±)-90.2. To a solution of (±)-90.2 (0.15 g, 0.21 mmol, 1.0 equiv) in DCM (5 mL) at 0° C. was added trifluoroacetic acid (0.8 mL). The reaction mixture was stirred at room temperature for 1 h. It was concentrated under reduced pressure to afford (±)-90.2. It was used in the next step without purification. MS(ES): m/z: 584.2 [M+H]$^+$.

Synthesis of compound (±)-I-90. To a solution of (±)-90.2 (0.1 g, 0.17 mmol, 1.0 equiv) in 1,2-dichloroethane (5 mL) at 0° C. was added formaldehyde solution (37% in H$_2$O) (0.020 g, 0.25 mmol, 1.5 equiv) and stirred for 15 min. To the mixture was added sodium triacetoxyborohydride (0.109 g, 0.51 mmol, 3 equiv) and stirred at room temperature for 16 h. It was transferred into ice-water and extracted with DCM. The combined organic layers were washed with brine, dried over anhydrous sodium sulfate, filtered, and concentrated under reduced pressure. The residue was purified by flash column chromatography on silica gel (CombiFlash®, 3.2% methanol in DCM) to afford (±)-I-90. MS(ES): m/z: 598.3 [M+H]$^+$.

I-90-a and I-90-b. The racemate was subjected to chiral HPLC separation (column: CHIRALPAK IH (250 mm*21 mm), 5 µm; mobile phases: (A) 0.1% DEA in n-hexane (B) 0.1% DEA in propane-2-ol:acetonitrile (70:30); flow rate=20 mL/min) to afford first eluting fraction (I-90-a) and second eluting fraction (I-90-b).

I-90-a: MS(ES): m/z 598.4 [M+H]$^+$; $^1$H NMR (DMSO-d$_6$, 400 MHz): δ 10.65 (s, 1H), 9.05 (s, 1H), 8.66 (s, 1H), 8.33 (s, 1H), 8.27-8.25, (d, J=8 Hz, 1H), 8.20 (s, 1H), 7.77 (s, 1H), 6.82-6.80 (m, 1H), 3.97 (s, 3H), 3.82 (bs, 1H), 3.74-3.71 (m, 1H), 3.67 (m, 3H), 3.47-3.40 (t, J=8 Hz, 1H), 2.69-2.67 (d, J=8 Hz, 1H), 2.47-2.42 (m, 2H), 2.16 (s, 3H), 1.99-1.94 (t, J=12 Hz, 1H), 1.74-1.69 (t, J=8 Hz, 1H).

I-90-b: MS(ES): m/z 598.4 [M+H]$^+$; $^1$H NMR (DMSO-d$_6$, 400 MHz): δ 10.65 (s, 1H), 9.05 (bs, 1H), 8.66 (s, 1H), 8.33 (s, 1H), 8.27, (d, J=4 Hz, 1H), 8.20 (s, 1H), 7.77 (s, 1H), 6.82-6.80 (m, 1H), 4.66-4.60 (m, 1H), 3.98 (s, 3H), 3.81 (bs, 1H), 3.74-3.71 (m, 1H), 3.67 (s, 3H), 3.45 (t, J=8 Hz, 1H), 2.68 (d, J=8 Hz, 1H), 2.47-2.43 (m, 2H), 2.16 (s, 3H), 1.94 (t, J=8 Hz, 1H), 1.72 (t, J=8 Hz, 1H).

Example 91: (R)-N-(4-((7-chloro-1-methyl-2-((2-(tetrahydrofuran-3-yl)-6-(trifluoromethyl)pyridin-4-yl)amino)-1H-imidazo[4,5-b]pyridin-6-yl)oxy)pyridin-2-yl)acetamide and (S)-N-(4-((7-chloro-1-methyl-2-((2-(tetrahydrofuran-3-yl)-6-(trifluoromethyl)pyridin-4-yl)amino)-1H-imidazo[4,5-b]pyridin-6-yl)oxy)pyridin-2-yl)acetamide

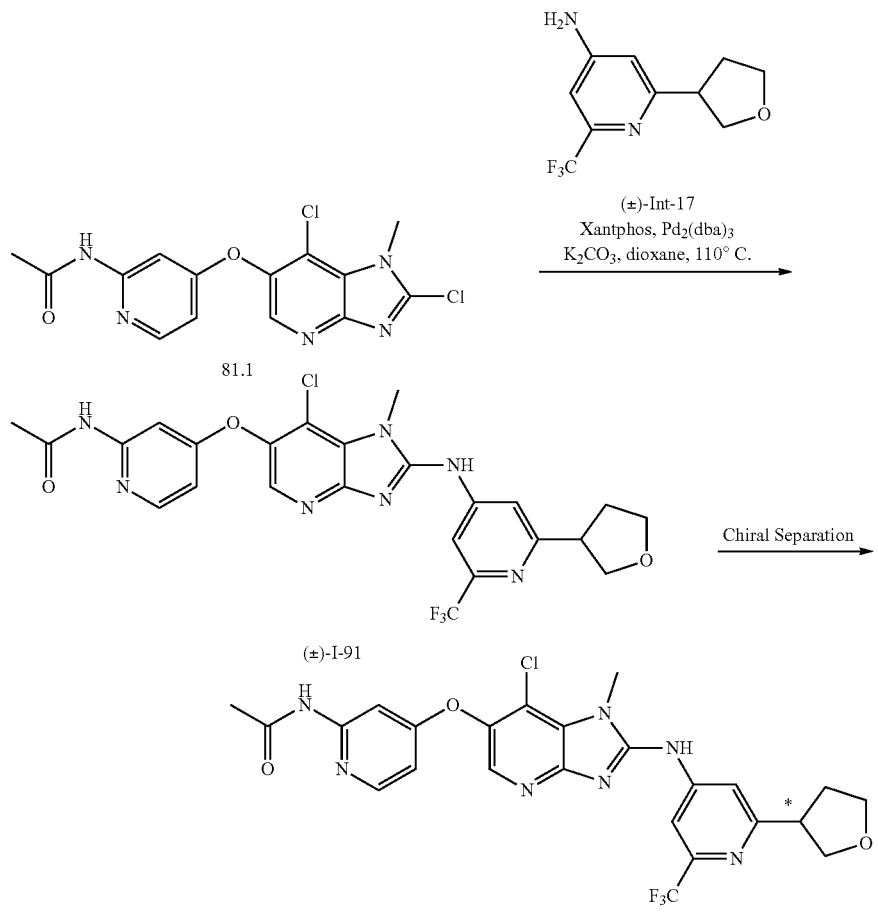

Synthesis of compound (±)-I-91. A mixture of 81.1 (0.120 g, 0.516 mmol, 1.0 equiv), (±)-Int-17 (0.145 g, 0.413 mmol, 0.5 equiv) and potassium carbonate (0.214 g, 1.55 mmol, 3 equiv) in 1,4-dioxane (5 mL) was degassed by bubbling through a stream of argon for 10 min. 4,5-Bis(diphenylphosphino)-9,9-dimethylxanthene (0.059 g, 0.103 mmol, 0.2 equiv) and tris(dibenzylideneacetone)dipalladium(0) (0.047 g, 0.051 mmol, 0.1 equiv) were added and degassed for 5 min. The reaction mixture was stirred at 120° C. for 3 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford (±)-I-91. MS(ES): m/z: 548.92 [M+H]$^+$.

I-91-a and I-91-b. The racemate was subjected to chiral HPLC separation: (column: CHIRALPAK IC (250 mm*21 mm, 5 µm); mobile phases: (A) 0.1% DEA in n-hexane (B) 0.1% DEA in propane-2-ol:acetonitrile (70:30); flow rate=20 mL/min) to afford first eluting fraction (I-91-a) and second eluting fraction (I-91-b).

I-91-a: MS(ES): m/z: 548.25 [M+H]$^+$; $^1$H NMR (DMSO-d$_6$, 400 MHz): δ 10.59 (s, 1H), 8.31 (s, 1H), 8.20 (s, 2H), 7.90 (s, 2H), 7.67 (s, 1H), 6.67 (m, 1H), 4.10 (m, 1H), 3.99 (s, 3H), 3.37 (m, 3H), 2.05 (s, 2H), 1.25 (m, 1H), 1.15 (m, 1H), 1.12 (m, 1H), 1.05 (m, 1H).

I-91-b: MS(ES): m/z: 548.25 [M+H]$^+$; $^1$H NMR (DMSO-d$_6$, 400 MHz): δ 10.59 (s, 1H), 8.31 (s, 1H), 8.20 (s, 2H), 7.90 (s, 2H), 7.67 (s, 1H), 6.67 (m, 1H), 4.10 (m, 1H), 3.99 (s, 3H), 3.37 (m, 3H), 2.05 (s, 2H), 1.25 (m, 1H), 1.15 (m, 1H), 1.12 (m, 1H), 1.05 (m, 1H).

Example 92: N-(4-((7-chloro-2-((4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)acetamide

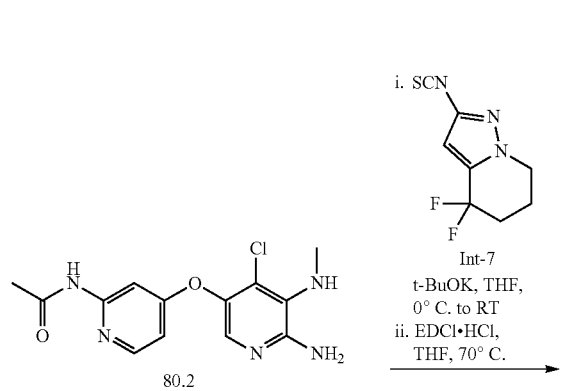

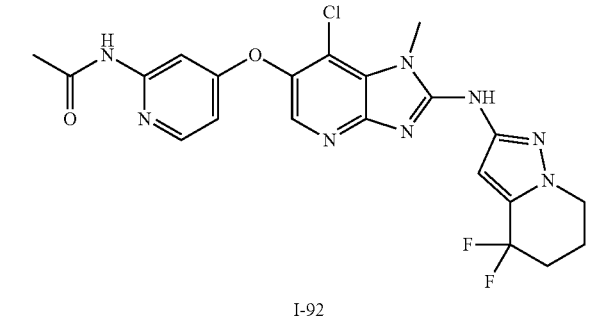

Synthesis of compound I-92. Compound I-92 was prepared from 80.2 and Int-7, following the procedure described in the synthesis of I-19. The product was purified by flash column chromatography on silica gel (CombiFlash®, 3.0% methanol in DCM) to afford I-92. MS(ES): m/z: 489.6 [M+H]$^+$ $^1$H NMR (DMSO-d$_6$, 400 MHz): δ 10.58 (s, 1H), 10.38 (s, 1H), 8.18 (d, J=4 Hz, 2H), 7.65 (s, 1H), 7.09 (s, 1H), 6.67-6.66 (m, 1H), 4.16 (bs, 2H), 3.96 (s, 3H), 2.46 (m, 2H), 2.36 (bs, 2H), 2.05 (bs, 4H).

Example 93: N-(4-((7-cyano-2-((4,4-difluoro-4,5,6,7-tetrahydropyrazolo[1,5-a]pyridin-2-yl)amino)-1-methyl-1H-imidazo[4,5-b]pyridin-6-yl)oxy)pyridin-2-yl)acetamide

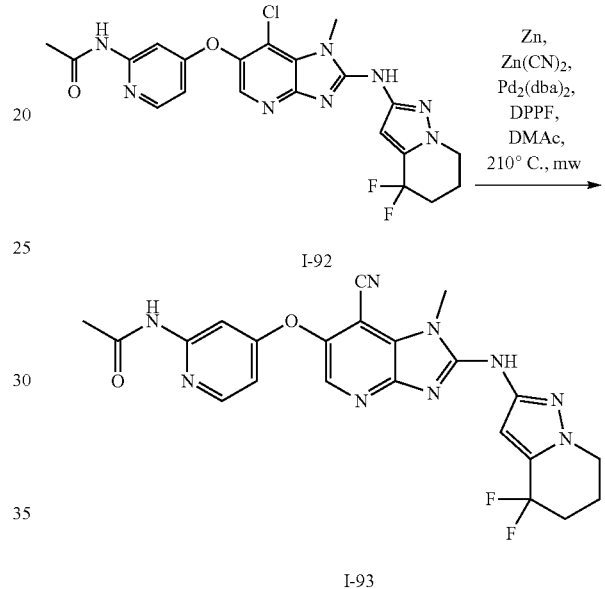

Synthesis of compound I-93. Compound I-93 was prepared from I-92, following the procedure described in the synthesis of 31.5. The product was purified by flash column chromatography on silica gel (CombiFlash®, 4.5% methanol in DCM). MS (ES): m/z 438.2 [M+H]$^+$; $^1$H NMR (DMSO-d$_6$, 400 MHz): δ 10.68-10.64 (d, 2H), 8.24-8.20 (m, 2H), 7.73 (bs, 1H), 7.09 (s, 1H), 6.74-6.73 (s, 1H), 4.16 (bs, 2H), 3.92 (s, 3H), 2.46 (m, 2H), 2.36 (bs, 2H), 2.05 (bs, 4H).

Example 94: N-(4-((7-chloro-2-((4-((dimethylamino)methyl)-3-(trifluoromethyl)phenyl)amino)-1-methyl-1H-imidazo[4,5-b]pyridin-6-yl)oxy)pyridin-2-yl)acetamide

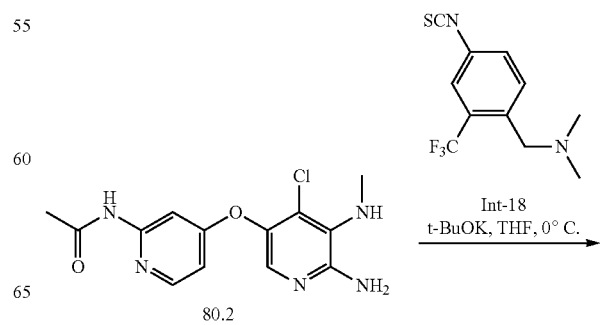

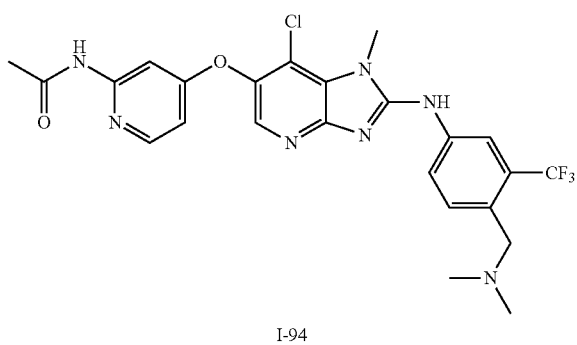

Synthesis of I-94. Compound I-94 was prepared from 80.2 and Int-18, following the procedure described in the synthesis of 3.7. The product was purified by flash column chromatography on silica gel (CombiFlash®, 3.9% methanol in DCM. MS(ES): m/z: 526.85 [M+H]⁺; ¹H NMR (DMSO-d₆, 400 MHz): δ 10.6 (s, 1H), 9.67 (s, 1H), 8.29 (s, 1H), 8.18 (t, J=6.8 Hz, 3H), 7.73 (d, J=8 Hz, 1H), 7.659 (s, 1H), 6.66 (t, J=8 Hz, 1H), 4.00 (s, 3H), 3.51 (s, 2H), 2.19 (s, 6H), 2.04 (s, 3H).

Example 95: (R)-N-(4-((7-cyano-1-methyl-2-((2-(tetrahydrofuran-3-yl)-6-(trifluoromethyl)pyridin-4-yl)amino)-1H-imidazo[4,5-b]pyridin-6-yl)oxy)pyridin-2-yl)acetamide and (S)-N-(4-((7-cyano-1-methyl-2-((2-(tetrahydrofuran-3-yl)-6-(trifluoromethyl)pyridin-4-yl)amino)-1H-imidazo[4,5-b]pyridin-6-yl)oxy)pyridin-2-yl)acetamide

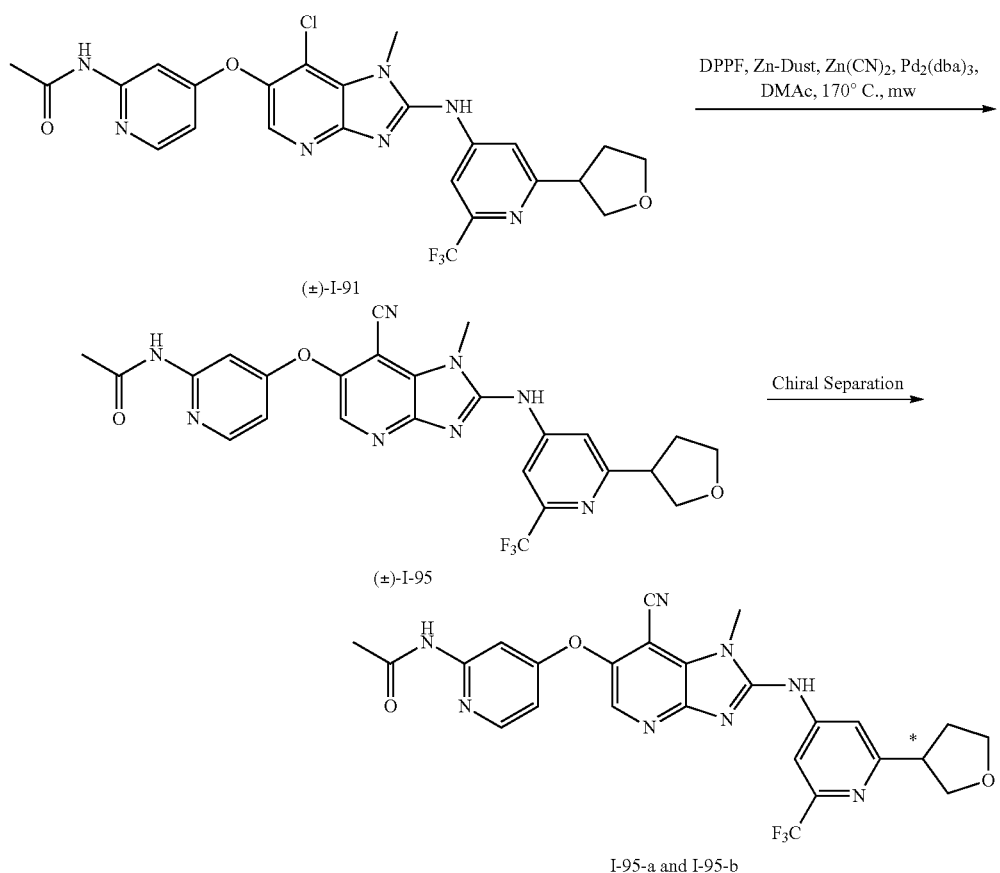

Synthesis of compound (±)-I-95. Compound (±)-I-95 was prepared from (±)-I-91, following the procedure described in the synthesis of (±)-I-74. The product was purified by flash column chromatography on silica gel (CombiFlash®, 2.5% methanol in DCM). MS(ES): m/z: 539.49 [M+H]⁺.

I-95-a and I-95-b. The racemate was subjected to chiral HPLC separation: (column: CHIRALPAK IC (250 mm*21 mm, 5 µm); mobile phases: (A) 0.1% DEA in n-hexane (B) 0.1% DEA in propan-2-ol:acetonitrile (70:30); flow rate=20 mL/min) to afford first eluting fraction (I-95-a) and second eluting fraction (I-95-b).

I-95-a: MS(ES): m/z: 539.22 [M+H]⁺; Chiral HPLC: 96.88%, ¹H NMR (DMSO-d₆, 400 MHz): δ 10.68 (s, 1H), 10.28 (s, 1H), 8.40 (s, 1H), 8.33 (s, 1H), 8.27 (d, J=4 Hz, 1H), 8.05 (s, 1H), 7.76 (s, 1H), 6.77 (s, 1H), 4.14 (m, 1H), 4.00 (s, 3H), 3.86-3.80 (m, 3H), 2.18-2.16 (m, 2H), 2.03 (m, 3H), 1.42 (s, 1H).

I-95-b: MS(ES): m/z: 539.22 [M+H]⁺, ¹H NMR (DMSO-d₆, 400 MHz): δ 10.68 (s, 1H), 10.28 (s, 1H), 8.40 (s, 1H), 8.33 (s, 1H), 8.27 (d, J=4 Hz, 1H), 8.05 (s, 1H), 7.76 (s, 1H), 6.77 (s, 1H), 4.14 (m, 1H), 4.00 (s, 3H), 3.86-3.80 (m, 3H), 2.18-2.16 (m, 2H), 2.03 (m, 3H), 1.42 (s, 1H).

Example 96: (S)-N-(4-((7-chloro-1-methyl-2-((3-((1-methylpyrrolidin-2-yl)methoxy)-5-(trifluoromethyl)phenyl)amino)-1H-imidazo[4,5-b]pyridin-6-yl)oxy)pyridin-2-yl)acetamide

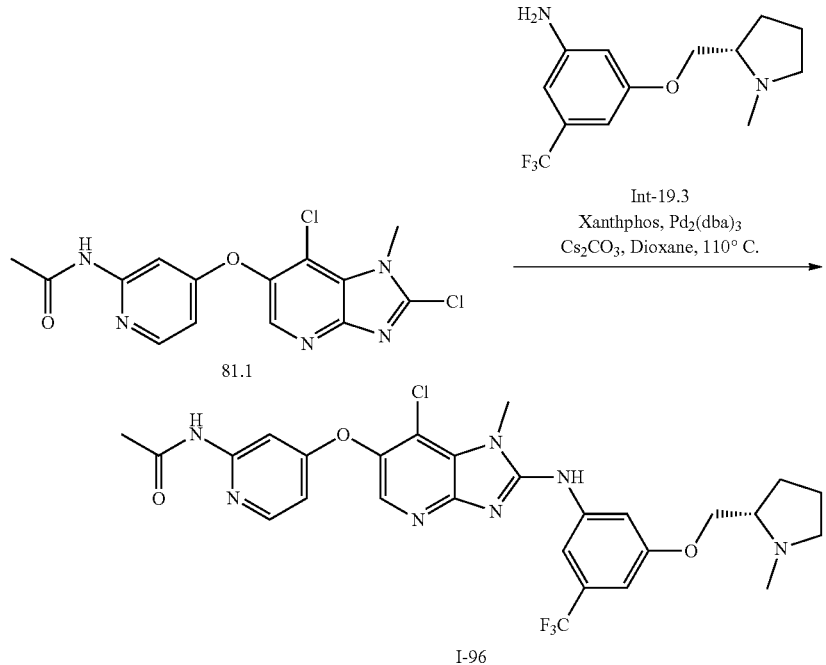

Synthesis of I-96. Compound I-96 was prepared from 81.1 and Int-19.3, following the procedure described in the synthesis of I-10. The product was purified by flash column chromatography on silica gel (CombiFlash®, 5.6% methanol in DCM). MS(ES): m/z: 588.41 [M–H]$^+$; $^1$H NMR (DMSO-d$_6$, 400 MHz): δ 10.61 (s, 1H), 9.70 (s, 1H), 8.21 (d, J=7.2 Hz, 2H), 8.01 (s, 1H), 7.90 (s, 1H), 7.66 (s, 1H), 6.98 (s, 1H), 6.69-6.67 (m, 1H), 4.186-4.130 (m, 1H), 4.02 (s, 3H), 3.18 (s, 1H), 2.59 (s, 3H), 2.05 (s, 5H), 1.82 (s, 4H).

Example 97: (R)-N-(4-((7-chloro-1-methyl-2-((3-((1-methylpyrrolidin-2-yl)methoxy)-5-(trifluoromethyl)phenyl)amino)-1H-imidazo[4,5-b]pyridin-6-yl)oxy)pyridin-2-yl)acetamide

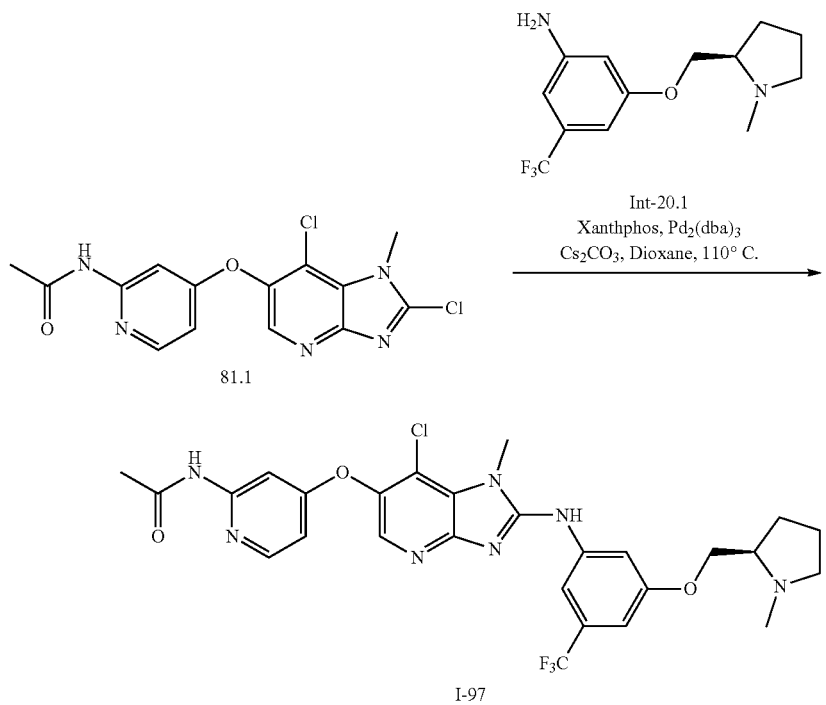

Synthesis of I-97. Compound I-97 was prepared from 81.1 and Int-20.1, following the procedure described in the synthesis of I-10. The product was purified by flash column chromatography on silica gel (CombiFlash®, 5.6% methanol in DCM). MS(ES): m/z: 592.2 [M+H]⁺; ¹H NMR (DMSO-d₆, 400 MHz): δ 10.60 (s, 1H), 9.69 (s, 1H), 8.22-8.20 (m, 2H), 8.00 (s, 1H), 7.89 (s, 1H), 7.67 (s, 1H), 6.98 (s, 1H), 6.69-6.67 (m, 1H), 4.17-4.12 (m, 2H), 4.02 (s, 3H), 2.47 (s, 3H), 2.05 (s, 4H), 1.93 (s, 1H), 1.81-1.74 (m, 3H), 1.69 (s, 1H).

Example 98: N-(4-((2-((1-(2-oxaspiro[3.3]heptan-6-yl)-5-(trifluoromethyl)-1H-pyrazol-3-yl)amino)-7-chloro-1-methyl-1H-imidazo[4,5-b]pyridin-6-yl)oxy)pyridin-2-yl)acetamide

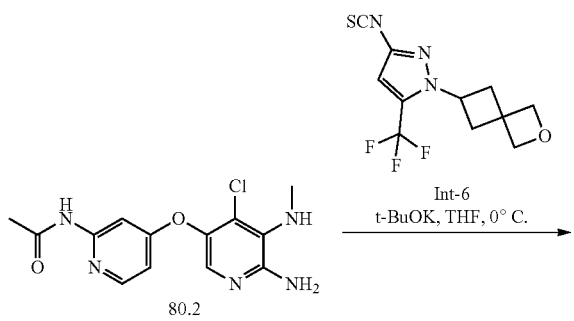

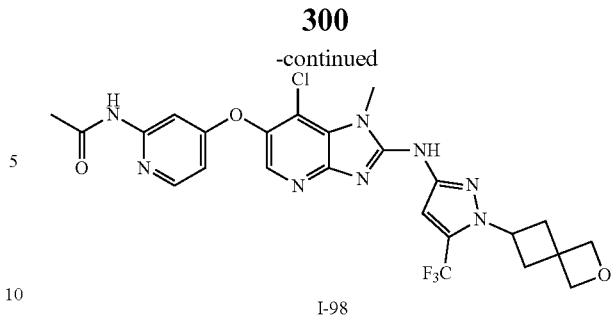

I-98

Synthesis of compound I-98. Compound I-98 was prepared from 80.2 and Int-6, following the procedure described in the synthesis of 3.7. The product was purified by flash column chromatography on silica gel (CombiFlash®, 5.0% methanol in DCM). MS(ES): m/z: 539.22 [M+H]⁺; ¹H NMR (DMSO-d₆, 400 MHz): δ 10.59 (s, 2H), 8.18 (d, J=8 Hz, 1H), 8.14 (s, 1H), 7.64 (s, 1H), 7.31 (s, 1H), 6.66 (d, J=4 Hz, 1H), 4.85 (m, 1H), 4.70 (s, 2H), 4.58 (s, 2H), 3.96 (s, 3H), 3.17 (s, 3H), 2.80 (d, J=8 Hz, 2H), 2.03 (s, 2H).

Example 99: (S)-N-(4-((7-chloro-1-methyl-2-((3-((1-methylpyrrolidin-3-yl)oxy)-5-(trifluoromethyl)phenyl)amino)-1H-imidazo[4,5-b]pyridin-6-yl)oxy)pyridin-2-yl)acetamide

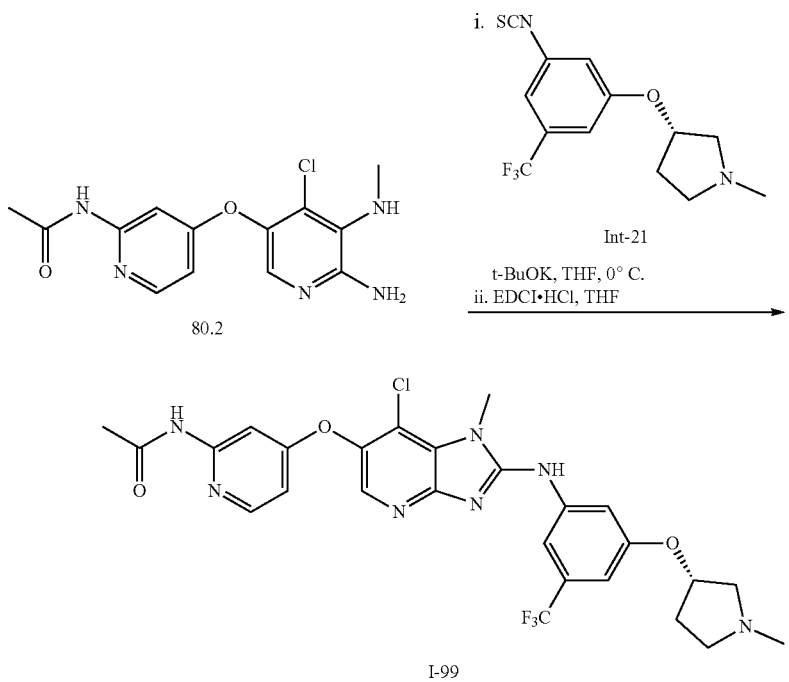

Synthesis of I-99. Compound I-99 was prepared from 80.2 and Int-21, following the procedure described in the synthesis of I-19. The product was purified by flash column chromatography on silica gel (CombiFlash®, 3.2% methanol in DCM). MS(ES): m/z: 576.3 [M+H]⁺, ¹H NMR (DMSO-d₆, 400 MHz): δ 10.60 (s, 1H), 9.69 (s, 1H), 8.20 (d, J=4.8 Hz, 2H), 7.98 (s, 1H), 7.85 (s, 1H), 7.65 (s, 1H), 6.87 (s, 1H), 6.79-6.65 (m, 1H), 5.03 (s, 1H), 4.12 (s, 3H), 2.73-2.67 (m, 4H), 2.45-2.41 (m, 5H), 2.04 (s, 3H).

Example 100: (R)-N-(4-((7-chloro-1-methyl-2-((3-((1-methylpyrrolidin-3-yl)oxy)(trifluoromethyl)phenyl)amino)-1H-imidazo[4,5-b]pyridin-6-yl)oxy)pyridin-2-yl)acetamide

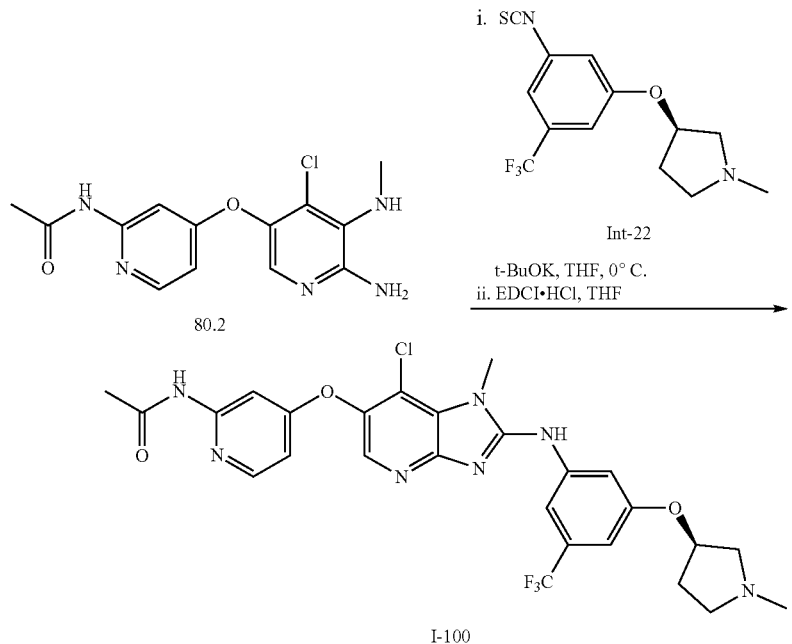

Synthesis of I-100. Compound I-100 was prepared from 80.2 and Int-22, following the procedure described in the synthesis of I-19. The product was purified by flash column chromatography on silica gel (CombiFlash®, 3.2% methanol in DCM) to afford I-100 (0.025 g, Yield: 19.08%). MS(ES): m/z: 574.8 [M–H]⁺, ¹H NMR (DMSO-$d_6$, 400 MHz): δ 10.61 (s, 1H), 9.70 (s, 1H), 8.21-8.20 (d, J=4.4 Hz, 2H), 7.99 (s, 1H), 7.86 (s, 1H), 7.67 (s, 1H), 6.88 (s, 1H), 6.68 (d, J=5.2, 1H), 5.03 (s, 1H), 4.02 (s, 3H), 2.97-2.86 (m, 3H), 2.40-2.41 (m, 5H), 2.05 (s, 3H), 1.93 (s, 1H).

Example 101: N-(4-((7-chloro-1-methyl-2-((3-(((1-methylazetidin-3-yl)oxy)methyl)-5-(trifluoromethyl)phenyl)amino)-1H-imidazo[4,5-b]pyridin-6-yl)oxy)pyridin-2-yl)acetamide

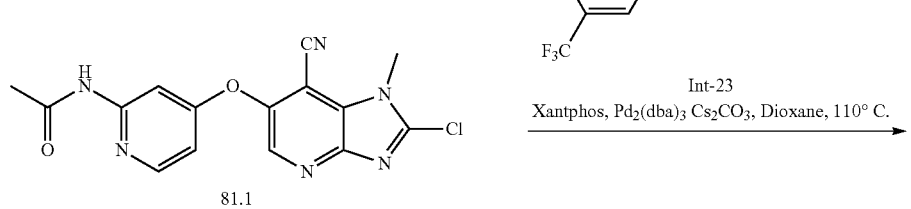

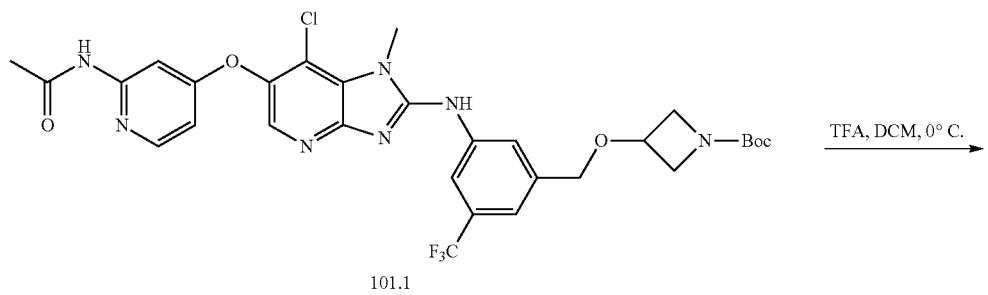

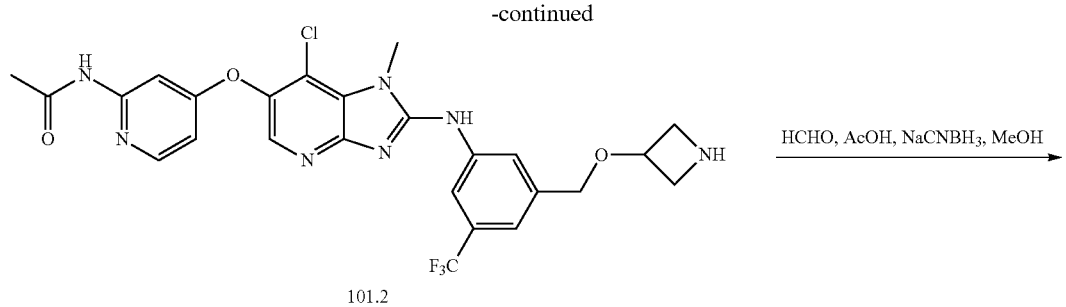

101.2

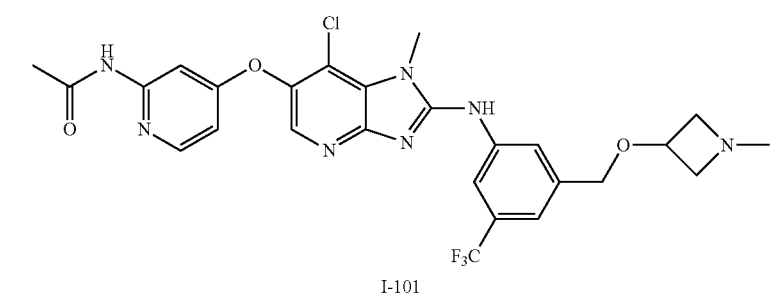

I-101

Synthesis of compound 101.1. Compound 101.1 was prepared from 81.1 and Int-23, following the procedure described in the synthesis of I-10. The product was purified by flash column chromatography on silica gel (CombiFlash®, 5.0% methanol in DCM. MS (ES): m/z 663.43 [M−H]+.

Synthesis of compound 101.2. To a solution of 101.1 (0.145 g, 0.219 mmol, 1.0 equiv) in DCM (5 mL) was added TFA (2.0 mL) dropwise at 0° C. The reaction mixture was stirred for 30 min. It was transferred into a saturated aqueous solution of sodium bicarbonate and extracted with 15% methanol in DCM. The combined organic layers were washed with brine, dried over anhydrous sodium sulfate, filtered, and concentrated under reduced pressure. The residue was further triturated with diethyl ether to afford 101.2. MS(ES): m/z 563.36 [M+H]+.

Synthesis of I-101. A solution of 101.2 (0.100 g, 0.177 mmol, 1.0 equiv), formaldehyde (37% in water, 0.043 g, 0.533 mmol, 3.0 equiv) and acetic acid (0.026 g, 0.444 mmol, 2.5 equiv) in 1,2-dichloroethane (6 mL) was stirred for 10 min and sodium triacetoxyborohydride (0.112 g, 0.533 mmol, 3.0 equiv) was added. The mixture was stirred for 15 min, transferred into a saturated aqueous solution of sodium bicarbonate and extracted with 15% methanol in DCM. The combined organic layers were washed with brine, dried over anhydrous sodium sulfate, filtered, and concentrated under reduced pressure. The residue was purified by flash column chromatography on silica gel (CombiFlash®, 18% methanol in DCM) to afford I-101. MS(ES): m/z: 576.16 [M+H]+, 1H NMR (DMSO-d6, 400 MHz): δ 10.60 (s, 1H), 9.80 (s, 1H), 8.36 (s, 1H), 8.20-8.13 (m, 3H), 7.66 (s, 1H), 7.34 (s, 1H), 6.67-6.65 (dd, J=2.4 Hz, 1H), 4.53 (s, 2H), 4.28 (t, J=5.6 Hz, 1H), 4.01 (s, 3H), 3.54 (s, 3H), 3.00 (s, 3H), 2.32 (s, 2H), 2.04 (s, 2H).

Example 102: (R)-N-(4-((7-chloro-1-methyl-2-((3-(1-methylpyrrolidin-2-yl)-5-(trifluoromethyl)phenyl)amino)-1H-imidazo[4,5-b]pyridin-6-yl)oxy)pyridin-2-yl)acetamide and (S)-N-(4-((7-chloro-1-methyl-2-((3-(1-methylpyrrolidin-2-yl)-5-(trifluoromethyl)phenyl)amino)-1H-imidazo[4,5-b]pyridin-6-yl)oxy)pyridin-2-yl)acetamide

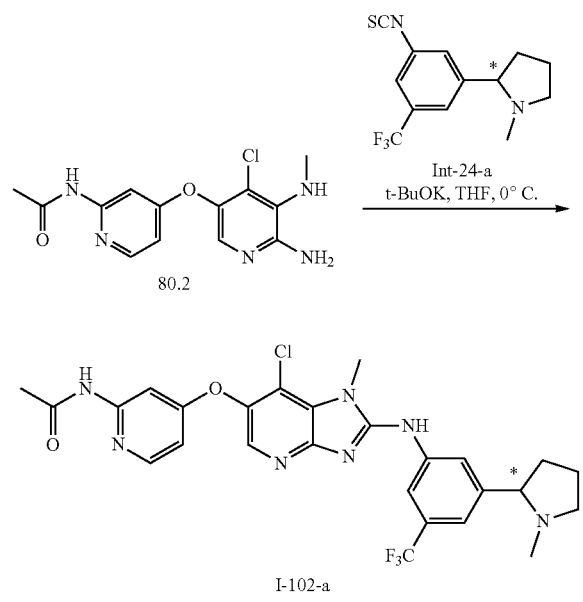

-continued

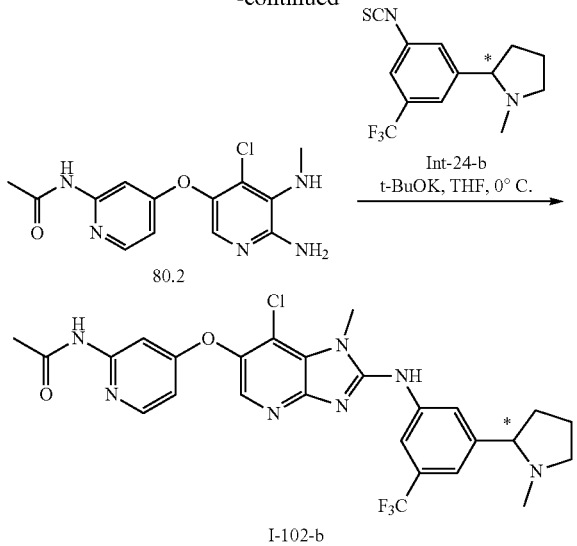

Synthesis of compound I-102-a. Compound I-102-a was prepared from 80.2 and Int-24-a, following the procedure described in the synthesis of 3.7. The product was purified by flash column chromatography on silica gel (Combi-Flash®, 5.0% methanol in DCM). MS(ES): m/z: 539.22 [M+H]$^+$; $^1$H NMR (DMSO-d$_6$, 400 MHz): δ 10.70 (s, 1H), 9.72 (s, 1H), 8.40 (s, 1H), 8.21-8.20 (d, J=4 Hz, 2H), 8.09 (s, 1H), 7.67 (s, 1H), 7.33 (s, 1H), 6.67 (s, 1H), 4.02 (s, 3H), 3.99 (m, 1H), 3.29-3.23 (m, 3H), 2.34-2.30 (m, 2H), 2.05 (s, 3H), 1.89 (m, 2H), 1.84 (m, 2H).

Synthesis of compound I-102-b. Compound I-102-b was prepared from 80.2 and Int-24-b, following the procedure described in the synthesis of 3.7. The product was purified by flash column chromatography on silica gel (Combi-Flash®, 5.0% methanol in DCM). MS(ES): m/z: 539.22 [M+H]$^+$; $^1$H NMR (DMSO-d$_6$, 400 MHz): δ 10.70 (s, 1H), 9.72 (s, 1H), 8.40 (s, 1H), 8.21 (d, J=4 Hz, 2H), 8.09 (s, 1H), 7.67 (s, 1H), 7.33 (s, 1H), 6.67 (s, 1H), 4.02 (s, 3H), 3.99 (m, 1H), 3.29-3.23 (m, 3H), 2.34-2.30 (m, 2H), 2.05 (s, 3H), 1.89 (m, 2H), 1.84 (m, 2H).

Example 103: N-(4-((7-chloro-1-methyl-2-((3-((1-methylazetidin-3-yl)oxy)-5-(trifluoromethyl)phenyl)amino)-1H-imidazo[4,5-b]pyridin-6-yl)oxy)pyridin-2-yl)acetamide

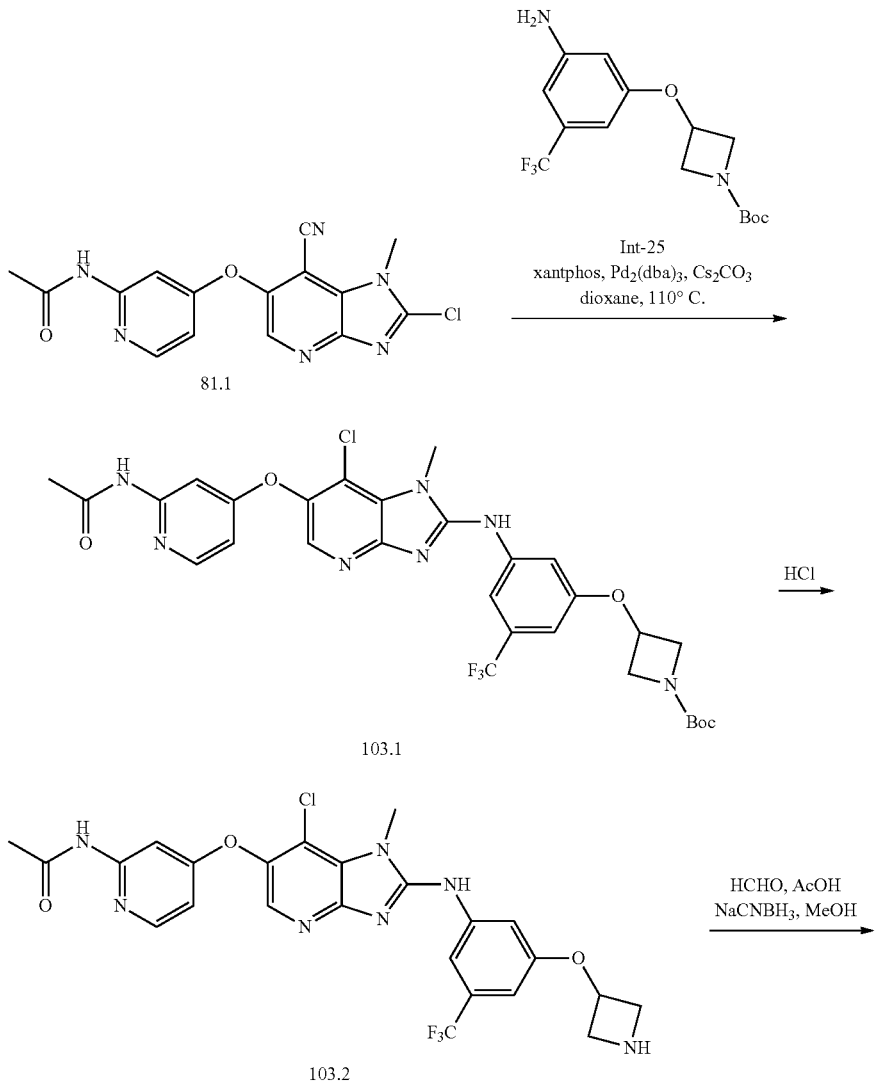

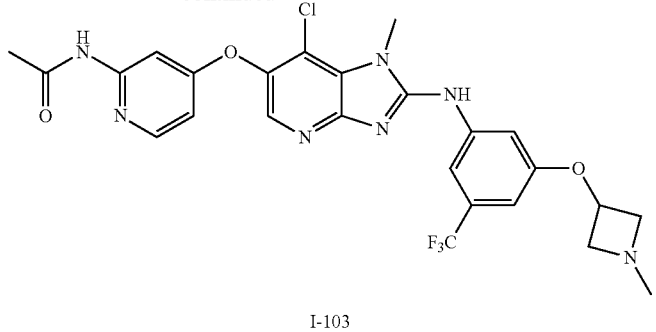

I-103

Synthesis of compound 103.1. Compound 103.1 was prepared from 81.1 and Int-25, following the procedure described in the synthesis of I-10. The product was purified by flash column chromatography on silica gel (CombiFlash®, 5.3% methanol in DCM). MS(ES): m/z: 649.04 [M−H]+.

Synthesis of compound 103.2. To a solution of 103.1 (0.090 g, 3.32 mmol, 1.0 equiv) in DCM (3 mL) at 0° C. and added a solution of HCl in dioxane (4 M, 1.0 mL). The reaction mixture was stirred at room temperature for 1 h. It was transferred into ice-water and neutralized with sodium bicarbonate and was extracted with DCM. The combined organic layers were washed with brine, dried over anhydrous sodium sulfate, filtered, and concentrated under reduced pressure to give 103.2. It was used as in the next step without purification. MS(ES): m/z: 548.92 [M+H]+.

Synthesis of I-103. Compound I-103 was prepared from 103.2, following the procedure described in the synthesis of I-101. The product was purified by flash column chromatography on silica gel (CombiFlash®, 4.2% methanol in DCM). MS(ES): m/z: 562.95 [M+H]+; $^1$H NMR (DMSO-$d_6$, 400 MHz): δ 10.60 (s, 1H), 9.81 (s, 1H), 8.20 (d, J=3.6 Hz, 2H), 7.96 (s, 1H), 7.90 (s, 1H), 7.66 (s, 1H), 6.79 (s, 1H), 6.66-6.67 (m, 1H), 4.91-4.89 (m, 1H), 4.02 (s, 3H), 3.92 (s, 2H), 3.19 (s, 3H), 2.39 (s, 3H), 2.04 (s, 3H).

Example 104: N-(4-((7-cyano-1-methyl-2-((5-(1,1,1-trifluoro-2-methylpropan-2-yl)isoxazol-3-yl)amino)-1H-imidazo[4,5-b]pyridin-6-yl)oxy)pyridin-2-yl)acetamide

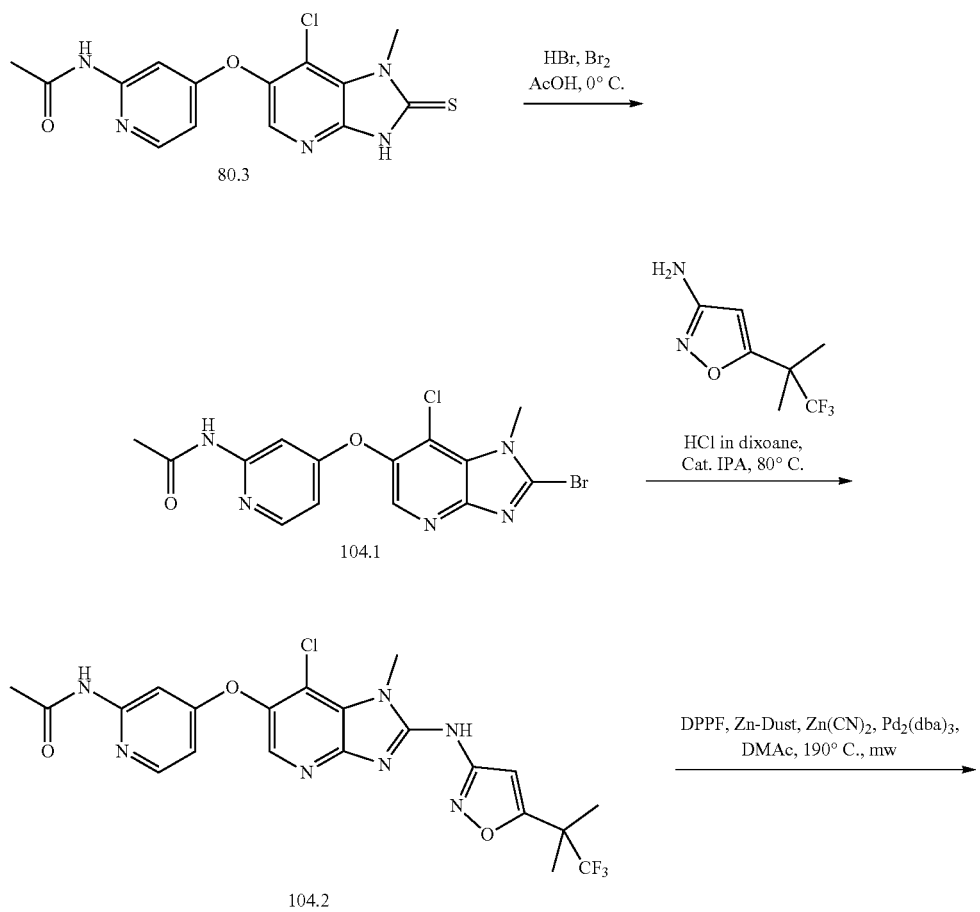

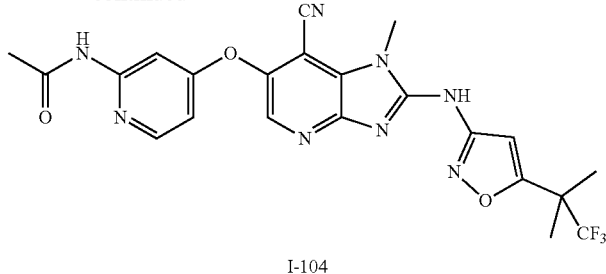

I-104

Synthesis of compound 104.1. To a solution of 80.3 (0.110 g, 0.314 mmol, 1.0 equiv) in acetic acid (5 mL) was added aqueous hydrobromic acid (0.037 g, 0.471 mmol, 1.5 equiv) at 0° C. followed by bromine (0.200 g, 1.25 mmol, 4.0 equiv) and reaction mixture was stirred for 10 min. It was transferred into a saturated aqueous solution of sodium bicarbonate, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford 104.1. MS (ES): m/z 397.6 [M+H]$^+$.

Synthesis of compound 104.2. To a solution of 104.1 (0.120 g, 0.320 mmol, 1.0 equiv) and 5-(1,1,1-trifluoro-2-methylpropan-2-yl)isoxazol-3-amine (0.117 g, 0.605 mmol, 2.0 equiv) in isopropyl alcohol (8 mL) was added hydrochloric acid in 1,4-dioxane (4 M, 0.5 mL). The reaction mixture was stirred at 80° C. for 16 h. It was cooled to room temperature, transferred into water, basified using aqueous sodium bicarbonate solution and extracted with ethyl acetate. The combined organic layers were washed with brine, dried over anhydrous sodium sulfate, filtered, and concentrated under reduced pressure. The residue was purified by flash column chromatography on silica gel (CombiFlash®, 1.9% methanol in DCM) to afford 104.2. MS(ES): m/z: 510.87 [M]$^+$.

Synthesis of I-104. A mixture of 104.2 (0.070 g, 0.137 mmol, 1.0 equiv), zinc dust (0.0019 g, 0.027 mmol, 0.2 equiv) and zinc cyanide (0.080 g, 0.068 mmol, 0.5 equiv) in dimethylacetamide (5 mL) was degassed by bubbling through a stream of argon for 10 min. 1,1'-Ferrocenediyl-bis(diphenylphosphine) (0.023 g, 0.041 mmol, 0.3 equiv) and tris(dibenzylideneacetone)dipalladium(0) (0.025 g, 0.027 mmol, 0.2 equiv) were added and degassed for 5 min. The reaction mixture was stirred at 190° C. in a microwave reactor for 3 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.2% methanol in DCM) to afford I-104. MS(ES): m/z: 499.21 [M+H]$^+$; $^1$H NMR (DMSO-$d_6$, 400 MHz): δ 10.95 (s, 1H), 10.62 (s, 1H), 8.19 (d, J=8 Hz, 2H), 7.64 (s, 1H), 7.25 (bs, 1H), 6.66 (d, J=4 Hz, 1H), 3.95 (s, 3H), 2.04 (s, 3H), 1.61 (s, 6H).

Example 105: N-(4-((7-cyano-2-((4-((dimethylamino)methyl)-3-(trifluoromethyl)phenyl)amino)-1-methyl-1H-imidazo[4,5-b]pyridin-6-yl)oxy)pyridin-2-yl)acetamide

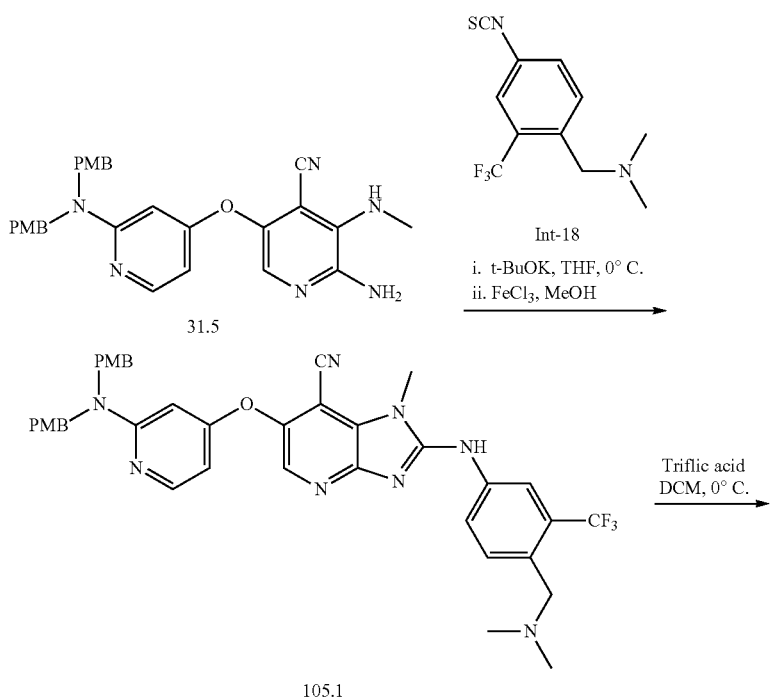

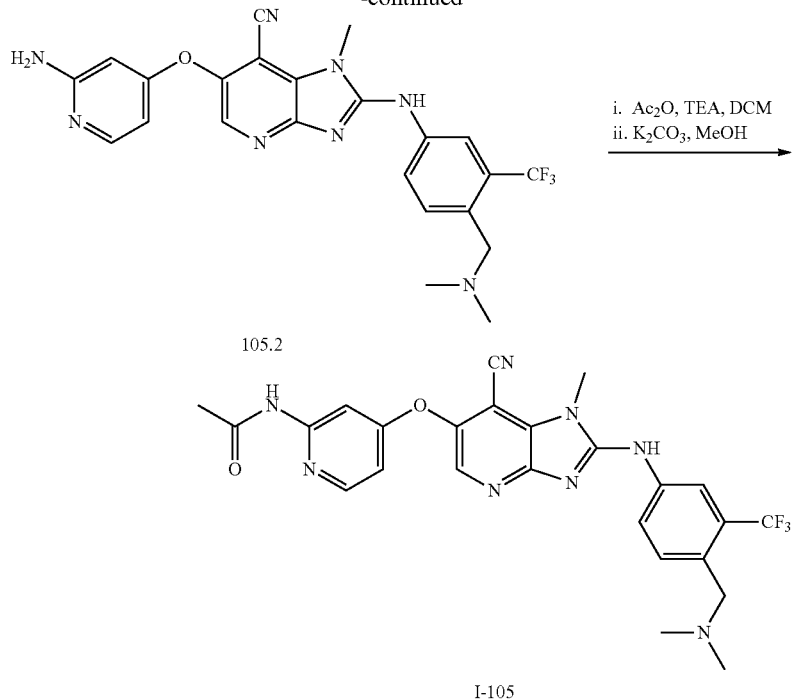

Synthesis of compound 105.1. Compound 105.1 was prepared from 31.5 and Int-18, following the procedure described in the synthesis of 40.1. The product was purified by flash column chromatography on silica gel (CombiFlash®, 3.9% methanol in DCM). MS(ES): m/z 723.77 [M+H]$^+$.

Synthesis of compound 105.2. Compound 105.2 was prepared from 105.1, following the procedure described in the synthesis of 40.2. The product was purified by flash column chromatography on silica gel (CombiFlash®, 3.9% methanol in DCM). MS(ES): m/z 483.47 [M+H]$^+$.

Synthesis of I-105. To a solution of 105.2 (0.04 g, 0.082 mmol, 1.0 equiv) in DCM (5 mL) was added acetic anhydride (0.016 mg, 0.16 mmol, 2.0 equiv) and triethylamine (0.2 mL, 0.16 mmol, 2.0 equiv) at 0° C. The reaction mixture was allowed to stir at room temperature for 1 h. It was transferred into water and extracted with DCM. The combined organic layers were washed with brine, dried over anhydrous sodium sulfate, filtered, and concentrated under reduced pressure. The residue was stirred with methanol and potassium carbonate for 30 min at room temperature. It was transferred into ice-water and extracted with DCM. The combined organic layers were washed with brine, dried over anhydrous sodium sulfate, filtered, and concentrated under reduced pressure. The residue was purified by a reverse phase column to afford I-105. MS(ES): m/z 525.51 [M+H]$^+$; $^1$H NMR (DMSO-$d_6$, 400 MHz): δ 10.67 (s, 1H), 8.31 (s, 1H), 8.22 (d, J=8 Hz, 4H), 7.76-7.74 (d, J=7.8 Hz, 2H), 6.74 (m, J=8 Hz, 4H), 3.97 (s, 3H), 3.51 (s, 2H), 2.20 (s, 6H), 2.06 (s, 3H).

Example 106: N-(4-((2-((1-(2-oxaspiro[3.3]heptan-6-yl)-5-(trifluoromethyl)-1H-pyrazol-3-yl)amino)-7-cyano-1-methyl-1H-imidazo[4,5-b]pyridin-6-yl)oxy)pyridin-2-yl)acetamide

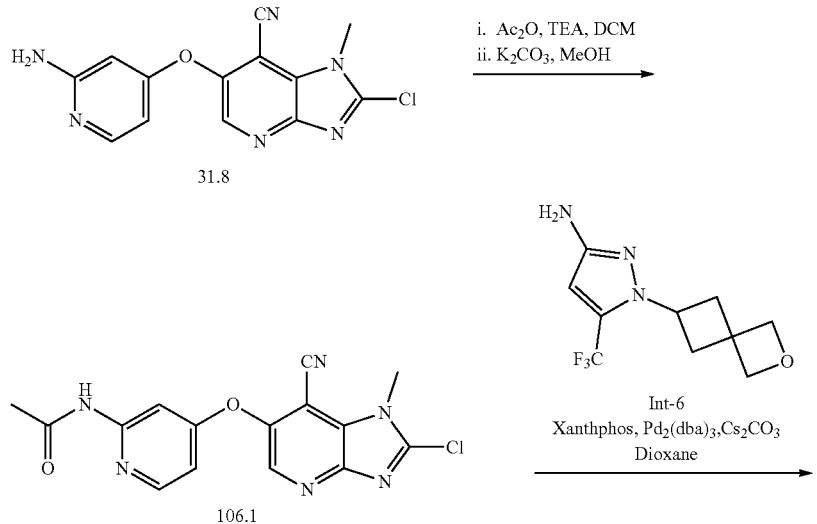

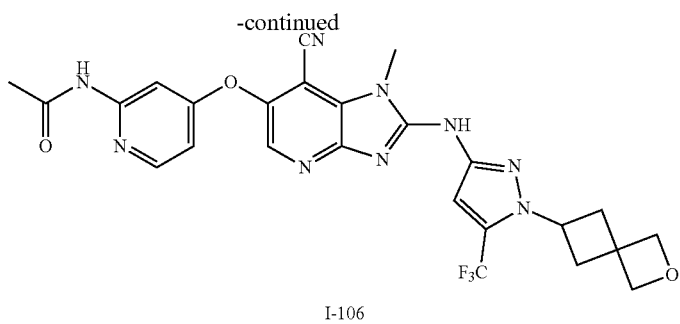

I-106

Synthesis of compound 106.1. Compound 106.1 was prepared from 31.8, following the procedure described in the synthesis of I-105. The product was purified by flash column chromatography on silica gel (CombiFlash®, 2.8% methanol in DCM). MS(ES): m/z: 343.74 [M+H]⁺.

Synthesis of I-106. Compound I-106 was prepared from 106.1 and Int-6, following the procedure described in the synthesis of I-10. The product was purified by flash column chromatography on silica gel (CombiFlash®, 3.5% methanol in DCM). MS(ES): m/z: 554.21 [M+H]⁺; $^1$H NMR (DMSO-d$_6$, 400 MHz): δ 10.62 (s, 1H), 8.21 (d, J=5.6 Hz, 1H), 8.01 (bs, 2H), 7.68 (s, 1H), 7.33 (s, 1H), 6.69-6.59 (m, 1H), 4.69 (s, 4H), 4.32 (s, 1H), 3.76 (bs, 3H), 2.73-2.69 (m, 4H), 2.06 (s, 3H).

Example 107: N-(4-((2-((1-(7-oxaspiro[3.5]nonan-2-yl)-5-(trifluoromethyl)-1H-pyrazol-3-yl)amino)-7-chloro-1-methyl-1H-imidazo[4,5-b]pyridin-6-yl)oxy)pyridin-2-yl)-2-methoxyacetamide

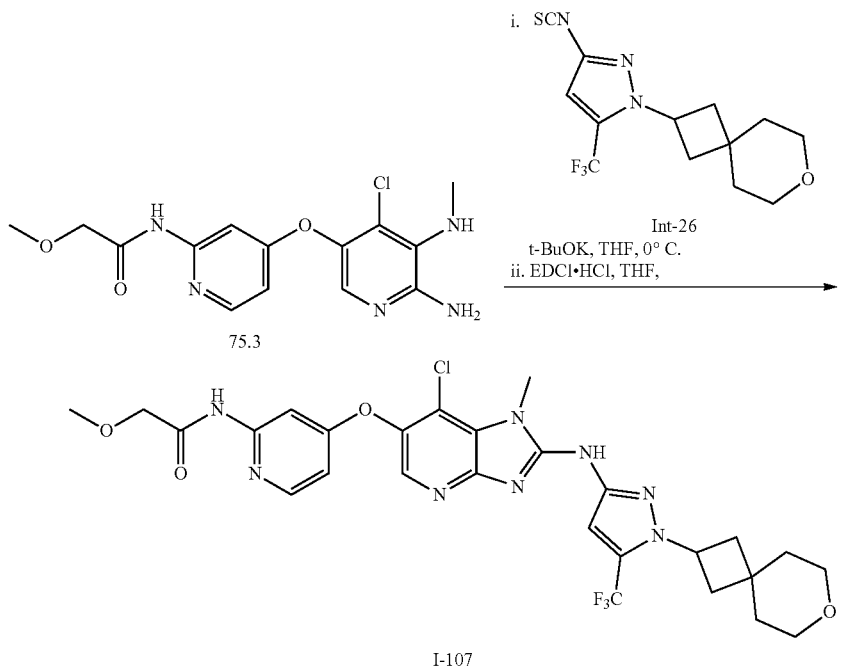

Synthesis of I-107. Compound I-107 was prepared from 75.3 and Int-26, following the procedure described in the synthesis of I-19. The product was purified by flash column chromatography on silica gel (CombiFlash®, 1.5-1.8% methanol in DCM). MS(ES): m/z: 621.31 [M+H]⁺; $^1$H NMR (DMSO-d$_6$, 400 MHz): δ 10.53 (s, 1H), 10.11 (s, 1H), 8.22-8.16 (m, 2H), 7.64 (s, 1H), 7.34 (s, 1H), 6.73 (s, 1H), 4.94-4.92 (d, J=8.8 Hz, 1H), 4.03-3.99 (m, 6H), 3.58 (s, 2H), 3.51 (s, 2H), 3.33 (s, 3H), 2.52 (s, 3H), 1.71 (s, 2H), 1.63 (s, 2H).

Example 108: (R)-N-(4-((7-chloro-1-methyl-2-((4-(1-methylpyrrolidin-2-yl)-3-(trifluoromethyl)phenyl)amino)-1H-imidazo[4,5-b]pyridin-6-yl)oxy)pyridin-2-yl)acetamide and (S)-N-(4-((7-chloro-1-methyl-2-((4-(1-methylpyrrolidin-2-yl)-3-(trifluoromethyl)phenyl)amino)-1H-imidazo[4,5-b]pyridin-6-yl)oxy)pyridin-2-yl)acetamide

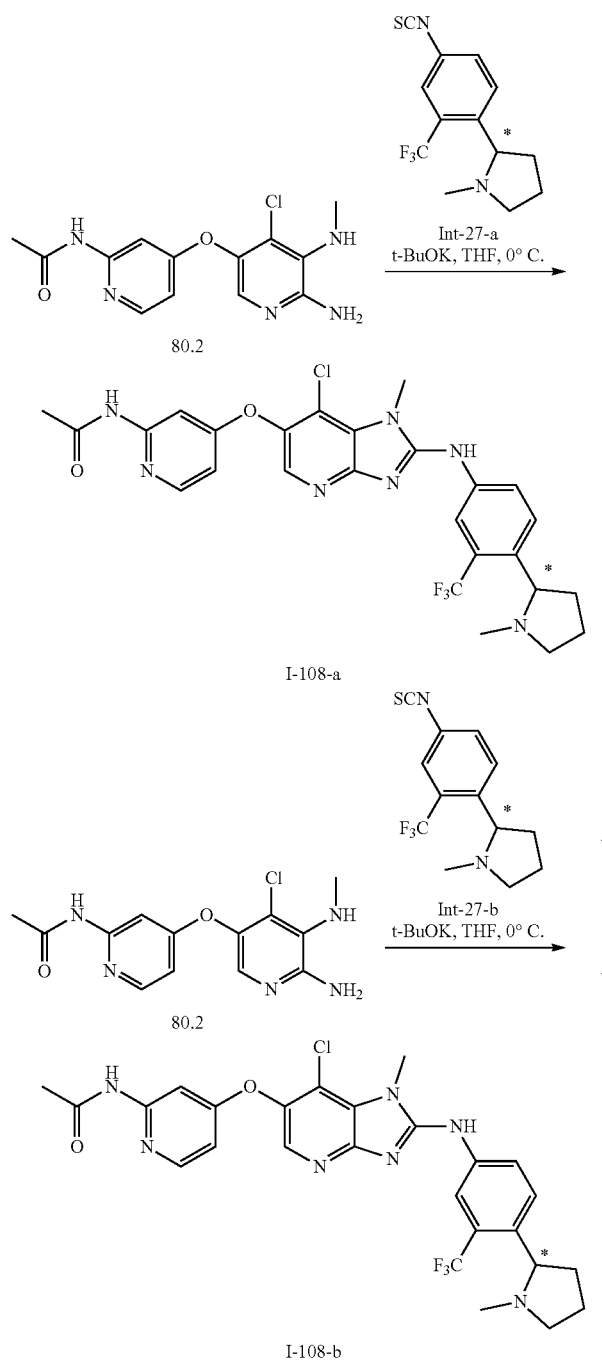

Synthesis of I-108-a. Compound I-108-a was prepared from 80.2 and Int-27-a, following the procedure described in the synthesis of 3.7. The product was purified by flash column chromatography on silica gel (CombiFlash®, 2.8% methanol in DCM). MS(ES): m/z: 559.98 [M+H]$^+$; $^1$H NMR (DMSO-d$_6$, 400 MHz): δ 10.59 (s, 1H), 9.71 (s, 1H), 8.29 (s, 1H), 8.21-8.18 (m, 3H), 7.91 (d, J=8.4 Hz, 1H), 7.67 (s, 1H), 6.68 (t, J=5.2 Hz, 1H), 4.01 (s, 3H), 3.29 (bs, 1H), 2.34-2.16 (m, 4H), 2.05 (m, 4H), 1.93-1.83 (m, 3H), 1.61 (bs, 1H).

Synthesis of I-108-b. Compound I-108-b was prepared from 80.2 and Int-27-b, following the procedure described in the synthesis of 3.7. The product was purified by flash column chromatography on silica gel (CombiFlash®, 2.9% methanol in DCM). MS(ES): m/z: 559.98 [M+H]$^+$; $^1$H NMR (DMSO-d$_6$, 400 MHz): δ 10.60 (s, 1H), 9.69 (s, 1H), 8.27 (s, 1H), 8.20-8.16 (m, 3H), 7.90 (d, J=8.4, 1H), 7.65 (s, 1H), 6.68-6.65 (dd, J=2.0 Hz, 1H), 4.00 (s, 3H), 3.24 (bs, 1H), 2.20-2.13 (m, 4H), 2.04 (m, 4H), 1.91-1.83 (m, 3H), 1.59 (bs, 1H).

Example 109: (R)-N-(4-((7-cyano-1-methyl-2-((4-(1-methylpyrrolidin-2-yl)-3-(trifluoromethyl)phenyl)amino)-1H-imidazo[4,5-b]pyridin-6-yl)oxy)pyridin-2-yl)acetamide and (S)-N-(4-((7-cyano-1-methyl-2-((4-(1-methylpyrrolidin-2-yl)-3-(trifluoromethyl)phenyl)amino)-1H-imidazo[4,5-b]pyridin-6-yl)oxy)pyridin-2-yl)acetamide

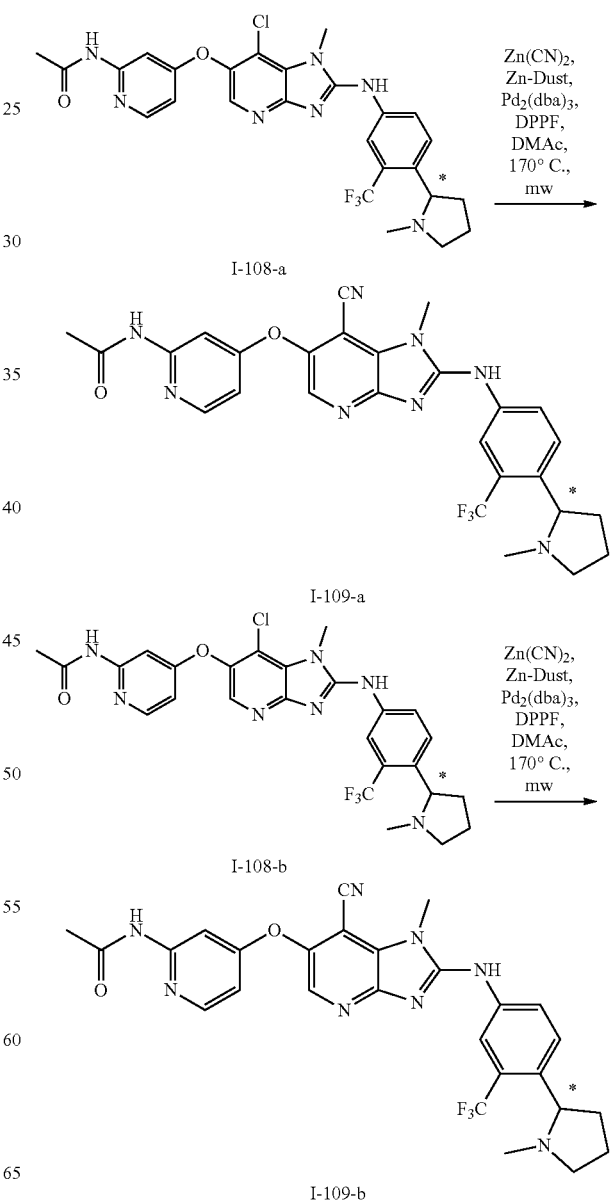

Synthesis of I-109-a Compound I-109-a was prepared from I-108-a, following the procedure described in the synthesis of (±)-I-74. The product was purified by flash column chromatography on silica gel (CombiFlash®, 3.3% methanol in DCM). MS (ES): m/z 551.4, [M+H]$^+$; $^1$H NMR (DMSO-d$_6$, 400 MHz): δ 10.66 (s, 1H), 9.96 (s, 1H), 8.30 (s, 1H), 8.26-8.21 (m, 3H), 7.91 (d, J=8.4 Hz, 1H), 7.76 (s, 1H), 6.76 (d, J=3.6 Hz, 1H), 3.98 (s, 3H), 3.25 (bs, 1H), 2.26-2.21 (m, 4H), 1.97 (m, 4H), 1.90-1.80 (m, 3H), 1.51 (bs, 1H).

Synthesis of I-109-b. Compound I-109-b was prepared from I-108-b, following the procedure described in the synthesis of (±)-I-74. The product was purified by flash column chromatography on silica gel (CombiFlash®, 3.4% methanol in DCM). MS (ES): m/z 551.3, [M+H]$^+$; $^1$H NMR (DMSO-d$_6$, 400 MHz): δ 10.66 (s, 1H), 9.94 (s, 1H), 8.30 (s, 1H), 8.26-8.21 (m, 3H), 7.92 (d, J=8.4 Hz, 1H), 7.76 (s, 1H), 6.76 (d, J=3.6 Hz, 1H), 3.98 (s, 3H), 3.25 (bs, 1H), 2.26-2.21 (m, 4H), 1.97 (m, 4H), 1.90-1.80 (m, 3H), 1.51 (bs, 1H).

Example 110: N-(4-((2-(((1-(7-oxaspiro[3.5]nonan-2-yl)-5-(trifluoromethyl)-1H-pyrazol-3-yl)amino)-7-cyano-1-methyl-1H-imidazo[4,5-b]pyridin-6-yl)oxy)pyridin-2-yl)-2-methoxyacetamide

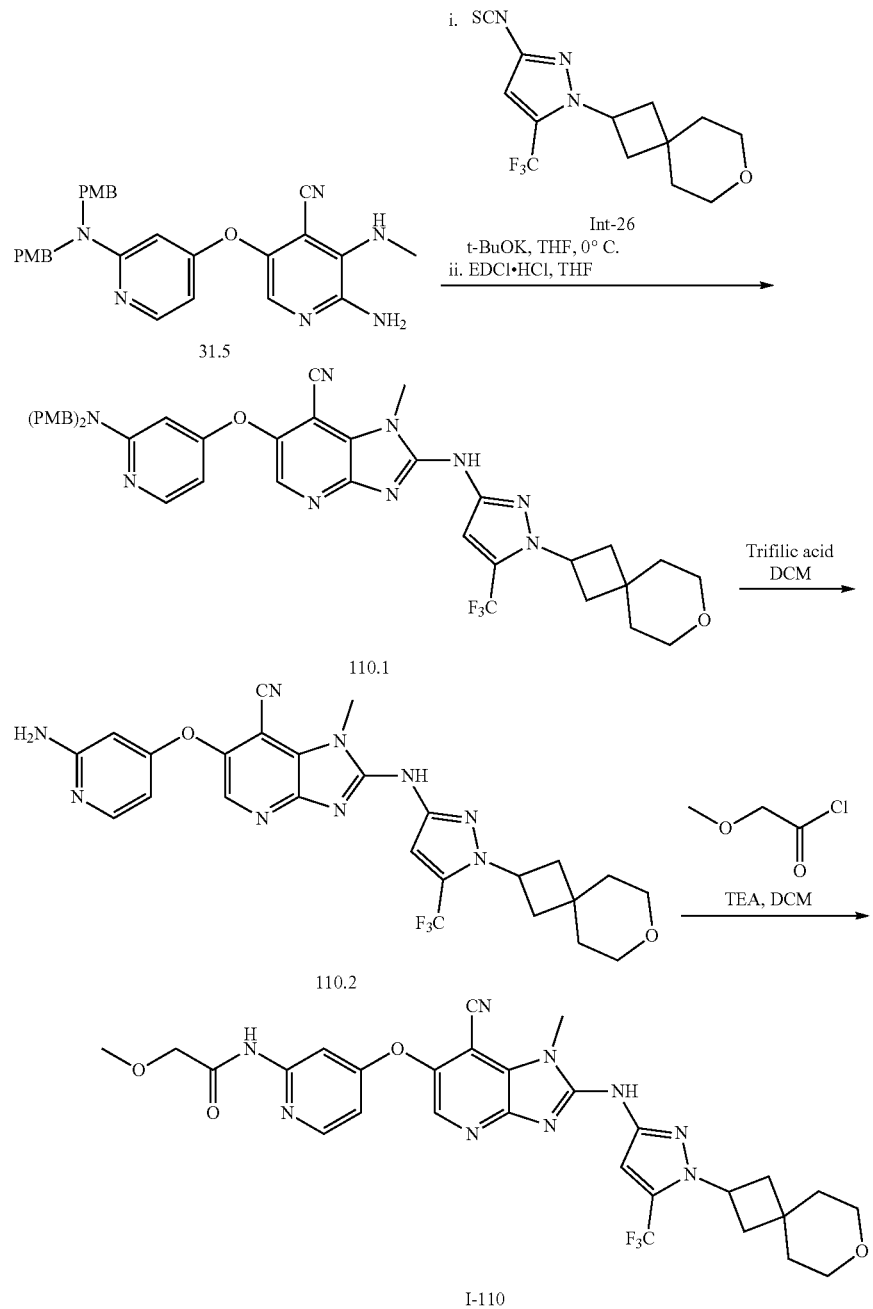

Synthesis of compound 110.1. Compound 110.1 was prepared from 31.5 and Int-26, following the procedure described in the synthesis of I-19. The product was purified by flash column chromatography on silica gel (Combi-Flash®, 38-48% ethyl acetate in hexane). MS(ES): m/z 780.83 [M+H]$^+$.

Synthesis of compound 110.2. Compound 110.2 was prepared from 110.1, following the procedure described in the synthesis of 40.2. The product was purified by flash column chromatography on silica gel (CombiFlash®, 45-55% methanol in DCM). MS(ES): m/z 540.52 [M+H]$^+$.

Synthesis of I-110. To a solution of 110.2 (0.080 g, 0.148 mmol, 1.0 equiv) and triethylamine (2.0 mL) in DCM (5 mL) was added 2-methoxyacetyl chloride (0.024 g, 0.222 mmol, 1.5 equiv). The reaction mixture was stirred at room temperature for 30 min. It was transferred into water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 1.5-1.8% methanol in DCM) to afford I-110. MS(ES): m/z: 612.41 [M+H]$^+$, $^1$H NMR (DMSO-d$_6$, 400 MHz): δ 10.83 (s, 1H), 10.21 (s, 1H), 8.26-8.24 (m, 2H), 7.72 (s, 1H), 7.34 (s, 1H), 6.79 (d, J=3.6 Hz, 1H), 4.96-4.92 (m, 1H), 4.04 (s, 3H), 3.95 (s, 3H), 3.57-3.50 (m, 4H), 3.34 (s, 2H), 2.50 (s, 4H), 1.70 (s, 2H), 1.62 (s, 2H).

Example 111: N-(4-((7-chloro-1-methyl-2-((2-(pyr-rolidin-1-yl)-6-(trifluoromethyl)pyridin-4-yl)amino)-1H-imidazo[4,5-b]pyridin-6-yl)oxy)pyridin-2-yl)acetamide

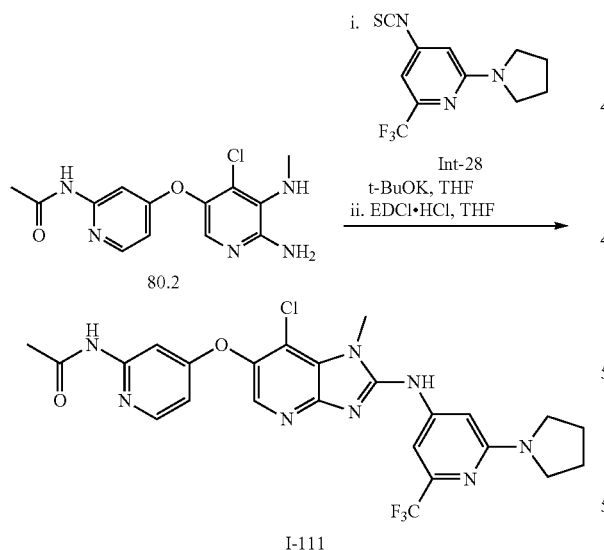

Synthesis of compound I-111. Compound I-111 was prepared from 80.2 and Int-28, following the procedure described in the synthesis of I-19. The product was purified by flash column chromatography on silica gel (Combi-Flash®, 85-90% ethyl acetate in hexane). MS(ES): m/z: 547.21 [M+H]$^+$; $^1$H NMR (DMSO-d$_6$, 400 MHz): δ 10.60 (s, 1H), 9.82 (s, 1H), 8.22-8.19 (m, 2H), 7.66 (s, 1H), 7.59 (s, 1H), 7.33 (s, 1H), 6.67 (d, J=3.6 Hz, 1H), 4.01 (s, 3H), 3.46 (s, 3H), 2.50 (s, 4H), 2.01 (s, 4H).

Example 112: N-(4-((7-cyano-2-((4,4-dimethyl-6,7-dihydro-4H-pyrazolo[5,1-c][1,4]oxazin-2-yl)amino)-1-methyl-1H-imidazo[4,5-b]pyridin-6-yl)oxy)pyridin-2-yl)acetamide

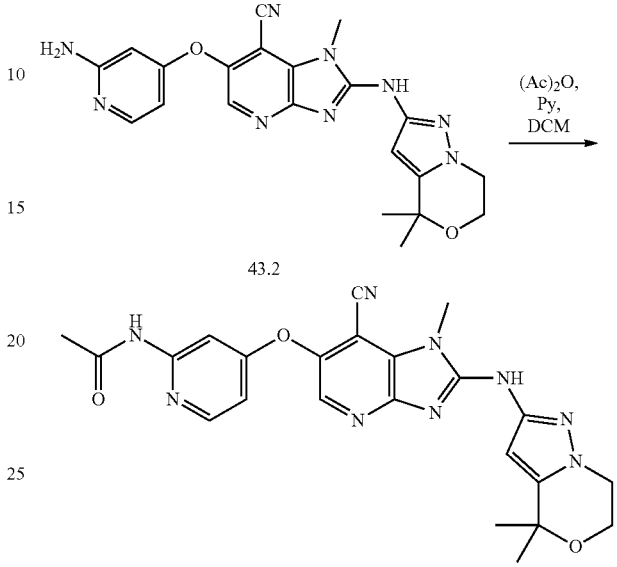

Synthesis of I-112. To a solution of 43.2 (0.050 g, 0.116 mmol, 1.0 equiv) in DCM (3 mL) was added pyridine (0.091 g, 1.16 mmol, 10.0 equiv) followed by acetic anhydride (0.027 g, 2.32 mmol, 20.0 equiv). The reaction mixture was stirred at room temperature for 16 h. It was transferred into water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.0% methanol in DCM) to afford I-112. MS(ES): m/z: 474.5 [M+H]$^+$; $^1$H NMR (DMSO-d$_6$, 400 MHz): δ 10.65 (s, 1H), 10.45 (s, 1H), 8.25-8.23 (d, J=5.6 Hz, 1H), 8.16 (bs, 1H), 7.74 (s, 1H), 6.75-6.74 (d, J=3.6 Hz, 1H), 6.64 (s, 1H), 4.11 (bs, 2H), 4.01 (bs, 2H), 3.91 (s, 3H), 2.07 (s, 3H), 1.55 (s, 6H).

Example 113: N-(4-((7-cyano-2-((5',6'-dihydrospiro [cyclobutane-1,4'-pyrrolo[1,2-b]pyrazol]-2'-yl)amino)-1-methyl-1H-imidazo[4,5-b]pyridin-6-yl)oxy)pyridin-2-yl)acetamide

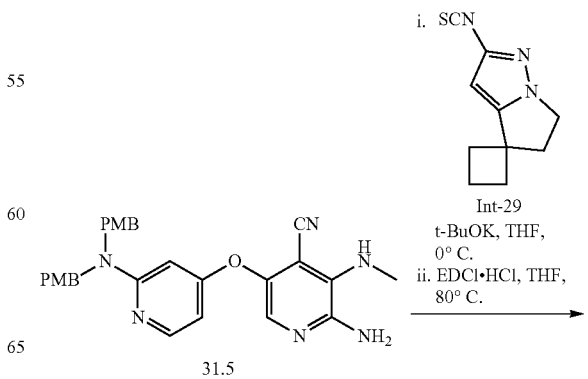

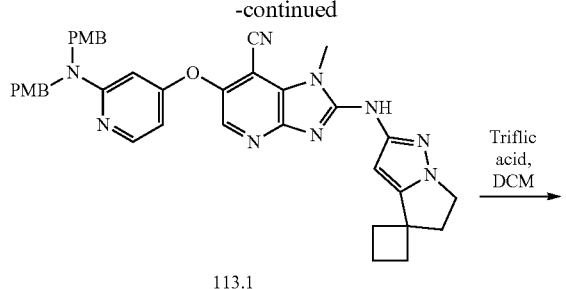

113.1

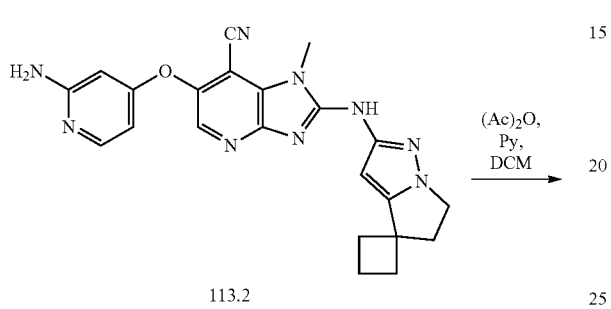

113.2

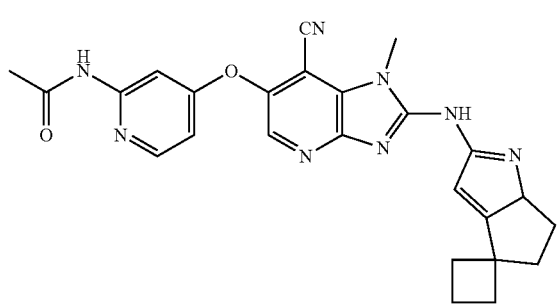

I-113

Synthesis of compound 113.1. Compound 113.1 was prepared from 31.5 and Int-29, following the procedure described in the synthesis of I-19. The product was purified by flash column chromatography on silica gel (CombiFlash®, dichloromethane) to afford 113.1. MS(ES): m/z 668 [M+H]⁺.

Synthesis of compound 113.2. Compound 113.2 was prepared from 113.1, following the procedure described in the synthesis of 40.2. The product was purified by trituration with diethyl ether. MS(ES): m/z 428 [M+H]⁺.

Synthesis of I-113. Compound I-113 was prepared from 113.2, following the procedure described in I-112. The product was purified by flash column chromatography on silica gel (CombiFlash®, 2.8% methanol in DCM). MS(ES): m/z 470.32 [M+H]⁺; ¹H NMR (DMSO-d₆, 400 MHz): δ 10.65 (s, 1H), 10.39 (s, 1H), 8.19 (s, 1H), 7.62 (s, 1H) 7.15 (d, J=7.6 Hz, 2H), 6.74 (s, 2H), 4.12-3.98 (m, 2H), 3.93 (s, 3H), 32.70 (s, 3H), 2.43-2.46 (m, 2H), 2.22 (s, 2H), 2.02 (s, 2H), 1.58 (s, 2H).

Example 114: N-(4-((7-cyano-2-((6',7'-dihydro-5'H-spiro[cyclopropane-1,4'-pyrazolo[1,5-a]pyridin]-2'-yl)amino)-1-methyl-1H-imidazo[4,5-b]pyridin-6-yl)oxy)pyridin-2-yl)acetamide

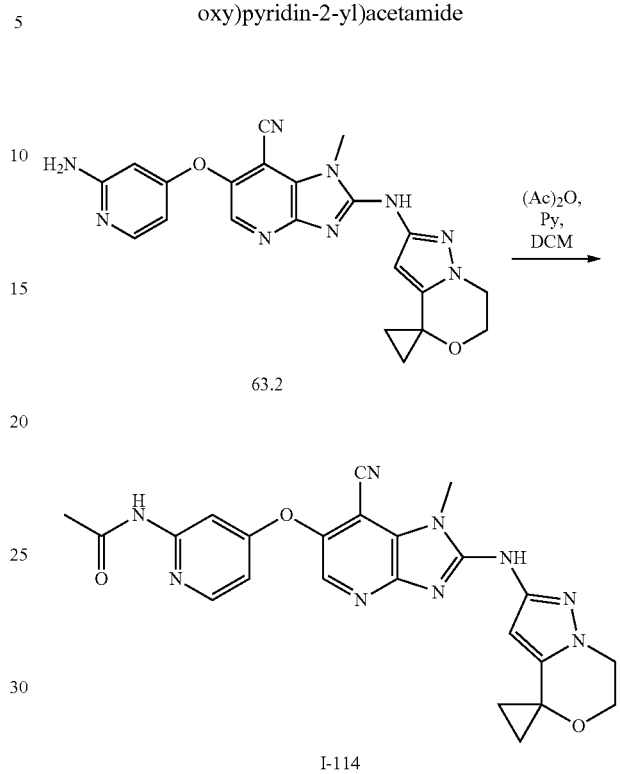

Synthesis of I-114. Compound I-114 was prepared from 63.2, following the procedure described in the synthesis of I-112. The product was purified by flash column chromatography on silica gel (CombiFlash®, 3.0% methanol in DCM). MS(ES): m/z: 469.51 [M+H]⁺; ¹H NMR (DMSO-d₆, 400 MHz): δ 10.66 (s, 1H), 8.25 (d, J=4.0 Hz, 1H), 8.16 (s, 1H), 7.740 (s, 1H), 6.74 (bs, 1H), 6.24 (s, 1H), 3.90 (bs, 4H), 3.36 (s, 3H), 2.07 (s, 3H), 1.80 (bs, 1H), 1.26 (s, 3H), 0.97 (bs, 3H).

Example 115: N-(4-((2-((1-(tert-butyl)-2,3-dihydro-1H-imidazo[1,2-b]pyrazol-6-yl)amino)-7-cyano-1-methyl-1H-imidazo[4,5-b]pyridin-6-yl)oxy)pyridin-2-yl)acetamide

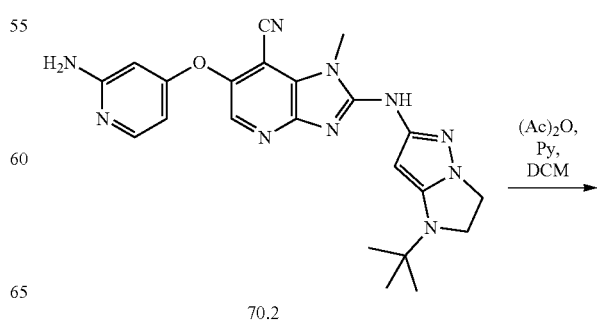

70.2

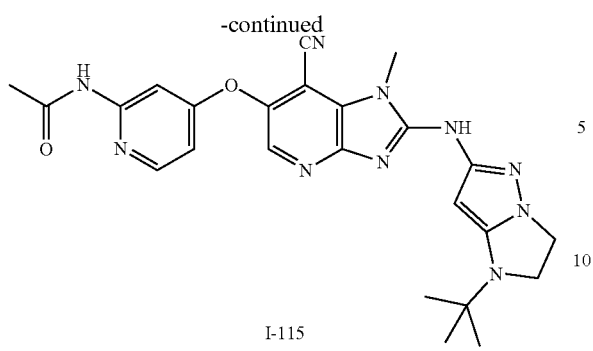

I-115

Synthesis of I-115. Compound I-115 was prepared from 70.2, following the procedure described in the synthesis of I-112. The product was purified by flash column chromatography on silica gel (CombiFlash®, 3.1-3.7% methanol in DCM). MS(ES): m/z: 487.36 [M+H]⁺; ¹H NMR (DMSO-$d_6$, 400 MHz): δ 10.59 (s, 1H), 10.22 (s, 1H), 8.20 (d, J=6 Hz, 1H), 8.135 (s, 1H), 7.77-7.65 (m, 1H), 6.70 (s, 1H), 6.03 (s, 1H), 3.92-3.86 (m, 3H), 3.64 (s, 2H), 3.84 (s, 2H), 2.03 (s, 3H), 1.25 (s, 9H).

Example 118: N-(4-((7-cyano-2-((4,4-dimethyl-4,5,7,8-tetrahydropyrazolo[1,5-d][1,4]oxazepin-2-yl)amino)-1-methyl-1H-imidazo[4,5-b]pyridin-6-yl)oxy)pyridin-2-yl)acetamide

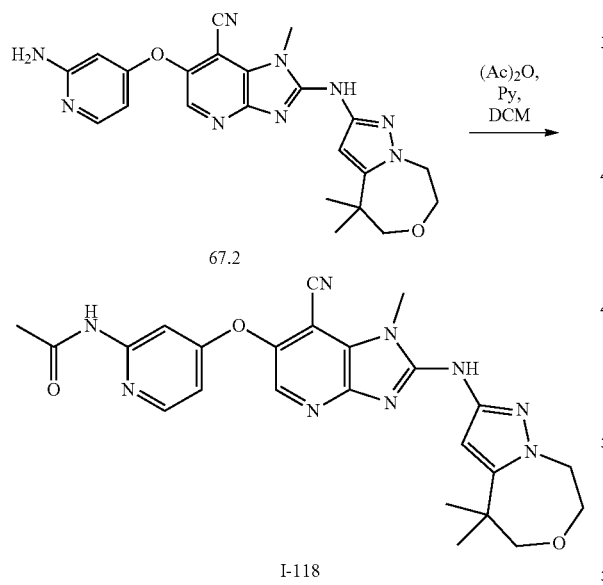

Synthesis of compound I-118. Compound I-118 was prepared from 67.2, following the procedure described in the synthesis of I-112. The product was purified by flash column chromatography on silica gel (CombiFlash®, 4.7% methanol in DCM). MS(ES): m/z: 488.36 [M+H]⁺; ¹H NMR (DMSO-$d_6$, 400 MHz): δ 10.66 (s, 1H), 10.38 (s, 1H), 8.24 (d, J=5.6 Hz, 1H), 8.17 (s, 1H), 7.73 (s, 1H), 6.74 (d, J=3.2 Hz, 1H), 6.67 (s, 1H), 4.38 (s, 2H), 3.90 (s, 3H), 3.86 (s, 2H), 3.58 (s, 2H), 2.06 (s, 3H), 1.31 (s, 6H).

Example 119: N-(4-((7-cyano-1-methyl-2-((5'-methyl-6',7'-dihydro-5'H-spiro[cyclopropane-1,4'-pyrazolo[1,5-a]pyrazin]-2'-yl)amino)-1H-imidazo[4,5-b]pyridin-6-yl)oxy)pyridin-2-yl)acetamide

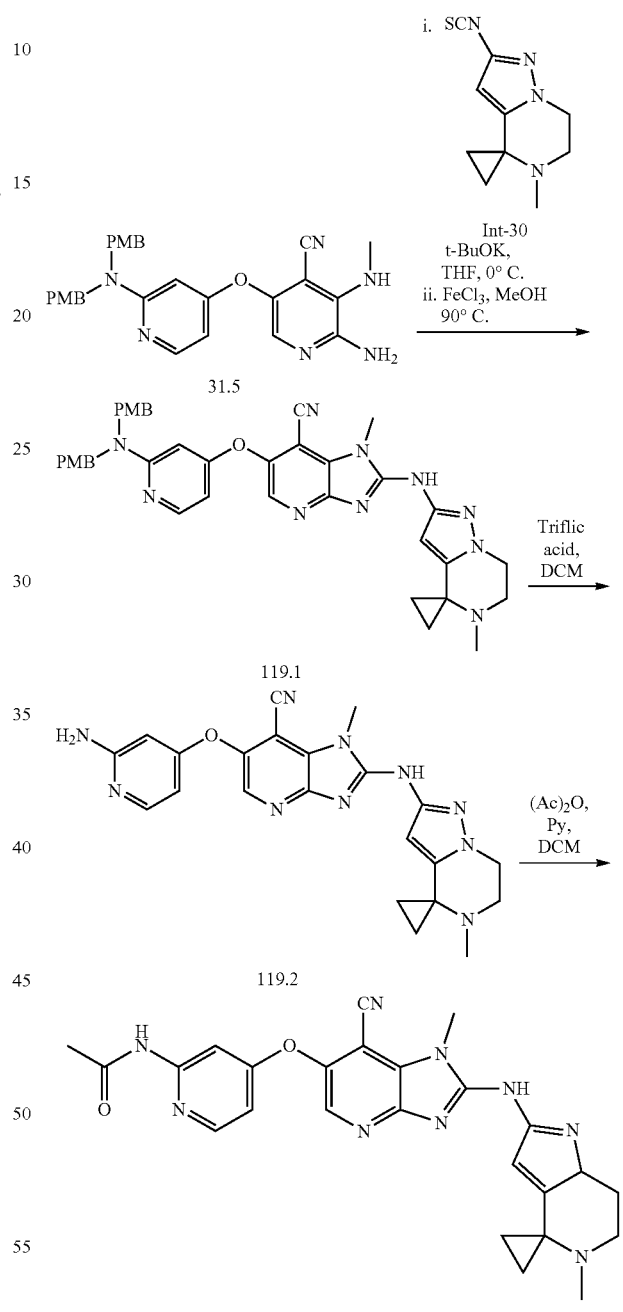

Synthesis of compound 119.1. Compound 119.1 was prepared from 31.5 and Int-30, following the procedure described in the synthesis of I-19. The product was purified by flash column chromatography on silica gel (CombiFlash®, 3.0% methanol in DCM). MS(ES): m/z: 683.7 [M+H]⁺.

Synthesis of compound 119.2. Compound 119.2 was prepared from 119.1, following the procedure described in the synthesis of 40.2. The product was purified by trituration with diethyl ether. MS(ES): m/z: 443.5 [M+H]+.

Synthesis of compound I-119. Compound I-119 was prepared from 119.2, following the procedure described in the synthesis of I-118. The product was purified by flash column chromatography on silica gel (CombiFlash®, 5.0% methanol in DCM). MS(ES): m/z: 485 [M+H]+; $^1$H NMR (DMSO-d$_6$, 400 MHz): δ 10.62 (bs, 1H), 10.38 (bs, 1H), 8.23-8.14 (m, 2H), 7.37 (s, 1H), 6.73 (bs, 1H), 6.30 (bs, 1H), 4.10 (bs, 2H), 3.90 (bs, 2H), 3.32 (s, 3H), 2.36 (m, 3H), 2.06 (bs, 1H) 1.25 (m, 2H), 1.025 (m, 2H).

Example 120: (S)-tetrahydrofuran-3-yl(4-((7-cyano-2-((5',6'-dihydrospiro[cyclobutane-1,4'-pyrrolo[1,2-b]pyrazol]-2'-yl)amino)-1-methyl-1H-imidazo[4,5-b]pyridin-6-yl)oxy)pyridin-2-yl)carbamate

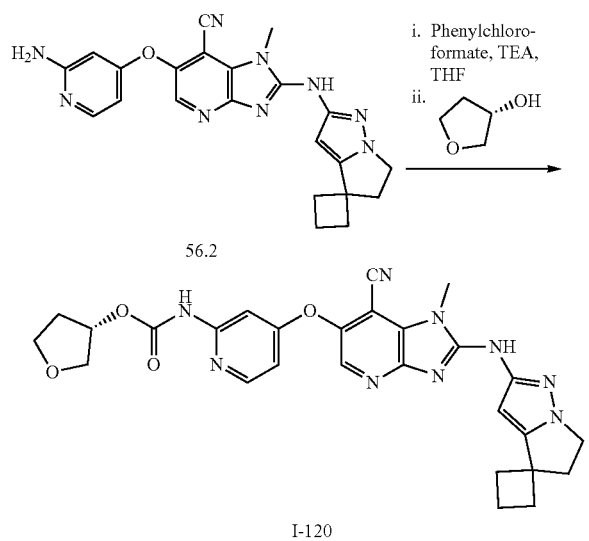

I-120

Synthesis of compound I-120. To a solution of 56.2 (0.05 g, 0.116 mmol, 1.0 equiv) and triethylamine (0.035 g, 0.348 mmol, 3.0 equiv) in THF (5 mL) at 0° C. was added phenyl chloroformate (0.027 g, 0.174 mmol, 1.5 equiv). The reaction mixture was stirred for 15 min and to it were added trimethylamine (0.035 g, 0.348 mmol, 3 equiv) and (S)-tetrahydrofuran-3-ol (0.031 g, 0.35 mmol, 3 equiv). The reaction mixture was stirred at 70° C. for 16 h. It was poured into water and extracted by ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford I-120. MS(ES): m/z: 541.57 [M+H]+; $^1$H NMR (DMSO-d$_6$, 400 MHz): δ 10.38-10.34 (bs, 2H), 8.20-8.17 (bs, 2H), 7.413 (s, 1H), 6.73-6.71 (bs, 2H), 5.20 (s, 1H), 4.04 (t, J=13.6 Hz, 2H), 3.910 (s, 3H), 3.78-3.63 (bs, 4H), 2.67-2.60 (bs, 2H), 2.40-2.33 (bs, 2H), 2.27-2.25 (bs, 2H), 2.18-2.09 (bs, 1H), 2.04-2.02 (bs, 2H), 1.92-1.89 (bs, 1H).

Example 121: (R)-tetrahydrofuran-3-yl (4-((7-cyano-2-((5',6'-dihydrospiro[cyclobutane-1,4'-pyrrolo[1,2-b]pyrazol]-2'-yl)amino)-1-methyl-1H-imidazo[4,5-b]pyridin-6-yl)oxy)pyridin-2-yl)carbamate

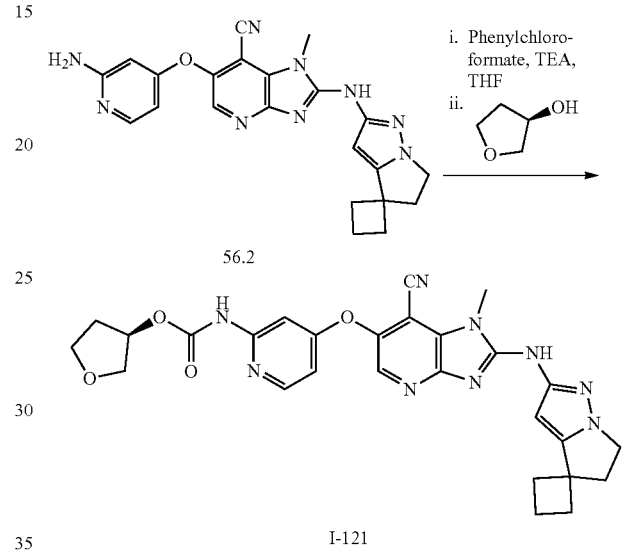

I-121

Synthesis of compound I-121. Compound I-121 was prepared from 56.2 and (R)-tetrahydrofuran-3-ol, following the procedure described in the synthesis of I-120. The product was purified by flash column chromatography on silica gel (CombiFlash®, 2.5% methanol in DCM). MS(ES): m/z: 541.57 [M+H]+; $^1$H NMR (DMSO-d$_6$, 400 MHz): δ 10.38-10.35 (bs, 2H), 8.20-8.17 (bs, 2H), 7.414 (s, 1H), 6.73-6.72 (bs, 2H), 5.20 (s, 1H), 4.04 (t, J=13.6 Hz, 2H), 3.91 (s, 3H), 3.78-3.67 (bs, 4H), 2.67-2.64 (bs, 2H), 2.40-2.33 (bs, 2H), 2.27-2.25 (bs, 2H), 2.16-2.08 (bs, 1H), 2.04-2.02 (bs, 2H), 1.93-1.91 (bs, 1H).

Example 122: N-(4-((7-cyano-2-((5',6'-dihydrospiro[cyclobutane-1,4'-pyrrolo[1,2-b]pyrazol]-2'-yl)amino)-1-methyl-1H-imidazo[4,5-b]pyridin-6-yl)oxy)pyridin-2-yl)cyclopropanecarboxamide

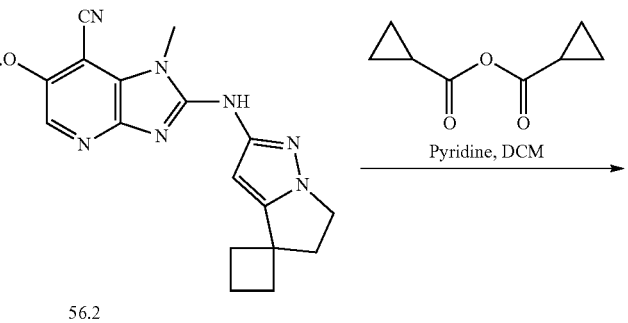

56.2

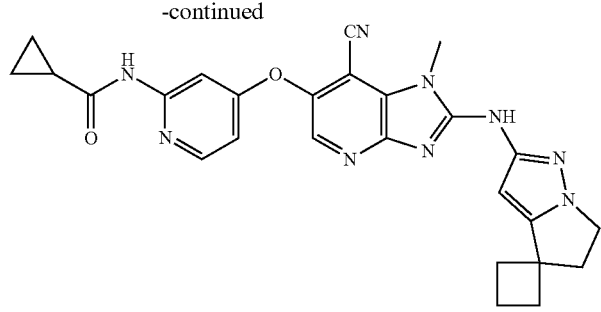

I-122

Synthesis of I-122. A solution of 56.2 (0.05 g, 0.116 mmol, 1 equiv) and cyclopropanecarboxylic anhydride (0.238 g, 2.3 mmol, 20 equiv) and pyridine (0.093 g, 1.2 mmol, 10 equiv) in DCM (3 mL) was stirred for 16 h at room temperature. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.0% methanol in DCM) to afford 1-122. MS(ES): m/z: 495.55 [M+H]$^+$; $^1$H NMR (DMSO-$d_6$, 400 MHz): δ 12.08 (s, 1H), 10.95 (s, 1H), 10.38 (s, 1H), 8.24 (d, J=5.6 Hz, 1H), 8.19 (d, J=8 Hz, 1H), 7.71 (s, 1H), 6.77-6.76 (bs, 1H), 4.04 (t, J=13.6 Hz, 2H), 3.907 (s, 3H), 2.67-2.63 (bs, 1H), 2.40-2.33 (bs, 2H), 2.29-2.25 (bs, 2H), 2.04-1.98 (bs, 2H), 1.51-1.49 (bs, 1H), 1.24 (bs, 1H), 0.77 (bs, 4H).

Example 123: 1-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-3-(oxetan-3-yl)urea

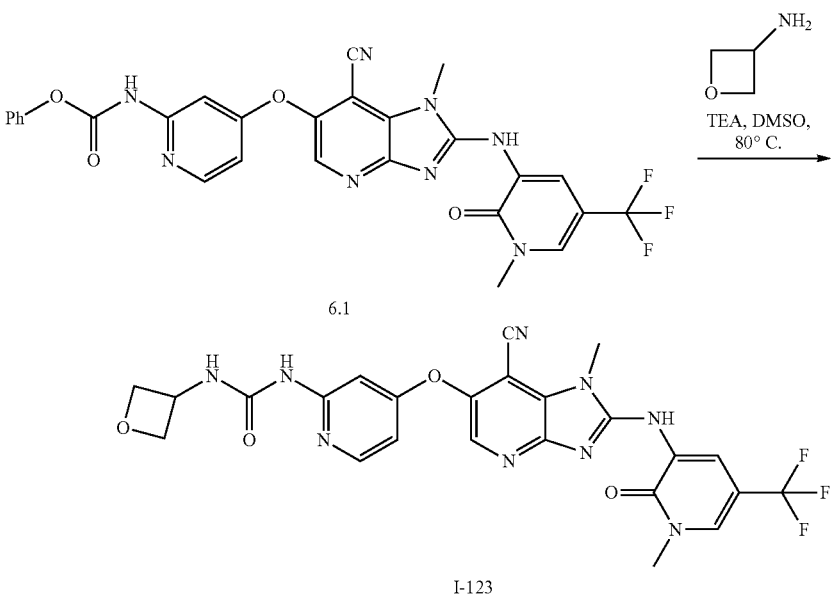

Synthesis of I-123. Compound I-123 was prepared from 6.1 and oxetan-3-amine, following the procedure described in the synthesis of I-6. The product was purified by flash column chromatography on silica gel (7.0% methanol in DCM) to afford I-123. MS(ES): m/z 556.4 [M+H]$^+$; $^1$H NMR (DMSO-$d_6$, 400 MHz): δ 9.25 (s, 1H), 9.08 (s, 1H), 8.66 (d, J=2.4 Hz, 1H), 8.46 (s, 1H), 8.33 (s, 1H), 8.20 (t, J=3.6 Hz, 2H), 7.09 (d, J=2.4 Hz, 2H), 6.70 (m, 1H), 4.79-4.72 (m, 3H), 4.44 (t, J=4.8 Hz, 2H), 3.98 (s, 3H), 3.68 (s, 3H).

Reference Compound

A compound R-1 is described in WO 2020/097396 (see compound I-2 therein):

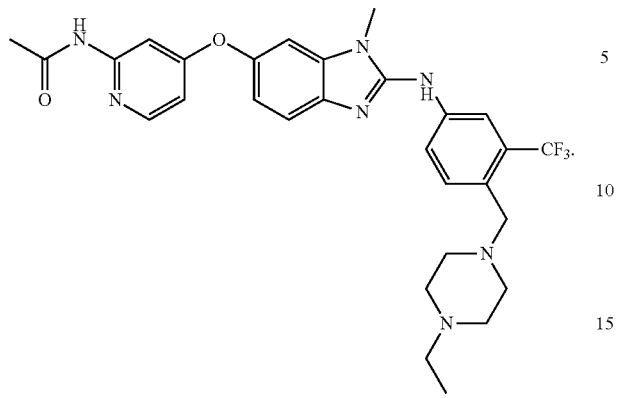

R-1

JAK2 Binding Assay

JAK2 (JH1 domain-catalytic, Y1007F,Y1008F) kinase was expressed as N-terminal fusion to the DNA binding domain of NFκB in transiently transfected HEK293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mmol/L DTT) to remove unbound ligand and to reduce nonspecific phage binding. Binding reactions were assembled by combining kinases, liganded affinity beads, and test compounds in 1× binding buffer (1×PBS, 0.05% Tween 20, 0.1% BSA, 1 mmol/L DTT). Test compound was prepared as 111× stocks in 100% DMSO and directly diluted into the assay wells. All reactions were performed in polypropylene 384-well plates in a final volume of 0.02 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μm on non-biotinylated affinity ligand) and incubated at room temperature with shaking for 30 minutes. The kinase concentration in the eluate was measured by qPCR.

Results of the JAK2 JH1 Domain Binding Assay described above are presented in Table 2. Compounds denoted as "A" had a $K_d$<10 nM; compounds denoted as "B" had a $K_d$≥10 nM and <50 nM; compounds denoted as "C" had a $K_d$≥50 nM and <1 μM; compounds denoted as "D" had a $K_d$≥1 μM and <5 μM; and compounds denoted as "E" had a $K_d$≥5 μM.

TABLE 2

| Compound | JAK2 $K_d$ |
| --- | --- |
| I-3 | A |
| I-4 | A |
| I-5 | A |
| I-6 | A |
| I-7 | A |
| I-8 | A |
| I-9 | A |
| I-10 | A |
| I-11 | A |
| I-12 | A |
| I-13 | A |
| I-14 | A |
| I-15 | A |

TABLE 2-continued

| Compound | JAK2 $K_d$ |
| --- | --- |
| I-16 | A |
| I-17 | A |
| I-18 | A |
| I-19 | A |
| I-20 | A |
| I-21 | A |
| I-22 | A |
| I-23 | A |
| I-24 | B |
| I-25 | B |
| I-26 | A |
| I-27 | A |
| I-28 | A |
| I-29 | B |
| I-30 | A |
| I-31 | B |
| I-32 | A |
| I-33 | A |
| I-34 | A |
| I-35 | A |
| I-36 | A |
| I-37 | A |
| I-38 | A |
| I-39 | C |
| I-40 | D |
| I-41 | C |
| I-42 | A |
| I-43 | A |
| I-44 | A |
| I-45 | A |
| I-46 | E |
| I-47 | A |
| I-48 | A |
| I-49 | A |
| I-52 | A |
| I-53 | E |
| I-54 | D |
| I-55 | D |
| I-56 | A |
| I-57 | A |
| I-58 | A |
| I-59 | A |
| I-60 | A |
| I-61 | A |
| I-62 | A |
| I-63 | A |
| I-64 | A |
| I-65 | A |
| I-66 | A |
| I-67 | A |
| I-68 | A |
| I-69 | A |
| I-70 | B |
| I-71 | A |
| I-72 | A |
| I-73 | B |
| I-74-a | A |
| I-74-b | A |
| I-75 | A |
| I-76 | A |
| I-77 | A |
| I-78-a | A |
| I-78-b | A |
| I-79 | A |
| I-80 | A |
| I-81 | A |
| I-82 | A |
| I-83 | A |
| I-84 | A |
| I-85 | A |
| I-86 | A |
| I-87 | A |
| I-88 | A |
| I-89 | A |
| I-90-a | A |
| I-90-b | A |
| I-91-a | A |
| I-91-b | A |

TABLE 2-continued

| Compound | JAK2 $K_d$ |
|---|---|
| I-92 | A |
| I-93 | A |
| I-94 | A |
| I-95-i | A |
| I-95-ii | A |
| I-96 | A |
| I-97 | A |
| I-98 | A |
| I-99 | A |
| I-100 | A |
| I-101 | A |
| I-102-a | A |
| I-102-b | A |
| I-103 | A |
| I-104 | E |
| I-105 | A |
| I-106 | B |
| I-107 | B |
| I-108-a | A |
| I-108-b | A |
| I-109-a | A |
| I-109-b | A |
| I-110 | A |
| I-111 | C |
| I-112 | A |
| I-113 | A |
| I-114 | A |
| I-115 | A |
| I-118 | A |
| I-119 | B |
| I-120 | A |
| I-121 | A |
| I-122 | A |
| I-123 | A |
| R-1 | A |

JAK Family Selectivity Assays

Provided compounds are evaluated for selectivity by comparing their JAK2 binding affinity ($K_d$) in the above JAK2 Binding Assay with their binding affinity ($K_d$) for one or more other kinases. Binding affinity for other kinases is determined as follows: Kinase-tagged T7 phage strains are prepared in an E. coli host derived from the BL21 strain. E. coli are grown to log-phase and infected with T7 phage and incubated with shaking at 32° C. until lysis. The lysates are centrifuged and filtered to remove cell debris. The remaining kinases are produced in HEK-293 cells and subsequently tagged with DNA for qPCR detection. Streptavidin-coated magnetic beads are treated with biotinylated small molecule ligands for 30 minutes at room temperature to generate affinity resins for kinase assays. The liganded beads are blocked with excess biotin and washed with blocking buffer (SeaBlock (Pierce), 1% BSA, 0.05% Tween 20, 1 mM DTT) to remove unbound ligand and to reduce non-specific binding. Binding reactions are assembled by combining kinases, liganded affinity beads, and test compounds in 1× binding buffer (20% SeaBlock, 0.17×PBS, 0.05% Tween 20, 6 mM DTT). Test compounds are prepared as 111× stocks in 100% DMSO. Kds are determined using an 11-point 3-fold compound dilution series with three DMSO control points. All compounds for Kd measurements are distributed by acoustic transfer (non-contact dispensing) in 100% DMSO. The compounds are then diluted directly into the assays such that the final concentration of DMSO is 0.9%. All reactions are performed in polypropylene 384-well plate. Each has a final volume of 0.02 ml. The assay plates are incubated at room temperature with shaking for 1 hour and the affinity beads are washed with wash buffer (1×PBS, 0.05% Tween 20). The beads are then re-suspended in elution buffer (1× PBS, 0.05% Tween 20, 0.5 µM non-biotinylated affinity ligand) and incubated at room temperature with shaking for 30 minutes. The kinase concentration in the eluates is measured by qPCR. Compounds that exhibit a better binding affinity for JAK2 compared to one or more other kinases are considered to be JAK2-selective compounds. In some embodiments, provided compounds may be JAK2-selective over one or more of the following kinases: JAK1, JAK3, and Tyk2.

Results of the JAK2 Selectivity Assay described above are presented in Table 3. Compounds denoted as "A" had a $K_d/K_d$ ratio ≥1000; compounds denoted as "B" had a $K_d/K_d$ ratio <1000 and ≥300; compounds denoted as "C" had a $K_d/K_d$ ratio <300 and ≥100; compounds denoted as "D" had a $K_d/K_d$ ratio <100.

TABLE 3

| Compound | JAK1/JAK2 $K_d/K_d$ ratio | JAK3/JAK2 $K_d/K_d$ ratio | TYK2/JAK2 $K_d/K_d$ ratio |
|---|---|---|---|
| I-3 | A | A | C |
| I-4 | B | A | C |
| I-7 | A | A | D |
| I-14 | A | A | C |
| I-15 | B | A | B |
| I-18 | C | A | C |
| I-30 | A | B | D |
| I-60 | B | B | D |
| I-61 | A | A | D |
| I-62 | B | A | C |
| I-75 | A | A | C |
| I-79 | C | A | C |
| I-88 | B | A | D |
| I-122 | D | B | D |
| R-1 | C | A | C |

SET2-pSTAT5 Cellular Assay

This assay measures inhibition of JAK2-mediated pSTAT5 signaling in constitutively active essential thrombocytopenia cells carrying the V617F mutation. Cells are harvested from a flask into cell culture medium, and the number of cells is counted. The cells are diluted with culture medium and 100 µL of cell suspension (50000/well) is added into each well of a 96-well cell culture plate. A solution of test compound is added to the assay plate. The plates are covered with a lid and placed in a 37° C. 5% $CO_2$ incubator for 4 hours. After 4 hours, the cells are spun, and the cell pellets are re-suspended with 100 µL cold PBS. Then, the cells are spun again at 4° C. and 4000 rpm for 5 min. PBS is aspirated, and 25 µL lysis buffer (with protease and phosphatase inhibitor cocktail) is added to each cell pellet. The cell lysate is shaken at 4° C. for 20 min to fully lyse the cells. The cell lysate is spun at 4° C. and 4000 rpm for 15 min, and then the supernatant is transferred into a new plate and stored at −80° C. Meso-scale discovery (MSD) is used to analyze plates as follows: a standard MSD plate is coated with capture antibody in PBS (40 µL/well) and is incubated at 4° C. overnight with shaking. The MSD plate is washed three times with 150 µL/well of 1×MSD Wash Buffer (Tris-buffered saline with 0.1% Tween® 20 detergent, TBST). The MSD plates are then blocked with 150 µL of blocking buffer (5% BSA in TBST) and shaken for 1 h at room temperature and 600 rpm. The MSD plate is washed three times with 150 µL/well of 1×MSD Wash Buffer (TBST). Sample lysates are then added to MSD plates (25 µL/well) and shaken for 1 h at room temperature and 600 rpm. The MSD plate is washed three times with 150 µL/well of 1×MSD Wash Buffer (TBST). Detection antibody (prepared in Antibody Detection buffer, 1% BSA in 1×TBST) is then added to the MSD plates, and they are shaken for 1 h at room temperature and 600 rpm. The MSD plate is washed three times with 150 µL/well of 1×MSD Wash Buffer (TBST). A secondary detection antibody (prepared in Antibody Detection buffer, 1% BSA in 1×TBST) is then added to the MSD plates, and they are shaken for 1 h at room temperature and 600 rpm. The MSD plate is washed three times with 150 µL/well of 1×MSD Wash Buffer (TBST). MSD reading buffer (1×) is added to the plates (150 µL/well), and they are diluted from 4× with water. The plates are imaged using an MSD imaging instrument according to the manufacturer's instructions.

Results of the SET2-pSTAT5 Cellular Assay described above are presented in Table 4. Compounds denoted as "A" had a $IC_{50} \leq 125$ nM; compounds denoted as "B" had a $IC_{50} \geq 125$ nM and <200 nM; compounds denoted as "C" had a $IC_{50} \geq 200$ nM and <1 µM; compounds denoted as "D" had a $IC_{50} \geq 1$ µM and <5 µM.

TABLE 4

| Compound | $IC_{50}$ |
|---|---|
| I-3 | A |
| I-4 | A |
| I-7 | A |
| I-14 | A |
| I-15 | A |
| I-18 | A |
| I-26 | C |
| I-30 | B |
| I-48 | D |
| I-56 | B |
| I-57 | B |
| I-60 | A |
| I-61 | A |
| I-62 | A |
| I-75 | A |
| I-79 | A |
| I-88 | A |
| I-114 | C |
| I-118 | C |
| I-122 | A |
| R-1 | C | hPBMC-GMCSF-STAT5 Assay

This assay measures inhibition of JAK2-homodimeric-mediated STAT5 signaling in human peripheral blood mononuclear cells. PBMCs are thawed with assay media comprising:

| Reagent | Cat # | Final conc |
|---|---|---|
| RPMI + L-glutamine | Gibco 21870 | 90% |
| Heat Inactivated FBS | Gibco 10082-147 | 10% |
| 1M HEPES | Gibco 15630 | 10 mM |
| 2-mercaptoethanol | Gibco 21985-0231 | 8.6 µL bME/10 mL media |
| Pen/Strep/Glut | Gibco 15140 | 1X |

Then, cells are counted. The cells are diluted with culture medium and 120 µL of cell suspension (500000/well) is added into each well of a 96-well cell culture plate. The test compound is diluted to 10× in assay media, and 15 µL of the solution is added to the assay plates. The plates are covered with a lid and placed in a 37° C., 5% $CO_2$ incubator for 4 hours. After 4 hours, GM-CSF stock solution (100 µg/mL) is diluted to 50 ng/mL in assay media, and 15 µL of the solution is added to the assay plates, such that the final concentration in the assay is 5 ng/mL. The plates are covered with a lid and placed in a 37° C., 5% $CO_2$ incubator for 5 min. After 5 min, the cells are spun and culture medium aspirated. Then, 50 µL lysis buffer (with protease and phosphatase inhibitor cocktail) is added to each cell pallet, and the cell lysate is shaken at 4° C. for 20 min. The cell lysate is then spun at 4° C., 4000 rpm for 5 min, and the supernatant is transferred into a new plate and stored at −80° C. until further use. An MSD standard plate is coated with capture antibody in PBS (40 µL/well) and incubated at 4° C. overnight with shaking. The MSD plate is then washed three times with 150 µL/well of TBST. Sample lysates (50 µL/well) are added to the MSD plates and shaken for 1 h at RT, 600 rpm. The MSD plates are then washed three times with 150 µL/well of TBST. Detection antibody is added (25 µL/well) and shaken for 1 h at RT, 600 rpm. The detection antibody is prepared in Antibody Detection buffer (1% Blocker A in TBST). The MSD plates are then washed three times with 150 µL/well of TBST. The second detection antibody is added (25 µL/well), shaken for 1 h at RT, 600 rpm. The second detection antibody is prepared in Antibody Detection buffer (1% Blocker A in TBST). The MSD plates are then washed three times with 150 µL/well of TBST. Then, MSD reading buffer (2×) is added (150 µL/well) and diluted from 4× with water. The plates are imaged using an MSD imaging instrument according to the manufacturer's instructions.

hPBMC-IL12-STAT4 Assay

This assay measures inhibition of Tyk2/JAK2-mediated STAT4 signaling in human peripheral blood mononuclear cells. PBMCs are thawed with assay media comprising:

| Reagent | Cat # | Final conc |
|---|---|---|
| RPMI + L-glutamine | Gibco 21870 | 90% |
| Heat Inactivated FBS | Gibco 10082-147 | 10% |
| 1M HEPES | Gibco 15630 | 10 mM |
| 2-mercaptoethanol | Gibco 21985-0231 | 8.6 µL bME/10 mL media |
| Pen/Strep/Glut | Gibco 15140 | 1X |

Then, cells are counted. The cells are diluted with culture medium and 120 µL of cell suspension (200000/well) is added into each well of a 96-well cell culture plate. The test compound is diluted to 10× in assay media, and 15 µL of the solution is added to the assay plates. The plates are covered with a lid and placed in a 37° C., 5% $CO_2$ incubator for 1 hour. After 1 hour, IL12 stock solution (50 ng/mL) is diluted to 50 ng/mL in assay media, and 15 µL of the solution is added to the assay plates, such that the final concentration in the assay is 1.7 ng/mL. The plates are covered with a lid and placed in a 37° C., 5% $CO_2$ incubator for 25 min. After 25 min, the cells are spun and culture medium aspirated. Then, 65 µL lysis buffer (with protease and phosphatase inhibitor cocktail) is added to each cell pallet, and the cell lysate is shaken at 4° C. for 30 min. The cell lysate is then spun at 4° C., 4000 rpm for 5 min, and the supernatant is transferred into a new plate and stored at −80° C. until further use. An MSD standard plate is blocked with blocking buffer (3% Blocker A in Wash buffer) and shaken for 1 h at RT, 600 rpm. The MSD plate is then washed three times with 150 µL/well of Wash buffer. Sample lysates (25 µL/well) are added to the MSD plates and shaken for 1 h at RT, 600 rpm. The MSD plates are then washed three times with 150 µL/well of Wash buffer. Detection antibody is added (25 µL/well) and shaken for 1 h at RT, 600 rpm. The detection antibody is prepared in Antibody Detection buffer (for one plate, 150 µL 2% Blocker D-M, 30 µL 10% Blocker D-R, 1 mL of Blocker A solution, 1.82 mL of 1× Wash buffer). The MSD plates are then washed three times with 150 µL/well of TBST. Then, MSD reading buffer (1×) is added (150 µL/well) and diluted from 4× with water. The plates are imaged using an MSD imaging instrument according to the manufacturer's instructions.

hPBMC-IL2-STAT5 Assay

This assay measures inhibition of JAK1/JAK3-mediated STAT5 signaling in human peripheral blood mononuclear cells. PBMCs are thawed with assay media comprising:

| Reagent | Cat # | Final conc |
|---|---|---|
| RPMI + L-glutamine | Gibco 21870 | 90% |
| Heat Inactivated FBS | Gibco 10082-147 | 10% |
| 1M HEPES | Gibco 15630 | 10 mM |
| 2-mercaptoethanol | Gibco 21985-0231 | 8.6 µL bME/10 mL media |
| Pen/Strep/Glut | Gibco 15140 | 1X |

Then, cells are counted. The cells are diluted with culture medium and 120 µL of cell suspension (200000/well) is added into each well of a 96-well cell culture plate. The test compound is diluted to 10× in assay media, and 15 µL of the solution is added to the assay plates. The plates are covered with a lid and placed in a 37° C., 5% $CO_2$ incubator for 1 hour. After 1 hour, IL2 stock solution (100 µg/mL) is diluted to 250 ng/mL in assay media, and 15 µL of the solution is added to the assay plates, such that the final concentration in the assay is 25 ng/mL. The plates are covered with a lid and placed in a 37° C., 5% $CO_2$ incubator for 5 min. After 5 min, the cells are spun and culture medium aspirated. Then, 40 µL lysis buffer (with protease and phosphatase inhibitor cocktail) is added to each cell pallet, and the cell lysate is shaken at 4° C. for 20 min. The cell lysate is then spun at 4° C., 4000 rpm for 5 min, and the supernatant is transferred into a new plate and stored at −80° C. until further use. An MSD standard plate is coated with capture antibody in PBS (40 µL/well) and incubated at 4° C. overnight with shaking. The MSD plate is then washed three times with 150 µL/well of TBST. The MSD plates are then blocked with blocking buffer (150 µL of 3% Blocker A in TBST) and shaken for 1 h at RT, 600 rpm. The MSD plate is then washed three times with 150 µL/well of TBST. Sample lysates (40 µL/well) are added to the MSD plates and shaken for 1 h at RT, 600 rpm. The MSD plates are then washed three times with 150 µL/well of TBST. Detection antibody is added (25 µL/well) and shaken for 1 h at RT, 600 rpm. The detection antibody is prepared in Antibody Detection buffer (1% Blocker A in TBST). The MSD plates are then washed three times with 150 µL/well of TBST. The second detection antibody is added (25 µL/well), shaken for 1 h at RT, 600 rpm. The second detection antibody is prepared in Antibody Detection buffer (1% Blocker A in TBST). The MSD plates are then washed three times with 150 µL/well of TBST. Then, MSD reading buffer (2×) is added (150 µL/well) and diluted from 4× with water. The plates are imaged using an MSD imaging instrument according to the manufacturer's instructions.

Kinome Profiling Assay

Kinome profiling is performed as described in Anastassiadis T, et al. Comprehensive assay of kinase catalytic activity reveals features of kinase inhibitor selectivity. Nat Biotechnol. 2011 Oct. 30; 29(11):1039-45. doi:10.1038/nbt.2017. Generally, substrate is prepared in freshly prepared Reaction Buffer (20 mM Hepes (pH 7.5), 10 mM $MgCl_2$, 1 mM EGTA, 0.01% Brij35, 0.02 mg/mL BSA, 0.1 mM $Na_3VO_4$, 2 mM DTT, 1% DMSO). Any required cofactors are then added to the substrate solution. Then, the kinase is delivered into the substrate solution and is gently mixed. Test compounds in 100% DMSO are then added to the kinase reaction mixture using Acoustic technology (Echo550; nanoliter range) and incubated for 20 min at RT. $^{33}$P-ATP is added to the reaction mixture and incubated for 2 h at RT. Kinase activity is detected by a P981 filter-binding method.

Caco2 Permeability Assay

Preparation of Caco-2 Cells: 50 µL and 25 mL of cell culture medium are added to each well of a Transwell® insert and reservoir, respectively. Then, the HTS Transwell® plates are incubated at 37° C., 5% $CO_2$ for 1 hour before cell seeding. Caco-2 cell cells are diluted to 6.86×105 cells/mL with culture medium, and 50 µL of cell suspension are dispensed into the filter well of the 96-well HTS Transwell® plate. Cells are cultivated for 14-18 days in a cell culture incubator at 37° C., 5% $CO_2$, 95% relative humidity. Cell culture medium is replaced every other day, beginning no later than 24 hours after initial plating.

Preparation of Stock Solutions: 10 mM stock solutions of test compounds are prepared in DMSO. The stock solutions of positive controls are prepared in DMSO at the concentration of 10 mM. Digoxin and propranolol are used as control compounds in this assay.

Assessment of Cell Monolayer Integrity: Medium is removed from the reservoir and each Transwell® insert and is replaced with prewarmed fresh culture medium. Transepithelial electrical resistance (TEER) across the monolayer is measured using Millicell Epithelial Volt-Ohm measuring system (Millipore, USA). The Plate is returned to the incubator once the measurement is done. The TEER value is calculated according to the following equation: TEER measurement (ohms)×Area of membrane ($cm^2$)=TEER value (ohm•$cm^2$). A TEER value greater than 230 ohm•$cm^2$ indicates a well-qualified Caco-2 monolayer.

Assay Procedure: The Caco-2 plate is removed from the incubator and washed twice with pre-warmed HBSS (10 mM HEPES, pH 7.4), and then incubated at 37° C. for 30 minutes. The stock solutions of control compounds are diluted in DMSO to get 1 mM solutions and then diluted with HBSS (10 mM HEPES, pH 7.4) to get 5 µM working solutions. The stock solutions of the test compounds are diluted in DMSO to get 1 mM solutions and then diluted with HBSS (10 mM HEPES and 4% BSA, pH 7.4) to get 5 µM working solutions. The final concentration of DMSO in the incubation system is 0.5%. To determine the rate of drug transport in the apical to basolateral direction. 75 µL of 5 µM working solutions of test compounds are added to the Transwell® insert (apical compartment) and the wells in the receiver plate (basolateral compartment) are filled with 235 µL of HBSS (10 mM HEPES and 4% BSA, pH 7.4). To determine the rate of drug transport in the basolateral to apical direction, 235 µL of 5 µM working solutions of test compounds are added to the receiver plate wells (basolateral compartment) and then the Transwell® inserts (apical compartment) are filled with 75 µL of HBSS (10 mM HEPES and 4% BSA, pH 7.4). Time 0 samples are prepared by transferring 50 µL of 5 µM working solution to wells of the 96-deepwell plate, followed by the addition of 200 µL cold methanol containing appropriate internal standards (IS). The plates are incubated at 37° C. for 2 hours. At the end of the incubation, 50 µL samples from donor sides (apical compartment for Ap→*Bl flux, and basolateral compartment for Bl→Ap) and receiver sides (basolateral compartment for Ap→Bl flux, and apical compartment for Bl→Ap) are transferred to wells of a new 96-well plate, followed by the addition of 4 volume of cold acetonitrile or methanol containing appropriate internal standards (IS). Samples are vortexed for 5 minutes and then centrifuged at 3,220 g for 40 minutes. An aliquot of 100 µL of the supernatant is mixed with an appropriate volume of ultra-pure water before LC-MS/MS analysis. To determine the Lucifer Yellow leakage after 2 hour transport period, stock solution of Lucifer yellow is prepared in ultra-pure water and diluted with HBSS (10 mM HEPES, pH 7.4) to reach the final concentration of 100 μM. 100 μL of the Lucifer yellow solution is added to each Transwell® insert (apical compartment), followed by filling the wells in the receiver plate (basolateral compartment) with 300 μL of HBSS (10 mM HEPES, pH 7.4). The plates are incubated at 37° C. for 30 minutes. 80 μL samples are removed directly from the apical and basolateral wells (using the basolateral access holes) and transferred to wells of new 96 wells plates. The Lucifer Yellow fluorescence (to monitor monolayer integrity) signal is measured in a fluorescence plate reader at 485 nM excitation and 530 nM emission.

Results of the Caco-2 Permeability Assay described above are presented in Table 5. Compounds denoted as "A" had a ER≤2; compounds denoted as "B" had a ER>2 and ≤5; compounds denoted as "C" had a ER>5 and ≤10; compounds denoted as "D" had a ER>10 and ≤30.

TABLE 5

| Compound | Papp (A-B, $10^{-6}$ cm/s) | Efflux Ratio (ER) |
|---|---|---|
| I-3 | 12 | A |
| I-4 | 7 | B |
| I-7 | 6 | B |
| I-14 | 4 | B |
| I-15 | 4 | B |
| I-18 | 2 | B |
| I-26 | 2 | C |
| I-30 | 3 | B |
| I-48 | 2 | C |
| I-56 | 5 | A |
| I-57 | 5 | A |
| I-60 | 6 | A |
| I-61 | 3 | B |
| I-62 | 5 | A |
| I-75 | 12 | A |
| I-79 | 15 | A |
| I-88 | 5 | A |
| I-114 | 4 | A |
| I-118 | 5 | B |
| I-122 | 2 | B |
| R-1 | 0.4 | D |

Cytotoxicity Assay

HEK293T cells are harvested from flask into cell culture medium, and then the cells are counted. The cells are diluted with culture medium to the desired density, and 40 μL of cell suspension is added into each well of a 384-well cell culture plate. The plates are covered with a lid and spun at room temperature at 1,000 RPM for 1 minute and then transferred into 37° C. 5% $CO_2$ incubator overnight. Test compounds are dissolved at 10 mM DMSO stock solution. 45 μL of stock solution is then transferred to a 384 PP-plate. A 3-fold, 10-point dilution is performed via transferring 15 μL compound into 30 μL DMSO by using TECAN (EVO200) liquid handler. The plates are spun at room temperature at 1,000 RPM for 1 minute and shaken on a plate shaker for 2 minutes. 40 nL of diluted compound is transferred from compound source plate into the cell plate by using liquid handler Echo550. After compound treatment for 48 hours, CTG detection is performed for compound treatment plates: the plates are removed from incubators and equilibrated to room temperature for 15 minutes. 30 μL of CellTiter-Glo reagent is added into each well to be detected. The plates are then placed at room temperature for 30 min followed by reading on EnVision. Inhibition activity is calculated with the following formula: % Inhibition=100×(LumHC−LumSample)/(LumHC−LumLC), wherein HC is reading obtained from cells treated with 0.1% DMSO only and LC is reading from cells treated with 10 μL staurosporine. $IC_{50}$ values are calculated using XLFit (equation 201).

Hepatocyte Stability Assay 10 mM stock solutions of test compound and positive control are prepared in DMSO. Stock solutions are diluted to 100 μM by combining 198 μL of 50% acetonitrile/50% water and 2 μL of 10 mM stock solution. Verapamil is used as positive control in the assay. Vials of cryopreserved hepatocytes are thawed in a 37° C. water bath with gently shaking. The contents are poured into the 50 mL thawing medium conical tube. Vials are centrifuged at 100 g for 10 minutes at room temperature. Thawing medium is aspirated and hepatocytes are re-suspended with serum-free incubation medium to yield ~1.5×106 cells/mL. Cell viability and density are counted using a Trypan Blue exclusion, and then cells are diluted with serum-free incubation medium to a working cell density of 0.5×106 viable cells/mL. A portion of the hepatocytes at 0.5×106 viable cells/mL are boiled for 5 min prior to adding to the plate as negative control to eliminate the enzymatic activity so that little or no substrate turnover should be observed. Aliquots of 198 μL hepatocytes are dispensed into each well of a 96-well non-coated plate. The plate is placed in the incubator for approximately 10 minutes. Aliquots of 2 μL of the 100 μM test compound and 2 μL positive control are added into respective wells of a non-coated 96-well plate to start the reaction. The final concentration of test compound is 1 μM. This assay is performed in duplicate. The plate is incubated in the incubator for the designed time points. 25 μL of contents are transferred and mixed with 6 volumes (150 μL) of cold acetonitrile with internal standard (100 nM alprazolam, 200 nM labetalol, 200 nM caffeine and 200 nM diclofenac) to terminate the reaction at time points of 0, 15, 30, 60, 90 and 120 minutes. Samples are centrifuged for 25 minutes at 3,220 g and aliquots of 150 μL of the supernatants are used for LC-MS/MS analysis.

Results of the Hepatocyte Stability Assay described above are presented in Table 6, with human or rat hepatocytes. For human heps $CL_{int}$: compounds denoted as "A" had a $CL_{int}$≤6 mL/min/kg; compounds denoted as "B" had a $CL_{int}$>6 mL/min/kg and ≤12 mL/min/kg; compounds denoted as "C" had a $CL_{int}$>12 mL/min/kg and <20 mL/min/kg. For rat heps $CL_{int}$: compounds denoted as "A" had a $CL_{int}$<17 mL/min/kg; compounds denoted as "B" had a $CL_{int}$≥17 mL/min/kg and <35 mL/min/kg; compounds denoted as "C" had a $CL_{int}$≥35 mL/min/kg and <45 mL/min/kg.

TABLE 6

| Compound | Human Heps $CL_{int}$ | Rat Heps $CL_{int}$ |
|---|---|---|
| I-3 | A | A |
| I-4 | A | B |
| I-7 | A | B |
| I-14 | A | A |
| I-15 | A | A |
| I-18 | B | B |
| I-26 | B | A |
| I-30 | A | B |
| I-48 | B | n.d. |
| I-56 | A | B |
| I-57 | B | C |
| I-60 | B | B |
| I-61 | A | C |

TABLE 6-continued

| Compound | Human Heps $CL_{int}$ | Rat Heps $CL_{int}$ |
|---|---|---|
| I-62 | B | B |
| I-75 | C | A |
| I-79 | C | B |
| I-88 | C | B |
| I-114 | B | C |
| I-118 | A | A |
| I-122 | C | A |
| R-1 | C | C | n.d. = not determined

Kinetic Solubility Assay

Stock solutions of test compounds are prepared in DMSO at the concentration of 10 mM, and a stock solution of control compound is prepared in DMSO at the concentration of 30 mM. Diclofenac is used as positive control in the assay. 30 µL stock solution of each compound is placed into their a 96-well rack, followed by adding 970 µL of PBS at pH 4.0 and pH 7.4 into each vial of the cap-less solubility sample plate. This study is performed in duplicate. One stir stick is added to each vial and then vials are sealed using a molded PTDE/SIL 96-Well Plate Cover. The solubility sample plate is transferred to the Thermomixer comfort plate shaker and incubated at RT for 2 hours with shaking at 1100 rpm. After 2 hours incubation, stir sticks are removed using a big magnet and all samples from the solubility sample plate are transferred into the filter plate. All the samples are filtered by vacuum manifold. The filtered samples are diluted with methanol. Samples are analyzed by LC-MS/MS and quantified against a standard of known concentration in DMSO using LC coupled with Mass spectral peak identification and quantitation. The solubility values of the test compounds are calculated as follows, wherein INJ VOL is injection volume, DF is dilution factor, and STD is standard:

$$[Sample] = \frac{AREA_{Sample} \times INJ\ VOL_{Std} \times DF_{Sample} \times [STD]}{AREA_{Std} \times INJ\ VOL_{Sample}}$$

Results of the Kinetic Solubility Assay described above are presented in Table 7. Compounds denoted as "A" had a solubility ≥0.1 µM and <9 µM; compounds denoted as "B" had a solubility ≥9 µM and <100 µM; compounds denoted as "C" had a solubility ≥100 µM and <200 µM.

TABLE 7

| Compound | Solubility |
|---|---|
| I-3 | A |
| I-4 | B |
| I-7 | A |
| I-14 | A |
| I-15 | B |
| I-18 | A |
| I-26 | B |
| I-30 | B |
| I-48 | A |
| I-56 | B |
| I-57 | A |
| I-60 | B |
| I-61 | A |
| I-62 | A |
| I-75 | A |
| I-79 | A |
| I-88 | A |
| I-114 | B |
| I-118 | B |
| I-122 | A |
| R-1 | C |

Plasma Protein Binding Assay

Working solutions of test compounds and control compound are prepared in DMSO at the concentration of 200 µM, and then the working solutions are spiked into plasma. The final concentration of compound is 1 µM. The final concentration of DMSO is 0.5%. Ketoconazole is used as positive control in the assay. Dialysis membranes are soaked in ultrapure water for 60 minutes to separate strips, then in 20% ethanol for 20 minutes, finally in dialysis buffer for 20 minutes. The dialysis set up is assembled according to the manufacturer's instruction. Each Cell is with 150 µL of plasma sample and dialyzed against equal volume of dialysis buffer (PBS). The assay is performed in duplicate. The dialysis plate is sealed and incubated in an incubator at 37° C. with 5% $CO_2$ at 100 rpm for 6 hours. At the end of incubation, 50 µL of samples from both buffer and plasma chambers are transferred to wells of a 96-well plate. 50 µL of plasma is added to each buffer samples and an equal volume of PBS is supplemented to the collected plasma sample. 400 µL of precipitation buffer acetonitrile containing internal standards (IS, 100 nM alprazolam, 200 nM labetalol, 200 nM imipramine and 2 µM ketoplofen) is added to precipitate protein and release compounds. Samples are vortexed for 2 minutes and centrifuged for 30 minutes at 3,220 g. Aliquot of 50 µL of the supernatant is diluted by 150 µL acetonitrile containing internal standards:ultra-pure $H_2O=1:1$, and the mixture is used for LC-MS/MS analysis.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The invention claimed is:
1. A compound selected from:

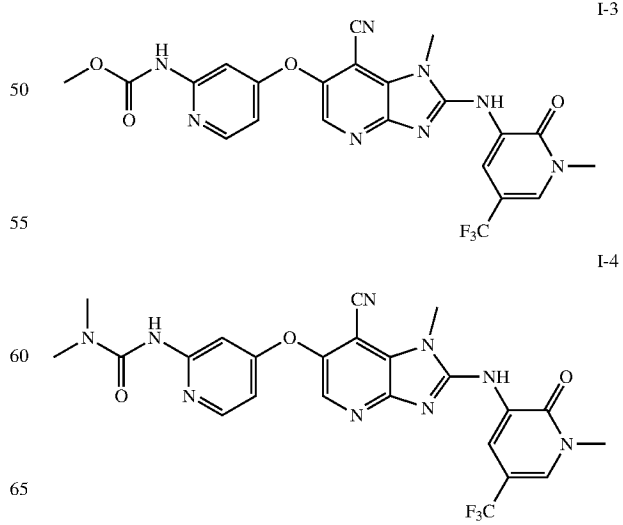

I-5
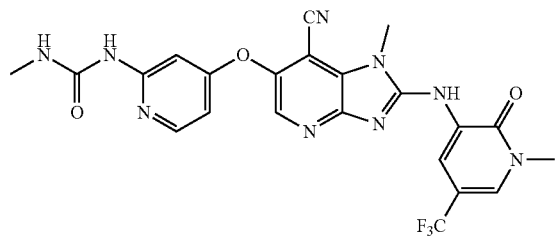
I-6
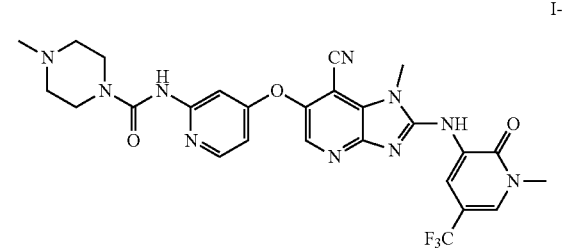
I-7
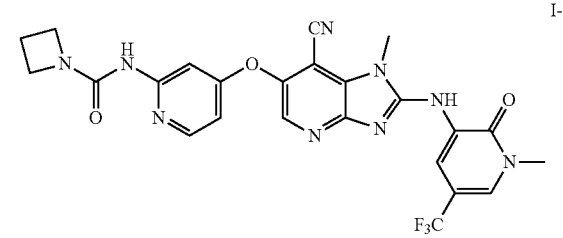
I-8
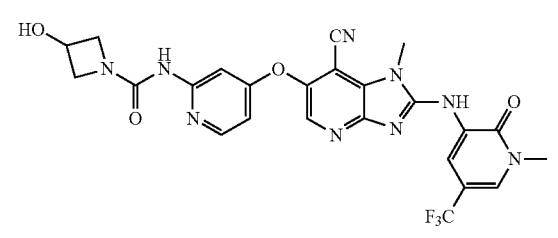
I-9
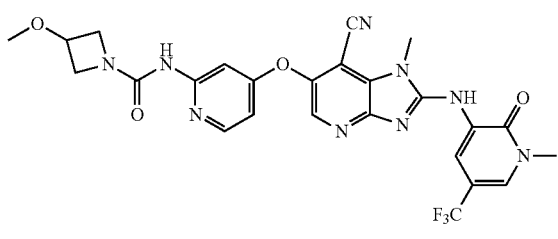
I-10
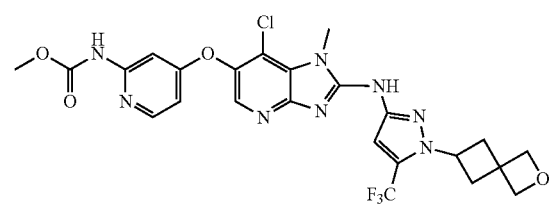
I-11
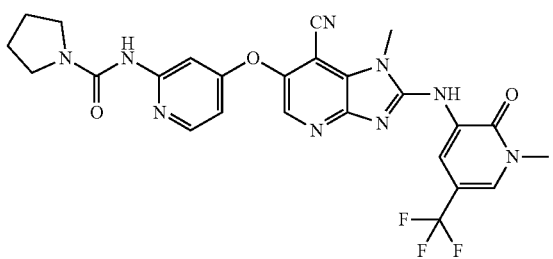
I-12
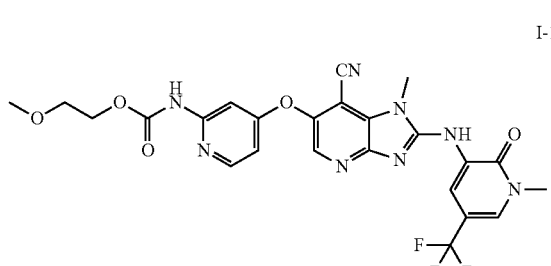
I-13'
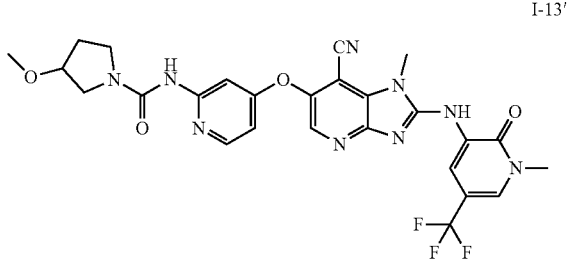
I-13
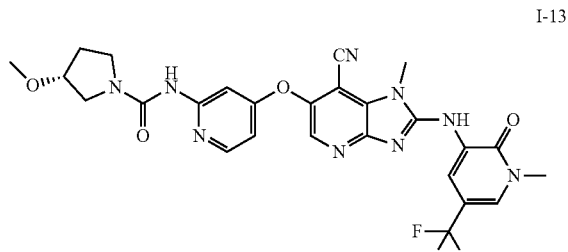
I-14
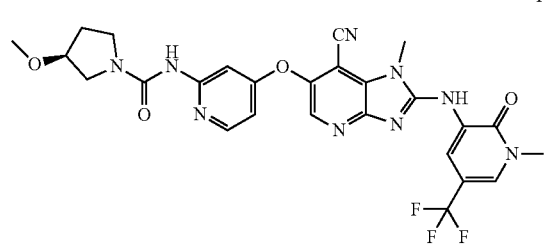
I-15
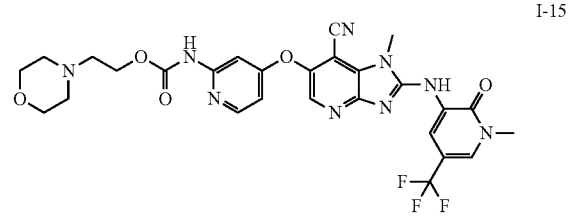

I-16
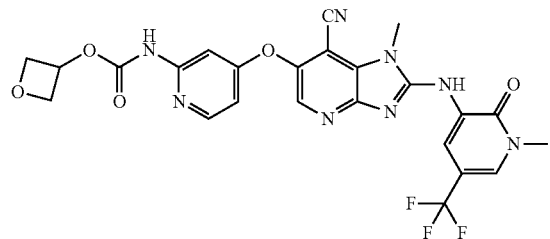
I-17'
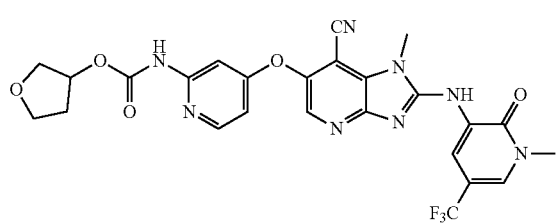
I-17
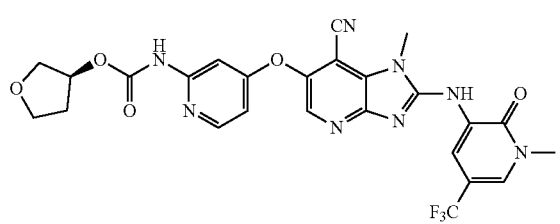
I-18
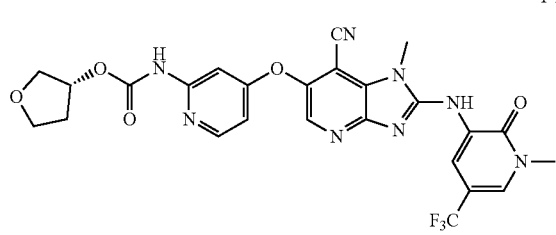
I-19
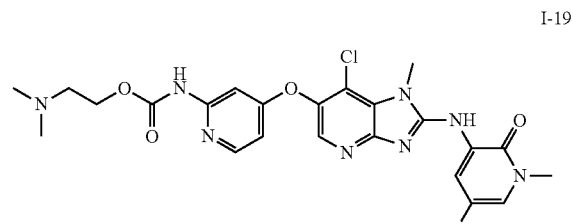
I-20
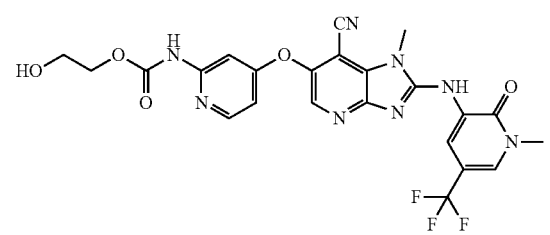
I-21
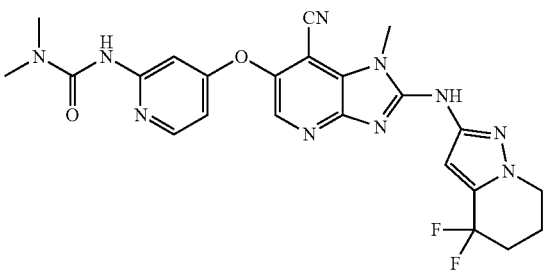
I-22
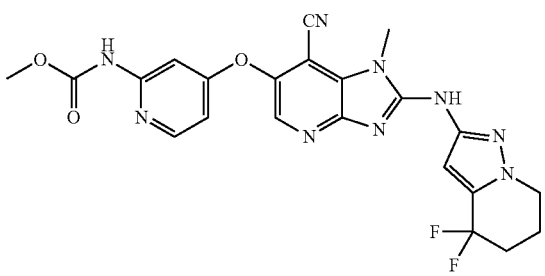
I-23
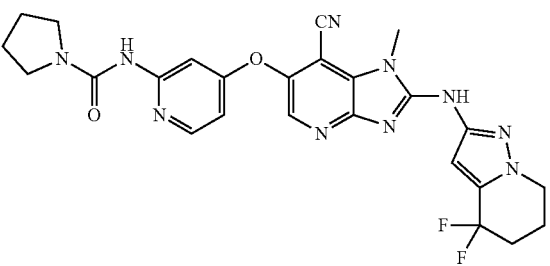
I-24
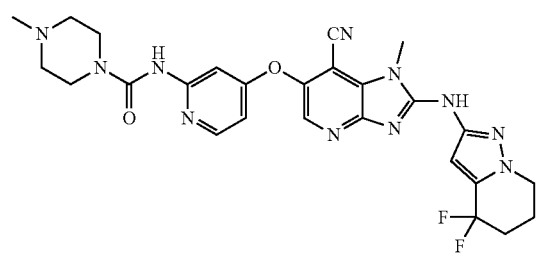
I-25
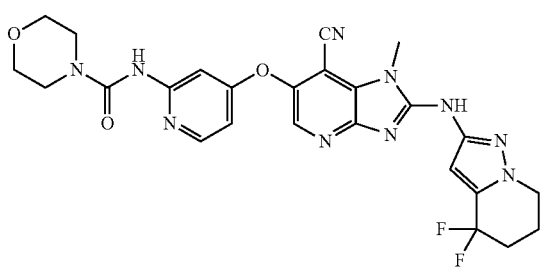

I-26
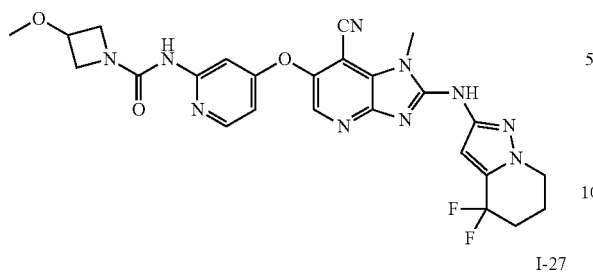
I-31
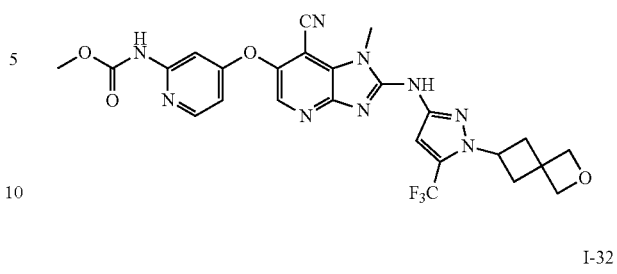
I-27
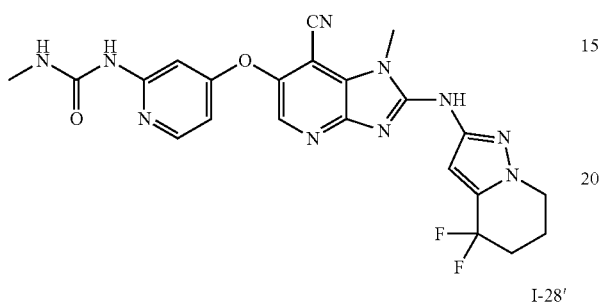
I-32
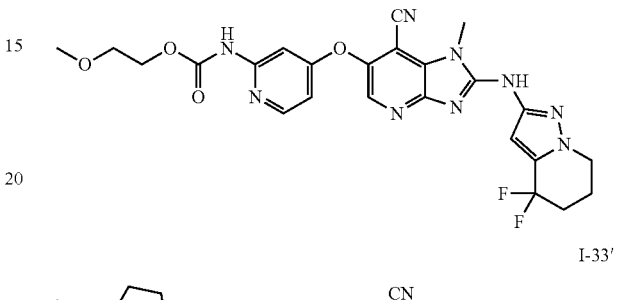
I-28'
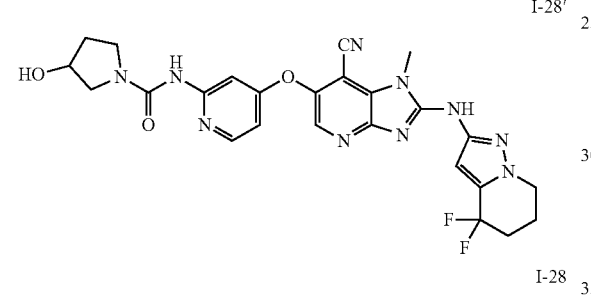
I-33'
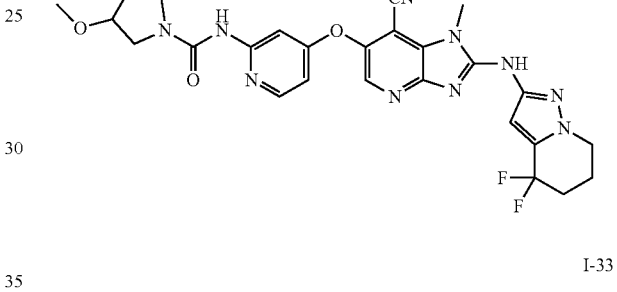
I-28
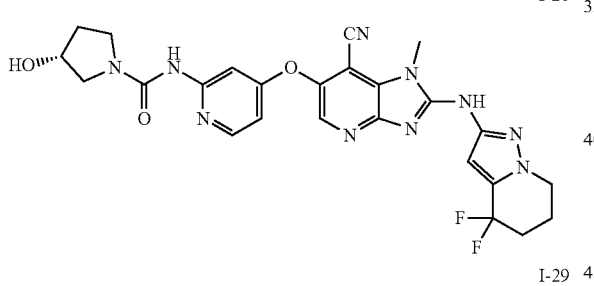
I-33
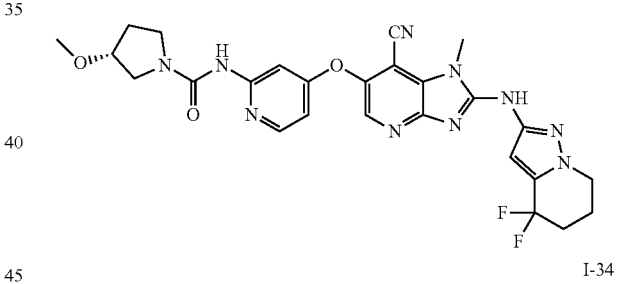
I-29
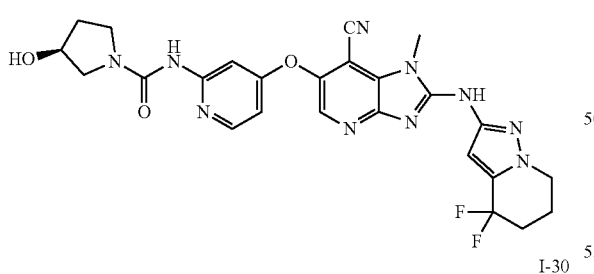
I-34
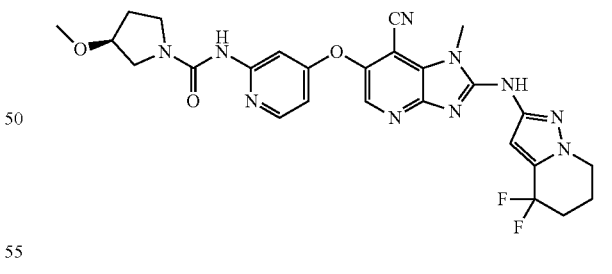
I-30
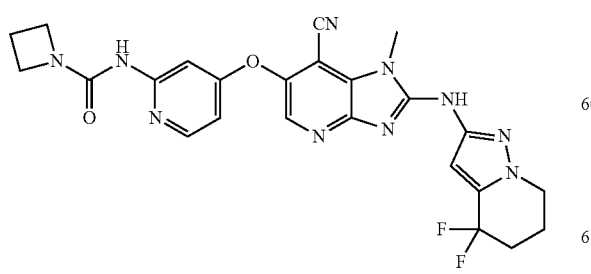
I-35
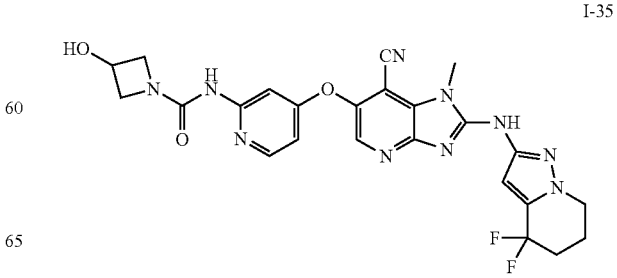

I-36'
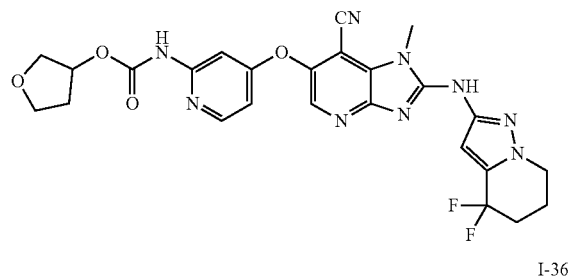
I-36
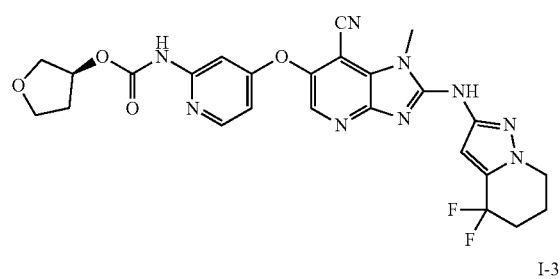
I-37
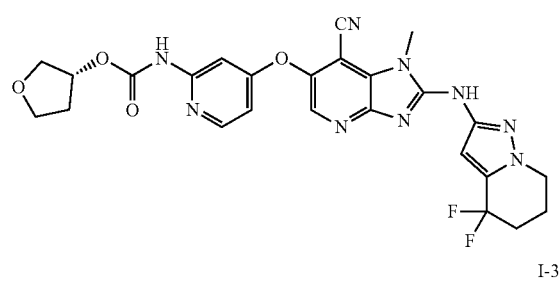
I-38
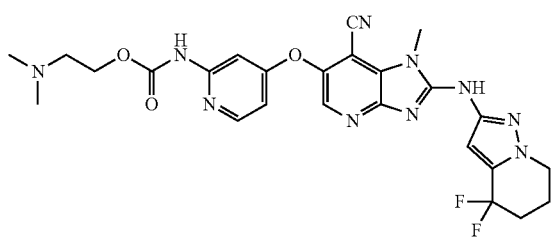
I-39
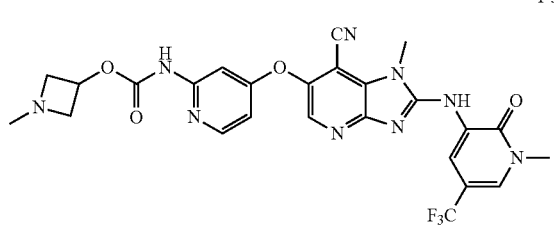
I-40
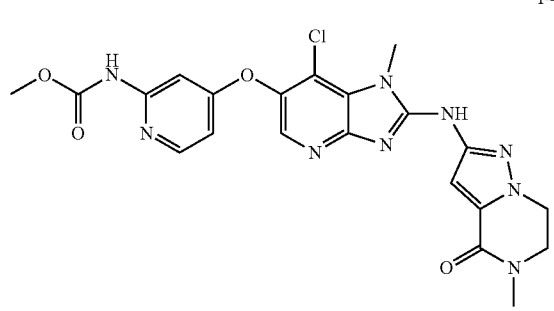
I-41
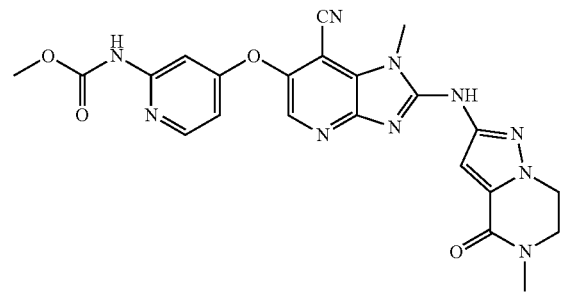
I-42
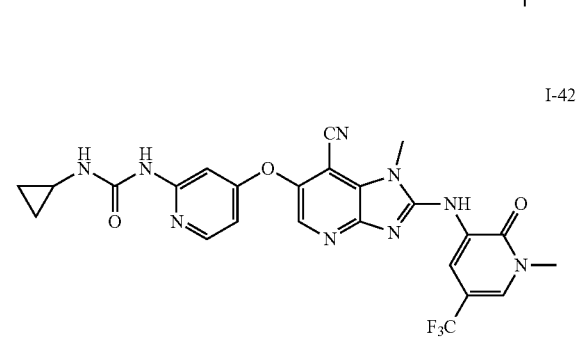
I-43
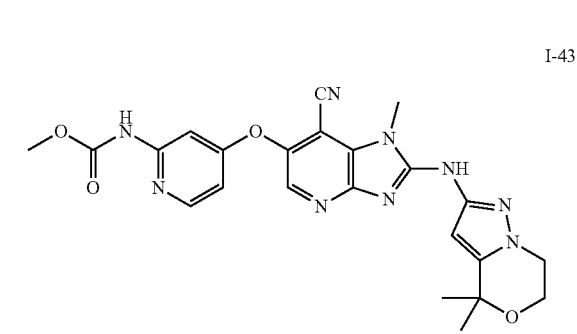
I-44
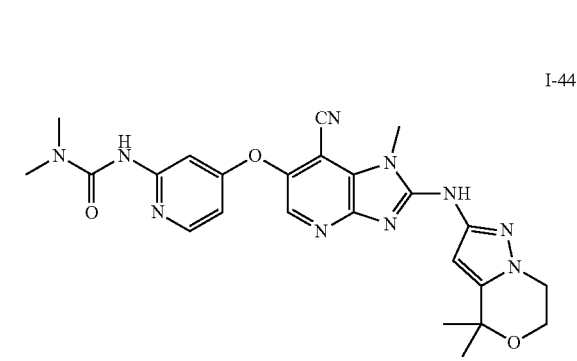
I-45
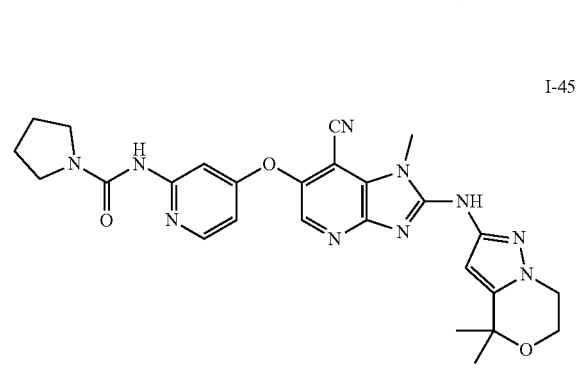

I-46
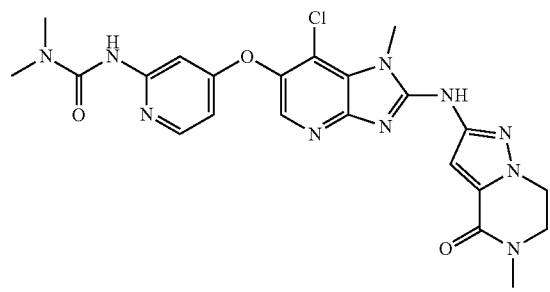
I-47
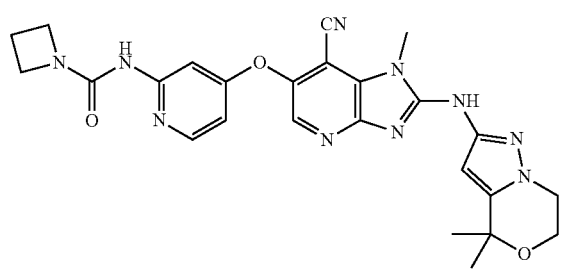
I-48'
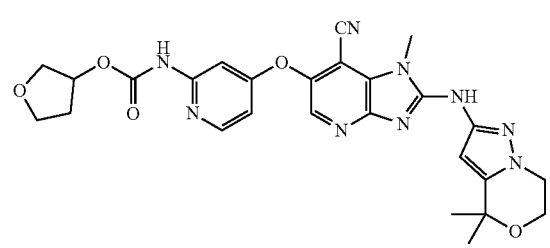
I-48
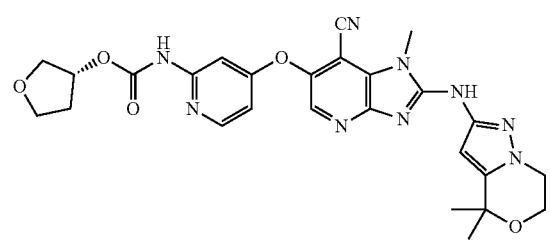
I-49
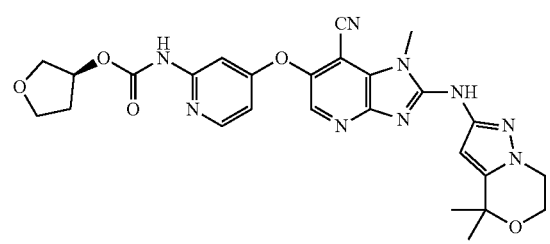
I-52
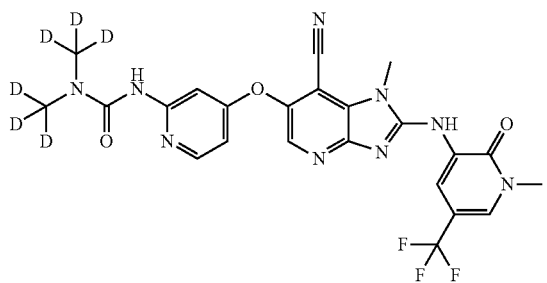
I-53'
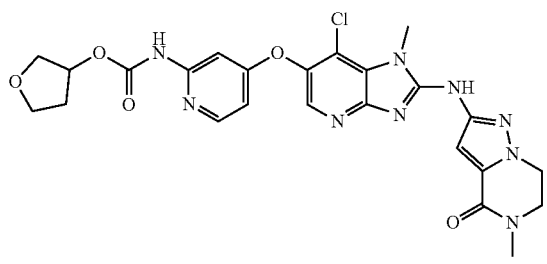
I-53
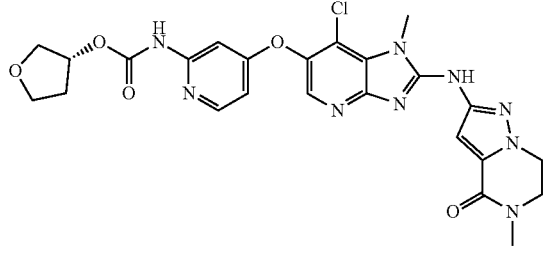
I-54
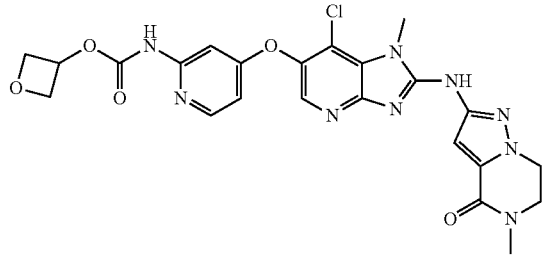
I-55
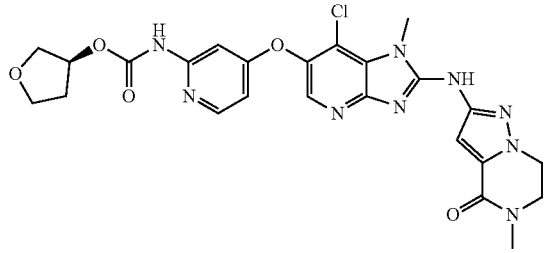

I-56
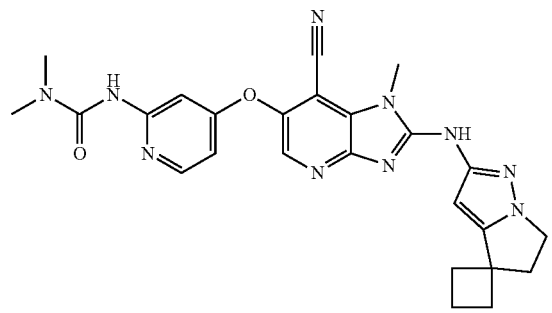
I-57
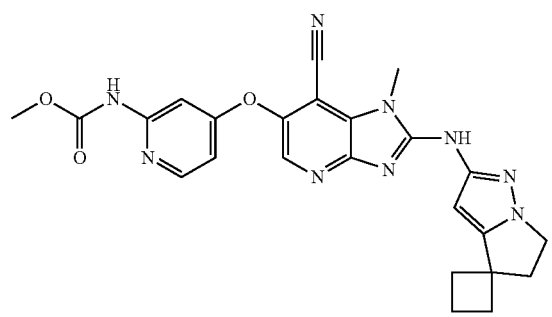
I-58
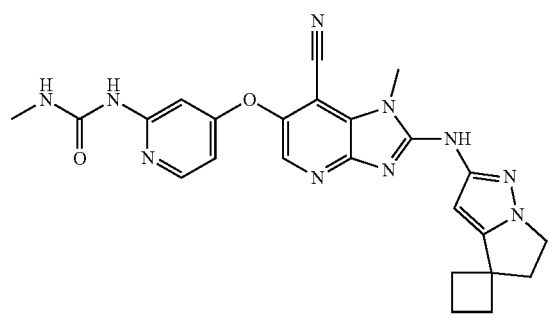
I-59'
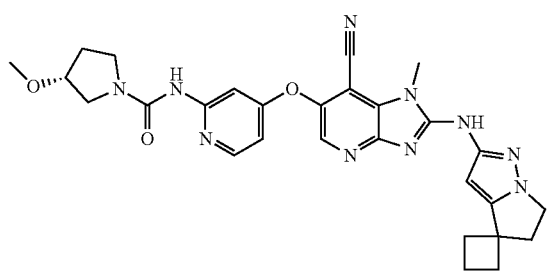
I-59
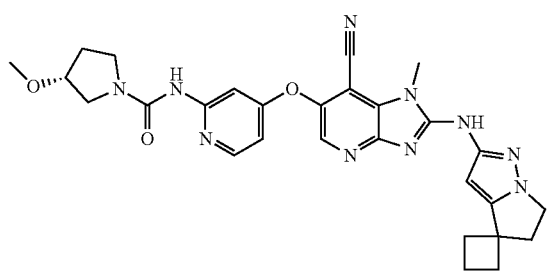
I-60
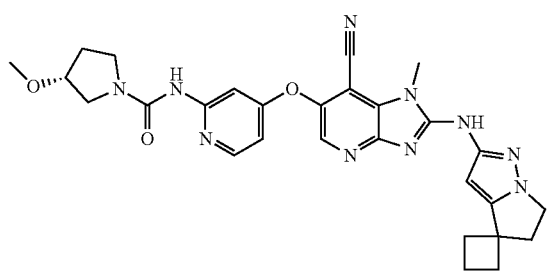
I-61
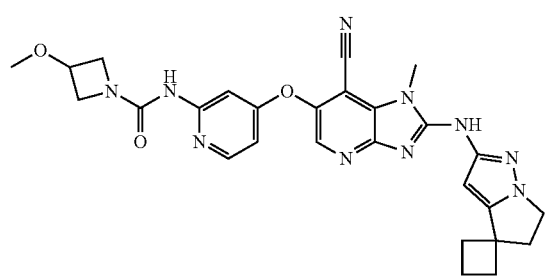
I-62
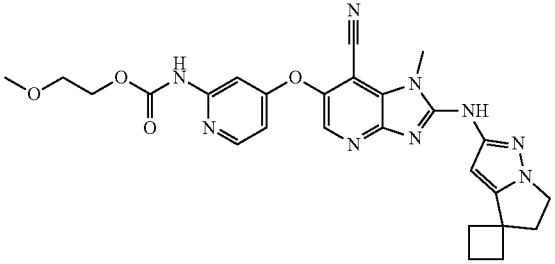
I-63
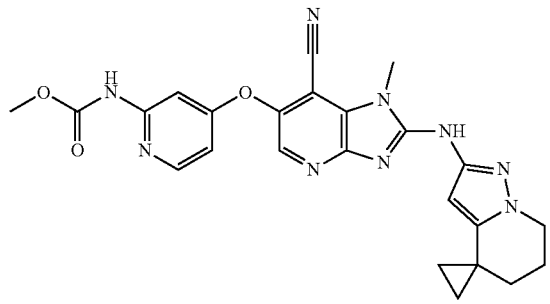
I-64
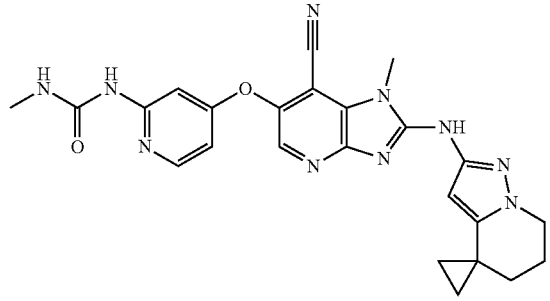

I-65
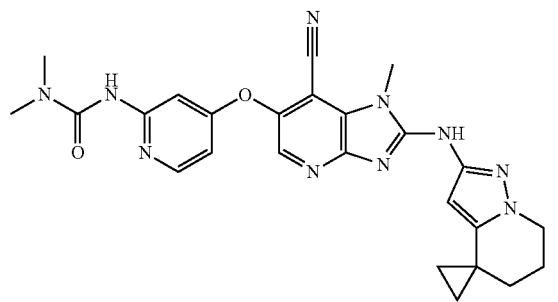
I-66
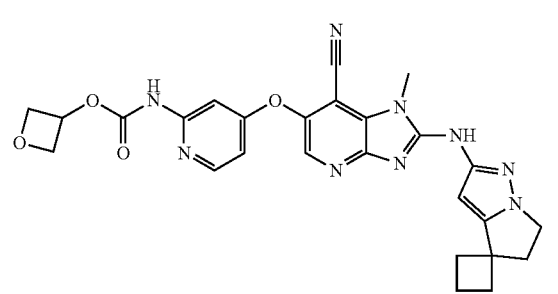
I-67
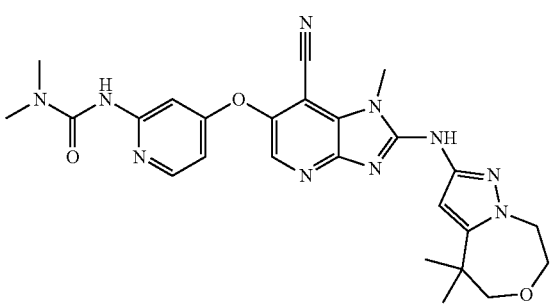
I-68
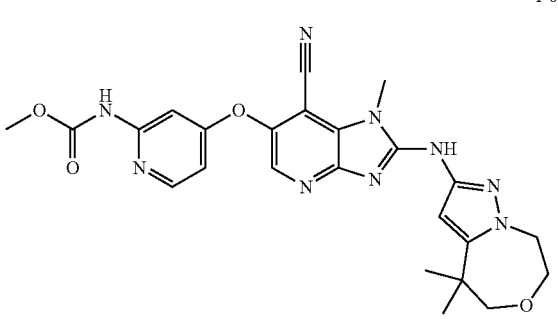
I-69
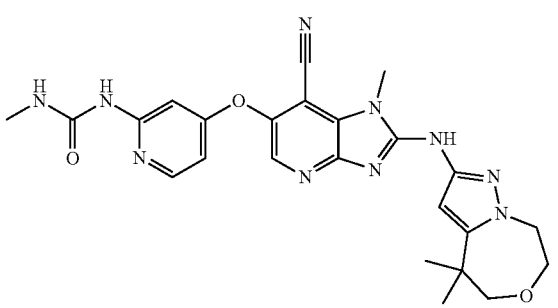
I-70
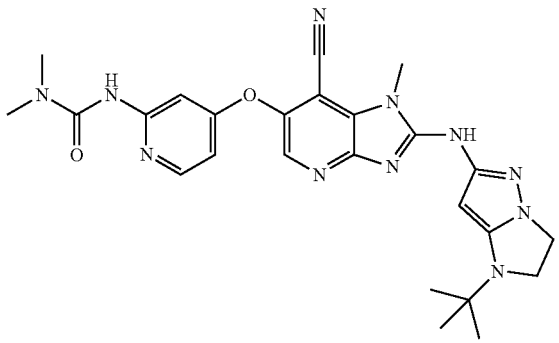
I-71
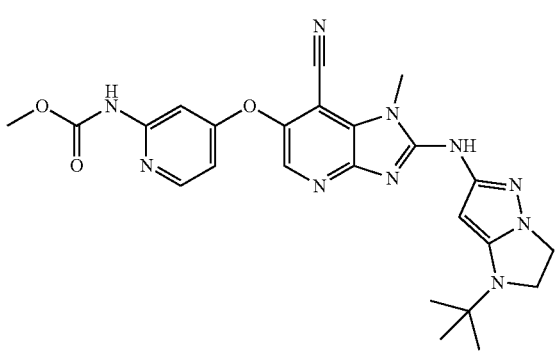
I-72
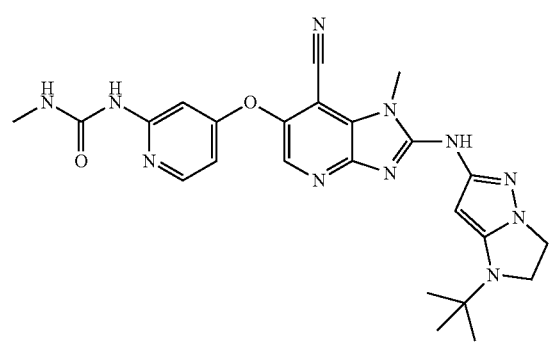
I-73

-continued

I-120'

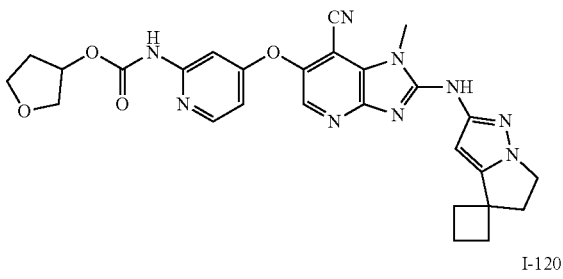

I-120

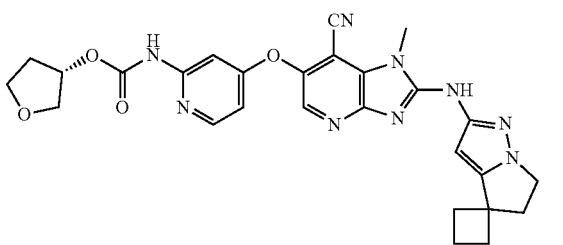

I-121

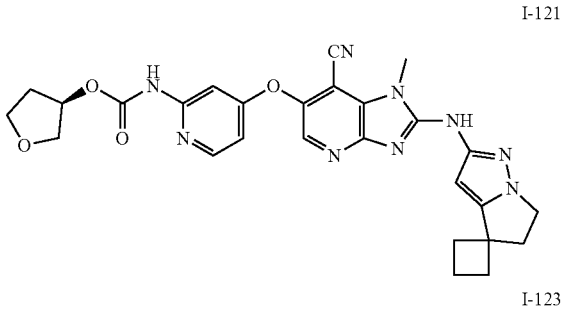

I-123

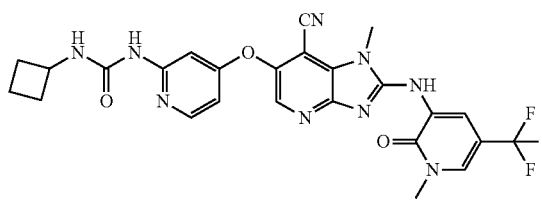

or a pharmaceutically acceptable salt thereof.

2. A pharmaceutical composition comprising a compound of claim 1, or a pharmaceutically acceptable salt thereof, and a pharmaceutically acceptable carrier.

3. The compound of claim 1, wherein the compound is:

I-3

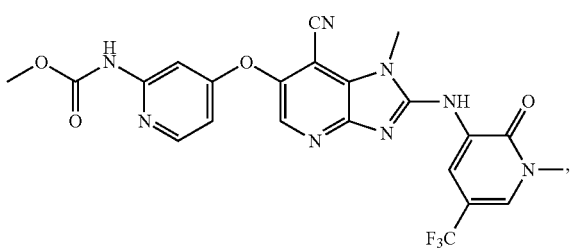

or a pharmaceutically acceptable salt thereof.

4. A pharmaceutical composition comprising the compound of claim 3, or a pharmaceutically acceptable salt thereof, and a pharmaceutically acceptable carrier.

5. The compound of claim 1, wherein the compound is:

I-4

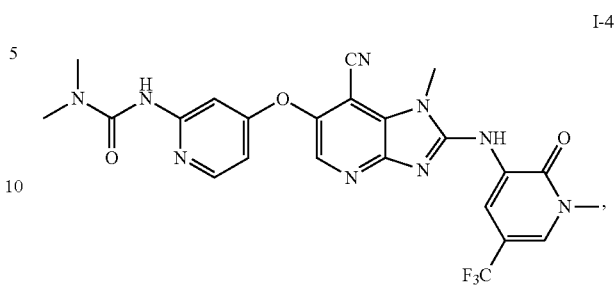

or a pharmaceutically acceptable salt thereof.

6. A pharmaceutical composition comprising the compound of claim 5, or a pharmaceutically acceptable salt thereof, and a pharmaceutically acceptable carrier.

7. The compound of claim 1, wherein the compound is:

I-7

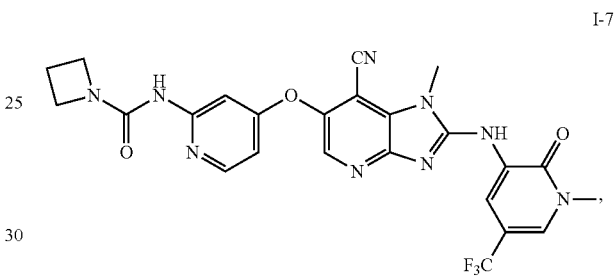

or a pharmaceutically acceptable salt thereof.

8. A pharmaceutical composition comprising the compound of claim 7, or a pharmaceutically acceptable salt thereof, and a pharmaceutically acceptable carrier.

9. The compound of claim 1, wherein the compound is:

I-14

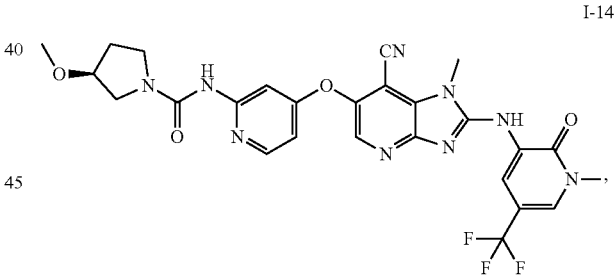

or a pharmaceutically acceptable salt thereof.

10. A pharmaceutical composition comprising the compound of claim 9, or a pharmaceutically acceptable salt thereof, and a pharmaceutically acceptable carrier.

11. The compound of claim 1, wherein the compound is:

I-15

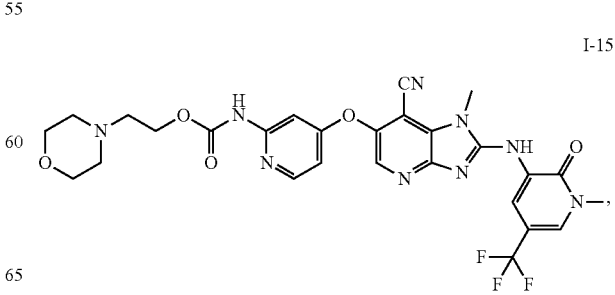

or a pharmaceutically acceptable salt thereof.

12. A pharmaceutical composition comprising the compound of claim 11, or a pharmaceutically acceptable salt thereof, and a pharmaceutically acceptable carrier.

13. The compound of claim 1, wherein the compound is:

I-18 or pharmaceutically acceptable salt thereof.

14. A pharmaceutical composition comprising the compound of claim 13, or a pharmaceutically acceptable salt thereof, and a pharmaceutically acceptable carrier.

15. The compound of claim 1, wherein the compound is:

I-26 or a pharmaceutically acceptable salt thereof.

16. A pharmaceutical composition comprising the compound of claim 15, or a pharmaceutically acceptable salt thereof, and a pharmaceutically acceptable carrier.

17. The compound of claim 1, wherein the compound is:

I-30 or a pharmaceutically acceptable salt thereof.

18. A pharmaceutical composition comprising the compound of claim 17, or a pharmaceutically acceptable salt thereof, and a pharmaceutically acceptable carrier.

19. The compound of claim 1, wherein the compound is:

I-48 or pharmaceutically acceptable salt thereof.

20. A pharmaceutical composition comprising the compound of claim 19, or a pharmaceutically acceptable salt thereof, and a pharmaceutically acceptable carrier.

21. The compound of claim 1, wherein the compound is:

I-56 or a pharmaceutically acceptable salt thereof.

22. A pharmaceutical composition comprising the compound of claim 21, or a pharmaceutically acceptable salt thereof, and a pharmaceutically acceptable carrier.

23. The compound of claim 1, wherein the compound is:

I-57 or a pharmaceutically acceptable salt thereof.

24. A pharmaceutical composition comprising the compound of claim 23, or a pharmaceutically acceptable salt thereof, and a pharmaceutically acceptable carrier.

25. The compound of claim 1, wherein the compound is:

I-60 or a pharmaceutically acceptable salt thereof.

26. A pharmaceutical composition comprising the compound of claim 25, or a pharmaceutically acceptable salt thereof, and a pharmaceutically acceptable carrier.

27. The compound of claim 1, wherein the compound is:

I-61

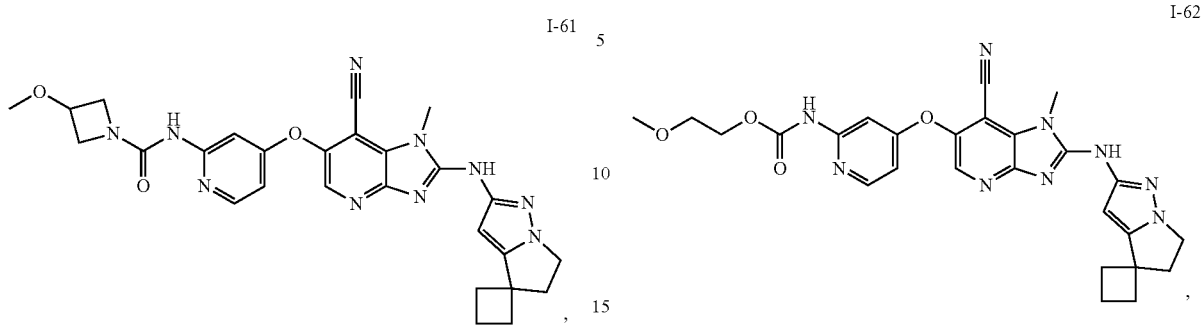

or a pharmaceutically acceptable salt thereof.

28. A pharmaceutical composition comprising the compound of claim 27, or a pharmaceutically acceptable salt thereof, and a pharmaceutically acceptable carrier.

29. The compound of claim 1, wherein the compound is:

I-62 or a pharmaceutically acceptable salt thereof.

30. A pharmaceutical composition comprising the compound of claim 29, or a pharmaceutically acceptable salt thereof, and a pharmaceutically acceptable carrier.

* * * * *

UNITED STATES PATENT AND TRADEMARK OFFICE
CERTIFICATE OF CORRECTION

Page 1 of 2

PATENT NO.       : 11,970,494 B2
APPLICATION NO.  : 17/982663
DATED            : April 30, 2024
INVENTOR(S)      : Craig E. Masse et al.

It is certified that error appears in the above-identified patent and that said Letters Patent is hereby corrected as shown below:

In the Specification

At Column 81, beginning at Line 17, please delete:

"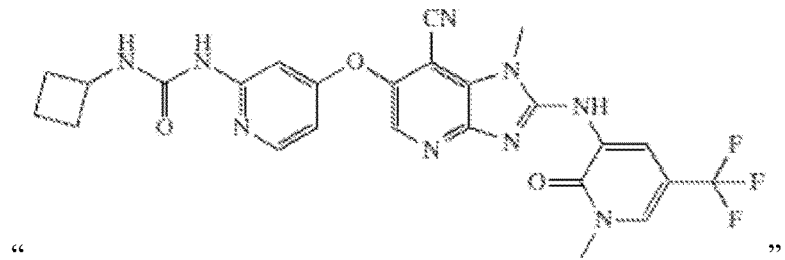"

And insert:

-- 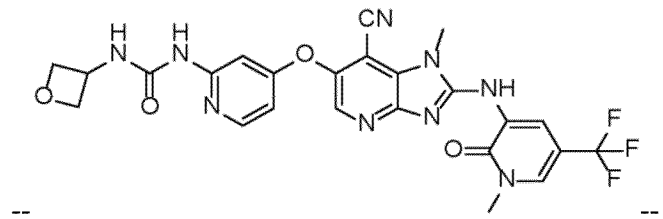 --

Column 256, beginning at Line 31, Example 77, please delete:

"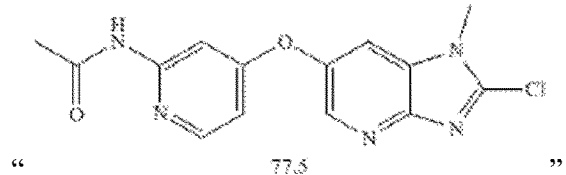"

Signed and Sealed this
Ninth Day of July, 2024

Katherine Kelly Vidal
*Director of the United States Patent and Trademark Office*

CERTIFICATE OF CORRECTION (continued)
U.S. Pat. No. 11,970,494 B2

And insert:

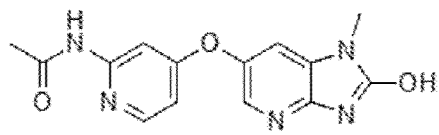

|    | 77.5 |    |
|----|------|----|
| -- |      | -- |

In the Claims

At Claim 1, Column 355, Line 40, please delete:

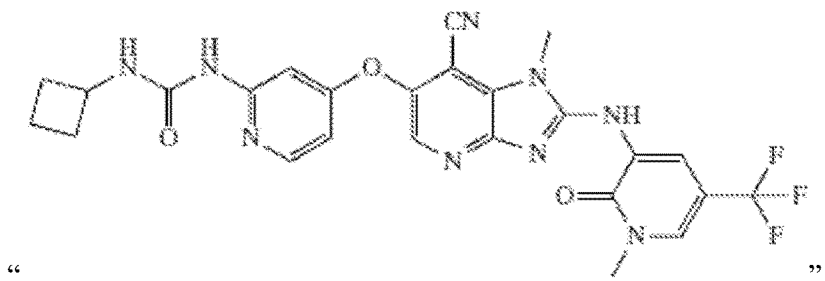

"                                                                              "

And insert:

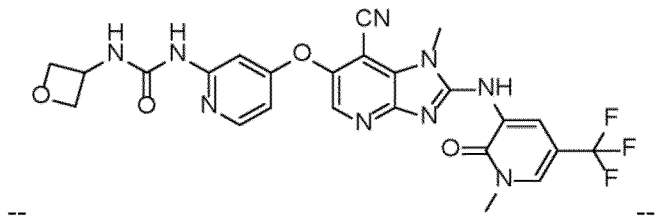

--                                                                              --